(12) United States Patent
Mikami et al.

(10) Patent No.: US 10,017,508 B2
(45) Date of Patent: *Jul. 10, 2018

(54) NITROGENATED HETEROCYCLIC COMPOUND

(71) Applicant: Takeda Pharmaceutical Company Limited, Osaka-shi, Osaka (JP)

(72) Inventors: Satoshi Mikami, Kanagawa (JP); Shinji Nakamura, Kanagawa (JP); Tomoko Ashizawa, New York, NY (US); Shigekazu Sasaki, Kanagawa (JP); Takahiko Taniguchi, Kanagawa (JP); Izumi Nomura, Kanagawa (JP); Masanori Kawasaki, New York, NY (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/264,213

(22) Filed: Sep. 13, 2016

(65) Prior Publication Data

US 2017/0129887 A1    May 11, 2017

Related U.S. Application Data

(63) Continuation of application No. 14/397,066, filed as application No. PCT/JP2013/062140 on Apr. 24, 2013, now Pat. No. 9,469,637.

(30) Foreign Application Priority Data

Apr. 25, 2012 (JP) .................................. 2012-100374
Dec. 26, 2012 (JP) .................................. 2012-283470

(51) Int. Cl.
C07D 241/36    (2006.01)
A61K 31/498    (2006.01)
(Continued)

(52) U.S. Cl.
CPC ............. *C07D 471/04* (2013.01); *A61K 9/20* (2013.01); *A61K 31/498* (2013.01);
(Continued)

(58) Field of Classification Search
None
See application file for complete search history.

(56) References Cited

U.S. PATENT DOCUMENTS 6,066,649 A    5/2000    Podzuweit
7,135,498 B1   11/2006   Chopp et al.
(Continued)

FOREIGN PATENT DOCUMENTS

CL    2014001110    8/2014
EP    2 873 669     5/2015
(Continued)

OTHER PUBLICATIONS

Menniti, et al., "Phosphodiesterases in the CNS: targets for drug development", Nat. Rev. Drug Discov. Aug. 2006, vol. 5: 660-670—Abstract; 1 page.
(Continued)

*Primary Examiner* — Marcos L Sznaidman
*Assistant Examiner* — Rayna Rodriguez
(74) *Attorney, Agent, or Firm* — Hamre, Schumann, Mueller & Larson, P.C.

(57) ABSTRACT

The present invention provides a compound having a PDE2A selective inhibitory action, which is useful as an agent for the prophylaxis or treatment of schizophrenia, Alzheimer's disease and the like.

The present invention is a compound represented by the formula (1):

(Continued)

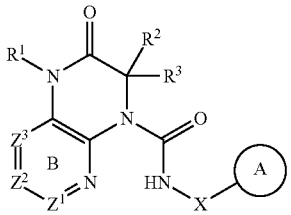

(1)

wherein each symbol is as described in the specification, or a salt thereof.

11 Claims, 1 Drawing Sheet

(51) Int. Cl.
    *C07D 471/04*     (2006.01)
    *C07D 519/00*     (2006.01)
    *A61K 9/20*     (2006.01)
    *A61K 31/555*     (2006.01)
    *C07F 7/18*     (2006.01)

(52) U.S. Cl.
    CPC .......... *A61K 31/555* (2013.01); *C07D 519/00* (2013.01); *C07F 7/1844* (2013.01)

(56) References Cited

U.S. PATENT DOCUMENTS

| | | |
|---|---|---|
| 2002/0032203 A1 | 3/2002 | Swope |
| 2002/0119978 A1 | 8/2002 | Swope et al. |
| 2002/0132754 A1 | 9/2002 | Boss et al. |
| 2002/0155173 A1 | 10/2002 | Chopp et al. |
| 2002/0198377 A1 | 12/2002 | Niewohner et al. |
| 2004/0127538 A1 | 7/2004 | Oinuma et al. |
| 2005/0143388 A1 | 6/2005 | Chopp |
| 2005/0282880 A1 | 12/2005 | Oinuma et al. |
| 2006/0106037 A1 | 5/2006 | Bar et al. |
| 2006/0128695 A1 | 6/2006 | Bourguignon et al. |
| 2006/0148802 A1 | 7/2006 | Haning et al. |
| 2007/0135457 A1 | 6/2007 | Beyer et al. |
| 2007/0299079 A1 | 12/2007 | Norbert et al. |
| 2008/0027064 A1 | 1/2008 | Hofgen et al. |
| 2008/0280907 A1 | 11/2008 | Schmidt et al. |
| 2008/0312225 A1 | 12/2008 | Schmidt et al. |
| 2009/0203691 A1 | 8/2009 | Oinuma et al. |
| 2009/0239874 A1 | 9/2009 | Hofgen et al. |
| 2010/0035882 A1 | 2/2010 | Ellinghaus et al. |
| 2010/0120762 A1 | 5/2010 | Stange et al. |
| 2010/0120763 A1 | 5/2010 | Stange et al. |
| 2010/0150839 A1 | 6/2010 | Kelleher |
| 2011/0071168 A1 | 3/2011 | Chopp et al. |
| 2011/0136803 A1 | 6/2011 | Schmidt et al. |
| 2011/0144153 A1 | 6/2011 | Nozawa et al. |
| 2012/0009152 A1 | 1/2012 | Chopp |
| 2012/0136012 A1 | 5/2012 | Breslin et al. |
| 2012/0136064 A1 | 5/2012 | Nixon et al. |
| 2012/0252780 A1 | 10/2012 | Ng et al. |
| 2013/0115194 A1 | 5/2013 | Long et al. |
| 2014/0088080 A1 | 3/2014 | Koga et al. |
| 2015/0105373 A1 | 4/2015 | Mikami et al. |
| 2015/0158863 A1 | 6/2015 | Nakamura et al. |

FOREIGN PATENT DOCUMENTS

| | | |
|---|---|---|
| GB | 2 404 658 | 2/2005 |
| JP | 6-145169 | 5/1994 |
| JP | 9-221423 | 8/1997 |
| JP | 11-292877 | 10/1999 |
| JP | 2004-525098 | 8/2004 |
| JP | 2005-145840 | 6/2005 |
| JP | 2006-519243 | 8/2006 |
| JP | 2007-513996 | 5/2007 |
| JP | 2008-526716 | 7/2008 |
| JP | 2008-526717 | 7/2008 |
| JP | 2009-538853 | 11/2009 |
| WO | 92/01938 | 2/1992 |
| WO | 00/23091 | 4/2000 |
| WO | 00/32575 | 6/2000 |
| WO | 01/09125 | 2/2001 |
| WO | 02/50078 | 6/2002 |
| WO | 2004/044234 | 5/2004 |
| WO | 2004/056823 | 7/2004 |
| WO | 2004/060872 | 7/2004 |
| WO | 2005/035534 | 4/2005 |
| WO | 2005/058892 | 6/2005 |
| WO | 2006/015159 | 2/2006 |
| WO | 2007/020521 | 2/2007 |
| WO | 2007/125405 | 11/2007 |
| WO | 2007/137819 | 12/2007 |
| WO | 2007/146230 | 12/2007 |
| WO | 2008/043461 | 4/2008 |
| WO | 2008/085302 | 7/2008 |
| WO | 2009/026276 | 2/2009 |
| WO | 2010/054253 | 5/2010 |
| WO | 2010/054260 | 5/2010 |
| WO | 2010/097410 | 9/2010 |
| WO | 2011/022213 | 2/2011 |
| WO | 2011/044157 | 4/2011 |
| WO | 2011/059839 | 5/2011 |
| WO | 2012/018909 | 2/2012 |
| WO | 2012/042541 | 4/2012 |
| WO | 2012/051036 | 4/2012 |
| WO | 2012/087861 | 6/2012 |
| WO | 2012/165399 | 12/2012 |
| WO | 2012/178124 | 12/2012 |
| WO | 2013/161913 | 10/2013 |
| WO | 2015/012328 | 1/2015 |

OTHER PUBLICATIONS

Houslay, et al., "cAMP-Specific Phosphodiesterase-4 Enzymes in the Cardiovascular System", Circ. Res. 2007, vol. 100: pp. 950-966.
Beavo, et al., "Stimulation of Adenosine 3',5'-Monophosphate Hydrolysis by Guanosine 3',5'-Monophosphate", J. Biol. Chem. 1971, vol. 246: pp. 3841-3846.
Russell, et al., "Separate Phosphodiesterases for the Hydrolysis of Cyclic Adenosine 3',5'-Monophosphate and Cyclic Guanosine 3',5'Monophosphate in Rat Liver", J. Biol. Chem. 1973, vol. 248: pp. 1334-1340.
Martinez, et al., "The two GAF domains in phosphodiesterase 2A have distinct roles in dimerization and in cGMP binding", PNAS 2002, vol. 99: pp. 13260-13265.
Jager, et al., "Activation of PDE2 and PDE5 by specific GAF ligands: delayed activation of PDE5", British J. Pharmacol. 2010, vol. 161: pp. 1645-1660.
Wu, et al, "Molecular Determinants for Cyclic Nucleotide Binding to the Regulatory Domains of Phosphodiesterase 2A", J. Biol. Chem. 2004, vol. 279: pp. 37928-37938.
Martins, et al., "Purification and Characterization of a Cyclic GMP-stimulated Cyclic Nucleotide Phosphodiesterase from Bovine Tissues", J. Biol. Chem. 1982, vol. 257: pp. 1973-1979.
Yamamoto, et al., "Purification and Characterization of Cyclic GMP-stimulated Cyclic Nucleotide Phosphodiesterase from Calf Liver", J. Biol. Chem. 1983, vol. 258: pp. 12526-12533.
Juilfs, et al., "Cyclic GMP as Substrate and Regulator of Cyclic Nucleotide Phosphodiesterases (PDEs)" Rev. Physiol. Biochem. Pharmacol. 1999, vol. 135: pp. 67-104.
Bender, et al., "Differentiation of human monocytes in vitro with granulocyte-macrophage colony-stimulating factor and macrophage colony-stimulating factor produces distinct changes in cGMP", Cellular Signalling 2004, vol. 16:, abstract, 1 page.
Stephenson, et al., "Immunohistochemical Localization of Phosphodiesterase 2A in Multiple Mammalian Species", J. Histochem. Cytochem. 2009, vol. 57: pp. 933-949.

(56) References Cited

OTHER PUBLICATIONS

Lakics, et al., "Quantitative comparison of phosphodiesterase mRNA distribution in human brain and peripheral tissues", Neuropharmacology 2010, vol. 59: abstract, 1 page.

Boess, et al., "Inhibition of phosphodiesterase 2 increases neuronal cGMP, synaptic plasticity and memory performance", Neuropharmacology 2004, vol. 47: abstract, 1 page.

Domek-Lopacinaska, et al., "Cyclic GMP and Nitric Oxide Synthase in Aging and Alzheimer's Disease", Mol. Neurobiol. 2010, vol. 41: abstract, 1 page.

Rodefer, et al., "Selective phosphodiesterase inhibitors improve performance on the ED/ID cognitive task in rates", Neuropharmacology 2012, vol. 62: abstract, 1 page.

Masood, et al., "Reversal of Oxidative Stress-Induced Anxiety by Inhibition of Phosphodiesterase-2 in Mice", J. Pharmacol. Exp. Ther. 2008, vol. 326: pp. 369-379.

Masood, et al., "Anxiolytic Effects of Phosphodiesterase-2 Inhibitors Associated with Increase cGMP Signaling", J. Pharmacol. Exp. Ther. 2009, vol. 331: pp. 690-699.

Jordan, V.C., "Tamoxifen: A most Unlikely Pioneering Medicine", Nature Reviews: Drug Discovery, vol. 2, Mar. 2003, pp. 205-213.

Dorwald, "Side Reactions in Organic Synthesis: A Guide to Successful Synthesis Design", Weinheim: Wiley-VCH Verlag GmbH & Co. KGaA, 2005, Preface.

Tenor, et al., "Analysis of PDE Isoenzymer Profiles in Cells and Tissues by Pharmacological Methods", Phosphodiesterase Inhibitors, Academic Press, 1996, pp. 21-40.

Juilfs, et al., Cyclic GMP as Substrate and Regulator of Cyclic Nucleotide Phosphodiesterases (PDEs), Rev. Physiol. Biochem. Pharmacol. 1999, vol. 135, pp. 67-104.

Shen, et al., "Discovery of pyrazolopyrimidines as the first class of allosteric agonists for the high affinity nicotinic acid receptor GPR109A", Bioorganic & Medicinal Chemistry Letters, vol. 18, Aug. 14, 2008, pp. 4948-4951.

Banerjee, et al., Second-Generation DBFOX Ligands for the Synthesis of β-Substituted α-Amino Acids via Enantioselective Radical Conjugate Additions, J. Org. Chem., vol. 73, No. 22, 2008, pp. 8973-8978.

Klimkowski, et al., "D-Phenylglycinol-derived non-covalent factor Xa inhibitors: Effect of non-peptidic S4 linkage elements on affinity and anticoagulant activity", Bioorganic & Medicinal Chemistry Letters, vol. 17, No. 21, 2007, pp. 5801-5805.

Chemical Library, RN 1422628-80-5, Mar. 8, 2013, 1 page.

STN Registry File, RN 1422576-26-8, Mar. 7, 2013, 1 page.

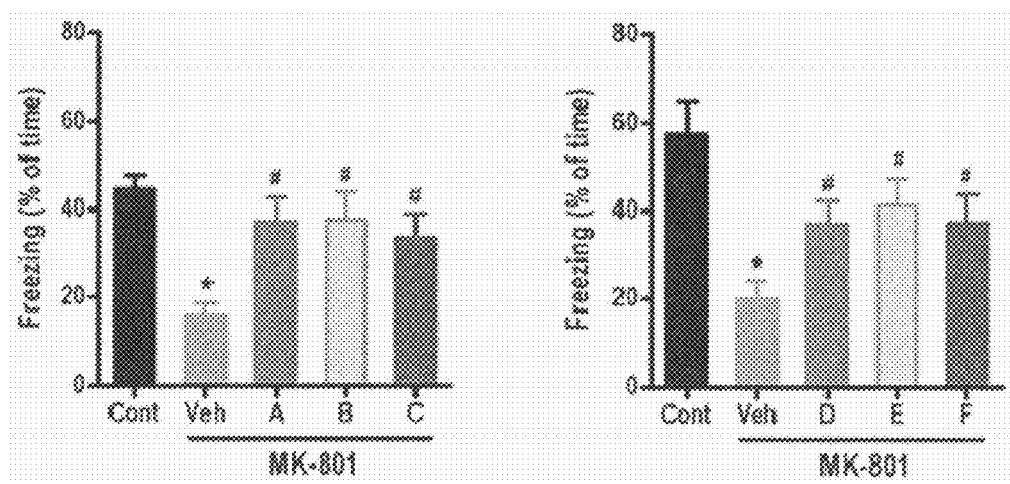

NITROGENATED HETEROCYCLIC COMPOUND

TECHNICAL FIELD

The present invention relates to a nitrogen-containing heterocyclic compound having a PDE2A selective inhibitory action, which is useful as an agent for the prophylaxis or treatment of schizophrenia, Alzheimer's disease and the like.

BACKGROUND OF THE INVENTION

Cyclic nucleotide phosphodiesterases (PDEs) are enzymes that regulate the cellular levels of the second messengers, cyclic adenosine monophosphate (cAMP) and cyclic guanosine monophosphate (cGMP), by controlling their rates of degradation. PDEs are a superfamily of enzymes encoded by 21 genes and subdivided into 11 distinct families according to structural and functional properties. The PDE enzymes selectively catalyze the hydrolysis of the 3'-ester bond of cAMP and/or cGMP, forming the inactive 5'-monophosphate. On the basis of substrate specificity, the PDE families can be further classified into three groups: i) the cAMP-PDEs (PDE4, PDE7 and PDE8), ii) the cGMP-PDEs (PDE5, PDE6 and PDE9), and iii) the dual-substrate PDEs (PDE1, PDE2, PDE3, PDE10 and PDE11).

cAMP and cGMP are involved in the regulation of virtually every physiological process such as pro-inflammatory mediator production and action, ion channel function, muscle relaxation, learning and memory formation, differentiation, apoptosis, lipogenesis, glycogenolysis and gluconeogenesis. Especially, in neurons, these second messengers have an important role in the regulation of synaptic transmission as well as in neuronal differentiation and survival (Non-Patent Document 1). Regulation of these processes by cAMP and cGMP are accompanied by activation of protein kinase A (PKA) and protein kinase G (PKG), which in turn phosphorylate a variety of substrates, including transcription factors, ion channels and receptors that regulate a variety of physiological processes. Intracellular cAMP and cGMP concentrations seem to be temporally, spatially, and functionally compartmentalized by regulation of adenylate and guanylate cyclases in response to extracellular signaling and their degradation by PDEs (Non-Patent Document 2). PDEs provide the only means of degrading the cyclic nucleotides cAMP and cGMP in cells, thus PDEs play an essential role in cyclic nucleotide signaling. Thereby, PDEs could be promising targets for various therapeutic drugs.

Phosphodiesterase 2A (PDE2A) is a dual substrate enzyme that hydrolyzes both cAMP and cGMP. It is organized into four domains, N-terminus, GAF-A, GAF-B, and catalytic domains, and functions as a homodimer. PDE2A catalytic activity is allosterically stimulated by cGMP binding. GAF-B domain binds with a high affinity and a high selectivity to cGMP. A conformational change is caused by the cGMP binding in the PDE2A homodimer which causes an increase in the catalytic activity of the enzyme (Non-Patent Document 3-6). In contrast, there are as yet no known in vivo examples that cAMP stimulates PDE2A catalytic activity, even though it can also bind to the GAF-B domain with a 30-100-fold lower affinity than cGMP (Non-Patent Document 6 and 7). PDE2A activity may become functionally significant under conditions in which cellular cGMP concentrations are elevated, which shows a physiological role for GAF domain-regulation of the enzyme.

PDE2A is expressed in a wide variety of tissues and highly in the brain. The protein was originally purified from heart, liver, adrenal gland, platelets, endothelial cells, and macrophages (Non-Patent Document 8-13). In the brain, the PDE2A mRNA levels are the highest in the caudate lobe, nucleus accumbens, cortex (frontal, parietal and temporal) and the hippocampus, and are at least 10-fold lower expression in other brain regions (Non-Patent Document 14). This suggests that PDE2A may control intraneuronal cAMP and cGMP levels in areas that are important for learning and memory formation.

Inhibition of PDE2A results in increased cAMP and cGMP levels that could improve cognitive function. In both cortical neurons and hippocampal slices, a PDE2A inhibitor potently increased cGMP concentrations in the presence of guanylate cyclase activators and also increased cAMP concentrations in the presence of forskolin (Non-Patent Document 15). The PDE2A inhibitor was also found to potently increase the induction of long-term potentiation (LTP) in hippocampal slices in response to a weak tetanizing stimulus. This effect on LTP in slices suggests that PDE2A inhibition has positive effects on learning and memory in vivo (Non-Patent Document 15). In fact, the same PDE2A inhibitor increased retention on both novel object and social recognition tasks in rats, and improved object memory and object recognition task in 3-, 12-, and 24-month old rats. It also attenuated the extradimensional (ED) shift deficit on extradimensional-intradimensional (ED/ID) cognitive task in subchronic PCP-treated rats (Non-Patent Document 15-17). These results suggest that PDE2A inhibition could facilitate learning and memory processes through potentiation of cAMP and cGMP-regulated signaling cascades.

Increased cGMP levels by PDE2A inhibition could also influence anxiety and stress-related events. PDE2A inhibitors decreased oxidative stress and induced the expression of NADPH oxidase subunits in oxidative stress inducer-treated mice. It improved anxiety-like behavior in elevated plus maze, open-field, and hole-board tests through the NADPH oxidase pathway (Non-Patent Document 18). In addition, PDE2A inhibitors also produced anxiolytic effects on behavior in non-stressed mice in the elevated plus-maze and hole-board tests (Non-Patent Document 19). PDE2A may be a novel pharmacological target for treatment of not only cognitive deficit, but also anxiety in neuropsychiatric and neurodegenerative disorders.

These unique distribution and functions in the brain indicate that PDE2A represents an important novel target for the treatment of neuropsychiatric and neurodegenerative disorders, in particular schizophrenia and Alzheimer's disease.

Patent Document 1 discloses, as a nitrogen-containing heterocyclic compound, a compound represented by the formula (I):

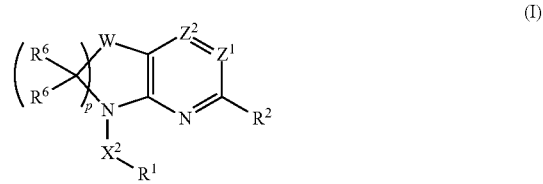

wherein
$Z^1$ and $Z^2$ are each independently N or CR (at least one is CR, and R is halogen, —OH, —CN, fluoro-substituted $C_{1-2}$ alkyl, —O—($C_{1-2}$) fluoro-substituted alkyl, —S—$C_{1-2}$ fluoro-substituted alkyl or the like);

W is —O—, —NH—, —N($C_{1-4}$ alkyl)-, —S—, —S(O)—, —S(O)$_2$— or the like;

$R^6$ is H, $C_{1-4}$ alkyl or fluoro-substituted $C_{1-4}$ alkyl, or two $R^6$, which are bonded to the single carbon atom, in combination optionally form =O;

$R^1$ is carbocycle or heterocycle, each of which is optionally substituted by halo, —CN, $C_{1-4}$ alkyl or the like;

$R^2$ is carbocycle or heterocycle, each of which is optionally substituted by halo, —CN, $C_{1-4}$ alkyl or the like;

P is 1, 2 or 3;

$X^2$ is C(=O), —C(=O)—O—*, —C(=O)—NH—*, —C(=O)—NHCR$^4$R$^5$—* or the like (* means the binding position to $R^1$);

$R^4$ and $R^5$ are each independently H, $C_{1-4}$ alkyl, —$CF_3$ or ($C_{1-3}$ alkyl) —$CF_3$, which is a sirtuin modulator, and useful for treatment of Alzheimer's disease, Parkinson's disease.

However, the structure of the present invention is different from that of the above-mentioned compound.

DOCUMENT LIST

Patent Document

Patent Document 1: WO 2011/059839

Non-Patent Document

Non-Patent Document 1: Nat. Rev. Drug Discov. 2006, vol. 5: 660-670
Non-Patent Document 2: Circ. Res. 2007, vol. 100: 950-966
Non-Patent Document 3: J. Biol. Chem. 1971, vol. 246: 3841-3846
Non-Patent Document 4: J. Biol. Chem. 1973, vol. 248: 1334-1340
Non-Patent Document 5: PNAS 2005, vol. 99: 13260-13265
Non-Patent Document 6: British J. Pharmacol. 2010, vol. 161: 1645-1660
Non-Patent Document 7: J. Biol. Chem. 2004, vol. 279: 37928-37938
Non-Patent Document 8: J. Biol. Chem. 1982, vol. 257: 1973-1979
Non-Patent Document 9: J. Biol. Chem. 1983, vol. 258: 12526-12533
Non-Patent Document 10: Phosphodiesterase Inhibitors, Academic Press: 21-40
Non-Patent Document 11: Rev. Physiol. Biochem. Pharmacol. 1999, vol. 135: 67-104
Non-Patent Document 12: Cell Signal 2004, vol. 16: 365-374
Non-Patent Document 13: J. Histochem. Cytochem. 2009, vol. 57: 933-949
Non-Patent Document 14: Neuropharmacology 2010, vol. 59: 367-374
Non-Patent Document 15: Neuropharmacology 2004, vol. 47: 1081-1092
Non-Patent Document 16: Mol. Neurobiol. 2010, vol. 41: 129-137
Non-Patent Document 17: Neuropharmacology 2012, vol. 62: 1182-1190
Non-Patent Document 18: J. Pharmacol. Exp. Ther. 2008, vol. 326: 369-379
Non-Patent Document 19: J. Pharmacol. Exp. Ther. 2009, vol. 331: 690-699

SUMMARY OF THE INVENTION

Problems to be Solved by the Invention

The present invention aims to provide a compound having a PDE2A selective inhibitory action, which is useful as a prophylactic or therapeutic drug for schizophrenia, Alzheimer's disease and the like.

Means of Solving the Problems

The present inventors have conducted intensive studies, and have found that a compound represented by the formula (1) shown below unexpectedly has a superior PDE2A selective inhibitory action, and therefore, is useful as a prophylactic or therapeutic drug for schizophrenia, Alzheimer's disease and the like, and completed the present invention based on these findings.

Accordingly, the present invention provides the following:

[1] A compound represented by the formula (1):

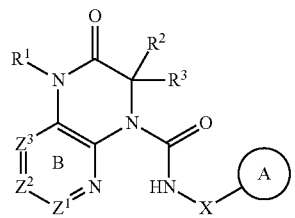

(1)

wherein $R^1$ is a hydrogen atom or an optionally substituted $C_{1-6}$ alkyl group, $R^2$ and $R^3$ are each independently a hydrogen atom or an optionally substituted $C_{1-6}$ alkyl group, or $R^2$ and $R^3$ in combination optionally form, together with the adjacent carbon atom, an optionally substituted ring, X is a bond or an optionally substituted $C_{1-6}$ alkylene group, A is an optionally substituted cyclic group, $Z^1$ is a group represented by $CR^{Z1}$ wherein $R^{Z1}$ is a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted amino group, a cyano group or an optionally substituted cyclic group, or a nitrogen atom, $Z^2$ is a group represented by $CR^{Z2}$ wherein $R^{Z2}$ is a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted amino group, a cyano group or an optionally substituted cyclic group, or a nitrogen atom, $Z^3$ is a group represented by $CR^{Z3}$ wherein $R^{Z3}$ is a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted amino group, a cyano group, an optionally substituted $C_{1-6}$ alkyl-carbonyl group or an optionally substituted cyclic group, or a nitrogen atom, and B is a nitrogen-containing aromatic heterocycle containing 1 or 2 nitrogen atoms, provided that 2,3-dihydro-1-methyl-2-oxo-N-2-thiazolyl-6-[3-(trifluoromethyl)phenyl]-pyrido[2,3-b]pyrazine-4(1H)carboxamide, 2,3-dihydro-1-methyl-N-(4-methyl-2-thiazolyl)-2-oxo-6-[3-(trifluoromethyl)phenyl]-pyrido[2,3-b]pyrazine-4(1H) carboxamide, 2,3-dihydro-1-methyl-2-oxo-N-(tetrahydro-2-oxo-3-furanyl)-6-[3-(trifluoromethyl)phenyl]-pyrido[2,3-b]pyrazine-4(1H)carboxamide, 2,3-dihydro-1-methyl-N-2-oxazolyl-2-oxo-6-[3-(trifluoromethyl)phenyl]-pyrido[2,3-b]pyrazine-4(1H)carboxamide, 2,3-dihydro-1-methyl-2-oxo-N-1H-1,2,4-triazol-3-yl-6-[3-(trifluoromethyl)phenyl]-pyrido[2,3-b]pyrazine-4(1H) carboxamide, 2,3-dihydro-1-methyl-2-oxo-N-4-pyridinyl-6-[3-(trifluoromethyl)phenyl]-pyrido[2,3-b]pyrazine-4(1H)carboxamide, 2,3-dihydro-1-methyl-2-oxo-N-4-pyrimidinyl-6-[3-(trifluoromethyl)phenyl]-pyrido[2,3-b]pyrazine-4(1H)carboxamide, 2,3-dihydro-1-methyl-2-oxo-N-5-pyrimidinyl-6-[3-(trifluoromethyl)phenyl]-pyrido[2,3-b]pyrazine-4(1H)carboxamide, 2,3-dihydro-1-methyl-2-oxo-N-3-pyridazinyl-6-[3-(trifluoromethyl)phenyl]-pyrido[2,3-b]pyrazine-4(1H)carboxamide, 2,3-dihydro-1-methyl-N-[6-(4-morpholinyl)-2-pyridinyl]-2-oxo-6-[3-(trifluoromethyl)phenyl]-pyrido[2,3-b]pyrazine-4(1H) carboxamide, N-(4,5-dimethyl-2-thiazolyl)-2,3-dihydro-1-methyl-2-oxo-6-[3-(trifluoromethyl)phenyl]-pyrido[2,3-b]pyrazine-4(1H)carboxamide, 2,3-dihydro-1-methyl-N-(5-methyl-2-thiazolyl)-2-oxo-6-[3-(trifluoromethyl)phenyl]-pyrido[2,3-b]pyrazine-4(1H) carboxamide, N-[5-[(dimethylamino)carbonyl]-4-methyl-thiazolyl]-2,3-dihydro-1-methyl-2-oxo-6-[3-(trifluoromethyl)phenyl]-pyrido[2,3-b]pyrazine-4(1H)carboxamide, N-(4,6-dimethyl-2-pyridinyl)-2,3-dihydro-1-methyl-2-oxo-6-[3-(trifluoromethyl)phenyl]-pyrido[2,3-b]pyrazine-4(1H)carboxamide, 2,3-dihydro-1-methyl-2-oxo-N-2-pyrazinyl-6-[3-(trifluoromethyl)phenyl]-pyrido[2,3-b]pyrazine-4(1H)carboxamide, 2,3-dihydro-1-methyl-2-oxo-N-2-pyrimidinyl-6-[3-(trifluoromethyl)phenyl]-pyrido[2,3-b]pyrazine-4(1H)carboxamide, N-[2-(1-azetidinyl)-4-pyridinyl]-2,3-dihydro-1-methyl-2-oxo-6-[3-(trifluoromethyl)phenyl]-pyrido[2,3-b]pyrazine-4(1H)carboxamide, 2,3-dihydro-1-methyl-N-[6-(4-morpholinylmethyl)-2-pyridinyl]-2-oxo-6-[3-(trifluoromethyl)phenyl]-pyrido[2,3-b]pyrazine-4(1H)carboxamide, and N-[6-(1-azetidinyl)-2-pyridinyl]-2,3-dihydro-1-methyl-2-oxo-6-[3-(trifluoromethyl)phenyl]-pyrido[2,3-b]pyrazine-4(1H)carboxamide are excluded, or a salt thereof (hereinafter to be referred as compound (1)).

[2] The compound or salt of the above-mentioned [1], wherein $R^{Z1}$ is a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted amino group or a cyano group, and $Z^3$ is $CR^{Z3}$ wherein $R^{Z3}$ is a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted amino group, a cyano group or an optionally substituted cyclic group.

[3] The compound or salt of the above-mentioned [1], wherein $R^1$ is a hydrogen atom.

[4] The compound or salt of the above-mentioned [1], wherein $R^2$ and $R^3$ are both hydrogen atoms.

[5] The compound or salt of the above-mentioned [1], wherein $Z^1$, $Z^2$ and $Z^3$ are respectively $CR^{Z1}$, $CR^{Z2}$ and $CR^{Z3}$.

[6] The compound or salt of the above-mentioned [5], wherein $R^{Z1}$ and $R^{Z3}$ are both hydrogen atoms.

[7] The compound or salt of the above-mentioned [5], wherein $R^{Z2}$ is an optionally substituted $C_{1-6}$ alkoxy group, an optionally substituted $C_{1-6}$ alkyl group or an optionally substituted $C_{3-8}$ cycloalkyl group.

[8] The compound or salt of the above-mentioned [1], wherein X is an optionally substituted $C_{1-6}$ alkylene group.

[9] The compound or salt of the above-mentioned [1], wherein A is an optionally substituted phenyl group.

[10] The compound or salt of the above-mentioned [1], wherein $R^1$ is a hydrogen atom, $R^2$ and $R^3$ are both hydrogen atoms, X is an optionally substituted $C_{1-6}$ alkylene group, A is an optionally substituted phenyl group, $Z^1$ is CH, $Z^2$ is a group represented by $CR^{Z2}$ wherein $R^{Z2}$ is an optionally substituted $C_{1-6}$ alkyl group, an optionally substituted $C_{1-6}$ alkoxy group or an optionally substituted $C_{3-8}$ cycloalkyl group, and $Z^3$ is CH.

[11] 7-Methoxy-N-((1S)-2-methoxy-1-(4-(trifluoromethoxy)phenyl)ethyl)-2-oxo-2,3-dihydropyrido[2,3-b]pyrazine-4(1H)-carboxamide or a salt thereof.

[12] N-((1S)-1-(3-Fluoro-4-(trifluoromethoxy)phenyl)-2-methoxyethyl)-7-methoxy-2-oxo-2,3-dihydropyrido[2,3-b]pyrazine-4(1H)-carboxamide or a salt thereof.

[13] 7-Cyclopropyl-N-((1S)-2-hydroxy-2-methyl-1-(4-(trifluoromethoxy)phenyl)propyl)-2-oxo-2,3-dihydropyrido[2,3-b]pyrazine-4(1H)-carboxamide or a salt thereof.

[14] 7-Cyclopropyl-N-(1-(3-fluoro-4-(trifluoromethoxy)phenyl)-2-hydroxy-2-methylpropyl)-2-oxo-2,3-dihydropyrido[2,3-b]pyrazine-4(1H)-carboxamide or a salt thereof.

[15] N-(1-(3-Fluoro-4-(trifluoromethoxy)phenyl)-2-hydroxy-2-methylpropyl)-7-methyl-2-oxo-2,3-dihydropyrido[2,3-b]pyrazine-4(1H)-carboxamide or a salt thereof.

[16] A medicament comprising the compound or salt of the above-mentioned [1].

[17] The medicament of the above-mentioned [16], which is a phosphodiesterase 2A inhibitor.

[18] The medicament of the above-mentioned [16], which is an agent for the prophylaxis or treatment of schizophrenia.

[19] A method of inhibiting phosphodiesterase 2A, which comprises administering an effective amount of a compound represented by the formula (1):

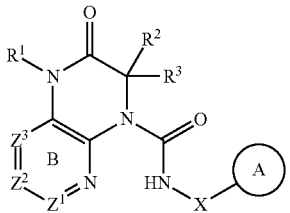

(1)

wherein
$R^1$ is a hydrogen atom or an optionally substituted $C_{1-6}$ alkyl group,
$R^2$ and $R^3$ are each independently a hydrogen atom or an optionally substituted $C_{1-6}$ alkyl group, or $R^2$ and $R^3$ in combination optionally form, together with the adjacent carbon atom, an optionally substituted ring,
X is a bond or an optionally substituted $C_{1-6}$ alkylene group,
A is an optionally substituted cyclic group,
$Z^1$ is a group represented by $CR^{Z1}$ wherein $R^{Z1}$ is a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted amino group, a cyano group or an optionally substituted cyclic group, or a nitrogen atom,
$Z^2$ is a group represented by $CR^{Z2}$ wherein $R^{Z2}$ is a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted amino group, a cyano group or an optionally substituted cyclic group, or a nitrogen atom,
$Z^3$ is a group represented by $CR^{Z3}$ wherein $R^{Z3}$ is a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted amino group, a cyano group, an optionally substituted $C_{1-6}$ alkyl-carbonyl group or an optionally substituted cyclic group, or a nitrogen atom, and
B is a nitrogen-containing aromatic heterocycle containing 1 or 2 nitrogen atoms,
or a salt thereof, to a mammal.

[20] A method for the prophylaxis or treatment of schizophrenia, which comprises administering an effective amount of a compound represented by the formula (1):

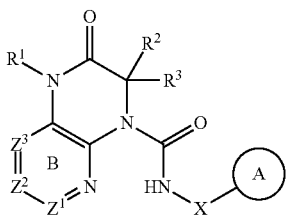

(1)

wherein
$R^1$ is a hydrogen atom or an optionally substituted $C_{1-6}$ alkyl group,
$R^2$ and $R^3$ are each independently a hydrogen atom or an optionally substituted $C_{1-6}$ alkyl group, or $R^2$ and $R^3$ in combination optionally form, together with the adjacent carbon atom, an optionally substituted ring,
X is a bond or an optionally substituted $C_{1-6}$ alkylene group,
A is an optionally substituted cyclic group,
$Z^1$ is a group represented by $CR^{Z1}$ wherein $R^{Z1}$ is a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted amino group, a cyano group or an optionally substituted cyclic group, or a nitrogen atom,
$Z^2$ is a group represented by $CR^{Z2}$ wherein $R^{Z2}$ is a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted amino group, a cyano group or an optionally substituted cyclic group, or a nitrogen atom,
$Z^3$ is a group represented by $CR^{Z3}$ wherein $R^{Z3}$ is a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted amino group, a cyano group, an optionally substituted $C_{1-6}$ alkyl-carbonyl group or an optionally substituted cyclic group, or a nitrogen atom, and B is a nitrogen-containing aromatic heterocycle containing 1 or 2 nitrogen atoms,
or a salt thereof, to a mammal.

[21] Use of a compound represented by the formula (1):

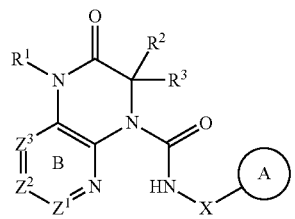

(1)

wherein
$R^1$ is a hydrogen atom or an optionally substituted $C_{1-6}$ alkyl group,
$R^2$ and $R^3$ are each independently a hydrogen atom or an optionally substituted $C_{1-6}$ alkyl group, or $R^2$ and $R^3$ in combination optionally form, together with the adjacent carbon atom, an optionally substituted ring,
X is a bond or an optionally substituted $C_{1-6}$ alkylene group,
A is an optionally substituted cyclic group,
$Z^1$ is a group represented by $CR^{Z1}$ wherein $R^{Z1}$ is a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted amino group, a cyano group or an optionally substituted cyclic group, or a nitrogen atom,
$Z^2$ is a group represented by $CR^{Z2}$ wherein $R^{Z2}$ is a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted amino group, a cyano group or an optionally substituted cyclic group, or a nitrogen atom, $Z^3$ is a group represented by $CR^{Z3}$ wherein $R^{Z3}$ is a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted amino group, a cyano group, an optionally substituted $C_{1-6}$ alkyl-carbonyl group or an optionally substituted cyclic group, or a nitrogen atom, and B is a nitrogen-containing aromatic heterocycle containing 1 or 2 nitrogen atoms, or a salt thereof, for the production of an agent for the prophylaxis or treatment of schizophrenia.

[22] A compound represented by the formula (1):

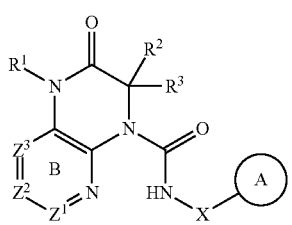

(1)

wherein $R^1$ is a hydrogen atom or an optionally substituted $C_{1-6}$ alkyl group, $R^2$ and $R^3$ are each independently a hydrogen atom or an optionally substituted $C_{1-6}$ alkyl group, or $R^2$ and $R^3$ in combination optionally form, together with the adjacent carbon atom, an optionally substituted ring, X is a bond or an optionally substituted $C_{1-6}$ alkylene group, A is an optionally substituted cyclic group, $Z^1$ is a group represented by $CR^{Z1}$ wherein $R^{Z1}$ is a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted amino group, a cyano group or an optionally substituted cyclic group, or a nitrogen atom, $Z^2$ is a group represented by $CR^{Z2}$ wherein $R^{Z2}$ is a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted amino group, a cyano group or an optionally substituted cyclic group, or a nitrogen atom, $Z^3$ is a group represented by $CR^{Z3}$ wherein $R^{Z3}$ is a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted amino group, a cyano group, an optionally substituted $C_{1-6}$ alkyl-carbonyl group or an optionally substituted cyclic group, or a nitrogen atom, and B is a nitrogen-containing aromatic heterocycle containing 1 or 2 nitrogen atoms, or a salt thereof, for use in the prophylaxis or treatment of schizophrenia.

Effect of the Invention

According to the present invention, the compound having a PDE2A selective inhibitory action, which is useful as an agent for the prophylaxis or treatment of schizophrenia, Alzheimer's disease and the like, can be provided.

BRIEF DESCRIPTION OF THE DRAWINGS

FIG. 1 shows a graph that a test compound has an improvement effect for MK-801 induced disorder in Contextual fear conditioning test (Experimental Example 2).

DETAILED DESCRIPTION OF THE INVENTION

The present invention is explained in detail in the following.

The "halogen atom" in the present specification means, unless otherwise specified, a fluorine atom, a chlorine atom, a bromine atom or an iodine atom.

The "optionally substituted hydrocarbon group" in the present specification means, unless otherwise specified, for example, an "optionally substituted $C_{1-10}$ alkyl", an "optionally substituted $C_{2-10}$ alkenyl", an "optionally substituted $C_{2-10}$ alkynyl", an "optionally substituted $C_{3-8}$ cycloalkyl", an "optionally substituted $C_{3-8}$ cycloalkenyl", an "optionally substituted $C_{6-14}$ aryl", an "optionally substituted $C_{7-14}$ aralkyl" or the like.

The "$C_{1-10}$ alkyl" in the present specification means, unless otherwise specified, for example, methyl, ethyl, propyl, isopropyl, butyl, isobutyl, sec-butyl, tert-butyl, pentyl, isopentyl, neopentyl, hexyl, heptyl, octyl, nonyl, decyl or the like. The "$C_{1-6}$ alkyl" in the present specification means $C_{1-6}$ alkyl from among the above-mentioned "$C_{1-10}$ alkyl". The "$C_{1-5}$ alkyl" in the present specification means $C_{1-5}$ alkyl from among the above-mentioned "$C_{1-10}$ alkyl".

The "$C_{2-10}$ alkenyl" in the present specification means, unless otherwise specified, for example, vinyl, propenyl, isopropenyl, 2-buten-1-yl, 4-penten-1-yl, 5-hexen-1-yl or the like. The "$C_{2-6}$ alkenyl" in the present specification means $C_{2-6}$ alkenyl from among the above-mentioned "$C_{2-10}$ alkenyl".

The "$C_{2-10}$ alkynyl" in the present specification means, unless otherwise specified, for example, 2-butyn-1-yl, 4-pentyn-1-yl, 5-hexyn-1-yl or the like. The "$C_{2-6}$ alkynyl" in the present specification means $C_{2-6}$ alkynyl from among the above-mentioned "$C_{2-10}$ alkynyl".

The "$C_{3-8}$ cycloalkyl" in the present specification means, unless otherwise specified, for example, cyclopropyl, cyclobutyl, cyclopentyl, cyclohexyl, cycloheptyl, cyclooctyl or the like.

The "$C_{3-8}$ cycloalkenyl" in the present specification means, unless otherwise specified, for example, cyclopropenyl(e.g., 2-cyclopropen-1-yl), cyclobutenyl(e.g., 2-cyclobuten-1-yl), cyclopentenyl(e.g., 1-cyclopenten-1-yl, 2-cyclopenten-1-yl, 3-cyclopenten-1-yl), cyclohexenyl(e.g., 1-cyclohexen-1-yl, 2-cyclohexen-1-yl, 3-cyclohexen-1-yl) or the like.

The "$C_{6-14}$ aryl" in the present specification means, unless otherwise specified, for example, phenyl, 1-naphthyl, 2-naphthyl, 2-biphenylyl, 3-biphenylyl, 4-biphenylyl, 2-anthryl or the like. The $C_{6-14}$ aryl may be partially saturated, and examples of the partially saturated $C_{6-14}$ aryl include tetrahydronaphthyl and the like.

The "$C_{7-14}$ aralkyl" in the present specification means, unless otherwise specified, for example, benzyl, phenethyl, 1-methyl-2-phenylethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl or the like.

The "optionally substituted hydroxy" in the present specification means, unless otherwise specified, for example, "hydroxy", "optionally substituted $C_{1-6}$ alkoxy", "optionally substituted heterocyclyl-oxy", "optionally substituted $C_{6-14}$ aryloxy", "optionally substituted $C_{7-14}$ aralkyloxy" or the like.

The "$C_{1-6}$ alkoxy" in the present specification means, unless otherwise specified, for example, methoxy, ethoxy, propoxy, isopropoxy, butoxy, isobutoxy, tert-butoxy, pentyloxy, hexyloxy or the like.

The "$C_{1-6}$ alkoxy-$C_{1-6}$ alkoxy" in the present specification means, unless otherwise specified, for example, methoxymethoxy, methoxyethoxy, ethoxymethoxy, ethoxyethoxy or the like.

The "heterocyclyl-oxy" in the present specification means hydroxyl substituted by the below-mentioned "heterocyclic group". Preferable examples of the heterocyclyl-oxy include tetrahydropyranyloxy, thiazolyloxy, pyridyloxy, pyrazolyloxy, oxazolyloxy, thienyloxy, furyloxy and the like.

The "$C_{6-14}$ aryloxy" in the present specification means, unless otherwise specified, for example, phenoxy, 1-naphthyloxy, 2-naphthyloxy or the like.

The "$C_{7-14}$ aralkyloxy" in the present specification means, unless otherwise specified, for example, benzyloxy, phenethyloxy or the like.

The "optionally substituted sulfanyl" in the present specification means, unless otherwise specified, for example, "sulfanyl", "optionally substituted $C_{1-6}$ alkylsulfanyl", "optionally substituted heterocyclyl-sulfanyl", "optionally substituted $C_{6-14}$ arylsulfanyl", "optionally substituted $C_{7-14}$ aralkylsulfanyl" or the like.

The "$C_{1-6}$ alkylsulfanyl" in the present specification means, unless otherwise specified, for example, methylsulfanyl, ethylsulfanyl, propylsulfanyl, isopropylsulfanyl, butylsulfanyl, sec-butylsulfanyl, tert-butylsulfanyl or the like.

The "heterocyclyl-sulfanyl" in the present specification means sulfanyl substituted by the below-mentioned "heterocyclic group". Preferable examples of the heterocyclyl-sulfanyl include tetrahydropyranylsulfanyl, thiazolylsulfanyl, pyridylsulfanyl, pyrazolylsulfanyl, oxazolylsulfanyl, thienylsulfanyl, furylsulfanyl and the like.

The "$C_{6-14}$ arylsulfanyl" in the present specification means, unless otherwise specified, for example, phenylsulfanyl, 1-naphthylsulfanyl, 2-naphthylsulfanyl or the like.

The "$C_{7-14}$ aralkylsulfanyl" in the present specification means, unless otherwise specified, for example, benzylsulfanyl, phenethylsulfanyl or the like.

The "heterocyclic group" in the present specification means, unless otherwise specified, for example, a 5- to 14-membered (monocyclic, bicyclic or tricyclic) heterocyclic group containing, as a ring-constituting atom besides carbon atom, 1 or 2 kinds of 1 to 4 hetero atoms selected from a nitrogen atom, a sulfur atom and an oxygen atom, preferably (i) a 5- to 14-membered (preferably 5- to 10-membered) aromatic heterocyclic group, (ii) a 5- to 10-membered nonaromatic heterocyclic group or the like. Of these, a 5- or 6-membered aromatic heterocyclic group is preferable. Specifically, for example, aromatic heterocyclic groups such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl, 5-oxazolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1-triazolyl, 2-triazolyl), tetrazolyl, pyridazinyl (e.g., 3-pyridazinyl, 4-pyridazinyl), isothiazolyl (e.g., 3-isothiazolyl, 4-isothiazolyl, 5-isothiazolyl), isoxazolyl (e.g., 3-isoxazolyl, 4-isoxazolyl, 5-isoxazolyl), indolyl (e.g., 1-indolyl, 2-indolyl, 3-indolyl), 2-benzothiazolyl, 2-benzoxazolyl, benzimidazolyl (e.g., 1-benzimidazolyl, 2-benzimidazolyl), benzo[b]thienyl (e.g., 2-benzo[b]thienyl, 3-benzo[b]thienyl), benzo[b]furyl (e.g., 2-benzo[b]furanyl, 3-benzo[b]furanyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazolopyridinyl (e.g., pyrazolo[1,5-a]pyridin-3-yl) and the like;

for example, nonaromatic heterocyclic groups such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidyl (e.g., piperidino, 2-piperidyl, 3-piperidyl, 4-piperidyl), piperazinyl (e.g., 1-piperazinyl, 2-piperazinyl), morpholinyl (e.g., 2-morpholinyl, 3-morpholinyl, morpholino), thiomorpholinyl (e.g., 2-thiomorpholinyl, 3-thiomorpholinyl, thiomorpholino), tetrahydrofuryl, tetrahydropyranyl and the like can be mentioned.

The "optionally substituted cyclic group" in the present specification means, unless otherwise specified, for example, "optionally substituted $C_{6-14}$ aryl", "optionally substituted $C_{3-8}$ cycloalkyl", "optionally substituted $C_{3-8}$ cycloalkenyl", "optionally substituted heterocyclic group" or the like.

The "optionally substituted ring" in the present specification means, unless otherwise specified, for example, an optionally substituted ring corresponding to the above-mentioned "optionally substituted cyclic group".

The "$C_{6-14}$ aromatic hydrocarbon" in the present specification means a ring corresponding to the above-mentioned "$C_{6-14}$ aryl".

The "$C_{3-8}$ cycloalkane" in the present specification means a ring corresponding to the above-mentioned "$C_{3-8}$ cycloalkyl".

The "$C_{3-8}$ cycloalkene" in the present specification means a ring corresponding to the above-mentioned "$C_{3-8}$ cycloalkenyl".

The "heterocycle" in the present specification means a ring corresponding to the above-mentioned "heterocyclic group".

The "nitrogen-containing aromatic heterocycle containing 1 to 2 nitrogen atoms" means, unless otherwise specified, for example, a nitrogen-containing aromatic heterocycle containing, as a ring-constituting atom besides carbon atom and 1 to 2 nitrogen atoms, one or two kinds of 1 to 3 hetero atoms selected from a sulfur atom and an oxygen atom. Specifically, for example, pyridine ring, pyridazine ring, pyrimidine ring, pyrazine ring and the like can be mentioned.

The "$C_{1-6}$ alkyl-carbonyl" in the present specification means, unless otherwise specified, for example, acetyl, isobutanoyl, isopentanoyl or the like.

The "$C_{1-6}$ alkoxy-carbonyl" in the present specification means, unless otherwise specified, for example, methoxycarbonyl, ethoxycarbonyl, propoxycarbonyl, tert-butoxycarbonyl or the like.

The "$C_{3-8}$ cycloalkyl-carbonyl" in the present specification means, unless otherwise specified, for example, cyclopentylcarbonyl, cyclohexylcarbonyl or the like.

The "$C_{6-14}$ aryl-carbonyl" in the present specification means, unless otherwise specified, for example, benzoyl, 1-naphthoyl, 2-naphthoyl or the like.

The "$C_{7-14}$ aralkyl-carbonyl" in the present specification means, unless otherwise specified, for example, phenylacetyl, 2-phenylpropanoyl or the like.

The "$C_{6-14}$ aryloxy-carbonyl" in the present specification means, unless otherwise specified, for example, phenoxycarbonyl, naphthyloxycarbonyl or the like.

The "$C_{7-14}$ aralkyloxy-carbonyl" in the present specification means, unless otherwise specified, for example, benzyloxycarbonyl, phenethyloxycarbonyl or the like.

The "nitrogen-containing heterocyclyl-carbonyl" in the present specification means, unless otherwise specified, for example, pyrrolidinylcarbonyl, piperidinocarbonyl or the like.

The "$C_{1-6}$ alkylsulfonyl" in the present specification means, unless otherwise specified, for example, methylsulfonyl, ethylsulfonyl or the like.

The "$C_{6-14}$ arylsulfonyl" in the present specification means, unless otherwise specified, for example, phenylsulfonyl, 1-naphthylsulfonyl, 2-naphthylsulfonyl or the like.

The "$C_{1-6}$ alkylsulfinyl" in the present specification means, unless otherwise specified, for example, methylsulfinyl, ethylsulfinyl or the like.

The "$C_{6-14}$ arylsulfinyl" in the present specification means, unless otherwise specified, for example, phenylsulfinyl, 1-naphthylsulfinyl, 2-naphthylsulfinyl or the like.

The "optionally esterified carboxyl" in the present specification means, unless otherwise specified, for example, carboxyl, $C_{1-6}$ alkoxy-carbonyl, $C_{6-14}$ aryloxy-carbonyl, $C_{7-14}$ aralkyloxy-carbonyl or the like.

The "optionally halogenated $C_{1-6}$ alkyl" in the present specification means, unless otherwise specified, the above-mentioned "$C_{1-6}$ alkyl" optionally substituted by 1 to 5 of the above-mentioned "halogen atom". For example, methyl, ethyl, propyl, isopropyl, butyl, tert-butyl, isobutyl, trifluoromethyl and the like can be mentioned.

The "optionally halogenated $C_{1-6}$ alkoxy" in the present specification means, unless otherwise specified, the above-mentioned "$C_{1-6}$ alkoxy" optionally substituted by 1 to 5 of the above-mentioned "halogen atom". For example, methoxy, ethoxy, isopropoxy, tert-butoxy, trifluoromethoxy and the like can be mentioned.

The "mono- or di-$C_{1-6}$ alkyl-amino" in the present specification means, unless otherwise specified, amino mono- or di-substituted by the above-mentioned "$C_{1-6}$ alkyl". For example, methylamino, ethylamino, propylamino, dimethylamino, diethylamino and the like can be mentioned.

The "mono- or di-$C_6$-14 aryl-amino" in the present specification means, unless otherwise specified, amino mono- or di-substituted by the above-mentioned "$C_{6-14}$ aryl". For example, phenylamino, diphenylamino, 1-naphthylamino, 2-naphthylamino and the like can be mentioned.

The "mono- or di-$C_{7-14}$ aralkyl-amino" in the present specification means, unless otherwise specified, amino mono- or di-substituted by the above-mentioned "$C_{7-14}$ aralkyl". For example, benzylamino, phenethylamino and the like can be mentioned.

The "N—$C_{1-6}$ alkyl-N—$C_{6-14}$ aryl-amino" in the present specification means, unless otherwise specified, amino substituted by the above-mentioned "$C_{1-6}$ alkyl" and the above-mentioned "$C_{6-14}$ aryl". For example, N-methyl-N-phenylamino, N-ethyl-N-phenylamino and the like can be mentioned.

The "N—$C_{1-6}$ alkyl-N—$C_{7-14}$ aralkyl-amino" in the present specification means, unless otherwise specified, amino substituted by the above-mentioned "$C_{1-6}$ alkyl" and the above-mentioned "$C_{7-14}$ aralkyl". For example, N-methyl-N-benzylamino, N-ethyl-N-benzylamino and the like can be mentioned.

The "$C_{1-6}$ alkyl-carbonylamino" in the present specification means, unless otherwise specified, amino substituted by the above-mentioned "$C_{1-6}$ alkyl-carbonyl". For example, acetyl amino, propionylamino and the like can be mentioned.

The "mono- or di-$C_{1-6}$ alkyl-carbamoyl" in the present specification means, unless otherwise specified, carbamoyl mono- or di-substituted by the above-mentioned "$C_{1-6}$ alkyl". For example, methylcarbamoyl, ethylcarbamoyl, dimethylcarbamoyl, diethylcarbamoyl, ethylmethylcarbamoyl and the like can be mentioned.

The "mono- or di-$C_{6-14}$ aryl-carbamoyl" in the present specification means, unless otherwise specified, carbamoyl mono- or di-substituted by the above-mentioned "$C_{6-14}$ aryl". For example, phenylcarbamoyl, 1-naphthylcarbamoyl, 2-naphthylcarbamoyl and the like can be mentioned.

The "mono- or di-$C_{3-8}$ cycloalkyl-carbamoyl" in the present specification means, unless otherwise specified, carbamoyl mono- or di-substituted by the above-mentioned "$C_{3-8}$ cycloalkyl". For example, cyclopropylcarbamoyl and the like can be mentioned.

The "mono- or di-$C_{7-14}$ aralkyl-carbamoyl" in the present specification means, unless otherwise specified, carbamoyl mono- or di-substituted by the above-mentioned "$C_{7-14}$ aralkyl". For example, benzylcarbamoyl and the like can be mentioned.

The "N—$C_{1-6}$ alkyl-N—$C_{6-14}$ aryl-carbamoyl" in the present specification means, unless otherwise specified, carbamoyl substituted by the above-mentioned "$C_{1-6}$ alkyl" and "$C_{6-14}$ aryl". For example, (n-butyl) (phenyl) carbamoyl and the like can be mentioned.

The "mono- or di-5- to 7-membered heterocyclyl-carbamoyl" in the present specification means, unless otherwise specified, carbamoyl mono- or di-substituted by a 5- to 7-membered heterocyclic group. Here, examples of the 5- to 7-membered heterocyclic group include a heterocyclic group containing, as a ring-constituting atom besides carbon atom, 1 or 2 kinds of 1 to 4 hetero atoms selected from a nitrogen atom, a sulfur atom and an oxygen atom can be mentioned. Preferable examples of the "mono- or di-5- to 7-membered heterocyclyl-carbamoyl" include 2-pyridylcarbamoyl, 3-pyridylcarbamoyl, 4-pyridylcarbamoyl, 2-thienylcarbamoyl, 3-thienylcarbamoyl and the like.

As the "mono- or di-$C_{1-6}$ alkyl-sulfamoyl" in the present specification, unless otherwise specified, sulfamoyl mono- or di-substituted by the above-mentioned "$C_{1-6}$ alkyl" can be used. For example, methylsulfamoyl, ethylsulfamoyl, dimethylsulfamoyl, diethylsulfamoyl and the like can be mentioned.

As the "mono- or di-$C_{6-14}$ aryl-sulfamoyl" in the present specification, unless otherwise specified, sulfamoyl mono- or di-substituted by the above-mentioned "$C_{6-14}$ aryl" can be used. For example, phenylsulfamoyl, diphenylsulfamoyl, 1-naphthylsulfamoyl, 2-naphthylsulfamoyl and the like can be mentioned.

The "mono- or di-$C_{7-14}$ aralkyl-sulfamoyl" in the present specification means, unless otherwise specified, sulfamoyl mono- or di-substituted by the above-mentioned "$C_{7-14}$ aralkyl". For example, benzylsulfamoyl and the like can be mentioned.

The "$C_{1-6}$ alkyl-carbonyloxy" in the present specification means, unless otherwise specified, for example, methylcarbonyloxy, ethylcarbonyloxy or the like.

The "$C_{1-6}$ alkylene" in the present specification means, unless otherwise specified, for example, —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH(CH_3)$—, —$C(CH_3)_2$—, —$CH(CH_2CH_3)$—, —$C(CH_2CH_3)_2$—, —$CH(CH(CH_3)_2)$—, —$CH(CH_3)CH_2$—, —$CH_2CH(CH_3)$—, —$CH(CH_2CH_3)CH_2$—, —$CH_2CH(CH_2CH_3)$— or the like. The "$C_{1-5}$ alkylene" in the present specification means $C_{1-5}$ alkylene from among the above-mentioned "$C_{1-6}$ alkylene".

Examples of the "optionally substituted $C_{1-10}$ (or $C_{1-6}$ or $C_{1-5}$) alkyl", "optionally substituted $C_{2-10}$ (or $C_{2-6}$) alkenyl", "optionally substituted $C_{2-10}$ (or $C_{2-6}$) alkynyl", "optionally substituted $C_{1-6}$ alkoxy", "optionally substituted $C_{1-6}$ alkylsulfanyl" and "optionally substituted $C_{1-6}$ alkylene" in the present specification include "$C_{1-10}$ (or $C_{1-6}$ or $C_{1-5}$) alkyl", "$C_{2-6}$ alkenyl", "$C_{2-10}$ (or $C_{2-6}$) alkynyl", "$C_{2-10}$ (or $C_{2-6}$) alkoxy", "$C_{1-6}$ alkylsulfanyl" and "$C_{1-6}$ alkylene", each of which optionally has, at substitutable position(s), 1 to 5 substituents selected from (1) a halogen atom;
(2) hydroxy;
(3) amino;
(4) nitro;
(5) cyano;
(6) a heterocyclic group optionally substituted by 1 to 3 substituents selected from a halogen atom, hydroxy, oxo, amino, nitro, cyano, an optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(7) mono- or di-$C_{1-6}$ alkyl-amino;
(8) mono- or di-$C_{6-14}$ aryl-amino;
(9) mono- or di-$C_{7-14}$ aralkyl-amino;
(10) N—$C_{1-6}$ alkyl-N—$C_{6-14}$ aryl-amino;
(11) N—$C_{1-6}$ alkyl-N—$C_{7-14}$ aralkyl-amino;
(12) $C_{3-8}$ cycloalkyl;
(13) optionally halogenated $C_{1-6}$ alkoxy;
(14) $C_{1-6}$ alkylsulfanyl;
(15) $C_{1-6}$ alkylsulfinyl;
(16) $C_{1-6}$ alkylsulfonyl;
(17) optionally esterified carboxyl;
(18) $C_{1-6}$ alkyl-carbonyl;
(19) $C_{3-8}$ cycloalkyl-carbonyl;
(20) $C_{6-14}$ aryl-carbonyl;
(21) carbamoyl;
(22) thiocarbamoyl;
(23) mono- or di-$C_{1-6}$ alkyl-carbamoyl;
(24) mono- or di-$C_{6-14}$ aryl-carbamoyl;
(25) N—$C_{1-6}$ alkyl-N—$C_{6-14}$ aryl-carbamoyl;
(26) mono- or di-5- to 7-membered heterocyclyl-carbamoyl;
(27) $C_{1-6}$ alkyl-carbonylamino optionally substituted by carboxyl;
(28) $C_{6-14}$ aryloxy optionally substituted by 1 to 3 substituents selected from a halogen atom, hydroxy, amino, nitro, cyano, an optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or alkyl-sulfamoyl and mono- or di-$C_{6-14}$ aryl-sulfamoyl;
(29) a $C_{6-14}$ aryl optionally substituted by 1 to 3 substituents selected from a halogen atom, hydroxy, amino, nitro, cyano, an optionally halogenated $C_{1-6}$ alkyl, mono- or di-$C_{1-6}$ alkyl-amino, $C_{6-14}$ aryl, mono- or di-$C_{6-14}$ aryl-amino, $C_{3-6}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or alkyl-sulfamoyl and mono- or di-$C_{6-14}$ aryl-sulfamoyl;
(30) heterocyclyl-oxy;
(31) sulfamoyl;
(32) mono- or di-$C_{1-6}$ alkyl-sulfamoyl;
(33) mono- or di-$C_{6-14}$ aryl-sulfamoyl;
(34) $C_{7-14}$ aralkyloxy optionally substituted by 1 to 3 substituents selected from a halogen atom, hydroxy, amino, nitro, cyano, an optionally halogenated $C_{1-6}$ alkyl, mono- or di-$C_{1-6}$ alkyl-amino, $C_{6-14}$ aryl, mono- or di-$C_6$-14 aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(35) $C_{1-6}$ alkyl-carbonyloxy;
(36) $C_{1-6}$ alkoxy-carbonyl;
and the like. When the number of the substituents is plural, the respective substituents may be the same or different.

Examples of the "optionally substituted $C_{3-8}$ cycloalkyl", "optionally substituted $C_{3-8}$ cycloalkenyl", "optionally substituted $C_{6-14}$ aryl", "optionally substituted $C_{7-14}$ aralkyl", "optionally substituted heterocyclic group", "optionally substituted heterocyclyl-oxy", "optionally substituted $C_{6-14}$ aryloxy", "optionally substituted $C_{7-14}$ aralkyloxy", "optionally substituted heterocyclyl-sulfanyl", "optionally substituted $C_{6-14}$ arylsulfanyl" and "optionally substituted $C_{7-14}$ aralkylsulfanyl" in the present specification include "$C_{3-8}$ cycloalkyl", "$C_{3-8}$ cycloalkenyl", "$C_{6-14}$ aryl", "$C_{7-14}$ aralkyl", "heterocyclic group", "heterocyclyl-oxy", "$C_{6-14}$ aryloxy", "$C_{7-14}$ aralkyloxy", "heterocyclyl-sulfanyl", "$C_{6-14}$ arylsulfanyl" and "$C_{7-14}$ aralkylsulfanyl", each of which optionally have, at substitutable position(s), 1 to 5 substituents selected from (1) a halogen atom;
(2) hydroxy;
(3) amino;
(4) nitro;
(5) cyano;
(6) optionally substituted $C_{1-6}$ alkyl;
(7) optionally substituted $C_{2-6}$ alkenyl;
(8) optionally substituted $C_{2-6}$ alkynyl;
(9) $C_{6-14}$ aryl optionally substituted by 1 to 3 substituents selected from a halogen atom, hydroxy, amino, nitro, cyano, an optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(10) $C_{6-14}$ aryloxy optionally substituted by 1 to 3 substituents selected from a halogen atom, hydroxy, amino, nitro, cyano, an optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;

(11) $C_{7-14}$ aralkyloxy optionally substituted by 1 to 3 substituents selected from a halogen atom, hydroxy, amino, nitro, cyano, an optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;

(12) a heterocyclic group optionally substituted by 1 to 3 substituents selected from a halogen atom, hydroxy, amino, nitro, cyano, an optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;

(13) mono- or di-$C_{1-6}$ alkyl-amino;
(14) mono- or di-$C_{6-14}$ aryl-amino;
(15) mono- or di-$C_{7-14}$ aralkyl-amino;
(16) N—$C_{1-6}$ alkyl-N—$C_{6-14}$ aryl-amino;
(17) N—$C_{1-6}$ alkyl-N—$C_{7-14}$ aralkyl-amino;
(18) $C_{3-8}$ cycloalkyl;
(19) optionally substituted $C_{1-6}$ alkoxy;
(20) optionally substituted $C_{1-6}$ alkylsulfanyl;
(21) $C_{1-6}$ alkylsulfinyl;
(22) $C_{1-6}$ alkylsulfonyl;
(23) optionally esterified carboxyl;
(24) $C_{1-6}$ alkyl-carbonyl;
(25) $C_{3-8}$ cycloalkyl-carbonyl;
(26) $C_{6-14}$ aryl-carbonyl;
(27) carbamoyl;
(28) thiocarbamoyl;
(29) mono- or di-$C_{1-6}$ alkyl-carbamoyl;
(30) mono- or di-$C_{6-14}$ aryl-carbamoyl;
(31) N—$C_{1-6}$ alkyl-N—$C_{6-14}$ aryl-carbamoyl;
(32) mono- or di-5- to 7-membered heterocyclyl-carbamoyl;
(33) sulfamoyl;
(34) mono- or di-$C_{1-6}$ alkyl-sulfamoyl;
(35) mono- or di-$C_{6-14}$ aryl-sulfamoyl;
(36) $C_{1-6}$ alkyl-carbonylamino optionally substituted by carboxyl;
(37) heterocyclyl-oxy;
(38) $C_{1-6}$ alkyl-carbonyloxy;
(39) $C_{1-6}$ alkoxy-carbonyl;

and the like. When the number of the substituents is plural, the respective substituents may be the same or different.

The "optionally substituted amino" in the present specification means, unless otherwise specified, amino optionally substituted by 1 or 2 substituents selected from
(1) optionally substituted $C_{1-6}$ alkyl;
(2) optionally substituted $C_{2-6}$ alkenyl;
(3) optionally substituted $C_{2-6}$ alkynyl;
(4) optionally substituted $C_{3-8}$ cycloalkyl;
(5) optionally substituted $C_{6-14}$ aryl;
(6) optionally substituted $C_{1-6}$ alkoxy;
(7) optionally substituted acyl;
(8) optionally substituted heterocyclic group (preferably furyl, pyridyl, thienyl, pyrazolyl, thiazolyl, oxazolyl);
(9) sulfamoyl;
(10) mono- or di-$C_{1-6}$ alkyl-sulfamoyl;
(11) mono- or di-$C_{6-14}$ aryl-sulfamoyl;

or the like. In addition, when the "optionally substituted amino" is amino substituted by two substituents, these substituents may be same or different, and these substituents may form, together with the adjacent nitrogen atom, a nitrogen-containing heterocycle. Examples of the "nitrogen-containing heterocycle" include a 5- to 7-membered nitrogen-containing heterocycle optionally containing, as a ring-constituting atom besides carbon atom, at least one nitrogen atom, and further, 1 or 2 hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine, thiazolidine, oxazolidine and the like.

The "optionally substituted aminocarbonyl" in the present specification means, unless otherwise specified, aminocarbonyl wherein the "optionally substituted amino" moiety is the above-mentioned "optionally substituted amino".

The "optionally substituted acyl" in the present specification means, unless otherwise specified, a group represented by the formula: —$COR^{18}$, —CO—$OR^{18}$, —$SO_2R^{18}$, —$SOR^{18}$, —$PO(OR^{18})(OR^{19})$, —CO—$NR^{18a}R^{19a}$ and —CS—$NR^{18a}R^{19a}$ wherein $R^{18}$ and $R^{19}$ are the same or different and each is a hydrogen atom, an optionally substituted hydrocarbon group or an optionally substituted heterocyclic group, $R^{18a}$ and $R^{19a}$ are the same or different and each is a hydrogen atom, an optionally substituted hydrocarbon group or an optionally substituted heterocyclic group, $R^{18a}$ and $R^{19a}$ may form, together with the adjacent nitrogen atom, an optionally substituted nitrogen-containing heterocycle, or the like.

Examples of the "nitrogen-containing heterocycle" of the "optionally substituted nitrogen-containing heterocycle" formed by $R^{18a}$ and $R^{19a}$ together with the adjacent nitrogen atom include a 5- to 7-membered nitrogen-containing heterocycle optionally containing, as a ring-constituting atom besides carbon atom, at least one nitrogen atom, and further, 1 or 2 hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine, thiazolidine, oxazolidine and the like.

The nitrogen-containing heterocycle may have 1 or 2 substituents at substitutable position(s). Examples of such substituent include hydroxy, an optionally halogenated $C_{1-6}$ alkyl, $C_{6-14}$ aryl, $C_{7-14}$ aralkyl and the like. When the number of the substituents is 2, these substituents may be the same or different.

Preferable examples of the "optionally substituted acyl" include
formyl;
carboxyl;
carbamoyl;
$C_{1-6}$ alkyl-carbonyl;
$C_{1-6}$ alkoxy-carbonyl;
$C_{3-8}$ cycloalkyl-carbonyl;
$C_{6-14}$ aryl-carbonyl;
$C_{7-14}$ aralkyl-carbonyl;
$C_{6-14}$ aryloxy-carbonyl;
$C_{7-14}$ aralkyloxy-carbonyl;
mono- or di-$C_{1-6}$ alkyl-carbamoyl;
mono- or di-$C_{6-14}$ aryl-carbamoyl;
mono- or di-$C_{3-8}$ cycloalkyl-carbamoyl;
mono- or di-$C_{7-14}$ aralkyl-carbamoyl;
$C_{1-6}$ alkylsulfonyl;

$C_{6-14}$ arylsulfonyl optionally substituted by nitro;
nitrogen-containing heterocyclyl-carbonyl;
$C_{1-6}$ alkylsulfinyl;
$C_{6-14}$ arylsulfinyl;
thiocarbamoyl;
sulfamoyl;
mono- or di-$C_{1-6}$ alkyl-sulfamoyl;
mono- or di-$C_{6-14}$ aryl-sulfamoyl;
mono- or di-$C_{7-14}$ aralkyl-sulfamoyl;
and the like.

The definition of each symbol in the formula (1) is explained in detail in the following.

$R^1$ is a hydrogen atom or an optionally substituted $C_{1-6}$ alkyl group.

$R^1$ is preferably a hydrogen atom or a $C_{1-6}$ alkyl group.

$R^1$ is more preferably a hydrogen atom or a $C_{1-3}$ alkyl group (preferably methyl).

$R^1$ is particularly preferably a hydrogen atom.

$R^2$ and $R^3$ are each independently a hydrogen atom or an optionally substituted $C_{1-6}$ alkyl group, or $R^2$ and $R^3$ in combination optionally form, together with the adjacent carbon atom, an optionally substituted ring.

$R^2$ and $R^3$ are preferably each independently a hydrogen atom or a $C_{1-6}$ alkyl group (e.g., methyl).

$R^2$ and $R^3$ are more preferably both hydrogen atoms.

Examples of the "optionally substituted ring" formed by $R^2$ and $R^3$ in combination together with the adjacent carbon atom include a ring represented by

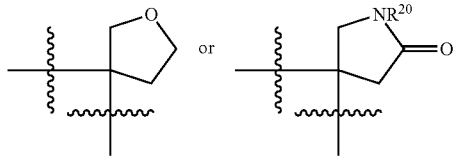

wherein $R^{20}$ is an optionally substituted $C_{1-6}$ alkyl group, and the like.

Examples of the substituent for "ring" of the "optionally substituted ring" formed by $R^2$ and $R^3$ in combination together with the adjacent carbon atom include those similar to the substituent for the "heterocyclic group" of the above-mentioned "optionally substituted heterocyclic group".

X is a bond or an optionally substituted $C_{1-6}$ alkylene group.

The "$C_{1-6}$ alkylene group" of the "optionally substituted $C_{1-6}$ alkylene group" for X is preferably a $C_{1-5}$ alkylene group, more preferably —$CH_2$—, —$CH(CH_3)$—, —$CH(CH_2CH_3)$—, —$CH(CH_2CH_2CH_3)$— or —$CH(CH(CH_3)_2)$—.

In another embodiment, the "$C_{1-6}$ alkylene group" of the "optionally substituted $C_{1-6}$ alkylene group" for X is more preferably —$CH_2$—, —$CH(CH_3)$—, —$CH(CH_2CH_3)$—, —$CH(CH_2CH_2CH_3)$—, —$CH(CH(CH_3)_2)$—, —$CH(C(CH_3)_3)$—, —$CH(CH_2CH_2CH_2CH_3)$—, —$CH(CH(CH_2CH_3)_2)$— or —$CH_2CH_2$—.

In yet another embodiment, the "$C_{1-6}$ alkylene group" of the "optionally substituted $C_{1-6}$ alkylene group" for X is more preferably —$CH_2$—, —$CH(CH_3)$—, —$CH(CH_2CH_3)$—, —$CH(CH_2CH_2CH_3)$—, —$CH(CH(CH_3)_2)$—, —$CH(C(CH_3)_3)$—, —$CH(CH_2CH_2CH_2CH_3)$— or —$CH(CH(CH_2CH_3)_2)$—.

X is preferably an optionally substituted $C_{1-6}$ alkylene group (preferably an optionally substituted $C_{1-5}$ alkylene group).

X is more preferably a $C_{1-6}$ alkylene group (preferably a $C_{1-5}$ alkylene group, more preferably —$CH_2$—, —$CH(CH_3)$—, —$CH(CH_2CH_3)$—, —$CH(CH_2CH_2CH_3)$— or —$CH(CH(CH_3)_2)$—) optionally substituted by 1 to 3 substituents selected from
(1) hydroxy,
(2) cyano,
(3) carbamoyl,
(4) $C_{1-6}$ alkoxy (e.g., methoxy),
(5) $C_{1-6}$ alkylsulfanyl (e.g., methylsulfanyl),
(6) $C_{1-6}$ alkylsulfonyl (e.g., methylsulfonyl),
(7) mono- or di-$C_{1-6}$ alkyl-amino (e.g., dimethylamino),
(8) $C_{3-8}$ cycloalkyl (e.g., cyclopropyl),
(9) $C_{6-14}$ aryl (e.g., phenyl) optionally substituted by 1 to 3 substituents selected from optionally halogenated $C_{1-6}$ alkoxy (e.g., methoxy) (preferably optionally substituted by 1 to 3 halogen atoms (e.g., a fluorine atom)), and
(10) a heterocyclic group (preferably a 5- or 6-membered aromatic heterocyclic group) (e.g., pyridyl, isoxazolyl, pyrazolyl) optionally substituted by 1 to 3 $C_{1-6}$ alkyl (e.g., methyl).

In another embodiment, X is more preferably a $C_{1-6}$ alkylene group (preferably —$CH_2$—, —$CH(CH_3)$—, —$CH(CH_2CH_3)$—, —$CH(CH_2CH_2CH_3)$—, —$CH(CH(CH_3)_2)$—, —$CH(C(CH_3)_3)$—, —$CH(CH_2CH_2CH_2CH_3)$—, —$CH(CH(CH_2CH_3)_2)$— or —$CH_2CH_2$—) optionally substituted by 1 to 5 substituents selected from
(1) a halogen atom (e.g., a fluorine atom),
(2) hydroxy,
(3) amino,
(4) cyano,
(5) carbamoyl,
(6) mono- or di-$C_{1-6}$ alkyl-carbamoyl (e.g., methylcarbamoyl, dimethylcarbamoyl),
(7) $C_{1-6}$ alkoxy (e.g., methoxy, ethoxy, isopropoxy) optionally substituted by 1 to 3 substituents selected from
 (i) a halogen atom (e.g., a fluorine atom), and
 (ii) $C_{1-6}$ alkoxy (e.g., methoxy),
(8) $C_{1-6}$ alkylsulfanyl (e.g., methylsulfanyl),
(9) $C_{1-6}$ alkylsulfinyl (e.g., methylsulfinyl),
(10) $C_{1-6}$ alkylsulfonyl (e.g., methylsulfonyl),
(11) mono- or di-$C_{1-6}$ alkyl-amino (e.g., dimethylamino),
(12) $C_{3-8}$ cycloalkyl (e.g., cyclopropyl),
(13) $C_{6-14}$ aryl (e.g., phenyl) optionally substituted by 1 to 3 substituents selected from
 (i) a halogen atom (e.g., a fluorine atom, a bromine atom),
 (ii) hydroxy, and
 (iii) optionally halogenated $C_{1-6}$ alkoxy (e.g., methoxy) (preferably optionally substituted by 1 to 3 halogen atoms (e.g., a fluorine atom)),
(14) a heterocyclic group (preferably a 4- to 10-membered heterocyclic group) (e.g., pyridyl, isoxazolyl, pyrazolyl, pyrrolidinyl, triazolyl, oxetanyl, tetrahydrofuryl, tetrahydropyranyl, dihydroisoindolyl) optionally substituted by 1 to 3 substituents selected from
 (i) $C_{1-6}$ alkyl (e.g., methyl),
 (ii) hydroxy, and
 (iii) oxo,
(15) $C_{3-8}$ cycloalkyloxy (e.g., cyclopentyloxy),
(16) optionally halogenated heterocyclyl-oxy (e.g., pyridyloxy) (preferably optionally substituted by 1 to 3 halogen atoms (e.g., a bromine atom)),
(17) $C_{1-6}$ alkyl-carbonyloxy (e.g., acetoxy),
(18) $C_{1-6}$ alkyl(diaryl)silyloxy (e.g., tert-butyl(diphenyl)silyloxy),

(19) $C_{1-6}$ alkyl-carbonyl (e.g., acetyl), and
(20) $C_{3-8}$ cycloalkyl-carbonyl (e.g., cyclopropylcarbonyl), or a bond.

In yet another embodiment, X is more preferably a $C_{1-6}$ alkylene group (preferably —$CH_2$—, —$CH(CH_3)$—, —$CH(CH_2CH_3)$—, —$CH(CH_2CH_2CH_3)$—, —$CH(CH(CH_3)_2)$—, —$CH(C(CH_3)_3)$—, —$CH(CH_2CH_2CH_2CH_3)$— or —$CH(CH(CH_2CH_3)_2)$) optionally substituted by 1 to 5 substituents selected from
(1) a halogen atom (e.g., a fluorine atom),
(2) hydroxy,
(3) amino,
(4) cyano,
(5) carbamoyl,
(6) mono- or di-$C_{1-6}$ alkyl-carbamoyl (e.g., methylcarbamoyl, dimethylcarbamoyl),
(7) $C_{1-6}$ alkoxy (e.g., methoxy, ethoxy, isopropoxy) optionally substituted by 1 to 3 substituents selected from
 (i) a halogen atom (e.g., a fluorine atom), and
 (ii) $C_{1-6}$ alkoxy (e.g., methoxy),
(8) $C_{1-6}$ alkylsulfanyl (e.g., methylsulfanyl),
(9) $C_{1-6}$ alkylsulfinyl (e.g., methylsulfinyl),
(10) $C_{1-6}$ alkylsulfonyl (e.g., methylsulfonyl),
(11) mono- or di-$C_{1-6}$ alkyl-amino (e.g., dimethylamino),
(12) $C_{3-8}$ cycloalkyl (e.g., cyclopropyl),
(13) $C_{6-14}$ aryl (e.g., phenyl) optionally substituted by 1 to 3 substituents selected from
 (i) a halogen atom (e.g., a fluorine atom, a bromine atom),
 (ii) hydroxy, and
 (iii) optionally halogenated $C_{1-6}$ alkoxy (e.g., methoxy) (preferably optionally substituted by 1 to 3 halogen atoms (e.g., a fluorine atom)),
(14) a heterocyclic group (preferably a 4- to 10-membered heterocyclic group) (e.g., pyridyl, isoxazolyl, pyrazolyl, pyrrolidinyl, triazolyl, oxetanyl, tetrahydrofuryl, tetrahydropyranyl, dihydroisoindolyl) optionally substituted by 1 to 3 substituents selected from
 (i) $C_{1-6}$ alkyl (e.g., methyl),
 (ii) hydroxy, and
 (iii) oxo,
(15) $C_{3-8}$ cycloalkyloxy (e.g., cyclopentyloxy),
(16) optionally halogenated heterocyclyl-oxy (e.g., pyridyloxy) (preferably optionally substituted by 1 to 3 halogen atoms (e.g., a bromine atom)),
(17) $C_{1-6}$ alkyl-carbonyloxy (e.g., acetoxy),
(18) $C_{1-6}$ alkyl(diaryl)silyloxy (e.g., tert-butyl(diphenyl)silyloxy),
(19) $C_{1-6}$ alkyl-carbonyl (e.g., acetyl), and
(20) $C_{3-8}$ cycloalkyl-carbonyl (e.g., cyclopropylcarbonyl).

X is still more preferably a $C_{1-6}$ alkylene group (preferably a $C_{1-5}$ alkylene group, more preferably —$CH(CH_3)$— or —$CH(CH(CH_3)_2)$—) optionally substituted by 1 to 3 substituents selected from
(1) hydroxy, and
(2) $C_{1-6}$ alkoxy (e.g., methoxy).

A is an optionally substituted cyclic group.

The "optionally substituted cyclic group" for A is "optionally substituted $C_{6-14}$ aryl", "optionally substituted $C_{3-8}$ cycloalkyl", "optionally substituted $C_{3-8}$ cycloalkenyl" or "optionally substituted heterocyclic group". The "cyclic group" is optionally fused, for example, with a $C_{6-14}$ aromatic hydrocarbon, a $C_{3-8}$ cycloalkane, a $C_{3-8}$ cycloalkene, a heterocycle or the like.

The "cyclic group" of the "optionally substituted cyclic roup" for A is preferably a $C_{6-14}$ aryl group or a 5- or 6-membered aromatic heterocyclic group, more preferably a $C_{6-10}$ aryl group or a 5- or 6-membered nitrogen-containing aromatic heterocyclic group, still more preferably phenyl, pyridazinyl, pyridyl, pyrimidinyl, isoxazolyl or pyrazolyl, particularly preferably phenyl.

A is preferably a $C_{6-10}$ aryl group or a 5- or 6-membered nitrogen-containing aromatic heterocyclic group, each of which is optionally substituted, more preferably an optionally substituted phenyl group.

A is more preferably a $C_{6-10}$ aryl group or a 5- or 6-membered aromatic heterocyclic group (preferably a $C_{6-10}$ aryl group or a 5- or 6-membered nitrogen-containing aromatic heterocyclic group, more preferably phenyl, pyridazinyl, pyridyl, pyrimidinyl, isoxazolyl or pyrazolyl, particularly preferably phenyl), each of which is optionally substituted by 1 to 3 substituents selected from
(1) a halogen atom (e.g., a fluorine atom),
(2) hydroxy,
(3) optionally halogenated $C_{1-6}$ alkyl (e.g., methyl, isopropyl) (preferably optionally substituted by 1 to 3 halogen atoms (e.g., a fluorine atom)),
(4) $C_{2-6}$ alkenyl (e.g., prop-1-en-2-yl),
(5) $C_{1-6}$ alkoxy (e.g., methoxy) optionally substituted by 1 to 3 substituents selected from
 (i) a halogen atom (e.g., a fluorine atom), and
 (ii) $C_{3-8}$ cycloalkyl (e.g., cyclopropyl),
(6) $C_{6-14}$ aryl (e.g., phenyl), and
(7) a heterocyclic group (preferably a 5- or 6-membered heterocyclic group) (e.g., pyrazolyl, dihydropyranyl, tetrahydropyranyl) optionally substituted by 1 to 3 $C_{1-6}$ alkyl (e.g., methyl).

In another embodiment, A is more preferably a $C_{6-10}$ aryl group, a 4- to 10-membered heterocyclic group or a $C_{3-8}$ cycloalkyl group (preferably phenyl, pyridazinyl, pyridyl, pyrimidinyl, isoxazolyl, pyrazolyl, oxetanyl, pyrrolidinyl, tetrahydrofuryl, imidazolyl, triazolyl, thienyl, tetrahydropyranyl, imidazo[1,2-a]pyridyl, benzodioxolyl, pyrazolo[1,5-a]pyridyl, dihydroisoindolyl or cyclopropyl, more preferably phenyl), each of which is optionally substituted by 1 to 3 substituents selected from
(1) a halogen atom (e.g., a fluorine atom, a chlorine atom, a bromine atom),
(2) hydroxy,
(3) optionally halogenated $C_{1-6}$ alkyl (e.g., methyl, ethyl, isopropyl) (preferably optionally substituted by 1 to 3 halogen atoms (e.g., a fluorine atom)),
(4) $C_{2-6}$ alkenyl (e.g., prop-1-en-2-yl),
(5) $C_{1-6}$ alkoxy (e.g., methoxy, ethoxy, isopropoxy) optionally substituted by 1 to 3 substituents selected from
 (i) a halogen atom (e.g., a fluorine atom), and
 (ii) $C_{3-8}$ cycloalkyl (e.g., cyclopropyl),
(6) $C_{6-14}$ aryl (e.g., phenyl) optionally substituted by optionally halogenated $C_{1-6}$ alkoxy (e.g., methoxy) (preferably optionally substituted by 1 to 3 halogen atoms (e.g., a fluorine atom)),
(7) a heterocyclic group (preferably a 4- to 6-membered heterocyclic group) (e.g., azetidinyl, pyrazolyl, pyrrolyl, pyrrolidinyl, triazolyl, dihydropyranyl, tetrahydropyranyl) optionally substituted by 1 to 3 $C_{1-6}$ alkyl (e.g., methyl),
(8) $C_{3-8}$ cycloalkyl (e.g., cyclopropyl), and
(9) oxo.

In yet another embodiment, A is more preferably a $C_{6-10}$ aryl group or a 5- to 10-membered aromatic heterocyclic group (preferably phenyl, pyridazinyl, pyridyl, pyrimidinyl, isoxazolyl, pyrazolyl, imidazolyl, triazolyl, thienyl, imidazo[1,2-a]pyridyl or pyrazolo[1,5-a]pyridyl, more preferably phenyl), each of which is optionally substituted by 1 to 3 substituents selected from (1) a halogen atom (e.g., a fluorine atom, a chlorine atom, a bromine atom),
(2) hydroxy,
(3) optionally halogenated $C_{1-6}$ alkyl (e.g., methyl, ethyl, isopropyl) (preferably optionally substituted by 1 to 3 halogen atoms (e.g., a fluorine atom)),
(4) $C_{2-6}$ alkenyl (e.g., prop-1-en-2-yl),
(5) $C_{1-6}$ alkoxy (e.g., methoxy, ethoxy, isopropoxy) optionally substituted by 1 to 3 substituents selected from
   (i) a halogen atom (e.g., a fluorine atom), and
   (ii) $C_{3-8}$ cycloalkyl (e.g., cyclopropyl),
(6) $C_{6-14}$ aryl (e.g., phenyl),
(7) a heterocyclic group (preferably a 4- to 6-membered heterocyclic group) (e.g., azetidinyl, pyrazolyl, pyrrolyl, pyrrolidinyl, triazolyl, dihydropyranyl, tetrahydropyranyl) optionally substituted by 1 to 3 $C_{1-6}$ alkyl (e.g., methyl), and
(8) $C_{3-8}$ cycloalkyl (e.g., cyclopropyl).

In yet another embodiment, A is more preferably a $C_{6-10}$ aryl group (preferably phenyl), each of which is optionally substituted by 1 to 3 substituents selected from
(1) a halogen atom (e.g., a fluorine atom, a chlorine atom, a bromine atom),
(2) hydroxy,
(3) optionally halogenated $C_{1-6}$ alkyl (e.g., methyl, isopropyl) (preferably optionally substituted by 1 to 3 halogen atoms (e.g., a fluorine atom)),
(4) $C_{2-6}$ alkenyl (e.g., prop-1-en-2-yl),
(5) $C_{1-6}$ alkoxy (e.g., methoxy, ethoxy, isopropoxy) optionally substituted by 1 to 3 substituents selected from
   (i) a halogen atom (e.g., a fluorine atom), and
   (ii) $C_{3-8}$ cycloalkyl (e.g., cyclopropyl),
(6) $C_{6-14}$ aryl (e.g., phenyl),
(7) a heterocyclic group (preferably a 4- to 6-membered heterocyclic group) (e.g., azetidinyl, pyrazolyl, pyrrolyl, pyrrolidinyl, triazolyl, dihydropyranyl, tetrahydropyranyl) optionally substituted by 1 to 3 $C_{1-6}$ alkyl (e.g., methyl), and
(8) $C_{3-8}$ cycloalkyl (e.g., cyclopropyl).

A is particularly preferably a $C_{6-10}$ aryl group (e.g., phenyl) optionally substituted by 1 to 3 substituents selected from
(1) a halogen atom (e.g., a fluorine atom), and
(2) $C_{1-6}$ alkoxy (e.g., methoxy) optionally substituted by 1 to 3 halogen atoms (e.g., a fluorine atom).

Preferable examples of the group represented by

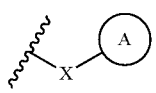

include a group represented by

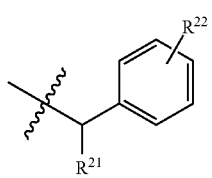

wherein
$R^{21}$ is a hydrogen atom, an optionally substituted $C_{1-5}$ alkyl group, a $C_{3-8}$ cycloalkyl group, a carbamoyl group or a cyano group, and
$R^{22}$ is a hydrogen atom or a substituent.

Another preferable examples of the group represented by

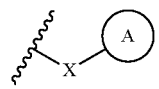

include a group represented by

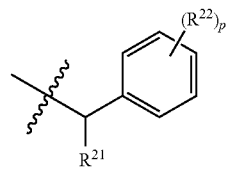

wherein
$R^{21}$ is a hydrogen atom, an optionally substituted $C_{1-5}$ alkyl group, a $C_{3-8}$ cycloalkyl group, a carbamoyl group, a cyano group or an optionally substituted heterocyclic group,
$R^{22}$ is a hydrogen atom or a substituent, and
p is an integer of 1 to 5.

The "substituent" for $R^{22}$ corresponds to the "substituent" of the "optionally substituted cyclic group" for A.

In another embodiment, another preferable examples of the group represented by

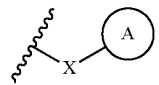

include a group represented by

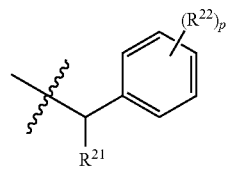

wherein
$R^{21}$ is a hydrogen atom, an optionally substituted $C_{1-6}$ alkyl group, a $C_{3-8}$ cycloalkyl group, an optionally substituted carbamoyl group, a cyano group, an optionally substituted heterocyclic group, a $C_{1-6}$ alkyl-carbonyl group, a $C_{3-8}$ cycloalkyl-carbonyl group or an optionally substituted $C_{6-14}$ aryl group,
$R^{22}$ is a hydrogen atom or a substituent, and
p is an integer of 1 to 5.

The "substituent" for $R^{22}$ corresponds to the "substituent" of the "optionally substituted cyclic group" for A.

The group represented by

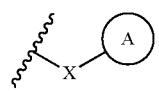

is more preferably

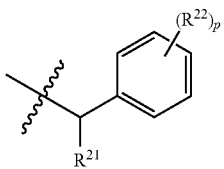

wherein
R²¹ is
(1) cyano
(2) carbamoyl
(3) $C_{1-5}$ alkyl (e.g., methyl, ethyl, isopropyl, propyl) optionally substituted by 1 to 3 substituents selected from
  (i) hydroxy,
  (ii) $C_{1-6}$ alkoxy (e.g., methoxy),
  (iii) mono- or di-$C_{1-6}$ alkyl-amino (e.g., dimethylamino),
  (iv) $C_{1-6}$ alkylsulfanyl (e.g., methylsulfanyl), and
  (v) $C_{1-6}$ alkylsulfonyl (e.g., methylsulfonyl),
(4) $C_{3-8}$ cycloalkyl (e.g., cyclopropyl), or
(5) a heterocyclic group (preferably a 5- or 6-membered aromatic heterocyclic group) (e.g., pyridyl, isoxazolyl, pyrazolyl) optionally substituted by 1 to 3 $C_{1-6}$ alkyl (e.g., methyl),
R²² is
(1) a halogen atom (e.g., a fluorine atom),
(2) hydroxy,
(3) optionally halogenated $C_{1-6}$ alkyl (e.g., methyl, isopropyl) (preferably optionally substituted by 1 to 3 halogen atoms (e.g., a fluorine atom)),
(4) $C_{2-6}$ alkenyl (e.g., prop-1-en-2-yl),
(5) $C_{1-6}$ alkoxy (e.g., methoxy) optionally substituted by 1 to 3 substituents selected from
  (i) a halogen atom (e.g., a fluorine atom), and
  (ii) $C_{3-8}$ cycloalkyl (e.g., cyclopropyl),
(6) $C_{6-14}$ aryl (e.g., phenyl), or
(7) a heterocyclic group (preferably a 5- or 6-membered heterocyclic group) (e.g., pyrazolyl, dihydropyranyl, tetrahydropyranyl) optionally substituted by 1 to 3 $C_{1-6}$ alkyl (e.g., methyl), and
p is an integer of 1 to 3.

In another embodiment, the group represented by

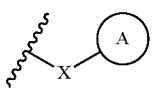

is more preferably

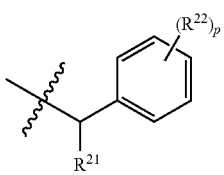

wherein
R²¹ is
(1) cyano,
(2) carbamoyl,
(3) mono- or di-$C_{1-6}$ alkyl-carbamoyl (e.g., methylcarbamoyl, dimethylcarbamoyl),
(4) $C_{1-6}$ alkyl (e.g., methyl, ethyl, isopropyl, propyl, butyl, tert-butyl, 1-ethylpropyl) optionally substituted by 1 to 5 substituents selected from
  (i) a halogen atom (e.g., a fluorine atom),
  (ii) hydroxy,
  (iii) amino,
  (iv) cyano,
  (v) $C_{3-8}$ cycloalkyl (e.g., cyclopropyl),
  (vi) $C_{1-6}$ alkoxy (e.g., methoxy, ethoxy, isopropoxy) optionally substituted by 1 to 3 substituents selected from
    (a) a halogen atom (e.g., a fluorine atom), and
    (b) $C_{1-6}$ alkoxy (e.g., methoxy),
  (vii) $C_{3-8}$ cycloalkyloxy (e.g., cyclopentyloxy),
  (viii) mono- or di-$C_{1-6}$ alkyl-amino (e.g., dimethylamino),
  (ix) $C_{1-6}$ alkylsulfanyl (e.g., methylsulfanyl),
  (x) $C_{1-6}$ alkylsulfinyl (e.g., methylsulfinyl),
  (xi) $C_{1-6}$ alkylsulfonyl (e.g., methylsulfonyl),
  (xii) carbamoyl,
  (xiii) mono- or di-$C_{1-6}$ alkyl-carbamoyl (e.g., dimethylcarbamoyl),
  (xiv) a heterocyclic group (e.g., oxetanyl, pyrrolidinyl, pyrazolyl, triazolyl, tetrahydropyranyl, dihydroisoindolyl) optionally substituted by 1 to 3 substituents selected from
    (a) hydroxy, and
    (b) oxo,
  (xv) $C_{1-6}$ alkyl-carbonyloxy (e.g., acetoxy),
  (xvi) $C_{1-6}$ alkyl(diaryl)silyloxy (e.g., tert-butyl(diphenyl) silyloxy), and
  (xvii) optionally halogenated heterocyclyl-oxy (e.g., pyridyloxy) (preferably optionally substituted by 1 to 3 halogen atoms (e.g., a bromine atom)),
(5) $C_{3-8}$ cycloalkyl (e.g., cyclopropyl),
(6) a heterocyclic group (preferably a 4- to 6-membered heterocyclic group) (e.g., pyridyl, isoxazolyl, pyrazolyl, oxetanyl, tetrahydrofuryl, tetrahydropyranyl) optionally substituted by 1 to 3 $C_{1-6}$ alkyl (e.g., methyl),
(7) $C_{1-6}$ alkyl-carbonyl (e.g., acetyl),
(8) $C_{3-8}$ cycloalkyl-carbonyl (e.g., cyclopropylcarbonyl), or
(9) $C_{6-14}$ aryl (e.g., phenyl) optionally substituted by 1 to 3 substituents selected from
  (i) a halogen atom (e.g., a fluorine atom, a bromine atom), and
  (ii) hydroxy,
R²² is
(1) a halogen atom (e.g., a fluorine atom, a chlorine atom, a bromine atom),
(2) hydroxy,
(3) optionally halogenated $C_{1-6}$ alkyl (e.g., methyl, isopropyl) (preferably optionally substituted by 1 to 3 halogen atoms (e.g., a fluorine atom)),
(4) $C_{2-6}$ alkenyl (e.g., prop-1-en-2-yl),
(5) $C_{1-6}$ alkoxy (e.g., methoxy, ethoxy, isopropoxy) optionally substituted by 1 to 3 substituents selected from
  (i) a halogen atom (e.g., a fluorine atom), and
  (ii) $C_{3-8}$ cycloalkyl (e.g., cyclopropyl),
(6) $C_{6-14}$ aryl (e.g., phenyl),
(7) a heterocyclic group (preferably a 4- to 6-membered heterocyclic group) (e.g., azetidinyl, pyrazolyl, pyrrolyl, pyrrolidinyl, triazolyl, dihydropyranyl, tetrahydropyranyl) optionally substituted by 1 to 3 $C_{1-6}$ alkyl (e.g., methyl), or
(8) $C_{3-8}$ cycloalkyl (e.g., cyclopropyl), and
p is an integer of 1 to 3.

The group represented by

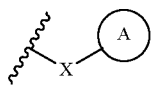

is still more preferably a group represented by

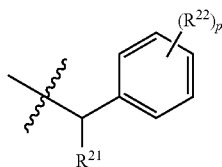

wherein
R$^{21}$ is a C$_{1-5}$ alkyl group (e.g., methyl, isopropyl) optionally substituted by hydroxyl or C$_{1-6}$ alkoxy (e.g., methoxy),
R$^{22}$ is
(1) a halogen atom (e.g., a fluorine atom), or
(2) optionally halogenated C$_{1-6}$ alkoxy (e.g., methoxy) (preferably optionally substituted by 1 to 3 halogen atoms (e.g., a fluorine atom)), and
p is an integer of 1 or 2.

Z$^1$ is a group represented by CR$^{Z1}$ wherein R$^{Z1}$ is a hydrogen atom, a halogen atom, an optionally substituted C$_{1-6}$ alkyl group, an optionally substituted C$_{2-6}$ alkenyl group, an optionally substituted C$_{2-6}$ alkynyl group, an optionally substituted C$_{1-6}$ alkoxy group, an optionally substituted amino group or a cyano group, or a nitrogen atom.

In another embodiment, Z$^1$ is a group represented by CR$^{Z1}$ wherein R$^{Z1}$ is a hydrogen atom, a halogen atom, an optionally substituted C$_{1-6}$ alkyl group, an optionally substituted C$_{2-6}$ alkenyl group, an optionally substituted C$_{2-6}$ alkynyl group, an optionally substituted C$_{1-6}$ alkoxy group, an optionally substituted amino group, a cyano group or an optionally substituted cyclic group, or a nitrogen atom.

Z$^1$ is preferably a group represented by CR$^{Z1}$ wherein R$^{Z1}$ is a hydrogen atom, a halogen atom, an optionally substituted C$_{1-6}$ alkyl group, an optionally substituted C$_{2-6}$ alkenyl group, an optionally substituted C$_{1-6}$ alkoxy group or a cyano group.

In another embodiment, Z$^1$ is preferably a group represented by CR$^{Z1}$ wherein R$^{Z1}$ is a hydrogen atom, a halogen atom, an optionally substituted C$_{1-6}$ alkyl group, an optionally substituted C$_{2-6}$ alkenyl group, an optionally substituted C$_{1-6}$ alkoxy group, a cyano group or an optionally substituted cyclic group, more preferably a group represented by CR$^{Z1}$ wherein R$^{Z1}$ is a hydrogen atom, a halogen atom, an optionally substituted C$_{1-6}$ alkyl group, an optionally substituted C$_{2-6}$ alkenyl group, an optionally substituted C$_{1-6}$ alkoxy group, a cyano group, an optionally substituted C$_{6-14}$ aryl group, an optionally substituted heterocyclic group or an optionally substituted C$_{3-8}$ cycloalkyl group.

Z$^1$ is more preferably
a group represented by CR$^{Z1}$ wherein R$^{Z1}$ is
(1) a hydrogen atom,
(2) a halogen atom (e.g., a chlorine atom),
(3) a C$_{1-6}$ alkyl group (e.g., methyl, ethyl) optionally substituted by 1 to 3 substituents selected from
    (i) a halogen atom (e.g., a fluorine atom), and
    (ii) C$_{6-14}$ aryl (e.g., phenyl),
(4) a C$_{2-6}$ alkenyl group (e.g., vinyl),
(5) a C$_{1-6}$ alkoxy group (e.g., methoxy), or
(6) a cyano group.

In another embodiment, Z$^1$ is more preferably a group represented by CR$^{Z1}$ wherein R$^{Z1}$ is
(1) a hydrogen atom,
(2) a halogen atom (e.g., a chlorine atom),
(3) a C$_{1-6}$ alkyl group (e.g., methyl, ethyl) optionally substituted by 1 to 3 substituents selected from
    (i) a halogen atom (e.g., a fluorine atom), and
    (ii) C$_{6-14}$ aryl (e.g., phenyl),
(4) a C$_{2-6}$ alkenyl group (e.g., vinyl),
(5) a C$_{1-6}$ alkoxy group (e.g., methoxy),
(6) a cyano group,
(7) a C$_{6-14}$ aryl group (e.g., phenyl) optionally substituted by 1 to 3 C$_{1-6}$ alkoxy (e.g., methoxy),
(8) a heterocyclic group (preferably a 5- or 6-membered heterocyclic group) (e.g., pyrazolyl, thienyl, furyl, isoxazolyl, pyridyl, dihydropyranyl, tetrahydropyranyl, tetrahydropyridyl, piperidyl) optionally substituted by 1 to 3 C$_{1-6}$ alkyl (e.g., methyl), or
(9) a C$_{3-8}$ cycloalkyl group (e.g., cyclopropyl).

Z$^1$ is still more preferably
a group represented by CR$^{Z1}$ wherein R$^{Z1}$ is a hydrogen atom.

Z$^2$ is a group represented by CR$^{Z2}$ wherein R$^{Z2}$ is a hydrogen atom, a halogen atom, an optionally substituted C$_{1-6}$ alkyl group, an optionally substituted C$_{2-6}$ alkenyl group, an optionally substituted C$_{2-6}$ alkynyl group, an optionally substituted C$_{1-6}$ alkoxy group, an optionally substituted amino group, a cyano group or an optionally substituted cyclic group, or a nitrogen atom.

Z$^2$ is preferably a group represented by CR$^{Z2}$ wherein R$^{Z2}$ is a hydrogen atom, a halogen atom, an optionally substituted C$_{1-6}$ alkyl group, an optionally substituted C$_{2-6}$ alkenyl group, a cyano group or an optionally substituted cyclic group.

Z$^2$ is more preferably a group represented by CR$^{Z2}$ wherein R$^{Z2}$ is a hydrogen atom, a halogen atom, an optionally substituted C$_{1-6}$ alkyl group, a cyano group, an optionally substituted C$_{6-14}$ aryl group or an optionally substituted C$_{3-8}$ cycloalkyl group.

Z$^2$ is particularly preferably
a group represented by CR$^{Z2}$ wherein R$^{Z2}$ is
(1) a hydrogen atom,
(2) a halogen atom (e.g., a bromine atom, an iodine atom),
(3) optionally halogenated C$_{1-6}$ alkyl (e.g., methyl, ethyl, isopropyl) (preferably optionally substituted by 1 to 3 halogen atoms (e.g., a fluorine atom)),
(4) a C$_{2-6}$ alkenyl group (e.g., vinyl),
(5) a cyano group,
(6) a C$_{6-14}$ aryl group (e.g., phenyl), or
(7) a C$_{3-8}$ cycloalkyl group (e.g., cyclopropyl).

Z$^2$ is preferably a group represented by CR$^{Z2}$ wherein R$^{Z2}$ is a hydrogen atom, a halogen atom, an optionally substituted C$_{1-6}$ alkyl group, an optionally substituted C$_{2-6}$ alkenyl group, an optionally substituted C$_{1-6}$ alkoxy group, a cyano group or an optionally substituted cyclic group.

In another embodiment, Z$^2$ is preferably a group represented by CR$^{Z2}$ wherein R$^{Z2}$ is a hydrogen atom, a halogen atom, an optionally substituted C$_{1-6}$ alkyl group, an optionally substituted C$_{2-6}$ alkenyl group, an optionally substituted C$_{1-6}$ alkoxy group, a cyano group or an optionally substituted cyclic group, or a nitrogen atom.

Z$^2$ is more preferably a group represented by CR$^{Z2}$ wherein R$^{Z2}$ is a hydrogen atom, a halogen atom, an optionally substituted C$_{1-6}$ alkyl group, an optionally substituted C$_{1-6}$ alkoxy group, a cyano group, an optionally substituted C$_{6-14}$ aryl group or an optionally substituted C$_{3-8}$ cycloalkyl group.

In another embodiment, $Z^2$ is more preferably a group represented by $CR^{Z2}$ wherein $R^{Z2}$ is a hydrogen atom, a halogen atom, an optionally substituted $C_{1-6}$ alkyl group, an optionally substituted $C_{2-6}$ alkenyl group, an optionally substituted $C_{1-6}$ alkoxy group, a cyano group, an optionally substituted $C_{6-14}$ aryl group, an optionally substituted heterocyclic group or an optionally substituted $C_{3-8}$ cycloalkyl group, or a nitrogen atom.

$Z^2$ is particularly preferably
a group represented by $CR^{Z2}$ wherein $R^{Z2}$ is
(1) a hydrogen atom,
(2) a halogen atom (e.g., a bromine atom, an iodine atom),
(3) optionally halogenated $C_{1-6}$ alkyl group (e.g., methyl, ethyl, isopropyl) (preferably optionally substituted by 1 to 3 halogen atoms (e.g., a fluorine atom)),
(4) a $C_{2-6}$ alkenyl group (e.g., vinyl),
(5) a $C_{1-6}$ alkoxy group (e.g., methoxy),
(6) a cyano group,
(7) a $C_{6-14}$ aryl group (e.g., phenyl), or
(8) a $C_{3-8}$ cycloalkyl group (e.g., cyclopropyl).

In another embodiment, $Z^2$ is particularly preferably a group represented by $CR^{Z2}$ wherein $R^{Z2}$ is
(1) a hydrogen atom,
(2) a halogen atom (e.g., a fluorine atom, a chlorine atom, a bromine atom, an iodine atom),
(3) a $C_{1-6}$ alkyl group (e.g., methyl, ethyl, isopropyl) optionally substituted by 1 to 3 substituents selected from
  (i) a halogen atom (e.g., a fluorine atom), and
  (ii) hydroxy,
(4) a $C_{2-6}$ alkenyl group (e.g., vinyl),
(5) an optionally halogenated $C_{1-6}$ alkoxy group (e.g., methoxy, ethoxy, isopropoxy) (preferably optionally substituted by 1 to 3 halogen atoms (e.g., a fluorine atom)),
(6) a cyano group,
(7) a $C_{6-14}$ aryl group (e.g., phenyl),
(8) a $C_{3-8}$ cycloalkyl group (e.g., cyclopropyl), or
(9) a heterocyclic group (e.g., azetidinyl, pyrazolyl) optionally substituted by 1 to 3 $C_{1-6}$ alkyl (e.g., methyl), or a nitrogen atom.

$Z^2$ is most preferably
a group represented by $CR^{Z2}$ wherein $R^{Z2}$ is
(1) a $C_{1-6}$ alkoxy group (e.g., methoxy), or
(2) a $C_{3-8}$ cycloalkyl group (e.g., cyclopropyl).

In another embodiment, $Z^2$ is most preferably a group represented by $CR^{Z2}$ wherein $R^{Z2}$ is an optionally substituted $C_{1-6}$ alkoxy group, an optionally substituted $C_{1-6}$ alkyl group or an optionally substituted $C_{3-8}$ cycloalkyl group.

In another embodiment, $Z^2$ is most preferably
a group represented by $CR^{Z2}$ wherein $R^{Z2}$ is
(1) a $C_{1-6}$ alkoxy group (e.g., methoxy),
(2) a $C_{3-8}$ cycloalkyl group (e.g., cyclopropyl), or
(3) a $C_{1-6}$ alkyl group (e.g., methyl).

$Z^3$ is a group represented by $CR^{Z3}$ wherein $R^{Z3}$ is a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted amino group, a cyano group or an optionally substituted cyclic group, or a nitrogen atom.

In another embodiment, $Z^3$ is a group represented by $CR^{Z3}$ wherein $R^{Z3}$ is a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted amino group, a cyano group, an optionally substituted $C_{1-6}$ alkyl-carbonyl group or an optionally substituted cyclic group, or a nitrogen atom.

$Z^3$ is preferably a group represented by $CR^{Z3}$ wherein $R^{Z3}$ is a hydrogen atom or an optionally substituted $C_{1-6}$ alkyl group, or a nitrogen atom.

In another embodiment, $Z^3$ is preferably a group represented by $CR^{Z3}$ wherein $R^{Z3}$ is a hydrogen atom, an optionally substituted $C_{1-6}$ alkyl group, an optionally substituted $C_{1-6}$ alkoxy group or an optionally substituted $C_{1-6}$ alkyl-carbonyl group, or a nitrogen atom.

$Z^3$ is more preferably a group represented by $CR^{Z3}$ wherein $R^{Z3}$ is a hydrogen atom or a $C_{1-6}$ alkyl group (e.g., methyl), or a nitrogen atom.

In another embodiment, $Z^3$ is more preferably a group represented by $CR^{Z3}$ wherein $R^{Z3}$ is
(1) a hydrogen atom,
(2) a $C_{1-6}$ alkyl group (e.g., methyl, isopropyl) optionally substituted by 1 to 3 hydroxy groups,
(3) a $C_{1-6}$ alkoxy group (e.g., methoxy), or
(4) a $C_{1-6}$ alkyl-carbonyl group (e.g., acetyl), or a nitrogen atom.

$Z^3$ is still more preferably a group represented by $CR^{Z3}$ wherein $R^{Z3}$ is a hydrogen atom.

B is a nitrogen-containing aromatic heterocycle containing 1 or 2 nitrogen atoms.

B is preferably a 6-membered nitrogen-containing aromatic heterocycle containing 1 or 2 nitrogen atoms.

B is more preferably a pyridine ring or a pyrazine ring.

In another embodiment, B is more preferably a pyridine ring, a pyrimidine ring or a pyrazine ring.

B is particularly preferably a pyridine ring.

Preferable examples of compound (1) include the following compounds.

[Compound A-1]
compound (1) wherein
$R^1$ is a hydrogen atom or an optionally substituted $C_{1-6}$ alkyl group;
$R^2$ and $R^3$ are a hydrogen atom or an optionally substituted $C_{1-6}$ alkyl group;
X is an optionally substituted $C_{1-6}$ alkylene group (preferably an optionally substituted $C_{1-5}$ alkylene group);
A is a $C_{6-10}$ aryl group or a 5- or 6-membered nitrogen-containing aromatic heterocyclic group, each of which is optionally substituted;
$Z^1$ is a group represented by $CR^{Z1}$ wherein $R^{Z1}$ is a hydrogen atom, a halogen atom, an optionally substituted $C_{1-6}$ alkyl group, an optionally substituted $C_{2-6}$ alkenyl group, an optionally substituted $C_{1-6}$ alkoxy group or a cyano group;
$Z^2$ is a group represented by $CR^{Z2}$ wherein $R^{Z2}$ is a hydrogen atom, a halogen atom, an optionally substituted $C_{1-6}$ alkyl group, an optionally substituted $C_{2-6}$ alkenyl group, a cyano group, an optionally substituted $C_{6-14}$ aryl group or an optionally substituted $C_{3-8}$ cycloalkyl group;
$Z^3$ is a group represented by $CR^{Z3}$ wherein $R^{Z3}$ is a hydrogen atom or an optionally substituted $C_{1-6}$ alkyl group, or a nitrogen atom; and
B is a 6-membered nitrogen-containing aromatic heterocycle containing 1 or 2 nitrogen atoms.

[Compound A-2]
compound (1) wherein
$R^1$ is a hydrogen atom or an optionally substituted $C_{1-6}$ alkyl group;
$R^2$ and $R^3$ are a hydrogen atom or an optionally substituted $C_{1-6}$ alkyl group;
X is an optionally substituted $C_{1-6}$ alkylene group (preferably an optionally substituted $C_{1-5}$ alkylene group);
A is a $C_{6-10}$ aryl group or a 5- or 6-membered nitrogen-containing aromatic heterocyclic group, each of which is optionally substituted;

$Z^1$ is a group represented by $CR^{Z1}$ wherein $R^{Z1}$ is a hydrogen atom, a halogen atom, an optionally substituted $C_{1-6}$ alkyl group, an optionally substituted $C_{2-6}$ alkenyl group, an optionally substituted $C_{1-6}$ alkoxy group or a cyano group;

$Z^2$ is a group represented by $CR^{Z2}$ wherein $R^{Z2}$ is a hydrogen atom, a halogen atom, an optionally substituted $C_{1-6}$ alkyl group, an optionally substituted $C_{2-6}$ alkenyl group, an optionally substituted $C_{1-6}$ alkoxy group, a cyano group, an optionally substituted $C_{6-14}$ aryl group or an optionally substituted $C_{3-8}$ ycloalkyl group;

$Z^3$ is a group represented by $CR^{Z3}$ wherein $R^{Z3}$ is a hydrogen atom or an optionally substituted $C_{1-6}$ alkyl group, or a nitrogen atom; and B is a 6-membered nitrogen-containing aromatic heterocycle containing 1 or 2 nitrogen atoms.

[Compound A-3]
compound (1) wherein
$R^1$ is a hydrogen atom or an optionally substituted $C_{1-6}$ alkyl group;
$R^2$ and $R^3$ are a hydrogen atom or an optionally substituted $C_{1-6}$ alkyl group;
X is an optionally substituted $C_{1-6}$ alkylene group (preferably an optionally substituted $C_{1-5}$ alkylene group);
A is a $C_{6-10}$ aryl group, a 4- to 10-membered heterocyclic group or a $C_{3-8}$ cycloalkyl group, each of which is optionally substituted;
$Z^1$ is a group represented by $CR^{Z1}$ wherein $R^{Z1}$ is a hydrogen atom, a halogen atom, an optionally substituted $C_{1-6}$ alkyl group, an optionally substituted $C_{2-6}$ alkenyl group, an optionally substituted $C_{1-6}$ alkoxy group or a cyano group;
$Z^2$ is a group represented by $CR^{Z2}$ wherein $R^{Z2}$ is a hydrogen atom, a halogen atom, an optionally substituted $C_{1-6}$ alkyl group, an optionally substituted $C_{2-6}$ alkenyl group, an optionally substituted $C_{1-6}$ alkoxy group, a cyano group, an optionally substituted $C_{6-14}$ aryl group or an optionally substituted $C_{3-8}$ cycloalkyl group, or a nitrogen atom;
$Z^3$ is a group represented by $CR^{Z3}$ wherein $R^{Z3}$ is a hydrogen atom or an optionally substituted $C_{1-6}$ alkyl group, or a nitrogen atom; and
B is a 6-membered nitrogen-containing aromatic heterocycle containing 1 or 2 nitrogen atoms.

[Compound A-4]
compound (1) wherein
$R^1$ is a hydrogen atom,
$R^2$ and $R^3$ are both hydrogen atoms,
X is an optionally substituted $C_{1-6}$ alkylene group,
A is an optionally substituted phenyl group,
$Z^1$ is CH,
$Z^2$ is a group represented by $CR^{Z2}$ wherein $R^{Z2}$ is an optionally substituted $C_{1-6}$ alkyl group, an optionally substituted $C_{1-6}$ alkoxy group or an optionally substituted $C_{3-8}$ cycloalkyl group, and
$Z^3$ is CH.

[Compound B-1]
compound (1) wherein
$R^1$ is a hydrogen atom or a $C_{1-6}$ alkyl group;
$R^2$ and $R^3$ are both hydrogen atoms;
X is a $C_{1-6}$ alkylene group (preferably a $C_{1-5}$ alkylene group, more preferably —$CH_2$—, —$CH(CH_3)$—, —$CH(CH_2CH_3)$—, —$CH(CH_2CH_2CH_3)$— or —$CH(CH(CH_3)_2)$—) optionally substituted by 1 to 3 substituents selected from
(1) hydroxy,
(2) cyano,
(3) carbamoyl,
(4) $C_{1-6}$ alkoxy (e.g., methoxy),
(5) $C_{1-6}$ alkylsulfanyl (e.g., methylsulfanyl),
(6) $C_{1-6}$ alkylsulfonyl (e.g., methylsulfonyl),
(7) mono- or di-$C_{1-6}$ alkyl-amino (e.g., dimethylamino),
(8) $C_{3-8}$ cycloalkyl (e.g., cyclopropyl),
(9) $C_{6-14}$ aryl (e.g., phenyl) optionally substituted by 1 to 3 substituents selected from optionally halogenated $C_{1-6}$ alkoxy (e.g., methoxy) (preferably optionally substituted by 1 to 3 halogen atoms (e.g., a fluorine atom)), and
(10) a heterocyclic group (preferably a 5- or 6-membered aromatic heterocyclic group) (e.g., pyridyl, isoxazolyl, pyrazolyl) optionally substituted by 1 to 3 $C_{1-6}$ alkyl (e.g., methyl);

A is a $C_{6-10}$ aryl group or a 5- or 6-membered aromatic heterocyclic group (preferably a $C_{6-10}$ aryl group or a 5- or 6-membered nitrogen-containing aromatic heterocyclic group, more preferably phenyl, pyridazinyl, pyridyl, pyrimidinyl, isoxazolyl or pyrazolyl, particularly preferably phenyl), each of which is optionally substituted by 1 to 3 substituents selected from
(1) a halogen atom (e.g., a fluorine atom),
(2) hydroxy,
(3) optionally halogenated $C_{1-6}$ alkyl (e.g., methyl, isopropyl) (preferably optionally substituted by 1 to 3 halogen atoms (e.g., a fluorine atom)),
(4) $C_{2-6}$ alkenyl (e.g., prop-1-en-2-yl),
(5) $C_{1-6}$ alkoxy (e.g., methoxy) optionally substituted by 1 to 3 substituents selected from
   (i) a halogen atom (e.g., a fluorine atom), and
   (ii) $C_{3-8}$ cycloalkyl (e.g., cyclopropyl),
(6) $C_{6-14}$ aryl (e.g., phenyl), and
(7) a heterocyclic group (preferably a 5- or 6-membered heterocyclic group) (e.g., pyrazolyl, dihydropyranyl, tetrahydropyranyl) optionally substituted by 1 to 3 $C_{1-6}$ alkyl (e.g., methyl);

[preferably the group represented by

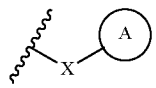

is a group represented by

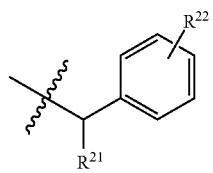

wherein
$R^{21}$ is a hydrogen atom, an optionally substituted $C_{1-5}$ alkyl group, a $C_{3-8}$ cycloalkyl group, a carbamoyl group or a cyano group, and
$R^{22}$ is a hydrogen atom or a substituent]

$Z^1$ is a group represented by $CR^{Z1}$ wherein $R^{Z1}$ is
(1) a hydrogen atom,
(2) a halogen atom (e.g., a chlorine atom),
(3) a $C_{1-6}$ alkyl group (e.g., methyl, ethyl) optionally substituted by 1 to 3 substituents selected from
   (i) a halogen atom (e.g., a fluorine atom), and
   (ii) a $C_{6-14}$ aryl group (e.g., phenyl),
(4) a $C_{2-6}$ alkenyl group (e.g., vinyl),
(5) a $C_{1-6}$ alkoxy group (e.g., methoxy), or
(6) a cyano group;

$Z^2$ is a group represented by $CR^{Z2}$ wherein $R^{Z2}$ is
(1) a hydrogen atom,
(2) a halogen atom (e.g., a bromine atom, an iodine atom),
(3) optionally halogenated $C_{1-6}$ alkyl (e.g., methyl, ethyl, isopropyl) (preferably optionally substituted by 1 to 3 halogen atoms (e.g., a fluorine atom)),
(4) a $C_{2-6}$ alkenyl group (e.g., vinyl),
(5) a cyano group,
(6) a $C_{6-14}$ aryl group (e.g., phenyl), or
(7) a $C_{3-6}$ cycloalkyl group (e.g., cyclopropyl);
$Z^3$ is a group represented by $CR^{Z3}$ wherein $R^{Z3}$ is a hydrogen atom or a $C_{1-6}$ alkyl group, or a nitrogen atom; and
B is a pyridine ring or a pyrazine ring.
[Compound B-2]
compound (1) wherein
$R^1$ is a hydrogen atom or a $C_{1-6}$ alkyl group (preferably methyl);
$R^2$ and $R^3$ are both hydrogen atoms;
X is a $C_{1-6}$ alkylene group (preferably a $C_{1-5}$ alkylene group, more preferably —$CH_2$—, —$CH(CH_3)$—, —CH($CH_2OH_3$)—, —$CH(CH_2CH_2CH_3)$— or —$CH(CH(CH_3)_2)$—) optionally substituted by 1 to 3 substituents selected from
(1) hydroxy,
(2) cyano,
(3) carbamoyl,
(4) $C_{1-6}$ alkoxy (e.g., methoxy),
(5) $C_{1-6}$ alkylsulfanyl (e.g., methylsulfanyl),
(6) $C_{1-6}$ alkylsulfonyl (e.g., methylsulfonyl),
(7) mono- or di-$C_{1-6}$ alkyl-amino (e.g., dimethylamino),
(8) $C_{3-8}$ cycloalkyl (e.g., cyclopropyl),
(9) $C_{6-14}$ aryl (e.g., phenyl) optionally substituted by 1 to 3 substituents selected from optionally halogenated $C_{1-6}$ alkoxy (e.g., methoxy) (preferably optionally substituted by 1 to 3 halogen atoms (e.g., a fluorine atom)), and
(10) a heterocyclic group (preferably a 5- or 6-membered aromatic heterocyclic group) (e.g., pyridyl, isoxazolyl, pyrazolyl) optionally substituted by 1 to 3 $C_{1-6}$ alkyl (e.g., methyl);
A is a $C_{6-10}$ aryl group or a 5- or 6-membered aromatic heterocyclic group (preferably a $C_{6-10}$ aryl group or a 5- or 6-membered nitrogen-containing aromatic heterocyclic group, more preferably phenyl, pyridazinyl, pyridyl, pyrimidinyl, isoxazolyl or pyrazolyl, particularly preferably phenyl), each of which is optionally substituted by 1 to 3 substituents selected from
(1) a halogen atom (e.g., a fluorine atom),
(2) hydroxy,
(3) optionally halogenated $C_{1-6}$ alkyl (e.g., methyl, isopropyl) (preferably optionally substituted by 1 to 3 halogen atoms (e.g., a fluorine atom)),
(4) $C_{2-6}$ alkenyl (e.g., prop-1-en-2-yl),
(5) $C_{1-6}$ alkoxy (e.g., methoxy) optionally substituted by 1 to 3 substituents selected from
  (i) a halogen atom (e.g., a fluorine atom), and
  (ii) $C_{3-8}$ cycloalkyl (e.g., cyclopropyl),
(6) $C_{6-14}$ aryl (e.g., phenyl), and
(7) a heterocyclic group (preferably a 5- or 6-membered heterocyclic group) (e.g., pyrazolyl, dihydropyranyl, tetrahydropyranyl) optionally substituted by 1 to 3 $C_{1-6}$ alkyl (e.g., methyl);
[preferably the group represented by

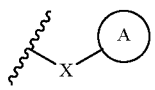

is a group represented by

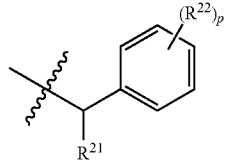

wherein
$R^{21}$ is
(1) cyano,
(2) carbamoyl,
(3) $C_{1-5}$ alkyl (e.g., methyl, ethyl, isopropyl, propyl) optionally substituted by 1 to 3 substituents selected from
  (i) hydroxy,
  (ii) $C_{1-6}$ alkoxy (e.g., methoxy),
  (iii) mono- or di-$C_{1-6}$ alkyl-amino (e.g., dimethylamino),
  (iv) $C_{1-6}$ alkylsulfanyl (e.g., methylsulfanyl), and
  (v) $C_{1-6}$ alkylsulfonyl (e.g., methylsulfonyl),
(4) $C_{3-8}$ cycloalkyl (e.g., cyclopropyl), or
(5) a heterocyclic group (preferably a 5- or 6-membered aromatic heterocyclic group) (e.g., pyridyl, isoxazolyl, pyrazolyl) optionally substituted by 1 to 3 $C_{1-6}$ alkyl (e.g., methyl),
$R^{22}$ is
(1) a halogen atom (e.g., a fluorine atom),
(2) hydroxy,
(3) optionally halogenated $C_{1-6}$ alkyl (e.g., methyl, isopropyl) (preferably optionally substituted by 1 to 3 halogen atoms (e.g., a fluorine atom)),
(4) $C_{2-6}$ alkenyl (e.g., prop-1-en-2-yl),
(5) $C_{1-6}$ alkoxy (e.g., methoxy) optionally substituted by 1 to 3 substituents selected from
  (i) a halogen atom (e.g., a fluorine atom), and
  (ii) $C_{3-8}$ cycloalkyl (e.g., cyclopropyl),
(6) $C_{6-14}$ aryl (e.g., phenyl), or
(7) a heterocyclic group (preferably a 5- or 6-membered heterocyclic group) (e.g., pyrazolyl, dihydropyranyl, tetrahydropyranyl) optionally substituted by 1 to 3 $C_{1-6}$ alkyl (e.g., methyl), and
p is an integer of 1 to 3],
$Z^1$ is a group represented by $CR^{Z1}$ wherein $R^{Z1}$ is
(1) a hydrogen atom,
(2) a halogen atom (e.g., a chlorine atom),
(3) a $C_{1-6}$ alkyl group (e.g., methyl, ethyl) optionally substituted by 1 to 3 substituents selected from
  (i) a halogen atom (e.g., a fluorine atom), and
  (ii) $C_{6-14}$ aryl (e.g., phenyl),
(4) a $C_{2-6}$ alkenyl group (e.g., vinyl),
(5) a $C_{1-6}$ alkoxy group (e.g., methoxy), or
(6) a cyano group;
$Z^2$ is a group represented by $CR^{Z2}$ wherein $R^{Z2}$ is
(1) a hydrogen atom,
(2) a halogen atom (e.g., a bromine atom, an iodine atom),
(3) an optionally halogenated $C_{1-6}$ alkyl group (e.g., methyl, ethyl, isopropyl) (preferably optionally substituted by 1 to 3 halogen atoms (e.g., a fluorine atom)),
(4) a $C_{2-6}$ alkenyl group (e.g., vinyl),
(5) a $C_{1-6}$ alkoxy group (e.g., methoxy),
(6) a cyano group,
(7) a $C_{6-14}$ aryl group (e.g., phenyl), or
(8) a $C_{3-8}$ cycloalkyl group (e.g., cyclopropyl);

$Z^3$ is a group represented by $CR^{Z3}$ wherein $R^{Z3}$ is a hydrogen atom or a $C_{1-6}$ alkyl group (e.g., methyl), or a nitrogen atom; and B is a pyridine ring or a pyrazine ring.

[Compound B-3]

compound (1) wherein $R^1$ is a hydrogen atom or a $C_{1-6}$ alkyl group (preferably methyl);

$R^2$ and $R^3$ are each independently a hydrogen atom or a $C_{1-6}$ alkyl group (preferably methyl);

X is a $C_{1-6}$ alkylene group (preferably $C_{1-6}$ alkylene group, more preferably —$CH_2$—, —$CH(CH_3)$—, —$CH(CH_2CH_3)$—, —$CH(CH_2CH_2CH_3)$—, —$CH(CH(CH_3)_2)$—, —$CH(C(CH_3)_3)$—, —$CH(CH_2CH_2CH_2CH_3)$—, —$CH(CH(CH_2CH_3)_2)$— or —$CH_2CH_2$—) optionally substituted by 1 to 5 substituents selected from
(1) a halogen atom (e.g., a fluorine atom),
(2) hydroxy,
(3) amino,
(4) cyano,
(5) carbamoyl,
(6) mono- or di-$C_{1-6}$ alkyl-carbamoyl (e.g., methylcarbamoyl, dimethylcarbamoyl),
(7) $C_{1-6}$ alkoxy (e.g., methoxy, ethoxy, isopropoxy) optionally substituted by 1 to 3 substituents selected from
  (i) a halogen atom (e.g., a fluorine atom), and
  (ii) $C_{1-6}$ alkoxy (e.g., methoxy),
(8) $C_{1-6}$ alkylsulfanyl (e.g., methylsulfanyl),
(9) $C_{1-6}$ alkylsulfinyl (e.g., methylsulfinyl),
(10) $C_{1-6}$ alkylsulfonyl (e.g., methylsulfonyl),
(11) mono- or di-$C_{1-6}$ alkyl-amino (e.g., dimethylamino),
(12) $C_{3-8}$ cycloalkyl (e.g., cyclopropyl),
(13) $C_{6-14}$ aryl (e.g., phenyl) optionally substituted by 1 to 3 substituents selected from
  (i) a halogen atom (e.g., a fluorine atom, a bromine atom),
  (ii) hydroxy, and
  (iii) optionally halogenated $C_{1-6}$ alkoxy (e.g., methoxy) (preferably optionally substituted by 1 to 3 halogen atoms (e.g., a fluorine atom)),
(14) a heterocyclic group (preferably a 4- to 10-membered heterocyclic group) (e.g., pyridyl, isoxazolyl, pyrazolyl, pyrrolidinyl, triazolyl, oxetanyl, tetrahydrofuryl, tetrahydropyranyl, dihydroisoindolyl) optionally substituted by 1 to 3 substituents selected from
  (i) $C_{1-6}$ alkyl (e.g., methyl),
  (ii) hydroxy, and
  (iii) oxo,
(15) $C_{3-8}$ cycloalkyloxy (e.g., cyclopentyloxy),
(16) optionally halogenated heterocyclyl-oxy (e.g., pyridyloxy) (preferably optionally substituted by 1 to 3 halogen atoms (e.g., a bromine atom)),
(17) $C_{1-6}$ alkyl-carbonyloxy (e.g., acetoxy),
(18) $C_{1-6}$ alkyl(diaryl)silyloxy (e.g., tert-butyl(diphenyl)silyloxy),
(19) $C_{1-6}$ alkyl-carbonyl (e.g., acetyl), and
(20) $C_{3-8}$ cycloalkyl-carbonyl (e.g., cyclopropylcarbonyl), or a bond;

A is a $C_{6-10}$ aryl group, a 4- to 10-membered heterocyclic group or a $C_{3-8}$ cycloalkyl group (preferably phenyl, pyridazinyl, pyridyl, pyrimidinyl, isoxazolyl, pyrazolyl, oxetanyl, pyrrolidinyl, tetrahydrofuryl, imidazolyl, triazolyl, thienyl, tetrahydropyranyl, imidazo[1,2-a]pyridyl, benzodioxolyl, pyrazolo[1,5-a]pyridyl, dihydroisoindolyl or cyclopropyl, more preferably phenyl), each of which is optionally substituted by 1 to 3 substituents selected from
(1) a halogen atom (e.g., a fluorine atom, a chlorine atom, a bromine atom),
(2) hydroxy,
(3) optionally halogenated $C_{1-6}$ alkyl (e.g., methyl, ethyl, isopropyl) (e.g., a fluorine atom)) (preferably optionally substituted by 1 to 3 halogen atoms,
(4) $C_{2-6}$ alkenyl (e.g., prop-1-en-2-yl),
(5) $C_{1-6}$ alkoxy (e.g., methoxy, ethoxy, isopropoxy) optionally substituted by 1 to 3 substituents selected from
  (i) a halogen atom (e.g., a fluorine atom), and
  (ii) $C_{3-8}$ cycloalkyl (e.g., cyclopropyl),
(6) $C_{6-14}$ aryl (e.g., phenyl) optionally substituted by optionally halogenated $C_{1-6}$ alkoxy (e.g., methoxy) (preferably optionally substituted by 1 to 3 halogen atoms (e.g., a fluorine atom)),
(7) a heterocyclic group (preferably a 4- to 6-membered heterocyclic group) (e.g., azetidinyl, pyrazolyl, pyrrolyl, pyrrolidinyl, triazolyl, dihydropyranyl, tetrahydropyranyl) optionally substituted by 1 to 3 $C_{1-6}$ alkyl (e.g., methyl),
(8) $C_{3-8}$ cycloalkyl (e.g., cyclopropyl), and
(9) oxo;

[preferably the group represented by

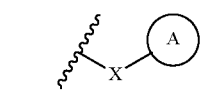

is a group represented by

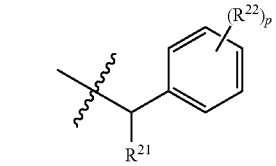

wherein $R^{21}$ is
(1) cyano,
(2) carbamoyl,
(3) mono- or di-$C_{1-6}$ alkyl-carbamoyl (e.g., methylcarbamoyl, dimethylcarbamoyl),
(4) $C_{1-6}$ alkyl (e.g., methyl, ethyl, isopropyl, propyl, butyl, tert-butyl, 1-ethylpropyl) optionally substituted by 1 to 5 substituents selected from
  (i) a halogen atom (e.g., a fluorine atom),
  (ii) hydroxy,
  (iii) amino,
  (iv) cyano,
  (v) $C_{3-8}$ cycloalkyl (e.g., cyclopropyl),
  (vi) $C_{1-6}$ alkoxy (e.g., methoxy, ethoxy, isopropoxy) optionally substituted by 1 to 3 substituents selected from
    (a) a halogen atom (e.g., a fluorine atom), and
    (b) $C_{1-6}$ alkoxy (e.g., methoxy),
  (vii) $C_{3-8}$ cycloalkyloxy (e.g., cyclopentyloxy),
  (viii) mono- or di-$C_{1-6}$ alkyl-amino (e.g., dimethylamino),
  (ix) $C_{1-6}$ alkylsulfanyl (e.g., methylsulfanyl),
  (x) $C_{1-6}$ alkylsulfinyl (e.g., methylsulfinyl),
  (xi) $C_{1-6}$ alkylsulfonyl (e.g., methylsulfonyl),
  (xii) carbamoyl,
  (xiii) mono- or di-$C_{1-6}$ alkyl-carbamoyl (e.g., dimethylcarbamoyl), (xiv) a heterocyclic group (e.g., oxetanyl, pyrrolidinyl, pyrazolyl, triazolyl, tetrahydropyranyl, dihydroisoindolyl) optionally substituted by 1 to 3 substituents selected from
(a) hydroxy, and
(b) oxo,
(xv) $C_{1-6}$ alkyl-carbonyloxy (e.g., acetoxy),
(xvi) $C_{1-6}$ alkyl(diaryl)silyloxy (e.g., tert-butyl(diphenyl)silyloxy), and
(xvii) optionally halogenated heterocyclyl-oxy (e.g., pyridyloxy) (preferably optionally substituted by 1 to 3 halogen atoms (e.g., a bromine atom)),
(5) $C_{3-8}$ cycloalkyl (e.g., cyclopropyl),
(6) a heterocyclic group (preferably a 4- to 6-membered heterocyclic group) (e.g., pyridyl, isoxazolyl, pyrazolyl, oxetanyl, tetrahydrofuryl, tetrahydropyranyl) optionally substituted by 1 to 3 $C_{1-6}$ alkyl (e.g., methyl),
(7) $C_{1-6}$ alkyl-carbonyl (e.g., acetyl),
(8) $C_{3-8}$ cycloalkyl-carbonyl (e.g., cyclopropylcarbonyl), or
(9) $C_{6-14}$ aryl (e.g., phenyl) optionally substituted by 1 to 3 substituents selected from
(i) a halogen atom (e.g., a fluorine atom, a bromine atom),
(ii) hydroxy,
(iii) optionally halogenated $C_{1-6}$ alkoxy (e.g., methoxy) (preferably optionally substituted by 1 to 3 halogen atoms (e.g., a fluorine atom)),
$R^{22}$ is
(1) a halogen atom (e.g., a fluorine atom, a chlorine atom, a bromine atom),
(2) hydroxy,
(3) optionally halogenated $C_{1-6}$ alkyl (e.g., methyl, isopropyl) (preferably optionally substituted by 1 to 3 halogen atoms (e.g., a fluorine atom)),
(4) $C_{2-6}$ alkenyl (e.g., prop-1-en-2-yl),
(5) $C_{1-6}$ alkoxy (e.g., methoxy, ethoxy, isopropoxy) optionally substituted by 1 to 3 substituents selected from
(i) a halogen atom (e.g., a fluorine atom), and
(ii) $C_{3-8}$ cycloalkyl (e.g., cyclopropyl),
(6) $C_{6-14}$ aryl (e.g., phenyl),
(7) a heterocyclic group (preferably a 4- to 6-membered heterocyclic group) (e.g., azetidinyl, pyrazolyl, pyrrolyl, pyrrolidinyl, triazolyl, dihydropyranyl, tetrahydropyranyl) optionally substituted by 1 to 3 $C_{1-6}$ alkyl (e.g., methyl), or
(8) $C_{3-8}$ cycloalkyl (e.g., cyclopropyl), and
p is an integer of 1 to 3],
$Z^1$ is a group represented by $CR^{Z1}$ wherein $R^{Z1}$ is
(1) a hydrogen atom,
(2) a halogen atom (e.g., a chlorine atom),
(3) a $C_{1-6}$ alkyl group (e.g., methyl, ethyl) optionally substituted by 1 to 3 substituents selected from
(i) a halogen atom (e.g., a fluorine atom), and
(ii) $C_{6-14}$ aryl (e.g., phenyl),
(4) a $C_{2-6}$ alkenyl group (e.g., vinyl),
(5) a $C_{1-6}$ alkoxy group (e.g., methoxy),
(6) a cyano group,
(7) a $C_{6-14}$ aryl group (e.g., phenyl) optionally substituted by 1 to 3 $C_{1-6}$ alkoxy (e.g., methoxy),
(8) a heterocyclic group (preferably a 5- or 6-membered heterocyclic group) (e.g., pyrazolyl, thienyl, furyl, isoxazolyl, pyridyl, dihydropyranyl, tetrahydropyranyl, tetrahydropyridyl, piperidyl) optionally substituted by 1 to 3 $C_{1-6}$ alkyl (e.g., methyl), or
(9) a $C_{3-8}$ cycloalkyl group (e.g., cyclopropyl);

$Z^2$ is a group represented by $CR^{Z2}$ wherein $R^{Z2}$ is
(1) a hydrogen atom,
(2) a halogen atom (e.g., a fluorine atom, a chlorine atom, a bromine atom, an iodine atom),
(3) $C_{1-6}$ alkyl (e.g., methyl, ethyl, isopropyl) optionally substituted by 1 to 3 substituents selected from
(i) a halogen atom (e.g., a fluorine atom), and
(ii) hydroxy,
(4) a $C_{2-6}$ alkenyl group (e.g., vinyl),
(5) an optionally halogenated $C_{1-6}$ alkoxy group (e.g., methoxy, ethoxy, isopropoxy) (preferably optionally substituted by 1 to 3 halogen atoms (e.g., a fluorine atom)),
(6) a cyano group,
(7) a $C_{6-14}$ aryl group (e.g., phenyl),
(8) a $C_{3-8}$ cycloalkyl group (e.g., cyclopropyl), or
(9) a heterocyclic group (e.g., azetidinyl, pyrazolyl) optionally substituted by 1 to 3 $C_{1-6}$ alkyl (e.g., methyl), or a nitrogen atom;
$Z^3$ is a group represented by $CR^{Z3}$ wherein $R^{Z3}$ is
(1) a hydrogen atom,
(2) a $C_{1-6}$ alkyl group (e.g., methyl, isopropyl) optionally substituted by 1 to 3 hydroxy,
(3) a $C_{1-6}$ alkoxy group (e.g., methoxy), or
(4) a $C_{1-6}$ alkyl-carbonyl group (e.g., acetyl), or a nitrogen atom; and
B is a pyridine ring, a pyrimidine ring or a pyrazine ring.
[Compound B-4]
compound (1) wherein
$R^1$ is a hydrogen atom or a $C_{1-6}$ alkyl group (preferably methyl);
$R^2$ and $R^3$ are each independently a hydrogen atom or a $C_{1-6}$ alkyl group (preferably methyl);
X is a $C_{1-6}$ alkylene group (preferably —CH$_2$—, —CH(CH$_3$)—, —CH(CH$_2$CH$_3$)—, —CH(CH$_2$CH$_2$CH$_3$)—, —CH(CH(CH$_3$)$_2$)—, —CH(C(CH$_3$)$_3$)—, —CH(CH$_2$CH$_2$CH$_2$CH$_3$)—, —CH(CH(CH$_2$CH$_3$)$_2$)— or —CH$_2$CH$_2$—) optionally substituted by 1 to 5 substituents selected from
(1) a halogen atom (e.g., a fluorine atom),
(2) hydroxy,
(3) amino,
(4) cyano,
(5) carbamoyl,
(6) mono- or di-$C_{1-6}$ alkyl-carbamoyl (e.g., methylcarbamoyl, dimethylcarbamoyl),
(7) $C_{1-6}$ alkoxy (e.g., methoxy, ethoxy, isopropoxy) optionally substituted by 1 to 3 substituents selected from
(i) a halogen atom (e.g., a fluorine atom), and
(ii) $C_{1-6}$ alkoxy (e.g., methoxy),
(8) $C_{1-6}$ alkylsulfanyl (e.g., methylsulfanyl),
(9) $C_{1-6}$ alkylsulfinyl (e.g., methylsulfinyl),
(10) $C_{1-6}$ alkylsulfonyl (e.g., methylsulfonyl),
(11) mono- or di-$C_{1-6}$ alkyl-amino (e.g., dimethylamino),
(12) $C_{3-8}$ cycloalkyl (e.g., cyclopropyl),
(13) $C_{6-14}$ aryl (e.g., phenyl) optionally substituted by 1 to 3 substituents selected from
(i) a halogen atom (e.g., a fluorine atom, a bromine atom),
(ii) hydroxy, and
(iii) optionally halogenated $C_{1-6}$ alkoxy (e.g., methoxy) (preferably optionally substituted by 1 to 3 halogen atoms (e.g., a fluorine atom)),
(14) a heterocyclic group (preferably a 4- to 10-membered heterocyclic group) (e.g., pyridyl, isoxazolyl, pyrazolyl, pyrrolidinyl, triazolyl, oxetanyl, tetrahydrofuryl, tetrahydropyranyl, dihydroisoindolyl) optionally substituted by 1 to 3 substituents selected from (i) $C_{1-6}$ alkyl (e.g., methyl),
(ii) hydroxy, and
(iii) oxo,
(15) $C_{3-8}$ cycloalkyloxy (e.g., cyclopentyloxy),
(16) optionally halogenated heterocyclyl-oxy (e.g., pyridyloxy) (preferably optionally substituted by 1 to 3 halogen atoms (e.g., a bromine atom)),
(17) $C_{1-6}$ alkyl-carbonyloxy (e.g., acetoxy),
(18) $C_{1-6}$ alkyl(diaryl)silyloxy (e.g., tert-butyl(diphenyl)silyloxy),
(19) $C_{1-6}$ alkyl-carbonyl (e.g., acetyl), and
(20) $C_{3-8}$ cycloalkyl-carbonyl (e.g., cyclopropylcarbonyl), or a bond;
A is a $C_{6-10}$ aryl group, a 4- to 10-membered heterocyclic group or a $C_{3-8}$ cycloalkyl group (preferably phenyl, pyridazinyl, pyridyl, pyrimidinyl, isoxazolyl, pyrazolyl, oxetanyl, pyrrolidinyl, tetrahydrofuryl, imidazolyl, triazolyl, thienyl, tetrahydropyranyl, imidazo[1,2-a]pyridyl, benzodioxolyl, pyrazolo[1,5-a]pyridyl, dihydroisoindolyl or cyclopropyl, more preferably phenyl), each of which is optionally substituted by 1 to 3 substituents selected from
(1) a halogen atom (e.g., a fluorine atom, a chlorine atom, a bromine atom),
(2) hydroxy,
(3) optionally halogenated $C_{1-6}$ alkyl (e.g., methyl, ethyl, isopropyl) (preferably optionally substituted by 1 to 3 halogen atoms (e.g., a fluorine atom)),
(4) $C_{2-6}$ alkenyl (e.g., prop-1-en-2-yl),
(5) $C_{1-6}$ alkoxy (e.g., methoxy, ethoxy, isopropoxy) optionally substituted by 1 to 3 substituents selected from
(i) a halogen atom (e.g., a fluorine atom), and
(ii) $C_{3-8}$ cycloalkyl (e.g., cyclopropyl),
(6) $C_{6-14}$ aryl (e.g., phenyl) optionally substituted by optionally halogenated $C_{1-6}$ alkoxy (e.g., methoxy) (preferably optionally substituted by 1 to 3 halogen atoms (e.g., a fluorine atom)),
(7) a heterocyclic group (preferably a 4- to 6-membered heterocyclic group) (e.g., azetidinyl, pyrazolyl, pyrrolyl, pyrrolidinyl, triazolyl, dihydropyranyl, tetrahydropyranyl) optionally substituted by 1 to 3 $C_{1-6}$ alkyl (e.g., methyl),
(8) $C_{3-8}$ cycloalkyl (e.g., cyclopropyl), and
(9) oxo;
$Z^1$ is a group represented by $CR^{Z1}$ wherein $R^{Z1}$ is
(1) a hydrogen atom,
(2) a halogen atom (e.g., a chlorine atom),
(3) a $C_{1-6}$ alkyl group (e.g., methyl, ethyl) optionally substituted by 1 to 3 substituents selected from
(i) a halogen atom (e.g., a fluorine atom), and
(ii) $C_{6-14}$ aryl (e.g., phenyl),
(4) a $C_{2-6}$ alkenyl group (e.g., vinyl),
(5) a $C_{1-6}$ alkoxy group (e.g., methoxy),
(6) a cyano group,
(7) a $C_{6-14}$ aryl group (e.g., phenyl) optionally substituted by 1 to 3 $C_{1-6}$ alkoxy (e.g., methoxy),
(8) a heterocyclic group (preferably a 5- or 6-membered heterocyclic group) (e.g., pyrazolyl, thienyl, furyl, isoxazolyl, pyridyl, dihydropyranyl, tetrahydropyranyl, tetrahydropyridyl, piperidyl) optionally substituted by 1 to 3 $C_{1-6}$ alkyl (e.g., methyl), or
(9) a $C_{3-8}$ cycloalkyl group (e.g., cyclopropyl);
$Z^2$ is a group represented by $CR^{Z2}$ wherein $R^{Z2}$ is
(1) a hydrogen atom,
(2) a halogen atom (e.g., a fluorine atom, a chlorine atom, a bromine atom, an iodine atom),
(3) a $C_{1-6}$ alkyl group (e.g., methyl, ethyl, isopropyl) optionally substituted by 1 to 3 substituents selected from (i) a halogen atom (e.g., a fluorine atom), and
(ii) hydroxy,
(4) a $C_{2-6}$ alkenyl group (e.g., vinyl),
(5) an optionally halogenated $C_{1-6}$ alkoxy group (e.g., methoxy, ethoxy, isopropoxy) (preferably optionally substituted by 1 to 3 halogen atoms (e.g., a fluorine atom)),
(6) a cyano group,
(7) a $C_{6-14}$ aryl group (e.g., phenyl),
(8) a $C_{3-8}$ cycloalkyl group (e.g., cyclopropyl), or
(9) a heterocyclic group (e.g., azetidinyl, pyrazolyl) optionally substituted by 1 to 3 $C_{1-6}$ alkyl (e.g., methyl), or a nitrogen atom;
$Z^3$ is a group represented by $CR^{Z3}$ wherein $R^{Z3}$ is
(1) a hydrogen atom,
(2) a $C_{1-6}$ alkyl group (e.g., methyl, isopropyl) optionally substituted by 1 to 3 hydroxy,
(3) a $C_{1-6}$ alkoxy group (e.g., methoxy), or
(4) a $C_{1-6}$ alkyl-carbonyl group (e.g., acetyl), or a nitrogen atom; and
B is a pyridine ring, a pyrimidine ring or a pyrazine ring.
[Compound B-5]
compound (1) wherein
$R^1$ is a hydrogen atom or a $C_{1-6}$ alkyl group (preferably methyl);
$R^2$ and $R^3$ are each independently a hydrogen atom or a $C_{1-6}$ alkyl group (preferably methyl);
the group represented by

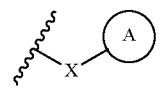

is a group represented by

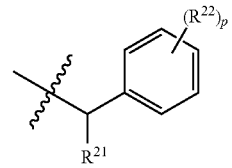

wherein
$R^{21}$ is
(1) cyano,
(2) carbamoyl,
(3) mono- or di-$C_{1-6}$ alkyl-carbamoyl (e.g., methylcarbamoyl, dimethylcarbamoyl),
(4) $C_{1-6}$ alkyl (e.g., methyl, ethyl, isopropyl, propyl, butyl, tert-butyl, 1-ethylpropyl) optionally substituted by 1 to 5 substituents selected from
(i) a halogen atom (e.g., a fluorine atom),
(ii) hydroxy,
(iii) amino,
(iv) cyano,
(v) $C_{3-8}$ cycloalkyl (e.g., cyclopropyl),
(vi) $C_{1-6}$ alkoxy (e.g., methoxy, ethoxy, isopropoxy) optionally substituted by 1 to 3 substituents selected from
(a) a halogen atom (e.g., a fluorine atom), and
(b) $C_{1-6}$ alkoxy (e.g., methoxy),
(vii) $C_{3-8}$ cycloalkyloxy (e.g., cyclopentyloxy),
(viii) mono- or di-$C_{1-6}$ alkyl-amino (e.g., dimethylamino), (ix) $C_{1-6}$ alkylsulfanyl (e.g., methylsulfanyl),
(x) $C_{1-6}$ alkylsulfinyl (e.g., methylsulfinyl),
(xi) $C_{1-6}$ alkylsulfonyl (e.g., methylsulfonyl),
(xii) carbamoyl,
(xiii) mono- or di-$C_{1-6}$ alkyl-carbamoyl (e.g., dimethylcarbamoyl),
(xiv) a heterocyclic group (e.g., oxetanyl, pyrrolidinyl, pyrazolyl, triazolyl, tetrahydropyranyl, dihydroisoindolyl) optionally substituted by 1 to 3 substituents selected from
  (a) hydroxy, and
  (b) oxo,
(xv) $C_{1-6}$ alkyl-carbonyloxy (e.g., acetoxy),
(xvi) $C_{1-6}$ alkyl(diaryl)silyloxy (e.g., tert-butyl(diphenyl)silyloxy), and
(xvii) optionally halogenated heterocyclyl-oxy (e.g., pyridyloxy) (preferably optionally substituted by 1 to 3 halogen atoms (e.g., a bromine atom)),
(5) $C_{3-8}$ cycloalkyl (e.g., cyclopropyl),
(6) a heterocyclic group (preferably a 4- to 6-membered heterocyclic group) (e.g., pyridyl, isoxazolyl, pyrazolyl, oxetanyl, tetrahydrofuryl, tetrahydropyranyl) optionally substituted by 1 to 3 $C_{1-6}$ alkyl (e.g., methyl),
(7) $C_{1-6}$ alkyl-carbonyl (e.g., acetyl),
(8) $C_{3-3}$ cycloalkyl-carbonyl (e.g., cyclopropylcarbonyl), or
(9) $C_{6-14}$ aryl (e.g., phenyl) optionally substituted by 1 to 3 substituents selected from
  (i) a halogen atom (e.g., a fluorine atom, a bromine atom), and
  (ii) hydroxy,
$R^{22}$ is
(1) a halogen atom (e.g., a fluorine atom, a chlorine atom, a bromine atom),
(2) hydroxy,
(3) optionally halogenated $C_{1-6}$ alkyl (e.g., methyl, isopropyl) (preferably optionally substituted by 1 to 3 halogen atoms (e.g., a fluorine atom)),
(4) $C_{2-6}$ alkenyl (e.g., prop-1-en-2-yl),
(5) $C_{1-6}$ alkoxy (e.g., methoxy, ethoxy, isopropoxy) optionally substituted by 1 to 3 substituents selected from
  (i) a halogen atom (e.g., a fluorine atom), and
  (ii) $C_{3-8}$ cycloalkyl (e.g., cyclopropyl),
(6) $C_{6-14}$ aryl (e.g., phenyl),
(7) a heterocyclic group (preferably a 4- to 6-membered heterocyclic group) (e.g., azetidinyl, pyrazolyl, pyrrolyl, pyrrolidinyl, triazolyl, dihydropyranyl, tetrahydropyranyl) optionally substituted by 1 to 3 $C_{1-6}$ alkyl (e.g., methyl), or
(8) $C_{3-8}$ cycloalkyl (e.g., cyclopropyl), and
p is an integer of 1 to 3,
$Z^1$ is a group represented by $CR^{Z1}$ wherein $R^{Z1}$ is
(1) a hydrogen atom,
(2) a halogen atom (e.g., a chlorine atom),
(3) a $C_{1-6}$ alkyl group (e.g., methyl, ethyl) optionally substituted by 1 to 3 substituents selected from
  (i) a halogen atom (e.g., a fluorine atom), and
  (ii) $C_{6-14}$ aryl (e.g., phenyl),
(4) a $C_{2-6}$ alkenyl group (e.g., vinyl),
(5) a $C_{1-6}$ alkoxy group (e.g., methoxy),
(6) a cyano group,
(7) a $C_{6-14}$ aryl group (e.g., phenyl) optionally substituted by 1 to 3 $C_{1-6}$ alkoxy (e.g., methoxy),
(8) a heterocyclic group (preferably a 5- or 6-membered heterocyclic group) (e.g., pyrazolyl, thienyl, furyl, isoxazolyl, pyridyl, dihydropyranyl, tetrahydropyranyl, tetrahydropyridyl, piperidyl) optionally substituted by 1 to 3 $C_{1-6}$ alkyl (e.g., methyl), or
(9) a $C_{3-8}$ cycloalkyl group (e.g., cyclopropyl);
$Z^2$ is a group represented by $CR^{Z2}$ wherein $R^{Z2}$ is
(1) a hydrogen atom,
(2) a halogen atom (e.g., a fluorine atom, a chlorine atom, a bromine atom, an iodine atom),
(3) a $C_{1-6}$ alkyl group (e.g., methyl, ethyl, isopropyl) optionally substituted by 1 to 3 substituents selected from
  (i) a halogen atom (e.g., a fluorine atom), and
  (ii) hydroxy,
(4) a $C_{2-6}$ alkenyl group (e.g., vinyl),
(5) an optionally halogenated $C_{1-6}$ alkoxy group (e.g., methoxy, ethoxy, isopropoxy) (preferably optionally substituted by 1 to 3 halogen atoms (e.g., a fluorine atom)),
(6) a cyano group,
(7) a $C_{6-14}$ aryl group (e.g., phenyl),
(8) a $C_{3-8}$ cycloalkyl group (e.g., cyclopropyl), or
(9) a heterocyclic group (e.g., azetidinyl, pyrazolyl) optionally substituted by 1 to 3 $C_{1-6}$ alkyl (e.g., methyl), or a nitrogen atom;
$Z^3$ is a group represented by $CR^{Z3}$ wherein $R^{Z3}$ is
(1) a hydrogen atom,
(2) a $C_{1-6}$ alkyl group (e.g., methyl, isopropyl) optionally substituted by 1 to 3 hydroxy,
(3) a $C_{1-6}$ alkoxy group (e.g., methoxy), or
(4) a $C_{1-6}$ alkyl-carbonyl group (e.g., acetyl), or a nitrogen atom; and
B is a pyridine ring, a pyrimidine ring or a pyrazine ring.
[Compound C-2]
compound (1) wherein
$R^1$ is a hydrogen atom;
$R^2$ and $R^3$ are both hydrogen atoms;
X is a $C_{1-6}$ alkylene group (preferably a $C_{1-5}$ alkylene group, more preferably —CH(CH$_3$)— or —CH(CH(CH$_3$)$_2$)—) optionally substituted by 1 to 3 substituents selected from
(1) hydroxy, and
(2) $C_{1-6}$ alkoxy (e.g., methoxy);
A is a $C_{6-10}$ aryl group (e.g., phenyl) optionally substituted by 1 to 3 substituents selected from
(1) a halogen atom (e.g., a fluorine atom), and
(2) $C_{1-6}$ alkoxy (e.g., methoxy) optionally substituted by 1 to 3 halogen atoms (e.g., a fluorine atom);
[preferably the group represented by

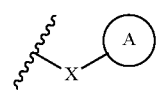

is a group represented by

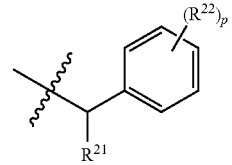

wherein
$R^{21}$ is a $C_{1-5}$ alkyl group (e.g., methyl, isopropyl) optionally substituted by hydroxy or $C_{1-6}$ alkoxy (e.g., methoxy), $R^{22}$ is
(1) a halogen atom (e.g., a fluorine atom), or
(2) optionally halogenated $C_{1-6}$ alkoxy (e.g., methoxy) (preferably optionally substituted by 1 to 3 halogen atoms (e.g., a fluorine atom)), and
p is an integer of 1 or 2];
$Z^1$ is CH;
$Z^2$ is a group represented by $CR^{Z2}$ wherein $R^{Z2}$ is
(1) a $C_{1-6}$ alkoxy group (e.g., methoxy), or
(2) a $C_{3-8}$ cycloalkyl group (e.g., cyclopropyl);
$Z^3$ is CH; and
B is a pyridine ring.
[Compound C-3]
compound (1) wherein
$R^1$ is a hydrogen atom;
$R^2$ and $R^3$ are both hydrogen atoms;
X is a $C_{1-6}$ alkylene group (preferably a $C_{1-5}$ alkylene group, more preferably —CH(CH$_3$)— or —CH(CH(CH$_3$)$_2$)—) optionally substituted by 1 to 3 substituents selected from
(1) hydroxy, and
(2) $C_{1-6}$ alkoxy (e.g., methoxy);
A is a $C_{6-10}$ aryl group (e.g., phenyl) optionally substituted by 1 to 3 substituents selected from
(1) a halogen atom (e.g., a fluorine atom), and
(2) $C_{1-6}$ alkoxy (e.g., methoxy) optionally substituted by 1 to 3 halogen atoms (e.g., a fluorine atom);
[preferably the group represented by

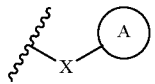

is a group represented by

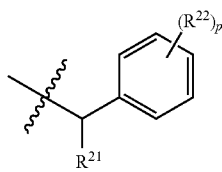

wherein
$R^{21}$ is a $C_{1-5}$ alkyl group (e.g., methyl, isopropyl) optionally substituted by hydroxy or $C_{1-6}$ alkoxy (e.g., methoxy),
$R^{22}$ is
(1) a halogen atom (e.g., a fluorine atom), or
(2) an optionally halogenated $C_{1-6}$ alkoxy group (e.g., methoxy) (preferably optionally substituted by 1 to 3 halogen atoms (e.g., a fluorine atom)),
p is an integer of 1 or 2];
$Z^1$ is CH;
$Z^2$ is a group represented by $CR^{Z2}$ wherein $R^{Z2}$ is
(1) a $C_{1-6}$ alkoxy group (e.g., methoxy),
(2) a $C_{3-8}$ cycloalkyl group (e.g., cyclopropyl), or
(3) a $C_{1-6}$ alkyl group (e.g., methyl);
$Z^3$ is CH; and
B is a pyridine ring.
Specific examples of compound (1) include compounds of Examples 1-280.
Examples of the salt of the compound represented by the formula (1) include metal salts, ammonium salts, salts with an organic base, salt with an inorganic acid, salts with an organic acid, salts with a basic or acidic amino acid, and the like.
Preferable examples of the metal salt include alkaline metal salts such as sodium salt, potassium salt and the like; alkaline earth metal salts such as calcium salt, magnesium salt, barium salt and the like; aluminum salt, and the like.
Preferable examples of the salt with an organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like.
Preferable examples of the salt with an inorganic acid include salts with hydrochloric acid, hydrobromic acid, nitric acid, sulfuric acid, phosphoric acid and the like.
Preferable examples of the salt with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.
Preferable examples of the salt with a basic amino acid include salts with arginine, lysine, ornithine and the like. Preferable examples of the salt with an acidic amino acid include salt with aspartic acid, glutamic acid and the like.
Among the above-mentioned salts, pharmaceutically acceptable salts are preferable.
The prodrug of compound (1) means a compound which is converted to compound (1) with a reaction due to an enzyme, gastric acid and the like under the physiological condition in the living body, that is, a compound which is converted to compound (1) by enzymatic oxidation, reduction, hydrolysis and the like; a compound which is converted to compound (1) by hydrolysis and the like due to gastric acid, and the like.
Examples of the prodrug of compound (1) include a compound obtained by subjecting an amino group in compound (1) to an acylation, alkylation or phosphorylation (e.g., a compound obtained by subjecting an amino group in compound (1) to an eicosanoylation, alanylation, pentylaminocarbonylation, (5-methyl-2-oxo-1,3-dioxolen-4-yl) methoxycarbonylation, tetrahydrofuranylation, pyrrolidylmethylation, pivaloyloxymethylation or tert-butylation); a compound obtained by subjecting a hydroxy group in compound (1) to an acylation, alkylation, phosphorylation or boration (e.g., a compound obtained by subjecting a hydroxy group in compound (1) to an acetylation, palmitoylation, propanoylation, pivaloylation, succinylation, fumarylation, alanylation or dimethylaminomethylcarbonylation); a compound obtained by subjecting a carboxyl group in compound (1) to an esterification or amidation (e.g., a compound obtained by subjecting a carboxyl group in compound (1) to a $C_{1-6}$ alkyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. Among them, a compound esterified by $C_{1-6}$ alkyl (e.g., methyl, ethyl, tert-butyl and the like) are preferably used. These compounds can be produced from compound (1) according to a method known per se.
The prodrug of compound (1) may also be one which is converted into compound (1) under a physiological condition, such as those described in IYAKUHIN no KAIHATSU (Development of Pharmaceuticals), Vol. 7, Design of Molecules, p. 163-198, 1990, Published by HIROKAWA SHOTEN.

Each symbol of the compound in the following Reaction Schemes is as defined above, unless otherwise specified. Each compound described in the following Reaction Schemes may be in the form of a salt as long as it does not inhibit the reaction. Examples of the salt include those similar to the salt of compound (1).

The compound obtained in each step can be used directly for the next reaction as the reaction mixture or as a crude product, or can also be isolated according to a conventional method from the reaction mixture, and can also be easily purified according to a separation means (e.g., recrystallization, distillation, chromatography etc.).

The production methods of the compound of the present invention are described in the following.

Compound (1) (compound (1a) and compound (1b) in the following Reaction Scheme 1) can be produced according to a method known per se, for example, the production method shown in Reaction Scheme 1 to Reaction Scheme 7 or a method analogous thereto.

In each of the following production methods, each starting compound used for the production of compound (1) may be in the form of a salt. Examples of the salt include those similar to the salt of compound (1).

Each starting compound to be used for the production of compound (1) can be used directly for the next reaction as the reaction mixture or as a crude product, or can also be isolated according to a conventional method from the reaction mixture, and can also be purified according to a separation means (e.g., extraction, concentration, neutralization, filtration, distillation, recrystallization, chromatography etc.). Examples of the solvent used for the above-mentioned recrystallization include water, alcohols, ethers, hydrocarbons, amides, halogenated hydrocarbons, nitriles, ketones, esters, sulfoxides, organic acids and the like. These solvents may be used alone, or two or more kinds of solvents may be mixed at a suitable ratio, for example, 1:1-1:10. In addition, the compounds in the Reaction Schemes may be commercially available, or can be produced according to a method known per se or a method analogous thereto.

When compound (1) and intermediate for the production of compound (1) have a convertible functional group (e.g., a carboxyl group, an amino group, a hydroxy group, a carbonyl group, a mercapto group, a $C_{1-6}$ alkoxy-carbonyl group, a $C_{6-14}$ aryloxy-carbonyl group, a $C_{7-16}$ aralkyloxy-carbonyl group, a sulfo group, a halogen atom, an optionally halogenated $C_{1-6}$ alkylsulfonyloxy group, a cyano group, an aminocarbonyl group, a boryl group etc.), various compounds can be produced by converting such functional group according to a method known per se or a method analogous thereto.

Carboxyl group can be converted, for example, by reactions such as esterification, reduction, amidation, conversion reaction to optionally protected amino group and the like.

Amino group can be converted, for example, by reactions such as amidation, sulfonylation, nitrosation, alkylation, arylation, imidation and the like.

Hydroxy group can be converted, for example, by reactions such as esterification, carbamoylation, sulfonylation, alkylation, fluorination, arylation, oxidation, halogenation and the like.

Carbonyl group can be converted, for example, by reactions such as reduction, oxidation, fluorination, imination (including oximation, hydrazonation), (thio)ketalization, alkylidenation, thiocarbonylation and the like.

Mercapto group can be converted, for example, by reactions such as alkylation, oxidation and the like.

$C_{1-6}$ alkoxy-carbonyl group, $C_{6-14}$ aryloxy-carbonyl group and $C_{7-16}$ aralkyloxy-carbonyl group can be converted, for example, by reactions such as reduction, hydrolysis and the like.

Sulfo group can be converted, for example, by reactions such as sulfonamidation, reduction and the like.

Halogen atom can be converted, for example, by various nucleophilic substitution reactions, various coupling reactions and the like.

Optionally halogenated $C_{1-6}$ alkylsulfonyloxy group can be converted, for example, by various nucleophilic substitution reactions, various coupling reactions and the like.

Cyano group can be converted, for example, by reactions such as reduction, hydrolysis and the like.

Aminocarbonyl group can be converted, for example, by reactions such as dehydration, reduction and the like.

Boryl group can be converted, for example, by oxidation, various coupling reactions and the like.

In each of the above-mentioned reactions, when the compound is obtained in a free form, it may be converted to a salt according to a conventional method. When it is obtained as a salt, it may be converted to a free form or other salt according to a conventional method.

The conversion of these functional group can be carried out according to a method known per se, for example, the method described in Comprehensive Organic Transformations, Second Edition, Wiley-VCH, Richard C. Larock, or the like.

In each reaction in the production method of compound (1) and each reaction of the synthesis of the starting materials, when the starting compound has an amino group, a carboxyl group, a hydroxy group, a carbonyl group or a mercapto group as a substituent, a protecting group generally used in peptide chemistry and the like may be introduced into these substituents. By removing the protecting group as necessary after the reaction, the object compound can be obtained.

Examples of the amino-protecting group include a formyl group; and a $C_{1-6}$ alkyl-carbonyl group (e.g., acetyl, ethylcarbonyl etc.), a phenylcarbonyl group, a $C_{1-6}$ alkyl-oxycarbonyl group (e.g., methoxycarbonyl, ethoxycarbonyl, tert-butoxycarbonyl (Boc) etc.), an allyloxycarbonyl (Alloc) group, a phenyloxycarbonyl group, a fluorenylmethoxycarbonyl (Fmoc) group, a $C_{7-10}$ aralkyl-carbonyl group (e.g., benzylcarbonyl etc.), a $C_{7-10}$ aralkyl-oxycarbonyl group (e.g., benzyloxycarbonyl (Z) etc.), a $C_{7-10}$ aralkyl group (e.g., benzyl etc.), a 2-(trimethylsilyl)ethoxymethyl (SEM) group, a trityl group, a phthaloyl group, an N,N-dimethylaminomethylene group, an allyl group and the like, each of which optionally has substituent(s), and the like. As these substituents, a phenyl group, a halogen atom (e.g., fluorine, chlorine, bromine, iodine etc.), a $C_{1-6}$ alkyl-carbonyl group (e.g., methylcarbonyl, ethylcarbonyl, butylcarbonyl etc.), a nitro group and the like are used, and the number of the substituents is about 1 to 3.

Examples of the carboxyl-protecting group include a $C_{1-6}$ alkyl group (e.g., methyl, ethyl, n-propyl, isopropyl, n-butyl, tert-butyl etc.), an allyl group, a benzyl group, a phenyl group, a trityl group, a trialkylsilyl group and the like, each of which optionally has substituent(s). As these substituents, a halogen atom (e.g., fluorine, chlorine, bromine, iodine etc.), a formyl group, a $C_{1-6}$ alkyl-carbonyl group (e.g., acetyl, ethylcarbonyl, butylcarbonyl etc.), a nitro group and the like are used, and the number of the substituents is about 1 to 3.

Examples of the hydroxyl-protecting group include a $C_{1-6}$ alkyl group (e.g., methyl, ethyl, n-propyl, isopropyl, n-butyl, tert-butyl etc.), a $C_{7-10}$ aralkyl group (e.g., benzyl etc.), a formyl group, a $C_{1-6}$ alkyl-carbonyl group (e.g., acetyl, ethylcarbonyl etc.), a benzoyl group, a $C_{7-10}$ aralkyl-carbonyl group (e.g., benzylcarbonyl etc.), a tetrahydropyranyl group, a furanyl group, a silyl group and the like, each of which optionally has substituent(s). As these substituents, a halogen atom (e.g., fluorine, chlorine, bromine, iodine etc.), a $C_{1-6}$ alkyl group (e.g., methyl, ethyl, n-propyl etc.), a phenyl group, a $C_{7-10}$ aralkyl group (e.g., benzyl etc.), a $C_{1-6}$ alkoxy group (e.g., methoxy, ethoxy, n-propoxy etc.), a nitro group and the like are used, and the number of the substituents is about 1 to 4.

Examples of the protected carbonyl group include cyclic acetal (e.g., 1,3-dioxane), noncyclic acetal (e.g., di-$C_{1-6}$ alkylacetal) and the like.

Examples of the mercapto-protecting group include a $C_{1-6}$ alkyl group, a phenyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl, 9-fluorenylmethoxycarbonyl), a 2-tetrahydropyranyl group, a $C_{1-6}$ alkylaminocarbonyl group (e.g., methylaminocarbonyl, ethylaminocarbonyl) and the like. These protecting groups are optionally substituted by 1 to 3 substituents selected from a halogen atom, a $C_{1-6}$ alkyl group, a $C_{1-6}$ alkoxy group and a nitro group.

These protecting groups can be introduced and removed by a method known per se, for example, the method described in Greene's Protective Groups in Organic Synthesis, 4th Edition, Wiley-Interscience, Theodora W. Greene, Peter G. M. Wuts or the like. Specifically, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like can be employed.

When compound (1) is present as a configurational isomer, a diastereomer, a conformer and the like, each can be isolated by a known means. When compound (1) has an optical isomer, racemates can be resolved by a general optical resolution means, whereby an optically active forms ((+) form, (−) form) can be obtained.

When compound (1) has an optical isomer, a stereoisomer, a positional isomer, a rotamer or a tautomer, these are also encompassed in compound (1), and can be obtained as a single product according to synthesis and separation methods known per se.

For example, the method of optical resolution may be a method known per se, such as a fractional recrystallization method, a chiral column method, a diastereomer method etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column (a chiral column) for separation of an optical isomer to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine, etc.) as an eluent, solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis and the like to separate an optically active reagent moiety, whereby an optical isomer is obtained. For example, when compound (1) contains hydroxy group, or primary or secondary amino group within a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (1) has a carboxyl group, the compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis.

The solvent, acid and base recited in the production methods of the compound of the present invention are explained in the following.

Examples of the "solvent" include "alcohols", "ethers", "hydrocarbons", "amides", "halogenated hydrocarbons", "nitriles", "ketones", "esters", "sulfoxides", "water" and the like.

Examples of the "alcohols" include methanol, ethanol, 1-propanol, 2-propanol, tert-butyl alcohol and the like.

Examples of the "ethers" include diethyl ether, diisopropyl ether, diphenyl ether, tetrahydrofuran, 1,4-dioxane, 1,2-dimethoxyethane, tert-butyl methyl ether and the like.

Examples of the "hydrocarbons" include benzene, toluene, cyclohexane, hexane, petroleum ether and the like.

Examples of the "amides" include N,N-dimethylformamide, N,N-dimethylacetamide, N-methylpyrrolidone, hexamethylphosphoric triamide and the like.

Examples of the "halogenated hydrocarbons" include dichloromethane, chloroform, carbon tetrachloride, 1,2-dichloroethane, chlorobenzene, benzotrifluoride and the like.

Examples of the "nitriles" include acetonitrile, propionitrile and the like.

Examples of the "ketones" include acetone, ethyl methyl ketone and the like.

Examples of the "esters" include ethyl acetate, tert-butyl acetate and the like.

Examples of the "sulfoxides" include dimethyl sulfoxide and the like.

Examples of the "acid" include "organic acids", "mineral acids", "Lewis acids" and the like.

Examples of the "organic acids" include formic acid, acetic acid, propionic acid, trifluoroacetic acid, citric acid, methanesulfonic acid, p-toluenesulfonic acid and the like.

Examples of the "mineral acids" include hydrochloric acid, sulfuric acid and the like.

Examples of the "Lewis acids" include boron trichloride, boron tribromide and the like.

Examples of the "base" include "inorganic bases", "basic salts", "aromatic amines", "tertiary amines", "alkali metal hydrides", "alkali metals", "metal amides", "alkyl metals", "aryl metals", "metal alkoxides" and the like.

Examples of the "inorganic bases" include sodium hydroxide, potassium hydroxide, lithium hydroxide, barium hydroxide and the like.

Examples of the "basic salts" include sodium carbonate, potassium carbonate, cesium carbonate, sodium hydrogen carbonate, sodium acetate, ammonium acetate and the like.

Examples of the "aromatic amines" include pyridine, 2,6-lutidine and the like.

Examples of the "tertiary amines" include triethylamine, tripropylamine, tributylamine, diisopropylethylamine, cyclohexyldimethylamine, 4-dimethylaminopyridine, N,N-dimethylaniline, N-methylpiperidine, N-methylpyrrolidine, N-methylmorpholine, 1,8-diazabicyclo[5,4,0]undec-7-ene and the like.

Examples of the "alkali metal hydrides" include sodium hydride, potassium hydride and the like.

Examples of the "alkali metals" include sodium, lithium, potassium and the like.

Examples of the "metal amides" include sodium amide, lithium diisopropylamide, lithium hexamethyldisilazide and the like.

Examples of the "alkyl metals" include butyllithium, sec-butyllithium, tert-butyllithium and the like.

Examples of the "aryl metals" include phenyllithium and the like.

Examples of the "metal alkoxides" include sodium methoxide, sodium ethoxide, sodium tert-butoxide, potassium tert-butoxide and the like.

Compound (1) can be produced, for example, according to the method shown in the following Reaction Scheme 1 or a method analogous thereto.

Reaction Scheme 1

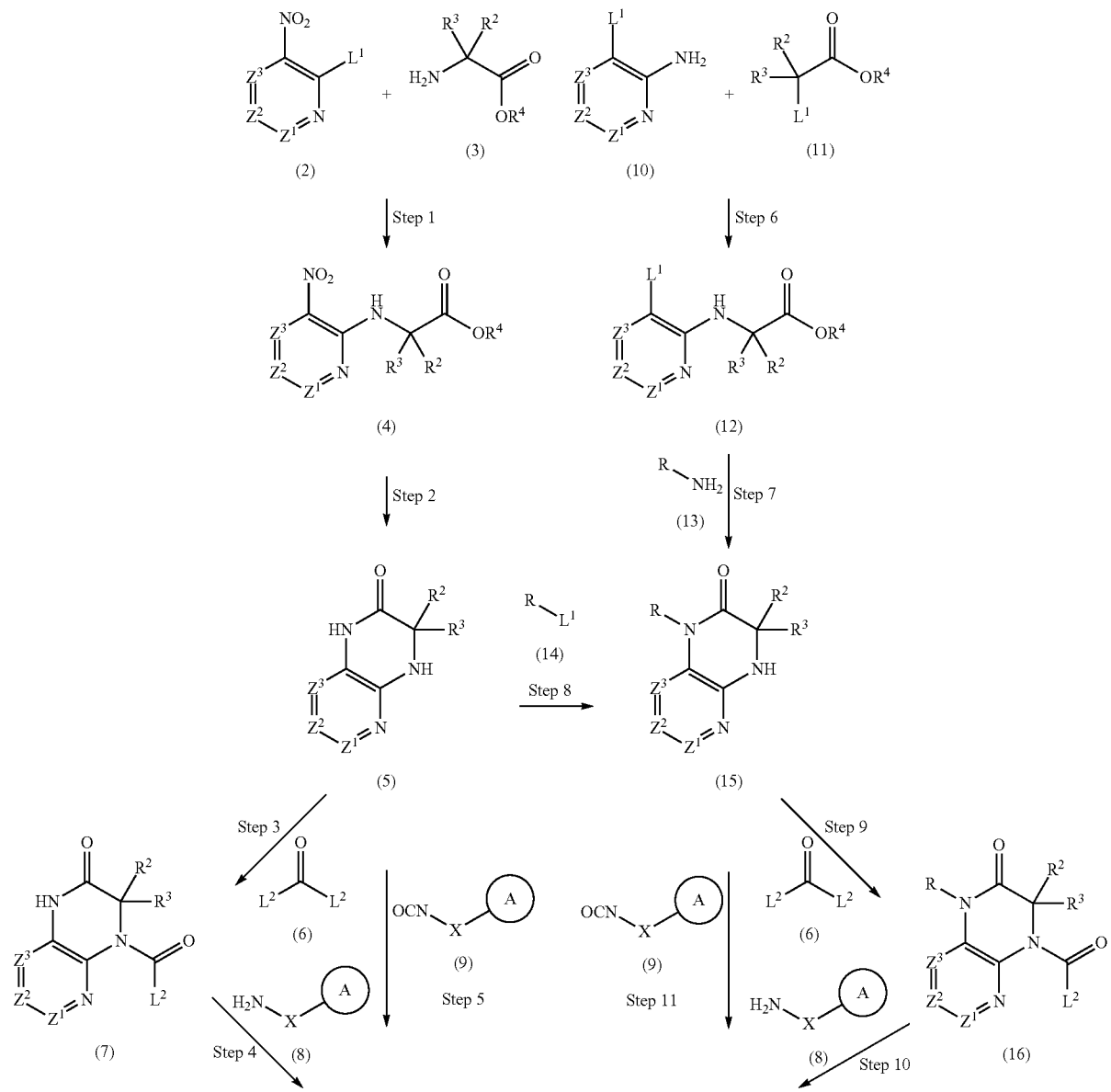

-continued

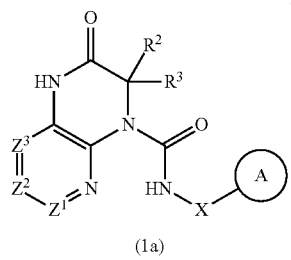

(1a)

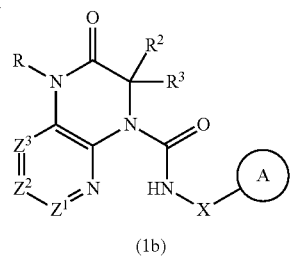

(1b)

wherein $R^4$ is an optionally substituted $C_{1-6}$ alkyl group, R is an optionally substituted $C_{1-6}$ alkyl group or an amino-protecting group, $L^1$ and $L^2$ are each independently a leaving group, and the other symbols are as defined above.

Examples of the amino-protecting group for R include a formyl group; a $C_{1-6}$ alkyl-carbonyl group (e.g., acetyl, ethylcarbonyl and the like), a phenylcarbonyl group, a $C_{1-6}$ alkyl-oxycarbonyl group (e.g., methoxycarbonyl, ethoxycarbonyl, tert-butoxycarbonyl (Boc) and the like), an allyloxycarbonyl (Alloc) group, a phenyloxycarbonyl group, a fluorenylmethoxycarbonyl (Fmoc) group, a $C_{7-10}$ aralkyl-carbonyl group (e.g., benzyl carbonyl and the like), a $C_{7-10}$ aralkyl-oxycarbonyl group (e.g., benzyloxycarbonyl (Z) and the like), a $C_{7-10}$ aralkyl group (e.g., benzyl and the like), a 2-(trimethylsilyl)ethoxymethyl (SEM) group, a trityl group, a phthaloyl group, an N,N-dimethylaminomethylene group and an allyl group, each optionally having substituent(s), and the like. The amino-protecting group is preferably a 2,4-dimethoxybenzyl (DMB) group or a 2-(trimethylsilyl)ethoxymethyl (SEM) group.

Examples of the leaving group for $L^1$ include a halogen atom, an optionally halogenated $C_{1-6}$ alkylsulfonyloxy group, a $C_{6-10}$ arylsulfonyloxy group optionally substituted by $C_{1-6}$ alkyl group(s), and the like. The leaving group is preferably a halogen atom or an optionally halogenated $C_{1-6}$ alkylsulfonyloxy group.

Examples of the leaving group for $L^2$ include a halogen atom, an optionally halogenated $C_{1-6}$ alkylsulfonyloxy group, an optionally halogenated $C_{1-6}$ alkoxy group, an optionally substituted aryloxy group, a 1-1H-imidazolyl group and the like. The leaving group is preferably a halogen atom, a 4-nitrophenoxy group or a trichloromethoxy group.

Compounds (2), (3), (6), (10), (11), (13) and (14) may be commercially available, or can also be produced according to a method known per se or a method analogous thereto.

<Step 1> Compound (4) can be produced by reacting compound (2) with compound (3).

The amount of compound (3) to be used is generally about 0.5-20 mol, preferably about 1-10 mol, per 1 mol of compound (2).

This reaction is generally carried out in the presence of a base. Examples of the base include tertiary amines, basic salts, metal hydrogen complex compounds, metal alkoxides, metal amides, alkyl metals, aryl metals and the like. The amount of the base to be used is generally about 1-100 mol, preferably about 1-10 mol, per 1 mol of compound (2).

This reaction is advantageously carried out in a solvent inert to the reaction. The solvent is not particularly limited as long as the reaction proceeds. Preferable examples thereof include alcohols, ethers, amides, sulfoxides, tertiary amines, mixed solvents thereof and the like.

While the reaction time varies depending on the reagent and solvent to be used, it is generally 0.1-48 hr, preferably 0.5-24 hr.

The reaction temperature is generally 0-300° C., preferably 20-150° C.

<Step 2> Compound (5) can be produced from compound (4).

The conversion of the nitro group to an amino group can be carried out according to a method known per se, for example, the method described in Reductions in Organic Chemistry, Second Edition, The American Chemical Society, 1996, or a method analogous thereto, for example, a hydrogenation reaction, a reaction using a metal or metal salt, or the like. The next intramolecular amidation reaction mostly proceeds under a condition of the reduction of the nitro group. Where necessary, this amidation reaction can be promoted by raising the reaction temperature or adding a suitable acid or base.

Examples of the acid include organic acids, mineral acids and the like. Examples of the base include tertiary amines, aromatic amines, alkali metal hydrides, basic salts and the like. The amount of the acid or base to be used is generally about 0.01-100 mol, preferably about 0.01-10 mol, per 1 mol of compound (4).

This reaction is advantageously carried out in a solvent inert to the reaction. The solvent is not particularly limited as long as the reaction proceeds. Preferable examples thereof include alcohols, ethers, esters, organic acids, amides, mixed solvents thereof and the like.

While the reaction time varies depending on the reagent and solvent to be used, it is generally 0.1-48 hr, preferably 0.5-24 hr.

The reaction temperature is generally 0-200° C., preferably 20-100° C.

<Step 3> Compound (7) can be produced by reacting compound (5) with compound (6).

The amount of compound (6) to be used is generally about 0.1-10 mol, preferably about 0.3-5 mol, per 1 mol of compound (5).

This reaction may be carried out in the presence of a base. Examples of the base include tertiary amines, aromatic amines, alkali metal hydrides, basic salts and the like. The amount of the base to be used is generally about 1-100 mol, preferably about 1-10 mol, per 1 mol of compound (5).

This reaction is advantageously carried out in a solvent inert to the reaction. The solvent is not particularly limited as long as the reaction proceeds. Preferable examples thereof include halogenated hydrocarbons, aromatic amines, amides, tertiary amines, ethers, nitriles, esters, hydrocarbons, mixed solvents thereof and the like.

While the reaction time varies depending on the reagent and solvent to be used, it is generally 0.1-48 hr, preferably The reaction temperature is generally −50-150° C., preferably −20-100° C.

<Step 4> Compound (1a) can be produced by reacting compound (7) with compound (8).

The amount of compound (8) to be used is generally about 1-10 mol, preferably about 1-5 mol, per 1 mol of compound (7).

This reaction is generally carried out in the presence of a base. Examples of the base include tertiary amines, aromatic amines, alkali metal hydrides, basic salts, metal alkoxides, inorganic bases and the like. The amount of the base to be used is generally about 1-100 mol, preferably about 1-10 mol, per 1 mol of compound (7).

This reaction is advantageously carried out in a solvent inert to the reaction. The solvent is not particularly limited as long as the reaction proceeds. Preferable examples thereof include halogenated hydrocarbons, aromatic amines, amides, sulfoxides, tertiary amines, ethers, nitriles, esters, hydrocarbons, mixed solvents thereof and the like.

While the reaction time varies depending on the reagent and solvent to be used, it is generally 0.1-48 hr, preferably 0.5-24 hr.

The reaction temperature is generally −20-150° C., preferably 0-100° C.

<Step 5> Compound (1a) can also be produced by reacting compound (5) with compound (9).

The amount of compound (9) to be used is generally about 1-10 mol, preferably about 1-3 mol, per 1 mol of compound (5).

This reaction may be carried out in the presence of a base. Examples of the base include tertiary amines, aromatic amines, alkali metal hydrides, basic salts, metal amides, alkyl metals, aryl metals and the like. The amount of the base to be used is generally about 1-10 mol, preferably about 1-3 mol, per 1 mol of compound (5).

This reaction is advantageously carried out in a solvent inert to the reaction. The solvent is not particularly limited as long as the reaction proceeds. Preferable examples thereof include halogenated hydrocarbons, ethers, nitriles, amides, sulfoxides, tertiary amines, aromatic amines, esters, mixed solvents thereof and the like.

While the reaction time varies depending on the reagent and solvent to be used, it is generally 0.1-48 hr, preferably 0.5-24 hr.

The reaction temperature is generally −20-150° C., preferably 0-100° C.

<Step 6> Compound (12) can be produced by reacting compound (10) with compound (11).

The amount of compound (11) to be used is generally about 0.5-10 mol, preferably about 1-3 mol, per 1 mol of compound (10).

This reaction is generally carried out in the presence of a base. Examples of the base include tertiary amines, aromatic amines, basic salts, alkali metal hydrides, metal alkoxides, metal amides, alkyl metals, aryl metals and the like. The amount of the base to be used is generally about 1-10 mol, preferably about 1-3 mol, per 1 mol of compound (10).

This reaction is advantageously carried out in a solvent inert to the reaction. The solvent is not particularly limited as long as the reaction proceeds. Preferable examples thereof include amides, sulfoxides, ethers, nitriles, hydrocarbons, mixed solvents thereof and the like.

While the reaction time varies depending on the reagent and solvent to be used, it is generally 0.1-48 hr, preferably 0.5-24 hr.

The reaction temperature is generally 0-200° C., preferably 20-150° C.

<Step 7> Compound (15) can be produced by reacting compound (12) with compound (13).

The amount of compound (13) to be used is generally about 1-10 mol, preferably about 1-3 mol, per 1 mol of compound (12).

This reaction is generally carried out in the presence of a base. Examples of the base include tertiary amines, basic salts, alkali metal hydrides, metal alkoxides, metal amides, alkyl metals, aryl metals and the like. The amount of the base to be used is generally about 1-10 mol, preferably about 1-3 mol, per 1 mol of compound (13).

This reaction is advantageously carried out in a solvent inert to the reaction. The solvent is not particularly limited as long as the reaction proceeds. Preferable examples thereof include sulfoxides, amides, tertiary amines, aromatic amines, alcohols, ethers, mixed solvents thereof and the like.

While the reaction time varies depending on the reagent and solvent to be used, it is generally 0.1-48 hr, preferably 0.5-24 hr.

The reaction temperature is generally 0-300° C., preferably 50-200° C.

<Step 8> Compound (15) can also be produced by reacting compound (5) with compound (14).

The amount of compound (14) to be used is generally about 1-10 mol, preferably about 1-3 mol, per 1 mol of compound (5).

This reaction is generally carried out in the presence of a base. Examples of the base include metal amides, alkyl metals, aryl metals, alkali metal hydrides, metal alkoxides, inorganic bases, basic salts, tertiary amines, aromatic amines and the like. The amount of the base to be used is generally 1-10 mol, preferably 1-3 mol, per 1 mol of compound (5).

This reaction is advantageously carried out in a solvent inert to the reaction. The solvent is not particularly limited as long as the reaction proceeds. Preferable examples thereof include amides, sulfoxides, ethers, mixed solvents thereof and the like.

While the reaction time varies depending on the reagent and solvent to be used, it is generally 0.1-48 hr, preferably 0.5-24 hr.

The reaction temperature is generally −100-200° C., preferably −80-150° C.

<Step 9> Compound (16) can be produced by reacting compound (15) with compound (6).

This reaction is carried out in the same manner as in Step 3.

<Step 10> Compound (1b) can be produced by reacting compound (16) with compound (8).

This reaction is carried out in the same manner as in Step 4.

<Step 11> Compound (1b) can also be produced by reacting compound (15) with compound (9).

This reaction is carried out in the same manner as in Step 5.

<Step 12> Compound (1a) can also be produced by subjecting compound (1b) wherein R is an amino-protecting group to a deprotection reaction.

The removal of the protecting group of compound (1b) can be carried out according to a method known per se, for example, the method described in Greene's Protective Groups in Organic Synthesis, 4th Edition, Wiley-Interscience, Theodora W. Greene, Peter G. M. Wuts or the like, or a method analogous thereto. For the removal of the protecting group, for example, a method using an acid, base or the like, a hydrogenation reaction or the like are employed.

Compound (5) in Reaction Scheme 1 (compound (5a) in the following Reaction Scheme 2 or compound (5) in Reaction Scheme 3) can be produced, for example, according to the method described in Reaction Scheme 2 or Reaction Scheme 3 or a method analogous thereto.

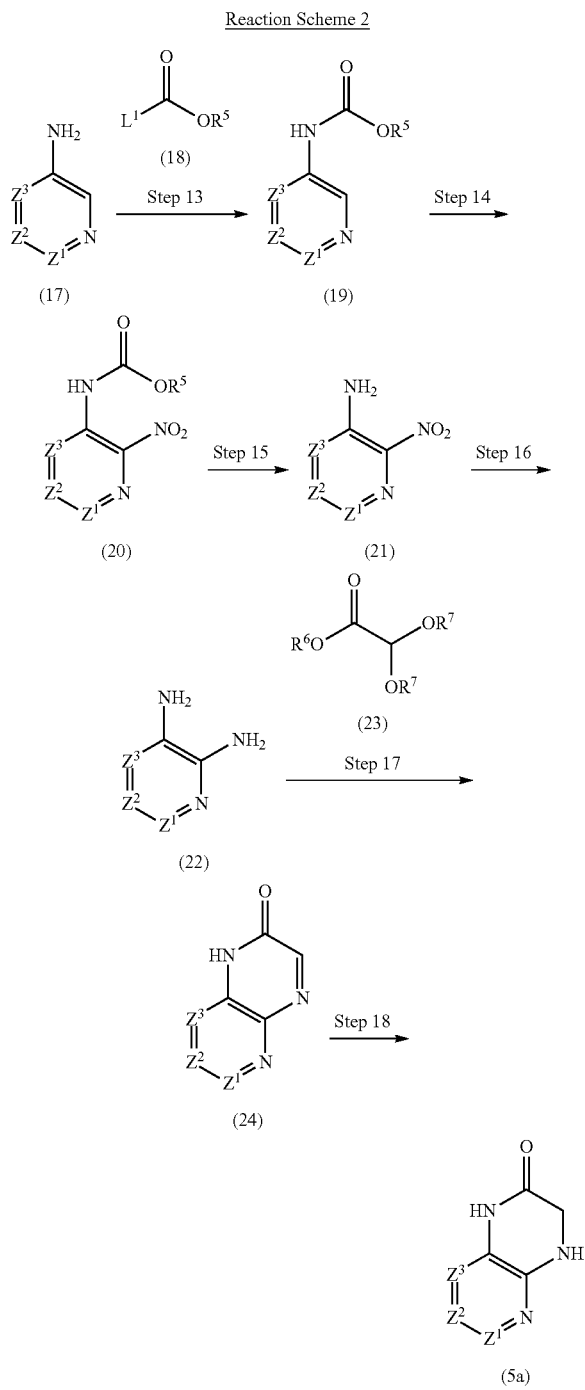

wherein $R^5$ is an optionally substituted $C_{1-6}$ alkyl group, $R^6$ and $R^7$ are each a hydrogen atom or an optionally substituted $C_{1-6}$ alkyl group, and the other symbols are as defined above.

Compounds (17), (18) and (23) may be commercially available, or can also be produced according to a method known per se or a method analogous thereto.

<Step 13> Compound (19) can be produced by reacting compound (17) with compound (18).

The amount of compound (18) to be used is generally about 1-10 mol, preferably about 1-3 mol, per 1 mol of compound (17).

This reaction is generally carried out in the presence of a base. Examples of the base include tertiary amines, aromatic amines, alkali metal hydrides, basic salts, metal alkoxides, inorganic bases and the like. The amount of the base to be used is generally about 1-10 mol, preferably about 1-3 mol, per 1 mol of compound (17).

This reaction is advantageously carried out in a solvent inert to the reaction. The solvent is not particularly limited as long as the reaction proceeds. Preferable examples thereof include aromatic amines, halogenated hydrocarbons, amides, sulfoxides, tertiary amines, ethers, nitriles, esters, hydrocarbons, mixed solvents thereof and the like.

While the reaction time varies depending on the reagent and solvent to be used, it is generally 0.1-48 hr, preferably 0.5-24 hr.

The reaction temperature is generally −20-150° C., preferably 0-100° C.

<Step 14> Compound (20) can be produced by reacting compound (19) with a nitrating reagent.

Examples of the nitrating reagent include metal nitrates such as sodium nitrate, potassium nitrate and the like, acetyl nitrate, dinitrogen pentoxide, nitronium salts, fuming nitric acid, nitric acid, mixed acids (a mixture of sulfuric acid and fuming nitric acid or nitric acid), and mixtures thereof.

The amount of the nitrating reagent to be used is generally about 0.8-100 mol, preferably about 1.0-20 mol, per 1 mol of compound (19). When fuming nitric acid, nitric acid, a mixed acid or the like is used as a nitrating reagent, it may be used in an excess amount as a reaction solvent.

This reaction is advantageously carried out in a solvent inert to the reaction. The solvent is not particularly limited as long as the reaction proceeds. Preferable examples thereof include alcohols, ethers, hydrocarbons, amides, halogenated hydrocarbons, nitriles, sulfoxides, organic acids, mineral acids, mixed solvents thereof and the like.

While the reaction time varies depending on the reagent and solvent to be used, it is generally 1-120 hr, preferably 1-96 hr.

The reaction temperature is −20-150° C., preferably 0-80° C.

<Step 15> Compound (21) can be produced by subjecting compound (20) to a deprotection reaction.

The removal of the protecting group of compound (20) can be carried out according to a method known per se, for example, the method described in Greene's Protective Groups in Organic Synthesis, 4$^{th}$ Edition, Wiley-Interscience, Theodora W. Greene, Peter G. M. Wuts or the like, or a method analogous thereto, for example, a method using an acid or base, hydrogenation reaction or the like.

<Step 16> Compound (22) can be produced from compound (21).

The conversion of the nitro group to an amino group can be carried out according to a method known per se, for example, the method described in Reductions in Organic Chemistry, Second Edition, The American Chemical Society, 1996 or a method analogous thereto, for example, a hydrogenation reaction, a reaction using a metal or metal salt, or the like.

This reaction is advantageously carried out in a solvent inert to the reaction. The solvent is not particularly limited as long as the reaction proceeds. Preferable examples thereof include alcohols, ethers, amides, esters, organic acids, mineral acids, water, mixed solvents thereof and the like.

While the reaction time varies depending on the reagent and solvent to be used, it is generally 0.1-48 hr, preferably 0.5-24 hr.

The reaction temperature is generally 0-200° C., preferably 20-100° C.

<Step 17> Compound (24) can be produced by reacting compound (22) with compound (23).

The amount of compound (23) to be used is generally about 1-10 mol, preferably about 1-5 mol, per 1 mol of compound (22).

This reaction is advantageously carried out in a solvent inert to the reaction. The solvent is not particularly limited as long as the reaction proceeds. Preferable examples thereof include water, alcohols, ethers, esters, amides, nitriles, aromatic amines, organic acids, mineral acids, halogenated hydrocarbons, mixed solvents thereof and the like.

While the reaction time varies depending on the reagent and solvent to be used, it is generally 0.1-48 hr, preferably 0.5-24 hr.

The reaction temperature is generally −20-150° C., preferably 0-100° C.

<Step 18> Compound (5a) can be produced by subjecting compound (24) to a reduction reaction.

Examples of the reducing agent include alkali metal hydrides, metal hydrogen complex compounds, borane complexes and the like. The amount of the reducing agent to be used is generally about 1-100 mol, preferably about 1-10 mol, per 1 mol of compound (24).

Alternatively, this reduction reaction can also be carried out by a hydrogenation reaction. In this case, for example, a catalyst such as palladium on carbon, palladium hydroxide on carbon, palladium black, platinum on carbon, platinum dioxide, Raney nickel, Raney cobalt and the like are can be used. The amount of the catalyst to be used is generally about 5-1000 wt %, preferably about 10-300 wt %, per 1 mol of compound (24).

The hydrogenation reaction can also be carried out by using various hydrogen sources instead of gaseous hydrogen. Examples of the hydrogen source include formic acid, ammonium formate, triethylammonium formate, sodium phosphinate, hydrazine and the like. The amount of the hydrogen source to be used is generally about 1-10 mol, preferably about 1-5 mol, per 1 mol of compound (24).

This reaction is advantageously carried out in a solvent inert to the reaction. The solvent is not particularly limited as long as the reaction proceeds. Preferable examples thereof include halogenated hydrocarbons, alcohols, ethers, esters, aromatic hydrocarbons, saturated hydrocarbons, amides, organic acids, water, mixed solvents thereof and the like.

While the reaction time varies depending on the reagent and solvent to be used, it is generally 0.1-100 hr, preferably 0.5-50 hr.

The reaction temperature is generally −20-100° C., preferably 0-80° C.

Reaction Scheme 3

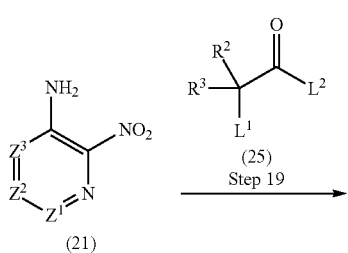

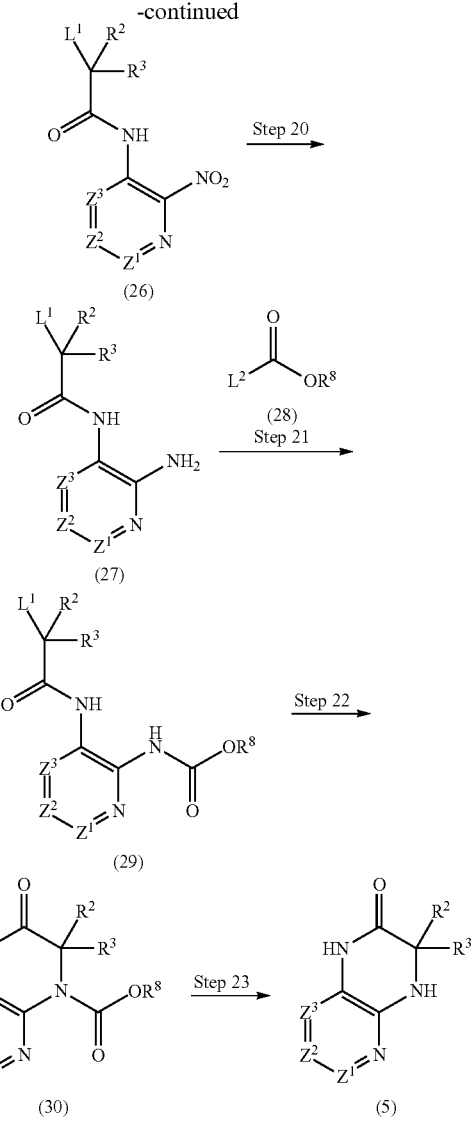

wherein $R^8$ is an optionally substituted $C_{1-6}$ alkyl group or an optionally substituted benzyl group, and the other symbols are as defined above.

Compounds (25) and (28) may be commercially available, or can also be produced according to a method known per se or a method analogous thereto.

<Step 19> Compound (26) can be produced by reacting compound (21) with compound (25).

The amount of compound (25) to be used is generally about 1-10 mol, preferably about 1-5 mol, per 1 mol of compound (21).

This reaction may be carried out in the presence of a base to promote the reaction. Examples of the base include tertiary amines, aromatic amines, inorganic bases, basic salts and the like. The amount of the base to be used is generally about 1-10 mol, preferably about 1-5 mol, per 1 mol of compound (25).

This reaction is advantageously carried out in a solvent inert to the reaction. The solvent is not particularly limited as long as the reaction proceeds. Preferable examples thereof include aromatic amines, amides, alcohols, ethers, halogenated hydrocarbons, esters, nitriles, sulfoxide, hydrocarbons, mixed solvents thereof and the like.

The reaction time is generally 0.1-48 hr, preferably 0.5-24 hr.

The reaction temperature is generally −30-120° C., preferably −10-100° C.

<Step 20> Compound (27) can be produced from compound (26).

This reaction is carried out in the same manner as in Step 16.

<Step 21> Compound (29) can be produced by reacting compound (27) with compound (28).

This reaction is carried out in the same manner as in Step 13.

<Step 22> Compound (30) can be produced by reacting compound (29) in the presence of a base.

Examples of the base include basic salts, alkali metal hydrides, metal alkoxides, metal amides, alkyl metals, aryl metals, aromatic amines, tertiary amines and the like. The amount of the base to be used is generally about 1-10 mol, preferably about 1-5 mol, per 1 mol of compound (29).

This reaction is advantageously carried out in a solvent inert to the reaction. The solvent is not particularly limited as long as the reaction proceeds. Preferable examples thereof include ethers, aromatic hydrocarbons, saturated hydrocarbons, amides, halogenated hydrocarbons, nitriles, ketones, esters, sulfoxides, aromatic amines, tertiary amines, mixed solvents thereof and the like.

The reaction time is generally 0.1-48 hr, preferably 0.3-24 hr.

The reaction temperature is generally −70-250° C., preferably −20-100° C.

<Step 23> Compound (5) can be produced from compound (30).

This reaction is carried out in the same manner as in Step 15.

Among compound (8) and compound (9) in Reaction Scheme 1, compounds (8a) and (9a) can be produced, for example, according to the method shown in Reaction Scheme 4 or a method analogous thereto.

Reaction Scheme 4

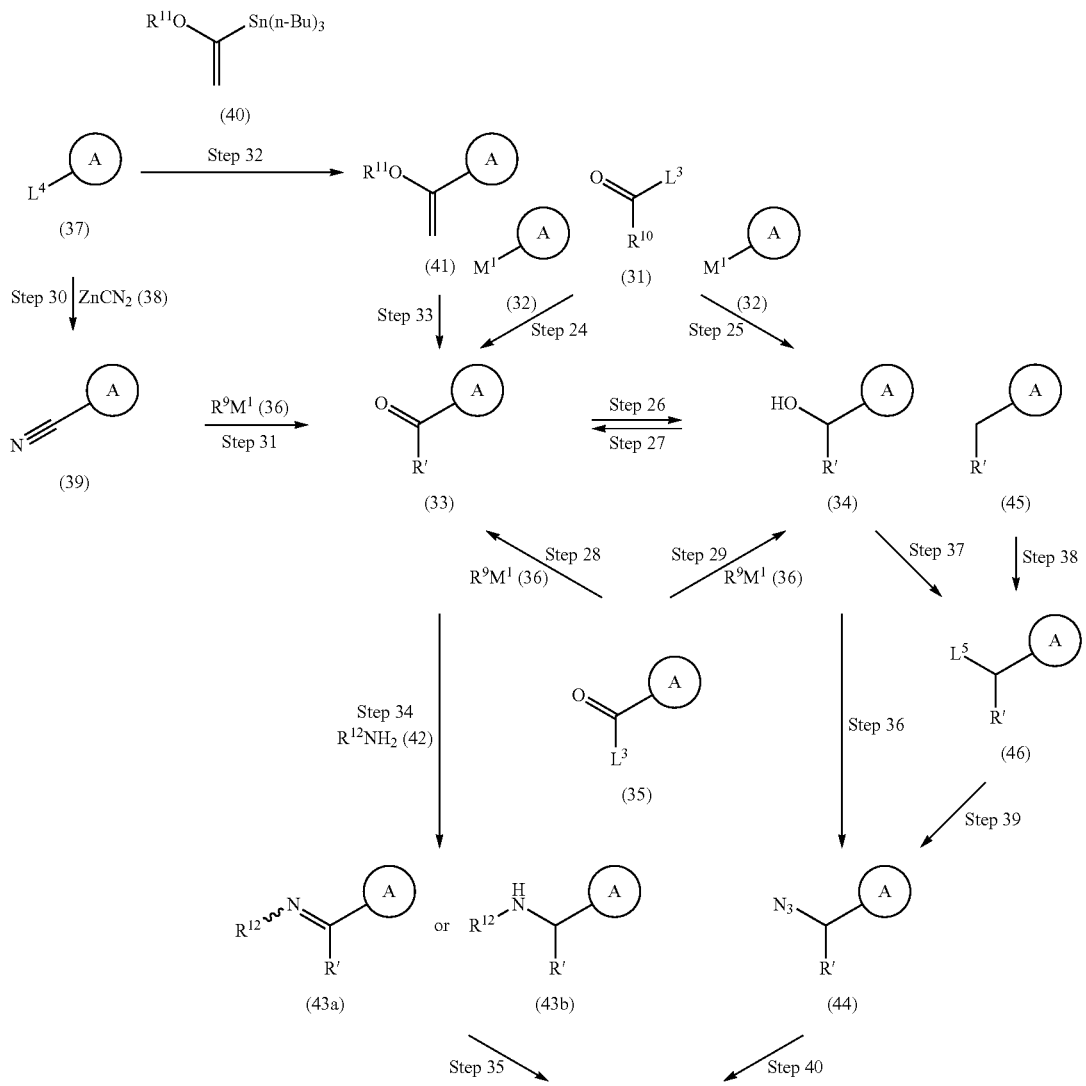

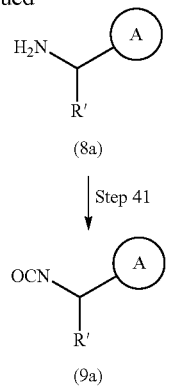

(8a)

Step 41

(9a)

wherein $R^9$ is a hydrogen atom, an optionally substituted $C_{1-6}$ alkyl group, an optionally substituted $C_{2-6}$ alkenyl group or an optionally substituted $C_{2-6}$ alkynyl group, $R^{10}$ is an optionally substituted $C_{1-6}$ alkyl group, an optionally substituted $C_{2-6}$ alkenyl group, an optionally substituted $C_{2-6}$ alkynyl group or an optionally esterified carboxyl group, $R^{11}$ is an optionally substituted $C_{1-6}$ alkyl group, $R^{12}$ is a hydroxy group, an optionally substituted $C_{1-3}$ alkoxy group or an optionally substituted benzyl group, R' is a substituent defined by $R^9$ and $R^{10}$, $L^3$ is a hydrogen atom or a leaving group, $L^4$ and $L^5$ are each a leaving group, $R^9M^1$ or ring $AM^1$ is an organic metal reagent for introducing a substituent defined by $R^9$ or ring A, and the other symbols are as defined above.

Examples of the leaving group for $L^3$ include an N,O-dimethylhydroxylamino group, an optionally substituted $C_{1-6}$ alkoxy group, a halogen atom and the like.

Examples of the leaving group for $L^4$ include a halogen atom, an optionally halogenated $C_{1-6}$ alkylsulfonyloxy group and the like.

Examples of the leaving group for $L^5$ include a halogen atom, an optionally halogenated $C_{1-6}$ alkylsulfonyloxy group, a $C_{6-10}$ arylsulfonyloxy group optionally substituted by $C_{1-6}$, and the like.

Compounds (31), (32), (35), (36), (37), (38), (39), (42) and (45) may be commercially available, or can be produced according to a method known per se or a method analogous thereto.

<Step 24> Compound (33) wherein R' is $R^{10}$ can be produced by reacting compound (31) wherein $L^3$ is a leaving group with compound (32).

The amount of compound (32) to be used is generally about 0.5-10 mol, preferably about 1-5 mol, per 1 mol of compound (31).

This reaction is advantageously carried out in a solvent inert to the reaction. The solvent is not particularly limited as long as the reaction proceeds. Preferable examples thereof include ethers, hydrocarbons, mixed solvents thereof and the like.

While the reaction time varies depending on the reagent and solvent to be used, it is generally 0.1-48 hr, preferably 0.5-24 hr.

The reaction temperature is generally −78-150° C., preferably −30-80° C.

<Step 25> Compound (34) wherein R' is $R^{10}$ can be produced by reacting compound (31) wherein $L^3$ is a hydrogen atom with compound (32).

The amount of compound (32) to be used is generally about 0.5-10 mol, preferably about 1-5 mol, per 1 mol of compound (31).

This reaction is advantageously carried out in a solvent inert to the reaction. The solvent is not particularly limited as long as the reaction proceeds. Preferable examples thereof include ethers, hydrocarbons, mixed solvents thereof and the like.

While the reaction time varies depending on the reagent and solvent to be used, it is generally 0.1-48 hr, preferably 0.5-24 hr.

The reaction temperature is generally −78-150° C., preferably −30-80° C.

<Step 26> Compound (34) can be produced by subjecting compound (33) to a reduction reaction.

Examples of the reducing agent include alkali metal hydrides, metal hydrogen complex compounds, borane complexes and the like. The amount of the reducing agent to be used is generally about 0.25-50 mol, preferably about 0.5-5 mol, per 1 mol of compound (33).

This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, water, mixed solvents thereof and the like.

While the reaction time varies depending on the reagent and solvent to be used, it is generally 0.1-100 hr, preferably 0.5-50 hr.

The reaction temperature is generally −78-100° C., preferably −30-80° C.

<Step 27> Compound (33) can be produced by subjecting compound (34) to an oxidation reaction.

This reaction is carried out using an oxidizing agent according to a conventional method.

Examples of the oxidizing agent include metal salts or metal oxides such as chromium(VI) oxide, pyridinium chlorochromate, manganese dioxide and the like, and organic oxidizing agents such as o-iodoxybenzoic acid (IBX), 1,1,1-triacetoxy-1,1-dihydro-1,2-benziodoxol-3(1H)-one (Dess-Martin periodinane) and the like. The amount of the oxidizing agent to be used is generally about 1-100 mol, preferably about 1-50 mol, per 1 mol of compound (34).

This reaction is advantageously carried out in a solvent inert to the reaction. The solvent is not particularly limited as long as the reaction proceeds. Preferable examples thereof include halogenated hydrocarbons, aromatic hydrocarbons, saturated hydrocarbons, nitriles, esters, ethers, sulfoxides, water, mixed solvents thereof and the like.

While the reaction time varies depending on the reagent and solvent to be used, it is generally 0.1-48 hr, preferably 0.1-24 hr.

The reaction temperature is generally −78-150° C., preferably −78-100° C.

<Step 28> Compound (33) wherein R' is $R^9$ can be produced by reacting compound (35) wherein $L^3$ is a leaving group with compound (36).

This reaction is carried out in the same manner as in Step 24.

<Step 29> compound (34) wherein R' is $R^9$ can be produced by reacting compound (35) wherein $L^3$ is a hydrogen atom with compound (36).

This reaction is carried out in the same manner as in Step 24.

<Step 30> Compound (39) can be produced by reacting compound (37) with zinc cyanide (38) in the presence of a palladium catalyst.

The amount of the zinc cyanide to be used is generally about 0.5-10 mol, preferably about 1-5 mol, per 1 mol of compound (37).

Examples of the palladium catalyst include palladium(II) acetate, tris(dibenzylideneacetone)dipalladium(0), tetrakis(triphenylphosphine)palladium(0), di-tert-butylphosphine palladium(0), bis(triphenylphosphine)palladium(II) chloride, [1,1'-bis(diphenylphosphino)ferrocene]palladium(II) chloride and the like. The amount of the palladium catalyst to be used is generally about 0.005-1 mol, preferably about 0.01-1 mol, per 1 mol of compound (37).

This reaction is generally under an inert gas (e.g., argon gas or nitrogen gas) atmosphere or stream in the presence of a phosphine ligand. Examples of the phosphine ligand include tert-butylphosphine, triphenylphosphine, 1,1'-bis(diphenylphosphino)ferrocene and the like. The amount of the phosphine ligand to be used is generally about 1-10 mol, preferably about 1-5 mol, per 1 mol of the palladium catalyst. Where necessary, a zinc metal may be added to the reaction system. The amount of the zinc metal to be used is generally about 0.005-10 mol, preferably about 0.01-5 mol, per 1 mol of compound (37).

This reaction is advantageously carried out in a solvent inert to the reaction. The solvent is not particularly limited as long as the reaction proceeds. Preferable examples thereof include amides, ethers, hydrocarbons, mixed solvents thereof and the like.

While the reaction time varies depending on the reagent and solvent to be used, it is generally 0.5-100 hr, preferably 1-48 hr.

The reaction temperature is generally 0-200° C., preferably 20-150° C.

<Step 31> Compound (33) wherein R' is $R^9$ can be produced by reacting (39) with compound (36).

This reaction is carried out in the same manner as in Step 24.

<Step 32> Compound (41) can be produced by reacting compound (37) with an organotin reagent (40) in the presence of a palladium catalyst.

Examples of the palladium catalyst include palladium(II) acetate, tris(dibenzylideneacetone)dipalladium(0), tetrakis(triphenylphosphine)palladium(0), di-tert-butylphosphine palladium(0), bis(triphenylphosphine)palladium(II) chloride, [1,1'-bis(diphenylphosphino)ferrocene]palladium(II) chloride and the like. The amount of the palladium catalyst to be used is generally about 0.005-1 mol, preferably about 0.01-1 mol, per 1 mol of compound (37).

The amount of the organotin reagent (40) to be used is generally about 1-10 mol, preferably about 1-5 mol, per 1 mol of compound (37).

This reaction is generally under an inert gas (e.g., argon gas or nitrogen gas) atmosphere or stream in the presence of a phosphine ligand. Examples of the phosphine ligand include tert-butylphosphine, triphenylphosphine, 1,1'-bis(diphenylphosphino)ferrocene and the like. The amount of the phosphine ligand to be used is generally about 1-10 mol, preferably about 1-5 mol, per 1 mol of the palladium catalyst.

This reaction is advantageously carried out in a solvent inert to the reaction. The solvent is not particularly limited as long as the reaction proceeds. Preferable examples thereof include hydrocarbons, amides, ethers, sulfoxides, nitriles, water, mixed solvents thereof and the like.

While the reaction time varies depending on the reagent and solvent to be used, it is generally 0.5-100 hr, preferably 1-48 hr.

The reaction temperature is generally 0-200° C., preferably 20-150° C.

<Step 33> Compound (33) wherein R' is a methyl group can be produced by subjecting compound (41) to an acid hydrolysis reaction.

Examples of the acid include mineral acids, organic acids and the like. The amount of the acid to be used is generally about 1-100 mol, preferably about 1-10 mol, per 1 mol of compound (41).

This reaction is advantageously carried out in a solvent inert to the reaction. The solvent is not particularly limited as long as the reaction proceeds. Preferable examples thereof include hydrocarbons, alcohols, ethers, nitriles, water, mixed solvents thereof and the like.

While the reaction time varies depending on the reagent and solvent to be used, it is generally 0.1-48 hr, preferably 0.5-24 hr.

The reaction temperature is generally 0-150° C., preferably 20-100° C.

<Step 34> Compound (43a) or compound (43b) can be produced by reacting compound (33) with compound (42).

(i) Compound (43a) can be produced by subjecting compound (33) to a dehydration and condensation reaction with compound (42).

The amount of compound (42) to be used is generally about 1-10 mol, preferably about 1-5 mol, per 1 mol of compound (33).

When compound (42) is in the form of a salt, this reaction is generally carried out in the presence of a base. Examples of the base include tertiary amines, aromatic amines, basic salts, inorganic bases, alkali metal hydrides, metal alkoxides and the like. The amount of the base to be used is generally about 1-10 mol, preferably about 1-5 mol, per 1 mol of compound (42).

This reaction can also be promoted by adding a dehydrating agent such as molecular sieves and the like, p-toluenesulfonic acid, zinc chloride, phosphoryl chloride, boron trifluoride, titanium tetrachloride, acetic acid, trifluoroacetic acid or the like to the reaction system, by removing water generated in the reaction system using Dean-Stark and the like, or by a combination thereof.

This reaction is advantageously carried out in a solvent inert to the reaction. The solvent is not particularly limited as long as the reaction proceeds. Preferable examples thereof include alcohols, ethers, hydrocarbons, esters, mixed solvents thereof and the like.

While the reaction time varies depending on the reagent and solvent to be used, it is generally 0.1-48 hr, preferably 0.5-24 hr.

The reaction temperature is generally 0-150° C., preferably 20-100° C.

(ii) Compound (43b) can be produced by subjecting compound (33) to a reductive amination reaction with compound (42) (e.g., described in 4th ed., Jikken Kagaku Koza, vol. 20, pages 282-284 and 366-368 (Japan Chemical Society); J. Am. Chem. Soc., vol. 93, pages 2897-2904, 1971; Synthesis, page 135, 1975, or the like).

In this reaction, compound (43b) is produced by subjecting the imine compound, which is produced by the dehydration reaction of compound (33) with compound (42), to a reduction reaction.

The amount of compound (42) to be used is generally about 1-10 mol, preferably about 1-3 mol, per 1 mol of compound (33).

The dehydration reaction can also be promoted by adding a dehydrating agent such as molecular sieves and the like, p-toluenesulfonic acid, zinc chloride, phosphoryl chloride, boron trifluoride, titanium tetrachloride, acetic acid, trifluoroacetic acid or the like to the reaction system, by removing water generated in the reaction system using Dean-Stark and the like, or by a combination thereof.

The reduction reaction is generally carried out using a reducing agent according to a conventional method. Examples of the reducing agent include metal hydrides such as aluminium hydride, diisobutylaluminium hydride, tributyltin hydride and the like, metal hydrogen complex compounds such as sodium cyanoborohydride, sodium triacetoxyborohydride, sodium borohydride, lithium aluminium hydride and the like, borane complexes such as borane tetrahydrofuran complex, borane dimethyl sulfide complex, picoline-borane complex and the like, alkyl boranes such as thexylborane, disiamyl borane and the like, and the like.

The amount of the reducing agent to be used is generally about 0.25-10 mol, preferably about 0.5-5 mol, per 1 mol of compound (33).

This reaction is advantageously carried out in a solvent inert to the reaction. The solvent is not particularly limited as long as the reaction proceeds. Preferable examples thereof include halogenated hydrocarbons, alcohols, ethers, nitriles, esters, hydrocarbons, amides, organic acids, mixed solvents thereof and the like.

While the reaction time varies depending on the reagent and solvent to be used, it is generally 0.1-100 hr, preferably 0.5-24 hr.

The reaction temperature is generally −20-200° C., preferably 0-100° C.

<Step 35> Compound (8a) can be produced from compound (43a) or compound (43b).

(i) This reaction is carried out, for example, using a catalyst such as palladium-carbon, palladium hydroxide, palladium black, platinum dioxide, Raney nickel, Raney cobalt and the like. The amount of the catalyst to be used is generally about 1-1000 wt %, preferably about 5-300 wt %, relative to compound (43a) or compound (43b).

This reaction is also carried out using various hydrogen sources instead of gaseous hydrogen. Examples of the hydrogen source include formic acid, ammonium formate, triethylammonium formate, sodium phosphinate, hydrazine and the like. The amount of the hydrogen source to be used is generally about 1-10 mol, preferably about 1-5 mol, per 1 mol of compound (43a) or compound (43b).

This reaction is advantageously carried out in a solvent inert to the reaction. The solvent is not particularly limited as long as the reaction proceeds. Preferable examples thereof include halogenated hydrocarbons, alcohols, ethers, esters, organic acids, amides, mixed solvents thereof and the like.

While the reaction time varies depending on the reagent and solvent to be used, it is generally 0.1-100 hr, preferably 0.5-50 hr.

The reaction temperature is generally −20-150° C., preferably 0-100° C.

(ii) When $R^{13}$ is a hydroxy group or an optionally substituted alkoxy group, compound (8a) can be produced, for example, by subjecting compound (43a) or compound (43b) to a reduction reaction.

Examples of the reducing agent include borane complexes, metal hydrogen complex compounds and the like.

The amount of the reducing agent to be used is generally about 0.25-100 mol, preferably about 0.5-10 mol, per 1 mol of compound (43a) or compound (43b).

This reaction is advantageously carried out in a solvent inert to the reaction. The solvent is not particularly limited as long as the reaction proceeds. Preferable examples thereof include ethers, alcohols, water, mixed solvents thereof and the like.

While the reaction time varies depending on the reagent and solvent to be used, it is generally 0.1-48 hr, preferably 0.5-24 hr.

The reaction temperature is generally −50-150° C., preferably −20-100° C.

<Step 36> Compound (44) can be produced from compound (34).

(i) Compound (44) can be produced, for example, by reacting compound (34) with diphenylphosphoryl azide (DPPA) under the Mitsunobu reaction conditions (e.g., described in Synthesis, pages 1-27, 1981, Tetrahedron Lett., vol. 36, pages 6373-6374, 1995, Tetrahedron Lett., vol. 38, pages 5831-5834, 1997, or the like).

The amount of the DPPA to be used is generally about 1-10 mol, preferably about 1-5 mol, per 1 mol of compound (34).

The amount of the azodicarboxylate and phosphine to be used for this reaction is generally about 1-10 mol, preferably about 1-5 mol, per 1 mol of compound (34), respectively.

This reaction is advantageously carried out in a solvent inert to the reaction. The solvent is not particularly limited as long as the reaction proceeds. Preferable examples thereof include ethers, aromatic hydrocarbons, saturated hydrocarbons, amides, halogenated hydrocarbons, nitriles, ketones, esters, sulfoxides, mixed solvent thereof and the like.

The reaction time is generally 0.1-100 hr, preferably 0.5-48 hr.

The reaction temperature is generally −20-200° C., preferably 0-100° C.

(ii) Compound (44) can also be produced, for example, by reacting compound (34) with DPPA in the presence of 1,8-diazabicyclo[5.4.0]undec-7-ene (DBU).

The amount of the DPPA to be used is generally about 1-10 mol, preferably about 1-5 mol, per 1 mol of compound (34).

The amount of the DBU to be used is generally about 1-10 mol, preferably about 1-5 mol, per 1 mol of compound (34).

This reaction is advantageously carried out in a solvent inert to the reaction. The solvent is not particularly limited as long as the reaction proceeds. Preferable examples thereof include aromatic hydrocarbons, saturated hydrocarbons and the like, ethers, amides, esters, nitriles, mixed solvents thereof and the like.

While the reaction time varies depending on the reagent and solvent to be used, it is generally 0.1-48 hr, preferably 0.5-24 hr.

The reaction temperature is generally 0-150° C., preferably 20-100° C.

<Step 37> Compound (46) can be produced from compound (34).

This reaction is generally carried out using methanesulfonyl chloride, p-toluenesulfonyl chloride or the like, in the presence of a base, according to a conventional method.

Examples of the base include tertiary amines, aromatic amines, basic salts and the like. The amount of the base to be used is generally about 1-10 mol, preferably about 1-5 mol, per 1 mol of compound (34).

The amount of the methanesulfonyl chloride, p-toluenesulfonyl chloride or the like to be used is generally about 1-10 mol, preferably about 1-5 mol, per 1 mol of compound (34).

This reaction can also be carried out by employing the conversion reaction known per se of alcohol to halide using triphenylphosphine/carbon tetrachloride, thionyl chloride or the like.

This reaction is advantageously carried out in a solvent inert to the reaction. The solvent is not particularly limited as long as the reaction proceeds. Preferable examples thereof include ethers, aromatic amines, tertiary amines, halogenated hydrocarbons, hydrocarbons, mixed solvents thereof and the like.

While the reaction time varies depending on the reagent and solvent to be used, it is generally 0.1-48 hr, preferably 0.1-24 hr.

The reaction temperature is generally −30-100° C., preferably −10-at 60° C.

<Step 38> Compound (46) wherein $L^5$ is a halogen atom can be produced by reacting compound (45) with a halogenating agent.

Examples of the halogenating agent include N-bromosuccinimide, N-chlorosuccinimide, bromine, chlorine, thionyl chloride and the like. The amount of the halogenating agent to be used is generally about 1-50 mol, preferably about 1-10 mol, per 1 mol of compound (45).

When N-bromosuccinimide or N-chlorosuccinimide is used as a halogenating agent, this reaction is generally carried out by heating together with a radical initiator such as azobisisobutyronitrile, benzoyl peroxide or the like, by light irradiation, or by a combination thereof. The amount of the radical initiator to be used is generally about 0.001-5 mol, preferably about 0.01-1 mol, per 1 mol of compound (45).

This reaction is advantageously carried out in a solvent inert to the reaction. The solvent is not particularly limited as long as the reaction proceeds. Preferable examples thereof include halogenated hydrocarbons, aromatic hydrocarbons, saturated hydrocarbons, esters, nitriles, ethers, mixed solvents thereof and the like.

While the reaction time varies depending on the reagent and solvent to be used, it is generally 0.1-100 hr, preferably 0.5-50 hr.

The reaction temperature is generally 0-150° C., preferably 20-100° C.

<Step 39> Compound (44) can be produced by reacting compound (46) with an azidating agent.

Examples of the azidating agent include sodium azide, cesium azide, tetrabutylammonium azide and the like. The amount of the azidating agent to be used is generally about 1-50 mol, preferably about 1-10 mol, per 1 mol of compound (46).

This reaction can be promoted by adding a crown ether. Examples of the crown ether include 18-crown-6 and the like. The amount of the crown ether to be used is generally about 0.01-20 mol, preferably about 0.1-5 mol, per 1 mol of compound (46).

This reaction is advantageously carried out in a solvent inert to the reaction. The solvent is not particularly limited as long as the reaction proceeds. Preferable examples thereof include amides, nitriles, ketones, sulfoxides, esters, ethers, water, mixed solvents thereof and the like.

While the reaction time varies depending on the reagent and solvent to be used, it is generally 0.1-100 hr, preferably 0.5-50 hr.

The reaction temperature is generally 0-150° C., preferably 20-100° C.

<Step 40> Compound (8a) can be produced from compound (44).

The conversion of the azide group to an amino group can be carried out according to a method known per se, for example, the method described in Comprehensive Organic Transformations, Second Edition, Wiley-VCH, Richard C. Larock or the like, or a method analogous thereto, for example, a hydrogenation reaction, Staudinger reaction using a triphenylphosphine, or the like.

<Step 41> Compound (9a) can be produced by reacting compound (8a) with phosgene or an equivalent thereof.

Examples of the equivalent of phosgene include bis(trichloromethyl)carbonate, trichloromethyl chloroformate, 1,1'-carbonyldiimidazole and the like. The amount of the phosgene or an equivalent thereof to be used is generally about 0.1-100 mol, preferably about 0.3-10 mol, per 1 mol of compound (8a).

This reaction is generally carried out in the presence of a base. Examples of the base include tertiary amines, aromatic amines, basic salts and the like. The amount of the base to be used is generally 1-100 mol, preferably 1-10 mol, per 1 mol of compound (8a).

This reaction is advantageously carried out in a solvent inert to the reaction. The solvent is not particularly limited as long as the reaction proceeds. Preferable examples thereof include halogenated hydrocarbons, ethers, hydrocarbons, nitriles, water, mixed solvents thereof and the like.

While the reaction time varies depending on the reagent and solvent to be used, it is generally 0.1-48 hr, preferably 0.5-24 hr.

The reaction temperature is generally −50-200° C., preferably −20-150° C.

Among compound (8) in Reaction Scheme 1, compounds (8b), (8c) and (8d) in Reaction Scheme 5 can be produced, for example, according to the method shown in Reaction Scheme 5 or a method analogous thereto.

Reaction Scheme 5

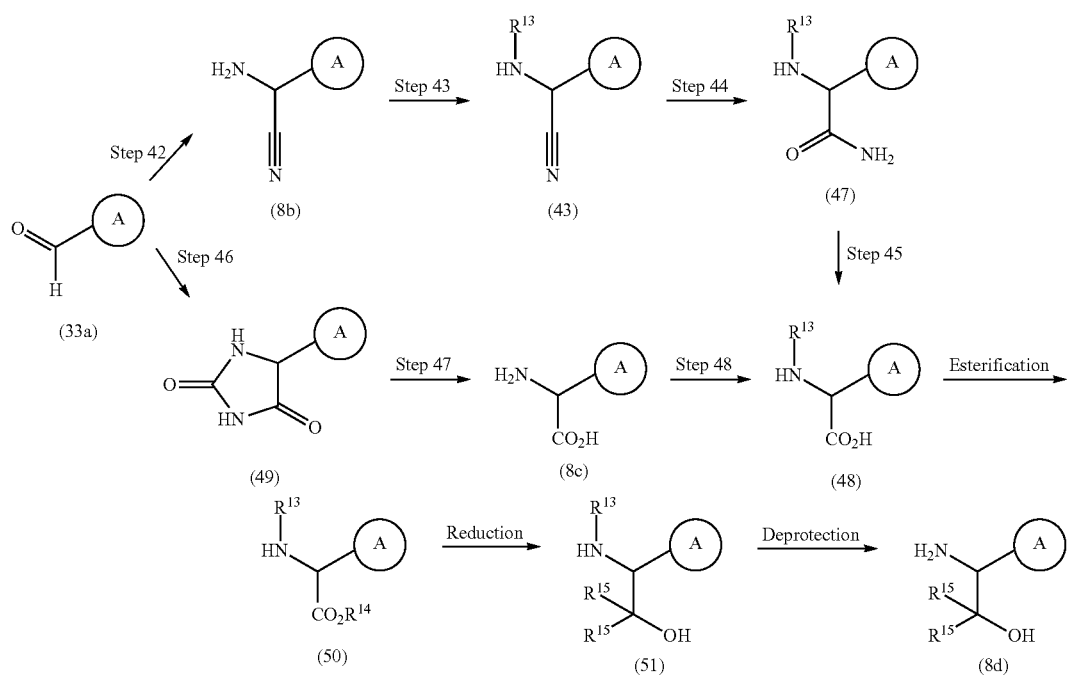

wherein $R^{13}$ is an amino-protecting group, $R^{14}$ is an optionally substituted $C_{1-6}$ alkyl group, $R^{15}$ is a hydrogen atom or an optionally substituted $C_{1-6}$ alkyl group, and the other symbols are as defined above.

Compound (33a) may be commercially available, or can be produced according to a method known per se or a method analogous thereto.

<Step 42> Compound (8b) can be produced by subjecting compound (33a) to Strecker reaction.

This reaction is generally carried out by condensing compound (33a) with ammonia or an equivalent thereof and hydrogen cyanide or an equivalent thereof to give the corresponding α-aminonitrile (8b).

Examples of the equivalent of ammonia include ammonium chloride, ammonium carbonate, benzyl amine and the like. The amount of the reagent to be used is generally about 1-50 mol, preferably about 1-10 mol, per 1 mol of compound (33a).

Examples of the equivalent of hydrogen cyanide include sodium cyanide, potassium cyanide, trimethylsilyl cyanide and the like. The amount of the reagent to be used is generally about 1-50 mol, preferably about 1-10 mol, per 1 mol of compound (33a).

This reaction may be carried out by adding a Lewis acid such as titanium(IV) tetraisopropoxide and the like. The amount of the Lewis acid to be used is generally about 0.05-50 mol, preferably about 0.1-10 mol, per 1 mol of compound (33a).

This reaction is advantageously carried out in a solvent inert to the reaction. The solvent is not particularly limited as long as the reaction proceeds. Preferable examples thereof include alcohols, halogenated hydrocarbons, ethers, hydrocarbons, nitriles, water, mixed solvents thereof and the like.

While the reaction time varies depending on the reagent and solvent to be used, it is generally 0.1-100 hr, preferably 0.5-48 hr.

The reaction temperature is generally −78-200° C., preferably −78-100° C.

<Step 43> Compound (43) can be produced by protecting the amino group of compound (8b).

The introduction of protecting group in this step can be carried out according to a method known per se, for example, the method described in Greene's Protective Groups in Organic Synthesis, 4$^{th}$ Edition, Wiley-Interscience, Theodora W. Greene, Peter G. M. Wuts or the like.

<Step 44> Compound (47) can be produced from compound (43).

This reaction can be carried out according to a method known per se, for example, the method described in Synthesis, vol. 12, pages 949-950, 1989, or a method analogous thereto.

This reaction is advantageously carried out in a solvent inert to the reaction. The solvent is not particularly limited as long as the reaction proceeds. Preferable examples thereof include sulfoxides, water, mixed solvents thereof and the like.

While the reaction time varies depending on the reagent and solvent to be used, it is generally 0.1-100 hr, preferably 0.5-24 hr.

The reaction temperature is generally −30-100° C., preferably 0-50° C.

<Step 45> Compound (48) can be produced by subjecting compound (47) to a hydrolysis reaction.

This reaction is carried out using an acid or base according to a conventional method.

Examples of the acid include mineral acids, organic acids and the like. Examples of the base include inorganic bases, basic salts and the like. The amount of the acid or base to be used is generally about 0.5-100 mol, preferably about 1-20 mol, per 1 mol of compound (47).

This reaction is advantageously carried out in a solvent inert to the reaction. The solvent is not particularly limited as long as the reaction proceeds. Preferable examples thereof include alcohols, ethers, water, mixed solvents thereof and the like.

While the reaction time varies depending on the reagent and solvent to be used, it is generally 0.1-100 hr, preferably 0.1-48 hr.

The reaction temperature is generally −10-200° C., preferably 0-150° C.

<Step 46> Compound (49) can be produced from compound (33a).

This reaction can be carried out according to a method known per se, for example, the method described in ORGANIC PREPARATIONS AND PROCEDURES INT., vol. 36, pages 391-443, 2004, or a method analogous thereto.

<Step 47> Compound (8c) can be produced by subjecting compound (49) to a hydrolysis reaction.

This reaction is carried out in the same manner as in Step 45.

<Step 48> Compound (48) can be produced by protecting the amino group of compound (8c).

This reaction is carried out in the same manner as in Step 43.

Compound (8d) can be produced, for example, from compound (48) successively according to an esterification reaction known per se, a reduction reaction known per se, and a deprotection reaction known per se of the protecting group.

Among compound (33) in Reaction Scheme 4, compound (33c) in Reaction Scheme 6 can be produced, for example, according to the method shown in Reaction Scheme 6 or a method analogous thereto.

as long as the reaction proceeds. Preferable examples thereof include organic acids, alcohols, ethers, amides, halogenated hydrocarbons, hydrocarbons, water, mixed solvents thereof and the like.

While the reaction time varies depending on the reagent and solvent to be used, it is generally 0.1-100 hr, preferably 0.1-48 hr.

The reaction temperature is generally −30-200° C., preferably 0-100° C.

<Step 50> Compound (33c) can be produced from compound (52).

(i) This reaction is carried out, for example, by reacting compound (52) with a desirable alcohol ($R^{16}OH$) in the presence of silver(I) carbonate or silver(I) oxide and boron trifluoride diethyl ether complex.

The amount of the silver(I) carbonate or silver(I) oxide to be used is generally about 1-10 mol, preferably about 1-5 mol, per 1 mol of compound (52).

The amount of the boron trifluoride diethyl ether complex to be used is generally about 1-10 mol, preferably about 1-5 mol, per 1 mol of compound (52).

This reaction is advantageously carried out in a solvent inert to the reaction. The solvent is not particularly limited as long as the reaction proceeds. Preferable examples thereof include alcohols corresponding to $R^{16}OH$, ethers, halogenated hydrocarbons, hydrocarbons, mixed solvents thereof and the like.

While the reaction time varies depending on the reagent and solvent to be used, it is generally 0.1-100 hr, preferably 0.1-48 hr.

The reaction temperature is generally −30-150° C., preferably 0-80° C.

Reaction Scheme 6 wherein $R^{16}$ is an optionally substituted $C_{1-6}$ alkyl group, and the other symbols are as defined above.

Compound (33a) and compound (33b) may be commercially available, or can be produced according to a method known per se or a method analogous thereto.

<Step 49> Compound (52) can be produced by subjecting compound (33b) to a bromination.

Examples of the brominating agent include bromine, phenyltrimethylammonium tribromide, N-bromosuccinimide and the like. The amount of the brominating agent to be used is generally about 0.5-2 mol, preferably about 0.8-1.5 mol, per 1 mol of compound (33b).

This reaction is advantageously carried out in a solvent inert to the reaction. The solvent is not particularly limited (ii) This reaction can also be carried out by reacting compound (52) with the desired alcohol ($R^{16}OH$) in the presence of a base.

Examples of the base include tertiary amines, basic salts, metal hydrogen complex compounds, metal alkoxides, metal amides, alkyl metals, aryl metals and the like. The amount of the base to be used is generally about 1-10 mol, preferably about 1-5 mol, per 1 mol of compound (52).

This reaction is advantageously carried out in a solvent inert to the reaction. The solvent is not particularly limited as long as the reaction proceeds. Preferable examples thereof include alcohols corresponding to $R^{16}OH$, ethers, amides, sulfoxides, halogenated hydrocarbons, hydrocarbons, mixed solvents thereof and the like.

While the reaction time varies depending on the reagent and solvent to be used, it is generally 0.1-48 hr, preferably 0.5-24 hr.

The reaction temperature is generally 0-150° C., preferably 20-100° C.

<Step 51> Compound (53) can be produced by subjecting compound (33a) to Wittig reaction.

This reaction is carried out, for example, by reacting compound (33a) with phosphorus ylide prepared by methyl (triphenyl)phosphonium salt and a base.

Examples of the base include metal alkoxides, alkyl metals, alkali metal hydrides, metal amides and the like. The amount of the base to be used is generally about 1-10 mol, preferably about 1-5 mol, per 1 mol of compound (33a).

The amount of the methyl(triphenyl)phosphonium salt to be used is generally about 1-10 mol, preferably about 1-5 mol, per 1 mol of compound (33a).

This reaction is advantageously carried out in a solvent inert to the reaction. The solvent is not particularly limited as long as the reaction proceeds. Preferable examples thereof include ethers, halogenated hydrocarbons, hydrocarbons, sulfoxides, mixed solvents thereof and the like.

While the reaction time varies depending on the reagent and solvent to be used, it is generally 0.1-48 hr, preferably 0.1-24 hr.

The reaction temperature is generally −78-100° C., preferably 0-100° C.

<Step 52> Compound (54) can be produced by reacting compound (53) with an oxidizing agent.

Examples of the oxidizing agent include 3-chloroperbenzoic acid, peracetic acid and the like.

The amount of the oxidizing agent to be used is generally about 1-10 mol, preferably about 1-5 mol, per 1 mol of compound (53).

This reaction is advantageously carried out in a solvent inert to the reaction. The solvent is not particularly limited as long as the reaction proceeds. Preferable examples thereof include halogenated hydrocarbons, organic acids, esters, ethers, hydrocarbons, nitriles, water, mixed solvents thereof and the like.

While the reaction time varies depending on the reagent and solvent to be used, it is generally 0.1-48 hr, preferably 0.1-24 hr.

The reaction temperature is generally −78-150° C., preferably −20-80° C.

<Step 53> Compound (55) can be produced by reacting compound (54) with the alcohol ($R^{16}OH$) in the presence of a base.

Examples of the base include metal alkoxides prepared from $R^{16}OH$, basic salts, metal hydrogen complex compounds, tertiary amines and the like. The amount of the base to be used is generally about 1-100 mol, preferably about 1-10 mol, per 1 mol of compound (54).

This reaction is advantageously carried out in a solvent inert to the reaction. The solvent is not particularly limited as long as the reaction proceeds. Preferable examples thereof include alcohols corresponding to $R^{16}OH$, amides, halogenated hydrocarbons, ethers, hydrocarbons, nitriles, water, mixed solvents thereof and the like.

While the reaction time varies depending on the reagent and solvent to be used, it is generally 0.1-48 hr, preferably 0.1-24 hr.

The reaction temperature is generally −30-150° C., preferably 0-100° C.

<Step 54> Compound (33c) can be produced by subjecting compound (55) to an oxidation reaction.

This reaction is carried out in the same manner as in Step 27.

Among compound (33) in Reaction Scheme 4, compound (33e) in Reaction Scheme 7 can be produced, for example, according to the method shown in Reaction Scheme 7 or a method analogous thereto.

Reaction Scheme 7

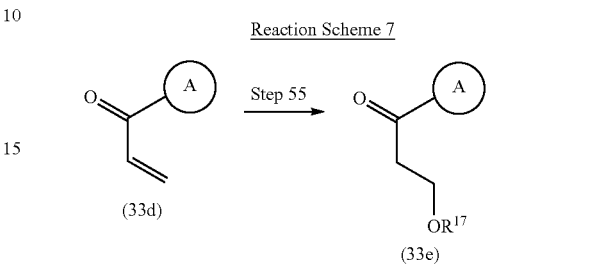

wherein $R^{17}$ is an optionally substituted $C_{1-6}$ alkyl group, and the other symbols are as defined above.

Compound (33d) may be commercially available, or can be produced according to a method known per se or a method analogous thereto.

<Step 55> Compound (33e) can be produced by reacting compound (33d) with the alcohol ($R^{17}OH$) in the presence of a palladium(II) catalyst.

Examples of the palladium(II) catalyst include bis(acetonitrile)palladium chloride, palladium chloride, palladium acetate and the like. The amount of the palladium(II) catalyst to be used is generally about 0.005-1 mol, preferably about 0.01-1 mol, per 1 mol of compound (33d).

The amount of the alcohol ($R^{17}OH$) to be used is generally about 1-10 mol, preferably about 1-3 mol, per 1 mol of compound (33d).

This reaction is advantageously carried out in a solvent inert to the reaction. The solvent is not particularly limited as long as the reaction proceeds. Preferable examples thereof include halogenated hydrocarbons, alcohols corresponding to $R^{17}OH$, ethers, hydrocarbons, mixed solvents thereof and the like.

While the reaction time varies depending on the reagent and solvent to be used, it is generally 0.5-48 hr, preferably 1-24 hr.

The reaction temperature is generally 0-100° C., preferably 20-80° C.

Compound (1) obtained in each reaction scheme can be isolated and purified by known separation and purification means such as concentration, concentration under reduced pressure, solvent extraction, crystallization, recrystallization, phase transfer, chromatography and the like. In addition, each material compound used in each reaction scheme can be isolated and purified by those similar to the above-mentioned known separation and purification means. The material compound may be used directly in the next step as the reaction mixture without isolation.

When compound (1) has isomers such as an optical isomer, a stereoisomer, a regioisomer and a rotamer and the like, such isomers and a mixture thereof are also encompassed in compound (1). For example, when compound (1) has an optical isomer, the optical isomer resolved from racemate is also encompassed in compound (I). These isomers can be obtained as single products according to synthetic methods known per se, separation methods known per se (e.g., concentration, solvent extraction, column chromatography, recrystallization etc.), optical resolutions (e.g., fractional recrystallization method, chiral column method, diastereomer method and the like).

Compound (1) may be a crystal, and the crystal form may be single or a mixture of crystal forms, both of which are encompassed in compound (1). The crystal can be produced according to a crystallization method known per se.

The compound (1) may be a solvate (e.g., hydrate) or a non-solvate (e.g., non-hydrate etc.) and both are encompassed in compound (1).

The compounds labeled with isotopes (e.g., 3H, $^{14}$C, $^{35}$S, $^{125}$I etc.) and the like are also encompassed in compound (1).

A deuterium conversion form wherein $^1$H is converted to $^2$H(D) is also encompassed in compound (1).

Compound (1) labeled or substituted with an isotope can be used as, for example, a tracer (PET tracer) used for Positron Emission Tomography (PET), and therefore, it is useful in the fields of medical diagnosis and the like.

Since the compound of the present invention has a superior PDE2A inhibitory action, shows low toxicity (e.g., phototoxicity, acute toxicity, chronic toxicity, genetic toxicity, reproductive toxicity, cardiac toxicity, drug interactions, carcinogenicity and the like, particularly phototoxicity), and is superior in stability (particularly metabolic stability), pharmacokinetics (absorption, distribution, metabolism, excretion etc.) and high solubility, it is useful as a medicament. The compound of the present invention has a PDE2A inhibitory action to mammals (e.g., mouse, rat, hamster, rabbit, cat, dog, bovine, horse, sheep, monkey, human etc.), and can be used for the prophylaxis or treatment of the following diseases and symptoms:

(1) psychotic disorder (e.g., brief psychotic disorder, shared psychotic disorder),
(2) psychosis induced by alcohol, amphetamine, cannabis, cocaine, hallucinogens, obesity, inhalants, opioids or phencyclidine,
(3) delusional disorder,
(4) anxiety disorder,
(5) movement disorder,
(6) mood disorder,
(7) major depressive disorder,
(8) a major depressive disorder superimposed on a psychotic disorder (including delusional disorder and schizophrenia),
(9) major depressive episode of the mild, moderate or severe type,
(10) manic or mixed mood episode,
(11) hypomanic mood episode,
(12) depressive episode with atypical features,
(13) depressive episode with melancholic features,
(14) depressive episode with catatonic features,
(15) mood episode with postpartum onset;
(16) post-stroke depression,
(17) dysthymic disorder,
(18) minor depressive disorder,
(19) autism;
(20) drug addiction,
(21) neurodegenerative disorder,
(22) neurodegeneration associated with cerebral trauma,
(23) neurodegeneration associated with stroke,
(24) neurodegeneration associated with cerebral infarct,
(25) neurodegeneration associated with hypoglycemia,
(26) neurodegeneration associated with epileptic seizure,
(27) neurodegeneration associated with neurotoxin poisoning,
(28) multi-system atrophy,
(29) Alzheimer's disease,
(30) dementia,
(31) multi-infarct dementia,
(32) alcoholic dementia or other drug-related dementia,
(33) dementia associated with intracranial tumors or cerebral trauma,
(34) dementia associated with Huntington's disease or Parkinson's disease,
(35) AIDS-related dementia,
(36) frontotemperal dementia,
(37) delirium,
(38) amnestic disorder,
(39) post-traumatic stress disorder,
(40) mental retardation,
(41) learning disorder (e.g., reading disorder, mathematics disorder, or a disorder of written expression),
(42) attention-deficit/hyperactivity disorder;
(43) age-related cognitive decline,
(44) premenstrual dysphoric disorder,
(45) post-psychotic depressive disorder of schizophrenia,
(46) bipolar disorder (including bipolar I disorder and bipolar II disorder),
(47) cyclothymic disorder,
(48) Parkinson's disease,
(49) Huntington's disease,
(50) paranoia,
(51) schizophrenia (e.g., paranoid schizophrenia, disorganized schizophrenia, catatonic schizophrenia, undifferentiated schizophrenia, residual schizophrenia),
(52) schizophreniform disorder,
(53) schizoaffective disorder of the delusional type or the depressive type,
(54) personality disorder of the paranoid type,
(55) personality disorder of the schizoid type,
(56) obesity,
(57) metabolic syndrome,
(58) non-insulin dependent diabetes (NIDDM),
(59) glucose intolerance,
(60) pneumonia, and/or
(61) osteoarthritis.

In particular, the compound of the present invention is useful for the prophylaxis or treatment of schizophrenia and Alzheimer's disease.

Since the compound of the present invention is superior in metabolic stability, it can be expected to have an excellent therapeutic effect on the above-mentioned diseases even in a low dose.

Since the compound of the present invention has low toxicity, a pharmaceutical composition containing the compound of the present invention (hereinafter to be referred to as the "medicament of the present invention") is obtained as, for example, tablet (including sugar-coated tablet, film-coated tablet, sublingual tablet, orally disintegrating tablet, buccal tablet and the like), pill, powder, granule, capsule (including soft capsule, microcapsule), troche, syrup, liquid, emulsion, suspension, controlled-release preparation (e.g., immediate-release preparation, sustained-release preparation, sustained-release microcapsule), aerosol, films (e.g., orally disintegrable films, oral cavity mucosa patch film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparations, pulmonary preparation (inhalant), eye drop and the like by using the compound of the present invention alone or along with a pharmacologically acceptable carrier according to a method known per se as a production method of pharmaceutical preparations (e.g., the method described in the Japanese Pharmacopoeia etc.). It can be safely administered orally or parenterally (e.g., intravenous, intramuscular, subcutaneous, intraorgan, intranasal, intradermal, instillation, intracerebral, rectal, vaginal, intraperitoneal, intratumor, tumor proximal administration, administration to a lesion and the like).

Examples of the pharmacologically acceptable carrier include various organic or inorganic carrier substances conventionally used as preparation materials, which are added as excipient, lubricant, binder or disintegrant for solid preparations; as solvent, solubilizing agent, suspending agent, isotonicity agent, buffer or soothing agent for liquid preparation, and the like. Where necessary, preparation additives such as preservative, antioxidant, colorant, sweetener, absorbent, humectant and the like can also be appropriately used in suitable amounts.

Examples of the excipient include lactose, sucrose, D-mannitol, D-sorbitol, starch, pregelatinized starch, cornstarch, dextrin, microcrystalline cellulose, low-substituted hydroxypropyl cellulose, sodium carboxymethylcellulose, gum arabic, pullulan, light anhydrous silicic acid, synthetic aluminum silicate, magnesium aluminate metasilicate and the like.

Examples of the lubricant include magnesium stearate, calcium stearate, talc, colloidal silica and the like.

Examples of the binder include pregelatinized starch, microcrystalline cellulose, sucrose, gum arabic, D-mannitol, trehalose, dextrin, pullulan, hydroxypropyl cellulose, hydroxypropyl methylcellulose, polyvinylpyrrolidone, starch, saccharose, gelatin, methylcellulose, carboxymethylcellulose, sodium carboxymethylcellulose and the like.

Examples of the disintegrant include lactose, sucrose, starch, carboxymethylcellulose, calcium carboxymethylcellulose, croscarmellose sodium, sodium carboxymethyl starch, light anhydrous silicic acid, low-substituted hydroxypropyl cellulose and the like.

Examples of the solvent include water for injection, physiological saline, Ringer's solution, alcohol, propylene glycol, polyethylene glycol, macrogol, sesame oil, corn oil, olive oil, cottonseed oil and the like.

Examples of the solubilizing agent include polyethylene glycol, propylene glycol, D-mannitol, trehalose, benzyl benzoate, ethanol, tris(hydroxymethyl)aminomethane, cholesterol, triethanolamine, sodium carbonate, sodium citrate, sodium salicylate, sodium acetate and the like.

Examples of the suspending agent include surfactants such as stearyltriethanolamine, sodium lauryl sulfate, laurylaminopropionic acid, lecithin, benzalkonium chloride, benzethonium chloride, glyceryl monostearate and the like; and hydrophilic polymers such as polyvinyl alcohol, polyvinylpyrrolidone, sodium carboxymethylcellulose, methylcellulose, hydroxymethyl cellulose, hydroxyethyl cellulose, hydroxypropyl cellulose, polysorbate, polyoxyethylene hydrogenated castor oil and the like.

Examples of the isotonicity agent include glucose, D-sorbitol, sodium chloride, glycerol, D-mannitol and the like.

Examples of the buffer include buffers such as phosphates, acetates, carbonates, citrates and the like, and the like.

Examples of the soothing agent include benzyl alcohol and the like.

Examples of the preservative include p-hydroxybenzoate, chlorobutanol, benzyl alcohol, phenethyl alcohol, dehydroacetic acid, sorbic acid and the like.

Preferred examples of the antioxidant include sulfites, ascorbic acid, α-tocopherols and the like.

Examples of the colorant include water-soluble edible tar pigments (e.g., Food Color Red Nos. 2 and 3, Food Color Yellow Nos. 4 and 5, Food Color Blue Nos. 1 and 2), water insoluble lake pigments (e.g., aluminum salts of the above-mentioned water-soluble edible tar pigment), natural pigments (e.g., beta-carotene, chlorophyll, red iron oxide) and the like.

Examples of the sweetening agent include saccharin sodium, dipotassium glycyrrhizinate, aspartame, stevia and the like.

While the content of the compound of the present invention in the medicament of the present invention varies depending on the dosage form, dose of the compound of the present invention, and the like, it is, for example, about 0.1 to 100 wt %, preferably about 0.1-95 wt %.

While the dose of the compound of the present invention varies depending on the subject of administration, administration route, target disease, symptom and the like, for example, for oral administration to a schizophrenia patient (adult, about 60 kg weight), it is generally about 0.1-about 20 mg/kg body weight, preferably about 0.2-about 10 mg/kg body weight, more preferably about 0.5-about 10 mg/kg body weight, which is desirably administered once to several times (e.g., once to 3 times) a day depending on the symptom.

The compound of the present invention can be administered as a single active substance, or can be administered in combination with other medicaments such as other drugs used in the treatment of psychotic disorder (particularly schizophrenia and bipolar disorder), obsessive-compulsive disorder, major depression, Parkinson's disease, Alzheimer's disease, cognitive disorder, memory loss and the like, (hereinafter to be abbreviated as concomitant drug).

Examples of the concomitant drug include nicotinic α7 agonists, nicotinic α7 partial agonists, nicotinic α7 positive allosteric modulators, PDE2 inhibitors, PDE4 inhibitors, PDE5 inhibitors, PDE10 inhibitors, other PDE inhibitors, calcium channel blockers, muscarinic m1 and m2 modulators, adenosine receptor modulators, ampakines, Glycine transporter 1 inhibitors, NMDA-R modulators, mGluR modulators, dopamine modulators, serotonin modulators, selective serotonin reuptake inhibitors, serotonin and norepinephrine reuptake inhibitors, norepinephrine and dopamine reuptake inhibitors, triple reuptake inhibitors, cannabinoid modulators, cholinesterase inhibitors (e.g., donepezil, rivastigmine, galantamine) and the like.

In addition, examples of the concomitant drug include, but are not limited to, other suitable schizophrenia drugs (e.g., Haloperidol, Clozapine, Olanzapine, Risperidone, Aripiprazole, Ziprasidone, Paliperidone, Quetiapine fumarate etc.), bipolar disorder drug (e.g., Lithium, Olanzapine, Aripiprazole, Valproic acid etc.), Parkinson's disease drugs (e.g., Levodopa, Bromocriptine, Pergolide, Pramipexole, Tolcapone, Procyclidine, Trihexyphenidyl, Benztropine etc.), agents used in the treatment of major depression (e.g., Amitriptyline, Imipramine, Desipramine, Nortriptyline, Paroxetine, Fluoxetine, Sertraline, Bupropion, Escitalopram, Mirtazapine, Venlafaxine, Duloxetine etc.), agents used in the treatment of Alzheimer's disease (e.g., Galantamine, Tacrine, Donepezil, Rivastigmine, Memantine, Neotropin, Selegiline, Estrogen, Clioquinol etc.), agents used in the treatment of dementia (e.g., Thioridazine, Haloperidol, Risperidone, Tacrine, Donepezil, Rivastigmine etc.), agents used in the treatment of epilepsy (e.g., Phenytoin, Phenobarbital, Carbamazepine, Valproic acid, Ethosuximide, Gabapentin, Solfeton, Felbatol etc.), agents used in the treatment of multiple sclerosis (e.g., Tolterodine, Oxybutynin, Oxycodone, Interferon beta-1b, Interferon beta-1a, Azathioprine, Methotrexate, Glatiramer etc.), agents used in the treatment of Huntington's disease (e.g., Amitriptyline, Imipramine, Desipramine, Nortriptyline, Paroxetine, Fluoxetine, Sertraline, Tetrabenazine, Haloperidol, Chlorpromazine, Thioridazine, Sulpiride, Quetiapine, Clozapine, Risperidone etc.), agents useful in the treatment of diabetes [e.g, PPAR ligands (e.g. agonists or antagonists such as Rosiglitazone, Troglitazone, Pioglitazone etc.), insulin secretagogues (e.g., sulfonylurea drugs such as Glyburide, Glimepiride, Chlopropamide, Tolbutamide, Glipizide etc., and non-sulfonyl secretagogues), α-glucosidase inhibitors (e.g., Acarbose, Miglitol, Voglibose etc), insulin sensitizers (e.g., PPAR-γ agonists (e.g., the glitazones); biguanides, PTP-1B inhibitors, DPP-IV inhibitors, 11beta-HSD inhibitors etc.), hepatic glucose output lowering compounds (e.g., glucagon antagonists and metformin (e.g., Glucophage, Glucophage XR etc.)), insulin and insulin derivatives (including both long and short acting forms and formulations of insulin)], antiobesity drugs [e.g., β-3 agonists, CB-1 agonists, neuropeptide Y5 inhibitors, Ciliary Neurotrophic Factor and derivatives (e.g., Axokine), appetite suppressants (e.g., Sibutramine), lipase inhibitors (e.g., Orlistat) etc.].

The dosage form of concomitant drugs is not particularly limited, and is acceptable as long as the compound of the present invention is combined with concomitant drugs at the time of administration. Examples of such dosage forms are as follows:

(1) Administration of a single formula obtained simultaneous formulation of the compound of the present invention with a concomitant drug,
(2) Simultaneous administration via the same administration route for two kinds of formulas obtained by independent formulations of the compound of the present invention and a concomitant drug,
(3) Administrations at different times via the same administration route for two kinds of formulas obtained by independent formulations of the compound of the present invention and a concomitant drug,
(4) Simultaneous administration via different administration routes for two kinds of formulas obtained by independent formulations of the compound of the present invention and a concomitant drug,
(5) Administrations at different times via different administration routes for two kinds of formulas obtained by independent formulations of the compound of the present invention and a concomitant drug (e.g., administration in the order of the compound of the present invention and then a concomitant drug, or administration in the reversed order).

These forms of administration are summarized below and abbreviated as a combination drug of the present invention.

When administering the combination drug of the present invention, the concomitant drug and the compound of the present invention can be administered simultaneously. Alternatively, the compound of the present invention can be administered after a concomitant drug is administered, or a concomitant drug can be administered after the compound of the present invention is administered. When administering at different times, the time difference depends upon the active ingredients to be administered, drug forms and methods of administration.

For example, when the concomitant drug or a pharmaceutical composition thereof is administered first, the compound of the present invention or a pharmaceutical composition thereof can be administered within 1 min. to 3 days, preferably within 10 min to 1 day and more preferably within 15 min to 1 hour after the concomitant drug or a pharmaceutical composition thereof is administered. When the compound of the present invention or a pharmaceutical composition thereof is administered first, the concomitant drug or a pharmaceutical composition thereof can be administered within 1 min to 1 day, preferably within 10 min to 6 hours and more preferably within 15 min to 1 hour after the compound of the present invention or a pharmaceutical composition thereof is administered.

If there are no problems with side effects of the concomitant drugs, any dosages can be set. A dosage as a concomitant drug varies depending on dosages, administration subjects, administration routes, target diseases, symptoms, etc. For example, in the case of oral administration in patients with schizophrenia (adults, body weight of approximately 60 kg), a dosage range is generally about 0.1 to 20 mg/kg body weight, preferably from about 0.2 to 10 mg/kg body weight and more preferably from about 0.5 to 10 mg/kg body weight. It is preferable that this dosage is administered once daily to several times daily (e.g., once to 3 times).

If the compound of the present invention is used in combination with a concomitant drug, the respective dosages can be reduced within a safe range with consideration of the opposite effects of the respective drugs.

The combination drug of the present invention exhibits low toxicity. For example, the compound of the present invention or(and) the concomitant drug can be combined with a pharmaceutically acceptable carrier according to the known method to prepare a pharmaceutical composition such as tablets (including sugar-coated tablets and film-coated tablets), powder agents, granular agents, capsules (including soft capsules), liquids, injection solutions, suppositories, sustained-release agents, etc. These compositions can be administered safely orally or non-orally (e.g., including local, rectal, venous routes etc.).

The pharmaceutically acceptable carriers that can be used for manufacturing the combination drug of the present invention can be the same as those used in the medicament of the present invention as mentioned above.

A mixing ratio between the compound of the present invention and the concomitant drug in the combination drug of the present invention can be selected appropriately based on the administration subjects, administration routes, diseases and the like.

The concomitant drug in the combination drug of the present invention can be combined at an appropriate proportion if two or more drugs are combined.

A dosage of the concomitant drug can be selected appropriately based on the dosages used clinically. In addition, a mixing ratio between the compound of the present invention and the concomitant drug can be selected appropriately based on the administration subjects, administration routes, target diseases, symptoms, combinations, etc. For example, if the administration subject is humans, a concomitant drug may be used in an amount ranging from about 0.01 to 100 parts by weight relative to 1 part by weight of the compound of the present invention.

For example, the content of the compound of the present invention in the combination drug of the present invention varies with the form of formulations. Generally, it is present in a range from about 0.01 to 99.9 wt %, preferably from about 0.1 to about 50 wt % and more preferably from about 0.5 to about 20 wt % relative to the entire formula.

The content of the concomitant drug in the combination drug of the present invention varies with the form of formulations. Generally it is present in a range from about 0.01 to 99.9 wt %, preferably from about 0.1 to about 50 wt % and more preferably from about 0.5 to about 20 wt % relative to the entire formula.

The content of an additive such as carriers in the combination drug of the present invention varies with the form of formulations. Generally it is present in a range from about 1 to 99.99 wt % and preferably from about 10 to about 90 wt % relative to the entire formula.

When the compound of the present invention and a concomitant drug are formulated independently, the same contents can be applied.

Since the dosages may fluctuate under various conditions as mentioned above, a dosage less than the dosages may be sufficient or it may be necessary to administer at a dosage exceeding the range.

EXAMPLE

The present invention is explained in detail in the following by referring to Examples, Formulation Examples and Experimental Examples and which are merely exemplified and not to be construed as limitative, and the invention may be changed within the scope of the present invention. In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bonded silica gel. In HPLC (high performance liquid chromatography), C18 means use of octadecyl-bound silica gel. The ratios of elution solvents are volume mixing ratios, unless otherwise specified.

$^1$H NMR (proton nuclear magnetic resonance spectrum) was measured by Fourier-transform type NMR. Peaks with very mild protons such as a hydroxyl group, an amino group and the like are not described.

In the following Reference Examples and Examples, mass spectrum (MS), nuclear magnetic resonance spectrum (NMR) and melting point were measured by the following apparatus.

MS (mass spectrum) was measured by LC/MS (liquid chromatograph mass spectrometer). As the ionization method, API (Atmospheric Pressure Ionization, atmospheric pressure chemical ionization) method or ESI (Electron Spray Ionization) method was used. The data indicate measured value (found) found. Generally, a molecular ion peak is observed. In the case of a compound having an amino group ($-NH_2$), a peak after elimination of $NH_3$ may be observed as a fragment ion. In the case of a salt, a molecular ion peak or fragment ion peak of free form is generally observed.

Example 1

N-(1-(4-methoxyphenyl)propyl)-2-oxo-2,3-dihydropyrido[2,3-b]pyrazine-4(1H)-carboxamide A) methyl N-(3-nitropyridin-2-yl)glycinate To a solution of methyl glycinate hydrochloride (1.98 g) and 2-chloro-3-nitropyridine (2.50 g) in N,N-dimethylformamide (16.0 mL) was added triethylamine (5.50 mL). The reaction mixture was stirred overnight at 80° C., and the solvent was evaporated under reduced pressure. The residue was dissolved in ethyl acetate, the ethyl acetate solution was washed successively with water and saturated brine, and dried over anhydrous sodium sulfate, and the solvent was evaporated under reduced pressure. The residue was purified by silica gel column chromatography (ethyl acetate/hexane) to give the title compound (2.25 g).
MS (API+): [M+H]$^+$ 212.0.

B) 3,4-dihydropyrido[2,3-b]pyrazin-2(1H)-one

To a solution of methyl N-(3-nitropyridin-2-yl)glycinate (50.0 mg) in ethanol (3.00 mL) was added 10% palladium-carbon (containing 50% water, 50.0 mg). The reaction mixture was stirred at room temperature for 2 hr under hydrogen atmosphere, and the catalyst was filtered off. The filtrate was stirred overnight at 70° C., and the solvent was evaporated under reduced pressure. The residue was purified by silica gel column chromatography (methanol/ethyl acetate) to give the title compound (23.5 mg).
MS (API+): [M+H]$^+$ 150.2.

C) N-hydroxy-1-(4-methoxyphenyl)propan-1-imine

To a solution of 1-(4-methoxyphenyl)propan-1-one (25.0 g) in ethanol (300 mL) were added hydroxylamine hydrochloride (11.6 g) and triethylamine (17.0 g). The reaction mixture was heated at reflux for 3 hr, and the solvent was evaporated under reduced pressure. To the residue was added water, and the mixture was extracted with ethyl acetate. The extract was washed with saturated brine, and dried over anhydrous sodium sulfate, and the solvent was evaporated under reduced pressure to give the title compound (26.7 g).
MS (API+): [M+H]$^+$ 180.0.

D) 1-(4-methoxyphenyl)propan-1-amine

To a solution of N-hydroxy-1-(4-methoxyphenyl)propan-1-imine (12.4 g) in ethanol (300 mL) was added 10% palladium-carbon (containing 50% water, 8.19 g). The reaction mixture was stirred overnight at room temperature under hydrogen atmosphere, the insoluble substance was filtered off, and the filtrate was concentrated under reduced pressure. The residue was purified by silica gel column chromatography (NH, hexane/ethyl acetate) to give the title compound (7.56 g).
$^1$H NMR (300 MHz, DMSO-d$_6$) δ 0.76 (3H, t, J=7.4 Hz), 1.30-1.64 (2H, m), 1.87 (2H, brs), 3.63 (1H, t, J=6.7 Hz), 3.72 (3H, s), 6.74-6.91 (2H, m), 7.15-7.29 (2H, m).

E) 1-(4-methoxyphenyl)propan-1-amine hydrochloride

To a solution of 1-(4-methoxyphenyl)propan-1-amine (6.74 g) in ethyl acetate (20 mL) was added 1 M hydrogen chloride/diethyl ether solution (50 mL). The reaction mixture was diluted with ethyl acetate, and the precipitated solid was collected by filtration. The obtained solid was washed with ethyl acetate, and dried under reduced pressure to give the title compound (7.46 g).
$^1$H NMR (300 MHz, DMSO-d$_6$) δ 0.73 (3H, t, J=7.4 Hz), 1.66-1.87 (1H, m), 1.89-2.10 (1H, m), 3.76 (3H, s), 3.96-4.11 (1H, m), 6.91-7.03 (2H, m), 7.36-7.50 (2H, m), 8.51 (3H, brs).

F) N-(1-(4-methoxyphenyl)propyl)-2-oxo-2,3-dihydropyrido[2,3-b]pyrazine-4(1H)-carboxamide To a solution of 3,4-dihydropyrido[2,3-b]pyrazin-2(1H)-one (23.5 mg) in a mixed solvent of tetrahydrofuran (5 mL) and N,N-dimethylacetamide (1 mL) were added triethylamine (65.9 μL) and bis(trichloromethyl)carbonate (46.8 mg) at 0° C. The reaction mixture was stirred at 0° C. for 2 hr, triethylamine (65.9 μL) and 1-(4-methoxyphenyl)propan-1-amine hydrochloride (159 mg) were added thereto at 0° C. The reaction mixture was stirred at room temperature for 2 hr, water was added thereto, and the mixture was extracted with ethyl acetate. The extract was washed with saturated brine, and dried over anhydrous sodium sulfate, and the solvent was evaporated under reduced pressure. The residue was purified by silica gel column chromatography (NH, ethyl acetate/hexane), and crystallized from hexane/isopropyl ether to give the title compound (6.3 mg).

MS (API−): [M−H]− 339.0.

$^1$H NMR (300 MHz, CDCl$_3$) δ 0.79-1.00 (3H, m), 1.76-1.97 (2H, m), 3.78 (3H, s), 4.68 (2H, s), 4.83 (1H, q, J=7.2 Hz), 6.86 (2H, d, J=8.7 Hz), 6.96 (1H, dd, J=7.7, 5.1 Hz), 7.08-7.37 (3H, m), 7.97 (1H, dd, J=5.1, 1.3 Hz), 9.69 (1H, brs), 10.35 (1H, d, J=7.6 Hz).

Example 2

2-oxo-N-(1-(4-(trifluoromethoxy)phenyl)propyl)-2,3-dihydropyrido[2,3-b]pyrazine-4(1H)-carboxamide A) 4-(trifluoromethoxy)benzoyl chloride To a suspension of 4-(trifluoromethoxy)benzoic acid (25.0 g) in toluene (300 mL) was added thionyl chloride (17.3 g) at room temperature. To the reaction mixture was added N,N-dimethylacetamide (1 mL) solution, the mixture was stirred at 60° C. for 2 hr, and the solvent was evaporated under reduced pressure to give the title compound (25.1 g).

$^1$H NMR (300 MHz, DMSO-d$_6$) δ 7.39-7.52 (2H, m), 8.01-8.11 (2H, m).

B) N-methoxy-N-methyl-4-(trifluoromethoxy)benzamide

To a solution of 4-(trifluoromethoxy)benzoyl chloride (25.0 g) in toluene (240 mL) were added N-methoxymethanamine hydrochloride (13.0 g) and N-ethyl-N-(propan-2-yl)propan-2-amine (36.0 g) at room temperature. The reaction mixture was stirred at 60° C. for 1 hr, water was added thereto, and the mixture was extracted with ethyl acetate. The extract was washed with saturated brine, and dried over anhydrous sodium sulfate. The residue was purified by silica gel column chromatography (NH, ethyl acetate), and the solvent was evaporated under reduced pressure to give the title compound (16.1 g).

$^1$H NMR (300 MHz, DMSO-d$_6$) δ 3.27 (3H, s), 3.55 (3H, s), 7.35-7.51 (2H, m), 7.64-7.83 (2H, m).

C) 1-(4-(trifluoromethoxy)phenyl)propan-1-one

To a solution of N-methoxy-N-methyl-4-(trifluoromethoxy)benzamide (16.1 g) in tetrahydrofuran (200 mL) was added 1 M ethylmagnesium bromide/tetrahydrofuran solution (97 mL) under ice-cooling. The reaction mixture was stirred at room temperature for 3 hr, 0.5 M hydrochloric acid was added thereto, and the mixture was extracted with ethyl acetate. The extract was washed successively with 0.5 M hydrochloric acid and saturated brine, and dried over anhydrous sodium sulfate, and the solvent was evaporated under reduced pressure. The residue was purified by silica gel column chromatography (hexane/ethyl acetate) to give the title compound (12.7 g).

$^1$H NMR (300 MHz, DMSO-d$_6$) δ 1.09 (3H, t, J=7.2 Hz), 3.07 (2H, q, J=7.2 Hz), 7.45-7.56 (2H, m), 8.04-8.15 (2H, m).

D) N-hydroxy-1-(4-(trifluoromethoxy)phenyl)propan-1-imine

To a solution of 1-(4-(trifluoromethoxy)phenyl)propan-1-one (12.7 g) in ethanol (120 mL) were added hydroxylamine hydrochloride (4.86 g) and triethylamine (7.08 g). The reaction mixture was heated at reflux for 4 hr, and the solvent was evaporated under reduced pressure. To the residue was added water, and the mixture was extracted with ethyl acetate. The extract was dried over anhydrous sodium sulfate, and the solvent was evaporated under reduced pressure to give the title compound (13.8 g).

$^1$H NMR (300 MHz, DMSO-d$_6$) δ 1.04 (3H, t, J=7.6 Hz), 2.72 (2H, q, J=7.6 Hz), 7.32-7.44 (2H, m), 7.71-7.81 (2H, m), 11.31 (1H, s).

E) 1-[4-(trifluoromethoxy)phenyl]propan-1-amine

To a solution of N-hydroxy-1-(4-(trifluoromethoxy)phenyl)propan-1-imine (13.8 g) in ethanol (130 mL) was added 10% palladium-carbon (containing 50% water, 3.0 g). The reaction mixture was stirred overnight at room temperature under hydrogen atmosphere, the insoluble substance was filtered off, and the filtrate was concentrated under reduced pressure to give the title compound (11.3 g).

$^1$H NMR (400 MHz, DMSO-d$_6$) δ 0.77 (3H, t, J=7.2 Hz), 1.48-1.63 (2H, m), 3.76 (1H, t, J=6.8 Hz), 7.27 (2H, d, J=8.4 Hz), 7.45 (2H, d, J=8.4 Hz).

F) 1-(4-(trifluoromethoxy)phenyl)propan-1-amine hydrochloride

To a solution of 1-(4-(trifluoromethoxy)phenyl)propan-1-amine (11.3 g) in a mixed solvent of ethyl acetate (70 mL) and methanol (10 mL) was added 4 M hydrogen chloride/ethyl acetate solution (40 mL). The reaction mixture was stirred for 20 min, the solvent was evaporated under reduced pressure, and diethyl ether was added thereto. The precipitated solid was collected by filtration, washed with diethyl ether, and dried under reduced pressure to give the title compound (10.12 g).

$^1$H NMR (300 MHz, DMSO-d$_6$) δ 0.76 (3H, t, J=7.4 Hz), 1.70-2.11 (2H, m), 4.20 (1H, dd, J=9.1, 5.7 Hz), 7.39-7.53 (2H, m), 7.61-7.71 (2H, m), 8.63 (3H, brs).

G) 2-oxo-N-(1-(4-(trifluoromethoxy)phenyl)propyl)-2,3-dihydropyrido[2,3-b]pyrazine-4(1H)-carboxamide The title compound was obtained in the same manner as in Step F of Example 1.

MS (API+): [M+H]+ 395.2.

$^1$H NMR (300 MHz, CDCl$_3$) δ 0.96 (3H, t, J=7.4 Hz), 1.76-1.96 (2H, m), 4.67 (2H, s), 4.90 (1H, q, J=7.2 Hz), 6.99 (1H, dd, J=7.6, 4.9 Hz), 7.12-7.25 (3H, m), 7.30-7.42 (2H, m), 7.99 (1H, dd, J=5.1, 1.7 Hz), 9.91 (1H, s), 10.46 (1H, d, J=7.2 Hz).

Example 3

N-(1-(4-methoxyphenyl)propyl)-7-methyl-2-oxo-2,3-dihydropyrido[2,3-b]pyrazine-4(1H)-carboxamide A) methyl N-(5-methyl-3-nitropyridin-2-yl)glycinate The title compound was obtained in the same manner as in Step A of Example 1.

MS (API+): [M+H]+ 226.1.

B) 7-methyl-3,4-dihydropyrido[2,3-b]pyrazin-2 (1H)-one hydrochloride

To an ethanol solution (100 mL) of methyl N-(5-methyl-3-nitropyridin-2-yl)glycinate (1.16 g) was added 10% palladium-carbon (containing 50% water, 1.00 g). The reaction mixture was stirred at room temperature for 2 hr under hydrogen atmosphere, and the catalyst was filtered off. The filtrate was stirred at 70° C. for 4 hr, 5-10% hydrochloric acid/methanol (10 mL) solution was added thereto, and the mixture was stirred overnight at 70° C. The solvent was evaporated under reduced pressure, and the obtained residue was crystallized from hexane/ethyl acetate to give the title compound (1.02 g).

MS (API+): [M+H]$^+$ 164.2.

C) N-(1-(4-methoxyphenyl)propyl)-7-methyl-2-oxo-2,3-dihydropyrido[2,3-b]pyrazine-4(1H)-carboxamide The title compound was obtained in the same manner as in Step F of Example 1.

MS (API+): [M+H]$^+$ 355.1.

$^1$H NMR (300 MHz, DMSO-d$_6$) δ 0.82 (3H, t, J=7.2 Hz), 1.67-1.83 (2H, m), 2.24 (3H, s), 3.72 (3H, s), 4.39 (2H, d, J=0.8 Hz), 4.70 (1H, q, J=7.1 Hz), 6.83-6.92 (2H, m), 7.12 (1H, d, J=1.5 Hz), 7.17-7.26 (2H, m), 7.81-7.88 (1H, m), 10.11 (1H, d, J=7.6 Hz), 10.78 (1H, brs).

Example 4

7-methyl-2-oxo-N-(1-(4-(trifluoromethoxy)phenyl) propyl)-2,3-dihydropyrido[2,3-b]pyrazine-4(1H)-carboxamide To a solution of 7-methyl-3,4-dihydropyrido[2,3-b] pyrazin-2(1H)-one hydrochloride (200 mg) in a mixed solvent of tetrahydrofuran (10 mL) and N,N-dimethylacetamide (10 mL) were added triethylamine (838 μL) and a solution of bis(trichloromethyl)carbonate (297 mg) in tetrahydrofuran (3 mL) at 0° C. The reaction mixture was stirred at 0° C. for 3 hr, triethylamine (698 μL) and a solution of 1-[4-(trifluoromethoxy)phenyl]propan-1-amine hydrochloride (1.28 g) in a mixed solvent of tetrahydrofuran (3 mL) and N,N-dimethylacetamide (5 mL) were added thereto at 0° C. The reaction mixture was stirred at room temperature for 1 hr, water was added thereto, and the mixture was extracted with ethyl acetate. The extract was washed successively with water and saturated brine, and dried over anhydrous sodium sulfate, and the solvent was evaporated under reduced pressure. The residue was purified by silica gel column chromatography (ethyl acetate) to give a crude product. The crude product was purified by HPLC (C18, mobile phase: water/acetonitrile (containing 10 mM NH$_4$HCO$_3$)), the obtained fraction was concentrated under reduced pressure, and the residue was crystallized from hexane/ethyl acetate to give the title compound (56.3 mg).

MS (API+): [M+H]$^+$ 409.2.

$^1$H NMR (300 MHz, DMSO-d$_6$) δ 0.76-0.95 (3H, m), 1.78 (2H, quin, J=7.2 Hz), 2.25 (3H, s), 4.38 (2H, s), 4.80 (1H, q, J=7.2 Hz), 7.13 (1H, d, J=1.9 Hz), 7.28-7.37 (2H, m), 7.38-7.48 (2H, m), 7.86 (1H, d, J=1.5 Hz), 10.21 (1H, d, J=7.2 Hz), 10.81 (1H, brs).

Example 5

Optically Active 7-methyl-2-oxo-N-(1-(4-(trifluoromethoxy)phenyl)propyl)-2,3-dihydropyrido[2,3-b] pyrazine-4(1H)-carboxamide Racemic 7-methyl-2-oxo-N-(1-(4-(trifluoromethoxy)phenyl)propyl)-2,3-dihydropyrido[2,3-b]pyrazine-4(1H)-carboxamide (56.3 mg) was resolved by HPLC (column: CHIRALPAK AD, 50 mmID×500 mmL, manufactured by Daicel Chemical Industries, Ltd., mobile phase: hexane/2-propanol=850/150) to give the title compound having a shorter retention time (10.2 mg).

MS (API+): [M+H]$^+$ 409.1.

$^1$H NMR (300 MHz, CDCl$_3$) δ 0.95 (3H, t, J=7.4 Hz), 1.85 (2H, quin, J=7.3 Hz), 2.31 (3H, s), 4.66 (2H, s), 4.89 (1H, q, J=6.9 Hz), 7.03 (1H, d, J=1.5 Hz), 7.16 (2H, d, J=8.0 Hz), 7.30-7.39 (2H, m), 7.83 (1H, d, J=1.1 Hz), 9.31 (1H, s), 10.33 (1H, d, J=7.2 Hz).

Example 6

Optically Active 7-methyl-2-oxo-N-(1-(4-(trifluoromethoxy)phenyl)propyl)-2,3-dihydropyrido[2,3-b] pyrazine-4(1H)-carboxamide Racemic 7-methyl-2-oxo-N-(1-(4-(trifluoromethoxy)phenyl)propyl)-2,3-dihydropyrido[2,3-b]pyrazine-4(1H)-carboxamide (56.3 mg) was resolved by HPLC (column: CHIRALPAK AD, 50 mmID×500 mmL, manufactured by Daicel Chemical Industries, Ltd., mobile phase: hexane/2-propanol=850/150) to give the title compound having a longer retention time (9.00 mg).

MS (API+): [M+H]$^+$ 409.1.

$^1$H NMR (300 MHz, CDCl$_3$) δ 0.95 (3H, t, J=7.4 Hz), 1.85 (2H, quin, J=7.3 Hz), 2.31 (3H, s), 4.66 (2H, s), 4.89 (1H, q, J=6.9 Hz), 7.04 (1H, d, J=1.5 Hz), 7.16 (2H, d, J=8.0 Hz), 7.29-7.38 (2H, m), 7.83 (1H, d, J=1.1 Hz), 9.49 (1H, s), 10.33 (1H, d, J=7.2 Hz).

Example 7

N-(2-methoxy-1-(4-(trifluoromethoxy)phenyl)ethyl)-2-oxo-2,3-dihydropyrido[2,3-b]pyrazine-4(1H)-carboxamide

A) 4-ethenylphenyl trifluoromethyl ether

To a suspension of potassium 2-methylpropan-2-olate (6.10 g) in tetrahydrofuran (80 mL) was added methyl (triphenyl)phosphonium iodide (22.1 g) over 5 min under ice-cooling. The reaction mixture was stirred for 30 min, and a solution of 4-(trifluoromethoxy)benzaldehyde (8.00 g) in tetrahydrofuran (20 mL) was added slowly thereto. The reaction mixture was stirred at room temperature for 1.5 hr, water was added thereto, and the mixture was extracted with ethyl acetate. The extract was washed successively with water and saturated brine, and dried over anhydrous sodium sulfate, and the solvent was evaporated under reduced pressure. The residue was purified by silica gel column chromatography (petroleum ether) to give the title compound (5.30 g).

$^1$H NMR (300 MHz, CDCl$_3$) δ 5.30 (1H, d, J=10.8 Hz), 5.75 (1H, d, J=17.7 Hz), 6.72 (1H, dd, J=17.7, 10.8 Hz), 7.19 (2H, d, J=7.8 Hz), 7.44 (2H, d, J=6.9 Hz).

B) 2-(4-(trifluoromethoxy)phenyl)oxirane

To a solution of 4-ethenylphenyl trifluoromethyl ether (5.30 g) in chloroform (50 mL) was added 3-chloroperbenzoic acid (11.4 g) at room temperature. The reaction mixture was stirred at room temperature for 2 hr, and washed successively with aqueous sodium thiosulfate solution and saturated brine. The organic layer was dried over anhydrous sodium sulfate, and the solvent was evaporated under reduced pressure. The residue was purified by silica gel column chromatography (petroleum ether/dichloromethane) to give the title compound (4.20 g).
$^1$H NMR (400 MHz, CDCl$_3$) δ 2.76 (1H, dd, J=5.6, 2.4 Hz), 3.16 (1H, dd, J=5.2, 4.0 Hz), 3.87 (1H, dd, J=4.0, 2.8 Hz), 7.20 (2H, d, J=8.0 Hz), 7.31 (2H, d, J=8.0 Hz).

C)
2-methoxy-1-(4-(trifluoromethoxy)phenyl)ethanol

To a solution of 2-(4-(trifluoromethoxy)phenyl)oxirane (4.20 g) in N,N-dimethylacetamide (20 mL) was added sodium methoxide (5.56 g) at room temperature. The reaction mixture was stirred at 60° C. for 3 hr. The reaction mixture was cooled to room temperature, and ethyl acetate was added thereto. The mixture was washed successively with water and saturated brine, and dried over anhydrous sodium sulfate, and the solvent was evaporated under reduced pressure. The residue was purified by silica gel column chromatography (dichloromethane/ethyl acetate) to give the title compound (2.75 g).
$^1$H NMR (300 MHz, CDCl$_3$) δ 2.87 (1H, d, J=2.7 Hz), 3.33-3.45 (4H, m), 3.55 (1H, dd, J=9.6, 3.0 Hz), 4.92 (1H, d, J=8.7 Hz), 7.22 (2H, d, J=8.1 Hz), 7.43 (2H, d, J=8.7 Hz).

D)
2-methoxy-1-(4-(trifluoromethoxy)phenyl)ethanone

To a solution of 2-methoxy-1-(4-(trifluoromethoxy)phenyl)ethanol (2.70 g) in dichloromethane (50 mL) was added 1,1,1-triacetoxy-1,1-dihydro-1,2-benziodoxol-3(1H)-one (6.28 g) at room temperature. The reaction mixture was stirred at room temperature for 2 hr, and the insoluble substance was filtered off. The filtrate was washed successively with sodium thiosulfate and saturated brine, and dried over anhydrous sodium sulfate, and the solvent was evaporated under reduced pressure. The residue was purified by silica gel column chromatography (dichloromethane) to give the title compound (2.00 g).
$^1$H NMR (400 MHz, CDCl$_3$) δ 3.51 (3H, s), 4.68 (2H, s), 7.30 (2H, d, J=8.0 Hz), 8.02 (2H, d, J=9.2 Hz).

E)
2-methoxy-1-(4-(trifluoromethoxy)phenyl)ethanamine

To a solution of 2-methoxy-1-(4-(trifluoromethoxy)phenyl)ethanone (2.00 g) in ethanol (80 mL) were added potassium carbonate (4.70 g) and hydroxylamine hydrochloride (1.18 g) at room temperature. The reaction mixture was heated at reflux overnight, and the solvent was evaporated under reduced pressure. To the residue was added ethyl acetate, and the mixture was washed successively with water and saturated brine, and dried over anhydrous sodium sulfate, and the solvent was evaporated under reduced pressure to give a crude product (1.50 g) of N-hydroxy-2-methoxy-1-(4-(trifluoromethoxy)phenyl)ethanimine. To a solution of the obtained crude product (1.50 g) of N-hydroxy-2-methoxy-1-(4-(trifluoromethoxy)phenyl)ethanimine in methanol (50 mL) was added 10% palladium-carbon (containing 50% water, 0.20 g) at room temperature. The reaction mixture was stirred overnight at room temperature under hydrogen atmosphere. The insoluble substance was filtered off, and the filtrate was concentrated under reduced pressure to give the title compound (1.3 g).
$^1$H NMR (300 MHz, CDCl$_3$) δ 3.72-3.40 (4H, m), 3.49 (1H, dd, J=9.0, 3.0 Hz), 4.22 (1H, dd, J=8.1, 3.6 Hz), 7.20 (2H, d, J=8.1 Hz), 7.42 (2H, d, J=8.1 Hz).

F) 4-nitrophenyl 2-oxo-2,3-dihydropyrido[2,3-b]pyrazine-4(1H)-carboxylate

To a solution of 3,4-dihydropyrido[2,3-b]pyrazin-2(1H)-one (1.00 g) in a mixed solvent of N,N-dimethylacetamide (60 mL) and pyridine (10 mL) was added slowly 4-nitrophenyl chloroformate (1.62 g) under ice-cooling. The reaction mixture was stirred at room temperature for 1.5 hr, and water was added thereto. The precipitated solid was collected by filtration, and washed with water to give the title compound (2.09 g).
MS (API+): [M+H]$^+$ 315.0.

G) N-(2-methoxy-1-(4-(trifluoromethoxy)phenyl) ethyl)-2-oxo-2,3-dihydropyrido[2,3-b]pyrazine-4 (1H)-carboxamide To a solution of 4-nitrophenyl 2-oxo-2,3-dihydropyrido[2,3-b]pyrazine-4(1H)-carboxylate (157 mg) in N,N-dimethylacetamide (5 mL) were added 2-methoxy-1-[4-(trifluoromethoxy)phenyl]ethanamine (118 mg) and triethylamine (191 μL) at room temperature. The reaction mixture was stirred at room temperature for 3 hr, aqueous sodium hydrogen carbonate solution was added thereto, and the mixture was extracted with ethyl acetate. The extract was washed successively with 1 M hydrochloric acid and saturated brine, and dried over anhydrous sodium sulfate, and the solvent was evaporated under reduced pressure. The residue was purified by silica gel column chromatography (hexane/ethyl acetate) to give the title compound (102 mg).
MS (API+): [M+H]$^+$ 411.1.
$^1$H NMR (300 MHz, DMSO-d$_6$) δ 3.28 (3H, s), 3.55-3.71 (2H, m), 4.33-4.50 (2H, m), 4.99-5.13 (1H, m), 7.11 (1H, dd, J=7.9, 4.9 Hz), 7.27-7.39 (3H, m), 7.42-7.53 (2H, m), 8.00 (1H, dd, J=4.9, 1.7 Hz), 10.51 (1H, d, J=7.4 Hz), 10.83 (1H, brs).

Example 8

Optically Active 2-oxo-N-(1-(4-(trifluoromethoxy) phenyl)propyl)-2,3-dihydropyrido[2,3-b]pyrazine-4 (1H)-carboxamide Racemic 2-oxo-N-(1-(4-(trifluoromethoxy)phenyl)propyl)-2,3-dihydropyrido[2,3-b]pyrazine-4(1H)-carboxamide (907 mg) was resolved by HPLC (column: CHIRALPAK IC, 50 mmID×500 mmL, manufactured by Daicel Chemical Industries, Ltd., mobile phase: hexane/ethanol=400/600) to give the title compound having a shorter retention time (429 mg).
MS (API+): [M+H]$^+$ 395.1.
$^1$H NMR (300 MHz, DMSO-d$_6$) δ 0.88 (3H, t, J=7.3 Hz), 1.70-1.90 (2H, m), 4.41 (2H, s), 4.81 (1H, q, J=7.0 Hz), 7.11 (1H, dd, J=7.7, 5.1 Hz), 7.26-7.38 (3H, m), 7.38-7.51 (2H, m), 8.02 (1H, dd, J=4.9, 1.5 Hz), 10.35 (1H, d, J=7.2 Hz), 10.83 (1H, brs).

Example 9

Optically Active 2-oxo-N-(1-(4-(trifluoromethoxy) phenyl)propyl)-2,3-dihydropyrido[2,3-b]pyrazine-4 (1H)-carboxamide Racemic 2-oxo-N-(1-(4-(trifluoromethoxy)phenyl)propyl)-2,3-dihydropyrido[2,3-b]pyrazine-4(1H)-carboxamide (907 mg) was resolved by HPLC (column: CHIRALPAK IC, 50 mmID×500 mmL, manufactured by Daicel Chemical Industries, Ltd., mobile phase: hexane/ethanol=400/600) to give the title compound having a longer retention time (439 mg).

MS (API+): [M+H]$^+$ 395.1.

$^1$H NMR (300 MHz, DMSO-d$_6$) δ 0.88 (3H, t, J=7.3 Hz), 1.70-1.89 (2H, m), 4.41 (2H, s), 4.81 (1H, q, J=6.9 Hz), 7.10 (1H, dd, J=7.7, 5.1 Hz), 7.25-7.37 (3H, m), 7.38-7.51 (2H, m), 8.02 (1H, dd, J=5.1, 1.7 Hz), 10.34 (1H, d, J=7.5 Hz), 10.82 (1H, brs).

Example 10

8-methyl-2-oxo-N-(1-(4-(trifluoromethoxy)phenyl)propyl)-2,3-dihydropyrido[2,3-b]pyrazine-4(1H)-carboxamide A) methyl N-(4-methyl-3-nitropyridin-2-yl)glycinate The title compound was obtained in the same manner as in Step A of Example 1.
MS (API+): [M+H]$^+$ 226.1.

B) 8-methyl-3,4-dihydropyrido[2,3-b]pyrazin-2(1H)-one

To an ethanol solution (120 mL) of methyl N-(4-methyl-3-nitropyridin-2-yl)glycinate (1.31 g) was added 10% palladium-carbon (containing 50% water, 1.00 g). The reaction mixture was stirred at room temperature for 2 hr under hydrogen atmosphere, and the catalyst was filtered off. The filtrate was stirred overnight at 80° C., and the solvent was evaporated under reduced pressure. The obtained residue was crystallized from hexane/ethyl acetate to give the title compound (870 mg).
MS (API+): [M+H]$^+$ 164.2.

C) 8-methyl-2-oxo-N-(1-(4-(trifluoromethoxy)phenyl)propyl)-2,3-dihydropyrido[2,3-b]pyrazine-4(1H)-carboxamide The title compound was obtained in the same manner as in Steps F-G of Example 7.
MS (API+): [M+H]$^+$ 409.1.
$^1$H NMR (300 MHz, CDCl$_3$) δ 0.95 (3H, t, J=7.4 Hz), 1.75-1.95 (2H, m), 2.32 (3H, s), 4.54-4.74 (2H, m), 4.89 (1H, q, J=7.2 Hz), 6.82-6.91 (1H, m), 7.16 (2H, d, J=7.7 Hz), 7.29-7.40 (2H, m), 7.90 (1H, d, J=5.1 Hz), 8.33 (1H, brs), 10.33 (1H, d, J=7.4 Hz).

Example 11

6-methyl-2-oxo-N-(1-(4-(trifluoromethoxy)phenyl)propyl)-2,3-dihydropyrido[2,3-b]pyrazine-4(1H)-carboxamide A) 4-nitrophenyl 6-methyl-2-oxo-2,3-dihydropyrido[2,3-b]pyrazine-4(1H)-carboxylate The title compound was obtained in the same manner as in Step A of Example 1, Step B of Example 10 and Step F of Example 7.
MS (API+): [M+H]$^+$ 164.2.

B) 6-methyl-2-oxo-N-(1-(4-(trifluoromethoxy)phenyl)propyl)-2,3-dihydropyrido[2,3-b]pyrazine-4(1H)-carboxamide The title compound was obtained in the same manner as in Step G of Example 7.
MS (API+): [M+H]$^+$ 409.1.
$^1$H NMR (300 MHz, CDCl$_3$) δ 0.96 (3H, t, J=7.5 Hz), 1.77-1.97 (2H, m), 2.47 (3H, s), 4.65 (2H, s), 4.90 (1H, q, J=7.0 Hz), 6.83 (1H, d, J=7.9 Hz), 7.17 (2H, d, J=7.9 Hz), 7.31-7.39 (2H, m), 7.50-7.58 (1H, m), 8.79 (1H, brs), 10.65 (1H, d, J=7.2 Hz).

Example 12

N-(2-methyl-1-(4-(trifluoromethoxy)phenyl)propyl)-2-oxo-2,3-dihydropyrido[2,3-b]pyrazine-4(1H)-carboxamide A) 2-methyl-1-[4-(trifluoromethoxy)phenyl]propan-1-amine hydrochloride The title compound was obtained in the same manner as in Steps C-F of Example 2.
MS (API+), found: 217.1.

B) N-(2-methyl-1-(4-(trifluoromethoxy)phenyl)propyl)-2-oxo-2,3-dihydropyrido[2,3-b]pyrazine-4(1H)-carboxamide The title compound was obtained in the same manner as in Step G of Example 7.
MS (API+): [M+H]$^+$ 409.1.
$^1$H NMR (300 MHz, CDCl$_3$) δ 0.89-1.02 (6H, m), 1.92-2.18 (1H, m), 4.57-4.73 (2H, m), 4.76-4.92 (1H, m), 6.96-7.06 (1H, m), 7.09-7.22 (3H, m), 7.24-7.35 (2H, m), 8.03 (1H, dd, J=5.1, 1.7 Hz), 8.74 (1H, brs), 10.60 (1H, d, J=7.9 Hz).

Example 13

N-(2-hydroxy-1-(4-(trifluoromethoxy)phenyl)ethyl)-2-oxo-2,3-dihydropyrido[2,3-b]pyrazine-4(1H)-carboxamide A) ethyl amino (4-(trifluoromethoxy)phenyl)acetate To a solution of 1-bromo-4-(trifluoromethoxy)benzene (10 g) in tetrahydrofuran (200 mL) was added 1.6 M n-butyllithium/hexane solution (31.1 mL) at −78° C., and the mixture was stirred at the same temperature for 50 min under nitrogen atmosphere. Ethyl 2-chloro-2-oxoacetate (6.23 g) was added thereto at the same temperature, and the reaction mixture was stirred overnight at room temperature. The reaction mixture was added to 1 M hydrochloric acid under ice-cooling, and the mixture was extracted with ethyl acetate. The extract was washed successively with water and saturated brine, and dried over anhydrous magnesium sulfate, and the solvent was evaporated under reduced pressure. The residue was purified by silica gel column chromatography (ethyl acetate/hexane) to give a crude product (2.50 g) of ethyl oxo-(4-(trifluoromethoxy)phenyl)acetate. The title compound (590 mg) was obtained in the same manner as in Steps D-E of Example 2 from the obtained crude product
MS (API+): [M+H]$^+$ 264.1.

B) ethyl ((tert-butoxycarbonyl) amino) (4-(trifluoromethoxy)phenyl)acetate

To a solution of ethyl amino (4-(trifluoromethoxy)phenyl)acetate (590 mg) in tetrahydrofuran (20 mL) was added tert-butyl dicarbonate (430 mg). The reaction mixture was stirred at room temperature for 2 days, and the solvent was evaporated under reduced pressure to give the title compound (952 mg).

$^1$H NMR (300 MHz, CDCl$_3$) δ 1.22 (3H, t, J=7.2 Hz), 1.53 (9H, s), 3.99-4.33 (2H, m), 5.32 (1H, d, J=6.8 Hz), 5.63 (1H, brs), 7.19 (2H, d, J=7.9 Hz), 7.41 (2H, d, J=8.7 Hz).

C) tert-butyl (2-hydroxy-1-(4-(trifluoromethoxy)phenyl)ethyl)carbamate

To a suspension of lithium aluminium hydride (41.8 mg) in tetrahydrofuran (5 mL) was added ethyl ((tert-butoxycarbonyl) amino) (4-(trifluoromethoxy)phenyl)acetate (100 mg) under ice-cooling, and the mixture was stirred at the same temperature for 30 min. Anhydrous magnesium sulfate was added thereto, and then one drop of water and ethyl acetate were successively added thereto, and the insoluble substance was filtered off using Celite. The filtrate was concentrated under reduced pressure to give the title compound (54.8 mg).

MS (API−): [M−H]$^-$ 320.1.

D) N-(2-hydroxy-1-(4-(trifluoromethoxy)phenyl)ethyl)-2-oxo-2,3-dihydropyrido[2,3-b]pyrazine-4(1H)-carboxamide Tert-butyl (2-hydroxy-1-(4-(trifluoromethoxy)phenyl)ethyl)carbamate (52 mg) was added 2 M hydrogen chloride/ethanol solution (2 mL). The reaction mixture was stirred at 60° C. for 2 min, and the solvent was evaporated under reduced pressure. To the residue were added N,N-dimethylformamide (2 mL), triethylamine (0.045 mL) and 4-nitrophenyl 2-oxo-2,3-dihydropyrido[2,3-b]pyrazine-4(1H)-carboxylate (50.9 mg) at room temperature. The reaction mixture was stirred overnight at room temperature, saturated brine was added thereto, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give a crude product containing N-(2-hydroxy-1-(4-(trifluoromethoxy)phenyl)ethyl)-2-oxo-2,3-dihydropyrido[2,3-b]pyrazine-4(1H)-carboxamide. The obtained crude product was purified by HPLC (C18, mobile phase: water/acetonitrile (containing 0.1% TFA)), to the obtained fraction was added saturated sodium carbonate aqueous solution, and the mixture was extracted with ethyl acetate. The extract was washed with saturated brine, and dried over anhydrous magnesium sulfate, and the solvent was evaporated under reduced pressure to give the title compound (32.2 mg).

MS (API+): [M+H]$^+$ 397.1.

$^1$H NMR (300 MHz, DMSO-d$_6$) δ 3.51-3.80 (2H, m), 4.29-4.53 (2H, m), 5.09 (1H, t, J=5.1 Hz), 7.11 (1H, dd, J=7.7, 5.1 Hz), 7.28-7.35 (4H, m), 7.40-7.51 (2H, m), 8.01 (1H, dd, J=4.9, 1.5 Hz), 10.39 (1H, d, J=7.2 Hz), 10.79 (1H, brs).

Example 14

N-(2-hydroxy-2-methyl-1-(4-(trifluoromethoxy)phenyl)propyl)-2-oxo-2,3-dihydropyrido[2,3-b]pyrazine-4(1H)-carboxamide

A) tert-butyl (2-hydroxy-2-methyl-1-(4-(trifluoromethoxy)phenyl)propyl)carbamate 1 M Methylmagnesium bromide/tetrahydrofuran solution (2.20 mL) was diluted with tetrahydrofuran (5 mL), ethyl ((tert-butoxycarbonyl) amino) (4-(trifluoromethoxy)phenyl)acetate (200 mg) was added thereto at 0° C. The reaction mixture was stirred at the same temperature for 2 hr, saturated aqueous ammonium chloride solution was added thereto, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (78 mg).

MS (API−): [M−H]$^-$ 348.2.

B) N-(2-hydroxy-2-methyl-1-(4-(trifluoromethoxy)phenyl)propyl)-2-oxo-2,3-dihydropyrido[2,3-b]pyrazine-4(1H)-carboxamide The title compound was obtained in the same manner as in. Step D of Example 13

MS (API+): [M+H]$^+$ 425.0.

$^1$H NMR (300 MHz, CDCl$_3$) δ 1.16 (3H, s), 1.37 (3H, s), 1.70 (1H, s), 4.55-4.76 (2H, m), 4.91 (1H, d, J=8.3 Hz), 7.02 (1H, dd, J=7.9, 4.9 Hz), 7.13-7.22 (3H, m), 7.37-7.46 (2H, m), 8.07 (1H, dd, J=4.9, 1.5 Hz), 8.51 (1H, s), 10.93 (1H, d, J=8.3 Hz).

Example 15

N-(cyclopropyl(4-(trifluoromethoxy)phenyl)methyl)-2-oxo-2,3-dihydropyrido[2,3-b]pyrazine-4(1H)-carboxamide

A) 1-cyclopropyl-N-hydroxy-1-(4-(trifluoromethoxy)phenyl)methanimine

The title compound was obtained in the same manner as in Step D of Example 2.

MS (API+): [M+H]$^+$ 246.1.

B) 1-cyclopropyl-1-(4-(trifluoromethoxy)phenyl)methanamine

To a solution of 1-cyclopropyl-N-hydroxy-1-(4-(trifluoromethoxy)phenyl)methanimine (4.2 g) in ethanol (100 mL) was added 10% palladium-carbon (containing 50% water, 1.823 g). The reaction mixture was stirred at room temperature for 1 hr under hydrogen atmosphere, 2 M hydrochloric acid/ethanol solution (1 mL) was added thereto, and the mixture was stirred overnight under hydrogen atmosphere. The insoluble substance was filtered off, and the filtrate was concentrated under reduced pressure. To the residue was added 4 M hydrogen chloride/ethyl acetate solution (45 mL), and the solvent was evaporated under reduced pressure. To the residue was added diisopropyl ether, and the precipitated solid was purified by HPLC (C18, mobile phase: water/acetonitrile (containing 0.1% TFA)). To the obtained fraction was added saturated aqueous sodium hydrogen carbonate solution, and the mixture was extracted with ethyl acetate. The extract was dried over anhydrous magnesium sulfate, and concentrated under reduced pressure to give 1-cyclopropyl-1-(4-(trifluoromethoxy)phenyl) methanamine (0.924 g).

MS (API+), found: 215.2.

C) 1-cyclopropyl-1-(4-(trifluoromethoxy)phenyl) methanamine hydrochloride

The title compound was obtained in the same manner as in Step F of Example 2.

MS (API+), found: 215.1.

D) N-(cyclopropyl(4-(trifluoromethoxy)phenyl) methyl)-2-oxo-2,3-dihydropyrido[2,3-b]pyrazine-4 (1H)-carboxamide The title compound was obtained in the same manner as in Step G of Example 7.

MS (API+): [M+H]$^+$ 407.0.

$^1$H NMR (300 MHz, CDCl$_3$) δ 0.35-0.55 (2H, m), 0.55-0.69 (2H, m), 1.14-1.31 (1H, m), 4.43-4.55 (1H, m), 4.59-4.77 (2H, m), 7.00 (1H, dd, J=7.9, 4.9 Hz), 7.11-7.22 (3H, m), 7.38-7.48 (2H, m), 8.01 (1H, dd, J=5.1, 1.7 Hz), 8.38 (1H, brs), 10.44 (1H, d, J=7.5 Hz).

Example 16

2-oxo-N-(1-(4-(trifluoromethoxy)phenyl)butyl)-2,3-dihydropyrido[2,3-b]pyrazine-4(1H)-carboxamide

A) 1-(4-(trifluoromethoxy)phenyl)butan-1-amine

To a solution of 1-butyl-N-hydroxy-1-(4-(trifluoromethoxy)phenyl)methanimine (4.2 g) in ethanol (100 mL) was added 10% palladium-carbon (containing 50% water, 1.823 g). The reaction mixture was stirred at room temperature for 1 hr under hydrogen atmosphere, 2 M hydrogen chloride/ethanol solution (1 mL) was added thereto, and the mixture was stirred overnight under hydrogen atmosphere. The insoluble substance was filtered off, and the filtrate was concentrated under reduced pressure. To the residue was added 4 M hydrogen chloride/ethyl acetate solution (45 mL), and the solvent was evaporated under reduced pressure. To the residue was added diisopropyl ether, and the precipitated solid was purified by HPLC (C18, mobile phase: water/acetonitrile (containing 0.1% TFA)). To the obtained fraction was added saturated aqueous sodium hydrogen carbonate solution, and the mixture was extracted with ethyl acetate. The extract was dried over anhydrous magnesium sulfate, and concentrated under reduced pressure to give 1-(4-(trifluoromethoxy)phenyl)butan-1-amine (0.524 g).

MS (API+), found: 217.2.

B) 1-(4-(trifluoromethoxy)phenyl)butan-1-amine hydrochloride

The title compound was obtained in the same manner as in Step F of Example 2.

MS (API+), found: 233.2.

C) 2-oxo-N-(1-(4-(trifluoromethoxy)phenyl)butyl)-2,3-dihydropyrido[2,3-b]pyrazine-4(1H)-carboxamide The title compound was obtained in the same manner as in Step G of Example 7.

MS (API+): [M+H]$^+$ 409.0.

$^1$H NMR (300 MHz, CDCl$_3$) δ 0.86-1.01 (3H, m), 1.23-1.51 (2H, m), 1.68-1.94 (2H, m), 4.58-4.75 (2H, m), 4.96 (1H, q, J=7.5 Hz), 7.00 (1H, dd, J=7.7, 5.1 Hz), 7.10-7.22 (3H, m), 7.31-7.38 (2H, m), 8.00 (1H, dd, J=4.9, 1.5 Hz), 8.99 (1H, s), 10.40 (1H, d, J=7.5 Hz).

Example 17

1-methyl-2-oxo-N-(1-(4-(trifluoromethoxy)phenyl) propyl)-2,3-dihydropyrido[2,3-b]pyrazine-4(1H)-carboxamide

A) 1-methyl-3,4-dihydropyrido[2,3-b]pyrazin-2 (1H)-one

To a solution of 3,4-dihydropyrido[2,3-b]pyrazin-2(1H)-one (1.40 g) in N,N-dimethylformamide (15 mL) was slowly added 1 M potassium 1,1,1,3,3,3-hexamethyldisilazane/tetrahydrofuran solution (6.6 mL) under ice-cooling. The reaction mixture was stirred at 0° C. for 30 min, and methyl iodide (2.00 g) was slowly added thereto at the same temperature. The reaction mixture was stirred overnight at room temperature, and the solvent was evaporated under reduced pressure. To the residue was added water, and the mixture was extracted with ethyl acetate. The extract was washed successively with water and saturated brine, and the solvent was evaporated under reduced pressure to give the title compound (1.10 g).

$^1$H NMR (400 MHz, CDCl$_3$) δ 3.33 (3H, s), 4.18 (2H, s), 6.73 (1H, dd, J=8.0, 5.2 Hz), 7.06 (1H, d, J=7.2 Hz), 7.78 (1H, d, J=4.4 Hz).

B) 4-nitrophenyl 1-methyl-2-oxo-2,3-dihydropyrido [2,3-b]pyrazine-4(1H)-carboxylate To a solution of 1-methyl-3,4-dihydropyrido[2,3-b] pyrazin-2(1H)-one (0.40 g) in a mixed solvent of N,N-dimethylacetamide (2 mL) and pyridine (1 mL) was added 4-nitrophenyl chloroformate (0.75 g). The reaction mixture was stirred at 45° C. for 30 min, and the solvent was evaporated under reduced pressure. To the residue was added water, and the mixture was extracted with ethyl acetate. The extract was washed with saturated brine, and dried over anhydrous sodium sulfate, and the solvent was evaporated under reduced pressure. The residue was purified by silica gel column chromatography (petroleum ether/ethyl acetate) to give the title compound (0.30 g).

$^1$H NMR (300 MHz, CDCl$_3$) δ 3.43 (3H, s), 4.67 (2H, s), 7.28 (1H, dd, J=8.1, 4.8 Hz), 7.42-7.47 (3H, m), 8.26-8.33 (3H, m).

C) 1-methyl-2-oxo-N-(1-(4-(trifluoromethoxy)phenyl)propyl)-2,3-dihydropyrido[2,3-b]pyrazine-4 (1H)-carboxamide The title compound was obtained in the same manner as in Step G of Example 7.

$^1$H NMR (300 MHz, CDCl$_3$) δ 0.97 (3H, t, J=7.5 Hz) 1.83-1.93 (2H, m), 3.36 (3H, s), 4.69 (2H, s), 4.91 (1H, q, J=6.9 Hz), 7.09 (1H, dd, J=7.8, 5.1 Hz), 7.18 (2H, d, J=8.4 Hz), 7.27-7.37 (3H, m), 8.02 (1H, d, J=4.8 Hz), 10.31 (1H, d, J=7.5 Hz).

Example 18

N-(1-(4-(difluoromethoxy)phenyl)propyl)-2-oxo-2,3-dihydropyrido[2,3-b]pyrazine-4(1H)-carboxamide

A) 4-(N-hydroxypropanimidoyl)phenol

The title compound was obtained in the same manner as in Step C of Example 1.
MS (API+): [M+H]$^+$ 166.1.

B) 4-(1-aminopropyl)phenol

The title compound was obtained in the same manner as in Step D of Example 1.
$^1$H NMR (300 MHz, DMSO-d$_6$) δ 0.74 (3H, t, J=7.5 Hz), 1.36-1.62 (2H, m), 3.56 (1H, t, J=6.6 Hz), 6.59-6.72 (2H, m), 7.02-7.14 (2H, m).

C) tert-butyl (1-(4-hydroxyphenyl)propyl)carbamate

To a solution of 4-(1-aminopropyl)phenol (10.4 g) in tetrahydrofuran (200 mL) were added triethylamine (11.5 mL) and di-tert-butyl dicarbonate (19.1 mL). The reaction mixture was stirred at room temperature for 2 hr, water was added thereto, and the mixture was extracted with ethyl acetate. The extract was washed with saturated brine, and dried over anhydrous sodium sulfate, and the solvent was evaporated under reduced pressure. The obtained solid was triturated with hexane/ethyl acetate, and washed with hexane/ethyl acetate to give the title compound (13.8 g).
MS (API−): [M−H]$^-$ 250.2.

D) tert-butyl (1-(4-(difluoromethoxy)phenyl)propyl)carbamate

Under chlorodifluoromethane atmosphere, to a solution of tert-butyl (1-(4-hydroxyphenyl)propyl)carbamate (833 mg) and benzyltriethylammonium chloride (226 mg) in tetrahydrofuran (20 mL) was slowly added 8 M aqueous sodium hydroxide solution under ice-cooling. The reaction mixture was stirred at room temperature for 2 hr, water was added thereto, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give the title compound (832 mg).
$^1$H NMR (300 MHz, DMSO-d$_6$) δ 0.81 (3H, t, J=7.3 Hz), 1.35 (9H, s), 1.49-1.71 (2H, m), 4.26-4.45 (1H, m), 6.90-7.47 (6H, m).

E) tert-butyl 1-(4-(difluoromethoxy)phenyl)propan-1-amine hydrochloride

To a solution of (1-(4-(difluoromethoxy)phenyl)propyl)carbamate (830 mg) in ethyl acetate (5 mL) was added 4 M hydrogen chloride/ethyl acetate (10 mL) solution. The reaction mixture was stirred at room temperature for 3 hr, and the solvent was evaporated under reduced pressure to give the title compound (643 mg).
$^1$H NMR (300 MHz, DMSO-d$_6$) δ 0.75 (3H, t, J=7.3 Hz), 1.67-2.10 (2H, m), 4.06-4.24 (1H, m), 6.99-7.62 (5H, m), 8.51 (3H, brs).

F) N-(1-(4-(difluoromethoxy)phenyl)propyl)-2-oxo-2,3-dihydropyrido[2,3-b]pyrazine-4(1H)-carboxamide The title compound was obtained in the same manner as in Step G of Example 7.
MS (API+): [M+H]$^+$ 377.1.
$^1$H NMR (300 MHz, DMSO-d$_6$) δ 0.86 (3H, t, J=7.3 Hz), 1.67-1.91 (2H, m), 4.41 (2H, s), 4.77 (1H, q, J=7.0 Hz), 6.91-7.50 (7H, m), 7.94-8.10 (1H, m), 10.30 (1H, d, J=7.5 Hz), 10.82 (1H, brs).

Example 19

2-oxo-N-(1-(4-(trifluoromethoxy)phenyl)propyl)-7-(trifluoromethyl)-2,3-dihydropyrido[2,3-b]pyrazine-4(1H)-carboxamide

A) methyl N-(3-nitro-5-(trifluoromethyl)pyridin-2-yl)glycinate

To a solution of methyl glycinate hydrochloride (13.9 g) and 2-chloro-3-nitro-5-(trifluoromethyl)pyridine (5.0 g) in ethanol (100 mL) was added triethylamine (15.4 mL). The reaction mixture was heated at reflux for 5 hr, and the solvent was evaporated under reduced pressure. The residue was triturated with water, and the solid was collected by filtration, and washed with ethanol to give the title compound (5.09 g).
$^1$H NMR (400 MHz, CDCl$_3$) δ 3.82 (3H, s), 4.43 (2H, d, J=5.2 Hz), 8.63 (1H, d, J=2.0 Hz), 8.68 (1H, d, J=2.4 Hz), 8.74 (1H, s).

B) 7-(trifluoromethyl)-3,4-dihydropyrido[2,3-b]pyrazin-2(1H)-one

To a solution of methyl N-(3-nitro-5-(trifluoromethyl)pyridin-2-yl)glycinate (5.09 g) in ethanol (200 mL) was added tin(II) chloride dihydrate (20.6 g). The reaction mixture was stirred at 80° C. for 2 hr, and the solvent was evaporated under reduced pressure. The residue was dissolved in ethyl acetate/ethanol, the pH of the solution was adjusted to 9 with saturated aqueous ammonia solution, and the insoluble substance was filtered off using Celite. The filtrate was concentrated under reduced pressure to give the title compound (1.10 g).
$^1$H NMR (400 MHz, DMSO-d$_6$) δ 4.04 (2H, s), 7.05 (1H, d, J=1.6 Hz), 7.61 (1H, s), 7.93 (1H, s), 10.61 (1H, brs).

C) 4-nitrophenyl 2-oxo-7-(trifluoromethyl)-2,3-dihydropyrido[2,3-b]pyrazine-4(1H)-carboxylate To a solution of 7-(trifluoromethyl)-3,4-dihydropyrido[2,3-b]pyrazin-2(1H)-one (300 mg) in a mixed solvent of N,N-dimethylacetamide (2 mL) and pyridine (0.5 mL) was added 4-nitrophenyl chloroformate (418 mg). The reaction mixture was stirred overnight at 45° C., and the solvent was evaporated under reduced pressure. The residue was purified by silica gel column chromatography (petroleum ether/ethyl acetate) to give the title compound (220 mg).
$^1$H NMR (400 MHz, CDCl$_3$) δ 4.63 (2H, s), 7.45 (2H, d, J=8.8 Hz), 7.57 (1H, s), 8.31 (2H, d, J=9.2 Hz), 8.44 (1H, s).

D) 2-oxo-N-(1-(4-(trifluoromethoxy)phenyl)propyl)-7-(trifluoromethyl)-2,3-dihydropyrido[2,3-b]pyrazine-4(1H)-carboxamide To a solution of 4-nitrophenyl 2-oxo-7-(trifluoromethyl)-2,3-dihydropyrido[2,3-b]pyrazine-4(1H)-carboxylate (220 mg) in N,N-dimethylformamide (3 mL) were added 1-(4-(trifluoromethoxy)phenyl)propan-1-amine hydrochloride (191 mg) and triethylamine (0.3 mL) at room temperature. The reaction mixture was stirred overnight at room temperature, and the solvent was evaporated under reduced pressure. The residue was purified by silica gel column chromatography (petroleum ether/ethyl acetate) to give a crude product. The crude product was purified by HPLC (C18, mobile phase: water/acetonitrile (containing 0.1% TFA)), to the obtained fraction was added saturated aqueous sodium hydrogen carbonate solution, and the mixture was extracted with ethyl acetate. The extract was dried over anhydrous sodium sulfate, and concentrated under reduced pressure to give the title compound (72 mg).

MS (API+): [M+H]$^+$ 463.2.

$^1$H NMR (400 MHz, CDCl$_3$) δ 0.97 (3H, t, J=4.0 Hz) 1.84-1.92 (2H, m), 4.71 (2H, s), 4.91 (1H, q, J=6.8 Hz), 7.17 (1H, d, J=8.0 Hz), 7.33-7.36 (3H, m), 8.28 (1H, s), 9.62 (1H, s), 10.33 (1H, d, J=7.2 Hz).

Example 20

2-oxo-7-phenyl-N-(1-(4-(trifluoromethoxy)phenyl) propyl)-2,3-dihydropyrido[2,3-b]pyrazine-4(1H)-carboxamide To a solution of 7-iodo-2-oxo-N-(1-(4-(trifluoromethoxy) phenyl)propyl)-2,3-dihydropyrido[2,3-b]pyrazine-4(1H)-carboxamide (140 mg), phenylboronic acid (49 mg) and tetrakis(triphenylphosphine)palladium(0) (37 mg) in 1,2-dimethoxyethane (4 mL) was added 2 M aqueous sodium carbonate solution (2 mL) at room temperature. The reaction mixture was stirred overnight at reflux, and extracted with ethyl acetate. The extract was washed with saturated brine, and dried over anhydrous sodium sulfate, and the solvent was evaporated under reduced pressure. The residue was purified by preparative TLC (petroleum ether/ethyl acetate) to give the title compound (72 mg).

MS (API+): [M+H]$^+$ 471.3.

$^1$H NMR (400 MHz, CDCl$_3$) δ 0.98 (3H, t, J=7.2 Hz), 1.87-1.93 (2H, m), 4.71 (1H, d, J=1.2 Hz), 4.92 (1H, q, J=6.8 Hz), 7.18 (2H, d, J=7.6 Hz), 7.36-7.38 (3H, m), 7.41-7.45 (1H, m), 7.47-7.51 (2H, m), 7.55-7.57 (2H, m), 8.24 (1H, d, J=2.0 Hz), 8.79 (1H, s), 10.41 (1H, d, J=7.2 Hz).

Example 21

6-bromo-3-oxo-N-(1-(4-(trifluoromethoxy)phenyl) propyl)-3,4-dihydropyrazino[2,3-b]pyrazine-1(2H)-carboxamide A) ethyl N-(3,5-dibromopyrazin-2-yl)glycinate To a solution of 3,5-dibromopyrazin-2-amine (16.0 g) and cesium carbonate (26.7 g) in N,N-dimethylformamide (90 mL) was slowly added 2-chloroethyl acetate (8.1 mL) at room temperature. The reaction mixture was stirred overnight at 65° C. under nitrogen atmosphere, water was added thereto, and the mixture was extracted with ethyl acetate. The extract was washed successively with water and saturated brine, and dried over anhydrous sodium sulfate, and the solvent was evaporated under reduced pressure. The residue was purified by silica gel column chromatography (petroleum ether/ethyl acetate) to give the title compound (8.6 g).

$^1$H NMR (400 MHz, CDCl$_3$) δ 1.31 (3H, t, J=7.2 Hz), 4.16 (2H, d, J=5.6 Hz), 4.25 (2H, q, J=7.2 Hz), 5.75 (1H, brs), 8.04 (1H, s).

B) 7-bromo-1-(2,4-dimethoxybenzyl)-3,4-dihydropyrazino[2,3-b]pyrazin-2(1H)-one

To a solution of ethyl N-(3,5-dibromopyrazin-2-yl)glycinate (4.20 g) and 2,4-dimethoxybenzyl amine (2.20 g) in dimethyl sulfoxide (5 mL) was added diisopropylethylamine (5 mL) at room temperature. The reaction mixture was stirred at 135° C. for 2.5 hr using microwave, and cooled to room temperature, water was added thereto, and the mixture was extracted with ethyl acetate. The extract was washed successively with water and saturated brine, and dried over anhydrous sodium sulfate, and the solvent was evaporated under reduced pressure. The residue was crystallized from methanol to give the title compound (1.2 g).

$^1$H NMR (300 MHz, CDCl$_3$) δ 3.77 (3H, s), 3.81 (3H, s), 4.29 (2H, s), 4.92 (1H, s), 5.22 (2H, s), 6.38-6.42 (2H, m), 7.10 (1H, d, J=8.1 Hz), 7.67 (1H, s).

C) 6-bromo-4-(2,4-dimethoxybenzyl)-3-oxo-N-(1-(4-(trifluoromethoxy)phenyl)propyl)-3,4-dihydropyrazino[2,3-b]pyrazine-1(2H)-carboxamide Under nitrogen atmosphere, to a solution of 7-bromo-1-(2,4-dimethoxybenzyl)-3,4-dihydropyrazino[2,3-b]pyrazin-2(1H)-one (1.7 g) in tetrahydrofuran (45 mL) was slowly added triphosgene (0.81 g) at room temperature. The reaction mixture was stirred at 50° C. for 2.5 hr, and the solvent was evaporated under reduced pressure. The residue was diluted with tetrahydrofuran (30 mL), and the mixture was slowly added to a solution of 1-(4-(trifluoromethoxy)phenyl)propan-1-amine hydrochloride (1.26 g) and triethylamine (2.15 mL) in tetrahydrofuran (45 mL) at room temperature. The reaction mixture was stirred at 60° C. for 30 min, and the solvent was evaporated under reduced pressure. The residue was purified by silica gel column chromatography (petroleum ether/ethyl acetate) to give the title compound (2.5 g).

$^1$H NMR (400 MHz, CDCl$_3$) δ 0.93 (3H, t, J=7.2 Hz), 1.79-1.91 (2H, m), 3.77 (3H, s), 3.79 (3H, s), 4.72 (2H, dd, J=18.8, 14.8 Hz), 4.86 (1H, q, J=7.2 Hz), 5.23 (2H, dd, J=16.8, 14.4 Hz), 6.38-6.41 (2H, m), 7.15-7.20 (3H, m), 7.27-7.33 (2H, m), 7.88 (1H, s), 9.69 (1H, d, J=7.2 Hz).

D) 6-bromo-3-oxo-N-(1-(4-(trifluoromethoxy)phenyl)propyl)-3,4-dihydropyrazino[2,3-b]pyrazine-1 (2H)-carboxamide To 6-bromo-4-(2,4-dimethoxybenzyl)-3-oxo-N-(1-(4-(trifluoromethoxy)phenyl)propyl)-3,4-dihydropyrazino[2,3-b] pyrazine-1(2H)-carboxamide (300 mg) was added trifluoroacetic acid (3 mL) at room temperature. The reaction mixture was stirred at 75° C. for 1 hr under nitrogen atmosphere, water was added thereto. The pH of the mixture was adjusted to 10 with 2 M aqueous sodium hydroxide solution, and the mixture was extracted with ethyl acetate. The extract was washed successively with water and saturated brine, and dried over anhydrous sodium sulfate, and the solvent was evaporated under reduced pressure. The residue was purified by silica gel column chromatography (petroleum ether/ethyl acetate) to give the title compound (40 mg).

MS (API−): [M−H]$^−$ 471.9.

$^1$H NMR (400 MHz, CDCl$_3$) δ 0.94 (3H, t, J=7.2 Hz), 1.83-1.91 (2H, m), 4.71 (2H, s), 4.87 (1H, q, J=7.2 Hz), 7.17 (2H, d, J=8.4 Hz), 7.31 (2H, d, J=8.4 Hz), 8.00 (1H, s), 8.42 (1H, s), 9.70 (1H, d, J=6.8 Hz).

Example 22

3-oxo-N-(1-(4-(trifluoromethoxy)phenyl)propyl)-3,4-dihydropyrazino[2,3-b]pyrazine-1(2H)-carboxamide A) 4-(2,4-dimethoxybenzyl)-3-oxo-N-(1-(4-(trifluoromethoxy)phenyl)propyl)-3,4-dihydropyrazino[2,3-b]pyrazine-1(2H)-carboxamide To a solution of 6-bromo-4-(2,4-dimethoxybenzyl)-3-oxo-N-(1-(4-(trifluoromethoxy)phenyl)propyl)-3,4-dihydropyrazino[2,3-b]pyrazine-1(2H)-carboxamide (800 mg) in a mixed solvent of tetrahydrofuran (10 mL) and methanol (10 mL) was added 10% palladium-carbon (containing 50% water, 120 mg). The reaction mixture was stirred overnight at 30° C. under hydrogen atmosphere, the catalyst was filtered off, and the filtrate was concentrated under reduced pressure. The residue was purified by silica gel column chromatography (petroleum ether/ethyl acetate) to give the title compound (610 mg).
$^1$H NMR (400 MHz, CDCl$_3$) δ 0.95 (3H, t, J=6.4 Hz), 1.85-1.91 (2H, m), 3.76 (3H, s), 3.79 (3H, s), 4.77 (2H, s), 4.90 (1H, q, J=7.2 Hz), 5.27 (2H, s), 6.35 (1H, dd, J=11.2, 3.2 Hz), 6.43 (1H, d, J=3.2 Hz), 6.94 (1H, d, J=11.2 Hz), 7.17 (2H, d, J=10.8 Hz), 7.34 (2H, d, J=10.8 Hz), 7.81 (1H, d, J=3.6 Hz), 7.93 (1H, d, J=3.6 Hz), 10.12 (1H, d, J=10.0 Hz).

B) 3-oxo-N-(1-(4-(trifluoromethoxy)phenyl)propyl)-3,4-dihydropyrazino[2,3-b]pyrazine-1(2H)-carboxamide The title compound was obtained in the same manner as in Step D of Example 21.
MS (API−): [M−H]$^−$ 394.0.
$^1$H NMR (400 MHz, CDCl$_3$) δ 0.96 (3H, t, J=7.6 Hz), 1.84-1.93 (2H, m), 4.72 (2H, s), 4.89 (1H, q, J=7.6 Hz), 7.17 (2H, d, J=8.8 Hz), 7.33 (2H, d, J=8.8 Hz), 7.91 (1H, d, J=2.8 Hz), 7.94 (1H, d, J=2.8 Hz), 9.01 (1H, s), 10.09 (1H, d, J=7.2 Hz).

Example 23

6-methyl-3-oxo-N-(1-(4-(trifluoromethoxy)phenyl)propyl)-3,4-dihydropyrazino[2,3-b]pyrazine-1(2H)-carboxamide A) 4-(2,4-dimethoxybenzyl)-6-methyl-3-oxo-N-(1-(4-(trifluoromethoxy)phenyl)propyl)-3,4-dihydropyrazino[2,3-b]pyrazine-1(2H)-carboxamide Under nitrogen atmosphere, to a solution of 6-bromo-4-(2,4-dimethoxybenzyl)-3-oxo-N-(1-(4-(trifluoromethoxy)phenyl)propyl)-3,4-dihydropyrazino[2,3-b]pyrazine-1(2H)-carboxamide (1.0 g) and (1,1-bis(diphenylphosphino)ferrocene)dichloropalladium(II) (150 mg) in 1,4-dioxane (15 mL) was added 1 M dimethylzinc(II)/hexane solution (4 mL) at room temperature. The reaction mixture was stirred at 80° C. for 30 min under nitrogen atmosphere, water was added thereto, and the mixture was extracted with ethyl acetate. The extract was washed successively with water and saturated brine, and dried over anhydrous sodium sulfate, and the solvent was evaporated under reduced pressure. The residue was purified by preparative TLC (petroleum ether/ethyl acetate) to give the title compound (730 mg).
$^1$H NMR (400 MHz, CDCl$_3$) δ 0.93 (3H, t, J=7.2 Hz), 1.83-1.88 (2H, m), 2.39 (3H, s), 3.76 (3H, s), 3.79 (3H, s), 4.73 (2H, s), 4.89 (1H, q, J=7.2 Hz), 5.27 (2H, s), 6.36 (1H, dd, J=8.0, 2.4 Hz), 6.41 (1H, d, J=2.4 Hz), 7.03 (1H, d, J=8.8 Hz), 7.16 (2H, d, J=8.0 Hz), 7.32 (2H, d, J=8.0 Hz), 7.66 (1H, s), 10.0 (1H, d, J=7.2 Hz).

B) 6-methyl-3-oxo-N-(1-(4-(trifluoromethoxy)phenyl)propyl)-3,4-dihydropyrazino[2,3-b]pyrazine-1(2H)-carboxamide To 4-(2,4-dimethoxybenzyl)-6-methyl-3-oxo-N-(1-(4-(trifluoromethoxy)phenyl)propyl)-3,4-dihydropyrazino[2,3-b]pyrazine-1(2H)-carboxamide (730 mg) was added trifluoroacetic acid (10 mL) at room temperature. The reaction mixture was stirred at 70° C. for 15 min, and water was added thereto. The pH of the mixture was adjusted to 10 or more with 4 M aqueous sodium hydroxide solution, and the mixture was extracted with dichloromethane. The extract was dried over anhydrous sodium sulfate, and the solvent was evaporated under reduced pressure. The residue was purified by HPLC (C18, mobile phase: water/acetonitrile (containing 0.1% TFA)), to the obtained fraction was added saturated aqueous sodium hydrogen carbonate solution, and the mixture was extracted with ethyl acetate. The extract was dried over anhydrous sodium sulfate, and concentrated under reduced pressure to give the title compound (150 mg).
MS (API+): [M+H]$^+$ 410.2.
$^1$H NMR (400 MHz, CDCl$_3$) δ 0.94 (3H, t, J=7.2 Hz), 1.82-1.90 (2H, m), 2.45 (3H, s), 4.70 (2H, s), 4.88 (1H, q, J=7.2 Hz), 7.17 (2H, d, J=8.4 Hz), 7.32 (2H, d, J=8.4 Hz), 7.77 (1H, s), 8.56 (1H, s), 9.98 (1H, d, J=6.8 Hz).

Example 24

N-((1R)-2-methoxy-1-(4-(trifluoromethoxy)phenyl)ethyl)-2-oxo-2,3-dihydropyrido[2,3-b]pyrazine-4(1H)-carboxamide Racemic N-(2-methoxy-1-(4-(trifluoromethoxy)phenyl)ethyl)-2-oxo-2,3-dihydropyrido[2,3-b]pyrazine-4(1H)-carboxamide (548 mg) was resolved by HPLC (column: CHIRALPAK IC, 50 mmID×500 mmL, manufactured by Daicel Chemical Industries, Ltd., mobile phase: hexane/ethanol=400/600) to give the title compound having a shorter retention time (265 mg).
MS (API+): [M+H]$^+$ 411.2.
$^1$H NMR (300 MHz, DMSO-d$_6$) δ 3.28 (3H, s), 3.54-3.73 (2H, m), 4.31-4.53 (2H, m), 4.97-5.14 (1H, m), 7.11 (1H, dd, J=7.9, 4.9 Hz), 7.25-7.39 (3H, m), 7.40-7.54 (2H, m), 8.00 (1H, dd, J=4.9, 1.5 Hz), 10.51 (1H, d, J=7.5 Hz), 10.83 (1H, brs).

Example 25

N-((1S)-2-methoxy-1-(4-(trifluoromethoxy)phenyl)ethyl)-2-oxo-2,3-dihydropyrido[2,3-b]pyrazine-4(1H)-carboxamide Racemic N-(2-methoxy-1-(4-(trifluoromethoxy)phenyl)ethyl)-2-oxo-2,3-dihydropyrido[2,3-b]pyrazine-4(1H)-carboxamide (548 mg) was resolved by HPLC (column: CHIRALPAK IC, 50 mmID×500 mmL, manufactured by Daicel Chemical Industries, Ltd., mobile phase: hexane/ethanol=400/600) to give the title compound having a longer retention time (273 mg).
MS (API+): [M+H]$^+$ 411.1.
$^1$H NMR (300 MHz, DMSO-d$_6$) δ 3.28 (3H, s), 3.55-3.71 (2H, m), 4.33-4.51 (2H, m), 4.99-5.14 (1H, m), 7.11 (1H, dd, J=7.7, 5.1 Hz), 7.26-7.37 (3H, m), 7.42-7.53 (2H, m), 8.00 (1H, dd, J=4.9, 1.9 Hz), 10.51 (1H, d, J=7.5 Hz), 10.83 (1H, brs).

Example 26

7-iodo-2-oxo-N-(1-(4-(trifluoromethoxy)phenyl)propyl)-2,3-dihydropyrido[2,3-b]pyrazine-4(1H)-carboxamide A) methyl N-(5-iodo-3-nitropyridin-2-yl)glycinate The title compound was obtained in the same manner as in Step A of Example 19.
$^1$H NMR (400 MHz, CDCl$_3$) δ 3.81 (3H, s), 4.37 (2H, d, J=7.6 Hz), 8.45 (1H, s), 8.54 (1H, d, J=2.8 Hz), 8.71 (1H, d, J=2.8 Hz).

B) 7-iodo-3,4-dihydropyrido[2,3-b]pyrazin-2(1H)-one

The title compound was obtained in the same manner as in. Step B of Example 19
$^1$H NMR (400 MHz, DMSO-d$_6$) δ 4.00 (2H, s), 7.17 (1H, d, J=1.6 Hz), 7.50 (1H, brs), 7.77 (1H, d, J=1.6 Hz), 10.66 (1H, s).

C) 7-iodo-1-((2-(trimethylsilyl)ethoxy)methyl)-3,4-dihydropyrido[2,3-b]pyrazin-2(1H)-one Under nitrogen atmosphere, to a solution of 7-iodo-3,4-dihydropyrido[2,3-b]pyrazin-2(1H)-one (12.5 g) in a mixed solvent of N,N-dimethylformamide (200 mL) and dimethyl sulfoxide (600 mL) was slowly added 1 M potassium 1,1,1,3,3,3-hexamethyldisilazane/tetrahydrofuran solution (63.6 mL) under ice-cooling. The reaction mixture was stirred at 0° C. for 30 min, and [2-(chloromethoxy)ethyl](trimethyl)silane (11.3 mL) was slowly added thereto at the same temperature. The reaction mixture was stirred at room temperature for 2 hr, and the solvent was evaporated under reduced pressure. To the residue was added aqueous sodium carbonate solution, and the mixture was extracted with ethyl acetate. The extract was washed successively with water and saturated brine, and the solvent was evaporated under reduced pressure. The residue was purified by silica gel column chromatography (dichloromethane/ethyl acetate) to give the title compound (6.86 g).
$^1$H NMR (400 MHz, DMSO-d$_6$) δ 0.01 (9H, s), 0.90 (2H, t, J=7.6 Hz), 3.59 (2H, t, J=8.0 Hz), 4.07 (2H, d, J=1.6 Hz), 5.31 (2H, s), 7.55 (1H, d, J=1.6 Hz), 7.92 (1H, d, J=2.0 Hz).

D) 7-iodo-2-oxo-N-(1-(4-(trifluoromethoxy)phenyl)propyl)-1-((2-(trimethylsilyl)ethoxy)methyl)-2,3-dihydropyrido[2,3-b]pyrazine-4(1H)-carboxamide Under nitrogen atmosphere, to a solution of 7-iodo-1-((2-(trimethylsilyl)ethoxy)methyl)-3,4-dihydropyrido[2,3-b]pyrazin-2(1H)-one (4.05 g) in tetrahydrofuran (150 mL) was slowly added a solution of triphosgene (2.37 g) in tetrahydrofuran (15 mL) at room temperature. The reaction mixture was stirred at 40° C. for 2 hr, and the solvent was evaporated under reduced pressure. The residue was diluted with tetrahydrofuran (40 mL), and the mixture was slowly added to a solution of 1-(4-(trifluoromethoxy)phenyl)propan-1-amine hydrochloride (3.07 g) and triethylamine (3.03 g) in tetrahydrofuran (50 mL) at room temperature. The reaction mixture was stirred overnight at 60° C., and the solvent was evaporated under reduced pressure. The residue was purified by silica gel column chromatography (petroleum ether/ethyl acetate) to give the title compound (4.08 g).
$^1$H NMR (400 MHz, CDCl$_3$) δ 0.01 (9H, s), 0.93 (3H, t, J=9.2 Hz), 1.80-1.86 (2H, m), 3.65 (1H, t, J=8.0 Hz), 4.66 (2H, dd, J=17.6, 7.6 Hz), 4.87 (1H, q, J=6.8 Hz), 5.27 (2H, dd, J=16.8, 10.8 Hz), 7.16 (2H, d, J=8.0 Hz), 7.31 (2H, d, J=8.8 Hz), 7.95 (1H, d, J=1.6 Hz), 8.24 (1H, d, J=1.6 Hz), 9.86 (1H, d, J=7.2 Hz).

E) 7-iodo-2-oxo-N-(1-(4-(trifluoromethoxy)phenyl)propyl)-2,3-dihydropyrido[2,3-b]pyrazine-4(1H)-carboxamide To 7-iodo-2-oxo-N-(1-(4-(trifluoromethoxy)phenyl)propyl)-1-((2-(trimethylsilyl)ethoxy)methyl)-2,3-dihydropyrido[2,3-b]pyrazine-4(1H)-carboxamide (4.08 g) were added trifluoroacetic acid (18 mL) and water (2 mL) at room temperature. The reaction mixture was stirred at room temperature for 1 hr, and the solvent was evaporated under reduced pressure. To the residue was added aqueous sodium hydrogen carbonate solution, and the mixture was extracted with ethyl acetate. The extract was washed with saturated brine, and dried over anhydrous sodium sulfate, and the solvent was evaporated under reduced pressure. The residue was purified by silica gel column chromatography (petroleum ether/ethyl acetate) to give the title compound (2.64 g).
MS (API+): [M+H]$^+$ 521.1.
$^1$H NMR (400 MHz, CDCl$_3$) δ 0.95 (3H, t, J=7.2 Hz), 1.81-1.87 (2H, m), 4.67 (1H, d, J=2.0 Hz), 4.87 (1H, q, J=6.8 Hz), 7.17 (2H, d, J=8.0 Hz), 7.32 (2H, d, J=8.4 Hz), 7.44 (1H, d, J=2.0 Hz), 8.19 (1H, d, J=2.0 Hz), 9.20 (1H, s), 10.07 (1H, d, J=7.2 Hz).

Example 27

2-oxo-N-(1-(4-(trifluoromethoxy)phenyl)propyl)-7-vinyl-2,3-dihydropyrido[2,3-b]pyrazine-4(1H)-carboxamide To a solution of 7-iodo-2-oxo-N-(1-(4-(trifluoromethoxy)phenyl)propyl)-2,3-dihydropyrido[2,3-b]pyrazine-4(1H)-carboxamide (520 mg), 2-ethenyl-4,4,5,5-tetramethyl-1,3,2-dioxaborolane (231 mg) and tetrakistriphenylphosphine palladium(0) (116 mg) in 1,2-dimethoxyethane (12 mL) was added 2 M aqueous sodium carbonate solution (4 mL) at room temperature. The reaction mixture was stirred overnight at reflux, and extracted with ethyl acetate. The extract was washed with saturated brine, and dried over anhydrous sodium sulfate, and the solvent was evaporated under reduced pressure. The residue was purified by silica gel column chromatography (petroleum ether/ethyl acetate) to give the title compound (372 mg).
MS (API+): [M+H]$^+$ 421.1.
$^1$H NMR (400 MHz, CDCl$_3$) δ 0.96 (3H, t, J=7.2 Hz), 1.83-1.90 (2H, m), 4.80 (1H, d, J=0.8 Hz), 4.90 (1H, q, J=6.8 Hz), 5.38 (1H, d, J=10.8 Hz), 5.76 (1H, d, J=17.6 Hz), 6.65 (1H, dd, J=18.0, 10.8 Hz), 7.17 (2H, d, J=7.6 Hz), 7.24 (1H, d, J=1.6 Hz), 7.34 (2H, d, J=8.8 Hz), 8.00 (1H, d, J=1.6 Hz), 9.12 (1H, s), 10.38 (1H, d, J=7.2 Hz).

Example 28

N-(1-(biphenyl-4-yl)propyl)-2-oxo-2,3-dihydropyrido[2,3-b]pyrazine-4(1H)-carboxamide A) 4-(1-(((2-oxo-2,3-dihydropyrido[2,3-b]pyrazine-4(1H)-yl)carbonyl) amino)propyl)phenyl trifluoromethanesulfonate To a solution of N-(1-(4-hydroxyphenyl)propyl)-2-oxo-2,3-dihydropyrido[2,3-b]pyrazine-4(1H)-carboxamide (1.00 g) in pyridine (30 mL) was slowly added trifluoromethanesulfonic anhydride (0.621 mL) under ice-cooling. The reaction mixture was stirred at room temperature for 3 hr, and the solvent was evaporated under reduced pressure. To the residue was added water, the mixture was washed with 0.5 M hydrochloric acid, and dried over anhydrous sodium sulfate, and the solvent was evaporated under reduced pressure. The residue was purified by silica gel column chromatography (hexane/ethyl acetate) to give the title compound (1.34 g).

MS (API+): [M+H]$^+$ 459.1.

B) N-(1-(biphenyl-4-yl)propyl)-2-oxo-2,3-dihydropyrido[2,3-b]pyrazine-4(1H)-carboxamide To a solution of 4-(1-(((2-oxo-2,3-dihydropyrido[2,3-b]pyrazine-4(1H)-yl)carbonyl) amino)propyl)phenyl trifluoromethanesulfonate (125 mg) in a mixed solvent of water (1.5 mL) and 1,2-dimethoxyethane (3 mL) were added phenylboronic acid (36.5 mg), potassium carbonate (150 mg) and tetrakistriphenylphosphine palladium(0) (15.7 mg) at room temperature. The reaction mixture was stirred at 150° C. for 20 min under nitrogen atmosphere using microwave, water was added thereto, and the mixture was extracted with ethyl acetate. The extract was dried over anhydrous sodium sulfate, and the solvent was evaporated under reduced pressure. The residue was purified by silica gel column chromatography (hexane/ethyl acetate) to give a crude product. The crude product was purified by HPLC (C18, mobile phase: water/acetonitrile (containing 0.1% TFA)), to the obtained fraction was added saturated aqueous sodium hydrogen carbonate solution, and the mixture was extracted with ethyl acetate. The extract was dried over anhydrous sodium sulfate, and concentrated under reduced pressure to give the title compound (29.8 mg).

MS (API+): [M+H]$^+$ 387.2.

$^1$H NMR (300 MHz, DMSO-d$_6$) δ 0.90 (3H, t, J=7.3 Hz), 1.73-1.94 (2H, m), 4.43 (2H, s), 4.82 (1H, q, J=6.9 Hz), 7.11 (1H, dd, J=7.5, 4.9 Hz), 7.26-7.52 (6H, m), 7.56-7.71 (4H, m), 8.03 (1H, dd, J=4.9, 1.5 Hz), 10.36 (1H, d, J=7.9 Hz), 10.82 (1H, brs).

Example 29

7-ethyl-2-oxo-N-(1-(4-(trifluoromethoxy)phenyl) propyl)-2,3-dihydropyrido[2,3-b]pyrazine-4(1H)-carboxamide To a solution of 2-oxo-N-(1-(4-(trifluoromethoxy)phenyl)propyl)-7-vinyl-2,3-dihydropyrido[2,3-b]pyrazine-4(1H)-carboxamide (177 mg) in methanol (25 mL) was added 10% palladium-carbon (containing 50% water, 18 mg) under nitrogen atmosphere. The reaction mixture was stirred at room temperature for 2 hr under hydrogen atmosphere, the catalyst was filtered off, and the filtrate was concentrated under reduced pressure. The residue was purified by HPLC (C18, mobile phase: water/acetonitrile (containing 0.1% TFA)), to the obtained fraction was added saturated aqueous sodium hydrogen carbonate solution, and the mixture was extracted with ethyl acetate. The extract was dried over anhydrous sodium sulfate, and concentrated under reduced pressure to give the title compound (135 mg).

MS (API+): [M+H]$^+$ 423.1.

$^1$H NMR (400 MHz, CDCl$_3$) δ 0.95 (3H, t, J=7.2 Hz), 1.26 (3H, t, J=7.6 Hz), 1.82-1.89 (2H, m), 2.63 (2H, q, J=7.6 Hz), 4.66 (2H, dd, J=20.0, 18.4 Hz), 4.90 (1H, q, J=7.2 Hz), 7.04 (1H, d, J=1.6 Hz), 7.16 (1H, d, J=8.4 Hz), 7.34 (2H, d, J=8.8 Hz), 7.85 (1H, d, J=1.6 Hz), 9.32 (1H, brs), 10.38 (1H, d, J=7.2 Hz).

Example 30

N-(1-(6-methoxypyridazin-3-yl)propyl)-2-oxo-2,3-dihydropyrido[2,3-b]pyrazine-4(1H)-carboxamide A) 6-methoxypyridazine-3-carbonitrile To a solution of 3-chloro-6-methoxypyridazine (5 g) and zinc cyanide (4.87 g) in N,N-dimethylformamide (100 mL) were added 1,1'-bis(diphenylphosphino)ferrocene (1.917 g) and tris(dibenzylideneacetone)dipalladium(0) (1.584 g). The reaction mixture was stirred at 100° C. for 2 days under nitrogen atmosphere, saturated brine was added thereto, and the mixture was extracted with ethyl acetate and tetrahydrofuran. The extract was washed with saturated brine, and dried over anhydrous magnesium sulfate, and the solvent was evaporated under reduced pressure. The residue was purified by silica gel column chromatography (ethyl acetate/hexane) to give the title compound (3.20 g).

$^1$H NMR (300 MHz, CDCl$_3$) δ 4.19-4.28 (3H, m), 7.03-7.15 (1H, m), 7.64-7.73 (1H, m).

B) 1-(6-methoxypyridazin-3-yl)propan-1-one

To a solution of 6-methoxypyridazine-3-carbonitrile (1.9 g) in tetrahydrofuran (30 mL) was added 3 M ethylmagnesium bromide/diethyl ether solution (5.62 mL) under ice-cooling. The reaction mixture was stirred at 0° C. for 1 hr under nitrogen atmosphere, 1 M hydrochloric acid was added thereto at the same temperature, and the mixture was stirred at room temperature for further 5 min. The reaction mixture was neutralized with saturated aqueous sodium hydrogen carbonate solution, and extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (0.323 g).

$^1$H NMR (300 MHz, CDCl$_3$) δ 1.25 (3H, t, J=7.2 Hz), 3.35 (2H, q, J=7.4 Hz), 4.23 (3H, s), 7.06 (1H, d, J=9.4 Hz), 8.05 (1H, d, J=9.0 Hz).

C) 1-(6-methoxypyridazin-3-yl)propan-1-amine

The title compound was obtained in the same manner as in Steps D-E of Example 2.

MS (API+): [M+H]$^+$ 168.2.

D) N-(1-(6-methoxypyridazin-3-yl)propyl)-2-oxo-2,3-dihydropyrido[2,3-b]pyrazine-4(1H)-carboxamide The title compound was obtained in the same manner as in Step G of Example 7.
MS (API+): [M+H]$^+$ 343.2.
$^1$H NMR (300 MHz, DMSO-d$_6$) δ 0.86 (3H, t, J=7.3 Hz), 1.70-1.99 (2H, m), 4.01 (3H, s), 4.43 (2H, s), 5.01 (1H, q, J=7.2 Hz), 7.11 (1H, dd, J=7.9, 4.9 Hz), 7.18 (1H, d, J=9.0 Hz), 7.32 (1H, dd, J=7.9, 1.5 Hz), 7.62 (1H, d, J=9.0 Hz), 8.02 (1H, dd, J=4.9, 1.5 Hz), 10.42 (1H, d, J=7.5 Hz), 10.81 (1H, s).

Example 31

N-(1-(3-fluoro-4-(trifluoromethoxy)phenyl)propyl)-2-oxo-2,3-dihydropyrido[2,3-b]pyrazine-4(1H)-carboxamide A) 3-fluoro-N-methoxy-N-methyl-4-(trifluoromethoxy)benzamide To a solution of 3-fluoro-4-(trifluoromethoxy)benzoic acid (20 g), N,O-dimethylhydroxylamine hydrochloride (10.5 g) and triethylamine (24.9 mL) in N,N-dimethylformamide (300 mL) were added 1-hydroxybenzotriazole monohydrate (16.4 g) and 1-(3-dimethylaminopropyl)-3-ethylcarbodiimide hydrochloride (20.5 g) at room temperature. The reaction mixture was stirred overnight at room temperature, saturated aqueous sodium hydrogen carbonate solution was added thereto, and the mixture was extracted with ethyl acetate. The extract was washed with saturated brine, and dried over anhydrous magnesium sulfate, and the solvent was evaporated under reduced pressure to give the title compound (22.9 g).
$^1$H NMR (300 MHz, CDCl$_3$) δ 3.38 (3H, s), 3.56 (3H, s), 7.30-7.42 (1H, m), 7.51-7.65 (2H, m).

B) 1-(3-fluoro-4-(trifluoromethoxy)phenyl)propan-1-amine hydrochloride

The title compound was obtained in the same manner as in Steps C-F of Example 2.
MS (API+), found: 221.1.

C) N-(1-(3-fluoro-4-(trifluoromethoxy)phenyl)propyl)-2-oxo-2,3-dihydropyrido[2,3-b]pyrazine-4(1H)-carboxamide The title compound was obtained in the same manner as in Step G of Example 7.
MS (API+): [M+H]$^+$ 413.1.
$^1$H NMR (300 MHz, DMSO-d$_6$) δ 0.77-0.95 (3H, m), 1.81 (2H, quin, J=7.3 Hz), 4.35-4.47 (2H, m), 4.81 (1H, q, J=7.2 Hz), 7.11 (1H, dd, J=7.7, 5.1 Hz), 7.27 (1H, d, J=8.3 Hz), 7.32 (1H, dd, J=7.9, 1.5 Hz), 7.44-7.58 (2H, m), 8.02 (1H, dd, J=4.9, 1.5 Hz), 10.30 (1H, d, J=7.2 Hz), 10.81 (1H, s).

Example 32

N-(1-(2-methoxy-4-(trifluoromethoxy)phenyl)propyl)-2-oxo-2,3-dihydropyrido[2,3-b]pyrazine-4(1H)-carboxamide The title compound was obtained in the same manner as in Step A of Example 31, Steps C-F of Example 2 and Step G of Example 7.

MS (API+): [M+H]$^+$ 425.1.
$^1$H NMR (300 MHz, CDCl$_3$) δ 0.92 (3H, t, J=7.5 Hz), 1.71-1.95 (2H, m), 3.88 (3H, s), 4.68 (2H, s), 5.05-5.26 (1H, m), 6.71 (1H, s), 6.77 (1H, d, J=9.4 Hz), 6.94-7.03 (1H, m), 7.13 (1H, brs), 7.22 (1H, d, J=8.3 Hz), 8.02 (1H, d, J=4.9 Hz), 10.43 (1H, brs).

Example 33

N-(1-(4-hydroxyphenyl)propyl)-2-oxo-2,3-dihydropyrido[2,3-b]pyrazine-4(1H)-carboxamide The title compound was obtained in the same manner as in Step G of Example 7.
MS (API+): [M+H]$^+$ 327.1.

Example 34

N-(1-(2-fluoro-4-(trifluoromethoxy)phenyl)propyl)-2-oxo-2,3-dihydropyrido[2,3-b]pyrazine-4(1H)-carboxamide The title compound was obtained in the same manner as in Steps A-B of Example 30, Steps D-E of Example 2 and Step G of Example 7.
MS (API+): [M+H]$^+$ 413.2.
$^1$H NMR (300 MHz, DMSO-d$_6$) δ 0.89 (3H, t, J=7.2 Hz), 1.70-1.88 (2H, m), 4.40 (2H, s), 5.00 (1H, q, J=7.4 Hz), 7.11 (1H, dd, J=7.9, 4.9 Hz), 7.22 (1H, d, J=8.7 Hz), 7.27-7.42 (2H, m), 7.49 (1H, t, J=8.5 Hz), 8.02 (1H, dd, J=4.9, 1.9 Hz), 10.43 (1H, d, J=7.5 Hz), 10.81 (1H, s).

Example 35

7-cyclopropyl-2-oxo-N-(1-(4-(trifluoromethoxy)phenyl)propyl)-2,3-dihydropyrido[2,3-b]pyrazine-4(1H)-carboxamide To a solution of N-methyl-N-nitrosourea (577 mg) in diethyl ether (10 mL) was slowly added 3 M potassium hydroxide solution (6 mL) under ice-cooling. The reaction mixture was stirred at the same temperature for 30 min, and the organic layer was dried over anhydrous sodium sulfate, and slowly added to a solution of 2-oxo-N-(1-(4-(trifluoromethoxy)phenyl)propyl)-7-vinyl-2,3-dihydropyrido[2,3-b]pyrazine-4(1H)-carboxamide (118 mg) in dichloromethane (10 mL) under ice-cooling. Then, palladium(II) acetate (25 mg) was added thereto, the reaction mixture was stirred at room temperature for 1 hr, and some drops of acetic acid was added thereto. The insoluble substance was filtered off, and the filtrate was concentrated under reduced pressure. The residue was purified by HPLC (C18, mobile phase: water/acetonitrile (containing 0.1% TFA)), to the obtained fraction was added saturated aqueous sodium hydrogen carbonate solution, and the mixture was extracted with ethyl acetate. The extract was dried over anhydrous sodium sulfate, and concentrated under reduced pressure to give the title compound (43 mg).
MS (API+): [M+H]$^+$ 435.1.
$^1$H NMR (400 MHz, CDCl$_3$) δ 0.69-0.73 (2H, m), 0.95 (3H, t, 7.2 Hz), 1.00-1.05 (2H, m), 1.82-1.90 (3H, m), 4.60-4.71 (2H, m), 4.89 (1H, q, J=6.8 Hz), 6.85 (1H, d, J=2.0

Hz), 7.16 (1H, d, J=7.6 Hz), 7.34 (2H, d, J=8.4 Hz), 7.81 (1H, d, J=2.0 Hz), 9.31 (1H, s), 10.30 (1H, d, J=7.2 Hz).

Example 36

7-isopropyl-2-oxo-N-(1-(4-(trifluoromethoxy)phenyl)propyl)-2,3-dihydropyrido[2,3-b]pyrazine-4(1H)-carboxamide A) 2-oxo-7-(prop-1-en-2-yl)-N-(1-[4-(trifluoromethoxy)phenyl]propyl)-2,3-dihydropyrido[2,3-b]pyrazine-4(1H)-carboxamide The title compound was obtained in the same manner as in Example 27.
$^{1}$H NMR (400 MHz, CDCl$_3$) δ 0.97 (3H, t, J=3.9 Hz), 1.84-1.93 (2H, m), 2.17 (3H, s), 4.69 (1H, d, J=3.9 Hz), 4.92 (1H, q, J=6.9 Hz), 5.19 (1H, s), 5.41 (1H, s), 7.18 (2H, d, J=7.8 Hz), 7.24 (1H, d, J=2.1 Hz), 7.34-7.38 (2H, m), 8.11 (1H, d, J=2.1 Hz), 8.82 (1H, s), 10.41 (1H, d, J=7.5 Hz).

B) 7-isopropyl-2-oxo-N-(1-(4-(trifluoromethoxy)phenyl)propyl)-2,3-dihydropyrido[2,3-b]pyrazine-4(1H)-carboxamide The title compound was obtained in the same manner as in Example 29.
MS (API+): [M+H]$^+$ 437.2.

Example 37

6-chloro-2-oxo-N-(1-(4-(trifluoromethoxy)phenyl)propyl)-2,3-dihydropyrido[2,3-b]pyrazine-4(1H)-carboxamide A) methyl N-(6-chloro-3-nitropyridin-2-yl)glycinate To a solution of methyl glycinate hydrochloride (15.0 g) and 2,6-dichloro-3-nitropyridine (21.0 g) in ethanol (100 mL) was added triethylamine (30.9 mL). The reaction mixture was heated at reflux overnight, and the solvent was evaporated under reduced pressure. The residue was diluted with ethyl acetate, and the mixture was washed successively with water and saturated brine, and the solvent was evaporated under reduced pressure. The residue was purified by silica gel column chromatography (petroleum ether/ethyl acetate) to give the title compound (16.3 g).
$^{1}$H NMR (400 MHz, DMSO-d$_6$) δ 3.67 (3H, s), 4.26 (2H, d, J=5.6 Hz), 6.87 (1H, d, J=8.8 Hz), 8.48 (1H, d, J=8.8 Hz), 8.98 (1H, t, J=5.2 Hz).

B) 6-chloro-3,4-dihydropyrido[2,3-b]pyrazin-2(1H)-one

To a solution of methyl N-(6-chloro-3-nitropyridin-2-yl)glycinate (13.3 g) in ethanol (650 mL) was added tin(II) chloride dihydrate (98.0 g). The reaction mixture was heated at reflux overnight, and the precipitated solid was collected by filtration, and dried under reduced pressure to give the title compound (9.4 g).
$^{1}$H NMR (400 MHz, DMSO-d$_6$) δ 3.95 (2H, s), 6.56 (1H, d, J=8.0 Hz), 6.91 (1H, d, J=7.6 Hz), 7.22 (1H, s), 10.49 (1H, s).

C) 6-chloro-1-((2-(trimethylsilyl)ethoxy)methyl)-3,4-dihydropyrido[2,3-b]pyrazin-2(1H)-one The title compound was obtained in the same manner as in Step C of Example 26.
$^{1}$H NMR (400 MHz, DMSO-d$_6$) δ 0.01 (9H, s), 0.90 (2H, t, J=8.4 Hz), 3.58 (2H, t, J=8.0 Hz), 4.09 (2H, s), 5.29 (2H, s), 6.74 (1H, d, J=7.6 Hz), 7.34 (1H, d, J=8.0 Hz), 7.39 (1H, brs).

D) 6-chloro-2-oxo-N-(1-(4-(trifluoromethoxy)phenyl)propyl)-1-((2-(trimethylsilyl)ethoxy)methyl)-2,3-dihydropyrido[2,3-b]pyrazine-4(1H)-carboxamide Under nitrogen atmosphere, to a solution of 6-chloro-1-((2-(trimethylsilyl)ethoxy)methyl)-3,4-dihydropyrido[2,3-b]pyrazin-2(1H)-one (7.9 g) and triethylamine (7.63 g) in tetrahydrofuran (150 mL) was slowly added triphosgene (5.98 g) at room temperature. The reaction mixture was stirred at 45° C. for 2 hr, 1-(4-(trifluoromethoxy)phenyl) propan-1-amine hydrochloride (7.72 g) was added thereto, and the mixture was stirred at 60° C. for further 12 hr. The reaction mixture was concentrated under reduced pressure, and the obtained residue was purified by silica gel column chromatography (petroleum ether/ethyl acetate) to give the title compound (7.0 g).
$^{1}$H NMR (400 MHz, DMSO-d$_6$) δ 0.02 (9H, s), 0.90-1.01 (5H, m), 1.86-1.92 (2H, m), 3.65 (2H, t, J=11.2 Hz), 4.68 (2H, t, J=6.4 Hz), 4.88-4.90 (1H, m), 5.30 (2H, d, J=4.0 Hz), 7.07 (1H, d, J=11.2 Hz), 7.19 (2H, d, J=10.8 Hz), 7.35-7.39 (2H, m), 7.67 (1H, d, J=11.6 Hz), 9.80 (1H, d, J=9.2 Hz).

E) 6-chloro-2-oxo-N-(1-(4-(trifluoromethoxy)phenyl)propyl)-2,3-dihydropyrido[2,3-b]pyrazine-4(1H)-carboxamide The title compound was obtained in the same manner as in Step E of Example 26.
MS (API+): [M+H]$^+$ 429.1.
$^{1}$H NMR (300 MHz, CDCl$_3$) δ 0.97 (3H, t, J=7.2 Hz), 1.84-1.93 (2H, m), 4.64 (2H, d, J=2.0 Hz), 4.85-4.90 (1H, m), 6.98 (1H, d, J=7.6 Hz), 7.17-7.19 (3H, m), 7.36 (2H, d, J=8.4 Hz), 9.81 (1H, s), 9.96 (1H, d, J=7.2 Hz).

Example 38

N-(1-(4-(1-methyl-1H-pyrazol-4-yl)phenyl)propyl)-2-oxo-2,3-dihydropyrido[2,3-b]pyrazine-4(1H)-carboxamide The title compound was obtained in the same manner as in Step B of Example 28.
MS (API+): [M+H]$^+$ 391.2.

Example 39

2-oxo-N-(1-(4-(prop-1-en-2-yl)phenyl)propyl)-2,3-dihydropyrido[2,3-b]pyrazine-4(1H)-carboxamide
The title compound was obtained in the same manner as in Step B of Example 28.
MS (API+): [M+H]$^+$ 351.2.

Example 40

N-(1-(4-isopropylphenyl)propyl)-2-oxo-2,3-dihydropyrido[2,3-b]pyrazine-4(1H)-carboxamide To a solution of 2-oxo-N-(1-(4-(prop-1-en-2-yl)phenyl) propyl)-2,3-dihydropyrido[2,3-b]pyrazine-4(1H)-carboxamide (46 mg) in methanol (3 mL) was added palladium-carbon-ethylene diamine complex (15 mg). The reaction mixture was stirred at room temperature for 2 hr under hydrogen atmosphere, and the insoluble substance was filtered off. The filtrate was concentrated under reduced pressure, the residue was dissolved in methanol (3 mL), and 10% palladium-carbon (containing 50% water, 15 mg) was added thereto. The reaction mixture was stirred at room temperature for 2 hr under hydrogen atmosphere, the insoluble substance was filtered off, and the filtrate was concentrated under reduced pressure. The residue was purified by HPLC (C18, mobile phase: water/acetonitrile (containing 0.1% TFA)), to the obtained fraction was added saturated aqueous sodium hydrogen carbonate solution, and the mixture was extracted with ethyl acetate. The extract was dried over anhydrous sodium sulfate, and concentrated under reduced pressure to give the title compound (22.0 mg).

MS (API+): [M+H]$^+$ 353.2.

$^1$H NMR (300 MHz, DMSO-d$_6$) δ 0.85 (3H, t, J=7.3 Hz), 1.18 (6H, d, J=6.8 Hz), 1.68-1.85 (2H, m), 2.75-2.94 (1H, m), 4.41 (2H, s), 4.73 (1H, q, J=7.0 Hz), 7.09 (1H, dd, J=7.9, 4.9 Hz), 7.15-7.25 (4H, m), 7.31 (1H, dd, J=7.9, 1.5 Hz), 8.01 (1H, dd, J=4.9, 1.5 Hz), 10.29 (1H, d, J=7.5 Hz), 10.81 (1H, brs).

Example 41

N-(1-(4-(3,6-dihydro-2H-pyran-4-yl)phenyl)propyl)-2-oxo-2,3-dihydropyrido[2,3-b]pyrazine-4(1H)-carboxamide The title compound was obtained in the same manner as in Step B of Example 28.
MS (API+): [M+H]$^+$ 393.2.

Example 42

N-(2-amino-2-oxo-1-(4-(trifluoromethoxy)phenyl)ethyl)-2-oxo-2,3-dihydropyrido[2,3-b]pyrazine-4(1H)-carboxamide A) amino (4-(trifluoromethoxy)phenyl)acetonitrile hydrochloride 4-(Trifluoromethoxy)benzaldehyde (10 g) was dissolved in 2 M ammonia/methanol solution (105 mL), and titanium (IV) tetraisopropoxide (15.4 mL) was added thereto under ice-cooling. The reaction mixture was stirred at the same temperature for 10 min, trimethylsilanecarbonitrile (7.83 g) was added thereto, and the mixture was stirred overnight at room temperature. Then, saturated aqueous sodium hydrogen carbonate solution was added thereto, the insoluble substance was filtered off using Celite, and the filtrate was extracted with ethyl acetate. The extract was washed successively with water and saturated brine, and dried over anhydrous magnesium sulfate, and the solvent was evaporated under reduced pressure. To the residue was added 4 M hydrogen chloride/ethyl acetate solution (20 mL) under ice-cooling, and the solvent was evaporated under reduced pressure to give the title compound (10.0 g).

MS (API+), found: 200.0.
$^1$H NMR (300 MHz, DMSO-d$_6$) δ 5.91-6.12 (1H, m), 7.47-7.62 (2H, m), 7.74-7.95 (2H, m), 9.61 (3H, brs).

B) 2-amino-2-(4-(trifluoromethoxy)phenyl)acetamide

To a mixture of amino (4-(trifluoromethoxy)phenyl)acetonitrile hydrochloride (3 g), potassium carbonate (4.92 g) and dimethyl sulfoxide (30 mL) was added 35% aqueous hydrogen peroxide (3.12 mL) under ice-cooling. The reaction mixture was stirred overnight at room temperature, saturated aqueous sodium thiosulfate solution was added thereto, and the mixture was stirred at room temperature for further 5 min. The reaction mixture was added to saturated brine, and the mixture was extracted with ethyl acetate. The extract was washed with saturated brine, and dried over anhydrous magnesium sulfate, and the solvent was evaporated under reduced pressure to give the title compound (2.15 g).

MS (API+): [M+H]$^+$ 235.1.

C) N-(2-amino-2-oxo-1-(4-(trifluoromethoxy)phenyl)ethyl)-2-oxo-2,3-dihydropyrido[2,3-b]pyrazine-4(1H)-carboxamide The title compound was obtained in the same manner as in Step G of Example 7.
MS (API+): [M+H]$^+$ 410.1.
$^1$H NMR (300 MHz, DMSO-d$_6$) δ 4.28-4.50 (2H, m), 5.45 (1H, d, J=6.8 Hz), 7.12 (1H, dd, J=7.9, 4.9 Hz), 7.24-7.41 (4H, m), 7.51-7.60 (2H, m), 7.87 (1H, s), 8.01 (1H, dd, J=4.9, 1.5 Hz), 10.66 (1H, d, J=6.8 Hz), 10.81 (1H, s).

Example 43

N-(cyano(4-(trifluoromethoxy)phenyl)methyl)-2-oxo-2,3-dihydropyrido[2,3-b]pyrazine-4(1H)-carboxamide The title compound was obtained in the same manner as in Step G of Example 7.
MS (API+): [M+H]$^+$ 392.1.
$^1$H NMR (300 MHz, DMSO-d$_6$) δ 4.46 (2H, s), 6.30 (1H, d, J=7.5 Hz), 7.13 (1H, dd, J=7.9, 4.9 Hz), 7.33 (1H, dd, J=7.9, 1.5 Hz), 7.47 (2H, d, J=8.3 Hz), 7.64-7.74 (2H, m), 7.93-8.00 (1H, m), 10.67 (1H, d, J=7.5 Hz), 10.86 (1H, s).

Example 44

7-cyano-2-oxo-N-(1-(4-(trifluoromethoxy)phenyl)propyl)-2,3-dihydropyrido[2,3-b]pyrazine-4(1H)-carboxamide A) 2-oxo-1-((2-(trimethylsilyl)ethoxy)methyl)-1,2,3,4-tetrahydropyrido[2,3-b]pyrazine-7-carbonitrile To a solution of 7-iodo-1-((2-(trimethylsilyl)ethoxy)methyl)-3,4-dihydropyrido[2,3-b]pyrazin-2(1H)-one (1.00 g), zinc cyanide (579 mg) and zinc (81 mg) in N,N-dimethylacetamide (10 mL) was added di-tert-butylphosphine palladium(0) (126 mg). The reaction mixture was stirred overnight at 110° C. under nitrogen atmosphere, and the solvent was evaporated under reduced pressure. The residue was purified by silica gel column chromatography (petroleum ether/ethyl acetate) to give the title compound (598 mg).

$^1$H NMR (400 MHz, CDCl$_3$) δ 0.01 (9H, s), 0.97 (2H, t, J=10.8 Hz), 3.65 (2H, t, J=11.0 Hz), 4.31 (2H, d, J=1.6 Hz), 5.34 (2H, s), 7.57 (1H, d, J=2.0 Hz), 8.14 (1H, s).

B) 7-cyano-2-oxo-N-(1-(4-(trifluoromethoxy)phenyl)propyl)-1-((2-(trimethylsilyl)ethoxy)methyl)-2,3-dihydropyrido[2,3-b]pyrazine-4(1H)-carboxamide The title compound was obtained in the same manner as in Step D of Example 26.

¹H NMR (300 MHz, CDCl₃) δ 0.01 (9H, s), 0.91-1.00 (5H, m), 1.84-1.94 (2H, m), 3.66 (2H, t, J=8.1 Hz), 4.66-4.79 (2H, m), 4.88 (1H, q, J=6.9 Hz), 5.29-5.37 (2H, m), 7.19 (2H, d, J=8.1 Hz), 7.34 (2H, d, J=8.7 Hz), 7.89 (1H, d, J=2.1 Hz), 8.34 (1H, d, J=1.8 Hz), 10.01 (1H, d, J=7.2 Hz).

C) 7-cyano-2-oxo-N-(1-(4-(trifluoromethoxy)phenyl)propyl)-2,3-dihydropyrido[2,3-b]pyrazine-4(1H)-carboxamide The title compound was obtained in the same manner as in Step E of Example 26.
MS (API−): [M−H]⁻ 418.0.
¹H NMR (400 MHz, CDCl₃) δ 0.96 (3H, t, J=7.2 Hz), 1.85-1.92 (2H, m), 4.65-4.75 (2H, m), 4.87 (1H, q, J=7.6 Hz), 7.17 (2H, d, J=8.0 Hz), 7.31-7.34 (2H, m), 7.36 (1H, d, J=2.0 Hz), 8.29 (1H, d, J=2.0 Hz), 9.79 (1H, s), 10.18 (1H, d, J=7.6 Hz).

Example 45

2-oxo-N-(1-(4-(trifluoromethoxy)phenyl)propyl)-6-(trifluoromethyl)-2,3-dihydropyrido[2,3-b]pyrazine-4(1H)-carboxamide A) 2-nitroacetamide An aqueous solution of nitroethyl acetate (45.0 g) in 28% ammonia (300 mL) was stirred at room temperature for 24 hr, and the solvent was evaporated under reduced pressure. To the residue was added water, the pH of the mixture was adjusted to 3 with 1 M hydrochloric acid, and the mixture was extracted with ethyl acetate. The extract was washed with saturated brine, and dried over anhydrous sodium sulfate, and the solvent was evaporated under reduced pressure to give the title compound (35 g).
¹H NMR (400 MHz, DMSO-d₆) δ 5.28 (2H, s), 7.64 (1H, s), 7.86 (1H, s).

B) 3-nitro-6-(trifluoromethyl)pyridin-2-ol

To a solution of 2-nitroacetamide (16.9 g) and (3E)-4-ethoxy-1,1,1-trifluorobut-3-en-2-one (30.0 g) in ethanol (700 mL) was slowly added sodium ethoxide (22.1 g) at room temperature. The reaction mixture was stirred at 90° C. for 2 hr, the pH of the mixture was adjusted to 2 with 1 M hydrochloric acid, and the mixture was stirred at room temperature for additional 30 min. To the reaction mixture was added water, and the mixture was extracted with ethyl acetate. The extract was washed with saturated brine, and dried over anhydrous sodium sulfate, and the solvent was evaporated under reduced pressure to give the title compound (5.5 g).
¹H NMR (400 MHz, CDCl₃) δ 7.46 (1H, d, J=8.0 Hz), 8.69 (1H, d, J=8.0 Hz), 11.02 (1H, brs).

C) 2-chloro-3-nitro-6-(trifluoromethyl)pyridine

To 3-nitro-6-(trifluoromethyl)pyridin-2-ol (5.5 g) was added phosphorous pentachloride (25.0 g) at room temperature. The reaction mixture was stirred at 170° C. for 2.5 hr, cooled to room temperature, and slowly poured into ice-water. The mixture was extracted with ethyl acetate, and the extract was washed successively with saturated brine and saturated aqueous sodium hydrogen carbonate solution, and dried over anhydrous sodium sulfate, and the solvent was evaporated under reduced pressure to give the title compound (5.0 g).
¹H NMR (300 MHz, CDCl₃) δ 7.84 (1H, d, J=8.1 Hz), 8.38 (1H, d, J=8.1 Hz).

D) methyl N-(6-trifluoromethyl-3-nitropyridin-2-yl)glycinate

The title compound was obtained in the same manner as in Step A of Example 1.
¹H NMR (300 MHz, CDCl₃) δ 3.81 (3H, s), 4.41 (2H, d, J=5.4 Hz), 7.07 (1H, d, J=8.4 Hz), 8.53 (1H, brs), 8.62 (1H, d, J=8.4 Hz).

E) 6-(trifluoromethyl)-3,4-dihydropyrido[2,3-b]pyrazin-2(1H)-one

To a solution of methyl N-(6-trifluoromethyl-3-nitropyridin-2-yl)glycinate (3.37 g) in ethanol (75 mL) was added tin(II) chloride dihydrate (14.2 g). The reaction mixture was stirred at 80° C. for 2 hr, and the solvent was evaporated under reduced pressure. The residue was dissolved in ethyl acetate, the pH of the solution was adjusted to 9 with saturated aqueous ammonia solution, and the insoluble substance was filtered off using Celite. The filtrate was concentrated under reduced pressure, and the obtained residue was purified by silica gel column chromatography (petroleum ether/ethyl acetate) to give the title compound (1.04 g).
¹H NMR (400 MHz, CDCl₃+CD₃D) δ 4.19 (2H, s), 6.97 (1H, d, J=7.6 Hz), 7.02 (1H, d, J=7.6 Hz).

F) 2-oxo-N-(1-(4-(trifluoromethoxy)phenyl)propyl)-6-(trifluoromethyl)-2,3-dihydropyrido[2,3-b]pyrazine-4(1H)-carboxamide The title compound was obtained in the same manner as in Step D of Example 26.
MS (API+): [M+H]⁺ 463.1.
¹H NMR (400 MHz, CDCl₃) δ 0.95 (3H, t, J=7.2 Hz), 1.79-1.93 (2H, m), 4.66-4.75 (2H, m), 4.85 (1H, q, J=7.2 Hz), 7.17 (2H, d, J=8.0 Hz), 7.28 (1H, d, J=8.0 Hz), 7.32-7.36 (3H, m), 7.63 (1H, brs), 10.12 (1H, d, J=7.6 Hz).

Example 46

2-oxo-N-(1-(4-(trifluoromethoxy)phenyl)propyl)-6-vinyl-2,3-dihydropyrido[2,3-b]pyrazine-4(1H)-carboxamide To a solution of 6-chloro-2-oxo-N-(1-(4-(trifluoromethoxy)phenyl)propyl)-2,3-dihydropyrido[2,3-b]pyrazine-4(1H)-carboxamide (1.10 g), 2-ethenyl-4,4,5,5-tetramethyl-1,3,2-dioxaborolane (539 mg) and (1,1-bis(diphenylphosphino)ferrocene)dichloropalladium(II) (100 mg) in a mixed solvent of 1,2-dimethoxyethane (15 mL) and water (5 mL) was added cesium carbonate (1.67 g) at room temperature. The reaction mixture was stirred at 120° C. for 4 hr under nitrogen atmosphere using microwave, water was added thereto, and the mixture was extracted with ethyl acetate. The extract was washed successively with water and saturated brine, and dried over anhydrous sodium sulfate, and the solvent was evaporated under reduced pressure. The residue was purified by silica gel column chromatography (petroleum ether/ethyl acetate) to give the title compound (500 mg).

MS (API+): [M+H]+ 421.2.

¹H NMR (300 MHz, CDCl₃) δ 0.98 (3H, t, J=7.2 Hz), 1.84-1.94 (2H, m), 4.70 (2H, s), 4.90 (1H, d, J=7.2 Hz), 5.41 (1H, d, J=10.8 Hz), 5.91 (1H, d, J=17.1 Hz), 6.68 (1H, dd, J=17.4, 7.8 Hz), 6.98 (1H, d, J=8.1 Hz), 7.16-7.22 (3H, m), 7.37 (2H, d, J=8.4 Hz), 10.14 (1H, s), 10.54 (1H, d, J=7.2 Hz).

Example 47

6-benzyl-2-oxo-N-(1-(4-(trifluoromethoxy)phenyl) propyl)-2,3-dihydropyrido[2,3-b]pyrazine-4(1H)-carboxamide To a solution of 6-chloro-2-oxo-N-(1-(4-(trifluoromethoxy)phenyl)propyl)-2,3-dihydropyrido[2,3-b]pyrazine-4(1H)-carboxamide (420 mg), 2-benzyl-4,4,5,5-tetramethyl-1,3,2-dioxaborolane (181 mg) and (1,1-bis(diphenylphosphino)ferrocene)dichloropalladium(II) (50 mg) in a mixed solvent of 1,2-dimethoxyethane (15 mL) and water (5 mL) was added cesium carbonate (645 mg) at room temperature. The reaction mixture was stirred at 100° C. for 40 min under nitrogen atmosphere using microwave, water was added thereto, and the mixture was extracted with ethyl acetate. The extract was washed successively with water and saturated brine, and dried over anhydrous sodium sulfate, and the solvent was evaporated under reduced pressure. The residue was purified by HPLC (C18, mobile phase: water/acetonitrile (containing 0.1% TFA)), to the obtained fraction was added saturated aqueous sodium hydrogen carbonate solution, and the mixture was extracted with ethyl acetate. The extract was dried over anhydrous sodium sulfate, and concentrated under reduced pressure to give the title compound (100 mg).

MS (API+): [M+H]+ 485.2.

¹H NMR (300 MHz, CDCl₃) δ 0.88 (3H, t, J=7.2 Hz), 1.60-1.68 (2H, m), 4.07 (2H, s), 4.65 (2H, s), 4.80 (1H, d, J=7.2 Hz), 6.89 (1H, d, J=8.1 Hz), 7.08-7.19 (8H, m), 7.25-7.34 (2H, m), 9.69 (1H, s), 10.34 (1H, d, J=7.5 Hz).

Example 48

2-oxo-N-(1-(4-(tetrahydro-2H-pyran-4-yl)phenyl) propyl)-2,3-dihydro pyrido[2,3-b]pyrazine-4(1H)-carboxamide To a solution of N-(1-(4-(3,6-dihydro-2H-pyran-4-yl)phenyl)propyl)-2-oxo-2,3-dihydropyrido[2,3-b]pyrazine-4 (1H)-carboxamide (42.5 mg) in methanol (3 mL) was added 10% palladium-carbon (containing 50% water, 15 mg). The reaction mixture was stirred at room temperature for 4 hr under hydrogen atmosphere, the insoluble substance was filtered off, and the filtrate was concentrated under reduced pressure. The residue was purified by HPLC (C18, mobile phase: water/acetonitrile (containing 0.1% TFA)), to the obtained fraction was added saturated aqueous sodium hydrogen carbonate solution, and the mixture was extracted with ethyl acetate. The extract was dried over anhydrous sodium sulfate, and concentrated under reduced pressure to give the title compound (27.9 mg).

MS (API+): [M+H]+ 395.2.

¹H NMR (300 MHz, DMSO-d₆) δ 0.85 (3H, t, J=7.3 Hz), 1.52-1.86 (6H, m), 2.62-2.82 (1H, m), 3.34-3.50 (2H, m), 3.86-4.00 (2H, m), 4.41 (2H, s), 4.74 (1H, q, J=6.9 Hz), 7.09 (1H, dd, J=7.9, 4.9 Hz), 7.15-7.28 (4H, m), 7.31 (1H, dd, J=7.7, 1.7 Hz), 8.01 (1H, dd, J=4.9, 1.5 Hz), 10.29 (1H, d, J=7.5 Hz), 10.80 (1H, brs).

Example 49

N-(1-(6-methoxypyridin-3-yl)propyl)-2-oxo-2,3-dihydropyrido[2,3-b]pyrazine-4(1H)-carboxamide A) 6-methoxynicotinonitrile To a solution of 6-chloronicotinonitrile (10.0 g) in methanol (100 mL) was added sodium methoxide (7.80 g). The reaction mixture was heated at reflux overnight, and the solvent was evaporated under reduced pressure. To the residue was added water, and the mixture was extracted with ethyl acetate. The extract was washed with saturated brine, and dried over sodium sulfate, and the solvent was evaporated under reduced pressure to give the title compound (8.8 g).

¹H NMR (400 MHz, DMSO-d₆) δ 4.00 (3H, s), 6.83 (1H, dd, J=8.8, 0.8 Hz), 7.78 (1H, dd, J=8.6, 2.4 Hz), 8.50 (1H, d, J=1.4 Hz).

B) 6-methoxynicotine acid

To a solution of 6-methoxynicotinonitrile (5.00 g) in ethanol (100 mL) was added 2 M aqueous potassium hydroxide solution (20 mL). The reaction mixture was heated at reflex for 2 hr, and the solvent was evaporated under reduced pressure. To the residue was added water, the pH of the mixture was adjusted to 4-5 with 2 M hydrochloric acid, and the mixture was extracted with ethyl acetate. The extract was washed with saturated brine, and dried over anhydrous sodium sulfate, and the solvent was evaporated under reduced pressure to give the title compound (4.2 g).

¹H NMR (400 MHz, DMSO-d₆) δ 3.92 (3H, s), 6.86-6.92 (1H, m), 8.11-8.15 (1H, m), 8.73 (1H, d, J=2.0 Hz), 13.0 (1H, s).

C) N,6-dimethoxy-N-methylnicotinamide

To a solution of 6-methoxynicotine acid (4.2 g) and N-methoxymethylamine hydrochloride (3.8 g) in dichloromethane (100 mL) were added 1-(3-dimethylaminopropyl)-3-ethylcarbodiimide hydrochloride (7.6 g) and 4-dimethylaminopyridine (0.32 g). The reaction mixture was stirred at room temperature for 10 min, diisopropylethylamine (10.0 g) was added thereto, and the mixture was stirred overnight at room temperature. The reaction mixture was washed with saturated brine, and dried over anhydrous sodium sulfate, and the solvent was evaporated under reduced pressure. The residue was purified by silica gel column chromatography (ethyl acetate/petroleum ether) to give the title compound (3.6 g).

¹H NMR (400 MHz, CDCl₃) δ 3.58 (3H, s), 3.77 (3H, s), 3.98 (3H, s), 6.72-6.77 (1H, m), 7.97-8.00 (1H, m), 8.62-8.65 (1H, m).

D) 1-(6-methoxypyridin-3-yl)propan-1-one

To a solution of N,6-dimethoxy-N-methylnicotinamide (3.6 g) in tetrahydrofuran (50 mL) was added 3 M ethylmagnesium bromide/tetrahydrofuran solution (18 mL) at −40° C. The reaction mixture was stirred at the same temperature for 2 hr, saturated aqueous ammonium chloride solution was added thereto, and the mixture was extracted with ethyl acetate. The extract was washed with saturated brine, and dried over anhydrous sodium sulfate, and the solvent was evaporated under reduced pressure to give the title compound (2.9 g).

¹H NMR (400 MHz, CDCl₃) δ 1.23 (3H, t, J=7.2 Hz), 2.95 (2H, q, J=7.2 Hz), 4.00 (3H, s), 6.78 (1H, dd, J=8.4, 0.4 Hz), 8.15 (1H, dd, J=8.8, 2.4 Hz), 8.80 (1H, d, J=2.4 Hz).

E) 1-(6-methoxypyridin-3-yl)propan-1-amine

To a solution of 1-(6-methoxypyridin-3-yl)propan-1-one (2.9 g) in ethanol (50 mL) were added hydroxylamine hydrochloride (1.5 g) and triethylamine (2.1 g). The reaction mixture was heated at reflux overnight, and the solvent was evaporated under reduced pressure. To the residue was added water, and the mixture was extracted with ethyl acetate. The extract was washed with saturated brine, and dried over anhydrous sodium sulfate, and the solvent was evaporated under reduced pressure. To a solution of the obtained solid (800 mg) in methanol (10 mL) was added Raney nickel (160 mg). The reaction mixture was stirred at 50° C. for 3 hr under hydrogen atmosphere (50 psi), the insoluble substance was filtered off using Celite, and the filtrate was concentrated under reduced pressure to give the title compound (600 mg).
¹H NMR (400 MHz, DMSO-d₆) δ 0.76 (3H, t, J=7.6 Hz), 1.45-1.61 (2H, m), 3.35 (2H, brs), 3.64-3.67 (1H, m), 3.81 (3H, s), 6.74 (1H, dd, J=13.6, 8.4 Hz), 7.67 (1H, dd, J=8.4, 2.4 Hz), 8.03 (1H, dd, J=8.4, 2.0 Hz).

F) N-(1-(6-methoxypyridin-3-yl)propyl)-2-oxo-2,3-dihydropyrido[2,3-b]pyrazine-4(1H)-carboxamide To a solution of 1-(6-methoxypyridin-3-yl)propan-1-amine (100 mg) in N,N-dimethylformamide (10 mL) were added 4-nitrophenyl 2-oxo-2,3-dihydropyrido[2,3-b]pyrazine-4(1H)-carboxylate (223 mg) and triethylamine (181 mg). The reaction mixture was stirred overnight at room temperature, and the solvent was evaporated under reduced pressure. The residue was purified by HPLC (C18, mobile phase: water/acetonitrile (containing 0.1% TFA)), to the obtained fraction was added saturated aqueous sodium hydrogen carbonate solution, and the mixture was extracted with ethyl acetate. The extract was dried over anhydrous sodium sulfate, and concentrated under reduced pressure to give the title compound (80 mg).
MS (API+): [M+H]⁺ 342.1.
¹H NMR (300 MHz, CDCl₃) δ 0.97 (3H, t, J=7.5 Hz), 1.83-1.95 (2H, m), 3.92 (3H, s), 4.62-4.75 (2H, m), 4.87 (1H, q, d, J=7.2 Hz), 6.72 (1H, d, J=8.4 Hz), 6.99 (1H, dd, J=7.8, 5.1 Hz), 7.20 (1H, dd, J=7.8, 1.5 Hz), 7.55 (1H, dd, J=8.7, 2.4 Hz), 8.00 (1H, dd, J=4.8, 1.5 Hz), 8.14 (1H, d, J=2.7 Hz), 9.16 (1H, s), 10.40 (1H, d, J=7.2 Hz).

Example 50

N-(1-(5-methoxypyrimidin-2-yl)propyl)-2-oxo-2,3-dihydropyrido[2,3-b]pyrazine-4(1H)-carboxamide A) 5-methoxypyrimidine-2-carbonitrile To a solution of 2-chloro-5-methoxypyrimidine (4.4 g) and 1,4-diazabicyclo[2.2.2]octane (6.7 g) in a mixed solvent of dimethyl sulfoxide (114 mL) and water (18 mL) was added potassium cyanide (4.00 g). The reaction mixture was stirred at 70° C. for 5 hr, water was added thereto, and the mixture was extracted with ethyl acetate. The extract was washed with saturated brine, and dried over sodium sulfate, and the solvent was evaporated under reduced pressure to give the title compound (3.5 g).
¹H NMR (400 MHz, CDCl₃) δ 4.02 (3H, s), 8.47 (2H, s).

B) 1-(5-methoxypyrimidin-2-yl)propan-1-one

The title compound was obtained in the same manner as in Step B of Example 30.
¹H NMR (300 MHz, CDCl₃) δ 1.25 (3H, t, J=7.2 Hz), 3.23 (2H, q, J=7.2 Hz), 4.02 (3H, s), 8.53 (2H, s).

C) N-benzyl-1-(5-methoxypyrimidin-2-yl)propan-1-amine

To a solution of 1-(5-methoxypyrimidin-2-yl)propan-1-one (500 mg) and benzyl amine (308 mg) in 1,2-dichloroethane (10 mL) was added sodium triacetoxyborohydride (953.5 mg). The reaction mixture was stirred overnight at 25° C., dichloromethane was added thereto, and washed with saturated brine. The organic layer was dried over anhydrous sodium sulfate, and the solvent was evaporated under reduced pressure to give the title compound (700 mg).
¹H NMR (300 MHz, CDCl₃) δ 0.85 (3H, t, J=7.5 Hz), 1.77-1.83 (2H, m), 3.61 (2H, dd, J=15.3, 12.9 Hz), 3.82 (1H, t, J=6.6 Hz), 3.94 (3H, s), 7.20-7.36 (5H, m), 8.40 (2H, s).

D) 1-(5-methoxypyrimidin-2-yl)propan-1-amine

To a solution of N-benzyl-1-(5-methoxypyrimidin-2-yl)propan-1-amine (700 mg) in methanol (10 mL) was added 10% palladium-carbon (containing 50% water, 100 mg). The reaction mixture was stirred at room temperature for 5 hr under hydrogen atmosphere (20 psi), the insoluble substance was filtered off, and the filtrate was concentrated under reduced pressure to give the title compound (500 mg).
¹H NMR (300 MHz, CDCl₃) δ 0.92 (3H, t, J=7.5 Hz), 1.69-1.79 (2H, m), 3.94 (3H, s), 3.92-4.02 (1H, m), 8.38 (2H, s).

E) N-(1-(5-methoxypyrimidin-2-yl)propyl)-2-oxo-2,3-dihydropyrido[2,3-b]pyrazine-4(1H)-carboxamide The title compound was obtained in the same manner as in Step G of Example 7.
MS (API+): [M+H]⁺ 343.2.
¹H NMR (400 MHz, CDCl₃) δ 0.95 (3H, t, J=7.2 Hz), 1.96-2.09 (2H, m), 3.91 (3H, s), 4.60 (2H, q, J=18.0 Hz), 5.17 (1H, q, J=6.8 Hz), 6.95-6.98 (1H, dd, J=8.0, 4.8 Hz), 7.14 (1H, dd, J=7.6, 1.6 Hz), 8.03 (1H, dd, J=4.8, 1.6 Hz), 8.40 (2H, s), 9.46 (1H, s), 10.63 (1H, d, J=7.2 Hz).

Example 51

6-ethyl-2-oxo-N-(1-(4-(trifluoromethoxy)phenyl)propyl)-2,3-dihydropyrido[2,3-b]pyrazine-4(1H)-carboxamide The title compound was obtained in the same manner as in Example 29.
MS (API+): [M+H]⁺ 423.1.
¹H NMR (400 MHz, CDCl₃) δ 0.97 (3H, t, J=7.2 Hz), 1.27 (3H, t, J=7.6 Hz), 1.83-1.93 (2H, m), 2.71-2.77 (2H, m), 4.66 (2H, s) 4.87-4.92 (1H, m), 6.82 (1H, d, J=7.6 Hz), 7.13-7.18 (3H, m), 7.33-7.37 (2H, m), 9.91 (1H, s), 10.65 (1H, d, J=7.6 Hz).

Example 52

6-methoxy-2-oxo-N-(1-(4-(trifluoromethoxy)phenyl)propyl)-2,3-dihydropyrido[2,3-b]pyrazine-4(1H)-carboxamide

A) methyl N-(6-methoxy-3-nitropyridin-2-yl)glycinate

To a solution of ethyl N-(6-chloro-3-nitropyridin-2-yl)glycinate (1.50 g) in methanol (40 mL) was added sodium methoxide (469 mg). The reaction mixture was stirred at 70° C. for 2 hr, water was added thereto, and the mixture was extracted with ethyl acetate. The extract was washed with saturated brine, and dried over anhydrous sodium sulfate, and the solvent was evaporated under reduced pressure to give the title compound (1.4 g).
$^1$H NMR (400 MHz, DMSO-d$_6$) δ 3.67 (3H, s), 3.84 (3H, s), 4.29 (2H, d, J=6.0 Hz), 6.22 (1H, t, J=4.4 Hz), 8.34 (1H, d, J=8.8 Hz), 9.11 (1H, s).

B) 6-methoxy-2-oxo-N-(1-(4-(trifluoromethoxy)phenyl)propyl)-2,3-dihydropyrido[2,3-b]pyrazine-4(1H)-carboxamide To a solution of methyl N-(6-methoxy-3-nitropyridin-2-yl)glycinate (1.40 g) in ethanol (40 mL) was added tin(II) chloride dihydrate (8.00 g). The reaction mixture was stirred overnight at 80° C., and the solvent was evaporated under reduced pressure to give a crude product (9.4 g) of 6-methoxy-3,4-dihydropyrido[2,3-b]pyrazin-2(1H)-one. To a solution of the crude product (4.00 g) of 6-methoxy-3,4-dihydropyrido[2,3-b]pyrazin-2(1H)-one and diisopropylethylamine (10 mL) in tetrahydrofuran (100 mL) was slowly added triphosgene (602 mg) at room temperature. The reaction mixture was stirred at 45° C. for 2 hr, and the solvent was evaporated under reduced pressure. The residue was dissolved in tetrahydrofuran (50 mL), and 1-(4-(trifluoromethoxy)phenyl)propan-1-amine hydrochloride (602 mg) was added thereto. The mixture was stirred overnight at 65° C., and the solvent was evaporated under reduced pressure. To the residue was added water, and the mixture was extracted with ethyl acetate. The extract was washed with saturated brine, and dried over anhydrous sodium sulfate, and the solvent was evaporated under reduced pressure. The residue was purified by HPLC (C18, mobile phase: water/acetonitrile (containing 0.1% TFA)), to the obtained fraction was added saturated aqueous sodium hydrogen carbonate solution, and the mixture was extracted with ethyl acetate. The extract was dried over anhydrous sodium sulfate, and concentrated under reduced pressure to give the title compound (90 mg).
MS (API+): [M+H]$^+$ 425.1.
$^1$H NMR (400 MHz, CDCl$_3$) δ 0.97 (3H, t, J=7.6 Hz), 1.82-1.91 (2H, m), 3.77 (3H, s), 4.56-4.68 (2H, m), 4.85-4.90 (1H, m), 6.46 (1H, d, J=8.4 Hz), 7.16-7.22 (3H, m), 7.36 (2H, d, J=8.4 Hz), 9.61 (1H, d, J=7.2 Hz), 9.64 (1H, s).

Example 53

N-(1-(4-(cyclopropylmethoxy)phenyl)propyl)-2-oxo-2,3-dihydropyrido[2,3-b]pyrazine-4(1H)-carboxamide

A) tert-butyl (1-(4-(cyclopropylmethoxy)phenyl)propyl)carbamate

To a solution of tert-butyl (1-(4-hydroxyphenyl)propyl)carbamate (303 mg), cyclopropylmethanol (104 mg) and tributylphosphine (394 mg) in tetrahydrofuran (10 mL) was added 1,1'-(azodicarbonyl)dipiperidine (457 mg). The reaction mixture was stirred at room temperature for 1 hr, and hexane was added thereto. The precipitated solid was filtered off, and the filtrate was concentrated under reduced pressure. The residue was purified by silica gel column chromatography (hexane/ethyl acetate) to give the title compound (292 mg).
MS (API+): [M+H]$^+$ 306.2.

B) N-(1-(4-(cyclopropylmethoxy)phenyl)propyl)-2-oxo-2,3-dihydropyrido[2,3-b]pyrazine-4(1H)-carboxamide To a solution of the hydrochloride (217 mg) (obtained from tert-butyl (1-(4-(cyclopropylmethoxy)phenyl)propyl)carbamate (292 mg) in the same manner as in Step E of Example 18) in N,N-dimethylacetamide (6 mL) were added 4-nitrophenyl 2-oxo-2,3-dihydropyrido[2,3-b]pyrazine-4(1H)-carboxylate (282 mg) and triethylamine (0.456 mL). The reaction mixture was stirred at room temperature for 16 hr, and the solvent was evaporated under reduced pressure. To the residue was added aqueous sodium hydrogen carbonate solution, and the mixture was extracted with ethyl acetate. The extract was washed with water, and dried over anhydrous sodium sulfate, and the solvent was evaporated under reduced pressure. The obtained solid was triturated with ethyl acetate/methanol, collected by filtration, and washed with ethyl acetate to give the title compound (136 mg).
MS (API+): [M+H]$^+$ 381.2.
$^1$H NMR (300 MHz, DMSO-d$_6$) δ 0.20-0.37 (2H, m), 0.48-0.64 (2H, m), 0.83 (3H, t, J=7.3 Hz), 1.09-1.32 (1H, m), 1.64-1.88 (2H, m), 3.77 (2H, d, J=6.8 Hz), 4.41 (2H, d, J=0.8 Hz), 4.70 (1H, q, J=7.0 Hz), 6.81-6.93 (2H, m), 7.09 (1H, dd, J=7.9, 4.9 Hz), 7.14-7.24 (2H, m), 7.30 (1H, dd, J=7.9, 1.5 Hz), 7.99 (1H, dd, J=4.9, 1.5 Hz), 10.23 (1H, d, J=7.5 Hz), 10.80 (1H, s).

Example 54

2-oxo-N-(1-(4-(trifluoromethyl)phenyl)propyl)-2,3-dihydropyrido[2,3-b]pyrazine-4(1H)-carboxamide

A) N-hydroxy-1-(4-(trifluoromethyl)phenyl)propan-1-imine

The title compound was obtained in the same manner as in Step C of Example 1.
$^1$H NMR (300 MHz, CDCl$_3$) δ 1.06-1.23 (3H, m), 2.54-2.90 (2H, m), 7.47-7.78 (4H, m), 8.14-8.53 (1H, m).

B) 1-(4-(trifluoromethyl)phenyl)propan-1-amine

To a solution of N-hydroxy-1-(4-(trifluoromethyl)phenyl)propan-1-imine (2.15 g) in ethanol (100 mL) was added 20% palladium hydroxide-carbon (200 mg). The reaction mixture was stirred overnight at room temperature under hydrogen atmosphere, the reaction mixture was filtered, and the filtrate was concentrated under reduced pressure. The residue was purified by silica gel column chromatography (NH, hexane/ethyl acetate) to give the title compound (988 mg).
$^1$H NMR (300 MHz, CDCl$_3$) δ 0.87 (3H, t, J=7.3 Hz), 1.62-1.77 (2H, m), 3.89 (1H, t, J=6.8 Hz), 7.44 (2H, d, J=7.9 Hz), 7.58 (2H, d, J=7.9 Hz).

C) 2-oxo-N-(1-(4-(trifluoromethyl)phenyl)propyl)-2,3-dihydropyrido[2,3-b]pyrazine-4(1H)-carboxamide The title compound was obtained in the same manner as in Step G of Example 7.

MS (API+): [M+H]$^+$ 379.2.

$^1$H NMR (300 MHz, CDCl$_3$) δ 0.97 (3H, t, J=7.3 Hz), 1.89 (2H, quin, J=7.3 Hz), 4.67 (2H, s), 4.93 (1H, q, J=6.8 Hz), 7.01 (1H, dd, J=7.7, 5.1 Hz), 7.19 (1H, dd, J=7.5, 1.5 Hz), 7.44 (2H, d, J=8.3 Hz), 7.58 (2H, d, J=8.3 Hz), 8.01 (1H, dd, J=4.9, 1.5 Hz), 9.16 (1H, brs), 10.48 (1H, d, J=7.2 Hz).

Example 55

2-oxo-N-((pyridin-2-yl)(4-(trifluoromethoxy)phenyl)methyl)-2,3-dihydropyrido[2,3-b]pyrazine-4(1H)-carboxamide A) N-methoxy-N-methylpyridine-2-carboxamide The title compound was obtained in the same manner as in Step A of Example 31.

MS (API+): [M+H]$^+$ 167.1.

B) pyridin-2-yl(4-(trifluoromethoxy)phenyl)methanone

To a solution of N-methoxy-N-methylpyridine-2-carboxamide (2.7 g) in tetrahydrofuran (60 mL) was added 0.5 M (4-(trifluoromethoxy)phenylmagnesium bromide/tetrahydrofuran solution (32.5 mL) at room temperature. The reaction mixture was stirred overnight at room temperature, saturated aqueous ammonium chloride solution was added thereto, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (2.69 g).

MS (API+): [M+H]$^+$ 268.0.

C) 1-(pyridin-2-yl)-1-(4-(trifluoromethoxy)phenyl)methanamine hydrochloride

The title compound was obtained in the same manner as in Steps C-E of Example 1.

MS (API+): [M+H]$^+$ 269.0.

D) 2-oxo-N-((pyridin-2-yl)(4-(trifluoromethoxy)phenyl)methyl)-2,3-dihydropyrido[2,3-b]pyrazine-4(1H)-carboxamide The title compound was obtained in the same manner as in Step G of Example 7.

MS (API+): [M+H]$^+$ 444.2.

$^1$H NMR (300 MHz, CDCl$_3$) δ 4.53-4.74 (2H, m), 6.25 (1H, d, J=6.8 Hz), 6.99 (1H, dd, J=7.9, 4.9 Hz), 7.09-7.25 (4H, m), 7.29 (1H, d, J=7.9 Hz), 7.43-7.53 (2H, m), 7.66 (1H, td, J=7.7, 1.9 Hz), 8.08 (1H, dd, J=5.1, 1.7 Hz), 8.64 (1H, dd, J=4.9, 0.8 Hz), 9.24 (1H, brs), 11.41 (1H, d, J=6.8 Hz).

Example 56

N-((3,5-dimethyl-1,2-oxazol-4-yl)(4-(trifluoromethoxy)phenyl)methyl)-2-oxo-2,3-dihydropyrido[2,3-b]pyrazine-4(1H)-carboxamide A) (3,5-dimethyl-1,2-oxazol-4-yl) (4-(trifluoromethoxy)phenyl)methanone The title compound was obtained in the same manner as in Step A of Example 31 and Step B of Example 55.

MS (API+): [M+H]$^+$ 286.0.

B) 1-(3,5-dimethyl-1,2-oxazol-4-yl)-N-hydroxy-1-(4-(trifluoromethoxy)phenyl)methanimine The title compound was obtained in the same manner as in Step C of Example 1.

MS (API+): [M+H]$^+$ 301.1.

C) 1-(3,5-dimethyl-1,2-oxazol-4-yl)-1-(4-(trifluoromethoxy)phenyl)methanamine

To a solution of 1-(3,5-dimethyl-1,2-oxazol-4-yl)-N-hydroxy-1-(4-(trifluoromethoxy)phenyl)methanimine (460 mg) in tetrahydrofuran (15 mL) was added 1.1 M borane-tetrahydrofuran complex/tetrahydrofuran solution (4.18 mL) at room temperature. The reaction mixture was stirred overnight at 80° C. under nitrogen atmosphere, 1 M hydrochloric acid was added thereto, and the mixture was stirred at room temperature for 15 min. Then, to the reaction mixture was added saturated aqueous sodium hydrogen carbonate solution, and the mixture was extracted with ethyl acetate. The extract was washed successively with saturated aqueous sodium hydrogen carbonate solution and saturated brine, and dried over anhydrous magnesium sulfate, and the solvent was evaporated under reduced pressure to give the title compound (398 mg).

MS (API+), found: 270.1.

D) N-((3,5-dimethyl-1,2-oxazol-4-yl) (4-(trifluoromethoxy)phenyl)methyl)-2-oxo-2,3-dihydropyrido[2,3-b]pyrazine-4(1H)-carboxamide The title compound was obtained in the same manner as in Step G of Example 7.

MS (API+): [M+H]$^+$ 462.1.

$^1$H NMR (300 MHz, CDCl$_3$) δ 2.12 (3H, s), 2.38 (3H, s), 4.62-4.83 (2H, m), 6.25 (1H, d, J=8.3 Hz), 7.02 (1H, dd, J=7.7, 5.1 Hz), 7.15-7.23 (3H, m), 7.27-7.36 (2H, m), 7.91 (1H, dd, J=5.1, 1.3 Hz), 8.38 (1H, brs), 10.79 (1H, d, J=8.3 Hz).

Example 57

N-((1-methyl-1H-pyrazol-4-yl) (4-(trifluoromethoxy)phenyl)methyl)-2-oxo-2,3-dihydropyrido[2,3-b]pyrazine-4(1H)-carboxamide The title compound was obtained in the same manner as in Step A of Example 31, Step B of Example 55, Steps C-E of Example 1 and Step G of Example 7.

MS (API+): [M+H]$^+$ 447.2.

$^1$H NMR (300 MHz, CDCl$_3$) δ 3.86 (3H, s), 4.60-4.77 (2H, m), 6.18 (1H, d, J=7.2 Hz), 6.99 (1H, dd, J=7.7, 5.1

Hz), 7.08-7.24 (4H, m), 7.33-7.48 (3H, m), 7.94 (1H, d, J=4.9 Hz), 9.00 (1H, brs), 10.68 (1H, d, J=7.5 Hz).

Example 58

N-(2-(dimethylamino)-1-(4-(trifluoromethoxy)phenyl)ethyl)-2-oxo-2,3-dihydropyrido[2,3-b]pyrazine-4(1H)-carboxamide A) tert-butyl (cyano(4-(trifluoromethoxy)phenyl)methyl)carbamate To a solution of amino (4-(trifluoromethoxy)phenyl)acetonitrile hydrochloride (3 g) and triethylamine (3.31 mL) in tetrahydrofuran (50 mL) was added di-tert-butyl dicarbonate (3.03 mL) at room temperature. The reaction mixture was stirred overnight at room temperature, further di-tert-butyl dicarbonate (500 mg) was added at room temperature, and the mixture was stirred for 2 days. The reaction mixture was filtered through silica gel pad, and eluted with ethyl acetate. The filtrate was concentrated under reduced pressure to give the title compound (4.14 g).
$^1$H NMR (300 MHz, CDCl$_3$) δ 1.49 (9H, s), 5.01-5.24 (1H, m), 5.82 (1H, brs), 7.22-7.34 (2H, m), 7.49-7.60 (2H, m).

B) tert-butyl (2-amino-1-(4-(trifluoromethoxy)phenyl)ethyl)carbamate

To a solution of cobalt(II) chloride (328 mg) and tert-butyl (cyano(4-(trifluoromethoxy)phenyl)methyl)carbamate (400 mg) in methanol (8 mL) was added sodium borohydride (478 mg) under ice-cooling. The reaction mixture was stirred for 40 min under ice-cooling, 1 M hydrochloric acid (10 mL) was added thereto, and the mixture was stirred at room temperature for 10 min. To the reaction mixture was added 8 M aqueous sodium hydroxide solution (5 mL), the insoluble substance was filtered off using Celite, and the filtrate was extracted with ethyl acetate. The extract was washed with saturated brine, and dried over anhydrous magnesium sulfate, and the solvent was evaporated under reduced pressure to give the title compound (360 mg).
MS (API+): [M+H]$^+$ 321.1.

C) tert-butyl (2-(dimethylamino)-1-(4-(trifluoromethoxy)phenyl)ethyl)carbamate

To a solution of tert-butyl (2-amino-1-(4-(trifluoromethoxy)phenyl)ethyl)carbamate (180 mg) and 37% aqueous formaldehyde solution (109 mg) in methanol (5 mL) was added borane-2-picoline complex (180 mg) under ice-cooling. The reaction mixture was stirred overnight at room temperature under nitrogen atmosphere, 1 M hydrochloric acid (5 mL) was added thereto at room temperature, and the mixture was stirred at the same temperature for 10 min. The reaction mixture was neutralized with saturated aqueous sodium hydrogen carbonate solution, and extracted with ethyl acetate. The extract was washed successively with water and saturated brine, and dried over anhydrous magnesium sulfate, and the solvent was evaporated under reduced pressure to give the title compound (118 mg).
MS (API+): [M+H]$^+$ 349.1.

D) N$^2$,N$^2$-dimethyl-1-(4-(trifluoromethoxy)phenyl)ethane-1,2-diamine dihydrochloride To tert-butyl (2-(dimethylamino)-1-(4-(trifluoromethoxy)phenyl)ethyl)carbamate (117 mg) was added 4 M hydrogen chloride/ethyl acetate solution (5 mL). The reaction mixture was stirred at room temperature for 10 min, and the solvent was evaporated under reduced pressure to give the title compound (128 mg).
MS (API+), found: 249.1.

E) N-(2-(dimethylamino)-1-(4-(trifluoromethoxy)phenyl)ethyl)-2-oxo-2,3-dihydropyrido[2,3-b]pyrazine-4(1H)-carboxamide The title compound was obtained in the same manner as in Step G of Example 7.
MS (API+): [M+H]$^+$ 424.1.
$^1$H NMR (300 MHz, DMSO-d$_6$) δ 2.20 (6H, s), 2.35-2.78 (2H, m), 4.29-4.52 (2H, m), 4.89 (1H, brs), 7.10 (1H, dd, J=7.5, 4.9 Hz), 7.25-7.35 (3H, m), 7.45 (2H, d, J=8.3 Hz), 7.99 (1H, dd, J=4.9, 1.9 Hz), 10.38 (1H, d, J=6.0 Hz), 10.81 (1H, s).

Example 59

N-(2-(methylsulfanyl)-1-(4-(trifluoromethoxy)phenyl)ethyl)-2-oxo-2,3-dihydropyrido[2,3-b]pyrazine-4(1H)-carboxamide A) 2-(methylsulfanyl)-1-(4-(trifluoromethoxy)phenyl)ethanone To a solution of 2-bromo-1-(4-(trifluoromethoxy)phenyl)ethanone (5 g) in tetrahydrofuran (150 mL) was added sodium thiomethoxide (1.24 g) under ice-cooling. The reaction mixture was stirred at room temperature for 1 hr, filtered through NH silica gel pad, and eluted with ethyl acetate/hexane. The filtrate was concentrated under reduced pressure to give the title compound (4.23 g).
$^1$H NMR (300 MHz, CDCl$_3$) δ 2.14 (3H, s), 3.74 (2H, s), 7.27-7.36 (2H, m), 7.99-8.10 (2H, m).

B) 2-(methylsulfanyl)-1-(4-(trifluoromethoxy)phenyl)ethanamine

The title compound was obtained in the same manner as in Step C of Example 1 and Step C of Example 56.
MS (API+), found: 235.0.

C) N-(2-(methylsulfanyl)-1-(4-(trifluoromethoxy)phenyl)ethyl)-2-oxo-2,3-dihydropyrido[2,3-b]pyrazine-4(1H)-carboxamide The title compound was obtained in the same manner as in Step G of Example 7.
MS (API+): [M+H]$^+$ 427.1.
$^1$H NMR (300 MHz, CDCl$_3$) δ 2.05 (3H, s), 2.97 (2H, d, J=6.0 Hz), 4.69 (2H, s), 5.24 (1H, q, J=6.4 Hz), 7.01 (1H, dd, J=7.7, 5.1 Hz), 7.12-7.25 (3H, m), 7.34-7.46 (2H, m), 8.03 (1H, dd, J=4.9, 1.5 Hz), 9.55 (1H, brs), 10.76 (1H, d, J=7.2 Hz).

Example 60

N-(2-(methylsulfonyl)-1-(4-(trifluoromethoxy)phenyl)ethyl)-2-oxo-2,3-dihydropyrido[2,3-b]pyrazine-4(1H)-carboxamide To a solution of N-(2-(methylsulfanyl)-1-(4-(trifluoromethoxy)phenyl)ethyl)-2-oxo-2,3-dihydropyrido[2,3-b]pyrazine-4(1H)-carboxamide (54.0 mg) in ethyl acetate (10 mL) was added 3-chloroperbenzoic acid (68.7 mg) at room temperature. The reaction mixture was stirred overnight at room temperature, saturated aqueous sodium thiosulfate solution was added thereto, and the mixture was stirred for 5 min. Then, to the reaction mixture was added saturated aqueous sodium hydrogen carbonate solution, and the mixture was extracted with ethyl acetate. The extract was washed successively with saturated aqueous sodium hydrogen carbonate solution and saturated brine, and dried over anhydrous magnesium sulfate, and the solvent was evaporated under reduced pressure. The obtained solid was triturated with hexane/ethyl acetate, collected by filtration, and washed with hexane/ethyl acetate to give the title compound (38.2 mg).

MS (API+): [M+H]$^+$ 459.2.

$^1$H NMR (300 MHz, DMSO-d$_6$) δ 2.91 (3H, s), 3.63 (1H, dd, J=14.7, 4.5 Hz), 4.00 (1H, dd, J=14.5, 9.2 Hz), 4.26-4.56 (2H, m), 5.46 (1H, td, J=8.5, 3.8 Hz), 7.11 (1H, dd, J=7.9, 4.9 Hz), 7.30 (1H, dd, J=7.9, 1.5 Hz), 7.33-7.41 (2H, m), 7.53-7.61 (2H, m), 7.98 (1H, dd, J=4.9, 1.5 Hz), 10.62 (1H, d, J=7.9 Hz), 10.82 (1H, s).

Example 61

N-(1-(5-methoxypyridin-2-yl)propyl)-2-oxo-2,3-dihydropyrido[2,3-b]pyrazine-4(1H)-carboxamide A) methyl 5-methoxypyridine-2-carboxylate To a solution of 2-bromo-5-methoxypyridine (21 g) and triethylamine (55 g) in a mixed solvent of N,N-dimethylformamide (100 mL) and methanol (100 mL) were added 1,3-bis(diphenylphosphino)-propane (7.0 g) and palladium (II) acetate (3.6 g). The reaction mixture was stirred at 100° C. for 24 hr under carbon monoxide atmosphere (5.0 MPa), and diluted with ethyl acetate, and the mixture was washed with saturated brine. The organic layer was dried over anhydrous sodium sulfate, and the solvent was evaporated under reduced pressure. The residue was purified by silica gel column chromatography (petroleum ether/ethyl acetate) to give the title compound (10.2 g).

$^1$H NMR (300 MHz, CDCl$_3$) δ 3.93 (3H, s), 3.99 (3H, s), 7.25-7.29 (1H, m), 8.12 (1H, d, J=8.4 Hz), 8.40 (1H, d, J=3.0 Hz).

B) 5-methoxypyridine-2-carboxylic acid

To a solution of methyl 5-methoxypyridine-2-carboxylate (4.0 g) in methanol (50 mL) was added a solution of lithium hydroxide monohydrate (5.0 g) in water (10 mL). The reaction mixture was stirred at room temperature for 12 hr, the pH of the mixture was adjusted to 4-5 with 2 M hydrochloric acid, and the precipitate was collected by filtration. The obtained solid was washed with water, and dried to give the title compound (2.4 g).

$^1$H NMR (400 MHz, DMSO-d$_6$) δ 3.93 (3H, s), 7.49-7.51 (1H, m), 8.03 (1H, d, J=7.2 Hz), 8.36 (1H, d, J=2.8 Hz), 12.85 (1H, s).

C) N-(1-(5-methoxypyridin-2-yl)propyl)-2-oxo-2,3-dihydropyrido[2,3-b]pyrazine-4(1H)-carboxamide The title compound was obtained in the same manner as in Steps C-E of Example 49 and Step G of Example 7.

MS (API+): [M+H]$^+$ 342.1.

$^1$H NMR (400 MHz, CDCl$_3$) δ 0.79 (3H, t, J=7.2 Hz), 1.77-1.85 (2H, m), 3.81 (3H, s), 4.43 (2H, s), 4.82 (1H, q, J=6.8 Hz), 7.09 (1H, dd, J=8.0, 5.2 Hz), 7.28-7.36 (3H, m), 8.00 (1H, d, J=4.0 Hz), 8.26 (1H, d, J=2.8 Hz), 10.35 (1H, d, J=7.6 Hz).

Example 62

6-cyano-2-oxo-N-(1-(4-(trifluoromethoxy)phenyl) propyl)-2,3-dihydropyrido[2,3-b]pyrazine-4(1H)-carboxamide A) 6-cyano-2-oxo-N-(1-(4-(trifluoromethoxy)phenyl)propyl)-1-((2-(trimethylsilyl)ethoxy)methyl)-2,3-dihydropyrido[2,3-b]pyrazine-4(1H)-carboxamide To a solution of 6-chloro-2-oxo-N-(1-(4-(trifluoromethoxy)phenyl)propyl)-1-((2-(trimethylsilyl)ethoxy)methyl)-2,3-dihydropyrido[2,3-b]pyrazine-4(1H)-carboxamide (1.00 g), zinc cyanide (126 mg) and zinc (200 mg) in N,N-dimethylformamide (10 mL) were added tris(dibenzylideneacetone)dipalladium(0) (100 mg) and 1,1'-bis(diphenylphosphino)ferrocene (100 mg). The reaction mixture was stirred at 120° C. for 6 hr under nitrogen atmosphere, water was added thereto, and the mixture was extracted with ethyl acetate. The extract was washed with saturated brine, and dried over anhydrous sodium sulfate, and the solvent was evaporated under reduced pressure. The residue was purified by silica gel column chromatography (petroleum ether/ethyl acetate) to give the title compound (320 mg).

$^1$H NMR (300 MHz, CDCl$_3$) δ 0.00 (9H, s), 0.92-1.00 (5H, m), 1.84-1.98 (2H, m), 3.61-3.67 (2H, m), 4.66-4.78 (2H, m), 4.85-4.90 (1H, m), 5.30-5.38 (2H, m), 7.20 (2H, d, J=8.4 Hz), 7.36 (2H, d, J=8.8 Hz), 7.46 (1H, d, J=8.4 Hz), 7.74 (1H, d, J=8.4 Hz), 9.82 (1H, d, J=7.6 Hz).

B) 6-cyano-2-oxo-N-(1-(4-(trifluoromethoxy)phenyl)propyl)-2,3-dihydropyrido[2,3-b]pyrazine-4(1H)-carboxamide To 6-cyano-2-oxo-N-(1-(4-(trifluoromethoxy)phenyl) propyl)-1-((2-(trimethylsilyl)ethoxy)methyl)-2,3-dihydropyrido[2,3-b]pyrazine-4(1H)-carboxamide (320 mg) was added trifluoroacetic acid (3 mL) at room temperature. The reaction mixture was stirred at room temperature for 2 hr, and the solvent was evaporated under reduced pressure. To the residue was added aqueous sodium hydrogen carbonate solution, and the mixture was extracted with ethyl acetate. The extract was washed with saturated brine, and dried over anhydrous sodium sulfate, and the solvent was evaporated under reduced pressure. The residue was purified by HPLC (C18, mobile phase: water/acetonitrile (containing 0.1% TFA)), to the obtained fraction was added saturated aqueous sodium hydrogen carbonate solution, and the mixture was extracted with ethyl acetate. The extract was dried over anhydrous sodium sulfate, and concentrated under reduced pressure to give the title compound (110 mg).

MS (API−): [M−H]$^−$ 418.2.

$^1$H NMR (400 MHz, DMSO-d$_6$) δ 0.94 (3H, t, J=7.2 Hz), 1.76-1.84 (2H, m), 4.34-4.43 (2H, m), 4.80-4.85 (2H, m), 7.31-7.36 (3H, m), 7.48 (2H, d, J=8.4 Hz), 7.71 (1H, d, J=8.0 Hz), 9.59 (1H, d, J=7.2 Hz), 11.27 (1H, s).

Example 63

7-methoxy-N-(2-methoxy-1-(4-(trifluoromethoxy) phenyl)ethyl)-2-oxo-2,3-dihydropyrido[2,3-b]pyrazine-4(1H)-carboxamide A) methyl N-(5-iodo-3-nitropyridin-2-yl)glycinate To a solution of 2-chloro-5-iodo-3-nitropyridine (12.0 g) in ethanol (200 mL) were added methyl glycinate hydrochloride (10.6 g) and triethylamine (11.8 mL) at room temperature. The reaction mixture was heated at reflux for 20 hr, and the solvent was evaporated under reduced pressure. To the residue was added water, and the mixture was extracted with ethyl acetate. The extract was washed successively with water and saturated brine, and dried over anhydrous magnesium sulfate, and the solvent was evaporated under reduced pressure. The residue was crystallized from hexane/ethyl acetate to give the title compound (11.1 g).

MS (API+): [M+H]$^+$ 338.0.

B) 7-iodo-3,4-dihydropyrido[2,3-b]pyrazin-2(1H)-one

To a solution of methyl N-(5-iodo-3-nitropyridin-2-yl)glycinate (6.00 g) in tetrahydrofuran (300 mL) was added 5% platinum-carbon (500 mg). The reaction mixture was stirred overnight at room temperature under hydrogen atmosphere, the catalyst was filtered off, and the filtrate was concentrated under reduced pressure. The residue was dissolved in ethanol (200 mL), the solution was heated at reflux for 16 hr, and the solvent was evaporated under reduced pressure. The residue was washed with diisopropyl ether to give the title compound (4.48 g).

MS (API+): [M+H]$^+$ 276.0.

C) 7-iodo-1-((2-(trimethylsilyl)ethoxy)methyl)-3,4-dihydropyrido[2,3-b]pyrazin-2(1H)-one To a suspension of 7-iodo-3,4-dihydropyrido[2,3-b]pyrazin-2(1H)-one (3.82 g) in N,N-dimethylformamide (160 mL) was slowly added 1 M potassium hexamethyldisilazide/tetrahydrofuran solution (17.4 mL) at 0° C. The reaction mixture was stirred at 0° C. for 1 hr, 2-(chloromethoxy)ethyltrimethylsilane (3.62 mL) was slowly added thereto, and the mixture was stirred at room temperature for 20 hr. To the reaction mixture was added water, the insoluble substance was filtered off using Celite, and the filtrate was extracted with ethyl acetate. The extract was washed successively with water and saturated brine, and dried over anhydrous magnesium sulfate, and the solvent was evaporated under reduced pressure. The residue was purified by silica gel column chromatography (NH, hexane/ethyl acetate) to give the title compound (2.71 g).

MS (API+): [M+H]$^+$ 406.0.

D) 2-methoxy-1-(4-(trifluoromethoxy)phenyl)ethanone

To a solution of 2-bromo-1-(4-(trifluoromethoxy)phenyl)ethanone (6.12 g) in methanol (150 mL) were added silver(I) carbonate (7.75 g) and boron trifluoride diethyl ether complex (3.29 mL) at room temperature. The reaction mixture was stirred at 50° C. for 20 hr, the insoluble substance was filtered off, and the filtrate was concentrated under reduced pressure. To the residue was added water, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate) to give the title compound (4.78 g).

MS (API+): [M+H]$^+$ 235.1.

E) 2-methoxy-1-(4-(trifluoromethoxy)phenyl)ethanamine hydrochloride

To a solution of 2-methoxy-1-(4-(trifluoromethoxy)phenyl)ethanone (4.78 g) in ethanol (120 mL) were added hydroxylamine hydrochloride (2.84 g) and triethylamine (5.69 mL) at room temperature. The reaction mixture was stirred at room temperature for 5.5 hr, and the solvent was evaporated under reduced pressure. To the residue was added water, and the mixture was extracted with ethyl acetate. The extract was washed successively with water and saturated brine, and dried over anhydrous magnesium sulfate, and the solvent was evaporated under reduced pressure to give a crude product of N-hydroxy-2-methoxy-1-(4-(trifluoromethoxy)phenyl)ethanimine. To a solution of the obtained crude product in ethanol (160 mL) was added 10% palladium-carbon (containing 50% water, 350 mg). The reaction mixture was stirred at room temperature for 16 hr under hydrogen atmosphere, the catalyst was filtered off, and the filtrate was concentrated under reduced pressure. To a solution of the residue in ethyl acetate (10 mL) was added 4 M hydrogen chloride/ethyl acetate solution (100 mL), the mixture was stirred at room temperature for 2 hr, and the solvent was evaporated under reduced pressure. The residue was washed with diisopropyl ether to give the title compound (4.2 g).

$^1$H NMR (300 MHz, DMSO-d$_6$) δ 3.34 (3H, s), 3.58-3.74 (2H, m), 4.58 (1H, dd, J=6.6, 5.5 Hz), 7.46 (2H, d, J=8.7 Hz), 7.65 (2H, d, J=8.3 Hz), 8.57 (3H, brs).

F) 7-iodo-N-(2-methoxy-1-(4-(trifluoromethoxy)phenyl)ethyl)-2-oxo-1-((2-(trimethylsilyl)ethoxy)methyl)-2,3-dihydropyrido[2,3-b]pyrazine-4(1H)-carboxamide To a solution of 7-iodo-1-((2-(trimethylsilyl)ethoxy)methyl)-3,4-dihydropyrido[2,3-b]pyrazin-2(1H)-one (1.11 g) in tetrahydrofuran (42.0 mL) was added a solution of bis(trichloromethyl)carbonate (647 mg) in tetrahydrofuran (6.30 mL) at room temperature under nitrogen atmosphere. The reaction mixture was stirred at 40° C. for 1 hr under nitrogen atmosphere, and the solvent was evaporated under reduced pressure. To the residue was added tetrahydrofuran, and the solvent was evaporated under reduced pressure. The operation (addition of tetrahydrofuran and then evaporation) was repeated three times. The residue was diluted with tetrahydrofuran (21.0 mL), and the mixture was added to a mixture of 2-methoxy-1-(4-(trifluoromethoxy)phenyl)ethanamine hydrochloride (889 mg) and triethylamine (1.15 mL) in tetrahydrofuran (14.0 mL) at room temperature. The reaction mixture was stirred overnight at 60° C., and the solvent was evaporated under reduced pressure. To the residue was added ethyl acetate, washed successively with water and saturated brine, and dried over anhydrous sodium sulfate, and the solvent was evaporated under reduced pressure. The residue was purified by silica gel chromatography (hexane/ethyl acetate) to give the title compound (1.17 g).

MS (API+):[M+H]$^+$ 667.1.

G) 7-hydroxy-N-(2-methoxy-1-(4-(trifluoromethoxy)phenyl)ethyl)-2-oxo-1-((2-(trimethylsilyl)ethoxy)methyl)-2,3-dihydropyrido[2,3-b]pyrazine-4(1H)-carboxamide To a solution of 7-iodo-N-(2-methoxy-1-(4-(trifluoromethoxy)phenyl)ethyl)-2-oxo-1-((2-(trimethylsilyl)ethoxy)methyl)-2,3-dihydropyrido[2,3-b]pyrazine-4(1H)-carboxamide (100 mg), 4,4,4',4',5,5,5',5'-octamethyl-2,2'-bi- 1,3,2-dioxaborolane (79.0 mg) and potassium acetate (60.7 mg) in N,N-dimethylformamide (1.50 mL) was added (1,1-bis(diphenylphosphino)ferrocene)dichloropalladium(II) (11.2 mg). The reaction mixture was stirred overnight at 80° C. under argon atmosphere, water was added thereto, and the mixture was extracted with ethyl acetate. The extract was washed with saturated brine, and dried over anhydrous sodium sulfate, and the solvent was evaporated under reduced pressure to give a crude product (100 mg) of N-(2-methoxy-1-(4-(trifluoromethoxy)phenyl)ethyl)-2-oxo-7-(4,4,5,5-tetramethyl-1,3,2-dioxaborolan-2-yl)-1-((2-(trimethylsilyl)ethoxy)methyl)-2,3-dihydropyrido[2,3-b]pyrazine-4(1H)-carboxamide. To a solution of the obtained crude product (100 mg) in tetrahydrofuran (1.50 mL) was added 2 M aqueous sodium hydroxide solution (0.300 mL) at 0° C. The reaction mixture was stirred at 0° C. for 30 min, and 35% aqueous hydrogen peroxide (53.0 µL) was added thereto. The reaction mixture was stirred at room temperature for 1.5 hr, ice water was added thereto, and the mixture was extracted with ethyl acetate. The extract was washed successively with water and saturated brine, and dried over anhydrous sodium sulfate, and the solvent was evaporated under reduced pressure. The residue was purified by silica gel chromatography (hexane/ethyl acetate) to give the title compound (43.3 mg).

MS (API+):[M+H]$^+$ 557.2.

H) 7-methoxy-N-(2-methoxy-1-(4-(trifluoromethoxy)phenyl)ethyl)-2-oxo-1-((2-(trimethylsilyl)ethoxy)methyl)-2,3-dihydropyrido[2,3-b]pyrazine-4(1H)-carboxamide To a solution of 7-hydroxy-N-(2-methoxy-1-(4-(trifluoromethoxy)phenyl)ethyl)-2-oxo-1-((2-(trimethylsilyl)ethoxy)methyl)-2,3-dihydropyrido[2,3-b]pyrazine-4(1H)-carboxamide (43.3 mg) in N,N-dimethylformamide (1.00 mL) were added potassium carbonate (10.8 mg) and iodomethane (7.33 µL). The reaction mixture was stirred overnight at room temperature, water was added thereto, and the mixture was extracted with ethyl acetate. The extract was washed with saturated brine, and dried over anhydrous sodium sulfate, and the solvent was evaporated under reduced pressure. The residue was purified by silica gel chromatography (hexane/ethyl acetate) to give the title compound (28.6 mg).

MS (API+):[M+H]$^+$ 571.2.

I) 7-methoxy-N-(2-methoxy-1-(4-(trifluoromethoxy)phenyl)ethyl)-2-oxo-2,3-dihydropyrido[2,3-b]pyrazine-4(1H)-carboxamide To 7-methoxy-N-(2-methoxy-1-(4-(trifluoromethoxy)phenyl)ethyl)-2-oxo-1-((2-(trimethylsilyl)ethoxy)methyl)-2,3-dihydropyrido[2,3-b]pyrazine-4(1H)-carboxamide (28.6 mg) were added trifluoroacetic acid (0.710 mL) and water (79.5 µL). The reaction mixture was stirred at room temperature for 3 hr, and the solvent was evaporated under reduced pressure. The residue was dissolved in N,N-dimethylformamide (1.35 mL), and 8 M ammonia/methanol solution (270 µL) was added thereto. The reaction mixture was stirred at room temperature for 2 hr, and the solvent was evaporated under reduced pressure. The residue was diluted with ethyl acetate, and the mixture was washed successively with water and saturated brine, and dried over anhydrous sodium sulfate, and the solvent was evaporated under reduced pressure. The residue was washed with hexane/ethyl acetate to give the title compound (18.8 mg).

MS (API+):[M+H]$^+$ 441.2.
$^1$H NMR (300 MHz, DMSO-d$_6$) δ 3.28 (3H, s), 3.54-3.68 (2H, m), 3.83 (3H, s), 4.30-4.49 (2H, m), 4.98-5.11 (1H, m), 6.96 (1H, d, J=2.6 Hz), 7.28-7.36 (2H, m), 7.40-7.52 (2H, m), 7.76 (1H, d, J=2.6 Hz), 10.02 (1H, d, J=7.5 Hz), 10.76 (1H, brs).

Example 64

7-methoxy-N-((1S)-2-methoxy-1-(4-(trifluoromethoxy)phenyl)ethyl)-2-oxo-2,3-dihydropyrido[2,3-b]pyrazine-4(1H)-carboxamide Racemic 7-methoxy-N-(2-methoxy-1-(4-(trifluoromethoxy)phenyl)ethyl)-2-oxo-2,3-dihydropyrido[2,3-b]pyrazine-4(1H)-carboxamide (200 mg) was resolved by SFC (column: CHIRALPAK IA, 20 mmID×250 mmL, manufactured by Daicel Chemical Industries, Ltd., mobile phase: carbon dioxide/methanol=860/140), and crystallized from hexane/ethyl acetate to give the title compound having a shorter retention time (78.3 mg).

MS (API+):[M+H]$^+$ 441.2.
$^1$H NMR (300 MHz, DMSO-d$_6$) δ 3.28 (3H, s), 3.52-3.70 (2H, m), 3.83 (3H, s), 4.26-4.52 (2H, m), 4.97-5.13 (1H, m), 6.96 (1H, d, J=2.6 Hz), 7.32 (2H, d, J=8.3 Hz), 7.46 (2H, d, J=8.7 Hz), 7.76 (1H, d, J=2.6 Hz), 10.02 (1H, d, J=7.5 Hz), 10.77 (1H, brs).

Example 65

7-methoxy-N-((1R)-2-methoxy-1-(4-(trifluoromethoxy)phenyl)ethyl)-2-oxo-2,3-dihydropyrido[2,3-b]pyrazine-4(1H)-carboxamide Racemic 7-methoxy-N-(2-methoxy-1-(4-(trifluoromethoxy)phenyl)ethyl)-2-oxo-2,3-dihydropyrido[2,3-b]pyrazine-4(1H)-carboxamide (200 mg) was resolved by SFC (column: CHIRALPAK IA, 20 mmID×250 mmL, manufactured by Daicel Chemical Industries, Ltd., mobile phase: carbon dioxide/methanol=860/140), and crystallized from hexane/ethyl acetate to give the title compound having a longer retention time (60.0 mg).

MS (API+):[M+H]$^+$ 441.2.
$^1$H NMR (300 MHz, DMSO-d$_6$) δ 3.28 (3H, s), 3.53-3.67 (2H, m), 3.83 (3H, s), 4.27-4.51 (2H, m), 4.96-5.16 (1H, m), 6.96 (1H, d, J=3.0 Hz), 7.32 (2H, d, J=8.3 Hz), 7.41-7.54 (2H, m), 7.76 (1H, d, J=2.6 Hz), 10.02 (1H, d, J=7.2 Hz), 10.76 (1H, brs).

Example 66

N-(1-(3-fluoro-4-(trifluoromethoxy)phenyl)-2-methoxyethyl)-7-methoxy-2-oxo-2,3-dihydropyrido[2,3-b]pyrazine-4(1H)-carboxamide A) methyl N-(5-iodo-3-nitropyridin-2-yl)glycinate To a solution of 2-chloro-5-iodo-3-nitropyridine (12.0 g) in ethanol (200 mL) were added methyl glycinate hydrochloride (10.6 g) and triethylamine (11.8 mL) at room temperature. The reaction mixture was heated at reflux for 20 hr, and the solvent was evaporated under reduced pressure. To the residue was added water, and the mixture was extracted with ethyl acetate. The extract was washed successively with water and saturated brine, and dried over anhydrous magnesium sulfate, and the solvent was evaporated under reduced pressure. The residue was crystallized from hexane/ethyl acetate to give the title compound (11.1 g).

MS (API+): [M+H]$^+$ 338.0.

B) 7-iodo-3,4-dihydropyrido[2,3-b]pyrazin-2(1H)-one

To a solution of methyl N-(5-iodo-3-nitropyridin-2-yl) glycinate (6.00 g) in tetrahydrofuran (300 mL) was added 5% platinum-carbon (500 mg). The reaction mixture was stirred overnight at room temperature under hydrogen atmosphere, the catalyst was filtered off, and the filtrate was concentrated under reduced pressure. The residue was dissolved in ethanol (200 mL), the solution was heated at reflux for 16 hr, and the solvent was evaporated under reduced pressure. The residue was washed with diisopropyl ether to give the title compound (4.48 g)

MS (API+): [M+H]$^+$ 276.0.

C) 7-iodo-1-((2-(trimethylsilyl)ethoxy)methyl)-3,4-dihydropyrido[2,3-b]pyrazin-2(1H)-one To a suspension of 7-iodo-3,4-dihydropyrido[2,3-b] pyrazin-2(1H)-one (3.82 g) in N,N-dimethylformamide (160 mL) was slowly added 1 M potassium hexamethyldisilazide/tetrahydrofuran solution (17.4 mL) at 0° C. The reaction mixture was stirred at 0° C. for 1 hr, 2-(chloromethoxy) ethyltrimethylsilane (3.62 mL) was slowly added thereto, and the mixture was stirred at room temperature for 20 hr. To the reaction mixture was added water, the insoluble substance was filtered off using Celite, and the filtrate was extracted with ethyl acetate. The extract was washed successively with water and saturated brine, and dried over anhydrous magnesium sulfate, and the solvent was evaporated under reduced pressure. The residue was purified by silica gel column chromatography (NH, hexane/ethyl acetate) to give the title compound (2.71 g).

MS (API+): [M+H]$^+$ 406.0.

D) 3-fluoro-N-methoxy-N-methyl-4-(trifluoromethoxy)benzamide

To a solution of 3-fluoro-4-(trifluoromethoxy)benzoic acid (20.0 g), N,O-dimethylhydroxylamine hydrochloride (10.5 g) and triethylamine (24.9 mL) in N,N-dimethylformamide (300 mL) were added 1-hydroxybenzotriazole monohydrate (16.4 g) and 1-(3-dimethylaminopropyl)-3-ethylcarbodiimide hydrochloride (20.5 g) at room temperature. The reaction mixture was stirred overnight at room temperature, saturated aqueous sodium hydrogen carbonate solution was added thereto, and the mixture was extracted with ethyl acetate. The extract was washed successively with water and saturated brine, and dried over anhydrous magnesium sulfate, and the solvent was evaporated under reduced pressure to give the title compound (22.9 g).

$^1$H NMR (300 MHz, CDCl$_3$) δ 3.38 (3H, s), 3.56 (3H, s), 7.30-7.42 (1H, m), 7.51-7.65 (2H, m).

E) 1-(3-fluoro-4-(trifluoromethoxy)phenyl)ethanone

To a solution of 3-fluoro-N-methoxy-N-methyl-4-(trifluoromethoxy)benzamide (3.52 g) in tetrahydrofuran (60 mL) was slowly added 1 M methylmagnesium bromide/tetrahydrofuran solution (39.5 mL) at 0° C. The reaction mixture was stirred at room temperature for 4 hr, and poured into saturated aqueous ammonium chloride solution, and the mixture was extracted with ethyl acetate. The extract was dried over anhydrous sodium sulfate, and the solvent was evaporated under reduced pressure. The residue was purified by silica gel column chromatography (hexane/ethyl acetate) to give the title compound (2.33 g).

$^1$H NMR (300 MHz, DMSO-d$_6$) δ 2.62 (3H, s), 7.68-7.80 (1H, m), 7.86-7.96 (1H, m), 8.04 (1H, dd, J=11.0, 2.1 Hz).

F) 2-bromo-1-(3-fluoro-4-(trifluoromethoxy)phenyl)ethanone

To a solution of 1-(3-fluoro-4-(trifluoromethoxy)phenyl) ethanone (4.51 g) in acetic acid (50 mL) was slowly added a solution of bromine (1.12 mL) in acetic acid (5 mL) at room temperature. The reaction mixture was stirred at 50° C. for 1.5 hr, and the solvent was evaporated under reduced pressure. Aqueous sodium hydrogen carbonate solution was added thereto, and the mixture was extracted with ethyl acetate. The extract was washed with saturated aqueous sodium hydrogen carbonate solution, dried over anhydrous sodium sulfate, and the solvent was evaporated under reduced pressure. The residue was purified by silica gel column chromatography (hexane/ethyl acetate) to give the title compound (6.01 g).

$^1$H NMR (300 MHz, DMSO-d$_6$) δ 4.99 (2H, s), 7.73-7.84 (1H, m), 7.92-8.00 (1H, m), 8.12 (1H, dd, J=11.0, 2.0 Hz).

G) 1-(3-fluoro-4-(trifluoromethoxy)phenyl)-2-methoxyethanone

To a solution of 2-bromo-1-(3-fluoro-4-(trifluoromethoxy)phenyl)ethanone (6.01 g) in methanol (60 mL) were added silver(I) carbonate (7.53 g) and boron trifluoride diethyl ether complex (3.10 mL). The reaction mixture was stirred at 60° C. for 4 hr under nitrogen atmosphere, and the insoluble substance was filtered off, and washed with ethyl acetate. The filtrate was concentrated under reduced pressure, and to the residue were added ethyl acetate and brine. The precipitated solid was filtered off, and the organic layer and aqueous layer of the filtrate were separated. The aqueous layer was extracted with ethyl acetate. The extract was dried over anhydrous sodium sulfate, and the solvent was evaporated under reduced pressure. The residue was purified by silica gel column chromatography (hexane/ethyl acetate) to give the title compound (3.57 g).

$^1$H NMR (300 MHz, DMSO-d$_6$) δ 3.36 (3H, s), 4.81 (2H, s), 7.70-7.81 (1H, m), 7.83-7.92 (1H, m), 8.01 (1H, dd, J=10.9, 2.3 Hz).

H) 1-(3-fluoro-4-(trifluoromethoxy)phenyl)-2-methoxyethanamine hydrochloride

To a mixture of 1-(3-fluoro-4-(trifluoromethoxy)phenyl)-2-methoxyethanone (3.57 g) and hydroxylamine hydrochloride (2.01 g) in ethanol (50 mL) was added triethylamine (3.99 mL). The reaction mixture was stirred at room temperature for 16 hr, and the solvent was evaporated under reduced pressure. To the residue was added water, and the mixture was extracted with ethyl acetate. The extract was washed with saturated brine, and dried over anhydrous sodium sulfate, and the solvent was evaporated under reduced pressure to give a crude product (3.89 g) of 1-(3-fluoro-4-(trifluoromethoxy)phenyl)-N-hydroxy-2-methoxyethanimine. To a solution of the obtained crude product (3.89 g) in ethanol (60 mL) was added 20% palladium hydroxide-carbon (1.00 g). The reaction mixture was stirred at room temperature for 5 hr under hydrogen atmosphere, the insoluble substance was filtered off, and the filtrate was concentrated under reduced pressure. The residue was dissolved in ethyl acetate (10 mL), and 4 M hydrogen chloride/ethyl acetate solution (10 mL) was added thereto. The solvent was evaporated under reduced pressure, and the precipitated solid was washed with diisopropyl ether to give the title compound (2.86 g).
$^1$H NMR (300 MHz, DMSO-d$_6$) δ 3.32 (3H, s), 3.60-3.78 (2H, m), 4.53-4.66 (1H, m), 7.46-7.55 (1H, m), 7.62-7.84 (2H, m), 8.70 (3H, brs).

I) N-(1-(3-fluoro-4-(trifluoromethoxy)phenyl)-2-methoxyethyl)-7-iodo-2-oxo-1-((2-(trimethylsilyl)ethoxy)methyl)-2,3-dihydropyrido[2,3-b]pyrazine-4(1H)-carboxamide To a solution of 7-iodo-1-((2-(trimethylsilyl)ethoxy)methyl)-3,4-dihydropyrido[2,3-b]pyrazin-2(1H)-one (1.00 g) in tetrahydrofuran (37.4 mL) was slowly added a solution of bis(trichloromethyl)carbonate (586 mg) in tetrahydrofuran (5.60 mL) at room temperature under nitrogen atmosphere. The reaction mixture was stirred at 40° C. for 3 hr under nitrogen atmosphere, and the solvent was evaporated under reduced pressure. To the residue was added tetrahydrofuran, and the solvent was evaporated under reduced pressure. The operation (addition of tetrahydrofuran and then evaporation) was repeated three times. The residue was diluted with tetrahydrofuran (18.7 mL), and the mixture was slowly added to a mixture of 1-(3-fluoro-4-(trifluoromethoxy)phenyl)-2-methoxyethanamine hydrochloride (858 mg) and triethylamine (1.04 mL) in tetrahydrofuran (12.4 mL) at room temperature. The reaction mixture was stirred overnight at 60° C., and the solvent was evaporated under reduced pressure. To the residue was added water, and the mixture was extracted with ethyl acetate. The extract was washed with saturated brine, and dried over anhydrous sodium sulfate, and the solvent was evaporated under reduced pressure. The residue was purified by silica gel chromatography (hexane/ethyl acetate) to give the title compound (1.58 g).
MS (API+):[M+H]$^+$ 685.1.

J) N-(1-(3-fluoro-4-(trifluoromethoxy)phenyl)-2-methoxyethyl)-7-hydroxy-2-oxo-1-((2-(trimethylsilyl)ethoxy)methyl)-2,3-dihydropyrido[2,3-b]pyrazine-4(1H)-carboxamide To a solution of N-(1-(3-fluoro-4-(trifluoromethoxy)phenyl)-2-methoxyethyl)-7-iodo-2-oxo-1-((2-(trimethylsilyl)ethoxy)methyl)-2,3-dihydropyrido[2,3-b]pyrazine-4(1H)-carboxamide (1.58 g), 4,4,4',4',5,5,5',5'-octamethyl-2,2'-bi-1,3,2-dioxaborolane (1.19 g) and potassium acetate (935 mg) in N,N-dimethylformamide (23.1 mL) was added (1,1-bis(diphenylphosphino)ferrocene)dichloropalladium(II) (173 mg). The reaction mixture was stirred overnight at 80° C. under argon atmosphere, water was added thereto, and the mixture was extracted with ethyl acetate. The extract was washed successively with water and saturated brine, and dried over anhydrous sodium sulfate, and the solvent was evaporated under reduced pressure to give a crude product (2.02 g) of N-(1-(3-fluoro-4-(trifluoromethoxy)phenyl)-2-methoxyethyl)-2-oxo-7-(4,4,5,5-tetramethyl-1,3,2-dioxaborolan-2-yl)-1-((2-(trimethylsilyl)ethoxy)methyl)-2,3-dihydropyrido[2,3-b]pyrazine-4(1H)-carboxamide. To a solution of the obtained crude product (2.02 g) in tetrahydrofuran (29.6 mL) was added 2 M aqueous sodium hydroxide solution (5.91 mL) at 0° C. The reaction mixture was stirred at 0° C. for 30 min, and 35% aqueous hydrogen peroxide (1.04 mL) was added thereto. The reaction mixture was stirred at room temperature for 2 hr, and ice water was added thereto. The mixture was acidified with 1 M hydrochloric acid, and extracted with ethyl acetate. The extract was washed successively with water and saturated brine, and dried over anhydrous sodium sulfate, and the solvent was evaporated under reduced pressure. The residue was purified by silica gel chromatography (hexane/ethyl acetate) to give the title compound (1.24 g).
MS (API+):[M+H]$^+$ 575.2.

K) N-(1-(3-fluoro-4-(trifluoromethoxy)phenyl)-2-methoxyethyl)-7-methoxy-2-oxo-1-((2-(trimethylsilyl)ethoxy)methyl)-2,3-dihydropyrido[2,3-b]pyrazine-4(1H)-carboxamide To a solution of N-(1-(3-fluoro-4-(trifluoromethoxy)phenyl)-2-methoxyethyl)-7-hydroxy-2-oxo-1-((2-(trimethylsilyl)ethoxy)methyl)-2,3-dihydropyrido[2,3-b]pyrazine-4(1H)-carboxamide (1.24 g) in N,N-dimethylformamide (27.7 mL) were added potassium carbonate (300 mg) and iodomethane (204 µL). The reaction mixture was stirred at room temperature for 3 hr, water was added thereto, and the mixture was extracted with ethyl acetate. The extract was washed with saturated brine, and dried over anhydrous sodium sulfate, and the solvent was evaporated under reduced pressure. The residue was purified by silica gel chromatography (hexane/ethyl acetate) to give the title compound (646 mg).
MS (API+):[M+H]$^+$ 589.2.

L) N-(1-(3-fluoro-4-(trifluoromethoxy)phenyl)-2-methoxyethyl)-7-methoxy-2-oxo-2,3-dihydropyrido[2,3-b]pyrazine-4(1H)-carboxamide To N-(1-(3-fluoro-4-(trifluoromethoxy)phenyl)-2-methoxyethyl)-7-methoxy-2-oxo-1-((2-(trimethylsilyl)ethoxy)methyl)-2,3-dihydropyrido[2,3-b]pyrazine-4(1H)-carboxamide (646 mg) were added trifluoroacetic acid (15.8 mL) and water (1.77 mL). The reaction mixture was stirred at room temperature for 1 hr, and the solvent was evaporated under reduced pressure. The residue was dissolved in N,N-dimethylformamide (30.1 mL), and 8 M ammonia/methanol solution (5.91 mL) was added thereto. The reaction mixture was stirred at room temperature for 2 hr, and the solvent was evaporated under reduced pressure. The residue was diluted with ethyl acetate, and the mixture was washed successively with water and saturated brine, and dried over anhydrous sodium sulfate, and the solvent was evaporated under reduced pressure. The obtained solid was washed with hexane/ethyl acetate to give the title compound (402 mg).
MS (API+):[M+H]$^+$ 459.1.
$^1$H NMR (300 MHz, DMSO-d$_6$) δ 3.29 (3H, s), 3.54-3.70 (2H, m), 3.83 (3H, s), 4.29-4.49 (2H, m), 5.00-5.13 (1H, m), 6.97 (1H, d, J=2.6 Hz), 7.29 (1H, d, J=8.7 Hz), 7.41-7.59 (2H, m), 7.75 (1H, d, J=2.6 Hz), 10.01 (1H, d, J=7.5 Hz), 10.76 (1H, brs).

Example 67-I

N-((1S)-1-(3-fluoro-4-(trifluoromethoxy)phenyl)-2-methoxyethyl)-7-methoxy-2-oxo-2,3-dihydropyrido[2,3-b]pyrazine-4(1H)-carboxamide Racemic N-(1-(3-fluoro-4-(trifluoromethoxy)phenyl)-2-methoxyethyl)-7-methoxy-2-oxo-2,3-dihydropyrido[2,3-b]

pyrazine-4(1H)-carboxamide (388 mg) was resolved by SFC (column: CHIRALPAK IA, 20 mmID×250 mmL, manufactured by Daicel Chemical Industries, Ltd., mobile phase: carbon dioxide/methanol=860/140), and crystallized from hexane/ethyl acetate to give the title compound having a shorter retention time (139 mg) as crystals.

MS (API+):[M+H]$^+$ 459.1.

$^1$H NMR (300 MHz, DMSO-d$_6$) δ 3.29 (3H, s), 3.55-3.70 (2H, m), 3.83 (3H, s), 4.28-4.51 (2H, m), 4.99-5.14 (1H, m), 6.97 (1H, d, J=3.0 Hz), 7.29 (1H, d, J=8.7 Hz), 7.41-7.59 (2H, m), 7.75 (1H, d, J=2.6 Hz), 10.02 (1H, d, J=7.5 Hz), 10.76 (1H, brs).

Example 67-II

N-((1S)-1-(3-fluoro-4-(trifluoromethoxy)phenyl)-2-methoxyethyl)-7-methoxy-2-oxo-2,3-dihydropyrido[2,3-b]pyrazine-4(1H)-carboxamide A) ethyl (5-bromopyridin-3-yl)carbamate To a mixture of 5-bromopyridin-3-amine (35.4 g) and pyridine (19.8 mL) in tetrahydrofuran (600 mL) was slowly added ethyl chloroformate (23.4 mL) at 0° C. The reaction mixture was stirred overnight at room temperature under nitrogen atmosphere, and poured into water, and the mixture was extracted with ethyl acetate. The extract was washed with saturated brine, and dried over anhydrous magnesium sulfate, and the solvent was evaporated under reduced pressure. To the residue was added diisopropyl ether (400 mL), the mixture was stirred at room temperature for 20 min, and the obtained solid was collected by filtration to give the title compound (29.0 g)

MS (API+):[M+H]$^+$ 245.1.

B) ethyl (5-bromo-2-nitropyridin-3-yl)carbamate

To a solution of ethyl (5-bromopyridin-3-yl)carbamate (19.0 g) in conc. sulfuric acid (37.2 mL) was slowly added fuming nitric acid (26.1 mL) at 0° C. The reaction mixture was stirred at room temperature for 72 hr under nitrogen atmosphere. The reaction mixture was slowly poured into ice, the pH of the mixture was adjusted to 9 with 28% aqueous ammonia, and the mixture was extracted with ethyl acetate. The extract was washed with saturated brine, and dried over anhydrous sodium sulfate, and the solvent was evaporated under reduced pressure. To the residue was added ethyl acetate/hexane, the mixture was stirred for 15 min, and the resulting solid was collected by filtration, and washed with hexane to give the title compound (13.9 g).

MS (API+):[M+H]$^+$ 290.1.

C) 5-methoxy-2-nitropyridin-3-amine

To a solution of ethyl (5-bromo-2-nitropyridin-3-yl)carbamate (31.1 g) in methanol (900 mL) was added 28% sodium methoxide/methanol solution (83.0 g) at room temperature. The reaction mixture was stirred at 65° C. for 4 hr under nitrogen atmosphere, and the solvent was evaporated to about 150 mL under reduced pressure. To the residue was added saturated aqueous ammonium chloride solution, the mixture was stirred at room temperature for 20 min, and the solvent was evaporated to about 100 mL under reduced pressure. The resulting solid was collected by filtration, and washed with water to give the title compound (16.6 g).

MS (API+):[M+H]$^+$ 170.2.

D) 2-chloro-N-(5-methoxy-2-nitropyridin-3-yl)acetamide

To a solution of 5-methoxy-2-nitropyridin-3-amine (24.7 g) in N,N-dimethylformamide (740 mL) was slowly added chloroacetyl chloride (23.2 mL) in tetrahydrofuran (40 mL) solution at 0° C. The reaction mixture was stirred at room temperature for 3 hr under nitrogen atmosphere, and the solvent was evaporated under reduced pressure. To the residue was added saturated aqueous sodium hydrogen carbonate solution, and the mixture was extracted with ethyl acetate. The extract was washed with saturated brine, and dried over anhydrous magnesium sulfate, and the solvent was evaporated under reduced pressure. To the residue was added diisopropyl ether/hexane, and the mixture was stirred at room temperature for 30 min. The obtained solid was collected by filtration, and washed with diisopropyl ether/hexane to give the title compound (34.1 g).

MS (API+):[M+H]$^+$ 246.0.

E) N-(2-amino-5-methoxypyridin-3-yl)-2-chloroacetamide

A mixture of 2-chloro-N-(5-methoxy-2-nitropyridin-3-yl)acetamide (34.1 g), ammonium chloride (44.6 g), iron (27.1 g), ethanol (823 mL) and water (206 mL) was stirred 75° C. for 40 min, and the solvent was evaporated under reduced pressure. To the residue were added tetrahydrofuran (500 mL) and saturated aqueous sodium hydrogen carbonate solution (300 mL), and the reaction mixture was stirred for 15 min. The insoluble substance was filtered off through Celite, and to the filtrate was added saturated brine, and the mixture was extracted with ethyl acetate. The extract was washed with saturated brine, and the solvent was evaporated under reduced pressure. To the residue was added diisopropyl ether/hexane, and the obtained solid was collected by filtration, and washed with diisopropyl ether/hexane to give the title compound (26.3 g).

MS (API+):[M+H]$^+$ 216.1.

F) benzyl (3-((chloroacetyl)amino)-5-methoxypyridin-2-yl)carbamate

To a mixture of N-(2-amino-5-methoxypyridin-3-yl)-2-chloroacetamide (2.74 g) and pyridine (5.14 mL) in tetrahydrofuran (85 mL) was slowly added benzyl chloroformate (2.72 mL) at 0° C. The reaction mixture was stirred at room temperature for 1 hr, ethyl acetate was added thereto, and the mixture was washed with a mixture of aqueous sodium hydrogen carbonate solution and brine. The organic layer was again washed with saturated brine, and the solvent was evaporated under reduced pressure. The residue was purified by silica gel column chromatography (hexane/ethyl acetate), and the obtained solid was washed with diisopropyl ether to give the title compound (3.79 g).

$^1$H NMR (300 MHz, DMSO-d$_6$) δ 3.82 (3H, s), 4.36 (2H, s), 5.13 (2H, s), 7.30-7.43 (5H, m), 7.87 (1H, d, J=3.0 Hz), 7.95 (1H, d, J=2.6 Hz), 9.46 (1H, s), 9.64 (1H, s).

G) benzyl 7-methoxy-2-oxo-2,3-dihydropyrido[2,3-b]pyrazine-4(1H)-carboxylate

To a solution of benzyl (3-((chloroacetyl)amino)-5-methoxypyridin-2-yl)carbamate (200 mg) in N,N-dimethylformamide (11 mL) was added cesium carbonate (279 mg)

at room temperature, and reaction mixture was stirred at 50° C. for 30 min. The reaction mixture was diluted with ethyl acetate, and washed with saturated brine, and the solvent was evaporated under reduced pressure. The residue was purified by silica gel column chromatography (hexane/ethyl acetate) to give the title compound (115 mg).

$^1$H NMR (300 MHz, DMSO-$d_6$) δ 3.81 (3H, s), 4.36 (2H, s), 5.20 (2H, s), 6.92 (1H, d, J=2.6 Hz), 7.27-7.43 (5H, m), 7.84 (1H, d, J=2.6 Hz), 10.72 (1H, s).

H) 7-methoxy-3,4-dihydropyrido[2,3-b]pyrazin-2 (1H)-one

To a solution of benzyl 7-methoxy-2-oxo-2,3-dihydropyrido[2,3-b]pyrazine-4(1H)-carboxylate (0.722 g) in tetrahydrofuran (46.1 mL) was added 10% palladium-carbon (containing 50% water, 0.049 g), and the reaction mixture was stirred at room temperature for 15 hr under hydrogen atmosphere. To the reaction mixture was added methanol at 50° C. to dissolve the precipitated solid, the catalyst was filtered off, and the filtrate was concentrated under reduced pressure. The obtained solid was washed with diisopropyl ether to give the title compound (0.380 g).

$^1$H NMR (300 MHz, DMSO-$d_6$) δ 3.68 (3H, s), 3.82 (2H, d, J=1.9 Hz), 6.32 (1H, s), 6.66 (1H, d, J=2.6 Hz), 7.37 (1H, d, J=2.6 Hz), 10.32 (1H, s).

I) N,2-dimethoxy-N-methylacetamide

To a mixture of N,O-dimethylhydroxylamine hydrochloride (24.7 g) and potassium carbonate (63.7 g) in acetonitrile (330 mL) was added 2-methoxyacetyl chloride (25.0 g) at the temperature of 10° C. or lower. The reaction mixture was stirred overnight at room temperature, the insoluble substance was filtered off, and the filtrate was concentrated under reduced pressure. The residue was distilled (boiling point: 60° C./0.8 KPa) to give the title compound (25.8 g).

$^1$H NMR (300 MHz, CDCl$_3$) δ 3.20 (3H, s), 3.47 (3H, d, J=0.8 Hz), 3.69 (3H, s), 4.22 (2H, s).

J) 1-(3-fluoro-4-(trifluoromethoxy)phenyl)-2-methoxyethanone

To a mixture of 4-bromo-2-fluoro-1-(trifluoromethoxy) benzene (25.0 g) and N,2-dimethoxy-N-methylacetamide (15.4 g) in tetrahydrofuran (400 mL) was slowly added 1.6 M n-butyllithium/hexane solution (72.4 mL) at −78° C. under nitrogen atmosphere. The reaction mixture was stirred at −78° C. for 20 min under nitrogen atmosphere, and neutralized with 0.1 M hydrochloric acid, and the mixture was extracted with ethyl acetate. The extract was washed successively with water and saturated brine, and dried over anhydrous sodium sulfate, and the solvent was evaporated under reduced pressure. The residue was purified by silica gel chromatography (hexane/ethyl acetate) to give the title compound (15.7 g).

$^1$H NMR (300 MHz, CDCl$_3$) δ 3.50 (3H, s), 4.63 (2H, s), 7.42 (1H, ddd, J=8.6, 7.3, 1.5 Hz), 7.75-7.81 (1H, m), 7.83 (1H, dd, J=10.2, 1.9 Hz).

K) 1-(3-fluoro-4-(trifluoromethoxy)phenyl)-N-hydroxy-2-methoxyethanimine

To a solution of 1-(3-fluoro-4-(trifluoromethoxy)phenyl)-2-methoxyethanone (7.56 g) in ethanol (250 mL) were added hydroxylamine hydrochloride (4.17 g) and triethylamine (8.36 mL) at room temperature. The reaction mixture was stirred at room temperature for 16 hr, and the solvent was evaporated under reduced pressure. To the residue was added water, and the mixture was extracted with ethyl acetate. The extract was washed successively with water and saturated brine, and dried over anhydrous magnesium sulfate, and the solvent was evaporated under reduced pressure. The residue was purified by silica gel chromatography (hexane/ethyl acetate) to give the title compound (7.88 g).

MS (API+): [M+H]$^+$ 268.0.

L) tert-butyl (1-(3-fluoro-4-(trifluoromethoxy)phenyl)-2-methoxyethyl)carbamate To a solution of 1-(3-fluoro-4-(trifluoromethoxy)phenyl)-N-hydroxy-2-methoxyethanimine (7.88 g) in ethanol (200 mL) was added 10% palladium-carbon (containing 50% water, 1.00 g). The reaction mixture was stirred overnight at room temperature under hydrogen atmosphere, the insoluble substance was filtered off, and the filtrate was concentrated under reduced pressure. To a tetrahydrofuran solution (200 mL) of the residue were added di-tert-butyl dicarbonate (7.53 mL) and triethylamine (6.17 mL), and the mixture was stirred at room temperature for 16 hr. To the reaction mixture was added water, and the mixture was extracted with ethyl acetate. The extract was washed with saturated brine, dried over anhydrous magnesium sulfate, and the solvent was evaporated under reduced pressure. The residue was purified by silica gel column chromatography (hexane/ethyl acetate) to give the title compound (8.25 g).

$^1$H NMR (300 MHz, CDCl$_3$) δ 1.42 (9H, brs), 3.35 (3H, s), 3.49-3.67 (2H, m), 4.78 (1H, brs), 5.34 (1H, brs), 7.08-7.29 (3H, m).

M) tert-butyl ((1S)-1-(3-fluoro-4-(trifluoromethoxy)phenyl)-2-methoxyethyl)carbamate Racemic tert-butyl (1-(3-fluoro-4-(trifluoromethoxy)phenyl)-2-methoxyethyl)carbamate (12.48 g) was resolved by HPLC (column: CHIRALPAK AD, 50 mmID×500 mmL, manufactured by Daicel Chemical Industries, Ltd., mobile phase: hexane/ethanol=950/50) to give the title compound having a shorter retention time (5.73 g).

MS (API+), found: 254.0.

N) (1S)-1-(3-fluoro-4-(trifluoromethoxy)phenyl)-2-methoxyethanamine hydrochloride A mixture of tert-butyl ((1S)-1-(3-fluoro-4-(trifluoromethoxy)phenyl)-2-methoxyethyl)carbamate (5.73 g) and 4 M hydrogen chloride/ethyl acetate solution (100 mL) was stirred at room temperature for 3 hr. The solvent was evaporated under reduced pressure, and the residue was washed with diisopropyl ether to give the title compound (3.22 g).

MS (API+), found: 254.0.

O) N-((1S)-1-(3-fluoro-4-(trifluoromethoxy)phenyl)-2-methoxyethyl)-7-methoxy-2-oxo-2,3-dihydropyrido[2,3-b]pyrazine-4(1H)-carboxamide To a mixture of 7-methoxy-3,4-dihydropyrido[2,3-b]pyrazin-2(1H)-one (2.49 g) and diisopropylethylamine (7.13 mL) in tetrahydrofuran (120 mL) was slowly added 4-nitrophenyl chloroformate (3.64 g) at 0° C. The reaction mixture was stirred at room temperature for 3 hr under nitrogen atmosphere, and the solvent was evaporated under reduced pressure. To the residue were added diisopropyl ether (200 mL) and saturated brine (150 mL), and the mixture was stirred at room temperature for 20 min. The resulting solid was collected by filtration, washed with water and diisopropyl ether to give 4-nitrophenyl 7-methoxy-2-oxo-2,3-dihydropyrido[2,3-b]pyrazine-4(1H)-carboxylate (4.20 g). A mixture of 4-nitrophenyl 7-methoxy-2-oxo-2,3-dihydropyrido[2,3-b]pyrazine-4(1H)-carboxylate (4.20 g), diisopropylethylamine (11.9 mL) and (S)-1-(3-fluoro-4-(trifluoromethoxy)phenyl)-2-methoxyethanamine hydrochloride (4.43 g) in N,N-dimethylformamide (130 mL) was stirred at room temperature for 16 hr, and the solvent was evaporated under reduced pressure. To the residue was added aqueous sodium hydrogen carbonate solution, and the mixture was extracted with a mixed solvent of ethyl acetate and tetrahydrofuran. The extract was washed with saturated brine, and dried over anhydrous sodium sulfate, and the solvent was evaporated under reduced pressure. The residue was purified by silica gel chromatography (NH, hexane/ethyl acetate) to give (S)—N-(1-(3-fluoro-4-(trifluoromethoxy)phenyl)-2-methoxyethyl)-7-methoxy-2-oxo-2,3-dihydropyrido[2,3-b]pyrazine-4(1H)-carboxamide (5.01 g). To a solution of the obtained (S)—N-(1-(3-fluoro-4-(trifluoromethoxy)phenyl)-2-methoxyethyl)-7-methoxy-2-oxo-2,3-dihydropyrido[2,3-b]pyrazine-4(1H)-carboxamide (5.00 g) in ethanol (200 mL) was added activated carbon (shirasagi) (10 g), and the mixture was stirred at room temperature for 30 min. The insoluble substance was filtered off, and washed with acetone. The filtrate was concentrated under reduced pressure to give (S)—N-(1-(3-fluoro-4-(trifluoromethoxy)phenyl)-2-methoxyethyl)-7-methoxy-2-oxo-2,3-dihydropyrido[2,3-b]pyrazine-4(1H)-carboxamide (4.17 g). To a solution of the obtained (S)—N-(1-(3-fluoro-4-(trifluoromethoxy)phenyl)-2-methoxyethyl)-7-methoxy-2-oxo-2,3-dihydropyrido[2,3-b]pyrazine-4(1H)-carboxamide (4.17 g) in acetone (35 mL) was slowly added heptane (70 mL) at 52° C. The mixture was stirred at 52° C. for 1 hr, heptane (35 mL) was slowly added thereto at 52° C., and the mixture was gradually cooled to room temperature. The mixture was stirred overnight at room temperature, and then at 5° C. for 1 hr. The resulting solid was collected by filtration, and washed with acetone/heptane to give the title compound (3.15 g) as crystals.

MS (API+): [M+H]$^+$ 459.2.

$^1$H NMR (300 MHz, DMSO-d$_6$) δ 3.29 (3H, s), 3.56-3.70 (2H, m), 3.83 (3H, s), 4.30-4.52 (2H, m), 4.95-5.16 (1H, m), 6.96 (1H, d, J=2.6 Hz), 7.29 (1H, d, J=8.3 Hz), 7.43-7.57 (2H, m), 7.75 (1H, d, J=3.0 Hz), 10.02 (1H, d, J=7.2 Hz), 10.78 (1H, brs).

Example 68

N-((1R)-1-(3-fluoro-4-(trifluoromethoxy)phenyl)-2-methoxyethyl)-7-methoxy-2-oxo-2,3-dihydropyrido[2,3-b]pyrazine-4(1H)-carboxamide Racemic N-(1-(3-fluoro-4-(trifluoromethoxy)phenyl)-2-methoxyethyl)-7-methoxy-2-oxo-2,3-dihydropyrido[2,3-b]pyrazine-4(1H)-carboxamide (388 mg) was resolved by SFC (column: CHIRALPAK IA, 20 mmID×250 mmL, manufactured by Daicel Chemical Industries, Ltd., mobile phase: carbon dioxide/methanol=860/140) to give the title compound having a longer retention time (145 mg).

MS (API+):[M+H]$^+$ 459.1.

$^1$H NMR (300 MHz, DMSO-d$_6$) δ 3.29 (3H, s), 3.57-3.69 (2H, m), 3.83 (3H, s), 4.29-4.50 (2H, m), 4.97-5.15 (1H, m), 6.97 (1H, d, J=2.6 Hz), 7.29 (1H, d, J=8.7 Hz), 7.41-7.59 (2H, m), 7.75 (1H, d, J=2.6 Hz), 10.02 (1H, d, J=7.5 Hz), 10.76 (1H, brs).

Example 69

7-methoxy-N-(2-methoxy-1-(4-(trifluoromethyl)phenyl)ethyl)-2-oxo-2,3-dihydropyrido[2,3-b]pyrazine-4(1H)-carboxamide A) methyl N-(5-iodo-3-nitropyridin-2-yl)glycinate To a solution of 2-chloro-5-iodo-3-nitropyridine (12.0 g) in ethanol (200 mL) were added methyl glycinate hydrochloride (10.6 g) and triethylamine (11.8 mL) at room temperature. The reaction mixture was heated at reflux for 20 hr, and the solvent was evaporated under reduced pressure. To the residue was added water, and the mixture was extracted with ethyl acetate. The extract was washed successively with water and saturated brine, and dried over anhydrous magnesium sulfate, and the solvent was evaporated under reduced pressure. The residue was crystallized from hexane/ethyl acetate to give the title compound (11.1 g).

MS (API+): [M+H]$^+$ 338.0.

B) 7-iodo-3,4-dihydropyrido[2,3-b]pyrazin-2(1H)-one

To a solution of methyl N-(5-iodo-3-nitropyridin-2-yl)glycinate (6.00 g) in tetrahydrofuran (300 mL) was added 5% platinum-carbon (500 mg). The reaction mixture was stirred overnight at room temperature under hydrogen atmosphere, the catalyst was filtered off, and the filtrate was concentrated under reduced pressure. The residue was dissolved in ethanol (200 mL), the mixture was heated at reflux for 16 hr, and the solvent was evaporated under reduced pressure. The residue was washed with diisopropyl ether to give the title compound (4.48 g).

MS (API+):[M+H]$^+$ 276.0.

C) 7-iodo-1-((2-(trimethylsilyl)ethoxy)methyl)-3,4-dihydropyrido[2,3-b]pyrazin-2(1H)-one To a suspension of 7-iodo-3,4-dihydropyrido[2,3-b]pyrazin-2(1H)-one (3.82 g) in N,N-dimethylformamide (160 mL) was slowly added 1 M potassium hexamethyldisilazide/tetrahydrofuran solution (17.4 mL) at 0° C. The reaction mixture was stirred at 0° C. for 1 hr, 2-(chloromethoxy)ethyltrimethylsilane (3.62 mL) was slowly added thereto, and the mixture was stirred at room temperature for 20 hr. To the reaction mixture was added water, the insoluble substance was filtered off using Celite, and the filtrate was extracted with ethyl acetate. The extract was washed successively with water and saturated brine, and dried over anhydrous magnesium sulfate, and the solvent was evaporated under reduced pressure. The residue was purified by silica gel column chromatography (NH, hexane/ethyl acetate) to give the title compound (2.71 g).

MS (API+): [M+H]$^+$ 406.0.

D) 2-methoxy-1-(4-(trifluoromethyl)phenyl)ethanone

To a solution of 2-bromo-1-(4-(trifluoromethyl)phenyl)ethanone (2.50 g) in methanol (50 mL) were added silver(I) carbonate (2.99 g) and boron trifluoride diethyl ether complex (1.42 mL) at room temperature. The reaction mixture was stirred overnight at 50° C., the insoluble substance was filtered off, and the solvent was evaporated under reduced pressure. To the residue was added water, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate) to give the title compound (1.84 g).
$^1$H NMR (300 MHz, CDCl$_3$) δ 3.51 (3H, s), 4.70 (2H, s), 7.75 (2H, d, J=8.3 Hz), 8.06 (2H, d, J=7.9 Hz).

E)
2-methoxy-1-(4-(trifluoromethyl)phenyl)ethanamine hydrochloride

To a solution of 2-methoxy-1-(4-(trifluoromethyl)phenyl)ethanone (1.84 g) in ethanol (100 mL) were added hydroxylamine hydrochloride (1.17 g) and triethylamine (2.35 mL) at room temperature. The reaction mixture was stirred at room temperature for 4.5 hr, and the solvent was evaporated under reduced pressure. To the residue was added water, and the mixture was extracted with ethyl acetate. The extract was washed with saturated brine, and dried over anhydrous magnesium sulfate, and the solvent was evaporated under reduced pressure to give a crude product of N-hydroxy-2-methoxy-1-(4-(trifluoromethyl)phenyl)ethanimine. To a solution of the obtained crude product in ethanol (100 mL) was added 10% palladium-carbon (containing 50% water, 200 mg). The reaction mixture was stirred overnight at room temperature under hydrogen atmosphere, the catalyst was filtered off, and the filtrate was concentrated under reduced pressure. A solution of the residue in ethyl acetate (5 mL) was added to 4 M hydrogen chloride/ethyl acetate solution (20 mL). The reaction mixture was stirred at room temperature for 30 min, and the solvent was evaporated under reduced pressure. The residue was crystallized from ethyl acetate to give the title compound (1.81 g).
$^1$H NMR (300 MHz, DMSO-d$_6$) δ 3.26-3.41 (3H, m), 3.59-3.78 (2H, m), 4.58-4.73 (1H, m), 7.66-7.91 (4H, m), 8.69 (3H, brs).

F) 7-iodo-N-(2-methoxy-1-(4-(trifluoromethyl)phenyl)ethyl)-2-oxo-1-((2-(trimethylsilyl)ethoxy)methyl)-2,3-dihydropyrido[2,3-b]pyrazine-4(1H)-carboxamide To a solution of 7-iodo-1-((2-(trimethylsilyl)ethoxy)methyl)-3,4-dihydropyrido[2,3-b]pyrazin-2(1H)-one (1.53 g) in tetrahydrofuran (60 mL) was added a solution of bis(trichloromethyl)carbonate (0.896 g) in tetrahydrofuran (8.0 mL) at room temperature. The reaction mixture was stirred at 40° C. for 5 hr, and the solvent was evaporated under reduced pressure. The residue was diluted with tetrahydrofuran (10.0 mL), and the mixture was added to a mixture of 2-methoxy-1-(4-(trifluoromethyl)phenyl)ethanamine hydrochloride (1.16 g) and triethylamine (1.58 mL) in tetrahydrofuran (60 mL) at room temperature. The reaction mixture was stirred at 60° C. for 16 hr, water was added thereto, and the mixture was extracted with ethyl acetate. The extract was washed successively with water and saturated brine, and dried over anhydrous magnesium sulfate, and the solvent was evaporated under reduced pressure. The residue was purified by silica gel column chromatography (NH, hexane/ethyl acetate) to give the title compound (2.18 g).
MS (API+): [M+H]$^+$ 651.1.

G) 7-hydroxy-N-(2-methoxy-1-(4-(trifluoromethyl)phenyl)ethyl)-2-oxo-1-((2-(trimethylsilyl)ethoxy)methyl)-2,3-dihydropyrido[2,3-b]pyrazine-4(1H)-carboxamide To a solution of 7-iodo-N-(2-methoxy-1-(4-(trifluoromethyl)phenyl)ethyl)-2-oxo-1-((2-(trimethylsilyl)ethoxy)methyl)-2,3-dihydropyrido[2,3-b]pyrazine-4(1H)-carboxamide (1.19 g), 4,4,4',4',5,5,5',5'-octamethyl-2,2'-bi-1,3,2-dioxaborolane (941 mg), potassium acetate (742 mg) in N,N-dimethylformamide (18.3 mL) was added (1,1-bis(diphenylphosphino)ferrocene)dichloropalladium(II) (137 mg). The reaction mixture was stirred overnight at 80° C. under argon atmosphere, water was added thereto, and the mixture was extracted with ethyl acetate. The extract was washed successively with water and saturated brine, and dried over anhydrous sodium sulfate, and the solvent was evaporated under reduced pressure to give a crude product (1.95 g) of N-(2-methoxy-1-(4-(trifluoromethyl)phenyl)ethyl)-2-oxo-7-(4,4,5,5-tetramethyl-1,3,2-dioxaborolan-2-yl)-1-((2-(trimethylsilyl)ethoxy)methyl)-2,3-dihydropyrido[2,3-b]pyrazine-4(1H)-carboxamide. To a solution of the obtained crude product (1.19 g) in tetrahydrofuran (18.3 mL) was added 2 M aqueous sodium hydroxide solution (3.67 mL) at 0° C. The reaction mixture was stirred at 0° C. for 30 min, and 35% aqueous hydrogen peroxide (642 µL) was added thereto. The reaction mixture was stirred at room temperature for 2 hr, ice water was added thereto, the mixture was acidified with 1 M hydrochloric acid, and extracted with ethyl acetate. The extract was washed successively with water and saturated brine, and dried over anhydrous sodium sulfate, and the solvent was evaporated under reduced pressure. The residue was purified by silica gel chromatography (hexane/ethyl acetate) to give the title compound (796 mg).
MS (API+):[M+H]$^+$ 541.2.

H) 7-methoxy-N-(2-methoxy-1-(4-(trifluoromethyl)phenyl)ethyl)-2-oxo-1-((2-(trimethylsilyl)ethoxy)methyl)-2,3-dihydropyrido[2,3-b]pyrazine-4(1H)-carboxamide To a solution of 7-hydroxy-N-(2-methoxy-1-(4-(trifluoromethyl)phenyl)ethyl)-2-oxo-1-((2-(trimethylsilyl)ethoxy)methyl)-2,3-dihydropyrido[2,3-b]pyrazine-4(1H)-carboxamide (796 mg) in N,N-dimethylformamide (18.9 mL) were added potassium carbonate (205 mg) and iodomethane (139 µL). The reaction mixture was stirred overnight at room temperature, water was added thereto, and the mixture was extracted with ethyl acetate. The extract was washed with saturated brine, and dried over anhydrous sodium sulfate, and the solvent was evaporated under reduced pressure. The residue was purified by silica gel chromatography (hexane/ethyl acetate) to give the title compound (665 mg).
MS (API+):[M+H]$^+$ 555.2.

I) 7-methoxy-N-(2-methoxy-1-(4-(trifluoromethyl)phenyl)ethyl)-2-oxo-2,3-dihydropyrido[2,3-b]pyrazine-4(1H)-carboxamide To 7-methoxy-N-(2-methoxy-1-(4-(trifluoromethyl)phenyl)ethyl)-2-oxo-1-((2-(trimethylsilyl)ethoxy)methyl)-2,3-dihydropyrido[2,3-b]pyrazine-4(1H)-carboxamide (665 mg) were added trifluoroacetic acid (17.3 mL) and water (1.93 mL). The reaction mixture was stirred at room temperature for 1 hr, and the solvent was evaporated under reduced pressure. The residue was dissolved in N,N-dimethylformamide (32.9 mL), and 8 M ammonia/methanol solution (6.46 mL) was added thereto. The reaction mixture was stirred at room temperature for 10 min, and the solvent was evaporated under reduced pressure. The residue was diluted with ethyl acetate, and the mixture was washed successively with water and saturated brine, and dried over anhydrous sodium sulfate, and the solvent was evaporated under reduced pressure. The residue was crystallized from hexane/ethyl acetate to give the title compound (474 mg).

MS (API+):[M+H]$^+$ 425.1.

$^1$H NMR (300 MHz, DMSO-d$_6$) δ 3.28 (3H, s), 3.59-3.68 (2H, m), 3.83 (3H, s), 4.25-4.55 (2H, m), 5.00-5.17 (1H, m), 6.97 (1H, d, J=3.0 Hz), 7.56 (2H, d, J=8.3 Hz), 7.64-7.73 (2H, m), 7.77 (1H, d, J=2.6 Hz), 10.07 (1H, d, J=7.5 Hz), 10.77 (1H, s).

Example 70

Optically Active 7-methoxy-N-(2-methoxy-1-(4-(trifluoromethyl)phenyl)ethyl)-2-oxo-2,3-dihydropyrido[2,3-b]pyrazine-4(1H)-carboxamide Racemic 7-methoxy-N-(2-methoxy-1-(4-(trifluoromethyl)phenyl)ethyl)-2-oxo-2,3-dihydropyrido[2,3-b]pyrazine-4(1H)-carboxamide (444 mg) was resolved by HPLC (column: CHIRALPAK AD, 50 mmID×500 mmL, manufactured by Daicel Chemical Industries, Ltd., mobile phase: hexane/ethanol=600/400), and crystallized from hexane/ethyl acetate to give the title compound having a shorter retention time (197 mg).

MS (API+):[M+H]$^+$ 425.1.

$^1$H NMR (300 MHz, DMSO-d$_6$) δ 3.28 (3H, s), 3.61-3.68 (2H, m), 3.83 (3H, s), 4.29-4.50 (2H, m), 5.03-5.16 (1H, m), 6.97 (1H, d, J=2.6 Hz), 7.56 (2H, d, J=8.3 Hz), 7.69 (2H, d, J=8.3 Hz), 7.77 (1H, d, J=2.6 Hz), 10.07 (1H, d, J=7.2 Hz), 10.77 (1H, brs).

Example 71

Optically Active 7-methoxy-N-(2-methoxy-1-(4-(trifluoromethyl)phenyl)ethyl)-2-oxo-2,3-dihydropyrido[2,3-b]pyrazine-4(1H)-carboxamide Racemic 7-methoxy-N-(2-methoxy-1-(4-(trifluoromethyl)phenyl)ethyl)-2-oxo-2,3-dihydropyrido[2,3-b]pyrazine-4(1H)-carboxamide (444 mg) was resolved by HPLC (column: CHIRALPAK AD, 50 mmID×500 mmL, manufactured by Daicel Chemical Industries, Ltd., mobile phase: hexane/ethanol=600/400), and crystallized from hexane/ethyl acetate to give the title compound having a longer retention time (189 mg).

MS (API+):[M+H]$^+$ 425.1.

$^1$H NMR (300 MHz, DMSO-d$_6$) δ 3.28 (3H, s), 3.61-3.67 (2H, m), 3.83 (3H, s), 4.30-4.50 (2H, m), 5.04-5.16 (1H, m), 6.97 (1H, d, J=2.6 Hz), 7.56 (2H, d, J=8.3 Hz), 7.69 (2H, d, J=8.3 Hz), 7.77 (1H, d, J=2.6 Hz), 10.07 (1H, d, J=7.5 Hz), 10.77 (1H, s).

Example 72-I 7-cyclopropyl-N-(2-hydroxy-2-methyl-1-(4-(trifluoromethoxy)phenyl)propyl)-2-oxo-2,3-dihydropyrido[2,3-b]pyrazine-4(1H)-carboxamide A) methyl N-(5-iodo-3-nitropyridin-2-yl)glycinate To a solution of 2-chloro-5-iodo-3-nitropyridine (12.0 g) in ethanol (200 mL) were added methyl glycinate hydrochloride (10.6 g) and triethylamine (11.8 mL) at room temperature. The reaction mixture was heated at reflux for 20 hr, and the solvent was evaporated under reduced pressure. To the residue was added water, and the mixture was extracted with ethyl acetate. The extract was washed successively with water and saturated brine, and dried over anhydrous magnesium sulfate, and the solvent was evaporated under reduced pressure. The residue was crystallized from hexane/ethyl acetate to give the title compound (11.1 g).

MS (API+): [M+H]$^+$ 338.0.

B) methyl N-(5-cyclopropyl-3-nitropyridin-2-yl)glycinate

A mixture of methyl N-(5-iodo-3-nitropyridin-2-yl)glycinate (1.00 g), cyclopropylboronic acid (0.510 g), palladium (II) acetate (0.100 g), tricyclohexylphosphine (0.250 g) and tripotassium phosphate (1.89 g) in toluene (30 mL) was stirred at 90° C. for 16 hr under argon atmosphere, and the solvent was evaporated under reduced pressure. The residue was purified by silica gel column chromatography (hexane/ethyl acetate) to give the title compound (0.130 g).

MS (API+): [M+H]$^+$ 252.1.

C) 7-cyclopropyl-3,4-dihydropyrido[2,3-b]pyrazin-2 (1H)-one

To a mixture of methyl N-(5-cyclopropyl-3-nitropyridin-2-yl)glycinate (73 mg) in a mixed solvent of ethanol (10 mL) and tetrahydrofuran (2 mL) was added 10% palladium-carbon (containing 50% water, 10 mg). The reaction mixture was stirred at room temperature for 2.5 hr under hydrogen atmosphere, the catalyst was filtered off, and the filtrate was concentrated under reduced pressure. The residue (64 mg) was dissolved in ethanol (8 mL), the reaction mixture was heated at reflux for 16 hr, and the solvent was evaporated under reduced pressure. The residue was washed with ethyl acetate to give the title compound (39.9 mg).

MS (API+): [M+H]$^+$ 190.1.

D) 5-cyclopropyl-3-nitropyridin-2-amine

A mixture of 5-bromo-3-nitropyridin-2-amine (2.27 g), cyclopropylboronic acid (1.79 g), palladium(II) acetate (0.117 g), tricyclohexylphosphine (0.292 g), tripotassium phosphate (5.53 g), toluene (30 mL), 1,2-dimethoxyethane (10 mL) and water (10 mL) was stirred overnight at 100° C. under nitrogen atmosphere, and the insoluble substance was filtered off using Celite. The filtrate was washed successively with water and saturated brine, and dried over anhydrous magnesium sulfate, and the solvent was evaporated under reduced pressure. The residue was purified by silica gel column chromatography (hexane/ethyl acetate) to give the title compound (2.04 g).

MS (API+): [M+H]$^+$180.2.

E) 7-cyclopropylpyrido[2,3-b]pyrazin-2(1H)-one

To a solution of 5-cyclopropyl-3-nitropyridin-2-amine (6.89 g) in ethanol (300 mL) was added 10% palladium-carbon (containing 50% water, 1.64 g). The reaction mixture was stirred at room temperature for 5 hr under hydrogen atmosphere, the catalyst was filtered off, and the filtrate was concentrated under reduced pressure. The residue was suspended in water (150 mL), 9 M aqueous glyoxylic acid solution (6.41 mL) was added thereto at room temperature.

The reaction mixture was stirred overnight at room temperature, and the resulting solid was collected by filtration, and washed with water and diisopropyl ether to give the title compound (4.52 g).

F) 7-cyclopropyl-3,4-dihydropyrido[2,3-b]pyrazin-2(1H)-one

To a solution of 7-cyclopropylpyrido[2,3-b]pyrazin-2(1H)-one (4.52 g) in ethanol (150 mL) was added sodium borohydride (1.83 g) at room temperature. The reaction mixture was stirred at 32° C. for 1 hr, and concentrated to about half of the volume under reduced pressure. To the residue was added water, and the resulting solid was collected by filtration, and washed with diisopropyl ether to give the title compound (3.45 g).
MS (API+): [M+H]$^+$190.2.

G) 7-cyclopropyl-3,4-dihydropyrido[2,3-b]pyrazin-2(1H)-one

To a solution of 7-cyclopropylpyrido[2,3-b]pyrazin-2(1H)-one (40.0 mg) in methanol (30 mL) was added 20% palladium hydroxide-carbon (15.0 mg). The reaction mixture was stirred at room temperature for 2 hr under hydrogen atmosphere, the catalyst was filtered off, and the filtrate was concentrated under reduced pressure to give the title compound (30.0 mg).
MS (API+): [M+H]$^+$190.2.

H) 4-nitrophenyl 7-cyclopropyl-2-oxo-2,3-dihydropyrido[2,3-b]pyrazine-4(1H)-carboxylate To a mixture of 7-cyclopropyl-3,4-dihydropyrido[2,3-b]pyrazin-2(1H)-one (35.0 mg) in a mixed solvent of N,N-dimethylacetamide (1.5 mL) and pyridine (0.3 mL) was added 4-nitrophenyl chloroformate (44.7 mg). The reaction mixture was stirred at room temperature for 2 hr, water was added thereto, and the mixture was extracted with ethyl acetate. The extract was washed successively with 1 M hydrochloric acid, water and saturated brine, and dried over anhydrous magnesium sulfate, and the solvent was evaporated under reduced pressure. The residue was crystallized from hexane/ethyl acetate to give the title compound (24.0 mg).
MS (API+): [M+H]$^+$ 355.1.

I) methyl 2-((tert-butoxycarbonyl) amino)-2-(4-(trifluoromethoxy)phenyl)acetate

To a mixture of 4-(trifluoromethoxy)benzaldehyde (19.0 g) and ammonium carbonate (25.9 g) in a mixed solvent of ethanol (114 mL) and water (45.6 mL) was slowly added an aqueous solution (71.1 mL) of potassium cyanide (8.14 g) at 50° C. The reaction mixture was stirred at 60° C. for 3 hr, and cooled to room temperature, and the ethanol was evaporated under reduced pressure. The pH of the residue was adjusted to 1 with conc. hydrochloric acid at 0° C., and the resulting solid was filtered off, and washed with water. To an aqueous solution (100 mL) of potassium hydroxide (23.6 g) was added the solid obtained by the above-mentioned operation at room temperature, and the reaction mixture was stirred at 90° C. for 3 days. The reaction mixture was cooled to room temperature, and neutralized with conc. hydrochloric acid. The resulting solid was filtered off, and washed with water to give a crude product (13.3 g) of 2-amino-2-(4-(trifluoromethoxy)phenyl)acetic acid. To a solution of the obtained crude product (13.3 g) in tetrahydrofuran (113 mL) were added di-tert-butyl dicarbonate (19.7 mL) and 2 M aqueous sodium hydroxide solution (85 mL) at room temperature. The reaction mixture was stirred overnight at room temperature, and poured into water, and the mixture was washed with diethyl ether. The pH of the aqueous layer was adjusted to 3 with 1 M hydrochloric acid at 0° C., and the mixture was extracted with ethyl acetate. The extract was washed with saturated brine, and dried over anhydrous magnesium sulfate, and the solvent was evaporated under reduced pressure to give a crude product (11.3 g) of 2-((tert-butoxycarbonyl) amino)-2-(4-(trifluoromethoxy)phenyl) acetic acid. To a solution of the obtained crude product (11.3 g) in N,N-dimethylformamide (84 mL) were added methyl iodide (2.53 mL) and potassium carbonate (5.59 g) at room temperature. The reaction mixture was stirred at room temperature for 2 hr, and poured into water, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (8.20 g).
MS (API−): [M−H]$^-$ 348.1.

J) tert-butyl (2-hydroxy-2-methyl-1-(4-(trifluoromethoxy)phenyl)propyl)carbamate To a solution of methyl 2-((tert-butoxycarbonyl) amino)-2-(4-(trifluoromethoxy)phenyl)acetate (5.00 g) in tetrahydrofuran (71.6 mL) was slowly added 1 M methylmagnesium bromide/tetrahydrofuran solution (57.3 mL) at 0° C. The reaction mixture was stirred at 0° C. for 1 hr under argon atmosphere, saturated aqueous ammonium chloride solution was added thereto at 0° C., and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (3.99 g).
MS (API−): [M−H]$^-$ 348.2.

K) 1-amino-2-methyl-1-(4-(trifluoromethoxy)phenyl)propan-2-ol hydrochloride

To tert-butyl (2-hydroxy-2-methyl-1-(4-(trifluoromethoxy)phenyl)propyl)carbamate (2.50 g) was added 4 M hydrogen chloride/ethyl acetate solution (71.6 mL). The reaction mixture was stirred at room temperature for 1 hr, and the solvent was evaporated under reduced pressure. To the residue was added diisopropyl ether, and the resulting crystals were collected by filtration to give the title compound (2.01 g).
MS (API+), found: 250.1.

L) 7-cyclopropyl-N-(2-hydroxy-2-methyl-1-(4-(trifluoromethoxy)phenyl)propyl)-2-oxo-2,3-dihydropyrido[2,3-b]pyrazine-4(1H)-carboxamide To a solution of 4-nitrophenyl 7-cyclopropyl-2-oxo-2,3-dihydropyrido[2,3-b]pyrazine-4(1H)-carboxylate (84 mg) in N,N-dimethylformamide (5 mL) were added 1-amino-2-methyl-1-(4-(trifluoromethoxy)phenyl)propan-2-ol hydrochloride (88 mg) and triethylamine (0.099 mL) at room temperature. The reaction mixture was stirred at room temperature for 20 hr, water was added thereto, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate), and recrystallized from hexane/ethyl acetate to give the title compound (52 mg).

MS (API+): [M+H]$^+$ 465.2.

$^1$H NMR (300 MHz, DMSO-d$_6$) δ 0.61-0.71 (2H, m), 0.94-1.05 (5H, m), 1.17 (3H, s), 1.91-2.04 (1H, m), 4.25-4.46 (2H, m), 4.68 (1H, d, J=8.3 Hz), 4.76 (1H, s), 6.94 (1H, d, J=2.3 Hz), 7.22-7.31 (2H, m), 7.38-7.48 (2H, m), 7.87 (1H, d, J=2.3 Hz), 10.50 (1H, d, J=8.3 Hz), 10.67 (1H, brs).

Example 72-II 7-cyclopropyl-N-(2-hydroxy-2-methyl-1-(4-(trifluoromethoxy)phenyl)propyl)-2-oxo-2,3-dihydropyrido[2,3-b]pyrazine-4(1H)-carboxamide A) methyl N-(5-iodo-3-nitropyridin-2-yl)glycinate To a solution of 2-chloro-5-iodo-3-nitropyridine (12.0 g) in ethanol (200 mL) were added methyl glycinate hydrochloride (10.6 g) and triethylamine (11.8 mL) at room temperature. The reaction mixture was heated at reflux for 20 hr, and the solvent was evaporated under reduced pressure. To the residue was added water, and the mixture was extracted with ethyl acetate. The extract was washed successively with water and saturated brine, and dried over anhydrous magnesium sulfate, and the solvent was evaporated under reduced pressure. The residue was crystallized from hexane/ethyl acetate to give the title compound (11.1 g).

MS (API+): [M+H]$^+$ 338.0.

B) 7-iodo-3,4-dihydropyrido[2,3-b]pyrazin-2(1H)-one

To a solution of methyl N-(5-iodo-3-nitropyridin-2-yl)glycinate (6.00 g) in tetrahydrofuran (300 mL) was added 5% platinum-carbon (500 mg). The reaction mixture was stirred overnight at room temperature under hydrogen atmosphere, the catalyst was filtered off, and the filtrate was concentrated under reduced pressure. The residue was dissolved in ethanol (200 mL), the reaction mixture was heated at reflux for 16 hr, and the solvent was evaporated under reduced pressure. The residue was washed with diisopropyl ether to give the title compound (4.48 g).

MS (API+): [M+H]$^+$ 276.0.

C) 7-iodo-1-((2-(trimethylsilyl)ethoxy)methyl)-3,4-dihydropyrido[2,3-b]pyrazin-2(1H)-one To a suspension of 7-iodo-3,4-dihydropyrido[2,3-b]pyrazin-2(1H)-one (3.82 g) in N,N-dimethylformamide (160 mL) was slowly added 1 M potassium hexamethyldisilazide/tetrahydrofuran solution (17.4 mL) at 0° C. The reaction mixture was stirred at 0° C. for 1 hr, 2-(chloromethoxy)ethyltrimethylsilane (3.62 mL) was slowly added thereto, and the mixture was stirred at room temperature for 20 hr. To the reaction mixture was added water, the insoluble substance was filtered off using Celite, and the filtrate was extracted with ethyl acetate. The extract was washed successively with water and saturated brine, and dried over anhydrous magnesium sulfate, and the solvent was evaporated under reduced pressure. The residue was purified by silica gel column chromatography (NH, hexane/ethyl acetate) to give the title compound (2.71 g).

MS (API+): [M+H]$^+$ 406.0.

D) methyl 2-((tert-butoxycarbonyl) amino)-2-(4-(trifluoromethoxy)phenyl)acetate

To a mixture of 4-trifluoromethoxybenzaldehyde (19.0 g) and ammonium carbonate (25.9 g) in a mixed solvent of ethanol (114 mL) and water (45.6 mL) was slowly added an aqueous solution (71.1 mL) of potassium cyanide (8.14 g) at 50° C. The reaction mixture was stirred at 60° C. for 3 hr, and cooled to room temperature, and the ethanol was evaporated under reduced pressure. The pH of the residue was adjusted to 1 with conc. hydrochloric acid at 0° C., and the resulting solid was filtered off, and washed with water. To an aqueous solution (100 mL) of potassium hydroxide (23.6 g) was added the solid obtained by the above-mentioned operation at room temperature, the reaction mixture was stirred at 90° C. for 3 days. The reaction mixture was cooled to room temperature, and neutralized with conc. hydrochloric acid. The resulting solid was collected by filtration, and washed with water to give a crude product (13.3 g) of 2-amino-2-(4-(trifluoromethoxy)phenyl)acetic acid. To a solution of the obtained crude product (13.3 g) in tetrahydrofuran (113 mL) were added di-tert-butyl dicarbonate (19.7 mL) and 2 M aqueous sodium hydroxide solution (85 mL) at room temperature. The reaction mixture was stirred overnight at room temperature, and poured into water, and the mixture was washed with diethyl ether. The pH of the aqueous layer was adjusted to 3 with 1 M hydrochloric acid at 0° C., and the mixture was extracted with ethyl acetate. The extract was washed with saturated brine, and dried over anhydrous magnesium sulfate, and the solvent was evaporated under reduced pressure to give a crude product (11.3 g) of 2-((tert-butoxycarbonyl) amino)-2-(4-(trifluoromethoxy)phenyl) acetic acid. To a solution of the obtained crude product (11.3 g) in N,N-dimethylformamide (84 mL) were added methyl iodide (2.53 mL) and potassium carbonate (5.59 g) at room temperature. The m reaction mixture was stirred at room temperature for 2 hr, and poured into water, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (8.20 g).

MS (API−): [M−H]$^−$ 348.1.

E) tert-butyl (2-hydroxy-2-methyl-1-(4-(trifluoromethoxy)phenyl)propyl)carbamate To a solution of methyl 2-((tert-butoxycarbonyl)amino)-2-(4-(trifluoromethoxy)phenyl)acetate (5.00 g) in tetrahydrofuran (71.6 mL) was slowly added 1 M methylmagnesium bromide/tetrahydrofuran solution (57.3 mL) at 0° C. The reaction mixture was stirred at 0° C. for 1 hr under argon atmosphere, saturated aqueous ammonium chloride solution was added thereto at 0° C., and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (3.99 g).

MS (API−): [M−H]$^−$ 348.2.

F) 1-amino-2-methyl-1-(4-(trifluoromethoxy)phenyl)propan-2-ol hydrochloride

To tert-butyl (2-hydroxy-2-methyl-1-(4-(trifluoromethoxy)phenyl)propyl)carbamate (2.50 g) was added 4 M hydrogen chloride/ethyl acetate solution (71.6 mL). The reaction mixture was stirred at room temperature for 1 hr, and the solvent was evaporated under reduced pressure. To the residue was added diisopropyl ether, and the resulting crystals were collected by filtration to give the title compound (2.01 g).
MS (API+), found: 250.1.

G) N-(2-hydroxy-2-methyl-1-(4-(trifluoromethoxy)phenyl)propyl)-7-iodo-2-oxo-1-((2-(trimethylsilyl)ethoxy)methyl)-2,3-dihydropyrido[2,3-b]pyrazine-4(1H)-carboxamide To a solution of 7-iodo-1-((2-(trimethylsilyl)ethoxy)methyl)-3,4-dihydropyrido[2,3-b]pyrazin-2(1H)-one (3.40 g) in tetrahydrofuran (120 mL) was slowly added a solution of bis(trichloromethyl)carbonate (1.99 g) in tetrahydrofuran (20 mL) at room temperature under nitrogen atmosphere. The reaction mixture was stirred at 40° C. for 5 hr under nitrogen atmosphere, and the solvent was evaporated under reduced pressure. To the residue was added tetrahydrofuran, and the solvent was evaporated under reduced pressure. The operation (addition of tetrahydrofuran and then evaporation) was repeated three times. The residue was diluted with tetrahydrofuran (120 mL), and slowly added to a mixture of 1-amino-2-methyl-1-(4-(trifluoromethoxy)phenyl)propan-2-ol hydrochloride (2.64 g) and triethylamine (3.51 mL) in tetrahydrofuran (20 mL) at room temperature. The reaction mixture was stirred overnight at 60° C., water was added thereto, and the mixture was extracted with ethyl acetate. The extract was washed with saturated brine, and dried over anhydrous magnesium sulfate, and the solvent was evaporated under reduced pressure. The residue was purified by silica gel chromatography (NH, hexane/ethyl acetate) to give the title compound (5.32 g).
MS (API+): [M+H]$^+$ 681.1.

H) 7-cyclopropyl-N-(2-hydroxy-2-methyl-1-(4-(trifluoromethoxy)phenyl)propyl)-2-oxo-1-((2-(trimethylsilyl)ethoxy)methyl)-2,3-dihydropyrido[2,3-b]pyrazine-4(1H)-carboxamide A mixture of N-(2-hydroxy-2-methyl-1-(4-(trifluoromethoxy)phenyl)propyl)-7-iodo-2-oxo-1-((2-(trimethylsilyl)ethoxy)methyl)-2,3-dihydropyrido[2,3-b]pyrazine-4(1H)-carboxamide (5.32 g), cyclopropylboronic acid (1.34 g), palladium(II) acetate (0.176 g), tricyclohexylphosphine (0.438 g) and tripotassium phosphate (4.98 g) in a mixed solvent of toluene (150 mL) and water (6.01 mL) was stirred under argon atmosphere at 80° C. for 3 hr, at 100° C. for 3 hr, at room temperature for 3 days, and at 100° C. for 2.5 hr, water was added thereto, and the mixture was extracted with ethyl acetate. The extract was washed successively with water and saturated brine, the aqueous layers were combined, and extracted with ethyl acetate. The extract was dried over anhydrous magnesium sulfate, and the solvent was evaporated under reduced pressure. The residue was purified by silica gel column chromatography (hexane/ethyl acetate) to give the title compound (3.80 g).
MS (API+): [M+H]$^+$ 595.3.

I) 7-cyclopropyl-N-(2-hydroxy-2-methyl-1-(4-(trifluoromethoxy)phenyl)propyl)-2-oxo-2,3-dihydropyrido[2,3-b]pyrazine-4(1H)-carboxamide To 7-cyclopropyl-N-(2-hydroxy-2-methyl-1-(4-(trifluoromethoxy)phenyl)propyl)-2-oxo-1-((2-(trimethylsilyl)ethoxy)methyl)-2,3-dihydropyrido[2,3-b]pyrazine-4(1H)-carboxamide (3.80 g) were slowly added trifluoroacetic acid (120 mL) and water (14 mL). The reaction mixture was stirred at room temperature for 1 hr, and the solvent was evaporated under reduced pressure. The residue was dissolved in N,N-dimethylformamide (220 mL), and 7 M ammonia/methanol solution (18.3 mL) was slowly added thereto. The reaction mixture was stirred at room temperature for 2 hr, ethyl acetate was added thereto, and the mixture was washed successively with water and saturated brine. The aqueous layer was neutralized with 1 M hydrochloric acid, and extracted with ethyl acetate. The extract was dried over anhydrous magnesium sulfate, and the solvent was evaporated under reduced pressure. The residue was dissolved in ethyl acetate, and the solution was washed successively with water and saturated brine, and dried over anhydrous magnesium sulfate. The solvent was evaporated under reduced pressure to give the title compound (2.65 g).
MS (API+):[M+H]$^+$ 465.2.
$^1$H NMR (300 MHz, DMSO-d$_6$) δ 0.60-0.71 (2H, m), 0.94-1.04 (5H, m), 1.18 (3H, s), 1.90-2.05 (1H, m), 4.25-4.47 (2H, m), 4.68 (1H, d, J=8.3 Hz), 4.78 (1H, s), 6.94 (1H, d, J=2.3 Hz), 7.23-7.33 (2H, m), 7.38-7.48 (2H, m), 7.88 (1H, d, J=2.3 Hz), 10.51 (1H, d, J=7.9 Hz), 10.68 (1H, brs).

Example 73

7-cyclopropyl-N-((1S)-2-hydroxy-2-methyl-1-(4-(trifluoromethoxy)phenyl)propyl)-2-oxo-2,3-dihydropyrido[2,3-b]pyrazine-4(1H)-carboxamide Racemic 7-cyclopropyl-N-(2-hydroxy-2-methyl-1-(4-(trifluoromethoxy)phenyl)propyl)-2-oxo-2,3-dihydropyrido[2,3-b]pyrazine-4(1H)-carboxamide (2.65 g) was resolved by HPLC (column: CHIRALPAK AD, 50 mmID×500 mmL, manufactured by Daicel Chemical Industries, Ltd., mobile phase: hexane/ethanol=850/150), and recrystallized from hexane/ethyl acetate to give the title compound having a shorter retention time (1.01 g).
MS (API+):[M+H]$^+$ 465.1.
$^1$H NMR (300 MHz, DMSO-d$_6$) δ 0.62-0.71 (2H, m), 0.95-1.05 (5H, m), 1.17 (3H, s), 1.91-2.04 (1H, m), 4.25-4.47 (2H, m), 4.68 (1H, d, J=7.9 Hz), 4.77 (1H, s), 6.94 (1H, d, J=1.9 Hz), 7.22-7.32 (2H, m), 7.38-7.47 (2H, m), 7.87 (1H, d, J=2.3 Hz), 10.50 (1H, d, J=8.3 Hz), 10.67 (1H, s).

Example 74

7-cyclopropyl-N-((1R)-2-hydroxy-2-methyl-1-(4-(trifluoromethoxy)phenyl)propyl)-2-oxo-2,3-dihydropyrido[2,3-b]pyrazine-4(1H)-carboxamide Racemic 7-cyclopropyl-N-(2-hydroxy-2-methyl-1-(4-(trifluoromethoxy)phenyl)propyl)-2-oxo-2,3-dihydropyrido[2,3-b]pyrazine-4(1H)-carboxamide (2.65 g) was resolved by HPLC (column: CHIRALPAK AD, 50 mmID×500 mmL, manufactured by Daicel Chemical Industries, Ltd., mobile phase: hexane/ethanol=850/150), and recrystallized from hexane/ethyl acetate to give the title compound having a longer retention time (0.792 g).
MS (API+): [M+H]$^+$ 465.1.

¹H NMR (300 MHz, DMSO-d₆) δ 0.62-0.71 (2H, m), 0.94-1.05 (5H, m), 1.17 (3H, s), 1.91-2.05 (1H, m), 4.25-4.46 (2H, m), 4.68 (1H, d, J=8.3 Hz), 4.77 (1H, s), 6.94 (1H, d, J=1.9 Hz), 7.23-7.32 (2H, m), 7.38-7.47 (2H, m), 7.87 (1H, d, J=2.3 Hz), 10.50 (1H, d, J=8.3 Hz), 10.67 (1H, s).

Example 75-I 7-cyclopropyl-N-(1-(3-fluoro-4-(trifluoromethoxy) phenyl)-2-hydroxy-2-methylpropyl)-2-oxo-2,3-dihydropyrido[2,3-b]pyrazine-4(1H)-carboxamide A) methyl N-(5-iodo-3-nitropyridin-2-yl)glycinate To a solution of 2-chloro-5-iodo-3-nitropyridine (12.0 g) in ethanol (200 mL) were added methyl glycinate hydrochloride (10.6 g) and triethylamine (11.8 mL) at room temperature. The reaction mixture was heated at reflux for 20 hr, and the solvent was evaporated under reduced pressure. To the residue was added water, and the mixture was extracted with ethyl acetate. The extract was washed successively with water and saturated brine, and dried over anhydrous magnesium sulfate, and the solvent was evaporated under reduced pressure. The residue was crystallized from hexane/ethyl acetate to give the title compound (11.1 g).
MS (API+): [M+H]⁺ 338.0.

B) 7-iodo-3,4-dihydropyrido[2,3-b]pyrazin-2(1H)-one

To a solution of methyl N-(5-iodo-3-nitropyridin-2-yl) glycinate (6.00 g) in tetrahydrofuran (300 mL) was added 5% platinum-carbon (500 mg). The reaction mixture was stirred overnight at room temperature under hydrogen atmosphere, the catalyst was filtered off, and the filtrate was concentrated under reduced pressure. The residue was dissolved in ethanol (200 mL), the solution was heated at reflux for 16 hr, and the solvent was evaporated under reduced pressure. The residue was washed with diisopropyl ether to give the title compound (4.48 g).
MS (API+): [M+H]⁺ 276.0.

C) 7-iodo-1-((2-(trimethylsilyl)ethoxy)methyl)-3,4-dihydropyrido[2,3-b]pyrazin-2(1H)-one To a suspension of 7-iodo-3,4-dihydropyrido[2,3-b] pyrazin-2(1H)-one (3.82 g) in N,N-dimethylformamide (160 mL) was slowly added 1 M potassium hexamethyldisilazide/ tetrahydrofuran solution (17.4 mL) at 0° C. The reaction mixture was stirred at 0° C. for 1 hr, 2-(chloromethoxy) ethyltrimethylsilane (3.62 mL) was slowly added thereto, and the mixture was stirred at room temperature for 20 hr. To the reaction mixture was added water, the insoluble substance was filtered off using Celite, and the filtrate was extracted with ethyl acetate. The extract was washed successively with water and saturated brine, and dried over anhydrous magnesium sulfate, and the solvent was evaporated under reduced pressure. The residue was purified by silica gel column chromatography (NH, hexane/ethyl acetate) to give the title compound (2.71 g).
MS (API+): [M+H]⁺ 406.0.

D) 3-fluoro-N-methoxy-N-methyl-4-(trifluoromethoxy)benzamide

To a solution of 3-fluoro-4-(trifluoromethoxy)benzoic acid (20 g), N,O-dimethylhydroxylamine hydrochloride (10.5 g) and triethylamine (24.9 mL) in N,N-dimethylformamide (300 mL) were added 1-hydroxybenzotriazole monohydrate (16.4 g) and 1-(3-dimethylaminopropyl)-3-ethylcarbodiimide hydrochloride (20.5 g) at room temperature. The reaction mixture was stirred overnight at room temperature, and then at 50° C. for 1.5 hr. To the reaction mixture was added saturated aqueous sodium hydrogen carbonate solution, and the mixture was extracted with ethyl acetate. The extract was washed successively with water and saturated brine, and dried over anhydrous magnesium sulfate, and the solvent was evaporated under reduced pressure. Toluene was added to the residue because the residue contained a small amount of N,N-dimethylformamide, and the solvent was evaporated under reduced pressure to give the title compound (22.0 g).
MS (API+): [M+H]⁺ 268.1.

E) 3-fluoro-4-(trifluoromethoxy)benzaldehyde

To a solution of 3-fluoro-N-methoxy-N-methyl-4-(trifluoromethoxy)benzamide (10.0 g) in tetrahydrofuran (101 mL) was added 1.5 M diisobutylaluminium hydride/toluene solution (27.4 mL) at 0° C. The reaction mixture was stirred overnight at room temperature, saturated aqueous ammonium chloride solution and 6 M hydrochloric acid was successively added, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ ethyl acetate) to give the title compound (3.55 g).
¹H NMR (300 MHz, DMSO-d₆) δ 7.71-7.97 (2H, m), 7.97-8.10 (1H, m), 10.02 (1H, d, J=1.9 Hz).

F) 2-amino-2-(3-fluoro-4-(trifluoromethoxy)phenyl) acetic acid

To a mixture of 3-fluoro-4-(trifluoromethoxy)benzaldehyde (3.50 g) and ammonium carbonate (4.36 g) in a mixed solvent of ethanol (21 mL) and water (8 mL) was slowly added an aqueous solution (13 mL) of potassium cyanide (1.37 g) at 50° C. The mixture was stirred at 60° C. for 4 hr, and cooled to room temperature, and the ethanol was evaporated under reduced pressure. The pH of the residue was adjusted to 1 with conc. hydrochloric acid at 0° C., and the mixture was left overnight at freezer. The resulting solid was collected by filtration, and washed with water. To an aqueous solution (100 mL) of potassium hydroxide (3.96 g) was added the obtained solid at room temperature, and the mixture was stirred at 90° C. for 60 hr, cooled to room temperature, and neutralized with conc. hydrochloric acid. The resulting solid was collected by filtration, and washed with water to give the title compound (937 mg).
¹H NMR (300 MHz, DMSO-d₆) δ 4.34 (1H, s), 7.22-7.42 (1H, m), 7.45-7.66 (2H, m).

G) 2-((tert-butoxycarbonyl) amino)-2-(3-fluoro-4-(trifluoromethoxy)phenyl)acetic acid To a solution of 2-amino-2-(3-fluoro-4-(trifluoromethoxy)phenyl)acetic acid (937 mg) in tetrahydrofuran (7.40 mL) were added di-tert-butyl dicarbonate (1.29 mL) and 2 M aqueous sodium hydroxide solution (5.55 mL) at room temperature. The reaction mixture was stirred at room temperature for 3 days, and poured into water, and the mixture was washed with diethyl ether. The pH of the aqueous layer was adjusted to 3 with 1 M hydrochloric acid at 0° C., and the mixture was extracted with ethyl acetate. The extract was washed with saturated brine, and dried over anhydrous magnesium sulfate, and the solvent was evaporated under reduced pressure to give the title compound (750 mg).

$^1$H NMR (300 MHz, DMSO-d$_6$) δ 1.39 (9H, s), 5.02-5.35 (1H, m), 7.15-7.64 (3H, m), 7.64-7.85 (1H, m).

H) methyl 2-((tert-butoxycarbonyl) amino)-2-(3-fluoro-4-(trifluoromethoxy)phenyl)acetate To a solution of 2-((tert-butoxycarbonyl) amino)-2-(3-fluoro-4-(trifluoromethoxy)phenyl)acetic acid (750 mg) in N,N-dimethylformamide (5.5 mL) were added methyl iodide (0.159 mL) and potassium carbonate (352 mg) at room temperature. The reaction mixture was stirred at room temperature for 4 hr under nitrogen atmosphere, and poured into water, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (630 mg).

MS (API–): [M–H]$^-$ 366.1.

I) tert-butyl (1-(3-fluoro-4-(trifluoromethoxy)phenyl)-2-hydroxy-2-methylpropyl)carbamate To a solution of methyl 2-((tert-butoxycarbonyl) amino)-2-(3-fluoro-4-(trifluoromethoxy)phenyl)acetate (630 mg) in tetrahydrofuran (9 mL) was slowly added 1 M methylmagnesium bromide/tetrahydrofuran solution (6.86 mL) at 0° C. under argon atmosphere. The reaction mixture was stirred at 0° C. for 4 hr under argon atmosphere, saturated aqueous ammonium chloride solution was added thereto, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (540 mg).

MS (API–): [M–H]$^-$ 366.2.

J) 1-amino-1-(3-fluoro-4-(trifluoromethoxy)phenyl)-2-methylpropan-2-ol hydrochloride To tert-butyl (1-(3-fluoro-4-(trifluoromethoxy)phenyl)-2-hydroxy-2-methylpropyl)carbamate (540 mg) was added 4 M hydrogen chloride/ethyl acetate solution (4 mL). The reaction mixture was stirred at room temperature for 30 min, and the solvent was evaporated under reduced pressure to give the title compound (510 mg).

MS (API+), found: 268.1.

K) N-(1-(3-fluoro-4-(trifluoromethoxy)phenyl)-2-hydroxy-2-methylpropyl)-7-iodo-2-oxo-1-((2-(trimethylsilyl)ethoxy)methyl)-2,3-dihydropyrido[2,3-b]pyrazine-4(1H)-carboxamide To a solution of 7-iodo-1-((2-(trimethylsilyl)ethoxy)methyl)-3,4-dihydropyrido[2,3-b]pyrazin-2(1H)-one (586 mg) in tetrahydrofuran (28 mL) was added bis(trichloromethyl)carbonate (343 mg) at room temperature. The reaction mixture was stirred at 40° C. for 5 hr under nitrogen atmosphere, and the solvent was evaporated under reduced pressure. To the residue was added tetrahydrofuran, and the solvent was evaporated under reduced pressure. The operation (addition of tetrahydrofuran and then evaporation) was repeated three times. The residue was diluted with tetrahydrofuran (14 mL), and the mixture was slowly added to a solution of 1-amino-1-(3-fluoro-4-(trifluoromethoxy)phenyl)-2-methylpropan-2-ol hydrochloride (439 mg) and triethylamine (0.604 mL) in tetrahydrofuran (9 mL) at room temperature. The reaction mixture was stirred at 60° C. for 16 hr, ethyl acetate was added thereto, washed successively with water and saturated brine. The organic layer was dried over anhydrous magnesium sulfate, and the solvent was evaporated under reduced pressure. The residue was purified by silica gel column chromatography (hexane/ethyl acetate) to give the title compound (590 mg).

MS (API+): [M+H]$^+$ 699.1.

L) 7-cyclopropyl-N-(1-(3-fluoro-4-(trifluoromethoxy)phenyl)-2-hydroxy-2-methylpropyl)-2-oxo-1-((2-(trimethylsilyl)ethoxy)methyl)-2,3-dihydropyrido[2,3-b]pyrazine-4(1H)-carboxamide To a mixture of N-(1-(3-fluoro-4-(trifluoromethoxy)phenyl)-2-hydroxy-2-methylpropyl)-7-iodo-2-oxo-1-((2-(trimethylsilyl)ethoxy)methyl)-2,3-dihydropyrido[2,3-b]pyrazine-4(1H)-carboxamide (590 mg), cyclopropylboronic acid (145 mg) and tripotassium phosphate (628 mg) in a mixed solvent of toluene (16.2 mL) and water (0.648 mL) were added palladium(II) acetate (37.9 mg) and tricyclohexylphosphine (95 mg) at room temperature. The reaction mixture was stirred overnight at 100° C. under argon atmosphere, the insoluble substance was filtered off, and the filtrate was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate) to give the title compound (160 mg).

MS (API+): [M+H]$^+$ 613.2.

M) 7-cyclopropyl-N-(1-(3-fluoro-4-(trifluoromethoxy)phenyl)-2-hydroxy-2-methylpropyl)-2-oxo-2,3-dihydropyrido[2,3-b]pyrazine-4(1H)-carboxamide To 7-cyclopropyl-N-(1-(3-fluoro-4-(trifluoromethoxy)phenyl)-2-hydroxy-2-methylpropyl)-2-oxo-1-((2-(trimethylsilyl)ethoxy)methyl)-2,3-dihydropyrido[2,3-b]pyrazine-4(1H)-carboxamide (160 mg) were slowly added trifluoroacetic acid (4 mL) and water (0.4 mL) at room temperature. The reaction mixture was stirred at room temperature for 1 hr, and the solvent was evaporated under reduced pressure. The residue was dissolved in N,N-dimethylformamide (3 mL), and 8 M ammonia/methanol solution (0.5 mL) was slowly added thereto. The reaction mixture was stirred at room temperature for 30 min, and the solvent was evaporated under reduced pressure. The residue was diluted with ethyl acetate, and the mixture was washed successively with water and saturated brine, and dried over anhydrous magnesium sulfate, and the solvent was evaporated under reduced pressure. The residue was purified by silica gel column chromatography (NH, hexane/ethyl acetate) to give the title compound (27.0 mg) and the title compound (100 mg) containing an impurity.

MS (API+): [M+H]+ 483.2.

$^1$H NMR (300 MHz, DMSO-d$_6$) δ 0.62-0.70 (2H, m), 0.94-1.04 (5H, m), 1.19 (3H, s), 1.91-2.04 (1H, m), 4.25-4.47 (2H, m), 4.68 (1H, d, J=8.3 Hz), 4.85 (1H, s), 6.94 (1H, d, J=1.9 Hz), 7.22-7.30 (1H, m), 7.35-7.43 (1H, m), 7.43-7.53 (1H, m), 7.87 (1H, d, J=1.9 Hz), 10.49 (1H, d, J=7.9 Hz), 10.67 (1H, brs).

Example 75-II 7-cyclopropyl-N-(1-(3-fluoro-4-(trifluoromethoxy)phenyl)-2-hydroxy-2-methylpropyl)-2-oxo-2,3-dihydropyrido[2,3-b]pyrazine-4(1H)-carboxamide To a mixture of 4-nitrophenyl 7-cyclopropyl-2-oxo-2,3-dihydropyrido[2,3-b]pyrazine-4(1H)-carboxylate (1.06 g) and 1-amino-1-(3-fluoro-4-(trifluoromethoxy)phenyl)-2-methylpropan-2-ol hydrochloride (1.09 g) in N,N-dimethylformamide (30 mL) was added triethylamine (1.25 mL) at room temperature. The reaction mixture was stirred at room temperature for 16 hr, water was added thereto, and the mixture was extracted with ethyl acetate. The extract was washed successively with water and saturated brine, and dried over anhydrous magnesium sulfate, and the solvent was evaporated under reduced pressure. The residue was crystallized from hexane/ethyl acetate to give the title compound (1.12 g).
MS (API+): [M+H]$^+$ 483.2.
$^1$H NMR (300 MHz, CDCl$_3$) δ 0.67-0.76 (2H, m), 0.99-1.09 (2H, m), 1.16 (3H, s), 1.37 (3H, s), 1.62 (1H, s), 1.83-1.96 (1H, m), 4.52-4.72 (2H, m), 4.85 (1H, d, J=8.3 Hz), 6.83 (1H, d, J=1.9 Hz), 7.13-7.34 (3H, m), 7.88 (1H, d, J=1.9 Hz), 8.57 (1H, s), 10.81 (1H, d, J=8.3 Hz).

Example 76-I

Optically Active 7-cyclopropyl-N-(1-(3-fluoro-4-(trifluoromethoxy)phenyl)-2-hydroxy-2-methylpropyl)-2-oxo-2,3-dihydropyrido[2,3-b]pyrazine-4(1H)-carboxamide 7-Cyclopropyl-N-(1-(3-fluoro-4-(trifluoromethoxy)phenyl)-2-hydroxy-2-methylpropyl)-2-oxo-2,3-dihydropyrido[2,3-b]pyrazine-4(1H)-carboxamide (100 mg) containing an impurity, which was obtained in Step M of Example 75, was purified by HPLC (C18, mobile phase: water (10 mM, containing NH$_4$HCO$_3$)/acetonitrile), and the obtained fraction was concentrated under reduced pressure. Then, the residue was optically resolved by HPLC (column: CHIRALPAK AD, 50 mmID×500 mmL, manufactured by Daicel Chemical Industries, Ltd., mobile phase: hexane/ethanol=850/150) to give the title compound having a shorter retention time (24 mg).
MS (API+): [M+H]$^+$ 483.2.
$^1$H NMR (300 MHz, DMSO-d$_6$) δ 0.62-0.70 (2H, m), 0.94-1.04 (5H, m), 1.19 (3H, s), 1.91-2.03 (1H, m), 4.25-4.46 (2H, m), 4.68 (1H, d, J=8.3 Hz), 4.86 (1H, s), 6.94 (1H, d, J=1.9 Hz), 7.22-7.30 (1H, m), 7.35-7.42 (1H, m), 7.43-7.54 (1H, m), 7.87 (1H, d, J=1.9 Hz), 10.49 (1H, d, J=7.9 Hz), 10.68 (1H, brs).

Example 76-II

Optically Active 7-cyclopropyl-N-(1-(3-fluoro-4-(trifluoromethoxy)phenyl)-2-hydroxy-2-methylpropyl)-2-oxo-2,3-dihydropyrido[2,3-b]pyrazine-4(1H)-carboxamide 7-Cyclopropyl-N-(1-(3-fluoro-4-(trifluoromethoxy)phenyl)-2-hydroxy-2-methylpropyl)-2-oxo-2,3-dihydropyrido[2,3-b]pyrazine-4(1H)-carboxamide (1.25 g) was optically resolved by HPLC (column: CHIRALPAK AD, 50 mmID×500 mmL, manufactured by Daicel Chemical Industries, Ltd., mobile phase: hexane/ethanol=850/150), and recrystallized from acetone/heptane to give the title compound having a shorter retention time (474 mg).
MS (API+): [M+H]$^+$ 483.2.
$^1$H NMR (300 MHz, CDCl$_3$) δ 0.67-0.76 (2H, m), 0.99-1.09 (2H, m), 1.16 (3H, s), 1.37 (3H, s), 1.64 (1H, s), 1.84-1.95 (1H, m), 4.52-4.73 (2H, m), 4.86 (1H, d, J=8.3 Hz), 6.84 (1H, d, J=1.9 Hz), 7.13-7.32 (6H, m), 7.88 (1H, d, J=1.9 Hz), 8.81 (1H, brs), 10.82 (1H, d, J=8.3 Hz).

Example 77

Optically Active 7-cyclopropyl-N-(1-(3-fluoro-4-(trifluoromethoxy)phenyl)-2-hydroxy-2-methylpropyl)-2-oxo-2,3-dihydropyrido[2,3-b]pyrazine-4(1H)-carboxamide 7-Cyclopropyl-N-(1-(3-fluoro-4-(trifluoromethoxy)phenyl)-2-hydroxy-2-methylpropyl)-2-oxo-2,3-dihydropyrido[2,3-b]pyrazine-4(1H)-carboxamide (100 mg) containing an impurity, which was obtained in Step M of Example 75, was purified by HPLC (C18, mobile phase: water/acetonitrile (containing 0.1% TFA)), and optically resolved by HPLC (column: CHIRALPAK AD, 50 mmID×500 mmL, manufactured by Daicel Chemical Industries, Ltd., mobile phase: hexane/ethanol=850/150) to give the title compound having a longer retention time (29 mg).
MS (API+): [M+H]$^+$ 483.2.
$^1$H NMR (300 MHz, DMSO-d$_6$) δ 0.62-0.70 (2H, m), 0.95-1.04 (5H, m), 1.19 (3H, s), 1.92-2.03 (1H, m), 4.26-4.46 (2H, m), 4.68 (1H, d, J=8.3 Hz), 4.86 (1H, s), 6.94 (1H, d, J=2.3 Hz), 7.22-7.29 (1H, m), 7.35-7.42 (1H, m), 7.43-7.53 (1H, m), 7.87 (1H, d, J=2.3 Hz), 10.49 (1H, d, J=8.3 Hz), 10.68 (1H, s).

Example 78

2-oxo-N-(1-(4-(2,2,2-trifluoroethoxy)phenyl)propyl)-2,3-dihydropyrido[2,3-b]pyrazine-4(1H)-carboxamide A) tert-butyl (1-(4-(2,2,2-trifluoroethoxy)phenyl)propyl)carbamate To a mixture of tert-butyl (1-(4-hydroxyphenyl)propyl)carbamate (302 mg) and 2,2,2-trifluoroethyl trifluoromethanesulfonate (418 mg) in N,N-dimethylformamide (10 mL) was added potassium carbonate (498 mg). The reaction mixture was stirred at 80° C. for 16 hr, and the solvent was evaporated under reduced pressure. To the residue was added ethyl acetate. The organic layer was washed with water, and dried over anhydrous sodium sulfate, and the solvent was evaporated under reduced pressure to give the title compound (362 mg).
MS (API−): [M−H]$^−$ 332.1.

B) 2-oxo-N-(1-(4-(2,2,2-trifluoroethoxy)phenyl)propyl)-2,3-dihydropyrido[2,3-b]pyrazine-4(1H)-carboxamide 1-(4-(2,2,2-Trifluoroethoxy)phenyl)propylamine hydrochloride was obtained from tert-butyl (1-(4-(2,2,2-trifluoroethoxy)phenyl)propyl)carbamate in the same manner as in Step E of Example 18. The title compound was obtained in the same manner as in Step B of Example 53.
MS (API+): [M+H]$^+$ 409.1.

Example 79

N-(2-(methylsulfinyl)-1-(4-(trifluoromethoxy)phenyl)ethyl)-2-oxo-2,3-dihydropyrido[2,3-b]pyrazine-4(1H)-carboxamide The title compound was obtained from N-(2-(methylsulfanyl)-1-(4-(trifluoromethoxy)phenyl)ethyl)-2-oxo-2,3-dihydropyrido[2,3-b]pyrazine-4(1H)-carboxamide in the same manner as in Example 60.
MS (API+): [M+H]$^+$ 443.1.

Example 80

2-oxo-N-(1-(1-(2,2,2-trifluoroethyl)-1H-imidazol-4-yl)propyl)-2,3-dihydropyrido[2,3-b]pyrazine-4(1H)-carboxamide

A) 1-trityl-1H-imidazol-4-carbaldehyde

A mixture of 1H-imidazol-4-carbaldehyde (3.00 g), triethylamine (7.00 g) and N,N-dimethylformamide (40 mL) was cooled to 0° C., trityl chloride (10.5 g) was added thereto. The reaction mixture was stirred at room temperature for 18 hr, water was added thereto, and the solid was collected by filtration. The obtained solid was washed with water and diethyl ether to give the title compound (10.0 g).
$^1$H NMR (400 MHz, DMSO-d$_6$) δ 7.11-7.14 (6H, m), 7.40-7.48 (9H, m), 7.67 (1H, d, J=0.8 Hz), 7.80 (1H, d, J=1.2 Hz), 9.23 (1H, s).

B) 1-(1-trityl-1H-imidazol-4-yl)propan-1-ol

To a mixture of 1-trityl-1H-imidazol-4-carbaldehyde (1.00 g) and tetrahydrofuran (100 mL) was slowly added 2.96 M ethylmagnesium bromide/tetrahydrofuran solution (1.50 mL) at 0° C. The reaction mixture was stirred at room temperature for 18 hr, saturated aqueous ammonium chloride solution was added thereto, and the mixture was extracted with ethyl acetate. The extract was washed successively with water and saturated brine, and dried over anhydrous sodium sulfate, and the solvent was evaporated under reduced pressure to give the title compound (1.00 g).
$^1$H NMR (400 MHz, DMSO-d$_6$) δ 0.78 (3H, t, J=7.6 Hz), 1.54-1.59 (1H, m), 1.68-1.72 (1H, m), 4.36 (1H, t, J=6.0 Hz), 4.81 (1H, d, J=5.6 Hz), 6.65 (1H, s), 7.02-7.12 (6H, m), 7.26 (1H, d, J=1.2 Hz), 7.35-7.43 (9H, m).

C) 1-(1-trityl-1H-imidazol-4-yl)propan-1-one

A mixture of 1-(1-trityl-1H-imidazol-4-yl)propan-1-ol (1.00 g), manganese dioxide (2.36 g) and dioxane (20 mL) was heated at reflux for 2 hr. The reaction mixture was cooled to room temperature, the insoluble substance was filtered off, and the filtrate was concentrated under reduced pressure to give the title compound (1.00 g).
$^1$H NMR (400 MHz, DMSO-d$_6$) δ 1.03 (3H, t, J=7.6 Hz), 2.86 (2H, q, J=7.6 Hz), 7.10-7.15 (6H, m), 7.35-7.80 (10H, m), 7.54 (1H, d, J=1.2 Hz).

D) 2-oxo-N-(1-(1-(2,2,2-trifluoroethyl)-1H-imidazol-4-yl)propyl)-2,3-dihydropyrido[2,3-b]pyrazine-4(1H)-carboxamide A mixture of 1-(1-trityl-1H-imidazol-4-yl)propan-1-one (1.00 g) and 4 M hydrogen chloride/ethyl acetate solution (40 mL) was stirred at room temperature for 2 hr, and the solvent was evaporated under reduced pressure. To the residue was added N,N-dimethylformamide (10 mL), potassium carbonate (829 mg) and 2,2,2-trifluoroethyl trifluoromethanesulfonate (950 mg) was added thereto. The reaction mixture was stirred overnight at room temperature, water was added thereto, and the mixture was extracted with ethyl acetate. The extract was washed successively with water and saturated brine, and dried over anhydrous sodium sulfate, and the solvent was evaporated under reduced pressure. The residue was purified by silica gel column chromatography (petroleum ether/ethyl acetate) to give 1-(1-(2,2,2-trifluoroethyl)-1H-imidazol-4-yl)propan-1-one containing an impurity. To the obtained residue were added hydroxylamine hydrochloride (202 mg), triethylamine (294 mg) and ethanol (20 mL), and the reaction mixture was heated at reflux for 4 hr. The reaction mixture was cooled to room temperature, and the solvent was evaporated under reduced pressure. To the residue was added water, and the mixture was extracted with ethyl acetate. The extract was washed successively with water and saturated brine, and dried over anhydrous sodium sulfate, and the solvent was evaporated under reduced pressure. To the residue were added methanol (50 mL) and Raney nickel (1.00 g), and the reaction mixture was stirred at 50° C. for 4 hr under hydrogen atmosphere (50 psi). The reaction mixture was cooled to room temperature, the insoluble substance was filtered off, and the filtrate was concentrated under reduced pressure. To the residue were added 4-nitrophenyl 2-oxo-2,3-dihydropyrido[2,3-b]pyrazine-4(1H)-carboxylate (491 mg), triethylamine (303 mg) and N,N-dimethylformamide (20 mL), and the reaction mixture was stirred overnight. The reaction mixture was purified by HPLC (C18, mobile phase: water/acetonitrile (containing 0.1% TFA)), and the obtained solid was crystallized from ethyl acetate to give the title compound (76 mg).
MS (API+): [M+H]$^+$ 383.1.

Example 81

2-oxo-N-(1-(1-(2,2,2-trifluoroethyl)-1H-1,2,4-triazol-3-yl)propyl)-2,3-dihydropyrido[2,3-b]pyrazine-4(1H)-carboxamide

A) methyl 1-trityl-1H-1,2,4-triazol-3-carboxylate

The title compound was obtained from methyl 1H-1,2,4-triazol-3-carboxylate in the same manner as in Step A of Example 80.
$^1$H NMR (400 MHz, DMSO-d$_6$) δ 3.84 (3H, s), 7.02-7.12 (6H, m), 7.30-7.42 (9H, m), 8.39 (1H, s).

B) 1-(1-(2,2,2-trifluoroethyl)-1H-1,2,4-triazol-3-yl)propan-1-one

A mixture of 3.0 M ethylmagnesium bromide/tetrahydrofuran solution (13.2 mL) and triethylamine (11.0 g) was stirred at room temperature for 30 min. The reaction mixture was cooled to −20° C., a solution of methyl 1-trityl-1H-1,2,4-triazol-3-carboxylate (7.30 g) in tetrahydrofuran (150 mL) was added thereto, and the mixture was stirred at −20° C. for 1 hr. To the reaction mixture was added water, and the mixture was extracted with ethyl acetate. The extract was washed successively with water and saturated brine, and dried over anhydrous sodium sulfate, and the solvent was evaporated under reduced pressure. The residue was purified by silica gel column chromatography (petroleum ether/ethyl acetate) to give the title compound (4.8 g).

$^1$H NMR (400 MHz, DMSO-d$_6$) δ 1.04 (3H, t, J=7.6 Hz), 2.97 (2H, q, J=7.6 Hz), 7.02-7.10 (6H, m), 7.35-7.43 (9H, m), 8.36 (1H, s).

C) 2-oxo-N-(1-(1-(2,2,2-trifluoroethyl)-1H-1,2,4-triazol-3-yl)propyl)-2,3-dihydropyrido[2,3-b]pyrazine-4(1H)-carboxamide The title compound was obtained from 1-(1-(2,2,2-trifluoroethyl)-1H-1,2,4-triazol-3-yl)propan-1-one in the same manner as in Step D of Example 80.
MS (API+): [M+H]$^+$384.1.

Example 82

N-(1-(4-isopropoxyphenyl)propyl)-2-oxo-2,3-dihydropyrido[2,3-b]pyrazine-4(1H)-carboxamide A) tert-butyl (1-(4-isopropoxyphenyl)propyl)carbamate To a mixture of tert-butyl (1-(4-hydroxyphenyl)propyl)carbamate (628 mg) and 2-iodopropane (0.324 mL) in N,N-dimethylformamide (15 mL) was added potassium carbonate (518 mg). The reaction mixture was stirred at room temperature for 16 hr, water was added thereto, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate) to give the title compound (309 mg).
$^1$H NMR (300 MHz, CDCl$_3$) δ 0.87 (3H, t, J=7.3 Hz), 1.32 (6H, d, J=6.0 Hz), 1.41 (9H, s), 1.66-1.83 (2H, m), 4.35-4.61 (2H, m), 4.73 (1H, brs), 6.80-6.87 (2H, m), 7.11-7.19 (2H, m).

B) N-(1-(4-isopropoxyphenyl)propyl)-2-oxo-2,3-dihydropyrido[2,3-b]pyrazine-4(1H)-carboxamide To tert-butyl (1-(4-isopropoxyphenyl)propyl)carbamate (305 mg) was added 4 M hydrogen chloride/ethyl acetate solution (5 mL), and the mixture was stirred at room temperature for 1 hr. The solvent was evaporated under reduced pressure to give 1-(4-isopropoxyphenyl)propan-1-amine hydrochloride. To a mixture of 4-nitrophenyl 2-oxo-2,3-dihydropyrido[2,3-b]pyrazine-4(1H)-carboxylate (297 mg) and 1-(4-isopropoxyphenyl)propan-1-amine hydrochloride in N,N-dimethylformamide (10 mL) was added triethylamine (0.395 mL), and the mixture was stirred at room temperature for 16 hr. To the reaction mixture was added water, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate), and crystallized from hexane/ethyl acetate to give the title compound (178 mg).
MS (API-): [M-H]$^-$367.2.

Example 83

N-(1-(4-chlorophenyl)propyl)-2-oxo-2,3-dihydropyrido[2,3-b]pyrazine-4(1H)-carboxamide A) 1-(4-chlorophenyl)propan-1-amine To a solution of 1-(4-chlorophenyl)propan-1-one (1.69 g) in ethanol (60 mL) were added hydroxylamine hydrochloride (1.39 g) and triethylamine (2.79 mL) at room temperature. The reaction mixture was stirred at room temperature for 16 hr, and the solvent was evaporated under reduced pressure. To the residue was added water, and the mixture was extracted with ethyl acetate. The extract was washed successively with water and saturated brine, and dried over anhydrous magnesium sulfate, and the solvent was evaporated under reduced pressure to give 1-(4-chlorophenyl)-N-hydroxypropan-1-imine. To a solution of 1-(4-chlorophenyl)-N-hydroxypropan-1-imine in tetrahydrofuran (100 mL) was added 1.1 M borane-tetrahydrofuran complex/tetrahydrofuran solution (27.3 mL), and the mixture was stirred at 80° C. for 16 hr. To the reaction mixture was added 1 M hydrochloric acid, and the mixture was extracted with ethyl acetate. The extract was washed successively with water and saturated brine, and dried over anhydrous magnesium sulfate, and the solvent was evaporated under reduced pressure. The residue was purified by silica gel column chromatography (NH, hexane/ethyl acetate) to give the title compound (520 mg).
$^1$H NMR (300 MHz, CDCl$_3$) δ 0.85 (3H, t, J=7.3 Hz), 1.58-1.74 (2H, m), 3.80 (1H, t, J=7.0 Hz), 7.21-7.40 (4H, m).

B) N-(1-(4-chlorophenyl)propyl)-2-oxo-2,3-dihydropyrido[2,3-b]pyrazine-4(1H)-carboxamide To a mixture of 4-nitrophenyl 2-oxo-2,3-dihydropyrido[2,3-b]pyrazine-4(1H)-carboxylate (300 mg) and 1-(4-chlorophenyl)propan-1-amine (211 mg) in N,N-dimethylformamide (10 mL) was added triethylamine (0.279 mL), and the mixture was stirred at room temperature for 16 hr. To the reaction mixture was added water, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate), and recrystallized from hexane/ethyl acetate to give the title compound (205 mg).
MS (API+): [M+H]$^+$ 345.1.

Example 84

2-oxo-N-(1-(2-(trifluoromethoxy)phenyl)propyl)-2,3-dihydropyrido[2,3-b]pyrazine-4(1H)-carboxamide A) N-methoxy-N-methyl-2-(trifluoromethoxy)benzamide To a mixture of 2-(trifluoromethoxy)benzoic acid (5.00 g), N,O-dimethylhydroxylamine hydrochloride (2.63 g), and triethylamine (7.36 g) in N,N-dimethylformamide (50 mL) were added 1-hydroxybenzotriazole monohydrate (4.94 g) and 1-(3-dimethylaminopropyl)-3-ethylcarbodiimide hydrochloride (2.63 g). The reaction mixture was stirred at 10° C. for 16 hr, water was added thereto, and the mixture was extracted with ethyl acetate. The extract was washed with saturated brine, and dried over anhydrous sodium sulfate, and the solvent was evaporated under reduced pressure to give the title compound (5.21 g).
$^1$H NMR (400 MHz, CDCl$_3$) δ 3.36 (3H, s), 3.45 (3H, s), 7.27-7.37 (2H, m), 7.39-7.50 (2H, m).

B) N-hydroxy-1-(2-(trifluoromethoxy)phenyl)propan-1-imine

The title compound was obtained from N-methoxy-N-methyl-2-(trifluoromethoxy)benzamide in the same manner as in Steps C-D of Example 2.

$^1$H NMR (400 MHz, CDCl$_3$) δ 1.05 (3H, t, J=7.6 Hz), 2.77 (2H, q, J=7.6 Hz), 7.27-7.35 (2H, m), 7.36-7.44 (2H, m), 8.28 (1H, s).

C) 1-(2-(trifluoromethoxy)phenyl)propan-1-amine hydrochloride

To a solution of N-hydroxy-1-(2-(trifluoromethoxy)phenyl)propan-1-imine (2.31 g) in methanol (100 mL) was added Raney nickel (1.00 g). The reaction mixture was stirred at 50° C. for 4 hr under hydrogen atmosphere (50 psi), the insoluble substance was filtered off, and the filtrate was concentrated under reduced pressure. The residue was dissolved in a mixed solvent of ethyl acetate (70 mL) and methanol (10 mL), 4 M hydrogen chloride/ethyl acetate solution (40 mL) was added thereto. The reaction mixture was stirred at 15° C. for 2 hr, and the solvent was evaporated under reduced pressure. The obtained solid was washed with tert-butyl methyl ether to give the title compound (1.36 g).
MS (API+): [M+H]$^+$219.9.

D) 2-oxo-N-(1-(2-(trifluoromethoxy)phenyl)propyl)-2,3-dihydropyrido[2,3-b]pyrazine-4(1H)-carboxamide The title compound was obtained from 1-(2-(trifluoromethoxy)phenyl)propan-1-amine hydrochloride in the same manner as in Step L of Example 72-I.
MS (API+): [M+H]$^+$395.1.

Example 85

N-(1-(4-methylphenyl)propyl)-2-oxo-2,3-dihydropyrido[2,3-b]pyrazine-4(1H)-carboxamide A) methyl 4-(difluoromethyl)benzoate To a solution of methyl 4-formylbenzoate (821 mg) in toluene (25 mL) was added N,N-diethylaminosulfur trifluoride (1.98 mL). The reaction mixture was stirred at room temperature for 20 hr, water was added thereto, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate), and crystallized from hexane/ethyl acetate to give the title compound (619 mg).
$^1$H NMR (300 MHz, CDCl$_3$) δ 3.95 (3H, s), 6.46-6.92 (1H, m), 7.59 (2H, d, J=8.3 Hz), 8.13 (2H, d, J=8.7 Hz).

B) 4-(difluoromethyl)-N-methoxy-N-methylbenzamide

To a solution of methyl 4-(difluoromethyl)benzoate (615 mg) in a mixed solvent of tetrahydrofuran (15 mL) and methanol (5 mL) was added 2 M aqueous sodium hydroxide solution (3.0 mL), and the mixture was stirred at room temperature for 3 hr. The reaction mixture was neutralized with 1 M hydrochloric acid, and the mixture was extracted with ethyl acetate. The extract was washed successively with water and saturated brine, and dried over anhydrous magnesium sulfate, and the solvent was evaporated under reduced pressure. A mixture of the obtained residue, N,O-dimethylhydroxylamine hydrochloride (387 mg), triethylamine (0.921 mL), 1-hydroxybenzotriazole monohydrate (607 mg) and 1-(3-dimethylaminopropyl)-3-ethylcarbodiimide hydrochloride (760 mg) in N,N-dimethylformamide (15 mL) was stirred at room temperature for 20 hr. To the reaction mixture was added water, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate) to give the title compound (540 mg).
$^1$H NMR (300 MHz, CDCl$_3$) δ 3.38 (3H, s), 3.54 (3H, s), 6.47-6.89 (1H, m), 7.56 (2H, d, J=8.3 Hz), 7.77 (2H, d, J=8.7 Hz).

C) 1-(4-(difluoromethyl)phenyl)propan-1-one

The title compound was obtained from 4-(difluoromethyl)-N-methoxy-N-methylbenzamide in the same manner as in Step C of Example 2.
$^1$H NMR (300 MHz, CDCl$_3$) δ 1.24 (3H, t, J=7.2 Hz), 3.03 (2H, q, J=7.2 Hz), 6.48-6.90 (1H, m), 7.61 (2H, d, J=8.3 Hz), 8.05 (2H, d, J=8.7 Hz).

D) 1-(4-methylphenyl)propan-1-amine

To a solution of 1-(4-(difluoromethyl)phenyl)propan-1-one (360 mg) in ethanol (10 mL) were added hydroxylamine hydrochloride (272 mg) and triethylamine (0.545 mL). The reaction mixture was stirred at room temperature for 16 hr, and the solvent was evaporated under reduced pressure. To the residue was added water, and the mixture was extracted with ethyl acetate. The extract was washed successively with water and saturated brine, and dried over anhydrous magnesium sulfate, and the solvent was evaporated under reduced pressure. To the residue were added ethanol (20 mL) and 20% palladium hydroxide-carbon (40 mg). The reaction mixture was stirred at room temperature for 16 hr under hydrogen atmosphere, the catalyst was filtered off, and the filtrate was concentrated under reduced pressure to give the title compound (280 mg).
$^1$H NMR (300 MHz, CDCl$_3$) δ 0.72 (3H, t, J=7.2 Hz), 1.66-1.94 (2H, m), 2.31 (3H, s), 3.73 (1H, dd, J=8.7, 5.7 Hz), 7.08-7.23 (4H, m), 8.26 (2H, brs).

E) N-(1-(4-methylphenyl)propyl)-2-oxo-2,3-dihydropyrido[2,3-b]pyrazine-4(1H)-carboxamide The title compound was obtained from 1-(4-methylphenyl)propan-1-amine in the same manner as in Step B of Example 83.
MS (API+): [M+H]$^+$325.2.

Example 86

2-oxo-N-(1-(1-(2,2,2-trifluoroethyl)-1H-pyrazol-4-yl)propyl)-2,3-dihydropyrido[2,3-b]pyrazine-4(1H)-carboxamide A) methyl 1H-pyrazol-4-carboxylate A mixture of 1H-pyrazol-4-carboxylic acid (4.00 g) and 4 M hydrogen chloride/methanol solution (150 mL) was stirred overnight at room temperature, and the solvent was evaporated under reduced pressure to give the title compound (5.0 g).
$^1$H NMR (400 MHz, DMSO-d$_6$) δ 3.72 (3H, s), 8.09 (2H, s), 11.62 (1H, s).

B) methyl 1-trityl-1H-pyrazol-4-carboxylate

The title compound was obtained from methyl 1H-pyrazole-4-carboxylate in the same manner as in Step A of Example 80.

$^1$H NMR (400 MHz, DMSO-$d_6$) δ 3.79 (3H, s), 7.11-7.14 (6H, m), 7.31-7.33 (9H, s) 7.93 (1H, s), 8.04 (1H, s).

C) N-methoxy-N-methyl-1-trityl-1H-pyrazole-4-carboxamide

A mixture of methyl 1-trityl-1H-pyrazol-4-carboxylate (8.00 g) and lithium hydroxide (2.70 g) in water/tetrahydrofuran/methanol (1:2:2) (100 mL) was stirred at 60° C. for 3 hr, and the solvent was evaporated under reduced pressure. To the residue were added N,N-dimethylformamide (50 mL), N,O-dimethylhydroxylamine hydrochloride (2.10 g), triethylamine (6.80 g) and O-(7-azabenzotriazol-1-yl)-N,N,N',N'-tetramethyluronium hexafluorophosphate (16.8 g) at room temperature. The reaction mixture was stirred overnight at room temperature, water was added thereto, and the mixture was extracted with ethyl acetate. The extract was washed successively with aqueous sodium carbonate solution, water and saturated brine, and dried over anhydrous sodium sulfate, and the solvent was evaporated under reduced pressure to give the title compound (5.7 g).

$^1$H NMR (400 MHz, DMSO-$d_6$) δ 3.29 (3H, s), 3.63 (3H, s), 7.13-7.16 (6H, m), 7.31-7.33 (9H, s) 7.98 (1H, s), 8.11 (1H, s).

D) 2-oxo-N-(1-(1-(2,2,2-trifluoroethyl)-1H-pyrazol-4-yl)propyl)-2,3-dihydropyrido[2,3-b]pyrazine-4(1H)-carboxamide The title compound was obtained from N-methoxy-N-methyl-1-trityl-1H-pyrazol-4-carboxamide in the same manner as in Step C of Example 2 and Step D of Example 80.

MS (API+): [M+H]$^+$383.1.

Example 87

N-(1-(3-methyl-4-(trifluoromethoxy)phenyl)propyl)-2-oxo-2,3-dihydropyrido[2,3-b]pyrazine-4(1H)-carboxamide The title compound was obtained from 1-bromo-3-methyl-4-(trifluoromethoxy)benzene in the same manner as in Steps A-B of Example 30, Step D of Example 2, Step C of Example 56 and Step G of Example 7.

MS (API+): [M+H]$^+$409.1.

Example 88

N-(2-(dimethylamino)-2-oxo-1-(4-(trifluoromethoxy)phenyl)ethyl)-2-oxo-2,3-dihydropyrido[2,3-b]pyrazine-4(1H)-carboxamide

A) tert-butyl (2-amino-2-oxo-1-(4-(trifluoromethoxy)phenyl)ethyl)carbamate

A mixture of 2-amino-2-(4-(trifluoromethoxy)phenyl)acetamide (2.15 g), di-tert-butyldicarbonate (2.41 g) and tetrahydrofuran (50 mL) was stirred overnight at room temperature. The solvent was evaporated under reduced pressure to give the title compound (2.99 g).

$^1$H NMR (300 MHz, CDCl$_3$) δ 1.41 (9H, s), 5.24 (1H, brs), 5.67 (1H, brs), 5.83 (1H, d, J=5.7 Hz), 5.91 (1H, brs), 7.16-7.24 (2H, m), 7.37-7.49 (2H, m).

B) tert-butyl (2-(dimethylamino)-2-oxo-1-(4-(trifluoromethoxy)phenyl)ethyl)carbamate A mixture of 2 M aqueous sodium hydroxide solution (20 mL), tert-butyl (2-amino-2-oxo-1-(4-(trifluoromethoxy)phenyl)ethyl)carbamate (1.5 g) and methanol (15 mL) was stirred at 70° C. for 2 days. The reaction mixture was neutralized with 1 M hydrochloric acid at 0° C., and the mixture was extracted with ethyl acetate. The extract was washed successively with water and saturated brine, and dried over anhydrous magnesium sulfate, and the solvent was evaporated under reduced pressure to give a pale yellow solid (1.26 g). A mixture of the obtained solid (400 mg), triethylamine (0.166 mL), 1-hydroxybenzotriazole monohydrate (219 mg), 1-(3-dimethylaminopropyl)-3-ethylcarbodiimide hydrochloride (274 mg), dimethylamine hydrochloride (117 mg) and N,N-dimethylformamide (5 mL) was stirred overnight at 80° C. The reaction mixture was poured into saturated aqueous sodium hydrogen carbonate solution, and the mixture was extracted with ethyl acetate. The extract was washed successively with saturated aqueous sodium hydrogen carbonate solution and saturated brine, and dried over anhydrous magnesium sulfate, and the solvent was evaporated under reduced pressure. The residue was purified by silica gel column chromatography (hexane/ethyl acetate) to give the title compound (254 mg).

$^1$H NMR (300 MHz, CDCl$_3$) δ 1.41 (9H, s), 2.90 (3H, s), 2.99 (3H, s), 5.56 (1H, d, J=7.5 Hz), 6.08 (1H, d, J=7.5 Hz), 7.14-7.23 (2H, m), 7.36-7.46 (2H, m).

C) N-(2-(dimethylamino)-2-oxo-1-(4-(trifluoromethoxy)phenyl)ethyl)-2-oxo-2,3-dihydropyrido[2,3-b]pyrazine-4(1H)-carboxamide A mixture of tert-butyl (2-(dimethylamino)-2-oxo-1-(4-(trifluoromethoxy)phenyl)ethyl)carbamate (270 mg) and 2 M hydrogen chloride/methanol solution (5 mL) was stirred at room temperature for 30 min, and the solvent was evaporated under reduced pressure. To the residue were added N,N-dimethylformamide (15 mL), triethylamine (226 mg) and 4-nitrophenyl-2-oxo-2,3-dihydropyrido[2,3-b]pyrazine-4(1H)-carboxylate (234 mg), and the mixture was stirred overnight at room temperature. To the reaction mixture was added saturated brine, and the mixture was extracted with ethyl acetate. The extract was washed with 1 M aqueous sodium hydroxide solution and saturated brine, and dried over anhydrous magnesium sulfate, and the solvent was evaporated under reduced pressure. The residue was purified by silica gel column chromatography (hexane/ethyl acetate) and then silica gel column chromatography (ethyl acetate/methanol) to give the title compound (83 mg).

MS (API+): [M+H]$^+$438.1.

Example 89

N-(2-(methylamino)-2-oxo-1-(4-(trifluoromethoxy)phenyl)ethyl)-2-oxo-2,3-dihydropyrido[2,3-b]pyrazine-4(1H)-carboxamide The title compound was obtained in the same manner as in Steps A-C of Example 88.

MS (API+): [M+H]$^+$424.1.

Example 90

N-(2-isopropoxy-1-(4-(trifluoromethoxy)phenyl)ethyl)-2-oxo-2,3-dihydropyrido[2,3-b]pyrazine-4(1H)-carboxamide A) 2-isopropoxy-1-(4-(trifluoromethoxy)phenyl)ethanamine The title compound was obtained in the same manner as in Step D of Example 63, Step C of Example 1 and Step B of Example 54.
MS (API+): [M+H]$^+$264.1.

B) N-(2-isopropoxy-1-(4-(trifluoromethoxy)phenyl)ethyl)-2-oxo-2,3-dihydropyrido[2,3-b]pyrazine-4(1H)-carboxamide The title compound was obtained from 2-isopropoxy-1-(4-(trifluoromethoxy)phenyl)ethanamine in the same manner as in Step B of Example 83.
MS (API+): [M+H]$^+$439.2.

Example 91

N-(2-(cyclopentyloxy)-1-(4-(trifluoromethoxy)phenyl)ethyl)-2-oxo-2,3-dihydropyrido[2,3-b]pyrazine-4(1H)-carboxamide A) 2-(cyclopentyloxy)-1-(4-(trifluoromethoxy)phenyl)ethanamine The title compound was obtained in the same manner as in Step D of Example 63, Step C of Example 1 and Step B of Example 54.
MS (API+): [M+H]$^+$290.2.

B) N-(2-(cyclopentyloxy)-1-(4-(trifluoromethoxy)phenyl)ethyl)-2-oxo-2,3-dihydropyrido[2,3-b]pyrazine-4(1H)-carboxamide The title compound was obtained from 2-(cyclopentyloxy)-1-(4-(trifluoromethoxy)phenyl)ethanamine in the same manner as in Step B of Example 83.
MS (API+): [M+H]$^+$465.2.

Example 92

N-(3-amino-3-oxo-1-(4-(trifluoromethoxy)phenyl)propyl)-2-oxo-2,3-dihydropyrido[2,3-b]pyrazine-4(1H)-carboxamide A) tert-butyl (3-amino-3-oxo-1-(4-(trifluoromethoxy)phenyl)propyl)carbamate To a solution of 3-((tert-butoxycarbonyl)amino)-3-(4-(trifluoromethoxy)phenyl)propanoic acid (700 mg) in N,N-dimethylformamide (25.0 mL) were added 1H-benzotriazol-1-ol ammonium salt (335 mg) and 1-(3-dimethylaminopropyl)-3-ethylcarbodiimide hydrochloride (431 mg). The reaction mixture was stirred overnight at room temperature, water was added thereto, and the precipitated solid was collected by filtration, and washed with water to give the title compound (740 mg).
MS (API–): [M–H]$^-$347.2.

B) 3-amino-3-(4-(trifluoromethoxy)phenyl)propanamide hydrochloride

To tert-butyl (3-amino-3-oxo-1-(4-(trifluoromethoxy)phenyl)propyl)carbamate (740 mg) was added 4 M hydrogen chloride/ethyl acetate solution (10 mL). The reaction mixture was stirred at room temperature for 1 hr, and the precipitated solid was collected by filtration, and washed with ethyl acetate to give the title compound (413 mg).
MS (API+), found: 249.1.

C) N-(3-amino-3-oxo-1-(4-(trifluoromethoxy)phenyl)propyl)-2-oxo-2,3-dihydropyrido[2,3-b]pyrazine-4(1H)-carboxamide The title compound was obtained from 3-amino-3-(4-(trifluoromethoxy)phenyl)propanamide hydrochloride in the same manner as in Step L of Example 72-I.
MS (API+): [M+H]$^+$424.1.

Example 93

N-(3-(dimethylamino)-3-oxo-1-(4-(trifluoromethoxy)phenyl)propyl)-2-oxo-2,3-dihydropyrido[2,3-b]pyrazine-4(1H)-carboxamide A) tert-butyl (3-(dimethylamino)-3-oxo-1-(4-(trifluoromethoxy)phenyl)propyl)carbamate To a solution of 3-((tert-butoxycarbonyl)amino)-3-(4-(trifluoromethoxy)phenyl)propanoic acid (600 mg) in N,N-dimethylformamide (25 mL) were added 1-hydroxybenzotriazole monohydrate (353 mg), 1-(3-dimethylaminopropyl)-3-ethylcarbodiimide hydrochloride (437 mg), N-methylmethanamine (1.12 mL) and triethylamine (725 µL). The reaction mixture was stirred overnight at room temperature, water was added thereto, and the precipitated solid was collected by filtration, and washed with water to give the title compound (600 mg).
MS (API–): [M–H]$^-$375.1.

B) 3-amino-N,N-dimethyl-3-(4-(trifluoromethoxy)phenyl)propanamide hydrochloride

The title compound was obtained from tert-butyl (3-(dimethylamino)-3-oxo-1-(4-(trifluoromethoxy)phenyl)propyl)carbamate in the same manner as in Step B of Example 92.
MS (API+), found: 277.1.

C) N-(3-(dimethylamino)-3-oxo-1-(4-(trifluoromethoxy)phenyl)propyl)-2-oxo-2,3-dihydropyrido[2,3-b]pyrazine-4(1H)-carboxamide The title compound was obtained from 3-amino-N,N-dimethyl-3-(4-(trifluoromethoxy)phenyl)propanamide hydrochloride in the same manner as in Step H of Example 72-I.
MS (API+): [M+H]$^+$452.2.

Example 94

N-(2-methoxy-1-(4-(trifluoromethoxy)phenyl)ethyl)-7-methyl-2-oxo-2,3-dihydropyrido[2,3-b]pyrazine-4(1H)-carboxamide The title compound was obtained from 2-methoxy-1-(4-(trifluoromethoxy)phenyl)ethylamine hydrochloride in the same manner as in Step L of Example 72-I.
MS (API+): [M+H]$^+$425.2.

Example 95

3-methyl-2-oxo-N-(1-(4-(trifluoromethoxy)phenyl) propyl)-2,3-dihydropyrido[2,3-b]pyrazine-4(1H)-carboxamide

A) methyl 2-((3-nitropyridin-2-yl)amino)propanoate

The title compound was obtained from methyl 2-aminopropanoate hydrochloride in the same manner as in Step A of Example 19.
MS (API+): [M+H]$^+$225.8.

B) 3-methyl-3,4-dihydropyrido[2,3-b]pyrazin-2(1H)-one

To a solution of methyl 2-((3-nitropyridin-2-yl) amino) propanoate (18.0 g) in ethanol (500 mL) were added iron powder (17.9 g) and conc. hydrochloric acid (2 mL). The reaction mixture was heated at reflux for 16 hr, the insoluble substance was filtered off, and the filtrate was concentrated under reduced pressure. The residue was purified by HPLC (C18, mobile phase: water/acetonitrile (containing 0.1% TFA)), and the obtained fraction was concentrated under reduced pressure. To the residue was added conc. hydrochloric acid (1 mL), and the mixture was concentrated under reduced pressure. To the residue was added saturated aqueous sodium hydrogen carbonate solution, the reaction mixture was stirred at 15° C. for 16 hr, and the solid was collected by filtration. The obtained solid was washed with water, and dried under reduced pressure to give the title compound (1.2 g).
MS (API+): [M+H]$^+$163.8.

C) 3-methyl-2-oxo-N-(1-(4-(trifluoromethoxy)phenyl)propyl)-2,3-dihydropyrido[2,3-b]pyrazine-4(1H)-carboxamide The title compound was obtained from 3-methyl-3,4-dihydropyrido[2,3-b]pyrazin-2(1H)-one in the same manner as in Step F of Example 1.
MS (API+): [M+H]$^+$409.1.

Example 96

N-(1-(4-(difluoromethyl)phenyl)propyl)-2-oxo-2,3-dihydropyrido[2,3-b]pyrazine-4(1H)-carboxamide The title compound was obtained from 1-(4-(difluoromethyl)phenyl)propan-1-one in the same manner as in Steps A-B of Example 83.
MS (API+): [M+H]$^+$361.2.

Example 97

N-(2-cyano-1-(4-(trifluoromethoxy)phenyl)ethyl)-2-oxo-2,3-dihydropyrido[2,3-b]pyrazine-4(1H)-carboxamide

A) tert-butyl (3-amino-3-oxo-1-(4-(trifluoromethoxy)phenyl)propyl)carbamate The title compound was obtained in the same manner as in Step A of Example 92.
MS (API−): [M−H]$^-$347.1.

B) tert-butyl (2-cyano-1-(4-(trifluoromethoxy)phenyl)ethyl)carbamate

To a solution of tert-butyl (3-amino-3-oxo-1-(4-(trifluoromethoxy)phenyl)propyl)carbamate (425 mg) in tetrahydrofuran (30.0 mL) was added thionyl chloride (281 μL). The reaction mixture was stirred overnight at 60° C., and the solvent was evaporated under reduced pressure. To the residue was added water, and the mixture was extracted with ethyl acetate. The extract was washed with saturated aqueous sodium hydrogen carbonate solution and saturated brine, dried over anhydrous sodium sulfate, and the solvent was evaporated under reduced pressure. The residue was purified by silica gel column chromatography (hexane/ethyl acetate) to give the title compound (251 mg).
MS (API−): [M−H]$^-$329.1.

C) 3-amino-3-(4-(trifluoromethoxy)phenyl)propanenitrile hydrochloride

The title compound was obtained from tert-butyl (2-cyano-1-(4-(trifluoromethoxy)phenyl)ethyl)carbamate in the same manner as in Step B of Example 92.
$^1$H NMR (300 MHz, DMSO-d$_6$) δ 3.23-3.44 (2H, m), 4.80 (1H, dd, J=8.3, 6.0 Hz), 7.52 (2H, d, J=7.9 Hz), 7.72-7.84 (2H, m), 9.01 (3H, brs).

D) N-(2-cyano-1-(4-(trifluoromethoxy)phenyl)ethyl)-2-oxo-2,3-dihydropyrido[2,3-b]pyrazine-4(1H)-carboxamide The title compound was obtained from 3-amino-3-(4-(trifluoromethoxy)phenyl)propanenitrile hydrochloride in the same manner as in Step L of Example 72-I.
MS (API+): [M+H]$^+$406.2.

Example 98

2-oxo-N-(1-(3-(trifluoromethoxy)phenyl)propyl)-2,3-dihydropyrido[2,3-b]pyrazine-4(1H)-carboxamide

A) 1-(3-(trifluoromethoxy)phenyl)propan-1-amine hydrochloride

The title compound was obtained from 3-(trifluoromethoxy)benzoic acid in the same manner as in Step A of Example 84, Steps C-D of Example 2 and Step C of Example 84.
$^1$H NMR (400 MHz, DMSO-d$_6$) δ 0.75 (3H, t, J=7.2 Hz), 1.71-1.85 (1H, m), 1.92-2.05 (1H, m), 4.17-4.28 (1H, m), 7.34-7.42 (1H, m), 7.51-7.61 (3H, m), 8.66 (3H, brs).

B) 2-oxo-N-(1-(3-(trifluoromethoxy)phenyl)propyl)-2,3-dihydropyrido[2,3-b]pyrazine-4(1H)-carboxamide The title compound was obtained from 1-(3-(trifluoromethoxy)phenyl)propan-1-amine hydrochloride in the same manner as in Step L of Example 72-I.
MS (API+): [M+H]$^+$395.2.

Example 99

N-(1-(4-cyclopropylphenyl)propyl)-2-oxo-2,3-dihydropyrido[2,3-b]pyrazine-4(1H)-carboxamide A) 1-(4-cyclopropylphenyl)propan-1-one A mixture of 1-(4-bromophenyl)propan-1-one (1.07 g), cyclopropylboronic acid (0.558 g), (1,1-bis(diphenylphosphino)ferrocene)dichloropalladium(II) (183 mg), tripotassium phosphate (2.12 g) in a mixed solvent of 1,2-dimethoxyethane (15 mL) and water (5 mL) was stirred at 85° C. for 20 hr under nitrogen atmosphere. To the reaction mixture was added water, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (679 mg).
MS (API+): $[M+H]^+$174.9.

B) N-(1-(4-cyclopropylphenyl)propyl)-2-oxo-2,3-dihydropyrido[2,3-b]pyrazine-4(1H)-carboxamide The title compound was obtained from 1-(4-cyclopropylphenyl)propan-1-one in the same manner as in Steps A-B of Example 83.
MS (API+): $[M+H]^+$351.2.

Example 100

N-(3-methoxy-1-(4-(trifluoromethoxy)phenyl)propyl)-2-oxo-2,3-dihydropyrido[2,3-b]pyrazine-4(1H)-carboxamide A) 1-(4-(trifluoromethoxy)phenyl)prop-2-en-1-ol To a solution of 4-(trifluoromethoxy)benzaldehyde (12.0 g) in tetrahydrofuran (200 mL) was slowly added 1 M vinylmagnesium bromide/tetrahydrofuran solution (69.5 mL) under nitrogen atmosphere, at −78° C. The reaction mixture was allowed to be slowly warmed to room temperature, and stirred at room temperature for 16 hr under nitrogen atmosphere. To the reaction mixture was added saturated aqueous ammonium chloride solution, and the mixture was extracted with ethyl acetate. The extract was washed with saturated brine, and dried over anhydrous sodium sulfate, and the solvent was evaporated under reduced pressure. The residue was purified by silica gel column chromatography (petroleum ether/ethyl acetate) to give the title compound (11.8 g).
$^1$H NMR (400 MHz, DMSO-$d_6$) δ 5.02-5.13 (2H, m), 5.26 (1H, dt, J=17.2, 1.6 Hz), 5.64 (1H, d, J=4.4 Hz), 5.87-5.99 (1H, m), 7.31 (2H, d, J=8.0 Hz), 7.44 (2H, dd, J=6.8, 1.6 Hz).

B) 1-(4-(trifluoromethoxy)phenyl)prop-2-en-1-one

To a solution of 1-(4-(trifluoromethoxy)phenyl)prop-2-en-1-ol (9.80 g) in dichloromethane (150 mL) was added manganese(IV) dioxide (39.1 g). The reaction mixture was stirred at room temperature for 2 days, the insoluble substance was filtered off, and the filtrate was concentrated under reduced pressure. The residue was purified by silica gel column chromatography (petroleum ether/ethyl acetate) to give the title compound (2.75 g).
$^1$H NMR (400 MHz, CDCl$_3$) δ 5.97 (1H, dd, J=10.8, 1.6 Hz), 6.46 (1H, dd, J=17.2, 1.6 Hz), 7.13 (1H, dd, J=17.2, 10.8 Hz), 7.31 (2H, dd, J=8.8, 0.8 Hz), 8.00 (2H, dd, J=6.8, 2.0 Hz).

C) 3-methoxy-1-(4-(trifluoromethoxy)phenyl)propan-1-one

A mixture of 1-(4-(trifluoromethoxy)phenyl)prop-2-en-1-one (2.75 g), methanol (407 mg) and bis(acetonitrile)dichloropalladium(II) (328 mg) in dichloromethane (30 mL) was stirred at room temperature for 16 hr under nitrogen atmosphere, dichloromethane was added thereto, and the insoluble substance was filtered off. The filtrate was concentrated under reduced pressure, and the residue was purified by silica gel column chromatography (petroleum ether/ethyl acetate) to give the title compound (2.80 g).
$^1$H NMR (400 MHz, CDCl$_3$) δ 3.22 (2H, t, J=6.4 Hz), 3.38 (3H, s), 3.82 (2H, t, J=6.4 Hz), 7.29 (2H, d, J=8.4 Hz), 8.02 (2H, dd, J=6.8, 2.0 Hz).

D) 3-methoxy-1-(4-(trifluoromethoxy)phenyl)propan-1-amine hydrochloride

The title compound was obtained from 3-methoxy-1-(4-(trifluoromethoxy)phenyl)propan-1-one in the same manner as in Steps D-F of Example 2.
MS (API+): $[M+H]^+$250.0.

E) N-(3-methoxy-1-(4-(trifluoromethoxy)phenyl)propyl)-2-oxo-2,3-dihydropyrido[2,3-b]pyrazine-4(1H)-carboxamide The title compound was obtained from 3-methoxy-1-(4-(trifluoromethoxy)phenyl)propan-1-amine hydrochloride in the same manner as in Step L of Example 72-I.
MS (API+): $[M+H]^+$425.2.

Example 101

2-oxo-N-(2-(pyrrolidin-1-yl)-1-(4-(trifluoromethoxy)phenyl)ethyl)-2,3-dihydropyrido[2,3-b]pyrazine-4(1H)-carboxamide A) 2-(pyrrolidin-1-yl)-1-(4-(trifluoromethoxy)phenyl)ethanamine To a mixture of 4-(trifluoromethoxy)phenacyl bromide (3.00 g) and triethylamine (1.61 g) in tetrahydrofuran (15 mL) was added pyrrolidine (0.902 g). The reaction mixture was stirred at room temperature for 1 hr, water was added thereto, and the mixture was extracted with dichloromethane. The extract was dried over anhydrous sodium sulfate, and the solvent was evaporated under reduced pressure to give 2-(pyrrolidin-1-yl)-1-(4-(trifluoromethoxy)phenyl)ethanone (3.20 g). To a solution of 2-(pyrrolidin-1-yl)-1-(4-(trifluoromethoxy)phenyl)ethanone (3.20 g) in ethanol (30 mL) were added hydroxylamine hydrochloride (0.805 g) and triethylamine (1.18 g). The reaction mixture was stirred at 78° C. for 16 hr, and the solvent was evaporated under reduced pressure. The residue was purified by silica gel column chromatography (petroleum ether/ethyl acetate) to give N-hydroxy-2-(pyrrolidin-1-yl)-1-(4-(trifluoromethoxy)phenyl)ethanimine (1.12 g). To a solution of N-hydroxy-2-(pyrrolidin-1-yl)-1-(4-(trifluoromethoxy)phenyl)ethanimine (1.12 g) in methanol (50 mL) was added Raney nickel (300 mg) at room temperature. The reaction mixture was stirred at 50° C. for 3 hr under hydrogen atmosphere (50 psi), the insoluble substance was filtered off, and the filtrate was concentrated under reduced pressure to give the title compound (1.01 g).
MS (API+): [M+H]$^+$274.9.

B) tert-butyl (2-(pyrrolidin-1-yl)-1-(4-(trifluoromethoxy)phenyl)ethyl)carbamate To a mixture of 2-(pyrrolidin-1-yl)-1-(4-(trifluoromethoxy)phenyl)ethanamine (1.01 g) and triethylamine (558 mg) in methanol (15 mL) was added di-tert-butyl dicarbonate (1.20 g) at room temperature. The reaction mixture was stirred at room temperature for 4 hr, and the solvent was evaporated under reduced pressure. The residue was purified by silica gel column chromatography (petroleum ether/ethyl acetate) and then HPLC (C18, mobile phase: water/acetonitrile (containing 0.1% NH$_4$HCO$_3$)) to give the title compound (560 mg).
$^1$H NMR (400 MHz, CDCl$_3$) δ 1.39 (9H, s), 1.71-1.85 (4H, m), 2.41-2.69 (5H, m), 2.73-2.86 (1H, m), 4.51-4.71 (1H, m), 5.58-5.78 (1H, m),7.16 (2H, d, J=8.0 Hz), 7.32 (2H, d, J=8.4 Hz).

C) 2-(pyrrolidin-1-yl)-1-(4-(trifluoromethoxy)phenyl)ethanamine hydrochloride

To tert-butyl (2-(pyrrolidin-1-yl)-1-(4-(trifluoromethoxy) phenyl)ethyl)carbamate (560 mg) was added 4 M hydrogen chloride/ethyl acetate solution (20 mL) at room temperature. The reaction mixture was stirred at room temperature for 2 hr, and the solvent was evaporated under reduced pressure to give the title compound (310 mg).
$^1$H NMR (400 MHz, CD$_3$OD) δ 2.02-2.15 (4H, m), 3.35-3.58 (4H, m), 3.97 (2H, d, J=6.8 Hz), 5.00 (1H, t, J=6.8 Hz), 7.49 (2H, d, J=8.0 Hz), 7.80 (2H, d, J=8.8 Hz).

D) 2-oxo-N-(2-(pyrrolidin-1-yl)-1-(4-(trifluoromethoxy)phenyl)ethyl)-2,3-dihydropyrido[2,3-b]pyrazine-4(1H)-carboxamide The title compound was obtained from 2-(pyrrolidin-1-yl)-1-(4-(trifluoromethoxy)phenyl)ethanamine hydrochloride in the same manner as in Step L of Example 72-I.
MS (API+): [M+H]$^+$450.2.

Example 102

2-oxo-N-(2-(2-oxopyrrolidin-1-yl)-1-(4-(trifluoromethoxy)phenyl)ethyl)-2,3-dihydropyrido[2,3-b]pyrazine-4(1H)-carboxamide A) 5-methoxy-3,4-dihydro-2H-pyrrole A mixture of pyrrolidine (7.30 g) and dimethyl sulfate (12.1 g) was stirred at 60° C. for 18 hr, water was added thereto, and the pH of the mixture was adjusted to 8-9 with saturated potassium carbonate aqueous solution. The reaction mixture was extracted with tert-butyl methyl ether, dried over anhydrous sodium sulfate, and the solvent was evaporated under reduced pressure to give the title compound (7.2 g).
$^1$H NMR (400 MHz, CDCl$_3$) δ 1.89-1.99 (2H, m), 2.30-2.40 (2H, m), 3.52-3.60 (2H, m), 3.71 (3H, s).

B) 1-(2-oxo-2-(4-(trifluoromethoxy)phenyl)ethyl)pyrrolidin-2-one

A mixture of 5-methoxy-3,4-dihydro-2H-pyrrole (5.60 g) and 2-bromo-1-(4-(trifluoromethoxy)phenyl)ethanone (3.00 g) in N,N-dimethylformamide (20 mL) was stirred at 50-60° C. for 5 hr, water was added thereto, and the mixture was extracted with ethyl acetate. The extract was washed with saturated brine, and dried over anhydrous sodium sulfate, and the solvent was evaporated under reduced pressure. The residue was purified by silica gel column chromatography (petroleum ether/ethyl acetate) to give the title compound (2.32 g).
$^1$H NMR (400 MHz, CDCl$_3$) δ 2.01-2.15 (2H, m), 2.48 (2H, t, J=8.0 Hz), 3.50 (2H, t, J=7.2 Hz), 4.70 (2H, s), 7.31 (2H, J=8.0 Hz), 8.03 (2H, d, J=8.8 Hz).

C) 1-(2-amino-2-(4-(trifluoromethoxy)phenyl)ethyl) pyrrolidin-2-one

A mixture of 1-(2-oxo-2-(4-(trifluoromethoxy)phenyl) ethyl)pyrrolidin-2-one (2.32 g) and hydroxylamine hydrochloride (1.12 g) in pyridine (20 mL) was stirred at 12° C. for 16 hr, water was added thereto, and the mixture was extracted with ethyl acetate. The extract was washed with saturated brine, and dried over anhydrous sodium sulfate, and the solvent was evaporated under reduced pressure to give 1-(2-(hydroxyimino)-2-(4-(trifluoromethoxy)phenyl) ethyl)pyrrolidin-2-one (2.19 g). A mixture of 1-(2-(hydroxyimino)-2-(4-(trifluoromethoxy)phenyl)ethyl)pyrrolidin-2-one (1.00 g) and 10% palladium-carbon (dry, 100 mg) in methanol (50 mL) was stirred at 25° C. for 18 hr under hydrogen atmosphere. The insoluble substance was filtered off through Celite, and the filtrate was concentrated under reduced pressure. The residue was purified by silica gel column chromatography (dichloromethane/methanol) to give the title compound (700 mg).
MS (API+): [M+H]$^+$288.9.

D) 2-oxo-N-(2-(2-oxopyrrolidin-1-yl)-1-(4-(trifluoromethoxy)phenyl)ethyl)-2,3-dihydropyrido[2,3-b]pyrazine-4(1H)-carboxamide The title compound was obtained in the same manner as in Step B of Example 83.
MS (API+): [M+H]$^+$464.2.

Example 103

3-(((2-oxo-2,3-dihydropyrido[2,3-b]pyrazin-4(1H)-yl)carbonyl) amino)-3-(4-(trifluoromethoxy)phenyl) propyl acetate The title compound was obtained from tert-butyl (3-hydroxy-1-(4-(trifluorofluoromethoxy)phenyl)propyl)carbamate in the same manner as in Step E of Example 18 and Step L of Example 72-I.
MS (API+): [M+H]$^+$453.2.

Example 104

N-(3-hydroxy-1-(4-(trifluoromethoxy)phenyl)propyl)-2-oxo-2,3-dihydropyrido[2,3-b]pyrazine-4(1H)-carboxamide To a solution of 3-(((2-oxo-2,3-dihydropyrido[2,3-b]pyrazine-4(1H)-yl)carbonyl)amino)-3-(4-(trifluoromethoxy)

phenyl)propyl acetate (115 mg) in methanol (5 mL) was added potassium carbonate (45.7 mg). The reaction mixture was stirred at room temperature for 1 hr, and the solvent was evaporated under reduced pressure. To the residue was added water, and the mixture was extracted with ethyl acetate. The extract was washed successively with water and saturated brine, and dried over anhydrous magnesium sulfate, and the solvent was evaporated under reduced pressure. The residue was recrystallized from hexane/ethyl acetate to give the title compound (89.4 mg).
MS (API+): [M+H]$^+$410.8.

Example 105

N-(1-(4-(azetidin-1-yl)phenyl)propyl)-2-oxo-2,3-dihydropyrido[2,3-b]pyrazine-4(1H)-carboxamide A) 1-(4-(azetidin-1-yl)phenyl)propan-1-one A mixture of 1-(4-bromophenyl)propan-1-one (639 mg), azetidine (0.303 mL), tris(dibenzylideneacetone)dipalladium(0) (137 mg), 4,5-bis(diphenylphosphino)-9,9-dimethylxanthene (174 mg) and sodium tert-butoxide (432 mg) in toluene (15 mL) was stirred at 85° C. for 20 hr under nitrogen atmosphere. To the reaction mixture was added water, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate) to give the title compound (414 mg).
$^1$H NMR (300 MHz, CDCl$_3$) δ 1.20 (3H, t, J=7.3 Hz), 2.42 (2H, quin, J=7.3 Hz), 2.90 (2H, q, J=7.2 Hz), 3.99 (4H, t, J=7.3 Hz), 6.32-6.39 (2H, m), 7.82-7.90 (2H, m).

B) N-(1-(4-(azetidin-1-yl)phenyl)propyl)-2-oxo-2,3-dihydropyrido[2,3-b]pyrazine-4(1H)-carboxamide The title compound was obtained from 1-(4-(azetidin-1-yl)phenyl)propan-1-one in the same manner as in Steps D-E of Example 2 and Step B of Example 83.
MS (API−): [M−H]$^-$364.2.

Example 106

N-((1R)-2-methoxy-1-(4-(trifluoromethoxy)phenyl)ethyl)-7-methyl-2-oxo-2,3-dihydropyrido[2,3-b]pyrazine-4(1H)-carboxamide Racemic N-(2-methoxy-1-(4-(trifluoromethoxy)phenyl)ethyl)-7-methyl-2-oxo-2,3-dihydropyrido[2,3-b]pyrazine-4(1H)-carboxamide (1.90 g) was resolved by HPLC (column: CHIRALPAK IC, 46 mmID×250 mmL, manufactured by Daicel Chemical Industries, Ltd., mobile phase: hexane/ethanol=400/600) to give the title compound having a shorter retention time (815 mg).
MS (API+): [M+H]$^+$425.2.

Example 107

N-((1S)-2-methoxy-1-(4-(trifluoromethoxy)phenyl)ethyl)-7-methyl-2-oxo-2,3-dihydropyrido[2,3-b]pyrazine-4(1H)-carboxamide Racemic N-(2-methoxy-1-(4-(trifluoromethoxy)phenyl)ethyl)-7-methyl-2-oxo-2,3-dihydropyrido[2,3-b]pyrazine-4(1H)-carboxamide (1.90 g) was resolved by HPLC (column: CHIRALPAK IC, 46 mmID×250 mmL, manufactured by Daicel Chemical Industries, Ltd., mobile phase: hexane/ethanol=400/600) to give the title compound having a longer retention time (772 mg).
MS (API+): [M+H]$^+$425.1.

Example 108

N-(2-(difluoromethoxy)-1-(4-(trifluoromethoxy)phenyl)ethyl)-2-oxo-2,3-dihydropyrido[2,3-b]pyrazine-4(1H)-carboxamide A) tert-butyl (2-(difluoromethoxy)-1-(4-(trifluoromethoxy)phenyl)ethyl)carbamate To a solution of tert-butyl (2-hydroxy-1-(4-(trifluoromethoxy)phenyl)ethyl)carbamate (4.00 g) in acetonitrile (120 mL) were added copper(I) iodide (3.57 g) and difluoro(fluorosulfonyl)acetic acid (1.93 mL) at room temperature. The reaction mixture was stirred overnight at room temperature, saturated aqueous ammonium chloride solution was added thereto, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give the title compound (673 mg).
MS (API−): [M−H]$^-$370.1.

B) 2-(difluoromethoxy)-1-(4-(trifluoromethoxy)phenyl)ethanamine hydrochloride

The title compound was obtained from tert-butyl (2-(difluoromethoxy)-1-(4-(trifluoromethoxy)phenyl)ethyl)carbamate in the same manner as in Step B of Example 92.
MS (API+): [M+H]$^+$272.1.

C) N-(2-(difluoromethoxy)-1-(4-(trifluoromethoxy)phenyl)ethyl)-2-oxo-2,3-dihydropyrido[2,3-b]pyrazine-4(1H)-carboxamide The title compound was obtained from 2-(difluoromethoxy)-1-(4-(trifluoromethoxy)phenyl)ethanamine hydrochloride in the same manner as in Step L of Example 72-I.
MS (API+): [M+H]$^+$447.1.

Example 109

N-(2-methoxy-1-(4-(trifluoromethyl)phenyl)ethyl)-2-oxo-2,3-dihydropyrido[2,3-b]pyrazine-4(1H)-carboxamide The title compound was obtained from 2-bromo-1-(4-(trifluoromethyl)phenyl)ethanone in the same manner as in Steps D-E of Example 63 and Step L of Example 72-I.
MS (API+): [M+H]$^+$395.1.

Example 110

N-(2-methoxy-1-(4-(trifluoromethyl)phenyl)ethyl)-7-methyl-2-oxo-2,3-dihydropyrido[2,3-b]pyrazine-4(1H)-carboxamide The title compound was obtained from 4-nitrophenyl 7-methyl-2-oxo-2,3-dihydropyrido[2,3-b]pyrazine-4(1H)- carboxylate and 2-methoxy-1-(4-(trifluoromethyl)phenyl)ethan-1-amine in the same manner as in Step L of Example 72-I.
MS (API+): [M+H]$^+$409.2.

Example 111

N-(1-(3-fluoro-4-(trifluoromethoxy)phenyl)-2-methoxyethyl)-2-oxo-2,3-dihydropyrido[2,3-b]pyrazine-4(1H)-carboxamide The title compound was obtained from 4-nitrophenyl 2-oxo-2,3-dihydropyrido[2,3-b]pyrazine-4(1H)-carboxylate and 2-methoxy-1-(3-fluoro-4-(trifluoromethoxy)phenyl)ethan-1-amine in the same manner as in Step L of Example 72-I.
MS (API+): [M+H]$^+$429.1.

Example 112

N-(1-(3-fluoro-4-(trifluoromethoxy)phenyl)-2-methoxyethyl)-7-methyl-2-oxo-2,3-dihydropyrido[2,3-b]pyrazine-4(1H)-carboxamide The title compound was obtained from 4-nitrophenyl 7-methyl-2-oxo-2,3-dihydropyrido[2,3-b]pyrazine-4(1H)-carboxylate and 2-methoxy-1-(3-fluoro-4-(trifluoromethoxy)phenyl)ethan-1-amine in the same manner as in Step L of Example 72-I.
MS (API+): [M+H]$^+$443.1.

Example 113

N-(1-(3-fluoro-4-(trifluoromethoxy)phenyl)-2-methoxyethyl)-2-oxo-6-(1H-pyrazol-1-yl)-2,3-dihydropyrido[2,3-b]pyrazine-4(1H)-carboxamide A) methyl N-(6-chloro-3-nitropyridin-2-yl)glycinate The title compound was obtained in the same manner as in Step A of Example 37.
$^1$H NMR (300 MHz, DMSO-d$_6$) δ 3.67 (3H, s), 4.27 (2H, d, J=6.0 Hz), 6.87 (1H, d, J=8.7 Hz), 8.48 (1H, d, J=8.7 Hz), 8.96 (1H, t, J=5.7 Hz).

B) methyl N-(3-nitro-6-(1H-pyrazol-1-yl)pyridin-2-yl)glycinate

To a solution of methyl N-(6-chloro-3-nitropyridin-2-yl)glycinate (1.02 g) in N,N-dimethylacetamide (10 mL) was added 1H-pyrazole (844 mg) at room temperature. The reaction mixture was stirred at 120° C. for 16 hr, water was added thereto, and the mixture was extracted with ethyl acetate/tetrahydrofuran. The extract was washed successively with water and saturated brine, and dried over anhydrous sodium sulfate, and the solvent was evaporated under reduced pressure. The residue was purified by silica gel column chromatography (hexane/ethyl acetate) to give the title compound (293 mg).
MS (API+): [M+H]$^+$278.1.

C) 6-(1H-pyrazol-1-yl)-3,4-dihydropyrido[2,3-b]pyrazin-2(1H)-one

The title compound was obtained from methyl 2-((3-nitro-6-(1H-pyrazol-1-yl)pyridin-2-yl) amino)acetate in the same manner as in Step C of Example 72-I.
MS (API–): [M–H]$^-$214.1.

D) 4-nitrophenyl 2-oxo-6-(1H-pyrazol-1-yl)-2,3-dihydropyrido[2,3-b]pyrazine-4(1H)-carboxylate The title compound was obtained from 6-(1H-pyrazol-1-yl)-3,4-dihydropyrido[2,3-b]pyrazin-2(1H)-one in the same manner as in Step F of Example 7.
MS (API+): [M+H]$^+$381.1.

E) N-(1-(3-fluoro-4-(trifluoromethoxy)phenyl)-2-methoxyethyl)-2-oxo-6-(1H-pyrazol-1-yl)-2,3-dihydropyrido[2,3-b]pyrazine-4(1H)-carboxamide The title compound was obtained from 4-nitrophenyl 2-oxo-6-(1H-pyrazol-1-yl)-2,3-dihydropyrido[2,3-b]pyrazine-4(1H)-carboxylate and 2-methoxy-1-(3-fluoro-4-(trifluoromethoxy)phenyl)ethan-1-amine in the same manner as in Step L of Example 72-I.
MS (API+): [M+H]$^+$495.2.

Example 114

7-cyclopropyl-N-(2-methoxy-1-(4-(trifluoromethoxy)phenyl)ethyl)-2-oxo-2,3-dihydropyrido[2,3-b]pyrazine-4(1H)-carboxamide The title compound was obtained from N-(1-(4-(trifluoromethoxy)phenyl)-2-methoxyethyl)-7-iodo-2-oxo-1-((2-(trimethylsilyl)ethoxy)methyl)-2,3-dihydropyrido[2,3-b]pyrazine-4(1H)-carboxamide in the same manner as in Step L of Example 75 and Step I of Example 63.
MS (API+): [M+H]$^+$451.2.

Example 115

7-cyclopropyl-N-(2-methoxy-1-(4-(trifluoromethyl)phenyl)ethyl)-2-oxo-2,3-dihydropyrido[2,3-b]pyrazine-4(1H)-carboxamide The title compound was obtained from 2-methoxy-1-(4-(trifluoromethyl)phenyl)ethan-1-amine hydrochloride in the same manner as in Step L of Example 72-I.
MS (API+): [M+H]$^+$435.2.

Example 116

N-(2-methoxy-1-(4-(trifluoromethoxy)phenyl)ethyl)-2-oxo-6-(1H-pyrazol-1-yl)-2,3-dihydropyrido[2,3-b]pyrazine-4(1H)-carboxamide The title compound was obtained from 4-nitrophenyl 2-oxo-6-(1H-pyrazol-1-yl)-2,3-dihydropyrido[2,3-b]pyrazine-4(1H)-carboxylate and 2-methoxy-1-(4-(trifluoromethyl)phenyl)ethan-1-amine hydrochloride in the same manner as in Step L of Example 72-I.
MS (API+): [M+H]$^+$477.2.

Example 117

N-((1S)-1-(3-fluoro-4-(trifluoromethoxy)phenyl)-2-methoxyethyl)-2-oxo-6-(1H-pyrazol-1-yl)-2,3-dihydropyrido[2,3-b]pyrazine-4(1H)-carboxamide Racemic N-(1-(3-fluoro-4-(trifluoromethoxy)phenyl)-2-methoxyethyl)-2-oxo-6-(1H-pyrazol-1-yl)-2,3-dihydropyrido[2,3-b]pyrazine-4(1H)-carboxamide (118 mg) was resolved by SFC (column: CHIRALCEL OJH, 20 mmID× 250 mmL, manufactured by Daicel Chemical Industries, Ltd., mobile phase: carbon dioxide/methanol=860/140) to give the title compound having a shorter retention time (31.0 mg).

MS (API+): [M+H]$^+$495.2.

Example 118

N-((1R)-1-(3-fluoro-4-(trifluoromethoxy)phenyl)-2-methoxyethyl)-2-oxo-6-(1H-pyrazol-1-yl)-2,3-dihydropyrido[2,3-b]pyrazine-4(1H)-carboxamide Racemic N-(1-(3-fluoro-4-(trifluoromethoxy)phenyl)-2-methoxyethyl)-2-oxo-6-(1H-pyrazol-1-yl)-2,3-dihydropyrido[2,3-b]pyrazine-4(1H)-carboxamide (118 mg) was resolved by SFC (column: CHIRALCEL OJH, 20 mmID× 250 mmL, manufactured by Daicel Chemical Industries, Ltd., mobile phase: carbon dioxide/methanol=860/140) to give the title compound having a longer retention time (41.8 mg).

MS (API+): [M+H]$^+$495.1.

Example 119

7-cyclopropyl-N-((1R)-2-methoxy-1-(4-(trifluoromethoxy)phenyl)ethyl)-2-oxo-2,3-dihydropyrido[2,3-b]pyrazine-4(1H)-carboxamide Racemic 7-cyclopropyl-N-(2-methoxy-1-(4-(trifluoromethoxy)phenyl)ethyl)-2-oxo-2,3-dihydropyrido[2,3-b]pyrazine-4(1H)-carboxamide (245 mg) was resolved by SFC (column: CHIRALCEL OJH, 20 mmID×250 mmL, manufactured by Daicel Chemical Industries, Ltd., mobile phase: carbon dioxide/methanol=860/140) to give the title compound having a shorter retention time (98.6 mg).

MS (API+): [M+H]$^+$451.2.

Example 120

7-cyclopropyl-N-((1S)-2-methoxy-1-(4-(trifluoromethoxy)phenyl)ethyl)-2-oxo-2,3-dihydropyrido[2,3-b]pyrazine-4(1H)-carboxamide Racemic 7-cyclopropyl-N-(2-methoxy-1-(4-(trifluoromethoxy)phenyl)ethyl)-2-oxo-2,3-dihydropyrido[2,3-b]pyrazine-4(1H)-carboxamide (245 mg) was resolved by SFC (column: CHIRALCEL OJH, 20 mmID×250 mmL, manufactured by Daicel Chemical Industries, Ltd., mobile phase: carbon dioxide/methanol=860/140) to give the title compound having a longer retention time (102 mg).

MS (API+): [M+H]$^+$451.2.

Example 121

N-((1S)-1-(3-fluoro-4-(trifluoromethoxy)phenyl)-2-methoxyethyl)-2-oxo-2,3-dihydropyrido[2,3-b]pyrazine-4(1H)-carboxamide Racemic N-(1-(3-fluoro-4-(trifluoromethoxy)phenyl)-2-methoxyethyl)-2-oxo-2,3-dihydropyrido[2,3-b]pyrazine-4(1H)-carboxamide (184 mg) was resolved by SFC (column: CHIRALPAK IA, 20 mmID×250 mmL, manufactured by Daicel Chemical Industries, Ltd., mobile phase: carbon dioxide/methanol=860/140) to give the title compound having a shorter retention time (70.1 mg).

MS (API+): [M+H]$^+$429.1.

Example 122

N-((1R)-1-(3-fluoro-4-(trifluoromethoxy)phenyl)-2-methoxyethyl)-2-oxo-2,3-dihydropyrido[2,3-b]pyrazine-4(1H)-carboxamide Racemic N-(1-(3-fluoro-4-(trifluoromethoxy)phenyl)-2-methoxyethyl)-2-oxo-2,3-dihydropyrido[2,3-b]pyrazine-4(1H)-carboxamide (184 mg) was resolved by SFC (column: CHIRALPAK IA, 20 mmID×250 mmL, manufactured by Daicel Chemical Industries, Ltd., mobile phase: carbon dioxide/methanol=860/140) to give the title compound having a longer retention time (73.6 mg).

MS (API+): [M+H]$^+$429.1.

Example 123

N-((1S)-1-(3-fluoro-4-(trifluoromethoxy)phenyl)-2-methoxyethyl)-7-methyl-2-oxo-2,3-dihydropyrido[2,3-b]pyrazine-4(1H)-carboxamide Racemic N-(1-(3-fluoro-4-(trifluoromethoxy)phenyl)-2-methoxyethyl)-7-methyl-2-oxo-2,3-dihydropyrido[2,3-b]pyrazine-4(1H)-carboxamide (203 mg) was resolved by SFC (column: CHIRALPAK IA, 20 mmID×250 mmL, manufactured by Daicel Chemical Industries, Ltd., mobile phase: carbon dioxide/methanol=860/140) to give the title compound having a shorter retention time (61.0 mg).

MS (API+): [M+H]$^+$443.1.

Example 124

N-((1R)-1-(3-fluoro-4-(trifluoromethoxy)phenyl)-2-methoxyethyl)-7-methyl-2-oxo-2,3-dihydropyrido[2,3-b]pyrazine-4(1H)-carboxamide Racemic N-(1-(3-fluoro-4-(trifluoromethoxy)phenyl)-2-methoxyethyl)-7-methyl-2-oxo-2,3-dihydropyrido[2,3-b]pyrazine-4(1H)-carboxamide (203 mg) was resolved by SFC (column: CHIRALPAK IA, 20 mmID×250 mmL, manufactured by Daicel Chemical Industries, Ltd., mobile phase: carbon dioxide/methanol=860/140) to give the title compound having a longer retention time (78.8 mg).

MS (API+): [M+H]$^+$443.1.

Example 125

7-cyclopropyl-N-(1-(3-fluoro-4-(trifluoromethoxy)phenyl)-2-methoxyethyl)-2-oxo-2,3-dihydropyrido[2,3-b]pyrazine-4(1H)-carboxamide The title compound was obtained from 2-methoxy-1-(3-fluoro-4-(trifluoromethoxy)phenyl)ethan-1-amine hydrochloride in the same manner as in Step L of Example 72-I.

MS (API+): [M+H]$^+$469.2.

Example 126

Optically Active N-(2-(difluoromethoxy)-1-(4-(trifluoromethoxy)phenyl)ethyl)-2-oxo-2,3-dihydropyrido[2,3-b]pyrazine-4(1H)-carboxamide Racemic N-(2-(difluoromethoxy)-1-(4-(trifluoromethoxy)phenyl)ethyl)-2-oxo-2,3-dihydropyrido[2,3-b]pyrazine-4(1H)-carboxamide (243 mg) was resolved by SFC (column: CHIRALPAK IC, 20 mmID×250 mmL, manufactured by Daicel Chemical Industries, Ltd., mobile phase: carbon dioxide/methanol=770/230) to give the title compound having a shorter retention time (81.1 mg).
MS (API+): [M+H]$^+$447.1.

Example 127

Optically Active N-(2-(difluoromethoxy)-1-(4-(trifluoromethoxy)phenyl)ethyl)-2-oxo-2,3-dihydropyrido[2,3-b]pyrazine-4(1H)-carboxamide Racemic N-(2-(difluoromethoxy)-1-(4-(trifluoromethoxy)phenyl)ethyl)-2-oxo-2,3-dihydropyrido[2,3-b]pyrazine-4(1H)-carboxamide (243 mg) was resolved by SFC (column: CHIRALPAK IC, 20 mmID×250 mmL, manufactured by Daicel Chemical Industries, Ltd., mobile phase: carbon dioxide/methanol=770/230) to give the title compound having a longer retention time (81.4 mg).
MS (API+): [M+H]$^+$447.1.

Example 128

7-cyclopropyl-N-((1R)-1-(3-fluoro-4-(trifluoromethoxy)phenyl)-2-methoxyethyl)-2-oxo-2,3-dihydropyrido[2,3-b]pyrazine-4(1H)-carboxamide Racemic 7-cyclopropyl-N-(1-(3-fluoro-4-(trifluoromethoxy)phenyl)-2-methoxyethyl)-2-oxo-2,3-dihydropyrido[2,3-b]pyrazine-4(1H)-carboxamide (129 mg) was resolved by HPLC (column: CHIRALPAK IC, 50 mmID× 500 mmL, manufactured by Daicel Chemical Industries, Ltd., mobile phase: hexane/ethanol=600/400) to give the title compound having a shorter retention time (58.2 mg).
MS (API+): [M+H]$^+$469.2.

Example 129

7-cyclopropyl-N-((1S)-1-(3-fluoro-4-(trifluoromethoxy)phenyl)-2-methoxyethyl)-2-oxo-2,3-dihydropyrido[2,3-b]pyrazine-4(1H)-carboxamide Racemic 7-cyclopropyl-N-(1-(3-fluoro-4-(trifluoromethoxy)phenyl)-2-methoxyethyl)-2-oxo-2,3-dihydropyrido[2,3-b]pyrazine-4(1H)-carboxamide (129 mg) was resolved by HPLC (column: CHIRALPAK IC, 50 mmID× 500 mmL, manufactured by Daicel Chemical Industries, Ltd., mobile phase: hexane/ethanol=600/400) to give the title compound having a longer retention time (60.7 mg).
MS (API+): [M+H]$^+$469.2.

Example 130

N-((1S)-2-methoxy-1-(4-(trifluoromethoxy)phenyl)ethyl)-2-oxo-6-(1H-pyrazol-1-yl)-2,3-dihydropyrido[2,3-b]pyrazine-4(1H)-carboxamide Racemic N-(2-methoxy-1-(4-(trifluoromethoxy)phenyl)ethyl)-2-oxo-6-(1H-pyrazol-1-yl)-2,3-dihydropyrido[2,3-b]pyrazine-4(1H)-carboxamide (142 mg) was resolved by SFC (column: CHIRALCEL OJH, 20 mmID×250 mmL, manufactured by Daicel Chemical Industries, Ltd., mobile phase: carbon dioxide/methanol=860/140) to give the title compound having a shorter retention time (53.5 mg).
MS (API+): [M+H]$^+$477.2.

Example 131

N-((1R)-2-methoxy-1-(4-(trifluoromethoxy)phenyl)ethyl)-2-oxo-6-(1H-pyrazol-1-yl)-2,3-dihydropyrido[2,3-b]pyrazine-4(1H)-carboxamide Racemic N-(2-methoxy-1-(4-(trifluoromethoxy)phenyl)ethyl)-2-oxo-6-(1H-pyrazol-1-yl)-2,3-dihydropyrido[2,3-b]pyrazine-4(1H)-carboxamide (142 mg) was resolved by SFC (column: CHIRALCEL OJH, 20 mmID×250 mmL, manufactured by Daicel Chemical Industries, Ltd., mobile phase: carbon dioxide/methanol=860/140) to give the title compound having a longer retention time (57.3 mg).
MS (API+): [M+H]$^+$477.2.

Example 132

N-(1-(4-bromophenyl)-2-methoxyethyl)-7-methyl-2-oxo-2,3-dihydropyrido[2,3-b]pyrazine-4(1H)-carboxamide A)
1-(4-bromophenyl)-N-hydroxy-2-methoxyethanimine The title compound was obtained from 2-bromo-1-(4-bromophenyl)ethanone in the same manner as in Step D of Example 63 and Step D of Example 2.
MS (API+): [M+H]$^+$244.1.

B) 1-(4-bromophenyl)-2-methoxyethanamine

A mixture of 1-(4-bromophenyl)-N-hydroxy-2-methoxyethanimine (7.5 g), 1.1 M borane-tetrahydrofuran complex/tetrahydrofuran solution (55.9 mL) and tetrahydrofuran (300 mL) was stirred at 80° C. for 2 days, 1 M aqueous sodium hydroxide solution was added thereto, and the mixture was stirred at 80° C. for 3 hr. To the reaction mixture was added saturated brine, and the mixture was extracted with ethyl acetate. The extract was washed with saturated brine, and dried over anhydrous magnesium sulfate, and the solvent was evaporated under reduced pressure to give the title compound containing an impurity (8.44 g).
MS (API+): [M+H]$^+$230.1.

C) N-(1-(4-bromophenyl)-2-methoxyethyl)-7-methyl-2-oxo-2,3-dihydropyrido[2,3-b]pyrazine-4(1H)-carboxamide The title compound was obtained from 4-nitrophenyl 7-methyl-2-oxo-2,3-dihydropyrido[2,3-b]pyrazine-4(1H)-carboxylate and 1-(4-bromophenyl)-2-methoxyethanamine in the same manner as in Step G of Example 7.
MS (API+): [M+H]$^+$419.1.

Example 133

N-(2-(2-methoxyethoxy)-1-(4-(trifluoromethoxy)phenyl)ethyl)-7-methyl-2-oxo-2,3-dihydropyrido[2,3-b]pyrazine-4(1H)-carboxamide The title compound was obtained from 4-(trifluoromethoxy)phenacyl bromide in the same manner as in Step D of Example 63, Step D of Example 2, Step B of Example and Step G of Example 7.
MS (API+): [M+H]$^+$469.2.

Example 134

N-(2-methoxy-1-(4-(1H-pyrazol-1-yl)phenyl)ethyl)-7-methyl-2-oxo-2,3-dihydropyrido[2,3-b]pyrazine-4(1H)-carboxamide

A) 1-(4-bromophenyl)-2-methoxyethanone

The title compound was obtained from 2-bromo-1-(4-bromophenyl)ethanone in the same manner as in Step D of Example 63.
$^1$H NMR (300 MHz, CDCl$_3$) δ 3.50 (3H, s), 4.65 (2H, s), 7.55-7.68 (2H, m), 7.75-7.87 (2H, m).

B) 2-(4-bromophenyl)-2-(methoxymethyl)-1,3-dioxolane

A mixture of 1-(4-bromophenyl)-2-methoxyethanone (3.00 g), p-toluenesulfonic acid monohydrate (0.249 g), ethylene glycol (1.63 g) and toluene (50 mL) was stirred overnight using Dean-Stark at 140° C. The reaction mixture was filtered through silica gel pad (NH), and the solvent was evaporated under reduced pressure to give the title compound (3.97 g).
$^1$H NMR (300 MHz, CDCl$_3$) δ 3.39 (3H, s), 3.57 (2H, s), 3.76-3.92 (2H, m), 4.02-4.19 (2H, m), 7.35-7.43 (2H, m), 7.43-7.52 (2H, m).

C) 1-(4-(2-(methoxymethyl)-1,3-dioxolane-2-yl)phenyl)-1H-pyrazole

A mixture of 2-(4-bromophenyl)-2-(methoxymethyl)-1,3-dioxolane (3.5 g), 1H-pyrazole (0.960 g), quinolin-8-ol (0.372 g), copper(I) iodide (0.244 g), potassium carbonate (3.54 g) and dimethyl sulfoxide (50 mL) was stirred overnight at 140° C. under nitrogen atmosphere, water was added thereto, and the mixture was extracted with ethyl acetate. The extract was washed successively with saturated aqueous ammonium chloride solution and saturated brine, dried over anhydrous magnesium sulfate, and filtered through NH silica gel pad. The filtrate was concentrated under reduced pressure, and the residue was purified by silica gel column chromatography (hexane/ethyl acetate) to give the title compound (2.53 g).
MS (API+): [M+H]$^+$261.1.

D) 2-methoxy-1-(4-(1H-pyrazol-1-yl)phenyl)ethanone

A mixture of 1-(4-(2-(methoxymethyl)-1,3-dioxolane-2-yl)phenyl)-1H-pyrazole (2.6 g), 1 M hydrochloric acid (15 mL) and tetrahydrofuran (30 mL) was stirred overnight at room temperature, saturated brine was added thereto, and the mixture was extracted with ethyl acetate. The extract was washed with saturated brine, and dried over anhydrous magnesium sulfate, and the solvent was evaporated under reduced pressure to give the title compound (2.15 g).
$^1$H NMR (300 MHz, CDCl$_3$) δ 3.52 (3H, s), 4.71 (2H, s), 6.48-6.56 (1H, m), 7.78 (1H, d, J=1.9 Hz), 7.79-7.87 (2H, m), 8.02 (1H, d, J=2.6 Hz), 8.03-8.10 (2H, m).

E) N-(2-methoxy-1-(4-(1H-pyrazol-1-yl)phenyl)ethyl)-7-methyl-2-oxo-2,3-dihydropyrido[2,3-b]pyrazine-4(1H)-carboxamide The title compound was obtained from 2-methoxy-1-(4-(1H-pyrazol-1-yl)phenyl)ethanone in the same manner as in Step D of Example 2, Step B of Example 15 and Step G of Example 7.
MS (API+): [M+H]$^+$407.2.

Example 135

N-(2-methoxy-1-(4-(trifluoromethoxy)phenyl)ethyl)-7-(1-methyl-1H-pyrazol-3-yl)-2-oxo-2,3-dihydropyrido[2,3-b]pyrazine-4(1H)-carboxamide

A) methyl N-(5-bromo-3-nitropyridin-2-yl)glycinate

The title compound was obtained from 5-bromo-2-chloro-3-nitropyridine in the same manner as in Step A of Example 19.
MS (API+): [M+H]$^+$290.0.

B) 7-bromo-3,4-dihydropyrido[2,3-b]pyrazin-2(1H)-one

A mixture of methyl N-(5-bromo-3-nitropyridin-2-yl)glycinate (18.0 g) and 5% platinum-carbon (1.80 g) in tetrahydrofuran (414 mL) was stirred at room temperature for 1 hr under hydrogen atmosphere. The catalyst was filtered off, and the solvent was evaporated under reduced pressure. The residue was dissolved in ethanol (200 mL), the solution was stirred overnight at 80° C. The reaction mixture was cooled to room temperature, and the solid was collected by filtration, and washed with ethyl acetate to give the title compound (9.60 g)
$^1$H NMR (300 MHz, DMSO-d$_6$) δ 3.94 (2H, d, J=1.7 Hz), 6.99 (1H, s), 7.01 (1H, d, J=2.1 Hz), 7.65 (1H, d, J=2.3 Hz), 10.46 (1H, s).

C) 7-bromo-N-(2-methoxy-1-(4-(trifluoromethoxy)phenyl)ethyl)-2-oxo-1-((2-(trimethylsilyl)ethoxy)methyl)-2,3-dihydropyrido[2,3-b]-pyrazine-4(1H)-carboxamide The title compound was obtained from 7-bromo-3,4-dihydropyrido[2,3-b]pyrazin-2(1H)-one in the same manner as in Steps C-D of Example 26.
MS (API+): [M+H]$^+$619.2.

D) N-(2-methoxy-1-(4-(trifluoromethoxy)phenyl)ethyl)-7-(1-methyl-1H-pyrazol-3-yl)-2-oxo-1-((2-(trimethylsilyl)ethoxy)methyl)-2,3-dihydropyrido[2,3-b]-pyrazine-4(1H)-carboxamide To a mixture of 7-bromo-N-(2-methoxy-1-(4-(trifluoromethoxy)phenyl)ethyl)-2-oxo-1-((2-(trimethylsilyl)ethoxy)methyl)-2,3-dihydropyrido[2,3-b]-pyrazine-4(1H)-carboxamide (100 mg) and 1-methyl-3-(4,4,5,5-tetramethyl-[1,3,2]-dioxaborolane-1H-pyrazole (101 mg), tripotassium phosphate (103 mg) in a mixed solvent of toluene (1.51 mL) and water (0.10 mL) was added bis(di-tert-butyl(4-dimethylaminophenyl)phosphine)dichloropalladium(II) (11.4 mg) at room temperature, the reaction mixture was stirred at 100° C. for 3 hr under argon atmosphere. The reaction mixture was cooled to room temperature, and the solvent was evaporated under reduced pressure. The residue was purified by silica gel column chromatography (hexane/ethyl acetate) to give the title compound (72 mg).
MS (API+): [M+H]$^+$621.3.

E) N-(2-methoxy-1-(4-(trifluoromethoxy)phenyl)ethyl)-7-(1-methyl-1H-pyrazol-3-yl)-2-oxo-2,3-dihydropyrido[2,3-b]pyrazine-4(1H)-carboxamide The title compound was obtained from N-(2-methoxy-1-(4-(trifluoromethoxy)phenyl)ethyl)-7-(1-methyl-1H-pyrazol-3-yl)-2-oxo-1-((2-(trimethylsilyl)ethoxy)methyl)-2,3-dihydropyrido[2,3-b]-pyrazine-4(1H)-carboxamide in the same manner as in Step I of Example 63.
MS (API+): [M+H]$^+$491.2.

Example 136

N-(2-methoxy-1-(4-(trifluoromethoxy)phenyl)ethyl)-7-(1-methyl-1H-pyrazol-4-yl)-2-oxo-2,3-dihydropyrido[2,3-b]pyrazine-4(1H)-carboxamide The title compound was obtained from 7-bromo-N-(2-methoxy-1-(4-(trifluoromethoxy)phenyl)ethyl)-2-oxo-1-((2-(trimethylsilyl)ethoxy)methyl)-2,3-dihydropyrido[2,3-b]-pyrazine-4(1H)-carboxamide (100 mg) and 1-methyl-4-(4,4,5,5-tetramethyl-[1,3,2]-dioxaborolane-1H-pyrazole in the same manner as in Step D of Example 135 and Step I of Example 63.
MS (API+): [M+H]$^+$491.2.

Example 137

N-(2-methoxy-1-(4-(trifluoromethoxy)phenyl)ethyl)-7-(1-methyl-1H-pyrazol-5-yl)-2-oxo-2,3-dihydropyrido[2,3-b]pyrazine-4(1H)-carboxamide The title compound was obtained from 7-bromo-N-(2-methoxy-1-(4-(trifluoromethoxy)phenyl)ethyl)-2-oxo-1-((2-(trimethylsilyl)ethoxy)methyl)-2,3-dihydropyrido[2,3-b]-pyrazine-4(1H)-carboxamide (100 mg) and 1-methyl-5-(4,4,5,5-tetramethyl-[1,3,2]-dioxaborolane-1H-pyrazole in the same manner as in Step D of Example 135 and Step I of Example 63.
MS (API+): [M+H]$^+$491.2.

Example 138

7-isopropoxy-N-(2-methoxy-1-(4-(trifluoromethoxy)phenyl)ethyl)-2-oxo-2,3-dihydropyrido[2,3-b]pyrazine-4(1H)-carboxamide The title compound was obtained from 2-iodopropane in the same manner as in Steps H-I of Example 63.
MS (API+): [M+H]$^+$469.1.

Example 139

7-(difluoromethoxy)-N-(2-methoxy-1-(4-(trifluoromethoxy)phenyl)ethyl)-2-oxo-2,3-dihydropyrido[2,3-b]pyrazine-4(1H)-carboxamide A) 7-(difluoromethoxy)-N-(2-methoxy-1-(4-(trifluoromethoxy)phenyl)ethyl)-2-oxo-1-((2-(trimethylsilyl)ethoxy)methyl)-2,3-dihydropyrido[2,3-b]pyrazine-4(1H)-carboxamide To a mixture of 7-hydroxy-N-(2-methoxy-1-(4-(trifluoromethoxy)phenyl)ethyl)-2-oxo-1-((2-(trimethylsilyl)ethoxy)methyl)-2,3-dihydropyrido[2,3-b]pyrazine-4(1H)-carboxamide (163 mg) and N-benzyl-N,N,N-triethylammonium chloride (20.4 mg) in tetrahydrofuran (2.00 mL) was added 8 M aqueous sodium hydroxide solution (36.3 µL) at 0° C. The reaction mixture was stirred overnight at room temperature under chloro(difluoro)methane atmosphere. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give the title compound (80.9 mg).
MS (API+): [M+H]$^+$607.2.

B) 7-(difluoromethoxy)-N-(2-methoxy-1-(4-(trifluoromethoxy)phenyl)ethyl)-2-oxo-2,3-dihydropyrido[2,3-b]pyrazine-4(1H)-carboxamide The title compound was obtained from 7-(difluoromethoxy)-N-(2-methoxy-1-(4-(trifluoromethoxy)phenyl)ethyl)-2-oxo-1-((2-(trimethylsilyl)ethoxy)methyl)-2,3-dihydropyrido[2,3-b]pyrazine-4(1H)-carboxamide in the same manner as in Step I of Example 63.
MS (API+): [M+H]$^+$477.2.

Example 140

N-(2-methoxy-1-(4-(trifluoromethoxy)phenyl)ethyl)-6-oxo-6,7-dihydropteridine-8(5H)-carboxamide A) methyl 2-((2-chloro-5-nitropyrimidin-4-yl)aminoacetate The title compound was obtained from 2,4-dichloro-5-nitropyrimidine in the same manner as in Step A of Example 1.
MS (API−): [M−H]$^-$245.0.

B) 7,8-dihydropteridin-6(5H)-one

To a solution of methyl 2-((2-chloro-5-nitropyrimidin-4-yl)aminoacetate (7.23 g) in ethanol (293 mL) was added 5% palladium-carbon (containing 50% water, 3.00 g) at room temperature. The reaction mixture was stirred at room temperature for 2 hr under hydrogen atmosphere, the catalyst was filtered off, and the solvent was evaporated under reduced pressure. To a solution of the residue in ethanol (293 mL) was added acetic acid (8.39 mL) at room temperature. The reaction mixture was stirred at 80° C. for 3 days, and cooled to room temperature, and the solid was collected by filtration. The obtained solid was suspended in saturated aqueous sodium bicarbonate solution, and the solid was collected by filtration, and washed with water to give the title compound (3.91 g).
$^1$H NMR (300 MHz, DMSO-d$_6$) δ 4.02 (2H, d, J=1.5 Hz), 7.66 (1H, s), 7.70 (1H, brs), 8.05 (1H, s), 10.49 (1H, brs).

D) N-(2-methoxy-1-(4-(trifluoromethoxy)phenyl)ethyl)-6-oxo-6,7-dihydropteridin-8(5H)-carboxamide The title compound was obtained from 7,8-dihydropteridin-6(5H)-one in the same manner as in Steps F-G of Example 7.
MS (API+): [M+H]$^+$412.2.

Example 141

7-ethoxy-N-(2-methoxy-1-(4-(trifluoromethoxy)phenyl)ethyl)-2-oxo-2,3-dihydropyrido[2,3-b]pyrazine-4(1H)-carboxamide The title compound was obtained from iodoethane in the same manner as in Steps H-I of Example 63.
MS (API+): [M+H]$^+$455.2.

Example 142

7-methyl-N-(oxetan-3-yl(4-(trifluoromethoxy)phenyl)methyl)-2-oxo-2,3-dihydropyrido[2,3-b]pyrazine-4(1H)-carboxamide A) diethyl (4-(trifluoromethoxy)benzyl)malonate A mixture of 1-(bromomethyl)-4-(trifluoromethoxy)benzene (10.0 g), diethyl malonate (6.91 g), sodium ethoxide (14.7 g) and ethanol (500 mL) was stirred at 80° C. for 2 days. To the reaction mixture was added saturated aqueous ammonium chloride solution, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (7.46 g).

MS (API−): [M−H]⁻333.1.

B) 2-(4-(trifluoromethoxy)benzyl)propane-1,3-diol

To a mixture of diethyl (4-(trifluoromethoxy)benzyl)malonate (5.3 g) and tetrahydrofuran (100 mL) was added lithium aluminium hydride (2.41 g) at 0° C. The reaction mixture was stirred at 0° C. for 30 min, 1 M hydrochloric acid was added thereto, and the mixture was extracted with ethyl acetate. The extract was washed with saturated brine, and dried over anhydrous magnesium sulfate, and the solvent was evaporated under reduced pressure to give a residue (4.32 g). The same reaction was repeated. The obtained residue (total 5.3 g) was purified by silica gel column chromatography (hexane/ethyl acetate) to give the title compound (2.9 g).

$^1$H NMR (300 MHz, CDCl$_3$) δ 1.89-2.12 (1H, m), 2.34 (2H, brs), 2.65 (2H, d, J=7.5 Hz), 3.60-3.72 (2H, m), 3.75-3.87 (2H, m), 7.08-7.17 (2H, m), 7.17-7.24 (2H, m).

C) 3-(4-(trifluoromethoxy)benzyl)oxetane

To a mixture of 2-(4-(trifluoromethoxy)benzyl)propane-1,3-diol (2.37 g) and tetrahydrofuran (100 mL) was added 1.6 M n-butyllithium/hexane solution (6.51 mL) at 0° C. The reaction mixture was stirred at 0° C. for 30 min under nitrogen atmosphere, p-toluenesulfonyl chloride (1.99 g) was added thereto at room temperature, and the mixture was stirred at room temperature for 1 hr under nitrogen atmosphere. To the reaction mixture was added 1.6 M n-butyllithium/hexane solution (7.10 mL) at room temperature, and the mixture was stirred at 80° C. for 4 hr under nitrogen atmosphere. To the reaction mixture was added saturated aqueous ammonium chloride solution, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (0.950 g).

$^1$H NMR (300 MHz, CDCl$_3$) δ 3.03 (2H, d, J=7.9 Hz), 3.15-3.43 (1H, m), 4.46 (2H, t, J=6.0 Hz), 4.80 (2H, dd, J=7.5, 6.0 Hz), 7.13 (4H, s).

D) 3-(bromo(4-(trifluoromethoxy)phenyl)methyl)oxetane

A mixture of 3-(4-(trifluoromethoxy)benzyl)oxetane (950 mg), N-bromosuccinimide (947 mg), 2,2'-azobis(2-methylpropionitrile) (67.2 mg) and benzotrifluoride (20 mL) was stirred overnight at 80° C. To the reaction mixture was added hexane, the insoluble substance was filtered off, and the filtrate was concentrated under reduced pressure. The residue was purified by silica gel column chromatography (hexane/ethyl acetate) to give the title compound (406 mg).

$^1$H NMR (300 MHz, CDCl$_3$) δ 3.68-3.87 (1H, m), 4.17 (1H, t, J=6.4 Hz), 4.54-4.66 (2H, m), 4.92 (1H, dd, J=7.4, 6.6 Hz), 5.32 (1H, d, J=11.1 Hz), 7.14-7.24 (2H, m), 7.35-7.43 (2H, m).

E) 3-(azido(4-(trifluoromethoxy)phenyl)methyl)oxetane

A mixture of 3-(bromo(4-(trifluoromethoxy)phenyl)methyl)oxetane (230 mg), sodium azide (80 mg), water (3 mL) and acetone (12 mL) was stirred overnight at room temperature, saturated aqueous sodium hydrogen carbonate solution was added thereto, and the mixture was extracted with ethyl acetate. The extract was washed with saturated brine, and dried over anhydrous magnesium sulfate, and the solvent was evaporated under reduced pressure to give the title compound (260 mg).

$^1$H NMR (300 MHz, CDCl$_3$) δ 3.18-3.41 (1H, m), 4.33 (1H, t, J=6.2 Hz), 4.54-4.71 (2H, m), 4.80-4.89 (2H, m), 7.21-7.27 (2H, 25 m), 7.29-7.36 (2H, m).

F) 7-methyl-N-(oxetan-3-yl(4-(trifluoromethoxy)phenyl)methyl)-2-oxo-2,3-dihydropyrido[2,3-b]pyrazine-4(1H)-carboxamide A mixture of 3-(azido(4-(trifluoromethoxy)phenyl)methyl)oxetane (260 mg), 5% palladium-carbon (containing 50% water, 30 mg) and tetrahydrofuran (5 mL) was stirred at room temperature for 1 hr under hydrogen atmosphere. Then, to the reaction mixture was added methanol (5 mL), the reaction mixture was stirred overnight at room temperature under hydrogen atmosphere. The insoluble substance was filtered off through Celite, and the filtrate was concentrated under reduced pressure to give oxetan-3-yl(4-(trifluoromethoxy)phenyl)methanamine (209 mg). The title compound was obtained from the obtained oxetan-3-yl(4-(trifluoromethoxy)phenyl)methanamine in the same manner as in Step G of Example 7.

MS (API+): [M+H]⁺437.1.

Example 143

N-(1-(3-fluoro-4-(1H-pyrazol-1-yl)phenyl)-2-methoxyethyl)-7-methyl-2-oxo-2,3-dihydropyrido[2,3-b]pyrazine-4(1H)-carboxamide A) 2-bromo-1-(4-bromo-3-fluorophenyl)ethanone To a solution of 1-(4-bromo-3-fluorophenyl)ethanone (2.8 g) (obtained from 4-bromo-3-fluorobenzonitrile in the same manner as in Step B of Example 30) in tetrahydrofuran (150 mL) was added phenyltrimethylammonium tribromide (4.35 g) at 0° C. The reaction mixture was stirred at room temperature for 2 days, and the solvent was evaporated under reduced pressure. The residue was purified by silica gel column chromatography (hexane/ethyl acetate) to give the title compound (3.58 g).

$^1$H NMR (300 MHz, CDCl$_3$) δ 4.33-4.42 (2H, m), 7.59-7.77 (3H, m).

B) N-(1-(3-fluoro-4-(1H-pyrazol-1-yl)phenyl)-2-methoxyethyl)-7-methyl-2-oxo-2,3-dihydropyrido[2,3-b]pyrazine-4(1H)-carboxamide The title compound was obtained from 2-bromo-1-(4-bromo-3-fluorophenyl)ethanone in the same manner as in Steps A-D of Example 134, Step D of Example 2, Step B of Example 15 and Step G of Example 7.
MS (API+): [M+H]$^+$425.2.

Example 144

N-(2-methoxy-1-(5-(1H-pyrazol-1-yl)pyridin-2-yl)ethyl)-7-methyl-2-oxo-2,3-dihydropyrido[2,3-b]pyrazine-4(1H)-carboxamide The title compound was obtained from 5-bromopicoline acid in the same manner as in Step A of Example 31, Steps D-F of Example 66, Steps A-D of Example 134, Step D of Example 2, Step B of Example 15 and Step G of Example 7.
MS (API+): [M+H]$^+$408.2.

Example 145

N-((1R)-2-hydroxy-2-methyl-1-(4-(trifluoromethoxy)phenyl)propyl)-2-oxo-2,3-dihydropyrido[2,3-b]pyrazine-4(1H)-carboxamide Racemic N-(2-hydroxy-2-methyl-1-(4-(trifluoromethoxy)phenyl)propyl)-2-oxo-2,3-dihydropyrido[2,3-b]pyrazine-4(1H)-carboxamide (30.1 mg) was resolved by HPLC (column: CHIRALPAK IC, 50 mmID×500 mmL, manufactured by Daicel Chemical Industries, Ltd., mobile phase: hexane/ethanol=800/200) to give the title compound having a shorter retention time (10.0 mg).
MS (API+): [M+H]$^+$425.2.

Example 146

N-((1S)-2-hydroxy-2-methyl-1-(4-(trifluoromethoxy)phenyl)propyl)-2-oxo-2,3-dihydropyrido[2,3-b]pyrazine-4(1H)-carboxamide
Racemic N-(2-hydroxy-2-methyl-1-(4-(trifluoromethoxy)phenyl)propyl)-2-oxo-2,3-dihydropyrido[2,3-b]pyrazine-4(1H)-carboxamide (30.1 mg) was resolved by HPLC (column: CHIRALPAK IC, 50 mmID×500 mmL, manufactured by Daicel Chemical Industries, Ltd., mobile phase: hexane/ethanol=800/200) to give the title compound having a longer retention time (9.4 mg).
MS (API+): [M+H]$^+$425.2.

Example 147

7-methyl-2-oxo-N-(1-(4-(1H-pyrrol-1-yl)phenyl)propyl)-2,3-dihydropyrido[2,3-b]pyrazine-4(1H)-carboxamide A) 1-(4-(1H-pyrrol-1-yl)phenyl)propan-1-one To a mixture of 1H-pyrrole (1.38 g), 1-(4-bromophenyl)propan-1-one (3.66 g), trans-N,N'-bismethyl-1,2-cyclohexane (489 mg) and tripotassium phosphate (7.66 g) in toluene (20 mL) was added copper(I) iodide (164 mg). The reaction mixture was heated at reflux for 16 hr under argon atmosphere, ethyl acetate and water were added thereto. The insoluble substance was filtered off, and the organic layer and aqueous layer of the filtrate were separated, and the aqueous layer was extracted with ethyl acetate. The extract was dried over anhydrous sodium sulfate, and the solvent was evaporated under reduced pressure. The residue was purified by silica gel column chromatography (hexane/ethyl acetate) to give the title compound (2.32 g).
$^1$H NMR (300 MHz, DMSO-d$_6$) δ 1.10 (3H, t, J=7.3 Hz), 3.06 (2H, q, J=7.2 Hz), 6.28-6.37 (2H, m), 7.46-7.57 (2H, m), 7.68-7.80 (2H, m), 7.96-8.10 (2H, m).

B) 7-methyl-2-oxo-N-(1-(4-(1H-pyrrol-1-yl)phenyl)propyl)-2,3-dihydropyrido[2,3-b]pyrazine-4(1H)-carboxamide The title compound was obtained from 1-(4-(1H-pyrrol-1-yl)phenyl)propan-1-one in the same manner as in Step C of Example 1, Step B of Example 54 and Step G of Example 7.
MS (API+): [M+H]$^+$390.2.

Example 148

7-methyl-2-oxo-N-(1-(4-(pyrrolidin-1-yl)phenyl)propyl)-2,3-dihydropyrido[2,3-b]pyrazine-4(1H)-carboxamide The title compound was obtained from 1-(4-(1H-pyrrol-1-yl)phenyl)propan-1-one in the same manner as in Step C of Example 1, Step B of Example 54 and Step G of Example 7.
MS (API+): [M+H]$^+$394.3.

Example 149

7-(2-hydroxypropan-2-yl)-N-(2-methoxy-1-(4-(trifluoromethoxy)phenyl)ethyl)-2-oxo-2,3-dihydropyrido[2,3-b]pyrazine-4(1H)-carboxamide A) methyl 4-((2-methoxy-1-(4-trifluoromethoxy)phenyl)ethyl) carbamoyl)-2-oxo-1-((2-(trimethylsilyl)ethoxy)methyl)-1,2,3,4-tetrahydropyrido[2,3-b]pyrazine-7-carboxylate A mixture of 7-bromo-N-(2-methoxy-1-(4-(trifluoromethoxy)phenyl)ethyl)-2-oxo-1-((2-(trimethylsilyl)ethoxy)methyl)-2,3-dihydropyrido[2,3-b]pyrazine-4(1H)-carboxamide (537 mg) and 1,1'-bis(diphenylphosphino)ferrocene dichloropalladium(II) dichloromethanecomplex (70.8 mg), triethylamine (0.242 mL) and methanol (1.5 mL) in N,N-dimethylformamide (15 mL) was stirred at 80° C. for 3 hr under carbon monoxide atmosphere (5 atm). The reaction mixture was cooled, and the solvent was evaporated under reduced pressure. The residue was purified by silica gel column chromatography (hexane/ethyl acetate) to give the title compound (403 mg).
MS (API+): [M+H]$^+$599.3.

C) methyl 4-((2-methoxy-1-(4-trifluoromethoxy)phenyl)ethyl) carbamoyl)-2-oxo-1,2,3,4-tetrahydropyrido[2,3-b]pyrazine-7-carboxylate The title compound was obtained from methyl 4-((2-methoxy-1-(4-trifluoromethoxy)phenyl)ethyl) carbamoyl)-2-oxo-1-((2-(trimethylsilyl)ethoxy)methyl)-1,2,3,4-tetrahydropyrido[2,3-b]pyrazine-7-carboxylate in the same manner as in Step I of Example 63.
MS (API+): [M+H]$^+$469.1.

D) 7-(2-hydroxypropan-2-yl)-N-(2-methoxy-1-(4-(trifluoromethoxy)phenyl)ethyl)-2-oxo-2,3-dihydropyrido[2,3-b]pyrazine-4(1H)-carboxamide To a solution of methyl 4-((2-methoxy-1-(4-trifluoromethoxy)phenyl)ethyl) carbamoyl)-2-oxo-1,2,3,4-tetrahydropyrido[2,3-b]pyrazine-7-carboxylate (40 mg) in tetrahydrofuran (0.85 mL) was added 1 M methylmagnesium bromide/tetrahydrofuran solution (0.43 mL) at 0° C. The reaction mixture was stirred at 0° C. for 2 hr under argon atmosphere, 1 M methylmagnesium bromide/tetrahydrofuran solution (0.85 mL) was added thereto. The reaction mixture was stirred at 0° C. for 30 min, saturated aqueous ammonium chloride solution was added thereto at 0° C., and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (27 mg).
MS (API+): [M+H]$^+$469.2.

Example 150

7-(azetidin-1-yl)-N-(2-methoxy-1-(4-(trifluoromethoxy)phenyl)ethyl)-2-oxo-2,3-dihydropyrido[2,3-b]pyrazine-4(1H)-carboxamide A) 7-(azetidin-1-yl)-N-(2-methoxy-1-(4-(trifluoromethoxy)phenyl)ethyl)-2-oxo-1-((2-(trimethylsilyl)ethoxy)methyl)-2,3-dihydropyrido[2,3-b]pyrazine-4(1H)-carboxamide To a mixture of 7-bromo-N-(2-methoxy-1-(4-(trifluoromethoxy)phenyl)ethyl)-2-oxo-1-((2-(trimethylsilyl)ethoxy)methyl)-2,3-dihydropyrido[2,3-b]pyrazine-4(1H)-carboxamide (300 mg), azetidine (32.6 μL), and cesium carbonate (249 mg) in toluene (4.84 mL) were added (9,9-dimethyl-9H-xanthene-4,5-diyl)bis(diphenylphosphine) (28.0 mg) and tris(dibenzylideneacetone)dipalladium(0) (29.6 mg), the reaction mixture was stirred overnight at 110° C. under nitrogen atmosphere. The reaction mixture was diluted with ethyl acetate, and the mixture was washed with saturated brine. The organic layer was dried over anhydrous sodium sulfate, and the solvent was evaporated under reduced pressure. The residue was purified by silica gel column chromatography (hexane/ethyl acetate) to give the title compound (19.3 mg).
MS (API+): [M+H]$^+$596.3.

B) 7-(azetidin-1-yl)-N-(2-methoxy-1-(4-(trifluoromethoxy)phenyl)ethyl)-2-oxo-2,3-dihydropyrido[2,3-b]pyrazine-4(1H)-carboxamide The title compound was obtained from 7-(azetidin-1-yl)-N-(2-methoxy-1-(4-(trifluoromethoxy)phenyl)ethyl)-2-oxo-1-((2-(trimethylsilyl)ethoxy)methyl)-2,3-dihydropyrido[2,3-b]pyrazine-4(1H)-carboxamide in the same manner as in Step I of Example 63.
MS (API+): [M+H]$^+$466.2.

Example 151

N-(1-(imidazo[1,2-a]pyridin-7-yl)propyl)-7-methyl-2-oxo-2,3-dihydropyrido[2,3-b]pyrazine-4(1H)-carboxamide The title compound was obtained from imidazo[1,2-a]pyridine-7-carboxylic acid in the same manner as in Step A of Example 31, Step B of Example 30, Step D of Example 2, Step B of Example 132 and Step G of Example 7.
MS (API+): [M+H]$^+$365.2.

Example 152

7-methyl-2-oxo-N-(1-(4-(trifluoromethoxy)phenyl)cyclopropyl)-2,3-dihydropyrido[2,3-b]pyrazine-4(1H)-carboxamide A)
1-(4-(trifluoromethoxy)phenyl)cyclopropaneamine To a mixture of 4-(trifluoromethoxy)benzonitrile (2.02 g) and titanium(IV) tetraisopropoxide (3.48 mL) in diethyl ether (50 mL) was slowly added 3 M ethylmagnesium bromide/tetrahydrofuran solution (7.91 mL) over 50 min at −78° C. The reaction mixture was stirred at room temperature for 1 hr, boron trifluoride diethyl ether complex (3.01 mL) was added thereto. The reaction mixture was stirred at room temperature for 16 hr, 1 M hydrochloric acid and diethyl ether were added thereto. Then, 2 M aqueous sodium hydroxide solution was added thereto, and the mixture was extracted with diethyl ether. The extract was dried over anhydrous sodium sulfate, and the solvent was evaporated under reduced pressure to give the to title compound (1.51 g).
MS (API+): [M+H]$^+$218.1.

B) 7-methyl-2-oxo-N-(1-(4-(trifluoromethoxy)phenyl)cyclopropyl)-2,3-dihydropyrido[2,3-b]pyrazine-4(1H)-carboxamide The title compound was obtained from 1-(4-(trifluoromethoxy)phenyl)cyclopropaneamine in the same manner as in Step G of Example 7.
MS (API+): [M+H]$^+$407.1.

Example 153

7-fluoro-N-(2-methoxy-1-(4-(trifluoromethoxy)phenyl)ethyl)-2-oxo-2,3-dihydropyrido[2,3-b]pyrazine-4(1H)-carboxamide A) methyl N-(5-fluoro-3-nitropyridin-2-yl)glycinate To a solution of methyl glycinate hydrochloride (1.39 g) and 2-chloro-5-fluoro-3-nitropyridine (2.00 g) in ethanol (35.9 mL) was added triethylamine (3.79 mL). The reaction mixture was stirred overnight at 80° C., and the solvent was evaporated under reduced pressure. The residue was diluted with ethyl acetate, and the mixture was washed successively with water and saturated brine, and dried over anhydrous sodium sulfate, and the solvent was evaporated under reduced pressure. The residue was purified by silica gel column chromatography (hexane/ethyl acetate) to give the title compound (93.0 mg).
MS (API+): [M+H]$^+$230.1.

B) 7-fluoro-3,4-dihydropyrido[2,3-b]pyrazin-2(1H)-one

To a solution of methyl N-(5-fluoro-3-nitropyridin-2-yl)glycinate (90.0 mg) in tetrahydrofuran (6.66 mL) was added 5% platinum-carbon (10.0 mg). The reaction mixture was stirred at room temperature for 2 hr under hydrogen atmosphere, the catalyst was filtered off, and the filtrate was concentrated under reduced pressure. The residue was dissolved in ethanol (5.00 mL), and the mixture was stirred at 87° C. for 1 hr. To the reaction mixture was added 2 M hydrogen chloride/methanol solution (1.00 mL), the mixture was stirred overnight at 87° C., and the solvent was evaporated under reduced pressure. The residue was diluted with ethyl acetate, and the mixture was neutralized with saturated aqueous sodium hydrogen carbonate solution, and extracted with ethyl acetate. The extract was washed with saturated brine, and the solvent was evaporated under reduced pressure to give the title compound (39.1 mg).
MS (API+): [M+H]$^+$168.1.

C) 7-fluoro-N-(2-methoxy-1-(4-(trifluoromethoxy)phenyl)ethyl)-2-oxo-2,3-dihydropyrido[2,3-b]pyrazine-4(1H)-carboxamide To a mixture of 7-fluoro-3,4-dihydropyrido[2,3-b]pyrazin-2(1H)-one (39.1 mg) and triethylamine (99.0 μL) in a mixed solvent of tetrahydrofuran (2.00 mL) and N,N-dimethylacetamide (2.00 mL) was added a solution of bis(trichloromethyl)carbonate (69.4 mg) in tetrahydrofuran (1.00 mL) at 0° C. The reaction mixture was stirred at 0° C. for 2 hr, a mixture of triethylamine (165 μL) and 2-methoxy-1-(4-(trifluoromethoxy)phenyl)ethanamine hydrochloride (318 mg) in a mixed solvent of tetrahydrofuran (1.00 mL) and N,N-dimethylacetamide (2.00 mL) was added thereto at 0° C. The reaction mixture was stirred overnight at room temperature, water was added thereto, and the mixture was extracted with ethyl acetate. The extract was washed successively with water and saturated brine, and dried over anhydrous sodium sulfate, and the solvent was evaporated under reduced pressure. The residue was purified by silica gel column chromatography (hexane/ethyl acetate), and crystallized from hexane/ethyl acetate to give the title compound (10.1 mg).
MS (API+): [M+H]$^+$429.1.

Example 154

N-(2-methoxy-1-(4-(1H-pyrrol-1-yl)phenyl)ethyl)-7-methyl-2-oxo-2,3-dihydropyrido[2,3-b]pyrazine-4(1H)-carboxamide A) 2-bromo-1-(4-iodophenyl)ethanone The title compound was obtained from 1-(4-iodophenyl)ethanone in the same manner as in Step F of Example 66.
$^1$H NMR (300 MHz, DMSO-d$_6$) δ 4.91 (2H, s), 7.72-7.80 (2H, m), 7.91-8.00 (2H, m).

B) 1-(4-iodophenyl)-2-methoxyethanone

The title compound was obtained from 2-bromo-1-(4-iodophenyl)ethanone in the same manner as in Step D of Example 63.
$^1$H NMR (300 MHz, DMSO-d$_6$) δ 3.35 (3H, s), 4.75 (2H, s), 7.63-7.73 (2H, m), 7.88-8.00 (2H, m).

C) 1-(4-(1H-pyrrol-1-yl)phenyl)-2-methoxyethanone

The title compound was obtained from 1H-pyrrole and 1-(4-iodophenyl)-2-methoxyethanone in the same manner as in Step A of Example 147.
$^1$H NMR (300 MHz, DMSO-d$_6$) δ 3.37 (3H, s), 4.79 (2H, s), 6.29-6.41 (2H, m), 7.50-7.58 (2H, m), 7.71-7.82 (2H, m), 7.95-8.05 (2H, m).

D) N-(2-methoxy-1-(4-(1H-pyrrol-1-yl)phenyl)ethyl)-7-methyl-2-oxo-2,3-dihydropyrido[2,3-b]pyrazine-4(1H)-carboxamide The title compound was obtained from 1-(4-(1H-pyrrol-1-yl)phenyl)-2-methoxyethanone in the same manner as in Step C of Example 1, Step B of Example 54 and Step G of Example 7.
MS (API+): [M+H]$^+$406.2.

Example 155

7-chloro-N-(2-methoxy-1-(4-(trifluoromethoxy)phenyl)ethyl)-2-oxo-2,3-dihydropyrido[2,3-b]pyrazine-4(1H)-carboxamide A) methyl N-(5-chloro-3-nitropyridin-2-yl)glycinate To a solution of methyl N-(5-bromo-3-nitropyridin-2-yl)glycinate (400 mg) in 1-methylpyrrolidin-2-one (13.8 mL) was added copper(I) chloride (410 mg). The reaction mixture was stirred at 150° C. for 2.5 hr under microwave irradiation, and water was added thereto. The insoluble substance was filtered off, and the filtrate was extracted with ethyl acetate. The extract was washed successively with water and saturated brine, and dried over anhydrous sodium sulfate, and the solvent was evaporated under reduced pressure. The residue was purified by silica gel column chromatography (hexane/ethyl acetate), and crystallized from diisopropyl ether to give the title compound (181 mg).
MS (API+): [M+H]$^+$246.0.

B) 7-chloro-3,4-dihydropyrido[2,3-b]pyrazin-2(1H)-one

To a solution of methyl N-(5-chloro-3-nitropyridin-2-yl)glycinate (181 mg) in tetrahydrofuran (12.5 mL) was added 5% platinum-carbon (20.0 mg). The reaction mixture was stirred at room temperature for 2 hr under hydrogen atmosphere, the catalyst was filtered off, and the filtrate was concentrated under reduced pressure. The residue was dissolved in ethanol (10.0 mL), and the solution was stirred overnight at 87° C. To the reaction mixture was added 2 M hydrogen chloride/methanol solution (1.00 mL), and the mixture was stirred at 87° C. for 10 min, and the solvent was evaporated under reduced pressure. The residue was diluted with ethyl acetate, and the mixture was neutralized with saturated aqueous sodium hydrogen carbonate solution, and extracted with ethyl acetate. The extract was washed with saturated brine, and dried over anhydrous sodium sulfate, and the solvent was evaporated under reduced pressure to give the title compound (132 mg).
MS (API+): [M+H]$^+$184.0.

C) 7-chloro-N-(2-methoxy-1-(4-(trifluoromethoxy)phenyl)ethyl)-2-oxo-2,3-dihydropyrido[2,3-b]pyrazine-4(1H)-carboxamide The title compound was obtained from 7-chloro-3,4-dihydropyrido[2,3-b]pyrazin-2(1H)-one in the same manner as in Step C of Example 153.
MS (API+): [M+H]$^+$445.1.

Example 156

N-(2-methoxy-1-(4-(pyrrolidin-1-yl)phenyl)ethyl)-7-methyl-2-oxo-2,3-dihydropyrido[2,3-b]pyrazine-4(1H)-carboxamide The title compound was obtained from 1-(4-(1H-pyrrol-1-yl)phenyl)-2-methoxyethanone in the same manner as in Step C of Example 1, Step E of Example 2 and Step G of Example 7.
MS (API+): [M+H]$^+$410.3.

Example 157

N-(2-methoxy-1-(4-(1H-pyrrol-1-yl)phenyl)ethyl)-2-oxo-2,3-dihydropyrido[2,3-b]pyrazine-4(1H)-carboxamide The title compound was obtained from 1-(4-(1H-pyrrol-1-yl)phenyl)-2-methoxyethanone in the same manner as in Step C of Example 1, Step E of Example 2 and Step G of Example 7.
MS (API+): [M+H]$^+$392.2.

Example 158

N-(2-methoxy-1-(4-(pyrrolidin-1-yl)phenyl)ethyl)-2-oxo-2,3-dihydropyrido[2,3-b]pyrazine-4(1H)-carboxamide The title compound was obtained from 1-(4-(1H-pyrrol-1-yl)phenyl)-2-methoxyethanone in the same manner as in Step C of Example 1, Step B of Example 54 and Step G of Example 7.
MS (API+): [M+H]$^+$396.2.

Example 159

N-(1-(2,2-difluoro-1,3-benzodioxol-5-yl)propyl)-2-oxo-2,3-dihydropyrido[2,3-b]pyrazine-4(1H)-carboxamide A) 1-(2,2-difluorobenzo[d][1,3]dioxol-5-yl)propan-1-ol To a solution of 2,2-difluorobenzo[d][1,3]dioxol-5-carbaldehyde (2.35 g) in tetrahydrofuran (50 mL) was slowly added 3 M ethylmagnesium bromide/tetrahydrofuran solution (6.30 mL) at 0° C. The reaction mixture was stirred at room temperature for 16 hr, saturated ammonium chloride solution was added thereto, and the mixture was extracted with ethyl acetate. The extract was dried over anhydrous sodium sulfate, and the solvent was evaporated under reduced pressure. The residue was purified by silica gel chromatography (hexane/ethyl acetate) to give the title compound (2.36 g).
$^1$H NMR (300 MHz, DMSO-d$_6$) δ 0.81 (3H, t, J=7.3 Hz), 1.51-1.67 (2H, m), 4.42-4.53 (1H, m), 5.27 (1H, d, J=4.5 Hz), 7.10-7.18 (1H, m), 7.27-7.36 (2H, m).

B) 1-(2,2-difluorobenzo[d][1,3]dioxol-5-yl)propan-1-one

To a solution of 1-(2,2-difluorobenzo[d][1,3]dioxol-5-yl)propan-1-ol (2.36 g) in toluene (50 mL) was added manganese dioxide (2.36 g). The reaction mixture was stirred at room temperature for 3 days, the insoluble substance was filtered off, and the filtrate was concentrated under reduced pressure. The residue was purified by silica gel chromatography (hexane/ethyl acetate) to give the title compound (0.492 g).
$^1$H NMR (300 MHz, DMSO-d$_6$) δ 1.08 (3H, t, J=7.2 Hz), 3.05 (2H, q, J=7.1 Hz), 7.55 (1H, d, J=8.3 Hz), 7.91 (1H, dd, J=8.5, 1.7 Hz), 7.96 (1H, d, J=1.7 Hz).

C) N-(1-(2,2-difluoro-1,3-benzodioxol-5-yl)propyl)-2-oxo-2,3-dihydropyrido[2,3-b]pyrazine-4(1H)-carboxamide The title compound was obtained from 1-(2,2-difluorobenzo[d][1,3]dioxol-5-yl)propan-1-one in the same manner as in Step C of Example 1, Step E of Example 2 and Step G of Example 7.
MS (API+): [M+H]$^+$391.1.

Example 160

7-methyl-2-oxo-N-(2-(1H-pyrazol-1-yl)-1-(4-(trifluoromethoxy)phenyl)ethyl)-2,3-dihydropyrido[2,3-b]pyrazine-4(1H)-carboxamide A) 2-(1H-pyrazol-1-yl)-1-(4-(trifluoromethoxy)phenyl)ethanone A mixture of 1H-pyrazole (0.722 g), 60% sodium hydride (459 mg) and N,N-dimethylformamide (50 mL) was stirred at 0° C. for 10 min, 2-bromo-1-(4-(trifluoromethoxy)phenyl)ethanone (2.5 g) was added thereto, and the mixture was stirred at 0° C. for 20 min under nitrogen atmosphere. To the reaction mixture was added saturated aqueous ammonium chloride solution, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (598 mg).
MS (API+): [M+H]$^+$271.1.

B) 7-methyl-2-oxo-N-(2-(1H-pyrazol-1-yl)-1-(4-(trifluoromethoxy)phenyl)ethyl)-2,3-dihydropyrido[2,3-b]pyrazine-4(1H)-carboxamide The title compound was obtained from 2-(1H-pyrazol-1-yl)-1-(4-(trifluoromethoxy)phenyl)ethanone in the same manner as in Step D of Example 2, Step B of Example 15 and Step G of Example 7.
MS (API+): [M+H]$^+$461.2.

Example 161

Optically Active 7-methyl-2-oxo-N-(1-(4-(1H-pyrrol-1-yl)phenyl)propyl)-2,3-dihydropyrido[2,3-b]pyrazine-4(1H)-carboxamide Racemic 7-methyl-2-oxo-N-(1-(4-(1H-pyrrol-1-yl)phenyl)propyl)-2,3-dihydropyrido[2,3-b]pyrazine-4(1H)-carboxamide (244 mg) was resolved by HPLC (column: CHIRALPAK IC, 4.6 mmID×250 mmL, manufactured by Daicel Chemical Industries, Ltd., mobile phase: ethanol) to give the title compound having a shorter retention time (93.7 mg).
MS (API+): [M+H]$^+$390.2.

Example 162

7-methyl-2-oxo-N-(1-(5-(1H-pyrazol-1-yl)-2-thienyl)propyl)-2,3-dihydropyrido[2,3-b]pyrazine-4(1H)-carboxamide The title compound was obtained from 5-bromothiophene-2-carboxylic acid in the same manner as in Step A of Example 31, Step C of Example 134, Step B of Example 30, Step D of Example 2, Step B of Example 15 and Step G of Example 7.
MS (API+): [M+H]$^+$397.0.

Example 163

Optically Active 7-methyl-2-oxo-N-(1-(4-(1H-pyrrol-1-yl)phenyl)propyl)-2,3-dihydropyrido[2,3-b]pyrazine-4(1H)-carboxamide Racemic 7-methyl-2-oxo-N-(1-(4-(1H-pyrrol-1-yl)phenyl)propyl)-2,3-dihydropyrido[2,3-b]pyrazine-4(1H)-carboxamide (244 mg) was resolved by HPLC (column: CHIRALPAK IC, 4.6 mmID×250 mmL, manufactured by Daicel Chemical Industries, Ltd., mobile phase: ethanol) to give the title compound having a longer retention time (93.0 mg).
MS (API+): [M+H]$^+$390.2.

Example 164

7-methyl-2-oxo-N-(2-(1H-1,2,4-triazol-1-yl)-1-(4-(trifluoromethoxy)phenyl)ethyl)-2,3-dihydropyrido[2,3-b]pyrazine-4(1H)-carboxamide The title compound was obtained from 2-bromo-1-(4-(trifluoromethoxy)phenyl)ethanone in the same manner as in Step A of Example 160, Step D of Example 2, Step B of Example 132 and Step G of Example 7.
MS (API+): [M+H]$^+$462.2.

Example 165

7-methyl-2-oxo-N-(1-(pyrazolo[1,5-a]pyridin-5-yl)propyl)-2,3-dihydropyrido[2,3-b]pyrazine-4(1H)-carboxamide A) diethyl pyrazolo[1,5-a]pyridine-3,5-dicarboxylate To a mixture of (aminooxy)(hydroxy)sulfane dioxide (15.0 g) and water (60 mL) was added saturated aqueous sodium hydrogen carbonate solution at 0° C. to adjust the pH of the mixture to 9-10, and a mixture of ethyl isonicotinate (10.0 g) and methanol (250 mL) was added thereto at 0° C. The reaction mixture was stirred overnight at 70° C., N,N-dimethylformamide was added thereto, and the solvent was evaporated under reduced pressure. To the residue were added potassium carbonate (27.4 g), N,N-dimethylformamide (250 mL) and ethyl propynoate (7.14 g) at 0° C., and the reaction mixture was stirred at room temperature for 3 hr. To the reaction mixture was added saturated brine, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (8.01 g).
MS (API+): [M+H]$^+$263.1.

B) pyrazolo[1,5-a]pyridine-5-carboxylic acid

A mixture of diethyl pyrazolo[1,5-a]pyridine-3,5-dicarboxylate (6.7 g), conc. sulfuric acid (50 mL) and water (50 mL) was stirred overnight at 100° C. The reaction mixture was cooled to room temperature, and the pH of the mixture was adjusted to about 3 with 8 M aqueous sodium hydroxide solution. The obtained solid was collected by filtration, and washed with water to give the title compound (3.15 g).
MS (API−) [M−H]$^−$161.1.

C) 7-methyl-2-oxo-N-(1-(pyrazolo[1,5-a]pyridin-5-yl)propyl)-2,3-dihydropyrido[2,3-b]pyrazine-4(1H)-carboxamide The title compound was obtained from pyrazolo[1,5-a]pyridine-5-carboxylic acid in the same manner as in Step A of Example 31, Step B of Example 30, Step D of Example 2, Step B of Example 132 and Step G of Example 7.
MS (API+): [M+H]$^+$365.2.

Example 166

7-methyl-N-(2-(oxetan-3-yl)-1-(4-(trifluoromethoxy)phenyl)ethyl)-2-oxo-2,3-dihydropyrido[2,3-b]pyrazine-4(1H)-carboxamide A) (2-oxo-2-(4-(trifluoromethoxy)phenyl)ethyl)triphenylphosphonium bromide To a solution of triphenylphosphine (6.29 g) in diethyl ether (20 mL) was slowly added a solution of 2-bromo-1-(4-(trifluoromethoxy)phenyl)ethanone (6.68 g) in diethyl ether (10 mL) at room temperature. The reaction mixture was stirred at room temperature for 1 hr, and the resulting solid was collected by filtration, washed with diethyl ether to give the title compound (9.47 g).
MS (API+), found: 465.3.

B) 2-(oxetan-3-ylidene)-1-(4-(trifluoromethoxy)phenyl)ethanone

A mixture of (2-oxo-2-(4-(trifluoromethoxy)phenyl)ethyl)triphenylphosphonium bromide (6.54 g) and potassium tert-butoxide (1.35 g) in tetrahydrofuran (50 mL) was stirred at 0° C. for 15 min. The reaction mixture was stirred at room temperature for 30 min, oxetan-3-one (721 mg) was added thereto, and the mixture was stirred overnight at 70° C. under argon atmosphere. The reaction mixture was cooled, and the solvent was evaporated under reduced pressure. The residue was purified by silica gel column chromatography (hexane/ethyl acetate) to give the title compound (2.18 g).
$^1$H NMR (300 MHz, CDCl$_3$) δ 5.39-5.48 (2H, m), 5.64-5.72 (2H, m), 6.77-6.85 (1H, m), 7.28-7.36 (2H, m), 7.93-8.02 (2H, m).

C) 2-(oxetan-3-yl)-1-(4-(trifluoromethoxy)phenyl)ethanone

To a solution of 2-(oxetan-3-ylidene)-1-(4-(trifluoromethoxy)phenyl)ethanone (1.03 g) in ethanol (35 mL) was added 10% palladium-carbon (containing 50% water, 200 mg). The reaction mixture was stirred at room temperature for 1 hr under hydrogen atmosphere, the insoluble substance was filtered off, and the solvent was evaporated under reduced pressure. To a solution of the residue (1.07 g) in acetonitrile (20.4 mL) was added Dess-Martin periodinane (1.90 g) at room temperature. The reaction mixture was stirred at oom temperature for 1 hr, and the solvent was evaporated under reduced pressure. The residue was purified by silica gel column chromatography (NH, hexane/ethyl acetate) to give the title compound (900 mg).
MS (API+): [M+H]$^+$261.1.

D) N-hydroxy-2-(oxetan-3-yl)-1-(4-(trifluoromethoxy)phenyl)ethanimine

The title compound was obtained from 2-(oxetan-3-yl)-1-(4-(trifluoromethoxy)phenyl)ethanone in the same manner as in Step C of Example 1.
MS (API+): [M+H]$^+$276.1.

E) 7-methyl-N-(2-(oxetan-3-yl)-1-(4-(trifluoromethoxy)phenyl)ethyl)-2-oxo-2,3-dihydropyrido[2,3-b]pyrazine-4(1H)-carboxamide To a solution of N-hydroxy-2-(oxetan-3-yl)-1-(4-(trifluoromethoxy)phenyl)ethanimine (275 mg) in ethanol (5 mL) was added 5% palladium-carbon (containing 50% water, 120 mg) at room temperature. The reaction mixture was stirred at room temperature for 5 hr under hydrogen atmosphere, and 20% palladium hydroxide-carbon (30 mg) was added thereto. The reaction mixture was stirred overnight at room temperature under hydrogen atmosphere, the catalyst was filtered off, and the solvent was evaporated under reduced pressure to give 2-(oxetan-3-yl)-1-(4-(trifluoromethoxy)phenyl)ethanamine (260 mg). To a solution of the obtained 2-(oxetan-3-yl)-1-(4-(trifluoromethoxy)phenyl)ethanamine in N,N-dimethylformamide (5.06 mL) were added 4-nitrophenyl 7-methyl-2-oxo-2,3-dihydropyrido[2,3-b]pyrazine-4-carboxylate (166 mg) and triethylamine (141 μL) at room temperature. The reaction mixture was stirred at room temperature for 2 hr, water was added thereto, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) and then silica gel column chromatography (NH, hexane/ethyl acetate) to give the title compound (92 mg).
MS (API+): [M+H]$^+$451.2.

Example 167

7-(difluoromethyl)-N-(2-methoxy-1-(4-(trifluoromethoxy)phenyl)ethyl)-2-oxo-2,3-dihydropyrido[2,3-b]pyrazine-4(1H)-carboxamide A) 6-hydroxy-5-nitronicotine acid To a mixture of 2-chloro-5-methyl-3-nitropyridine (25.0 g) in conc. sulfuric acid (540 mL) was slowly added sodium dichromate dihydrate (64.8 g). The reaction mixture was stirred at room temperature for 4 hr, poured into crushed ice, and the mixture was extracted with ethyl acetate. The extract was washed with saturated brine, and dried over anhydrous magnesium sulfate, and the solvent was evaporated under reduced pressure. The obtained solid was triturated with diisopropyl ether/hexane, and washed with diisopropyl ether/hexane to give the title compound (4.00 g).
$^1$H NMR (300 MHz, DMSO-d$_6$) δ 8.37 (1H, d, J=2.6 Hz), 8.64 (1H, d, J=2.6 Hz), 13.33 (2H, brs).

B) 6-chloro-N-methoxy-N-methyl-5-nitronicotinamide

To a mixture of 6-hydroxy-5-nitronicotine acid (552 mg) and thionyl chloride (6.57 mL) was added N,N-dimethylformamide (two drops). The reaction mixture was stirred overnight at 70° C., and the solvent was evaporated under reduced pressure. To a solution of the residue in N,N-dimethylacetamide (15.0 mL) was added N,O-dimethylhydroxylamine hydrochloride (322 mg) at 0° C. The reaction mixture was stirred at 0° C. for 2 hr, water was added thereto, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (647 mg).
$^1$H NMR (300 MHz, DMSO-d$_6$) δ 3.28-3.36 (3H, m), 3.58 (3H, s), 8.77 (1H, d, J=2.1 Hz), 8.94 (1H, d, J=2.1 Hz).

C) methyl 2-((5-(methoxy (methyl) carbamoyl)-3-nitropyridin-2-yl) amino)acetate

The title compound was obtained from 6-chloro-N-methoxy-N-methyl-5-nitronicotinamide in the same manner as in Step A of Example 1.
$^1$H NMR (300 MHz, DMSO-d$_6$) δ 3.28 (3H, s), 3.63 (3H, s), 3.67 (3H, s), 4.37 (2H, d, J=5.7 Hz), 8.68-8.80 (2H, m), 9.00-9.12 (1H, m).

D) methyl 2-((5-formyl-3-nitropyridin-2-yl) amino) acetate

To a solution of methyl 2-((5-(methoxy (methyl) carbamoyl)-3-nitropyridin-2-yl) amino)acetate (250 mg) in tetrahydrofuran (8.38 mL) was slowly added 1.5 M diisobutylaluminium hydride/toluene solution (1.12 mL) at −78° C. The reaction mixture was stirred at −78° C. for 1 hr under argon atmosphere, and methanol (170 μL) was added thereto. The reaction mixture was stirred for 5 min, silica gel was added thereto, and the solvent was evaporated under reduced pressure. The residue was purified by column chromatography (hexane/ethyl acetate) to give the title compound (72 mg).
MS (API−): [M−H]$^-$238.1.

E) methyl 2-((5-(difluoromethyl)-3-nitropyridin-2-yl) amino)acetate

To a solution of methyl 2-((5-formyl-3-nitropyridin-2-yl) amino)acetate (4.71 g) in acetonitrile (150 mL) was added N,N-diethylaminosulfur trifluoride (20.8 mL) at room temperature. The reaction mixture was stirred at room temperature for 2 hr, N,N-diethylaminosulfur trifluoride (20.8 mL) was added thereto at room temperature. The reaction mixture was stirred at room temperature for 1 hr, saturated aqueous sodium hydrogen carbonate solution was slowly added thereto at 0° C., and the mixture was extracted with ethyl acetate. The extract was washed with saturated brine, and dried over anhydrous magnesium sulfate, and the solvent was evaporated under reduced pressure. The residue was purified by silica gel column chromatography (NH, hexane/ethyl acetate) to give the title compound (2.78 g).

¹H NMR (300 MHz, CDCl₃) δ 3.81 (3H, s), 4.43 (2H, d, J=5.3 Hz), 6.44-6.88 (1H, m), 8.51-8.61 (2H, m), 8.65 (1H, brs).

F) 7-(difluoromethyl)-3,4-dihydropyrido[2,3-b]pyrazin-2(1H)-one

The title compound was obtained from methyl 2-((5-(difluoromethyl)-3-nitropyridin-2-yl) amino)acetate in the same manner as in Step B of Example 135.

¹H NMR (300 MHz, DMSO-d₆) δ 3.99 (2H, s), 6.63-7.12 (1H, m), 7.02 (1H, s), 7.27 (1H, s), 7.74-7.82 (1H, m), 10.55 (1H, s).

G) 7-(difluoromethyl)-N-(2-methoxy-1-(4-(trifluoromethoxy)phenyl)ethyl)-2-oxo-2,3-dihydropyrido[2,3-b]pyrazine-4(1H)-carboxamide The title compound was obtained from 7-(difluoromethyl)-3,4-dihydropyrido[2,3-b]pyrazin-2(1H)-one in the same manner as in Step F of Example 1.

MS (API+): [M+H]⁺461.1.

Example 168

7-methyl-2-oxo-N-(tetrahydro-2H-pyran-4-yl(4-(trifluoromethoxy)phenyl)methyl)-2,3-dihydropyrido[2,3-b]pyrazine-4(1H)-carboxamide A) N-methoxy-N-methyltetrahydro-2H-pyran-4-carboxamide To a solution of tetrahydro-2H-pyran-4-carboxylic acid (800 mg) in N,N-dimethylformamide (60.0 mL) were added 1-hydroxybenzotriazole monohydrate (1.17 g), 1-(3-dimethylaminopropyl)-3-ethylcarbodiimide hydrochloride (1.44 g), N,O-dimethylhydroxylamine hydrochloride (600 mg) and triethylamine (1.73 mL). The reaction mixture was stirred overnight at room temperature, water was added thereto, and the mixture was extracted with ethyl acetate. The extract was washed successively with saturated aqueous sodium hydrogen carbonate solution and saturated brine, dried over anhydrous sodium sulfate, and the solvent was evaporated under reduced pressure to give the title compound (831 mg).

MS (API+): [M+H]⁺174.3.

B) tetrahydro-2H-pyran-4-yl(4-(trifluoromethoxy)phenyl)methanone

To a solution of 1-bromo-4-(trifluoromethoxy)benzene (2.78 g) in tetrahydrofuran (76.8 mL) was slowly added 1.6 M n-butyllithium/hexane solution (7.20 mL) at −78° C. The reaction mixture was stirred at −78° C. for 30 min under nitrogen atmosphere, a solution of N-methoxy-N-methyltetrahydro-2H-pyran-4-carboxamide (665 mg) in tetrahydrofuran (1.00 mL) was added thereto at −78° C. The reaction mixture was stirred at room temperature for 2 hr under nitrogen atmosphere, saturated aqueous ammonium chloride solution was added thereto, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give the title compound (812 mg).

MS (API+): [M+H]⁺275.1.

C) N-hydroxy-1-(tetrahydro-2H-pyran-4-yl)-1-(4-(trifluoromethoxy)phenyl)methanimine To a mixture of tetrahydro-2H-pyran-4-yl(4-(trifluoromethoxy)phenyl)methanone (690 mg) and hydroxylamine hydrochloride (713 mg) in ethanol (16.8 mL) was added triethylamine (1.42 mL) at room temperature. The reaction mixture was stirred overnight at room temperature, and the solvent was evaporated under reduced pressure. The residue was diluted with ethyl acetate and water, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give the title compound (566 mg).

MS (API+): [M+H]⁺290.1.

D) 1-(tetrahydro-2H-pyran-4-yl)-1-(4-(trifluoromethoxy)phenyl)methanamine

To a solution of N-hydroxy-1-(tetrahydro-2H-pyran-4-yl)-1-(4-(trifluoromethoxy)phenyl)methanimine (566 mg) in tetrahydrofuran (25.0 mL) was added 1.1 M borane-tetrahydrofuran complex/tetrahydrofuran solution (5.33 mL) at room temperature. The reaction mixture was stirred overnight at 70° C., 1 M aqueous sodium hydroxide solution (19.6 mL) was added thereto, and the mixture was stirred at 60° C. for 3 hr. To the reaction mixture was added saturated brine, and the mixture was extracted with ethyl acetate. The extract was washed with saturated brine, and dried over anhydrous sodium sulfate, and the solvent was evaporated under reduced pressure to give the title compound (547 mg).

MS (API+): [M+H]⁺276.1.

E) 7-methyl-2-oxo-N-(tetrahydro-2H-pyran-4-yl(4-(trifluoromethoxy)phenyl)methyl)-2,3-dihydropyrido[2,3-b]pyrazine-4(1H)-carboxamide The title compound was obtained from 1-(tetrahydro-2H-pyran-4-yl)-1-(4-(trifluoromethoxy)phenyl)methanamine in the same manner as in Step B of Example 83.

MS (API+): [M+H]⁺465.2.

Example 169

N-(2-(4-hydroxytetrahydro-2H-pyran-4-yl)-1-(4-(trifluoromethoxy)phenyl)ethyl)-7-methyl-2-oxo-2,3-dihydropyrido[2,3-b]pyrazine-4(1H)-carboxamide A) 2-(4-hydroxytetrahydro-2H-pyran-4-yl)-1-(4-(trifluoromethoxy)phenyl)ethanone To a solution of diisopropylamine (3.36 mL) in tetrahydrofuran (100 mL) was slowly added 1.6 M n-butyllithium/hexane solution (15 mL) at −78° C. The reaction mixture was stirred at −78° C. for 30 min under argon atmosphere, and 4-trifluoromethoxyacetophenone (3.19 mL) was added thereto at −78° C. The reaction mixture was stirred at −78° C. for 1 hr under argon atmosphere, and tetrahydro-4H-pyran-4-one (1.85 mL) was added thereto at −78° C. The reaction mixture was stirred at −78° C. for 1 hr under argon atmosphere, saturated aqueous ammonium chloride solution was added thereto, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (4.34 g).
MS (API-): [M-H]⁻303.1.

B) N-(2-(4-hydroxytetrahydro-2H-pyran-4-yl)-1-(4-(trifluoromethoxy)phenyl)ethyl)-7-methyl-2-oxo-2,3-dihydropyrido[2,3-b]pyrazine-4(1H)-carboxamide The title compound was obtained from 2-(4-hydroxytetrahydro-2H-pyran-4-yl)-1-(4-(trifluoromethoxy)phenyl)ethanone in the same manner as in Steps C-D of Example 1 and Step L of Example 72-I.
MS (API+): [M+H]⁺495.1.

Example 170

7-methyl-2-oxo-N-(tetrahydrofuran-2-yl(4-(trifluoromethoxy)phenyl)methyl)-2,3-dihydropyrido[2,3-b]pyrazine-4(1H)-carboxamide A) tetrahydrofuran-2-yl(4-(trifluoromethoxy)phenyl)methanone To a solution of 1-bromo-4-(trifluoromethoxy)benzene (7.6 g) in tetrahydrofuran (50 mL) was slowly added 1.6 M n-butyllithium/hexane solution (19.7 mL) at −78° C. The reaction mixture was stirred at −78° C. for 40 min under nitrogen atmosphere, and N-methoxy-N-methyltetrahydrofuran-2-carboxamide (1.673 g) (obtained from tetrahydrofuran-2-carboxylic acid in the same manner as in Step A of Example 31) was added thereto at −78° C., and the reaction mixture was stirred at room temperature for 1 hr under nitrogen atmosphere. To the reaction mixture was added saturated aqueous ammonium chloride solution, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (2.49 g).
MS (API+): [M+H]⁺261.1.

B) 7-methyl-2-oxo-N-(tetrahydrofuran-2-yl(4-(trifluoromethoxy)phenyl)methyl)-2,3-dihydropyrido[2,3-b]pyrazine-4(1H)-carboxamide The title compound was obtained from tetrahydrofuran-2-yl(4-(trifluoromethoxy)phenyl)methanone in the same manner as in Step D of Example 2, Step B of Example 132 and Step G of Example 7.
MS (API+): [M+H]⁺451.2.

Example 171

N-(2-hydroxy-1-(4-(trifluoromethoxy)phenyl)pentyl)-7-methyl-2-oxo-2,3-dihydropyrido[2,3-b]pyrazine-4(1H)-carboxamide The title compound was obtained from 4-(trifluoromethoxy)benzaldehyde in the same manner as in Example 174.
MS (API+): [M+H]⁺453.2.

Example 172

N-(3-((tert-butyl(diphenyl)silyl)oxy)-2,2-dimethyl-1-(4-(trifluoromethoxy)phenyl)propyl)-7-methyl-2-oxo-2,3-dihydropyrido[2,3-b]pyrazine-4(1H)-carboxamide A) methyl 3-((tert-butyl(diphenyl)silyl)oxy)-2,2-dimethylpropanoate A mixture of methyl 3-hydroxy-2,2-dimethylpropanoate (18.3 g), tert-butyl(chloro)diphenylsilane (40.0 g), 1H-imidazole (12.3 g) and N,N-dimethylformamide (300 mL) was stirred overnight at room temperature, and the solvent was evaporated under reduced pressure. To the residue was added saturated brine, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (50.6 g).
¹H NMR (300 MHz, CDCl₃) δ 1.03 (9H, s), 1.20 (6H, s), 3.64 (2H, s), 3.67 (3H, s), 7.31-7.47 (6H, m), 7.58-7.68 (4H, m).

B) 3-((tert-butyl(diphenyl)silyl)oxy)-2,2-dimethylpropanoic acid

A mixture of methyl 3-((tert-butyl(diphenyl)silyl)oxy)-2,2-dimethylpropanoate (50.6 g), 8 M aqueous sodium hydroxide solution (150 mL) and tetrahydrofuran (150 mL) was stirred at 100° C. for 3 hr, and the pH of the mixture was adjusted to about 1 with 6 M hydrochloric acid, and the mixture was extracted with ethyl acetate. The extract was washed with saturated brine, and dried over anhydrous magnesium sulfate, and the solvent was evaporated under reduced pressure to give the title compound (50.1 g).
MS (API-): [M-H]⁻355.2.

C) N-(3-((tert-butyl(diphenyl)silyl)oxy)-2,2-dimethyl-1-(4-(trifluoromethoxy)phenyl)propyl)-7-methyl-2-oxo-2,3-dihydropyrido[2,3-b]pyrazine-4(1H)-carboxamide The title compound was obtained from 3-((tert-butyl(diphenyl)silyl)oxy)-2,2-dimethylpropanoic acid in the same manner as in Step A of Example 170, Step D of Example 2, Step B of Example 132 and Step G of Example 7.
MS (API+): [M+H]⁺691.4.

Example 173

N-(2-(1,3-dioxo-1,3-dihydro-2H-isoindol-2-yl)-1-(4-(trifluoromethoxy)phenyl)ethyl)-2-oxo-2,3-dihydropyrido[2,3-b]pyrazine-4(1H)-carboxamide A) tert-butyl (2-(1,3-dioxoisoindolin-2-yl)-1-(4-(trifluoromethoxy)phenyl)ethyl)carbamate A mixture of tert-butyl (2-amino-1-(4-(trifluoromethoxy)phenyl)ethyl)carbamate (762 mg) and isobenzofuran-1,3-dione (423 mg) in toluene (20 mL) was heated at reflux using Dean-Stark for 16 hr, and the solvent was evaporated under reduced pressure. The obtained solid was triturated with ethyl acetate, collected by filtration, and washed with ethyl acetate to give the title compound (399 mg).
MS (API+), found: 351.1.

B) 2-(2-amino-2-(4-(trifluoromethoxy)phenyl)ethyl) isoindoline-1,3-dione hydrochloride The title compound was obtained from tert-butyl (2-(1,3-dioxoisoindolin-2-yl)-1-(4-(trifluoromethoxy)phenyl)ethyl) carbamate in the same manner as in Step E of Example 18.
$^1$H NMR (300 MHz, DMSO-$d_6$) δ 3.89-4.01 (1H, m), 4.03-4.16 (1H, m), 4.67 (1H, t, J=6.9 Hz), 7.41-7.51 (2H, m), 7.64-7.74 (2H, m), 7.87 (4H, d, J=2.8 Hz), 8.65 (3H, brs).

C) N-(2-(1,3-dioxo-1,3-dihydro-2H-isoindol-2-yl)-1-(4-(trifluoromethoxy)phenyl)ethyl)-2-oxo-2,3-dihydropyrido[2,3-b]pyrazine-4(1H)-carboxamide The title compound was obtained from 2-(2-amino-2-(4-(trifluoromethoxy)phenyl)ethyl)isoindoline-1,3-dione hydrochloride in the same manner as in Step L of Example 72-I.
MS (API+): [M+H]$^+$526.2.

Example 174

N-(2-cyclopropyl-2-oxo-1-(4-(trifluoromethoxy) phenyl)ethyl)-2-oxo-2,3-dihydropyrido[2,3-b]pyrazine-4(1H)-carboxamide A) tert-butyl (cyano(4-(trifluoromethoxy)phenyl)methyl)carbamate To 2 M ammonia/methanol solution (112 mL) of 4-(trifluoromethoxy)benzaldehyde (10.6 g) was added titanium (IV) tetraisopropoxide (16.3 mL) at 0° C. The reaction mixture was stirred at 0° C. for 15 min, trimethylsilyl cyanide (11.2 mL) was added thereto, and the reaction mixture was stirred at room temperature for 20 hr, and concentrated to about ¼ of volume under reduced pressure, saturated aqueous sodium hydrogen carbonate solution was added thereto, the insoluble substance was filtered off using Celite, and the filtrate was extracted with ethyl acetate. The extract was washed successively with water and saturated brine, and dried over anhydrous magnesium sulfate, and the solvent was evaporated under reduced pressure. To a solution of the residue in tetrahydrofuran (300 mL) were added di-tert-butyl dicarbonate (12.94 mL) and triethylamine (9.32 mL). The reaction mixture was stirred at 45° C. for 16 hr, water was added thereto, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate) to give the title compound (9.39 g).
MS (API+): [M+H]$^+$317.1.

B) tert-butyl (2-amino-2-oxo-1-(4-(trifluoromethoxy)phenyl)ethyl)carbamate

To a mixture of tert-butyl (cyano(4-(trifluoromethoxy)phenyl)methyl)carbamate (3.00 g) and potassium carbonate (1.31 g) in dimethyl sulfoxide (70 mL) was added 35% aqueous hydrogen peroxide (1.66 mL) at 0° C. The reaction mixture was stirred at room temperature for 3 hr, water was added thereto, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate) to give the title compound (2.44 g).
$^1$H NMR (300 MHz, CDCl$_3$) δ 1.41 (9H, s), 5.11-5.28 (1H, m), 5.48 (1H, brs), 5.68 (1H, brs), 5.78 (1H, brs), 7.18-7.25 (2H, m), 7.40-7.47 (2H, m).

C) tert-butyl (2-(methoxy (methyl) amino)-2-oxo-1-(4-(trifluoromethoxy)phenyl)ethyl)carbamate To a solution of tert-butyl (2-amino-2-oxo-1-(4-(trifluoromethoxy)phenyl)ethyl)carbamate (2.44 g) in methanol (70 mL) was added 8 M aqueous sodium hydroxide solution (1.8 mL), the reaction mixture was heated at reflux for 20 hr. The solvent was evaporated under reduced pressure, the pH of the residue was adjusted to 3-4 with 1 M hydrochloric acid, and the mixture was extracted with ethyl acetate. The extract was washed successively with water and saturated brine, and dried over anhydrous magnesium sulfate, and the solvent was evaporated under reduced pressure. A mixture of the obtained residue, N,O-dimethylhydroxylamine hydrochloride (0.783 g), triethylamine (1.32 mL), 1-hydroxybenzotriazole monohydrate (1.45 g) and 1-(3-dimethylaminopropyl)-3-ethylcarbodiimide hydrochloride (1.82 g) in N,N-dimethylformamide (30 mL) was stirred at room temperature for 3 hr, water was added thereto, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate) to give the title compound (1.39 g).
$^1$H NMR (300 MHz, CDCl$_3$) δ 1.42 (9H, s), 3.19 (3H, s), 3.51 (3H, s), 5.63-5.91 (2H, m), 7.14-7.22 (2H, m), 7.37-7.45 (2H, m).

D) tert-butyl (2-cyclopropyl-2-oxo-1-(4-(trifluoromethoxy)phenyl)ethyl)carbamate To a solution of tert-butyl (2-(methoxy(methyl)amino)-2-oxo-1-(4-(trifluoromethoxy)phenyl)ethyl)carbamate (685 mg) in tetrahydrofuran (15 mL) was added 0.7 M cyclopropylmagnesium bromide/tetrahydrofuran solution (7.76 mL) at 0° C. The reaction mixture was stirred at room temperature for 20 hr, 1 M hydrochloric acid was added thereto, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate) to give the title compound (486 mg).
$^1$H NMR (300 MHz, CDCl$_3$) δ 0.75-0.86 (1H, m), 0.90-1.05 (2H, m), 1.08-1.17 (1H, m), 1.40 (9H, s), 1.79-1.90 (1H, m), 5.48 (1H, d, J=6.4 Hz), 5.92-6.04 (1H, m), 7.18-7.25 (2H, m), 7.33-7.41 (2H, m).

E) N-(2-cyclopropyl-2-oxo-1-(4-(trifluoromethoxy) phenyl)ethyl)-2-oxo-2,3-dihydropyrido[2,3-b]pyrazine-4(1H)-carboxamide A mixture of tert-butyl (2-cyclopropyl-2-oxo-1-(4-(trifluoromethoxy)phenyl)ethyl)carbamate (200 mg) and 4 M hydrogen chloride/ethyl acetate solution (5 mL) was stirred at room temperature for 1 hr, and the solvent was evaporated under reduced pressure. To a mixture of the residue and 4-nitrophenyl 2-oxo-2,3-dihydropyrido[2,3-b]pyrazine-4 (1H)-carboxylate (160 mg) in N,N-dimethylformamide (5 mL) was added triethylamine (0.213 mL). The reaction mixture was stirred at room temperature for 20 hr, water was added thereto, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate), and recrystallized from hexane/ethyl acetate to give the title compound (143 mg).

MS (API+): [M+H]$^+$435.1.

Example 175

N-(2-cyclopropyl-2-hydroxy-1-(4-(trifluoromethoxy) phenyl)ethyl)-2-oxo-2,3-dihydropyrido[2,3-b]pyrazine-4(1H)-carboxamide To a mixture of N-(2-cyclopropyl-2-oxo-1-(4-(trifluoromethoxy)phenyl)ethyl)-2-oxo-2,3-dihydropyrido[2,3-b]pyrazine-4(1H)-carboxamide (126 mg) in a mixed solvent of methanol (3 mL) and tetrahydrofuran (1 mL) was added sodium borohydride (13.2 mg) at 0° C. The reaction mixture was stirred at room temperature for 3 hr, water was added thereto, and the mixture was extracted with ethyl acetate. The extract was washed successively with water and saturated brine, and dried over anhydrous magnesium sulfate, and the solvent was evaporated under reduced pressure. The residue was crystallized from hexane/ethyl acetate to give the title compound (87.2 mg).

MS (API+): [M+H]$^+$ 437.2.

Example 176

7-methyl-2-oxo-N-(2-(tetrahydro-2H-pyran-4-yl)-1-(4-(trifluoromethoxy)phenyl)ethyl)-2,3-dihydropyrido[2,3-b]pyrazine-4(1H)-carboxamide A) 4-(2-azido-2-(4-(trifluoromethoxy)phenyl)ethyl) tetrahydro-2H-pyran To a solution of 2-(4-hydroxytetrahydro-2H-pyran-4-yl)-1-(4-(trifluoromethoxy)phenyl)ethanone (304 mg) in pyridine (5 mL) was added thionyl chloride (102 μL) at 0° C. The reaction mixture was stirred at 0° C. for 10 min, water was added thereto at 0° C., and the mixture was extracted with ethyl acetate. The extract was washed with saturated brine, and dried over anhydrous magnesium sulfate, and the solvent was evaporated under reduced pressure. A mixture of the residue (286 mg) and 10% palladium-carbon (containing 50% water, 60 mg) in ethanol (5 mL) was stirred at room temperature for 2 hr under hydrogen atmosphere. The insoluble substance was filtered off, and the filtrate was concentrated under reduced pressure. To a solution of the residue (290 mg) in tetrahydrofuran (5 mL) were added triphenylphosphine (315 mg), diphenylphosphoryl azide (259 μL) and 1.9 M diisopropyl azodicarboxylate/toluene solution (632 μL) at room temperature. The reaction mixture was stirred at room temperature for 30 min, and the solvent was evaporated under reduced pressure. The residue was purified by silica gel column chromatography (hexane/ethyl acetate) to give the title compound (274 mg).

$^1$H NMR (300 MHz, CDCl$_3$) δ 1.20-1.44 (2H, m), 1.52-1.72 (4H, m), 1.73-1.87 (1H, m), 3.30-3.43 (2H, m), 3.89-4.01 (2H, m), 4.48-4.59 (1H, m), 7.19-7.46 (4H, m).

B) 7-methyl-2-oxo-N-(2-(tetrahydro-2H-pyran-4-yl)-1-(4-(trifluoromethoxy)phenyl)ethyl)-2,3-dihydropyrido[2,3-b]pyrazine-4(1H)-carboxamide A mixture of 4-(2-azido-2-(4-(trifluoromethoxy)phenyl) ethyl)tetrahydro-2H-pyran (274 mg) and 10% palladium-carbon (containing 50% water, 92 mg) in ethanol (4.4 mL) was stirred at room temperature for 1 hr under hydrogen atmosphere. The catalyst was filtered off, and the solvent was evaporated under reduced pressure to give 2-(tetrahydro-2H-pyran-4-yl)-1-(4-(trifluoromethoxy)phenyl) ethanamine (254 mg). To a mixture of 4-nitrophenyl 7-methyl-2-oxo-2,3-dihydropyrido[2,3-b]pyrazine-4(1H)-carboxylate (144 mg) in N,N-dimethylformamide (2.19 mL) were added 2-(tetrahydro-2H-pyran-4-yl)-1-(4-(trifluoromethoxy)phenyl)ethanamine (254 mg) obtained above and triethylamine (122 μL) at room temperature. The reaction mixture was stirred overnight at room temperature, water was added thereto, and the mixture was extracted with ethyl acetate. The extract was washed with saturated brine, and dried over anhydrous magnesium sulfate, and the solvent was evaporated under reduced pressure. The residue was purified by silica gel column chromatography (NH, hexane/ethyl acetate) to give the title compound (184 mg).

MS (API+): [M+H]$^+$ 479.2.

Example 177

2-oxo-N-(2-oxo-1-(4-(trifluoromethoxy)phenyl)propyl)-2,3-dihydropyrido[2,3-b]pyrazine-4(1H)-carboxamide To a solution of N-(2-(methoxy (methyl) amino)-2-oxo-1-(4-(trifluoromethoxy)phenyl)ethyl)-2-oxo-2,3-dihydropyrido[2,3-b]pyrazine-4(1H)-carboxamide (290 mg) in tetrahydrofuran (7 mL) was added 1 M methylmagnesium bromide/tetrahydrofuran solution (7.0 mL) at 0° C. The reaction mixture was stirred at room temperature for 20 hr, 1 M hydrochloric acid was added thereto, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate), and recrystallized from hexane/ethyl acetate to give the title compound (174 mg).

MS (API+): [M+H]$^+$ 409.1.

Example 178

8-methoxy-N-(2-methoxy-1-(4-(trifluoromethoxy) phenyl)ethyl)-2-oxo-2,3-dihydropyrido[2,3-b]pyrazine-4(1H)-carboxamide The title compound was obtained from 2-chloro-4-methoxy-3-nitropyridine in the same manner as in Steps A-B of Example 1 and Steps C-D of Example 19.

MS (API+): [M+H]$^+$441.2.

Example 179

N-(2-hydroxy-1-(4-(trifluoromethoxy)phenyl)propyl)-2-oxo-2,3-dihydropyrido[2,3-b]pyrazine-4(1H)-carboxamide The title compound was obtained from 2-oxo-N-(2-oxo-1-(4-(trifluoromethoxy)phenyl)propyl)-2,3-dihydropyrido[2,3-b]pyrazine-4(1H)-carboxamide in the same manner as in Example 175.
MS (API+): [M+H]$^+$ 411.1.

Example 180

2-oxo-N-(2,2,2-trifluoro-1-(4-(trifluoromethoxy)phenyl)ethyl)-2,3-dihydropyrido[2,3-b]pyrazine-4(1H)-carboxamide A) 2,2,2-trifluoro-1-(4-(trifluoromethoxy)phenyl)ethanol To a solution of 1-bromo-4-(trifluoromethoxy)benzene (10.1 g) in tetrahydrofuran (90 mL) was slowly added 1.6 M n-butyllithium/hexane solution (28.7 mL) at −78° C. The reaction mixture was stirred at −78° C. for 30 min, a solution of 2,2,2-trifluoro-1-(piperidin-1-yl)ethanone (9.07 g) in tetrahydrofuran (10 mL) was slowly added thereto. The reaction mixture was stirred at −78° C. for 1.5 hr, saturated aqueous ammonium chloride solution was added thereto, and the mixture was extracted with diethyl ether. The extract was dried over anhydrous sodium sulfate, and the solvent was evaporated under reduced pressure to give a crude product of 2,2,2-trifluoro-1-(4-(trifluoromethoxy)phenyl)ethanone. To a solution of the obtained crude product (11.9 g) in ethanol (80 mL) was slowly added sodium borohydride (3.49 g) under ice-cooling. The reaction mixture was stirred at room temperature for 16 hr, and the ethanol was evaporated under reduced pressure. To the residue was added 1 M hydrochloric acid, and the mixture was extracted with ethyl acetate. The extract was washed successively with 1 M hydrochloric acid and saturated brine, dried over anhydrous sodium sulfate, and the solvent was evaporated under reduced pressure. The residue was purified by silica gel chromatography (hexane/ethyl acetate) to give the title compound (9.57 g).
MS (API−): [M−H]$^-$ 259.0.

B) 2,2,2-trifluoro-1-(4-(trifluoromethoxy)phenyl)ethyl methanesulfonate

To a mixture of 2,2,2-trifluoro-1-(4-(trifluoromethoxy)phenyl)ethanol (9.57 g) and triethylamine (7.69 mL) in tetrahydrofuran (100 mL) was slowly added methanesulfonyl chloride (3.42 mL) under ice-cooling. The reaction mixture was stirred at room temperature for 1.5 hr, water was added thereto, and the mixture was extracted with ethyl acetate. The extract was washed successively with water and saturated brine, and dried over anhydrous sodium sulfate, and the solvent was evaporated under reduced pressure to give the title compound (10.7 g).
$^1$H NMR (300 MHz, DMSO-d$_6$) δ 3.33 (3H, s), 6.62 (1H, q, J=6.8 Hz), 7.48-7.58 (2H, m), 7.68-7.78 (2H, m).

C) 1-(1-azido-2,2,2-trifluoroethyl)-4-(trifluoromethoxy)benzene

To a solution of 2,2,2-trifluoro-1-(4-(trifluoromethoxy)phenyl)ethyl methanesulfonate (10.7 g) in N,N-dimethylformamide (100 mL) was added sodium azide (5.15 g) at room temperature. The reaction mixture was stirred at 100° C. for 24 hr, and then at room temperature for 2 days. To the reaction mixture was added water, and the mixture was extracted with diethyl ether. The extract was washed successively with water and saturated brine, and dried over anhydrous sodium sulfate, and the solvent was evaporated under reduced pressure. The residue was purified by silica gel chromatography (hexane/ethyl acetate) to give the title compound (5.12 g).
$^1$H NMR (300 MHz, CDCl$_3$) δ 4.94 (1H, q, J=6.8 Hz), 7.26-7.33 (2H, m), 7.43-7.53 (2H, m).

D) 2,2,2-trifluoro-1-(4-(trifluoromethoxy)phenyl)ethanamine

To a solution of 1-(1-azido-2,2,2-trifluoroethyl)-4-(trifluoromethoxy)benzene (4.92 g) in methanol (30 mL) was added 10% palladium-carbon (containing 50% water, 1 g). The reaction mixture was stirred at room temperature for 2 hr under hydrogen atmosphere, the insoluble substance was filtered off, and the filtrate was concentrated under reduced pressure. To the residue was added brine, and the mixture was extracted with diethyl ether. The extract was washed with saturated brine, and dried over anhydrous sodium sulfate, solvent was evaporated under reduced pressure to give the title compound (4.31 g).
$^1$H NMR (300 MHz, DMSO-d$_6$) δ 2.57 (2H, brs), 4.49-4.68 (1H, m), 7.34-7.44 (2H, m), 7.58-7.68 (2H, m).

E) 2-oxo-N-(2,2,2-trifluoro-1-(4-(trifluoromethoxy)phenyl)ethyl)-2,3-dihydropyrido[2,3-b]pyrazine-4(1H)-carboxamide The title compound was obtained from 2,2,2-trifluoro-1-(4-(trifluoromethoxy)phenyl)ethanamine in the same manner as in Steps F-I of Example 63.
MS (API+): [M+H]$^+$435.1.

Example 181

7-methyl-2-oxo-N-(2-(pyridin-3-yloxy)-1-(4-(trifluoromethoxy)phenyl)ethyl)-2,3-dihydropyrido[2,3-b]pyrazine-4(1H)-carboxamide A) 2-((5-bromopyridin-3-yl)oxy)-1-(4-(trifluoromethoxy)phenyl)ethanone To a solution of 5-bromopyridin-3-ol (5 g) in N,N-dimethylformamide (100 mL) was added 60% sodium hydride (1.72 g) at 0° C. The reaction mixture was stirred at 0° C. for 30 min, 2-bromo-1-(4-(trifluoromethoxy)phenyl)ethanone (9.76 g) was added thereto at 0° C. The reaction mixture was stirred at room temperature for 3 hr, and added to saturated aqueous ammonium chloride solution, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate), and the obtained solid was washed with hexane to give the title compound (7.78 g).
MS (API+): [M+H]$^+$376.0.

B) 7-methyl-2-oxo-N-(2-(pyridin-3-yloxy)-1-(4-(trifluoromethoxy)phenylethyl)-2,3-dihydropyrido[2,3-b]pyrazine-4(1H)-carboxamide The title compound was obtained from 2-((5-bromopyridin-3-yl)oxy)-1-(4-(trifluoromethoxy)phenyl)ethanone in the same manner as in Step D of Example 2, Step B of Example 132 and Step G of Example 7.
MS (API+): [M+H]$^+$488.2.

Example 182

N-(2-hydroxy-1-(4-(trifluoromethoxy)phenyl)ethyl)-7-methyl-2-oxo-2,3-dihydropyrido[2,3-b]pyrazine-4(1H)-carboxamide The title compound was obtained from 2-((5-bromopyridin-3-yl)oxy)-1-(4-(trifluoromethoxy)phenyl)ethanone in the same manner as in Step D of Example 2, Step B of Example 132 and Step G of Example 7.
MS (API+): [M+H]$^+$ 411.1.

Example 183

N-(1-(3,5-difluoro-4-(trifluoromethoxy)phenyl)-2-methoxyethyl)-7-methyl-2-oxo-2,3-dihydropyrido[2,3-b]pyrazine-4(1H)-carboxamide A) 5-(1-ethoxyvinyl)-1,3-difluoro-2-(trifluoromethoxy)benzene A mixture of 5-bromo-1,3-difluoro-2-(trifluoromethoxy)benzene (5.00 g), tributyl(1-ethoxyvinyl)stannane (7.17 g), bis(triphenylphosphine)dichloropalladium(II) (0.38 g) and toluene (100 mL) was stirred overnight at 100° C. under nitrogen atmosphere, and 1 M hydrochloric acid (20 mL) was added thereto. The reaction mixture was stirred at room temperature for 3 hr, saturated brine was added thereto, and the mixture was extracted with ethyl acetate. The extract was washed with saturated brine, dried over anhydrous magnesium sulfate, and purified by silica gel column chromatography (NH, hexane/ethyl acetate) to give the title compound (4.24 g).
$^1$H NMR (300 MHz, CDCl$_3$) δ 1.42 (3H, t, J=7.0 Hz), 3.91 (2H, q, J=6.8 Hz), 4.31 (1H, d, J=3.4 Hz), 4.67 (1H, d, J=3.0 Hz), 7.21-7.35 (2H, m).

B) 1-(3,5-difluoro-4-(trifluoromethoxy)phenyl)ethanone

A mixture of 5-(1-ethoxyvinyl)-1,3-difluoro-2-(trifluoromethoxy)benzene (4.24 g), 6 M hydrochloric acid (15 mL), acetone (50 mL) and water (15 mL) was stirred at room temperature for 5 hr, and the mixture was extracted with ethyl acetate. The extract was washed with saturated brine, and dried over anhydrous magnesium sulfate, and the solvent was evaporated under reduced pressure to give the title compound (3.51 g).
$^1$H NMR (300 MHz, CDCl$_3$) δ 2.60 (3H, s), 7.56-7.67 (2H, m).

C) N-(1-(3,5-difluoro-4-(trifluoromethoxy)phenyl)-2-methoxyethyl)-7-methyl-2-oxo-2,3-dihydropyrido[2,3-b]pyrazine-4(1H)-carboxamide The title compound was obtained from 1-(3,5-difluoro-4-(trifluoromethoxy)phenyl)ethanone in the same manner as in Step A of Example 143, Step D of Example 63, Step D of Example 2, Step B of Example 15 and Step G of Example 7.
MS (API+): [M+H]$^+$ 461.1.

Example 184

N-(3-hydroxy-2,2-dimethyl-1-(4-(trifluoromethoxy)phenyl)propyl)-7-methyl-2-oxo-2,3-dihydropyrido[2,3-b]pyrazine-4(1H)-carboxamide To a mixture of N-(3-((tert-butyl(diphenyl)silyl)oxy)-2,2-dimethyl-1-(4-(trifluoromethoxy)phenyl)propyl)-7-methyl-2-oxo-2,3-dihydropyrido[2,3-b]pyrazine-4(1H)-carboxamide (90 mg) and acetic acid (23.5 mg) in tetrahydrofuran (5 mL) was added 1 M tetra-n-butylammonium fluoride/tetrahydrofuran solution (0.391 mL). The reaction mixture was stirred overnight at room temperature, and 1 M tetra-n-butylammonium fluoride/tetrahydrofuran solution (0.782 mL) was added. The reaction mixture was stirred at room temperature for 2 hr, and then overnight at 50° C. To the reaction mixture was added saturated brine, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (43.2 mg).
MS (API+): [M+H]$^+$453.2.

Example 185

N-(2-fluoro-2-methyl-1-(4-(trifluoromethoxy)phenyl)propyl)-2-oxo-2,3-dihydropyrido[2,3-b]pyrazine-4(1H)-carboxamide A) methyl (4-(trifluoromethoxy)phenyl)acetate To a solution of (4-(trifluoromethoxy)phenyl)acetic acid (5.00 g) in methanol (31.3 mL) was added conc. sulfuric acid (237 μL). The reaction mixture was stirred at 70° C. for 3 hr, and concentrated under reduced pressure to about 10 mL. To the residue was added water, and the mixture was extracted with ethyl acetate. The extract was washed successively with saturated aqueous sodium hydrogen carbonate solution and saturated brine, dried over anhydrous sodium sulfate, and the solvent was evaporated under reduced pressure to give the title compound (5.23 g).
$^1$H NMR (300 MHz, CDCl$_3$) δ 3.63 (2H, s), 3.71 (3H, s), 7.17 (2H, d, J=7.9 Hz), 7.27-7.37 (2H, m).

B) 2-methyl-1-(4-(trifluoromethoxy)phenyl)propan-2-ol

To a solution of methyl (4-(trifluoromethoxy)phenyl)acetate (5.23 g) in tetrahydrofuran (200 mL) was slowly added 1 M methylmagnesium bromide/tetrahydrofuran solution (55.8 mL). The reaction mixture was stirred overnight at room temperature, 1 M methylmagnesium bromide/tetrahydrofuran solution (55.8 mL) was added thereto, and the mixture was stirred at room temperature for 2 hr. To the reaction mixture was added saturated aqueous ammonium chloride solution at 0° C., and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give the title compound (2.65 g).
$^1$H NMR (300 MHz, CDCl$_3$) δ 1.23 (6H, s), 1.30 (1H, s), 2.77 (2H, s), 7.11-7.19 (2H, m), 7.21-7.29 (2H, m).

C) 1-(2-fluoro-2-methylpropyl)-4-(trifluoromethoxy) benzene

To 2-methyl-1-(4-(trifluoromethoxy)phenyl)propan-2-ol (2.55 g) was added N,N-diethylaminosulfur trifluoride (2.88 mL) at 0° C., and the reaction mixture was stirred overnight at room temperature. The reaction mixture was diluted with diethyl ether, water was added thereto at 0° C., and the mixture was extracted with diethyl ether. The extract was washed successively with saturated aqueous sodium hydrogen carbonate solution and saturated brine, dried over anhydrous sodium sulfate, and the solvent was evaporated under reduced pressure. The residue was purified by silica gel column chromatography (hexane) to give the title compound (1.59 g).

$^1$H NMR (300 MHz, CDCl$_3$) δ 1.30 (3H, s), 1.37 (3H, s), 2.83-2.97 (2H, m), 7.09-7.18 (2H, m), 7.20-7.28 (2H, m).

D) 1-(1-bromo-2-fluoro-2-methylpropyl)-4-(trifluoromethoxy)benzene

A mixture of 1-(2-fluoro-2-methylpropyl)-4-(trifluoromethoxy)benzene (1.59 g), N-bromosuccinimide (1.59 g) and 2,2'-azobis(2-methylpropionitrile) (113 mg) in trifluoromethylbenzene (33.7 mL) was stirred at 80° C. for 2 hr. To the reaction mixture was added hexane, the insoluble substance was filtered off, and the filtrate was concentrated under reduced pressure. The residue was purified by silica gel column chromatography (hexane) to give the title compound (1.66 g).

$^1$H NMR (300 MHz, CDCl$_3$) δ 1.48 (3H, d, J=3.8 Hz), 1.55 (3H, d, J=4.9 Hz), 4.92 (1H, d, J=17.3 Hz), 7.18 (2H, d, J=8.3 Hz), 7.49 (2H, d, J=8.7 Hz).

E) 1-(1-azido-2-fluoro-2-methylpropyl)-4-(trifluoromethoxy)benzene

A mixture of 1-(1-bromo-2-fluoro-2-methylpropyl)-4-(trifluoromethoxy)benzene (1.56 g) and sodium azide (1.65 g) in N,N-dimethylformamide (33.1 mL) was stirred overnight at 100° C., water was added thereto, and the mixture was extracted with diethyl ether. The extract was washed successively with water and saturated brine, and dried over anhydrous sodium sulfate, and the solvent was evaporated under reduced pressure to give the title compound (1.13 g).

$^1$H NMR (300 MHz, CDCl$_3$) δ 1.27-1.34 (3H, m), 1.35-1.42 (3H, m), 4.55 (1H, d, J=13.9 Hz), 7.18-7.26 (2H, m), 7.39 (2H, d, J=8.7 Hz).

F) 2-fluoro-2-methyl-1-(4-(trifluoromethoxy)phenyl) propan-1-amine

A mixture of 1-(1-azido-2-fluoro-2-methylpropyl)-4-(trifluoromethoxy)benzene (1.13 g) and 10% palladium-carbon (containing 50% water, 110 mg) in methanol (7 mL) was stirred at room temperature for 1 hr under hydrogen atmosphere, and the catalyst was filtered off. To the filtrate was added saturated brine, and the mixture was extracted with diethyl ether. The extract was washed successively with water and saturated brine, and dried over anhydrous sodium sulfate, and the solvent was evaporated under reduced pressure to give the title compound (971 mg).

MS (API+): [M+H]$^+$252.1.

G) N-(2-fluoro-2-methyl-1-(4-(trifluoromethoxy) phenyl)propyl)-2-oxo-2,3-dihydropyrido[2,3-b]pyrazine-4(1H)-carboxamide The title compound was obtained from 2-fluoro-2-methyl-1-(4-(trifluoromethoxy)phenyl)propan-1-amine in the same manner as in Step E of Example 168.

MS (API+): [M+H]$^+$427.1.

Example 186

2-oxo-N-(1-(4-(2H-1,2,3-triazol-2-yl)phenyl)propyl)-2,3-dihydropyrido[2,3-b]pyrazine-4(1H)-carboxamide

A) 1-(4-(2H-1,2,3-triazol-2-yl)phenyl)propan-1-one

A mixture of 2-di-tert-butylphosphino-3,4,5,6-tetramethyl-2',4',6'-triisopropyl-1,1'-biphenyl (181 mg) and tris(dibenzylideneacetone)dipalladium(0) (172 mg) in toluene (4 mL) was stirred at 120° C. for 3 min under argon atmosphere. The mixture was added to a mixture of 2H-1,2,3-triazole (389 mg), 1-(4-bromophenyl)propan-1-one (1 g) and tripotassium phosphate (1.99 g) in toluene (15 mL) at room temperature under argon atmosphere. The reaction mixture was heated at reflux for 16 hr under argon atmosphere, water was added thereto, and the mixture was extracted with ethyl acetate. The extract was dried over anhydrous sodium sulfate, and the solvent was evaporated under reduced pressure. The residue was purified by silica gel column chromatography (hexane/ethyl acetate) to give the title compound (858 mg).

$^1$H NMR (300 MHz, DMSO-d$_6$) δ 1.11 (3H, t, J=7.2 Hz), 3.09 (2H, q, J=7.2 Hz), 8.16 (4H, s), 8.21 (2H, s).

B) 2-oxo-N-(1-(4-(2H-1,2,3-triazol-2-yl)phenyl) propyl)-2,3-dihydropyrido[2,3-b]pyrazine-4(1H)-carboxamide The title compound was obtained from 1-(4-(2H-1,2,3-triazol-2-yl)phenyl)propan-1-one in the same manner as in Step C of Example 1, Step B of Example 54 and Step B of Example 53.

MS (API+): [M+H]$^+$378.2.

Example 187

N-(2-fluoro-2-methyl-1-(4-(trifluoromethoxy)phenyl)propyl)-7-methyl-2-oxo-2,3-dihydropyrido[2,3-b]pyrazine-4(1H)-carboxamide The title compound was obtained from 2-fluoro-2-methyl-1-(4-(trifluoromethoxy)phenyl)propan-1-amine in the same manner as in Step E of Example 168.

MS (API+): [M+H]$^+$441.2.

Example 188

N-(1-(3-fluoro-4-(pyrrolidin-1-yl)phenyl)-2-methoxyethyl)-7-methyl-2-oxo-2,3-dihydropyrido[2,3-b]pyrazine-4(1H)-carboxamide

A) 2-bromo-1-(4-bromo-3-fluorophenyl)ethanone

The title compound was obtained from 1-(4-bromo-3-fluorophenyl)ethanone in the same manner as in Step F of. Example 66.

¹H NMR (300 MHz, DMSO-d₆) δ 4.96 (2H, s), 7.77 (1H, dd, J=8.3, 1.9 Hz), 7.90-8.00 (2H, m).

B) 1-(4-bromo-3-fluorophenyl)-2-methoxyethanone

The title compound was obtained from 2-bromo-1-(4-bromo-3-fluorophenyl)ethanone in the same manner as in Step D of Example 63.
¹H NMR (300 MHz, CDCl₃) δ 3.50 (3H, s), 4.62 (2H, s), 7.56-7.76 (3H, m).

C) 2-(4-bromo-3-fluorophenyl)-2-(methoxymethyl)-1,3-dioxolane

A mixture of 1-(4-bromo-3-fluorophenyl)-2-methoxyethanone (1.01 g), p-toluenesulfonic acid monohydrate (77 mg) and 1,2-ethanediol (506 mg) in toluene (20 mL) heated at reflux using Dean-Stark for 5 hr, and the solvent was evaporated under reduced pressure. The residue was purified by silica gel column chromatography (NH, hexane/ethyl acetate) to give the title compound (1.00 g).
¹H NMR (300 MHz, DMSO-d₆) δ 3.24 (3H, s), 3.54 (2H, s), 3.73-3.87 (2H, m), 3.95-4.09 (2H, m), 7.21 (1H, dd, J=8.2, 2.0 Hz), 7.33 (1H, dd, J=9.8, 2.1 Hz), 7.70 (1H, dd, J=8.2, 7.3 Hz).

D) N-(1-(3-fluoro-4-(pyrrolidin-1-yl)phenyl)-2-methoxyethyl)-7-methyl-2-oxo-2,3-dihydropyrido[2,3-b]pyrazine-4(1H)-carboxamide The title compound was obtained from 2-(4-bromo-3-fluorophenyl)-2-(methoxymethyl)-1,3-dioxolane in the same manner as in Step A of Example 147, Step C of Example 1, Step B of Example 54 and Step B of Example 53.
MS (API+): [M+H]⁺428.2.

Example 189

N-(1-(3-fluoro-4-(1H-pyrrol-1-yl)phenyl)-2-methoxyethyl)-7-methyl-2-oxo-2,3-dihydropyrido[2,3-b]pyrazine-4(1H)-carboxamide The title compound was obtained from 2-(4-bromo-3-fluorophenyl)-2-(methoxymethyl)-1,3-dioxolane in the same manner as in Step A of Example 147, Step C of Example 1, Step B of Example 54 and Step B of Example 53.
MS (API+): [M+H]⁺424.2.

Example 190

8-(2-hydroxypropan-2-yl)-N-(2-methoxy-1-(4-(trifluoromethoxy)phenyl)ethyl)-2-oxo-2,3-dihydropyrido[2,3-b]pyrazine-4(1H)-carboxamide A) 2-chloro-3-nitroisonicotine acid The title compound was obtained from 2-chloro-4-methyl-3-nitropyridine in the same manner as in Step A of Example 167.
MS (API−): [M−H]⁻201.0.

B) methyl 2-chloro-3-nitroisonicotinate

To a mixture of 2-chloro-3-nitroisonicotine acid (2.03 g) and thionyl chloride (21.9 mL) was added N,N-dimethylformamide (two drops). The reaction mixture was stirred at 70° C. for 15 min, and the solvent was evaporated under reduced pressure. To the residue was added methanol (10 mL) at 0° C., and the reaction mixture was stirred at 0° C. for 10 min, and the solvent was evaporated under reduced pressure. The residue was purified by silica gel column chromatography (hexane/ethyl acetate) to give the title compound (2.15 g).
¹H NMR (300 MHz, CDCl₃) δ 3.97 (3H, s), 7.86 (1H, d, J=5.1 Hz), 8.68 (1H, d, J=4.9 Hz).

C) methyl 4-((2-methoxy-1-(4-(trifluoromethoxy)phenyl)ethyl) carbamoyl)-2-oxo-1,2,3,4-tetrahydropyrido[2,3-b]pyrazine-8-carboxylate The title compound was obtained from methyl 2-chloro-3-nitroisonicotinate in the same manner as in Steps A-B of Example 1 and Steps C-D of Example 19.
MS (API+): [M+H]⁺469.2.

D) 8-(2-hydroxypropan-2-yl)-N-(2-methoxy-1-(4-(trifluoromethoxy)phenyl)ethyl)-2-oxo-2,3-dihydropyrido[2,3-b]pyrazine-4(1H)-carboxamide To a solution of methyl 4-((2-methoxy-1-(4-(trifluoromethoxy)phenyl)ethyl)carbamoyl)-2-oxo-1,2,3,4-tetrahydropyrido[2,3-b]pyrazine-8-carboxylate (234 mg) in tetrahydrofuran (5 mL) was added 1 M methylmagnesium bromide/tetrahydrofuran solution (10 mL) at room temperature. The reaction mixture was stirred at room temperature for 20 hr, 1 M hydrochloric acid was added thereto at 0° C., and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate), and recrystallized from hexane/ethyl acetate to give the title compound (47 mg).
MS (API+): [M+H]⁺ 469.2.

Example 191

8-acetyl-N-(2-methoxy-1-(4-(trifluoromethoxy)phenyl)ethyl)-2-oxo-2,3-dihydropyrido[2,3-b]pyrazine-4(1H)-carboxamide To a solution of methyl 4-((2-methoxy-1-(4-(trifluoromethoxy)phenyl)ethyl)carbamoyl)-2-oxo-1,2,3,4-tetrahydropyrido[2,3-b]pyrazine-8-carboxylate (234 mg) in tetrahydrofuran (5 mL) was added 1 M methylmagnesium bromide/tetrahydrofuran solution (10 mL) at room temperature. The reaction mixture was stirred at room temperature for 20 hr, 1 M hydrochloric acid was added thereto at 0° C., and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate), and recrystallized from hexane/ethyl acetate to give the title compound (22 mg).
MS (API+): [M+H]⁺ 453.1.

Example 192

8-(hydroxymethyl)-N-(2-methoxy-1-(4-(trifluoromethoxy)phenyl)ethyl)-2-oxo-2,3-dihydropyrido[2,3-b]pyrazine-4(1H)-carboxamide

A) 4-((2-methoxy-1-(4-(trifluoromethoxy)phenyl)ethyl) carbamoyl)-2-oxo-1,2,3,4-tetrahydropyrido[2,3-b]pyrazine-8-carboxylic acid To a mixture of methyl 4-((2-methoxy-1-(4-(trifluoromethoxy)phenyl)ethyl)carbamoyl)-2-oxo-1,2,3,4-tetrahydropyrido[2,3-b]pyrazine-8-carboxylate (468 mg) in tetrahydrofuran (10 mL) and methanol (2.0 mL) was added 1 M aqueous sodium hydroxide solution (2.0 mL). The reaction mixture was stirred for 1 hr, and neutralized with 1 M hydrochloric acid, and the mixture was extracted with ethyl acetate. The extract was washed successively with water and saturated brine, and dried over anhydrous magnesium sulfate, and the solvent was evaporated under reduced pressure to give the title compound (452 mg).

MS (API+): [M+H]$^+$ 455.1.

B) 8-(hydroxymethyl)-N-(2-methoxy-1-(4-(trifluoromethoxy)phenyl)ethyl)-2-oxo-2,3-dihydropyrido[2,3-b]pyrazine-4(1H)-carboxamide To a solution of 4-((2-methoxy-1-(4-(trifluoromethoxy)phenyl)ethyl)carbamoyl)-2-oxo-1,2,3,4-tetrahydropyrido[2,3-b]pyrazine-8-carboxylic acid (445 mg) in tetrahydrofuran (10 mL) were added isobutyl chloroformate (0.153 mL) and triethylamine (0.205 mL). The reaction mixture was stirred at room temperature for 1 hr, and the insoluble substance was filtered off. To the filtrate was added an aqueous solution (1 mL) of sodium borohydride (74.1 mg). The reaction mixture was stirred for 1 hr, water was added thereto, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate), and recrystallized from hexane/ethyl acetate to give the title compound (13 mg).

MS (API+): [M+H]$^+$ 441.2.

Example 193

N-(2-ethyl-2-hydroxy-1-(4-(trifluoromethoxy)phenyl)butyl)-2-oxo-2,3-dihydropyrido[2,3-b]pyrazine-4(1H)-carboxamide

A) tert-butyl (2-oxo-1-(4-(trifluoromethoxy)phenyl)butyl)carbamate

To a solution of tert-butyl (2-(methoxy(methyl)amino)-2-oxo-1-(4-(trifluoromethoxy)phenyl)ethyl)carbamate (355 mg) in tetrahydrofuran (20 mL) was added 3 M ethylmagnesium bromide/diethyl ether solution (5.0 mL) at room temperature. The reaction mixture was stirred at room temperature for 20 hr, 1 M hydrochloric acid was added thereto, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate) to give the title compound (254 mg).

$^1$H NMR (300 MHz, CDCl$_3$) δ 1.00 (3H, t, J=7.3 Hz), 1.40 (9H, s), 2.29-2.49 (2H, m), 5.30 (1H, d, J=6.0 Hz), 5.91-6.01 (1H, m), 7.17-7.24 (2H, m), 7.30-7.37 (2H, m).

B) tert-butyl (2-ethyl-2-hydroxy-1-(4-(trifluoromethoxy)phenyl)butyl)carbamate To a solution of tert-butyl (2-oxo-1-(4-(trifluoromethoxy)phenyl)butyl)carbamate (320 mg) in tetrahydrofuran (10 mL) was added 3 M ethylmagnesium bromide/diethyl ether solution (5.0 mL) at 0° C. The reaction mixture was stirred at room temperature for 20 hr, 1 M hydrochloric acid was added thereto at 0° C., and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate) to give the title compound (170 mg).

MS (API−): [M−H]$^-$ 376.2.

C) N-(2-ethyl-2-hydroxy-1-(4-(trifluoromethoxy)phenyl)butyl)-2-oxo-2,3-dihydropyrido[2,3-b]pyrazine-4(1H)-carboxamide To tert-butyl (2-ethyl-2-hydroxy-1-(4-(trifluoromethoxy)phenyl)butyl)carbamate (170 mg) was added 4 M hydrogen chloride/ethyl acetate solution (5 mL) at room temperature. The reaction mixture was stirred at room temperature for 20 min, and the solvent was evaporated under reduced pressure. To a mixture of the residue and 4-nitrophenyl 2-oxo-2,3-dihydropyrido[2,3-b]pyrazine-4(1H)-carboxylate (128 mg) in N,N-dimethylformamide (5 mL) was added triethylamine (0.170 mL). The reaction mixture was stirred at room temperature for 20 hr, water was added thereto, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate), and recrystallized from hexane/ethyl acetate to give the title compound (161 mg).

MS (API+): [M+H]$^+$ 453.2.

Example 194

N-(2-amino-1-(4-(trifluoromethoxy)phenyl)ethyl)-2-oxo-2,3-dihydropyrido[2,3-b]pyrazine-4(1H)-carboxamide To a solution of N-(2-(1,3-dioxo-1,3-dihydro-2H-isoindol-2-yl)-1-(4-(trifluoromethoxy)phenyl)ethyl)-2-oxo-2,3-dihydropyrido[2,3-b]pyrazine-4(1H)-carboxamide (285 mg) in ethanol (15 mL) was added hydrazine monohydrate (0.211 mL) at room temperature. The reaction mixture was stirred at 80° C. for 3 hr, and the solvent was evaporated under reduced pressure. To the residue was added 1 M aqueous sodium hydroxide solution, and the mixture was purified by styrene/divinyl benzene synthetic adsorbent (HP-20, mobile phase: water-acetonitrile). The residue was purified by preparative HPLC (C18, mobile phase: water (10 mM, containing NH$_4$HCO$_3$)/acetonitrile), and the obtained fraction was concentrated under reduced pressure. The obtained solid was triturated with hexane/ethyl acetate, collected by filtration, and washed with hexane/ethyl acetate to give the title compound (151 mg).

MS (API+): [M+H]$^+$396.1.

Example 195

N-((4-bromo-2-fluorophenyl) (4-(trifluoromethoxy)phenyl)methyl)-7-methyl-2-oxo-2,3-dihydropyrido[2,3-b]pyrazine-4(1H)-carboxamide A)
4-bromo-2-fluoro-N-methoxy-N-methylbenzamide The title compound was obtained from 4-bromo-2-fluorobenzoic acid in the same manner as in Step A of Example 31.
MS (API+): [M+H]$^+$262.0.

B) (4-bromo-2-fluorophenyl)(4-(trifluoromethoxy)phenyl)methanone

To a solution of 4-bromo-2-fluoro-N-methoxy-N-methylbenzamide (10.8 g) in tetrahydrofuran (150 mL) was added 0.5 M (4-(trifluoromethoxy)phenyl)magnesium bromide/tetrahydrofuran solution (165 mL) at room temperature. The reaction mixture was stirred overnight at 70° C. under nitrogen atmosphere, saturated aqueous ammonium chloride solution was added thereto, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (11.6 g).
MS (API+): [M+H]$^+$363.0.

C) N-((4-bromo-2-fluorophenyl)(4-(trifluoromethoxy)phenyl)methyl)-7-methyl-2-oxo-2,3-dihydropyrido[2,3-b]pyrazine-4(1H)-carboxamide The title compound was obtained from (4-bromo-2-fluorophenyl)(4-(trifluoromethoxy)phenyl)methanone in the same manner as in Step D of Example 2, Step B of Example 132 and Step B of Example 83.
MS (API+): [M+H]$^+$ 553.1.

Example 196

N-((4-bromo-2-hydroxyphenyl) (4-(trifluoromethoxy)phenyl)methyl)-7-methyl-2-oxo-2,3-dihydropyrido[2,3-b]pyrazine-4(1H)-carboxamide The title compound was obtained from 4-bromo-2-fluorobenzoic acid in the same manner as in Step A of Example 31, Step B of Example 195, Step D of Example 2, Step B of Example 132 and Step B of Example 83.
MS (API+): [M+H]$^+$551.1.

Example 197

N-(2-((5-bromopyridin-3-yl)oxy)-1-(4-(trifluoromethoxy)phenyl)ethyl)-7-methyl-2-oxo-2,3-dihydropyrido[2,3-b]pyrazine-4(1H)-carboxamide The title compound was obtained in the same manner as in Step A of Example 181, Step D of Example 2, Step B of Example 132 and Step G of Example 7.
MS (API+): [M+H]$^+$566.1.

Example 198

N-((2-fluorophenyl) (4-(trifluoromethoxy)phenyl)methyl)-7-methyl-2-oxo-2,3-dihydropyrido[2,3-b]pyrazine-4(1H)-carboxamide A mixture of N-((4-bromo-2-fluorophenyl) (4-(trifluoromethoxy)phenyl)methyl)-7-methyl-2-oxo-2,3-dihydropyrido[2,3-b]pyrazine-4(1H)-carboxamide (60 mg), 5% palladium-carbon (containing 50% water, 15 mg) and methanol (5 mL) was stirred for 2 hr under hydrogen atmosphere. The catalyst was filtered off, and the filtrate was concentrated under reduced pressure to give the title compound (35.6 mg).
MS (API+): [M+H]$^+$475.2.

Example 199

N-((2-hydroxyphenyl) (4-(trifluoromethoxy)phenyl)methyl)-7-methyl-2-oxo-2,3-dihydropyrido[2,3-b]pyrazine-4(1H)-carboxamide The title compound was obtained from N-((4-bromo-2-hydroxyphenyl) (4-(trifluoromethoxy)phenyl)methyl)-7-methyl-2-oxo-2,3-dihydropyrido[2,3-b]pyrazine-4(1H)-carboxamide in the same manner as in Example 198.
MS (API+): [M+H]$^+$473.2.

Example 200

7-methyl-2-oxo-N-(tetrahydrofuran-2-yl(4-(trifluoromethoxy)phenyl)methyl)-2,3-dihydropyrido[2,3-b]pyrazine-4(1H)-carboxamide A diastereomeric mixture (110 mg) of 7-methyl-2-oxo-N-(tetrahydrofuran-2-yl(4-(trifluoromethoxy)phenyl)methyl)-2,3-dihydropyrido[2,3-b]pyrazine-4(1H)-carboxamide was resolved by HPLC (column: CHIRALPAK IA, 50 mmID×500 mmL, manufactured by Daicel Chemical Industries, Ltd., mobile phase: hexane/2-propanol=70/30) to give the title compound having a shortest retention time (28 mg).
MS (API+): [M+H]$^+$451.2.

Example 201

7-methyl-2-oxo-N-(tetrahydrofuran-2-yl(4-(trifluoromethoxy)phenyl)methyl)-2,3-dihydropyrido[2,3-b]pyrazine-4(1H)-carboxamide A diastereomeric mixture (110 mg) of 7-methyl-2-oxo-N-(tetrahydrofuran-2-yl(4-(trifluoromethoxy)phenyl)methyl)-2,3-dihydropyrido[2,3-b]pyrazine-4(1H)-carboxamide was resolved by HPLC (column: CHIRALPAK IA, 50 mmID×500 mmL, manufactured by Daicel Chemical Industries, Ltd., mobile phase: hexane/2-propanol=70/30) to give the title compound having a second shortest retention time (16 mg).
MS (API+): [M+H]$^+$451.2.

Example 202

7-methyl-2-oxo-N-(tetrahydrofuran-2-yl(4-(trifluoromethoxy)phenyl)methyl)-2,3-dihydropyrido[2,3-b]pyrazine-4(1H)-carboxamide A diastereomeric mixture (110 mg) of 7-methyl-2-oxo-N-(tetrahydrofuran-2-yl(4-(trifluoromethoxy)phenyl)

methyl)-2,3-dihydropyrido[2,3-b]pyrazine-4(1H)-carboxamide was resolved by HPLC (column: CHIRALPAK IA, 50 mmID×500 mmL, manufactured by Daicel Chemical Industries, Ltd., mobile phase: hexane/2-propanol=70/30) to give the title compound having a third shortest retention time (33 mg).

MS (API+): [M+H]$^+$451.2.

Example 203

7-methyl-2-oxo-N-(tetrahydrofuran-2-yl(4-(trifluoromethoxy)phenyl)methyl)-2,3-dihydropyrido[2,3-b]pyrazine-4(1H)-carboxamide A diastereomeric mixture (110 mg) of 7-methyl-2-oxo-N-(tetrahydrofuran-2-yl(4-(trifluoromethoxy)phenyl) methyl)-2,3-dihydropyrido[2,3-b]pyrazine-4(1H)-carboxamide was resolved by HPLC (column: CHIRALPAK IA, 50 mmID×500 mmL, manufactured by Daicel Chemical Industries, Ltd., mobile phase: hexane/2-propanol=70/30) to give the title compound having a longest retention time (14 mg).

MS (API+): [M+H]$^+$451.2.

Example 204

7-methoxy-2-oxo-N-(1-(4-(pyrrolidin-1-yl)phenyl) propyl)-2,3-dihydropyrido[2,3-b]pyrazine-4(1H)-carboxamide The title compound was obtained from 1-(4-(1H-pyrrol-1-yl)phenyl)propan-1-amine in the same manner as in Steps I-L of Example 66.

MS (API−): [M−H]$^−$408.2.

Example 205

N-(2-hydroxy-2-methyl-1-(4-(trifluoromethoxy)phenyl)propyl)-7-methoxy-2-oxo-2,3-dihydropyrido[2,3-b]pyrazine-4(1H)-carboxamide A) methyl N-(5-iodo-3-nitropyridin-2-yl)glycinate To a solution of 2-chloro-5-iodo-3-nitropyridine (12.0 g) in ethanol (200 mL) were added methyl glycinate hydrochloride (10.6 g) and triethylamine (11.8 mL) at room temperature. The reaction mixture was heated at reflux for 20 hr, and the solvent was evaporated under reduced pressure. To the residue was added water, and the mixture was extracted with ethyl acetate. The extract was washed successively with water and saturated brine, and dried over anhydrous magnesium sulfate, and the solvent was evaporated under reduced pressure. The residue was crystallized from hexane/ethyl acetate to give the title compound (11.1 g).

MS (API+): [M+H]$^+$338.0.

B) 7-iodo-3,4-dihydropyrido[2,3-b]pyrazin-2(1H)-one

To a solution of methyl N-(5-iodo-3-nitropyridin-2-yl) glycinate (6.00 g) in tetrahydrofuran (300 mL) was added 5% platinum-carbon (500 mg). The reaction mixture was stirred overnight at room temperature under hydrogen atmosphere, the catalyst was filtered off, and the filtrate was concentrated under reduced pressure. The residue was dissolved in ethanol (200 mL), the solution was heated at reflux for 16 hr, and the solvent was evaporated under reduced pressure. The residue was washed with diisopropyl ether to give the title compound (4.48 g).

MS (API+): [M+H]$^+$276.0.

C) 7-iodo-1-((2-(trimethylsilyl)ethoxy)methyl)-3,4-dihydropyrido[2,3-b]pyrazin-2(1H)-one To a suspension of 7-iodo-3,4-dihydropyrido[2,3-b] pyrazin-2(1H)-one (3.82 g) in N,N-dimethylformamide (160 mL) was slowly added 1 M potassium hexamethyldisilazide/ tetrahydrofuran solution (17.4 mL) at 0° C. The reaction mixture was stirred at 0° C. for 1 hr, 2-(chloromethoxy) ethyltrimethylsilane (3.62 mL) was slowly added thereto, and the mixture was stirred at room temperature for 20 hr. To the reaction mixture was added water, the insoluble substance was filtered off using Celite, and the filtrate was extracted with ethyl acetate. The extract was washed successively with water and saturated brine, and dried over anhydrous magnesium sulfate, and the solvent was evaporated under reduced pressure. The residue was purified by silica gel column chromatography (NH, hexane/ethyl acetate) to give the title compound (2.71 g).

MS (API+): [M+H]$^+$406.0.

D) methyl 2-((tert-butoxycarbonyl) amino)-2-(4-(trifluoromethoxy)phenyl)acetate

To a mixture of 4-trifluoromethoxybenzaldehyde (19.0 g) and ammonium carbonate (25.9 g) in a mixed solvent of ethanol (114 mL) and water (45.6 mL) was slowly added an aqueous solution (71.1 mL) of potassium cyanide (8.14 g) at 50° C. The reaction mixture was stirred at 60° C. for 3 hr, and cooled to room temperature, and the ethanol was evaporated under reduced pressure. The pH of the residue was adjusted to 1 with conc. hydrochloric acid at 0° C., and the resulting solid was collected by filtration, and washed with water. The obtained solid was added to an aqueous solution (100 mL) of potassium hydroxide (23.6 g) at room temperature, and the reaction mixture was stirred at 90° C. for 3 days. The reaction mixture was cooled to room temperature, and neutralized with conc. hydrochloric acid. The resulting solid was collected by filtration, and washed with water to give a crude product (13.3 g) of 2-amino-2-(4-(trifluoromethoxy)phenyl)acetic acid. To a solution of the obtained crude product (13.3 g) in tetrahydrofuran (113 mL) were added di-tert-butyl dicarbonate (19.7 mL) and 2 M aqueous sodium hydroxide solution (85 mL) at room temperature. The reaction mixture was stirred overnight at room temperature, and poured into water, and the mixture was washed with diethyl ether. The pH of the aqueous layer was adjusted to 3 with 1 M hydrochloric acid at 0° C., and the mixture was extracted with ethyl acetate. The extract was washed with saturated brine, and dried over anhydrous magnesium sulfate, and the solvent was evaporated under reduced pressure to give a crude product (11.3 g) of 2-((tert-butoxycarbonyl) amino)-2-(4-(trifluoromethoxy)phenyl)acetic acid. To a solution of the obtained crude product (11.3 g) in N,N-dimethylformamide (84 mL) were added methyl iodide (2.53 mL) and potassium carbonate (5.59 g) at room temperature. The reaction mixture was stirred at room temperature for 2 hr, and poured into water, and the mixture was extracted with ethyl acetate. The extract was washed with saturated brine, and dried over anhydrous magnesium sulfate, and the solvent was evaporated under reduced pressure.

The residue was purified by silica gel column chromatography (hexane/ethyl acetate) to give the title compound (8.20 g).

MS (API−): [M−H]⁻348.1.

E) tert-butyl (2-hydroxy-2-methyl-1-(4-(trifluoromethoxy)phenyl)propyl)carbamate To a solution of methyl 2-((tert-butoxycarbonyl)amino)-2-(4-(trifluoromethoxy)phenyl)acetate (5.00 g) in tetrahydrofuran (71.6 mL) was slowly added 1 M methylmagnesium bromide/tetrahydrofuran solution (57.3 mL) at 0° C. The reaction mixture was stirred at 0° C. for 1 hr under argon atmosphere, saturated aqueous ammonium chloride solution was added thereto at 0° C., and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (3.99 g).

MS (API−): [M−H]⁻348.2.

F) 1-amino-2-methyl-1-(4-(trifluoromethoxy)phenyl)propan-2-ol hydrochloride

To tert-butyl (2-hydroxy-2-methyl-1-(4-(trifluoromethoxy)phenyl)propyl)carbamate (2.50 g) was added 4 M hydrogen chloride/ethyl acetate solution (71.6 mL). The reaction mixture was stirred at room temperature for 1 hr, and the solvent was evaporated under reduced pressure. To the residue was added diisopropyl ether, and the resulting crystals were collected by filtration to give the title compound (2.01 g).

MS (API+), found: 250.1.

G) N-(2-hydroxy-2-methyl-1-(4-(trifluoromethoxy)phenyl)propyl)-7-iodo-2-oxo-1-((2-(trimethylsilyl)ethoxy)methyl)-2,3-dihydropyrido[2,3-b]pyrazine-4(1H)-carboxamide To a solution of 7-iodo-1-((2-(trimethylsilyl)ethoxy)methyl)-3,4-dihydropyrido[2,3-b]pyrazin-2(1H)-one (500 mg) in tetrahydrofuran (18.9 mL) was slowly added a solution of bis(trichloromethyl)carbonate (293 mg) in tetrahydrofuran (2.83 mL) at room temperature under nitrogen atmosphere. The reaction mixture was stirred at 40° C. for 3 hr under nitrogen atmosphere, and the solvent was evaporated under reduced pressure. To the residue was added tetrahydrofuran, and the solvent was evaporated under reduced pressure. The operation (addition of tetrahydrofuran and then evaporation) was repeated three times. The residue was diluted with tetrahydrofuran (9.42 mL), and the mixture was slowly added to a mixture of 1-amino-2-methyl-1-(4-(trifluoromethoxy)phenyl)propan-2-ol hydrochloride (423 mg) and triethylamine (521 μL) in tetrahydrofuran (6.28 mL) at room temperature. The reaction mixture was stirred at 60° C. overnight, and the solvent was evaporated under reduced pressure. To the residue was added water, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give the title compound (729 mg).

MS (API+): [M+11]⁺ 681.1.

H) 7-hydroxy-N-(2-hydroxy-2-methyl-1-(4-(trifluoromethoxy)phenyl)propyl)-2-oxo-1-((2-(trimethylsilyl)ethoxy)methyl)-2,3-dihydropyrido[2,3-b]pyrazine-4(1H)-carboxamide To a mixture of N-(2-hydroxy-2-methyl-1-(4-(trifluoromethoxy)phenyl)propyl)-7-iodo-2-oxo-1-((2-(trimethylsilyl)ethoxy)methyl)-2,3-dihydropyrido[2,3-b]pyrazine-4(1H)-carboxamide (699 mg), 4,4,4',4',5,5,5',5'-octamethyl-2,2'-bi-1,3,2-dioxaborolane (537 mg) and potassium acetate (415 mg) in N,N-dimethylformamide (10.3 mL) was added (1,1-bis(diphenylphosphino)ferrocene)dichloropalladium (II) (77.0 mg). The reaction mixture was stirred overnight at 80° C. under argon atmosphere, water was added thereto, and the mixture was extracted with ethyl acetate. The extract was washed successively with water and saturated brine, and dried over anhydrous sodium sulfate, and the solvent was evaporated under reduced pressure to give a crude product (986 mg) of N-(2-hydroxy-2-methyl-1-(4-(trifluoromethoxy)phenyl)propyl)-2-oxo-7-(4,4,5,5-tetramethyl-1,3-2-dioxaborolan-2-yl-1-((2-(trimethylsilyl)ethoxy)methyl)-2,3-dihydropyrido[2,3-b]pyrazine-4(1H)-carboxamide. To a solution of the obtained crude product (986 mg) in tetrahydrofuran (14.5 mL) was added 2 M aqueous sodium hydroxide solution (2.90 mL) at 0° C. The reaction mixture was stirred at 0° C. for 30 min, 35% aqueous hydrogen peroxide (508 μL) was added thereto. The reaction mixture was stirred at room temperature for 2 hr, ice water was added thereto, and the mixture was acidified with 1 M hydrochloric acid, and extracted with ethyl acetate. The extract was washed successively with water and saturated brine, and dried over anhydrous sodium sulfate, and the solvent was evaporated under reduced pressure. The residue was purified by silica gel column chromatography (hexane/ethyl acetate) to give the title compound (340 mg).

MS (API+): [M+H]⁺571.2.

I) N-(2-hydroxy-2-methyl-1-(4-(trifluoromethoxy)phenyl)propyl)-7-methoxy-2-oxo-1-((2-(trimethylsilyl)ethoxy)methyl)-2,3-dihydropyrido[2,3-b]pyrazine-4(1H)-carboxamide To a solution of 7-hydroxy-N-(2-hydroxy-2-methyl-1-(4-(trifluoromethoxy)phenyl)propyl)-2-oxo-1-((2-(trimethylsilyl)ethoxy)methyl)-2,3-dihydropyrido[2,3-b]pyrazine-4(1H)-carboxamide (340 mg) in N,N-dimethylformamide (7.64 mL) were added potassium carbonate (83.0 mg) and iodomethane (56.1 μL). The reaction mixture was stirred overnight at room temperature, water was added thereto, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) and then HPLC (C18, mobile phase: water (10 mM, containing NH₄HCO₃)/acetonitrile), and the obtained fraction was concentrated under reduced pressure to give the title compound (91.0 mg).

MS (API+): [M+H]⁺585.3.

J) N-(2-hydroxy-2-methyl-1-(4-(trifluoromethoxy)phenyl)propyl)-7-methoxy-2-oxo-2,3-dihydropyrido[2,3-b]pyrazine-4(1H)-carboxamide To N-(2-hydroxy-2-methyl-1-(4-(trifluoromethoxy)phenyl)propyl)-7-methoxy-2-oxo-1-((2-(trimethylsilyl)ethoxy)methyl)-2,3-dihydropyrido[2,3-b]pyrazine-4(1H)-carboxamide (90.9 mg) were added trifluoroacetic acid (2.24 mL) and water (251 µL). The reaction mixture was stirred at room temperature for 1 hr, and the solvent was evaporated under reduced pressure. The residue was dissolved in N,N-dimethylformamide (4.27 mL), and 8 M ammonia/methanol solution (838 µL) was added thereto. The reaction mixture was stirred at room temperature for 10 min, and the solvent was evaporated under reduced pressure. The residue was diluted with ethyl acetate, and the mixture was washed successively with water and saturated brine, and dried over anhydrous sodium sulfate, and the solvent was evaporated under reduced pressure. The obtained solid was washed with hexane/ethyl acetate to give the title compound (48.8 mg).

MS (API+): [M+H]$^+$455.3.

$^1$H NMR (300 MHz, DMSO-d$_6$) δ 0.98 (3H, s), 1.18 (3H, s), 3.84 (3H, s), 4.25-4.49 (2H, m), 4.67 (1H, d, J=8.3 Hz), 4.77 (1H, s), 6.96 (1H, d, J=2.6 Hz), 7.27 (2H, d, J=7.9 Hz), 7.42 (2H, d, J=8.7 Hz), 7.76 (1H, d, J=2.6 Hz), 10.19 (1H, d, J=8.3 Hz), 10.73 (1H, brs).

Example 206

7-methyl-2-oxo-N-(tetrahydrofuran-3-yl(4-(trifluoromethoxy)phenyl)methyl)-2,3-dihydropyrido[2,3-b]pyrazine-4(1H)-carboxamide The title compound was obtained from tetrahydrofuran-3-carboxylic acid in the same manner as in Step A of Example 170, Step D of Example 2, Step B of Example 132 and Step G of Example 7.

MS (API+): [M+H]$^+$451.2.

Example 207

N-((1S)-2-hydroxy-2-methyl-1-(4-(trifluoromethoxy)phenyl)propyl)-7-methoxy-2-oxo-2,3-dihydropyrido[2,3-b]pyrazine-4(1H)-carboxamide Racemic N-(2-hydroxy-2-methyl-1-(4-(trifluoromethoxy)phenyl)propyl)-7-methoxy-2-oxo-2,3-dihydropyrido[2,3-b]pyrazine-4(1H)-carboxamide (43.8 mg) was resolved by SFC (column: CHIRALPAK ADH, 20 mmID× 250 mmL, manufactured by Daicel Chemical Industries, Ltd., mobile phase: carbon dioxide/methanol=800/200), and crystallized from hexane/ethyl acetate to give the title compound having a shorter retention time (5.4 mg).

MS (API+): [M+H]$^+$455.2.

$^1$H NMR (300 MHz, DMSO-d$_6$) δ 0.98 (3H, s), 1.18 (3H, s), 3.84 (3H, s), 4.20-4.50 (2H, m), 4.67 (1H, d, J=8.3 Hz), 4.77 (1H, s), 6.96 (1H, d, J=3.0 Hz), 7.27 (2H, d, J=7.9 Hz), 7.42 (2H, d, J=8.7 Hz), 7.76 (1H, d, J=2.6 Hz), 10.19 (1H, d, J=8.3 Hz), 10.73 (1H, brs).

Example 208

N-((1R)-2-hydroxy-2-methyl-1-(4-(trifluoromethoxy)phenyl)propyl)-7-methoxy-2-oxo-2,3-dihydropyrido[2,3-b]pyrazine-4(1H)-carboxamide Racemic N-(2-hydroxy-2-methyl-1-(4-(trifluoromethoxy)phenyl)propyl)-7-methoxy-2-oxo-2,3-dihydropyrido[2,3-b]pyrazine-4(1H)-carboxamide (43.8 mg) was resolved by SFC (column: CHIRALPAK ADH, 20 mmID× 250 mmL, manufactured by Daicel Chemical Industries, Ltd., mobile phase: carbon dioxide/methanol=800/200), and crystallized from hexane/ethyl acetate to give the title compound having a longer retention time (5.2 mg).

MS (API+): [M+H]$^+$455.1.

Example 209

7-cyclopropyl-N-(1-(3-fluoro-4-(trifluoromethyl)phenyl)-2-methoxyethyl)-2-oxo-2,3-dihydropyrido[2,3-b]pyrazine-4(1H)-carboxamide A) 1-(3-fluoro-4-(trifluoromethyl)phenyl)-2-methoxyethanone The title compound was obtained from 2-bromo-1-(3-fluoro-4-(trifluoromethyl)phenyl)ethanone in the same manner as in Step D of Example 63.

MS (API−): [M−H]$^-$235.0.

B) 1-(3-fluoro-4-(trifluoromethyl)phenyl)-2-methoxyethanamine hydrochloride

The title compound was obtained from 1-(3-fluoro-4-(trifluoromethyl)phenyl)-2-methoxyethanone in the same manner as in Step E of Example 63.

MS (API+), found: 238.1.

C) N-(1-(3-fluoro-4-(trifluoromethyl)phenyl)-2-methoxyethyl)-7-iodo-2-oxo-1-((2-(trimethylsilyl)ethoxy)methyl)-2,3-dihydropyrido[2,3-b]pyrazine-4(1H)-carboxamide The title compound was obtained from 1-(3-fluoro-4-(trifluoromethyl)phenyl)-2-methoxyethanamine hydrochloride in the same manner as in Step F of Example 63.

MS (API+): [M+H]$^+$669.1.

D) 7-cyclopropyl-N-(1-(3-fluoro-4-(trifluoromethyl)phenyl)-2-methoxyethyl)-2-oxo-1-((2-(trimethylsilyl)ethoxy)methyl)-2,3-dihydropyrido[2,3-b]pyrazine-4(1H)-carboxamide The title compound was obtained from N-(1-(3-fluoro-4-(trifluoromethyl)phenyl)-2-methoxyethyl)-7-iodo-2-oxo-1-((2-(trimethylsilyl)ethoxy)methyl)-2,3-dihydropyrido[2,3-b]pyrazine-4(1H)-carboxamide in the same manner as in Step H of Example 72-II.

MS (API+): [M+H]$^+$583.2.

E) 7-cyclopropyl-N-(1-(3-fluoro-4-(trifluoromethyl)phenyl)-2-methoxyethyl)-2-oxo-2,3-dihydropyrido[2,3-b]pyrazine-4(1H)-carboxamide The title compound was obtained from 7-cyclopropyl-N-(1-(3-fluoro-4-(trifluoromethyl)phenyl)-2-methoxyethyl)-2-oxo-1-((2-(trimethylsilyl)ethoxy)methyl)-2,3-dihydropyrido[2,3-b]pyrazine-4(1H)-carboxamide in the same manner as in Step I of Example 72-11.

MS (API+): [M+H]$^+$453.1.

Example 210

7-methyl-2-oxo-N-(3,3,3-trifluoro-2-hydroxy-1-(4-(trifluoromethoxy)phenyl)propyl)-2,3-dihydropyrido[2,3-b]pyrazine-4(1H)-carboxamide A) (4-(trifluoromethoxy)phenyl)acetaldehyde To a mixture of 2-(4-(trifluoromethoxy)phenyl)ethanol (2.00 g) and sodium hydrogen carbonate (8.15 g) in acetonitrile (150 mL) was added Dess-Martin periodinane (8.23 g) at 0° C. The reaction mixture was stirred at 0° C. for 1 hr, saturated brine was added thereto, and the mixture was extracted with ethyl acetate. The extract was washed successively with saturated aqueous sodium hydrogen carbonate solution and saturated brine, and dried over anhydrous magnesium sulfate, and the solvent was evaporated under reduced pressure. The residue was purified by silica gel column chromatography (ethyl acetate) to give the title compound (1.72 g).

$^1$H NMR (300 MHz, CDCl$_3$) δ 3.72 (2H, d, J=1.9 Hz), 6.84-7.39 (4H, m), 9.77 (1H, t, J=2.1 Hz).

B) 1,1,1-trifluoro-3-(4-(trifluoromethoxy)phenyl)propan-2-ol

To a mixture of (4-(trifluoromethoxy)phenyl)acetaldehyde (800 mg) and trimethyl(trifluoromethyl)silane (2.79 g) in tetrahydrofuran (10 mL) was added 1 M tetra-n-butylammonium fluoride/tetrahydrofuran solution (7.84 mL) at 0° C. The reaction mixture was stirred at 0° C. for 2 hr, 1 M hydrochloric acid was added thereto, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (761 mg).

$^1$H NMR (300 MHz, CDCl$_3$) δ 2.13 (1H, d, J=5.7 Hz), 2.80-2.94 (1H, m), 2.97-3.11 (1H, m), 4.01-4.31 (1H, m), 7.04-7.24 (2H, m), 7.27-7.36 (2H, m).

C) tert-butyl(dimethyl)((1,1,1-trifluoro-3-(4-(trifluoromethoxy)phenyl)propan-2-yl)oxy)silane A mixture of 1,1,1-trifluoro-3-(4-(trifluoromethoxy)phenyl)propan-2-ol (750 mg), tert-butyldimethylsilyl trifluoromethanesulfonate (1.09 g), 2,6-dimethylpyridine (586 mg) and tetrahydrofuran (5 mL) was stirred at 0° C. for 2 hr. The reaction mixture was added to saturated aqueous sodium hydrogen carbonate solution, and the mixture was extracted with ethyl acetate. The extract was washed successively with 1 M hydrochloric acid and saturated aqueous sodium hydrogen carbonate solution, and dried over anhydrous magnesium sulfate, and the solvent was evaporated under reduced pressure. The residue was purified by silica gel column chromatography (hexane/ethyl acetate) to give the title compound (434 mg).

$^1$H NMR (300 MHz, CDCl$_3$) δ −0.48 (3H, s), −0.05 (3H, s), 0.72-0.79 (9H, m), 2.80 (1H, dd, J=13.8, 10.0 Hz), 3.03 (1H, dd, J=13.8, 2.8 Hz), 3.93-4.25 (1H, m), 7.07-7.20 (2H, m), 7.21-7.25 (2H, m).

D) ((3-bromo-1,1,1-trifluoro-3-(4-(trifluoromethoxy)phenyl)propan-2-yl)oxy)(tert-butyl)dimethylsilane A mixture of tert-butyl(dimethyl) ((1,1,1-trifluoro-3-(4-(trifluoromethoxy)phenyl)propan-2-yl)oxy)silane (165 mg), 2,2'-(diazene 1,2-diyl)bis(2-methylpropanenitrile) (6.98 mg), 1-bromopyrrolidine-2,5-dione (98 mg) and benzotrifluoride (5 mL) was stirred overnight at 130° C., were added 1-bromopyrrolidine-2,5-dione (227 mg) and 2,2'-(diazene-1,2-diyl)bis(2-methylpropanenitrile) (14.0 mg), and the reaction mixture was stirred at 130° C. for 6 hr. Separately, a mixture of tert-butyl(dimethyl)((1,1,1-trifluoro-3-(4-(trifluoromethoxy)phenyl)propan-2-yl)oxy)silane (200 mg), 2,2'-(diazene-1,2-diyl)bis(2-methylpropanenitrile) (42.3 mg), 1-bromopyrrolidine-2,5-dione (458 mg) and benzotrifluoride (10 mL) was stirred at 120° C. for 2 days. These mixtures were combined, hexane was added thereto, and the insoluble substance was filtered off. The filtrate was concentrated under reduced pressure, and the residue was purified by silica gel column chromatography (hexane/ethyl acetate) to give a pale yellow oil (385 mg). To a solution of this oil (380 mg) in N,N-dimethylformamide (15 mL) was added sodium azide (264 mg) at room temperature. The reaction mixture was stirred overnight at 100° C., saturated brine was added thereto, and the mixture was extracted with ethyl acetate. The extract was washed with saturated brine, and dried over anhydrous magnesium sulfate to give an orange oil (280 mg). To a solution of this oil (280 mg) in methanol (5 mL) was added 10% palladium-carbon (containing 50% water, 20 mg). The reaction mixture was stirred overnight under hydrogen atmosphere, the catalyst was filtered off, and the filtrate was concentrated under reduced pressure. To the residue were added triethylamine (92 mg), 4-nitrophenyl-7-methyl-2-oxo-2,3-dihydropyrido[2,3-b]pyrazine-4(1H)-carboxylate (100 mg) and N,N-dimethylformamide (5 mL). The reaction mixture was stirred overnight at room temperature, saturated aqueous sodium hydrogen carbonate solution was added thereto, and the mixture was extracted with ethyl acetate. The extract was washed successively with saturated aqueous sodium hydrogen carbonate solution and saturated brine, and dried over anhydrous magnesium sulfate, and the solvent was evaporated under reduced pressure. The residue was purified by HPLC (C18, mobile phase: water/acetonitrile (containing 0.1% TFA)), to the obtained fraction was added saturated aqueous sodium hydrogen carbonate solution, and the mixture was extracted with ethyl acetate. The extract was dried over anhydrous magnesium sulfate, and concentrated under reduced pressure. The residue was purified by silica gel column chromatography (hexane/ethyl acetate) to give the title compound (23.2 mg).

MS (API+): [M+H]$^+$479.1.

Example 211

N-(1-(3-fluoro-4-(1H-pyrrol-1-yl)phenyl)-2-methoxyethyl)-7-methoxy-2-oxo-2,3-dihydropyrido[2,3-b]pyrazine-4(1H)-carboxamide A) N-(1-(3-fluoro-4-(1H-pyrrol-1-yl)phenyl)-2-methoxyethyl)-7-methoxy-2-oxo-1-((2-(trimethylsilyl)ethoxy)methyl)-2,3-dihydropyrido[2,3-b]pyrazine-4(1H)-carboxamide The title compound was obtained from 1-(3-fluoro-4-(1H-pyrrol-1-yl)phenyl)-2-methoxyethanamine in the same manner as in Steps I-K of Example 66.

MS (API+): [M+H]$^+$570.3.

B) N-(1-(3-fluoro-4-(1H-pyrrol-1-yl)phenyl)-2-methoxyethyl)-7-methoxy-2-oxo-2,3-dihydropyrido[2,3-b]pyrazine-4(1H)-carboxamide To a solution of N-(1-(3-fluoro-4-(1H-pyrrol-1-yl)phenyl)-2-methoxyethyl)-7-methoxy-2-oxo-1-((2-(trimethylsilyl)ethoxy)methyl)-2,3-dihydropyrido[2,3-b]pyrazine-4(1H)-carboxamide (112 mg) in dichloromethane (3.72 mL) was added boron trifluoride diethyl ether complex (250 μL) at 0° C. The reaction mixture was stirred at 0° C. for 1 hr, and the solvent was evaporated under reduced pressure. To the residue was added water, and the mixture was extracted with diethyl ether. The extract was washed with saturated brine, and dried over anhydrous sodium sulfate, and the solvent was evaporated under reduced pressure. The residue was dissolved in methanol (5.00 mL), N-ethyl-N-isopropylpropan-2-amine (344 μL) was added thereto at room temperature. The reaction mixture was stirred at 50° C. for 1 hr, the solvent was evaporated under reduced pressure, and the obtained solid was washed with hexane/ethyl acetate to give the title compound (58.8 mg).
MS (API+): [M+H]$^+$440.2.

Example 212

6-(4-methoxyphenyl)-N-(2-methoxy-1-(4-(trifluoromethoxy)phenyl)ethyl)-2-oxo-2,3-dihydropyrido[2,3-b]pyrazine-4(1H)-carboxamide A) methyl 2-((6-chloro-3-nitropyridin-2-yl) amino) acetate The title compound was obtained from 2,6-dichloro-3-nitropyridine in the same manner as in Step A of Example 1.
$^1$H NMR (300 MHz, DMSO-d$_6$) δ 3.67 (3H, s), 4.27 (2H, d, J=6.0 Hz), 6.87 (1H, d, J=8.7 Hz), 8.48 (1H, d, J=8.7 Hz), 8.96 (1H, t, J=5.7 Hz).

B) 6-chloro-3,4-dihydropyrido[2,3-b]pyrazin-2(1H)-one

The title compound was obtained from methyl 2-((6-chloro-3-nitropyridin-2-yl) amino)acetate in the same manner as in Step B of Example 66.
$^1$H NMR (300 MHz, DMSO-d$_6$) δ 3.94 (2H, s), 6.55 (1H, d, J=7.9 Hz), 6.91 (1H, d, J=7.9 Hz), 7.19 (1H, s), 10.47 (1H, s).

C) 6-chloro-1-((2-(trimethylsilyl)ethoxy)methyl)-3,4-dihydropyrido[2,3-b]pyrazin-2(1H)-one The title compound was obtained from 6-chloro-3,4-dihydropyrido[2,3-b]pyrazin-2(1H)-one in the same manner as in Step C of Example 63.
MS (API+): [M+H]$^+$314.3.

D) 6-chloro-N-(2-methoxy-1-(4-(trifluoromethoxy) phenyl)ethyl)-2-oxo-1-((2-(trimethylsilyl)ethoxy) methyl)-2,3-dihydropyrido[2,3-b]pyrazine-4(1H)-carboxamide The title compound was obtained from 6-chloro-1-((2-(trimethylsilyl)ethoxy)methyl)-3,4-dihydropyrido[2,3-b]pyrazin-2(1H)-one in the same manner as in Step F of Example 63.
MS (API+): [M+H]$^+$575.2.

E) 6-(4-methoxyphenyl)-N-(2-methoxy-1-(4-(trifluoromethoxy)phenyl)ethyl)-2-oxo-2,3-dihydropyrido[2,3-b]pyrazine-4(1H)-carboxamide To a solution of 6-chloro-N-(2-methoxy-1-(4-(trifluoromethoxy)phenyl)ethyl)-2-oxo-1-((2-(trimethylsilyl) ethoxy)methyl)-2,3-dihydropyrido[2,3-b]pyrazine-4(1H)-carboxamide (69.0 mg) in 1,2-dimethoxyethane (1.5 mL) were added 4-methoxyphenylboronic acid (36.5 mg), 1 M potassium carbonate aqueous solution (0.24 mL) and bis(di-tert-butyl(4-dimethylaminophenyl)phosphine)dichloropalladium(II) (8.5 mg), and the mixture was heated at 120° C. for 1 hr using microwave generator (Biotage, Initiator Sixty). To a reaction solution were added water (1 mL) and ethyl acetate (2 mL), and the mixture was stirred, and filtered through phase separating filter, and the organic layer was concentrated using air spraying device. The residue was purified by HPLC (column: YMC Triart C18, mobile phase: acetonitrile/10 mM aqueous ammonium bicarbonate solution), and the solvent was evaporated using air spraying device. To the residue was added trifluoroacetic acid (1 mL), and the mixture was stirred at room temperature for 1 hr, and the solvent was evaporated using air spraying device. To the residue was added 8 M ammonia/methanol solution (1 mL), the mixture was stirred at room temperature for 1 hr, and the solvent was evaporated using air spraying device. The residue was purified by HPLC (column: YMC Triart C18, mobile phase: acetonitrile/10 mM aqueous ammonium bicarbonate solution), and the solvent was evaporated using air spraying device to give the title compound (36.7 mg).
MS (API+): [M+H]$^+$517.1.

Example 213

N-(2-methoxy-1-(4-(trifluoromethoxy)phenyl)ethyl)-2-oxo-6-(pyridin-3-yl)-2,3-dihydropyrido[2,3-b]pyrazine-4(1H)-carboxamide The title compound was obtained from pyridin-3-ylboronic acid in the same manner as in Step E of Example 212.
MS (API+): [M+H]$^+$488.1.

Example 214

N-(2-methoxy-1-(4-(trifluoromethoxy)phenyl)ethyl)-2-oxo-6-phenyl-2,3-dihydropyrido[2,3-b]pyrazine-4(1H)-carboxamide The title compound was obtained from phenylboronic acid in the same manner as in Step E of Example 212.
MS (API+): [M+H]$^+$487.1.

Example 215

6-(2-methoxyphenyl)-N-(2-methoxy-1-(4-(trifluoromethoxy)phenyl)ethyl)-2-oxo-2,3-dihydropyrido[2,3-b]pyrazine-4(1H)-carboxamide The title compound was obtained from 2-methoxyphenylboronic acid in the same manner as in Step E of Example 212.
MS (API+): [M+H]$^+$517.1.

Example 216

6-(3-methoxyphenyl)-N-(2-methoxy-1-(4-(trifluoromethoxy)phenyl)ethyl)-2-oxo-2,3-dihydropyrido[2,3-b]pyrazine-4(1H)-carboxamide The title compound was obtained from 3-methoxyphenylboronic acid in the same manner as in Step E of Example 212.
MS (API+): [M+H]$^+$517.2.

Example 217

N-(2-methoxy-1-(4-(trifluoromethoxy)phenyl)ethyl)-2-oxo-6-(pyridin-4-yl)-2,3-dihydropyrido[2,3-b]pyrazine-4(1H)-carboxamide The title compound was obtained from pyridin-4-ylboronic acid in the same manner as in Step E of Example 212.
MS (API+): [M+H]$^+$488.1.

Example 218

N-(2-methoxy-1-(4-(trifluoromethoxy)phenyl)ethyl)-2-oxo-6-(2-thienyl)-2,3-dihydropyrido[2,3-b]pyrazine-4(1H)-carboxamide The title compound was obtained from 2-thienylboronic acid in the same manner as in Step E of Example 212.
MS (API+): [M+H]$^+$493.1.

Example 219

6-(3-furyl)-N-(2-methoxy-1-(4-(trifluoromethoxy)phenyl)ethyl)-2-oxo-2,3-dihydropyrido[2,3-b]pyrazine-4(1H)-carboxamide The title compound was obtained from 3-furylboronic acid in the same manner as in Step E of Example 212.
MS (API+): [M+H]$^+$477.1.

Example 220

N-(2-methoxy-1-(4-(trifluoromethoxy)phenyl)ethyl)-2-oxo-6-(3-thienyl)-2,3-dihydropyrido[2,3-b]pyrazine-4(1H)-carboxamide The title compound was obtained from 3-thienylboronic acid in the same manner as in Step E of Example 212.
MS (API+): [M+H]$^+$493.1.

Example 221

N-(2-methoxy-1-(4-(trifluoromethoxy)phenyl)ethyl)-6-(1-methyl-1H-pyrazol-5-yl)-2-oxo-2,3-dihydropyrido[2,3-b]pyrazine-4(1H)-carboxamide The title compound was obtained from 1-methyl-5-(4,4,5,5-tetramethyl-1,3,2-dioxaborolan-2-yl)-1H-pyrazole in the same manner as in Step E of Example 212.
MS (API+): [M+H]$^+$491.1.

Example 222

N-(2-methoxy-1-(4-(trifluoromethoxy)phenyl)ethyl)-6-(1-methyl-1H-pyrazol-3-yl)-2-oxo-2,3-dihydropyrido[2,3-b]pyrazine-4(1H)-carboxamide The title compound was obtained from 1-methyl-3-(4,4,5,5-tetramethyl-1,3,2-dioxaborolan-2-yl)-1H-pyrazole in the same manner as in Step E of Example 212.
MS (API+): [M+H]$^+$491.1.

Example 223

N-(2-methoxy-1-(4-(trifluoromethoxy)phenyl)ethyl)-6-(1-methyl-1H-pyrazol-4-yl)-2-oxo-2,3-dihydropyrido[2,3-b]pyrazine-4(1H)-carboxamide The title compound was obtained from 1-methyl-4-(4,4,5,5-tetramethyl-1,3,2-dioxaborolan-2-yl)-1H-pyrazole in the same manner as in Step E of Example 212.
MS (API+): [M+H]$^+$491.1.

Example 224

6-(3,5-dimethyl-1,2-oxazol-4-yl)-N-(2-methoxy-1-(4-(trifluoromethoxy)phenyl)ethyl)-2-oxo-2,3-dihydropyrido[2,3-b]pyrazine-4(1H)-carboxamide The title compound was obtained from 3,5-dimethyl-1,2-oxazol-4-ylboronic acid in the same manner as in Step E of Example 212.
MS (API+): [M+H]$^+$506.1.

Example 225

N-(1-(3-fluoro-4-(trifluoromethyl)phenyl)-2-methoxyethyl)-7-methoxy-2-oxo-2,3-dihydropyrido[2,3-b]pyrazine-4(1H)-carboxamide The title compound was obtained from N-(1-(3-fluoro-4-(trifluoromethyl)phenyl)-2-methoxyethyl)-7-iodo-2-oxo-1-((2-(trimethylsilyl)ethoxy)methyl)-2,3-dihydropyrido[2,3-b]pyrazine-4(1H)-carboxamide in the same manner as in Steps J-L of Example 66.
MS (API+): [M+H]$^+$443.1.

Example 226

Optically Active 7-cyclopropyl-N-(1-(3-fluoro-4-(trifluoromethyl)phenyl)-2-methoxyethyl)-2-oxo-2,3-dihydropyrido[2,3-b]pyrazine-4(1H)-carboxamide Racemic 7-cyclopropyl-N-(1-(3-fluoro-4-(trifluoromethyl)phenyl)-2-methoxyethyl)-2-oxo-2,3-dihydropyrido[2,3-b]pyrazine-4(1H)-carboxamide (347 mg) was resolved by HPLC (column: CHIRALPAK AD, 50 mmID×500 manufactured by Daicel Chemical Industries, Ltd., mobile phase: hexane/ethanol=700/300) to give the title compound having a shorter retention time (107 mg).
MS (API+): [M+H]$^+$453.1.

Example 227

Optically Active 7-cyclopropyl-N-(1-(3-fluoro-4-(trifluoromethyl)phenyl)-2-methoxyethyl)-2-oxo-2,3-dihydropyrido[2,3-b]pyrazine-4(1H)-carboxamide Racemic 7-cyclopropyl-N-(1-(3-fluoro-4-(trifluoromethyl)phenyl)-2-methoxyethyl)-2-oxo-2,3-dihydropyrido[2,3-b]pyrazine-4(1H)-carboxamide (347 mg) was resolved by HPLC (column: CHIRALPAK AD, 50 mmID×500 mmL, manufactured by Daicel Chemical Industries, Ltd., mobile phase: hexane/ethanol=700/300) to give the title compound having a longer retention time (83 mg).
MS (API+): [M+H]$^+$453.1.

Example 228

N-(2-methoxy-2-methyl-1-(4-(trifluoromethoxy)phenyl)propyl)-7-methyl-2-oxo-2,3-dihydropyrido[2,3-b]pyrazine-4(1H)-carboxamide A) methyl 2-(4-(trifluoromethoxy)phenyl)acetate To a solution of 2-(4-(trifluoromethoxy)phenyl)acetic acid (5.00 g) in methanol (32 mL) was added conc. sulfuric acid (0.237 mL) at room temperature. The reaction mixture was stirred at 70° C. for 4 hr, and concentrated to about 10 mL under reduced pressure. To the residue was added water, and the mixture was extracted with ethyl acetate. The extract was washed with saturated brine, and dried over anhydrous magnesium sulfate, and the solvent was evaporated under reduced pressure to give the title compound (4.00 g).
MS (API−): [M−H]− 233.0.

B) 2-methyl-1-(4-(trifluoromethoxy)phenyl)propan-2-ol

To a solution of methyl 2-(4-(trifluoromethoxy)phenyl) acetate (4.00 g) in tetrahydrofuran (57 mL) was added 1 M methylmagnesium bromide/tetrahydrofuran solution (42.7 mL) at 0° C. The reaction mixture was stirred at room temperature for 4 hr, saturated aqueous ammonium chloride solution was added thereto at 0° C., and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (3.26 g).
$^1$H NMR (300 MHz, DMSO-$d_6$) δ 1.06 (6H, s), 2.67 (2H, s), 4.36 (1H, s), 7.31 (4H, s).

C) 1-(2-methoxy-2-methylpropyl)-4-(trifluoromethoxy)benzene

To a solution of 2-methyl-1-(4-(trifluoromethoxy)phenyl) propan-2-ol (6.72 g) in N,N-dimethylformamide (140 mL) was added 60% sodium hydride (5.74 g) at room temperature. The reaction mixture was stirred at room temperature for 30 min, methyl iodide (8.97 mL) was slowly added thereto at room temperature, and the mixture was stirred at room temperature for 18 hr. To the reaction mixture was added water, and the mixture was extracted with ethyl acetate. The extract was dried over anhydrous magnesium sulfate, and the solvent was evaporated under reduced pressure. The residue was purified by silica gel column chromatography (hexane/ethyl acetate) to give the title compound (6.01 g).
$^1$H NMR (300 MHz, DMSO-$d_6$) δ 1.05 (6H, s), 2.75 (2H, s), 3.16 (3H, s), 7.17-7.37 (4H, m).

D) 1-(1-bromo-2-methoxy-2-methylpropyl)-4-(trifluoromethoxy)benzene

The title compound was obtained from 1-(2-methoxy-2-methylpropyl)-4-(trifluoromethoxy)benzene in the same manner as in Step D of Example 142.
$^1$H NMR (300 MHz, DMSO-$d_6$) δ 1.13 (3H, s), 1.25 (3H, s), 3.20 (3H, s), 5.33-5.42 (1H, m), 7.18-7.38 (2H, m), 7.62-7.70 (2H, m).

E) 1-(1-azido-2-methoxy-2-methylpropyl)-4-(trifluoromethoxy)benzene

To a solution of 1-(1-bromo-2-methoxy-2-methylpropyl)-4-(trifluoromethoxy)benzene (2.10 g) in N,N-dimethylformamide (43 mL) were added sodium azide (2.09 g) and 18-crown-6 (6.8 g). The reaction mixture was stirred at 100° C. for 18 hr, water was added thereto, and the mixture was extracted with diethyl ether. The extract was washed with saturated brine, and dried over anhydrous magnesium sulfate, and the solvent was evaporated under reduced pressure to give the title compound (1.66 g).
$^1$H NMR (300 MHz, DMSO-$d_6$) δ 1.00-1.11 (6H, m), 3.20 (3H, s), 4.83-4.90 (1H, m), 7.33-7.40 (2H, m), 7.42-7.56 (2H, m).

F) N-(2-methoxy-2-methyl-1-(4-(trifluoromethoxy) phenyl)propyl)-7-methyl-2-oxo-2,3-dihydropyrido[2, 3-b]pyrazine-4(1H)-carboxamide The title compound was obtained from 1-(1-azido-2-methoxy-2-methylpropyl)-4-(trifluoromethoxy)benzene in the same manner as in Steps E-F of Example 2 and Step L of Example 72-I.
MS (API+): [M+H]+ 453.2.

Example 229

Optically Active N-(1-(3-fluoro-4-(1H-pyrrol-1-yl) phenyl)-2-methoxyethyl)-7-methoxy-2-oxo-2,3-dihydropyrido[2,3-b]pyrazine-4(1H)-carboxamide Racemic N-(1-(3-fluoro-4-(1H-pyrrol-1-yl)phenyl)-2-methoxyethyl)-7-methoxy-2-oxo-2,3-dihydropyrido[2,3-b] pyrazine-4(1H)-carboxamide (55.2 mg) was resolved by HPLC (column: CHIRALPAK AD, 50 mmID×500 mmL, manufactured by Daicel Chemical Industries, Ltd., mobile phase: hexane/ethanol=700/300) to give the title compound having a shorter retention time (13.7 mg).
MS (API+): [M+H]+440.2.

Example 230

Optically Active N-(1-(3-fluoro-4-(1H-pyrrol-1-yl) phenyl)-2-methoxyethyl)-7-methoxy-2-oxo-2,3-dihydropyrido[2,3-b]pyrazine-4(1H)-carboxamide Racemic N-(1-(3-fluoro-4-(1H-pyrrol-1-yl)phenyl)-2-methoxyethyl)-7-methoxy-2-oxo-2,3-dihydropyrido[2,3-b] pyrazine-4(1H)-carboxamide (55.2 mg) was resolved by HPLC (column: CHIRALPAK AD, 50 mmID×500 mmL, manufactured by Daicel Chemical Industries, Ltd., mobile phase: hexane/ethanol=700/300) to give the title compound having a longer retention time (15.4 mg).
MS (API+): [M+H]+440.2.

Example 231

Optically Active 7-cyclopropyl-N-(2-methoxy-1-(4-(trifluoromethyl)phenyl)ethyl)-2-oxo-2,3-dihydropyrido[2,3-b]pyrazine-4(1H)-carboxamide Racemic 7-cyclopropyl-N-(2-methoxy-1-(4-(trifluoromethyl)phenyl)ethyl)-2-oxo-2,3-dihydropyrido[2,3-b]pyrazine-4(1H)-carboxamide (426 mg) was resolved by HPLC (column: CHIRALPAK AD, 50 mmID×500 mmL, manufactured by Daicel Chemical Industries, Ltd., mobile phase: hexane/ethanol=700/300) to give the title compound having a shorter retention time (177 mg).
MS (API+): [M+H]+435.1.
$^1$H NMR (300 MHz, CDCl$_3$) δ 0.66-0.75 (2H, m), 0.98-1.08 (2H, m), 1.83-1.95 (1H, m), 3.40 (3H, s), 3.69 (2H, d, J=5.3 Hz), 4.64 (2H, s), 5.16-5.26 (1H, m), 6.83 (1H, d, J=2.3 Hz), 7.45-7.62 (4H, m), 7.84 (1H, d, J=1.9 Hz), 8.84-8.97 (1H, m), 10.55 (1H, d, J=7.2 Hz).

Example 232

Optically Active N-(1-(3-fluoro-4-(trifluoromethyl) phenyl)-2-methoxyethyl)-7-methoxy-2-oxo-2,3-dihydropyrido[2,3-b]pyrazine-4 (1H)-carboxamide Racemic N-(1-(3-fluoro-4-(trifluoromethyl)phenyl)-2-methoxyethyl)-7-methoxy-2-oxo-2,3-dihydropyrido[2,3-b]pyrazine-4(1H)-carboxamide (471 mg) was resolved by HPLC (column: CHIRALPAK AD, 50 mmID×500 mmL, manufactured by Daicel Chemical Industries, Ltd., mobile phase: hexane/ethanol=700/300), and recrystallized from hexane/ethyl acetate to give the title compound having a shorter retention time (208 mg).
MS (API+): [M+H]$^+$443.1.

Example 233

Optically Active 7-cyclopropyl-N-(2-methoxy-1-(4-(trifluoromethyl)phenyl)ethyl)-2-oxo-2,3-dihydropyrido[2,3-b]pyrazine-4(1H)-carboxamide Racemic 7-cyclopropyl-N-(2-methoxy-1-(4-(trifluoromethyl)phenyl)ethyl)-2-oxo-2,3-dihydropyrido[2,3-b]pyrazine-4(1H)-carboxamide (426 mg) was resolved by HPLC (column: CHIRALPAK AD, 50 mmID×500 mmL, manufactured by Daicel Chemical Industries, Ltd., mobile phase: hexane/ethanol=700/300), and recrystallized from hexane/ethyl acetate to give the title compound having a longer retention time (179 mg).
MS (API+): [M+H]$^+$435.1.
$^1$H NMR (300 MHz, CDCl$_3$) δ 0.66-0.75 (2H, m), 0.98-1.08 (2H, m), 1.81-1.94 (1H, m), 3.40 (3H, s), 3.69 (2H, d, J=5.3 Hz), 4.64 (2H, s), 5.14-5.26 (1H, m), 6.83 (1H, d, J=1.9 Hz), 7.45-7.64 (4H, m), 7.84 (1H, d, J=1.9 Hz), 9.01 (1H, s), 10.55 (1H, d, J=7.2 Hz).

Example 234

Optically Active N-(1-(3-fluoro-4-(trifluoromethyl) phenyl)-2-methoxyethyl)-7-methoxy-2-oxo-2,3-dihydropyrido[2,3-b]pyrazine-4(1H)-carboxamide Racemic N-(1-(3-fluoro-4-(trifluoromethyl)phenyl)-2-methoxyethyl)-7-methoxy-2-oxo-2,3-dihydropyrido[2,3-b]pyrazine-4(1H)-carboxamide (471 mg) was resolved by HPLC (column: CHIRALPAK AD, 50 mmID×500 mmL, manufactured by Daicel Chemical Industries, Ltd., mobile phase: hexane/ethanol=700/300) to give the title compound having a longer retention time (199 mg).
MS (API+): [M+H]$^+$443.1.

Example 235

6-(3,6-dihydro-2H-pyran-4-yl)-N-(2-methoxy-1-(4-(trifluoromethoxy)phenyl)ethyl)-2-oxo-2,3-dihydropyrido[2,3-b]pyrazine-4(1H)-carboxamide The title compound was obtained from 3,6-dihydro-2H-pyran-4-boronic acid pinacol ester in the same manner as in Step E of Example 212.
MS (API+): [M+H]$^+$493.1.

Example 236

N-(2-methoxy-1-(4-(trifluoromethoxy)phenyl)ethyl)-6-(1-methyl-1,2,3,6-tetrahydropyridin-4-yl)-2-oxo-2,3-dihydropyrido[2,3-b]pyrazine-4(1H)-carboxamide The title compound was obtained from 1-methyl-1,2,3,6-tetrahydropyridine-4-boronic acid pinacol ester in the same manner as in Step E of Example 212.
MS (API+): [M+H]$^+$506.1.

Example 237

N-(2-methoxy-1-(4-(trifluoromethoxy)phenyl)ethyl)-2-oxo-6-(1,2,3,6-tetrahydropyridin-4-yl)-2,3-dihydropyrido[2,3-b]pyrazine-4(1H)-carboxamide The title compound was obtained from tert-butyl 4-(4,4,5,5-tetramethyl-1,3,2-dioxaborolan-2-yl)-5,6-dihydropyridine-1(2H)-carboxylate in the same manner as in Step E of Example 212.
MS (API+): [M+H]$^+$492.1.

Example 238

N-(2-methoxy-1-(4-(trifluoromethoxy)phenyl)ethyl)-6-methyl-2-oxo-2,3-dihydropyrido[2,3-b]pyrazine-4 (1H)-carboxamide To a solution of 6-chloro-N-(2-methoxy-1-(4-(trifluoromethoxy)phenyl)ethyl)-2-oxo-1-((2-(trimethylsilyl) ethoxy)methyl)-2,3-dihydropyrido[2,3-b]pyrazine-4(1H)-carboxamide (46.0 mg) in 1,2-dimethoxyethane (1.0 mL) was added water (0.16 mL), trimethylboroxine (50.0 mg), cesium carbonate (52.0 mg) and bis(di-tert-butyl(4-dimethylaminophenyl)phosphine)dichloropalladium(II) (5.6 mg), and the mixture was heated at 110° C. for 1 hr using microwave generator (Biotage, Initiator Sixty). To the reaction mixture were added water (1 mL) and ethyl acetate (2 mL), and the mixture was stirred, and filtered through phase separating filter, and the organic layer was concentrated using air spraying device. The residue was purified by HPLC (column: YMC Triart C18, mobile phase: acetonitrile/10 mM aqueous ammonium bicarbonate solution), and the solvent was evaporated using air spraying device. To the residue was added trifluoroacetic acid (1 mL), and the mixture was stirred at room temperature for 1 hr, and the solvent was evaporated using air spraying device. To the residue was added 8 M ammonia/methanol solution (1 mL), and the mixture was stirred at room temperature for 1 hr, and the solvent was evaporated using air spraying device. The residue was purified by HPLC (column: YMC Triart C18, mobile phase: acetonitrile/10 mM aqueous ammonium bicarbonate solution), and the solvent was evaporated using air spraying device to give the title compound (16.5 mg).
MS (API+): [M+H]$^+$425.0.

Example 239

N-(2-methoxy-1-(4-(trifluoromethoxy)phenyl)ethyl)-2-oxo-6-(pyridin-2-yl)-2,3-dihydropyrido[2,3-b] pyrazine-4(1H)-carboxamide To a solution of 6-chloro-N-(2-methoxy-1-(4-(trifluoromethoxy)phenyl)ethyl)-2-oxo-1-((2-(trimethylsilyl) ethoxy)methyl)-2,3-dihydropyrido[2,3-b]pyrazine-4(1H)-carboxamide (46.0 mg) in N,N-dimethylformamide (0.5 mL) were added (2-pyridine)cyclic triolborate lithium (51.1 mg), cesium carbonate (78.1 mg), bis(di-tert-butyl(4-dimethylaminophenyl)phosphine)dichloropalladium(II) (5.6 mg) and copper(I) chloride (4.0 mg), and the mixture was heated at 100° C. for 1 hr using microwave generator (Biotage, Initiator Sixty). To the reaction mixture were added water (1 mL) and ethyl acetate (2 mL), and the mixture was stirred, and filtered through phase separating filter, and the organic layer was concentrated using air spraying device. The residue was purified by HPLC (column: YMC Triart C18, mobile phase: acetonitrile/10 mM aqueous ammonium bicarbonate solution), and the solvent was evaporated using air spraying device. To the residue was added trifluoroacetic acid (1 mL), and the mixture was stirred at room temperature for 1 hr, and the solvent was evaporated using air spraying device. To the residue was added 8 M ammonia/methanol solution (1 mL), and the mixture was stirred at room temperature for 1 hr, and the solvent was evaporated using air spraying device. The residue was purified by HPLC (column: YMC Triart C18, mobile phase: acetonitrile/10 mM aqueous ammonium bicarbonate solution), and the solvent was evaporated using air spraying device to give the title compound (6.3 mg).

MS (API+): [M+H]$^+$488.1.

Example 240

6-(2-furyl)-N-(2-methoxy-1-(4-(trifluoromethoxy)phenyl)ethyl)-2-oxo-2,3-dihydropyrido[2,3-b]pyrazine-4(1H)-carboxamide The title compound was obtained from sodium (2-furan)cyclic-triolborate in the same manner as in Example 239.

MS (API+): [M+H]$^+$477.1.

Example 241

6-cyclopropyl-N-(2-methoxy-1-(4-(trifluoromethoxy)phenyl)ethyl)-2-oxo-2,3-dihydropyrido[2,3-b]pyrazine-4(1H)-carboxamide To a solution of 6-chloro-N-(2-methoxy-1-(4-(trifluoromethoxy)phenyl)ethyl)-2-oxo-1-((2-(trimethylsilyl)ethoxy)methyl)-2,3-dihydropyrido[2,3-b]pyrazine-4(1H)-carboxamide (46.0 mg) in toluene (1.0 mL) were added water (0.2 mL), cyclopropylboronic acid (20.6 mg), cesium carbonate (78.1 mg), palladium(II) acetate (3.6 mg) and tricyclohexylphosphine (6.7 mg), and the mixture was heated at 100° C. for 30 min using microwave generator (Biotage, Initiator Sixty). To the reaction mixture were added water (1 mL) and ethyl acetate (2 mL), and the mixture was stirred, and filtered through phase separating filter, and the organic layer was concentrated using air spraying device. The residue was purified by HPLC (column: YMC Triart C18, mobile phase: acetonitrile/10 mM aqueous ammonium bicarbonate solution), and the solvent was evaporated using air spraying device. To the residue was added trifluoroacetic acid (1 mL), and the mixture was stirred at room temperature for 1 hr, and the solvent was evaporated using air spraying device. To the residue was added 8 M ammonia/methanol solution (1 mL), and the mixture was stirred at room temperature for 1 hr, and the solvent was evaporated using air spraying device. The residue was purified by HPLC (column: YMC Triart C18, mobile phase: acetonitrile/10 mM aqueous ammonium bicarbonate solution), and the solvent was evaporated using air spraying device to give the title compound (18.3 mg).

MS (API+): [M+H]$^+$451.1.

Example 242

N-(2-methoxy-1-(4-(trifluoromethoxy)phenyl)ethyl)-2-oxo-6-(tetrahydro-2H-pyran-4-yl)-2,3-dihydropyrido[2,3-b]pyrazine-4(1H)-carboxamide To a solution of 6-(3,6-dihydro-2H-pyran-4-yl)-N-(2-methoxy-1-(4-(trifluoromethoxy)phenyl)ethyl)-2-oxo-2,3-dihydropyrido[2,3-b]pyrazine-4(1H)-carboxamide (10 mg) in methanol (2 mL) were added ammonium formate (50 mg) and 5% palladium-carbon-ethylene diamine complex (50 mg), and the mixture was stirred at 60° C. for 2 hr. The reaction mixture was filtered, and concentrated using air spraying device. The residue was purified by HPLC (column: YMC Triart C18, mobile phase: acetonitrile/10 mM aqueous ammonium bicarbonate solution), and the solvent was evaporated using air spraying device to give the title compound (5.5 mg).

MS (API+): [M+H]$^+$495.1.

Example 243

N-(2-methoxy-1-(4-(trifluoromethoxy)phenyl)ethyl)-6-(1-methylpiperidine-4-yl)-2-oxo-2,3-dihydropyrido[2,3-b]pyrazine-4(1H)-carboxamide The title compound was obtained from N-(2-methoxy-1-(4-(trifluoromethoxy)phenyl)ethyl)-6-(1-methyl-1,2,3,6-tetrahydropyridin-4-yl)-2-oxo-2,3-dihydropyrido[2,3-b]pyrazine-4(1H)-carboxamide in the same manner as in Example 242.

MS (API+): [M+H]$^+$508.1.

Example 244

N-(2-methoxy-1-(4-(trifluoromethoxy)phenyl)ethyl)-2-oxo-6-(piperidin-4-yl)-2,3-dihydropyrido[2,3-b]pyrazine-4(1H)-carboxamide The title compound was obtained from N-(2-methoxy-1-(4-(trifluoromethoxy)phenyl)ethyl)-2-oxo-6-(1,2,3,6-tetrahydropyridin-4-yl)-2,3-dihydropyrido[2,3-b]pyrazine-4(1H)-carboxamide in the same manner as in Example 242.

MS (API+): [M+H]$^+$494.1.

Example 245

6-methoxy-N-(2-methoxy-1-(4-(trifluoromethoxy)phenyl)ethyl)-7-methyl-2-oxo-2,3-dihydropyrido[2,3-b]pyrazine-4(1H)-carboxamide A) 2-chloro-3-methyl-5-nitropyridine 1-oxide To a mixture of 2-chloro-3-methyl-5-nitropyridine (5.00 g) and hydrogen peroxide urea (5.72 g) in acetonitrile (37.6 mL) was slowly added trifluoroacetic anhydride (8.06 mL) at 0° C. The reaction mixture was stirred at 0° C. for 2 hr, 9% (w/w) aqueous sodium dithionite solution (60 mL) was added thereto, and the mixture was stirred at room temperature for 20 min. The reaction mixture was extracted with ethyl acetate. The extract was washed successively with saturated aqueous sodium hydrogen carbonate solution and saturated brine, and dried over anhydrous magnesium sulfate, and the solvent was evaporated under reduced pressure.

The residue was purified by silica gel column chromatography (hexane/ethyl acetate) to give the title compound (1.90 g).

$^1$H NMR (300 MHz, DMSO-d$_6$) δ 2.33 (3H, s, 7.98 (1H, d, J=0.8 Hz), 8.70 (1H, dd, J=1.7, 0.8 Hz).

B) 2,6-dichloro-3-methyl-5-nitropyridine

A mixture of 2-chloro-3-methyl-5-nitropyridine 1-oxide (8.17 g) and phosphorus oxychloride (101 mL) was stirred at 90° C. for 30 min, and the solvent was evaporated under reduced pressure. The residue was purified by silica gel column chromatography (hexane/ethyl acetate) to give the title compound (7.63 g).

$^1$H NMR (300 MHz, CDCl$_3$) δ 2.48 (3H, s), 8.14 (1H, d, J=0.8 Hz).

C) methyl 2-(6-chloro-5-methyl-3-nitropyridin-2-yl) acetate

The title compound was obtained from 2,6-dichloro-3-methyl-5-nitropyridine in the same manner as in Step A of Example 1.

MS (API+): [M+H]$^+$260.0.

D) methyl 2-(6-methoxy-5-methyl-3-nitropyridin-2-yl)acetate

A mixture of methyl 2-(6-chloro-5-methyl-3-nitropyridin-2-yl)acetate (2.63 g) and sodium methoxide (2.93 g) in methanol (50.6 mL) was stirred overnight at room temperature, and the solvent was evaporated under reduced pressure. The residue was purified by silica gel column chromatography (hexane/ethyl acetate) to give the title compound (1.12 g).

MS (API+): [M+H]$^+$256.1.

E) 6-methoxy-N-(2-methoxy-1-(4-(trifluoromethoxy)phenyl)ethyl)-7-methyl-2-oxo-2,3-dihydropyrido[2,3-b]pyrazine-4(1H)-carboxamide The title compound was obtained from methyl 2-(6-methoxy-5-methyl-3-nitropyridin-2-yl)acetate in the same manner as in Step B of Example 1 and Steps C-D of Example 19.

MS (API+): [M+H]$^+$455.1.

Example 246

7-methoxy-N-(2-methoxy-1-(4-(trifluoromethoxy) phenyl)ethyl)-6-methyl-2-oxo-2,3-dihydropyrido[2,3-b]pyrazine-4(1H)-carboxamide

A) 2-nitroacetamide ammonia salt

A mixture of 2-nitroethyl acetate (17.5 g) and 28% aqueous ammonia solution (88 mL) was stirred at room temperature for 4 days, and the solvent was evaporated under reduced pressure to give the title compound (15.0 g).

$^1$H NMR (300 MHz, D$_2$O) δ 6.43 (2H, s).

B) methyl 2-((5-methoxy-6-methyl-3-nitropyridin-2-yl) amino)acetate

To a solution of 28% sodium methoxide/methanol solution (16.7 g) in methanol (87 mL) was slowly added a mixture of 1-methoxypropan-2-one (7.63 g) and ethyl formate (7.68 mL) at −10° C. The reaction mixture was stirred at −10° C. for 1 hr under argon atmosphere, and then overnight at room temperature, and the solvent was evaporated under reduced pressure. To a solution of the residue (12.0 g) and 2-nitroacetamide ammonia salt (12.9 g) in water (54.1 mL) were added 3.4 M aqueous piperidine acetate solution (26.7 mL) and acetic acid (5.85 mL) at room temperature. The reaction mixture was stirred overnight at 50° C., water was added thereto, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give 5-methoxy-6-methyl-3-nitropyridin-2-ol (1.06 g) containing an impurity. To a solution of the 5-methoxy-6-methyl-3-nitropyridin-2-ol obtained above (153 mg) in pyridine (4.15 mL) was added trifluoromethanesulfonic anhydride (211 μL) at 0° C. The reaction mixture was stirred at 0° C., for 2 hr, water was added thereto, and the mixture was extracted with ethyl acetate. The extract was washed successively with 1 M hydrochloric acid, saturated aqueous sodium hydrogen carbonate solution and saturated brine, and dried over anhydrous magnesium sulfate, and the solvent was evaporated under reduced pressure. To a solution of the residue (262 mg) in N,N-dimethylacetamide (4.15 mL) were added glycinemethyl ester hydrochloride (125 mg) and triethylamine (289 μL) at room temperature. The reaction mixture was stirred overnight at 70° C., water was added thereto, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (70 mg).

MS (API+): [M+H]$^+$256.1.

C) 7-methoxy-N-(2-methoxy-1-(4-(trifluoromethoxy)phenyl)ethyl)-6-methyl-2-oxo-2,3-dihydropyrido[2,3-b]pyrazine-4(1H)-carboxamide The title compound was obtained from methyl 2-((5-methoxy-6-methyl-3-nitropyridin-2-yl) amino)acetate in the same manner as in Step B of Example 1 and Steps C-D of Example 19.

MS (API+): [M+H]$^+$455.1.

Example 247

N-(2-hydroxy-2-methyl-1-(4-(trifluoromethoxy)phenyl)propyl)-7-methoxy-6-methyl-2-oxo-2,3-dihydropyrido[2,3-b]pyrazine-4(1H)-carboxamide The title compound was obtained from 4-nitrophenyl 7-methoxy-6-methyl-2-oxo-2,3-dihydropyrido[2,3-b]pyrazine-4(1H)-carboxylate and 1-amino-2-methyl-1-(4-(trifluoromethoxy)phenyl)propan-2-ol hydrochloride in the same manner as in Step C of Example 19.

MS (API+): [M+H]$^+$469.1.

Example 248

N-(2-hydroxy-2-methyl-1-(4-(trifluoromethoxy)phenyl)propyl)-6-methoxy-7-methyl-2-oxo-2,3-dihydropyrido[2,3-b]pyrazine-4(1H)-carboxamide The title compound was obtained from 4-nitrophenyl 6-methoxy-7-methyl-2-oxo-2,3-dihydropyrido[2,3-b]pyrazine-4(1H)-carboxylate and 1-amino-2-methyl-1-(4-(trifluoromethoxy)phenyl)propan-2-ol hydrochloride in the same manner as in Step C of Example 19.
MS (API+): [M+H]$^+$469.1.

Example 249

N-(3-methoxy-1-(4-(trifluoromethoxy)phenyl)propyl)-7-methyl-2-oxo-2,3-dihydropyrido[2,3-b]pyrazine-4(1H)-carboxamide The title compound was obtained from 1-(3-methoxy-1-(4-(trifluoromethoxy)phenyl))propylamine hydrochloride in the same manner as in Step C of Example 19.
MS (API+): [M+H]$^+$439.1.

Example 250

N-(2-hydroxy-2-methyl-1-(4-(trifluoromethoxy)phenyl)propyl)-7-methyl-2-oxo-2,3-dihydropyrido[2,3-b]pyrazine-4(1H)-carboxamide A) methyl 2-((5-methyl-3-nitropyridin-2-yl) amino)acetate To a mixture of methyl glycinate hydrochloride (8.32 g) and 2-chloro-5-methyl-3-nitropyridine (7.62 g) in N,N-dimethylformamide (100 mL) was added triethylamine (18.5 mL). The reaction mixture was stirred at 80° C. for 16 hr, and the solvent was evaporated under reduced pressure. To the residue was added water, and the mixture was extracted with ethyl acetate. The extract was washed with water, and dried over anhydrous sodium sulfate, and the solvent was evaporated under reduced pressure. The residue was purified by silica gel column chromatography (ethyl acetate/hexane) to give the title compound (6.99 g).
$^1$H NMR (300 MHz, DMSO-d$_6$) δ 2.24 (3H, s), 3.64 (3H, s), 4.28 (2H, d, J=5.7 Hz), 8.27-8.37 (2H, m), 8.60 (1H, t, J=5.7 Hz).

B) 7-methyl-3,4-dihydropyrido[2,3-b]pyrazin-2(1H)-one

To a solution of methyl 2-((5-methyl-3-nitropyridin-2-yl)amino)acetate (6.99 g) in ethanol (100 mL) was added 10% palladium-carbon (containing 50% water, 2.00 g). The reaction mixture was stirred overnight at room temperature under hydrogen atmosphere, the catalyst was filtered off, and the filtrate was concentrated under reduced pressure. To the residue was added ethanol (100 mL), the reaction mixture was heated at reflux for 5 hr, and the solvent was evaporated to about ⅓ of the volume under reduced pressure. To the residue was added diisopropyl ether, and the precipitated solid was collected by filtration. The solid was washed with diisopropyl ether, and dried under reduced pressure to give the title compound (4.56 g).
$^1$H NMR (300 MHz, DMSO-d$_6$) δ 2.09 (3H, s), 3.85 (2H, d, J=1.5 Hz), 6.45 (1H, s), 6.72-6.80 (1H, m), 7.39-7.48 (1H, m), 10.31 (1H, s).

C) 4-nitrophenyl 7-methyl-2-oxo-2,3-dihydropyrido[2,3-b]pyrazine-4(1H)-carboxylate To a mixture of 7-methyl-3,4-dihydropyrido[2,3-b]pyrazin-2(1H)-one (1.00 g) in a mixed solvent of N,N-dimethylacetamide (40 mL) and pyridine (15 mL) was added 4-nitrophenyl chloroformate (1.48 g) at room temperature. The reaction mixture was stirred at room temperature for 16 hr, and water was added thereto. The precipitated solid was collected by filtration, washed with water, and dried under reduced pressure to give the title compound (1.63 g).
MS (API+): [M+H]$^+$ 329.1.

D) methyl 2-((tert-butoxycarbonyl) amino)-2-(4-(trifluoromethoxy)phenyl)acetate

To a mixture of 4-trifluoromethoxybenzaldehyde (19.0 g) and ammonium carbonate (25.9 g) in a mixed solvent of ethanol (114 mL) and water (45.6 mL) was slowly added an aqueous solution (71.1 mL) of potassium cyanide (8.14 g) at 50° C. The reaction mixture was stirred at 60° C. for 3 hr, and cooled to room temperature, and the ethanol was evaporated under reduced pressure. The pH of the residue was adjusted to 1 with conc. hydrochloric acid at 0° C., and the resulting solid was collected by filtration, and washed with water. To an aqueous solution (100 mL) of potassium hydroxide (23.6 g) was added the solid obtained above at room temperature, and the reaction mixture was stirred at 90° C. for 2 days. The reaction mixture was cooled to room temperature, and neutralized with conc. hydrochloric acid. The resulting solid was collected by filtration, and washed with water to give a crude product (13.3 g) of 2-amino-2-(4-(trifluoromethoxy)phenyl)acetic acid. To a solution of the obtained crude product (13.3 g) in tetrahydrofuran (113 mL) were added di-tert-butyl dicarbonate (19.7 mL) and 2 M aqueous sodium hydroxide solution (85 mL) at room temperature. The reaction mixture was stirred overnight at room temperature, and poured into water, and the mixture was washed with diethyl ether. The pH of the aqueous layer was adjusted to 3 with 1 M hydrochloric acid at 0° C., and the mixture was extracted with ethyl acetate. The extract was washed with saturated brine, and dried over anhydrous magnesium sulfate, and the solvent was evaporated under reduced pressure to give a crude product (11.3 g) of 2-((tert-butoxycarbonyl) amino)-2-(4-(trifluoromethoxy)phenyl) acetic acid. To a solution of the obtained crude product (11.3 g) in N,N-dimethylformamide (84 mL) were added methyl iodide (2.53 mL) and potassium carbonate (5.59 g) at room temperature. The reaction mixture was stirred at room temperature for 2 hr, and poured into water, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (8.20 g).
MS (API−): [M−H]$^-$348.1.

E) tert-butyl(2-hydroxy-2-methyl-1-(4-(trifluoromethoxy)phenyl)propyl)carbamate

To a solution of methyl 2-((tert-butoxycarbonyl)amino)-2-(4-(trifluoromethoxy)phenyl)acetate (5.00 g) in tetrahydrofuran (71.6 mL) was slowly added 1 M methylmagnesium bromide/tetrahydrofuran solution (57.3 mL) at 0° C. under argon atmosphere. The reaction mixture was stirred at 0° C. for 1 hr under argon atmosphere, saturated aqueous ammonium chloride solution was added thereto at 0° C., and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate) to give the title compound (3.99 g).
MS (API−): [M−H]⁻348.2.

F) 1-amino-2-methyl-1-(4-(trifluoromethoxy)phenyl)propan-2-ol hydrochloride

To tert-butyl(2-hydroxy-2-methyl-1-(4-(trifluoromethoxy)phenyl)propyl)carbamate (2.50 g) was added 4 M hydrogen chloride/ethyl acetate solution (71.6 mL). The reaction mixture was stirred at room temperature for 1 hr, and the solvent was evaporated under reduced pressure. To the residue was added diisopropyl ether, and the resulting crystals were collected by filtration to give the title compound (2.01 g).
MS (API+), found: 250.1.

G) N-(2-hydroxy-2-methyl-1-(4-(trifluoromethoxy)phenyl)propyl)-7-methyl-2-oxo-2,3-dihydropyrido[2,3-b]pyrazine-4(1H)-carboxamide To a suspension of 4-nitrophenyl 7-methyl-2-oxo-2,3-dihydropyrido[2,3-b]pyrazine-4(1H)-carboxylate (263 mg) in N,N-dimethylformamide (4.00 mL) were added 1-amino-2-methyl-1-(4-(trifluoromethoxy)phenyl)propan-2-ol hydrochloride (251 mg) and triethylamine (245 μL) at room temperature. The reaction mixture was stirred overnight at room temperature, and poured into water, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate), and the obtained solid was washed with diisopropyl ether to give the title compound (298 mg).
MS (API+): [M+H]⁺439.1.
¹H NMR (300 MHz, DMSO-d₆) δ 0.94-1.03 (3H, m), 1.18 (3H, s), 2.27 (3H, s), 4.27-4.36 (1H, m), 4.37-4.47 (1H, m), 4.68 (1H, d, J=8.3 Hz), 4.78 (1H, s), 7.13 (1H, d, J=1.5 Hz), 7.27 (2H, d, J=7.9 Hz), 7.42 (2H, d, J=8.7 Hz), 7.87 (1H, d, J=1.1 Hz), 10.54 (1H, d, J=8.3 Hz), 10.77 (1H, brs).

Example 251

7-methoxy-N-((1S)-2-methoxy-1-(4-(trifluoromethoxy)phenyl)ethyl)-6-methyl-2-oxo-2,3-dihydropyrido[2,3-b]pyrazine-4(1H)-carboxamide Racemic 7-methoxy-N-(2-methoxy-1-(4-(trifluoromethoxy)phenyl)ethyl)-6-methyl-2-oxo-2,3-dihydropyrido[2,3-b]pyrazine-4(1H)-carboxamide (80 mg) was resolved by HPLC (column: CHIRALPAK IA, 50 mmID× 500 mmL, manufactured by Daicel Chemical Industries, Ltd., mobile phase: hexane/ethanol=70/30, subsequently changed to 50/50) to give the title compound having a shorter retention time (23 mg).
MS (API+): [M+H]⁺455.1.

Example 252

7-methoxy-N-((1R)-2-methoxy-1-(4-(trifluoromethoxy)phenyl)ethyl)-6-methyl-2-oxo-2,3-dihydropyrido[2,3-b]pyrazine-4(1H)-carboxamide Racemic 7-methoxy-N-(2-methoxy-1-(4-(trifluoromethoxy)phenyl)ethyl)-6-methyl-2-oxo-2,3-dihydropyrido[2,3-b]pyrazine-4(1H)-carboxamide (80 mg) was resolved by HPLC (column: CHIRALPAK IA, 50 mmID× 500 mmL, manufactured by Daicel Chemical Industries, Ltd., mobile phase: hexane/ethanol=70/30, subsequently changed to 50/50) to give the title compound having a longer retention time (18 mg).
MS (API+): [M+H]⁺455.1.

Example 253

N-((1S)-2-hydroxy-2-methyl-1-(4-(trifluoromethoxy)phenyl)propyl)-7-methoxy-6-methyl-2-oxo-2,3-dihydropyrido[2,3-b]pyrazine-4(1H)-carboxamide Racemic N-(2-hydroxy-2-methyl-1-(4-(trifluoromethoxy)phenyl)propyl)-7-methoxy-6-methyl-2-oxo-2,3-dihydropyrido[2,3-b]pyrazine-4(1H)-carboxamide (33 mg) was resolved by HPLC (column: CHIRALPAK IA, 50 mmID×500 mmL, manufactured by Daicel Chemical Industries, Ltd., mobile phase: hexane/ethanol=70/30, subsequently changed to 50/50) to give the title compound having a shorter retention time (15 mg).
MS (API+): [M+H]⁺469.1.

Example 254

N-((1R)-2-hydroxy-2-methyl-1-(4-(trifluoromethoxy)phenyl)propyl)-7-methoxy-6-methyl-2-oxo-2,3-dihydropyrido[2,3-b]pyrazine-4(1H)-carboxamide Racemic N-(2-hydroxy-2-methyl-1-(4-(trifluoromethoxy)phenyl)propyl)-7-methoxy-6-methyl-2-oxo-2,3-dihydropyrido[2,3-b]pyrazine-4(1H)-carboxamide (33 mg) was resolved by HPLC (column: CHIRALPAK IA, 50 mmID×500 mmL, manufactured by Daicel Chemical Industries, Ltd., mobile phase: hexane/ethanol=70/30, subsequently changed to 50/50) to give the title compound having a longer retention time (15 mg).
MS (API+): [M+H]⁺469.1.

Example 255

7-methyl-2-oxo-N-(1-(5-(trifluoromethyl)pyridin-2-yl)propyl)-2,3-dihydropyrido[2,3-b]pyrazine-4(1H)-carboxamide The title compound was obtained from 5-(trifluoromethyl)pyridine-2-carboxylic acid in the same manner as in Step A of Example 84, Steps C-F of Example 2 and Example Step L of Example 72-I.
MS (API+): [M+H]⁺394.1.

Example 256

7-cyclopropyl-N-(2-hydroxy-2-methyl-1-(4-(trifluoromethyl)phenyl)propyl)-2-oxo-2,3-dihydropyrido[2,3-b]pyrazine-4(1H)-carboxamide The title compound was obtained from 1-amino-1-(4-(trifluoromethyl)phenyl)-2-methylpropan-2-ol hydrochloride in the same manner as in Steps K-M of Example 75.
MS (API+): [M+H]⁺ 449.2.

Example 257

Optically Active N-(3-methoxy-1-(4-(trifluoromethoxy)phenyl)propyl)-7-methyl-2-oxo-2,3-dihydropyrido[2,3-b]pyrazine-4(1H)-carboxamide Racemic N-(3-methoxy-1-(4-(trifluoromethoxy)phenyl)propyl)-7-methyl-2-oxo-2,3-dihydropyrido[2,3-b]pyrazine-4(1H)-carboxamide (300 mg) was resolved by HPLC (column: CHIRALPAK IA, 50 mmID×500 mmL, manufactured by Daicel Chemical Industries, Ltd., mobile phase: hexane/ethanol=70/30, subsequently changed to 50/50) to give the title compound having a shorter retention time (140 mg).

MS (API+): [M+H]$^+$439.1.

Example 258

Optically Active N-(3-methoxy-1-(4-(trifluoromethoxy)phenyl)propyl)-7-methyl-2-oxo-2,3-dihydropyrido[2,3-b]pyrazine-4(1H)-carboxamide Racemic N-(3-methoxy-1-(4-(trifluoromethoxy)phenyl)propyl)-7-methyl-2-oxo-2,3-dihydropyrido[2,3-b]pyrazine-4(1H)-carboxamide (300 mg) was resolved by HPLC (column: CHIRALPAK IA, 50 mmID×500 mmL, manufactured by Daicel Chemical Industries, Ltd., mobile phase: hexane/ethanol=70/30, subsequently changed to 50/50) to give the title compound having a longer retention time (134 mg).

MS (API+): [M+H]$^+$439.1.

Example 259

6-methoxy-N-((1S)-2-methoxy-1-(4-(trifluoromethoxy)phenyl)ethyl)-7-methyl-2-oxo-2,3-dihydropyrido[2,3-b]pyrazine-4(1H)-carboxamide Racemic N-(3-methoxy-1-(4-(trifluoromethoxy)phenyl)propyl)-7-methyl-2-oxo-2,3-dihydropyrido[2,3-b]pyrazine-4(1H)-carboxamide (100 mg) was resolved by HPLC (column: CHIRALPAK IA, 50 mmID×500 mmL, manufactured by Daicel Chemical Industries, Ltd., mobile phase: hexane/ethanol=70/30) to give the title compound having a shorter retention time (29.2 mg).

MS (API+): [M+H]$^+$455.1.

Example 260

6-methoxy-N-((1R)-2-methoxy-1-(4-(trifluoromethoxy)phenyl)ethyl)-7-methyl-2-oxo-2,3-dihydropyrido[2,3-b]pyrazine-4(1H)-carboxamide Racemic N-(3-methoxy-1-(4-(trifluoromethoxy)phenyl)propyl)-7-methyl-2-oxo-2,3-dihydropyrido[2,3-b]pyrazine-4(1H)-carboxamide (100 mg) was resolved by HPLC (column: CHIRALPAK IA, 50 mmID×500 mmL, manufactured by Daicel Chemical Industries, Ltd., mobile phase: hexane/ethanol=70/30) to give the title compound having a longer retention time (33.8 mg).

MS (API+): [M+H]$^+$455.1.

Example 261

N-((1S)-2-hydroxy-2-methyl-1-(4-(trifluoromethoxy)phenyl)propyl)-6-methoxy-7-methyl-2-oxo-2,3-dihydropyrido[2,3-b]pyrazine-4(1H)-carboxamide Racemic N-(2-hydroxy-2-methyl-1-(4-(trifluoromethoxy)phenyl)propyl)-6-methoxy-7-methyl-2-oxo-2,3-dihydropyrido[2,3-b]pyrazine-4(1H)-carboxamide (85 mg) was resolved by HPLC (column: CHIRALPAK AD, 50 mmID×500 mmL, manufactured by Daicel Chemical Industries, Ltd., mobile phase: hexane/ethanol=800/200) to give the title compound having a shorter retention time (29 mg).

MS (API+): [M+H]$^+$469.2.

Example 262

N-((1R)-2-hydroxy-2-methyl-1-(4-(trifluoromethoxy)phenyl)propyl)-6-methoxy-7-methyl-2-oxo-2,3-dihydropyrido[2,3-b]pyrazine-4(1H)-carboxamide Racemic N-(2-hydroxy-2-methyl-1-(4-(trifluoromethoxy)phenyl)propyl)-6-methoxy-7-methyl-2-oxo-2,3-dihydropyrido[2,3-b]pyrazine-4(1H)-carboxamide (85 mg) was resolved by HPLC (column: CHIRALPAK AD, 50 mmID×500 mmL, manufactured by Daicel Chemical Industries, Ltd., mobile phase: hexane/ethanol=800/200) to give the title compound having a longer retention time (23 mg).

MS (API+): [M+H]$^+$469.2.

Example 263

N-((1S)-2-hydroxy-2-methyl-1-(4-(trifluoromethoxy)phenyl)propyl)-7-methyl-2-oxo-2,3-dihydropyrido[2,3-b]pyrazine-4(1H)-carboxamide Racemic N-(2-hydroxy-2-methyl-1-(4-(trifluoromethoxy)phenyl)propyl)-7-methyl-2-oxo-2,3-dihydropyrido[2,3-b]pyrazine-4(1H)-carboxamide (270 mg) was resolved by HPLC (column: CHIRALPAK IA, 50 mmID×500 mmL, manufactured by Daicel Chemical Industries, Ltd., mobile phase: hexane/ethanol=70/30, subsequently changed to 50/50), crystallized from hexane/diisopropyl ether to give the title compound having a shorter retention time (116 mg).

MS (API+): [M+H]$^+$439.1.

$^1$H NMR (300 MHz, DMSO-$d_6$) δ 0.95-1.03 (3H, m), 1.18 (3H, s), 2.27 (3H, s), 4.26-4.37 (1H, m), 4.38-4.47 (1H, m), 4.60-4.93 (2H, m), 7.13 (1H, d, J=1.5 Hz), 7.27 (2H, d, J=7.9 Hz), 7.42 (2H, d, J=9.0 Hz), 7.87 (1H, d, J=1.5 Hz), 10.54 (1H, d, J=8.3 Hz), 10.77 (1H, s).

Example 264

N-((1R)-2-hydroxy-2-methyl-1-(4-(trifluoromethoxy)phenyl)propyl)-7-methyl-2-oxo-2,3-dihydropyrido[2,3-b]pyrazine-4(1H)-carboxamide Racemic N-(2-hydroxy-2-methyl-1-(4-(trifluoromethoxy)phenyl)propyl)-7-methyl-2-oxo-2,3-dihydropyrido[2,3-b]pyrazine-4(1H)-carboxamide (85 mg) was resolved by HPLC (column: CHIRALPAK IA, 50 mmID×500 mmL, manufactured by Daicel Chemical Industries, Ltd., mobile phase: hexane/ethanol=70/30, subsequently changed to 50/50), and crystallized from hexane/diisopropyl ether to give the title compound having a longer retention time (103 mg).
MS (API+): [M+H]$^+$439.1.

Example 265

Optically Active 7-cyclopropyl-N-(2-hydroxy-2-methyl-1-(4-(trifluoromethyl)phenyl)propyl)-2-oxo-2,3-dihydropyrido[2,3-b]pyrazine-4(1H)-carboxamide Racemic 7-cyclopropyl-N-(2-hydroxy-2-methyl-1-(4-(trifluoromethyl)phenyl)propyl)-2-oxo-2,3-dihydropyrido[2,3-b]pyrazine-4(1H)-carboxamide (478 mg) was resolved by HPLC (column: CHIRALPAK IA, 400 mmID×250 mmL, manufactured by Daicel Chemical Industries, Ltd., mobile phase: hexane/ethanol=700/300), and recrystallized from hexane/ethyl acetate to give the title compound having a longer retention time (170 mg).
MS (API+): [M+H]$^+$449.1.

Example 266

Optically Active 7-cyclopropyl-N-(2-hydroxy-2-methyl-1-(4-(trifluoromethyl)phenyl)propyl)-2-oxo-2,3-dihydropyrido[2,3-b]pyrazine-4(1H)-carboxamide Racemic 7-cyclopropyl-N-(2-hydroxy-2-methyl-1-(4-(trifluoromethyl)phenyl)propyl)-2-oxo-2,3-dihydropyrido[2,3-b]pyrazine-4(1H)-carboxamide (478 mg) was resolved by HPLC (column: CHIRALPAK IA, 400 mmID×250 mmL, manufactured by Daicel Chemical Industries, Ltd., mobile phase: hexane/ethanol=700/300), and recrystallized from hexane/ethyl acetate to give the title compound having a shorter retention time (156 mg).
MS (API+): [M+H]$^+$449.1.

Example 267

N-(2-hydroxy-2-methyl-1-(4-(trifluoromethyl)phenyl)propyl)-7-methoxy-2-oxo-2,3-dihydropyrido[2,3-b]pyrazine-4(1H)-carboxamide A) methyl 2-bromo-2-(4-(trifluoromethyl)phenyl)acetate The title compound was obtained from (4-(trifluoromethyl)phenyl)acetic acid in the same manner as in Steps A and Step D of Example 185.
$^1$H NMR (300 MHz, DMSO-d$_6$) δ 3.75 (3H, s), 5.98-6.21 (1H, m), 7.79 (4H, s).

B) methyl azido(4-(trifluoromethyl)phenyl)acetate

To a solution of methyl 2-bromo-2-(4-(trifluoromethyl)phenyl)acetate (11.8 g) in acetonitrile (265 mL) was added sodium azide (1.55 g) at 0° C. The reaction mixture was stirred at room temperature for 4 hr, and added to water, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give the title compound (10.8 g).
$^1$H NMR (300 MHz, CDCl$_3$) δ 3.80 (3H, s), 5.08 (1H, s), 7.53 (2H, d, J=8.3 Hz), 7.68 (2H, d, J=8.3 Hz).

C) methyl amino (4-(trifluoromethyl)phenyl)acetate

To a solution of methyl azido(4-(trifluoromethyl)phenyl)acetate (10.6 g) in methanol (408 mL) was added 10% palladium-carbon (containing 50% water, 1.10 g). The reaction mixture was stirred at room temperature for 6 hr under hydrogen atmosphere, the catalyst was filtered off, and the filtrate was concentrated under reduced pressure to give the title compound (9.13 g).
MS (API+): [M+H]$^+$234.1.

D) methyl ((tert-butoxycarbonyl) amino)(4-(trifluoromethyl)phenyl)acetate

The title compound was obtained from methyl 2-amino-2-(4-(trifluoromethoxy)phenyl)acetate in the same manner as in Step G of Example 75.
MS (API−): [M−H]$^-$332.1.

E) tert-butyl (2-hydroxy-2-methyl-1-(4-(trifluoromethyl)phenyl)propyl)carbamate

The title compound was obtained in the same manner as in Step B of Example 250.
MS (API−): [M−H]$^-$332.2.

F) 1-amino-2-methyl-1-(4-(trifluoromethyl)phenyl)propan-2-ol hydrochloride

The title compound was obtained in the same manner as in Step B of Example 92.
MS (API+), found: 234.1.

G) N-(2-hydroxy-2-methyl-1-(4-(trifluoromethyl)phenyl)propyl)-7-methoxy-2-oxo-2,3-dihydropyrido[2,3-b]pyrazine-4(1H)-carboxamide The title compound was obtained from 1-amino-2-methyl-1-(4-(trifluoromethyl)phenyl)propan-2-ol hydrochloride in the same manner as in Steps I-L of Example 66.
MS (API+): [M+H]$^+$439.2.

Example 268

Optically Active N-(2-hydroxy-2-methyl-1-(4-(trifluoromethyl)phenyl)propyl)-7-methoxy-2-oxo-2,3-dihydropyrido[2,3-b]pyrazine-4(1H)-carboxamide Racemic N-(2-hydroxy-2-methyl-1-(4-(trifluoromethyl)phenyl)propyl)-7-methoxy-2-oxo-2,3-dihydropyrido[2,3-b]pyrazine-4(1H)-carboxamide (221 mg) was resolved by HPLC (column: CHIRALPAK AD, 50 mmID×500 mmL, manufactured by Daicel Chemical Industries, Ltd., mobile phase: hexane/ethanol=50/50) to give the title compound having a shorter retention time (71.7 mg).
MS (API+): [M+H]$^+$439.2.

Example 269

Optically Active N-(2-hydroxy-2-methyl-1-(4-(trifluoromethyl)phenyl)propyl)-7-methoxy-2-oxo-2,3-dihydropyrido[2,3-b]pyrazine-4(1H)-carboxamide Racemic N-(2-hydroxy-2-methyl-1-(4-(trifluoromethyl)phenyl)propyl)-7-methoxy-2-oxo-2,3-dihydropyrido[2,3-b]

pyrazine-4(1H)-carboxamide (221 mg) was resolved by HPLC (column: CHIRALPAK AD, 50 mmIDx500 mmL, manufactured by Daicel Chemical Industries, Ltd., mobile phase: hexane/ethanol=50/50) to give the title compound having a longer retention time (78.3 mg).

MS (API+): [M+H]$^+$439.2.

Example 270

Optically Active 7-methyl-2-oxo-N-(1-(5-(trifluoromethyl)pyridin-2-yl)propyl)-2,3-dihydropyrido[2,3-b]pyrazine-4(1H)-carboxamide Racemic 7-methyl-2-oxo-N-(1-(5-(trifluoromethyl)pyridin-2-yl)propyl)-2,3-dihydropyrido[2,3-b]pyrazine-4(1H)-carboxamide (296 mg) was resolved by HPLC (column: CHIRALPAK AD, 50 mmIDx500 mmL, manufactured by Daicel Chemical Industries, Ltd., mobile phase: hexane/ethanol=450/550) to give the title compound having a shorter retention time (136 mg).

MS (API+): [M+H]$^+$ 394.1.

Example 271

Optically Active 7-methyl-2-oxo-N-(1-(5-(trifluoromethyl)pyridin-2-yl)propyl)-2,3-dihydropyrido[2,3-b]pyrazine-4(1H)-carboxamide Racemic 7-methyl-2-oxo-N-(1-(5-(trifluoromethyl)pyridin-2-yl)propyl)-2,3-dihydropyrido[2,3-b]pyrazine-4(1H)-carboxamide (296 mg) was resolved by HPLC (column: CHIRALPAK AD, 50 mmIDx500 mmL, manufactured by Daicel Chemical Industries, Ltd., mobile phase: hexane/ethanol=450/550) to give the title compound having a longer retention time (134 mg).

MS (API+): [M+H]$^+$ 394.1.

Example 272

N-(1-(3-fluoro-4-(trifluoromethoxy)phenyl)-2-hydroxy-2-methylpropyl)-7-methyl-2-oxo-2,3-dihydropyrido[2,3-b]pyrazine-4(1H)-carboxamide A) methyl 2-((5-methyl-3-nitropyridin-2-yl) amino) acetate To a mixture of methyl glycinate hydrochloride (8.32 g) and 2-chloro-5-methyl-3-nitropyridine (7.62 g) in N,N-dimethylformamide (100 mL) was added triethylamine (18.5 mL). The reaction mixture was stirred at 80° C. for 16 hr, and the solvent was evaporated under reduced pressure. To the residue was added water, and the mixture was extracted with ethyl acetate. The extract was washed with water, and dried over anhydrous sodium sulfate, and the solvent was evaporated under reduced pressure. The residue was purified by silica gel column chromatography (ethyl acetate/hexane) to give the title compound (6.99 g).

$^1$H NMR (300 MHz, DMSO-d$_6$) δ 2.24 (3H, s), 3.64 (3H, s), 4.28 (2H, d, J=5.7 Hz), 8.27-8.37 (2H, m), 8.60 (1H, t, J=5.7 Hz).

B) 7-methyl-3,4-dihydropyrido[2,3-b]pyrazin-2(1H)-one

To a solution of methyl 2-((5-methyl-3-nitropyridin-2-yl) amino)acetate (6.99 g) in ethanol (100 mL) was added 10% palladium-carbon (containing 50% water, 2.00 g). The reaction mixture was stirred overnight at room temperature under hydrogen atmosphere, the catalyst was filtered off, and the filtrate was concentrated under reduced pressure. To the residue was added ethanol (100 mL), the reaction mixture was heated at reflux for 5 hr, and the solvent was evaporated to about ⅓ of volume under reduced pressure. To the residue was added diisopropyl ether, and the precipitated solid was collected by filtration, washed with diisopropyl ether, and dried under reduced pressure to give the title compound (4.56 g).

$^1$H NMR (300 MHz, DMSO-d$_6$) δ 2.09 (3H, s), 3.85 (2H, d, J=1.5 Hz), 6.45 (1H, s), 6.72-6.80 (1H, m), 7.39-7.48 (1H, m), 10.31 (1H, s).

C) 4-nitrophenyl 7-methyl-2-oxo-2,3-dihydropyrido[2,3-b]pyrazine-4(1H)-carboxylate To a mixture of 7-methyl-3,4-dihydropyrido[2,3-b]pyrazin-2(1H)-one (1.00 g) in N,N-dimethylacetamide (40 mL) and pyridine (15 mL) was added 4-nitrophenyl chloroformate (1.48 g) at room temperature. The reaction mixture was stirred at room temperature for 16 hr, and water was added thereto. The precipitated solid was collected by filtration, washed with water, and dried under reduced pressure to give the title compound (1.63 g).

MS (API+): [M+H]$^+$ 329.1.

D) 2-amino-2-(3-fluoro-4-(trifluoromethoxy)phenyl) acetonitrile

3-Fluoro-4-(trifluoromethoxy)benzaldehyde (10 g) was dissolved in 2 M ammonia/methanol solution (96 mL), titanium(IV) tetraisopropoxide (15.5 mL) was added thereto under ice-cooling. The reaction mixture was stirred at the same temperature for 15 min, trimethylsilanecarbonitrile (9.61 mL) was added thereto, and the mixture was stirred at room temperature for 20 hr. The solvent was evaporated under reduced pressure, and to the residue were added ethyl acetate and saturated aqueous sodium hydrogen carbonate solution. The insoluble substance was filtered off using Celite, and the filtrate was extracted with ethyl acetate. The extract was washed successively with water and saturated brine, and dried over anhydrous magnesium sulfate, and the solvent was evaporated under reduced pressure. The residue was purified by silica gel column chromatography (ethyl acetate/hexane) to give the title compound (9.4 g).

$^1$H NMR (300 MHz, CDCl$_3$) δ 2.01 (2H, brs), 4.93 (1H, s), 7.29-7.53 (3H, m).

E) tert-butyl (cyano(3-fluoro-4-(trifluoromethoxy) phenyl)methyl)carbamate

To a solution of 2-amino-2-(3-fluoro-4-(trifluoromethoxy)phenyl)acetonitrile (9.4 g) in tetrahydrofuran (200 mL) was added di-tert-butyl dicarbonate (10.3 mL) and triethylamine (7.27 mL) at room temperature. The reaction mixture was stirred at 40° C. for 20 hr, water was added thereto, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (8.47 g).

MS (API+): [M+H]$^+$ 335.1.

F) tert-butyl (2-amino-1-(3-fluoro-4-(trifluoromethoxy)phenyl)-2-oxoethyl)carbamate To a mixture of tert-butyl (cyano(3-fluoro-4-(trifluoromethoxy)phenyl)methyl)carbamate (9.4 g), potassium carbonate (3.89 g) and dimethyl sulfoxide (200 mL) was added 35% aqueous hydrogen peroxide (4.66 mL) at room temperature. The reaction mixture was stirred at room temperature for 4 hr, water was added thereto, and the mixture was extracted with ethyl acetate. The extract was washed successively with water and saturated brine, and dried over anhydrous magnesium sulfate, and the solvent was evaporated under reduced pressure. The residue was purified by silica gel column chromatography (ethyl acetate/hexane) to give the title compound (3.84 g).

MS (API+), found: 253.0.

G) methyl 2-((tert-butoxycarbonyl)amino)-2-(3-fluoro-4-(trifluoromethoxy)phenyl)acetate To a solution of tert-butyl (2-amino-1-(3-fluoro-4-(trifluoromethoxy)phenyl)-2-oxoethyl)carbamate (3.84 g) in methanol (100 mL) was added 8 M aqueous sodium hydroxide solution (2.8 mL) at room temperature. The reaction mixture was heated at reflex overnight, and the methanol was evaporated under reduced pressure. The residue was neutralized with 1 M hydrochloric acid, and the mixture was extracted with ethyl acetate. The extract was washed with saturated brine, and dried over anhydrous magnesium sulfate, and the solvent was evaporated under reduced pressure. To a mixture of the residue (3.85 g) and potassium carbonate (1.81 g) in N,N-dimethylformamide (50 mL) was added methyl iodide (0.750 mL) at room temperature. The reaction mixture was stirred at room temperature for 2 hr, water was added thereto, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate) to give the title compound (1.90 g).

MS (API+), found: 268.0.

H) tert-butyl (1-(3-fluoro-4-(trifluoromethoxy)phenyl)-2-hydroxy-2-methylpropyl)carbamate To a solution of methyl 2-((tert-butoxycarbonyl)amino)-2-(3-fluoro-4-(trifluoromethoxy)phenyl)acetate (1.90 g) in tetrahydrofuran (60 mL) was slowly added 3 M methylmagnesium bromide/diethyl ether solution (5.17 mL) at 0° C. The reaction mixture was stirred at room temperature for 3 hr, 1 M hydrochloric acid at 0° C. was added thereto, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate) to give the title compound (1.53 g).

$^1$H NMR (300 MHz, CDCl$_3$) δ 1.06 (3H, s), 1.29-1.50 (13H, m), 4.38-4.52 (1H, m), 5.47-5.60 (1H, m), 7.07-7.30 (3H, m).

I) 1-amino-1-(3-fluoro-4-(trifluoromethoxy)phenyl)-2-methylpropan-2-ol hydrochloride To tert-butyl (1-(3-fluoro-4-(trifluoromethoxy)phenyl)-2-hydroxy-2-methylpropyl)carbamate (3.01 g) was added 4 M hydrogen chloride/ethyl acetate solution (30 mL). The reaction mixture was stirred at room temperature for 1 hr, and the solvent was evaporated under reduced pressure. The residue was washed with diisopropyl ether to give the title compound (2.22 g)

MS (API+), found: 268.1.

J) N-(1-(3-fluoro-4-(trifluoromethoxy)phenyl)-2-hydroxy-2-methylpropyl)-7-methyl-2-oxo-2,3-dihydropyrido[2,3-b]pyrazine-4(1H)-carboxamide To a solution of 4-nitrophenyl 7-methyl-2-oxo-2,3-dihydropyrido[2,3-b]pyrazine-4(1H)-carboxylate (328 mg) and 1-amino-1-(3-fluoro-4-(trifluoromethoxy)phenyl)-2-methylpropan-2-ol hydrochloride (334 mg) in N,N-dimethylformamide (10 mL) was added triethylamine (0.335 mL) at room temperature. The reaction mixture was stirred at room temperature for 16 hr, water was added thereto, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate), and recrystallized from hexane/ethyl acetate to give the title compound (357 mg).

MS (API+): [M+H]$^+$ 457.1.

$^1$H NMR (300 MHz, CDCl$_3$) δ 1.16 (3H, s), 1.37 (3H, s), 1.62 (1H, s), 2.32 (3H, s), 4.54-4.74 (2H, m), 4.85 (1H, d, J=8.3 Hz), 7.02 (1H, d, J=1.1 Hz), 7.14-7.21 (1H, m), 7.21-7.30 (2H, m), 7.86-7.95 (1H, m), 8.78 (1H, s), 10.84 (1H, d, J=8.3 Hz).

Example 273

Optically Active N-(1-(3-fluoro-4-(trifluoromethoxy)phenyl)-2-hydroxy-2-methylpropyl)-7-methyl-2-oxo-2,3-dihydropyrido[2,3-b]pyrazine-4(1H)-carboxamide Racemic N-(1-(3-fluoro-4-(trifluoromethoxy)phenyl)-2-hydroxy-2-methylpropyl)-7-methyl-2-oxo-2,3-dihydropyrido[2,3-b]pyrazine-4(1H)-carboxamide (349 mg) was resolved by HPLC (column: CHIRALPAK IA, 50 mmIDx 500 mmL, manufactured by Daicel Chemical Industries, Ltd., mobile phase: hexane/ethanol=90/10, subsequently changed to 70/30), and recrystallized from acetone/heptane to give the title compound having a shorter retention time (140 mg).

MS (API+): [M+H]$^+$ 457.1.

Example 274

Optically Active N-(1-(3-fluoro-4-(trifluoromethoxy)phenyl)-2-hydroxy-2-methylpropyl)-7-methyl-2-oxo-2,3-dihydropyrido[2,3-b]pyrazine-4(1H)-carboxamide Racemic N-(1-(3-fluoro-4-(trifluoromethoxy)phenyl)-2-hydroxy-2-methylpropyl)-7-methyl-2-oxo-2,3-dihydropyrido[2,3-b]pyrazine-4(1H)-carboxamide (349 mg) was resolved by HPLC (column: CHIRALPAK IA, 50 mmIDx 500 mmL, manufactured by Daicel Chemical Industries, Ltd., mobile phase: hexane/ethanol=90/10, subsequently changed to 70/30), and recrystallized from acetone/heptane to give the title compound having a longer retention time (107 mg).

MS (API+): [M+H]$^+$ 457.1.

Example 275

N-(1-(3-fluoro-4-(trifluoromethoxy)phenyl)-2-hydroxy-2-methylpropyl)-7-methoxy-2-oxo-2,3-dihydropyrido[2,3-b]pyrazine-4(1H)-carboxamide

A) ethyl (5-bromopyridin-3-yl)carbamate

To a mixture of 5-bromopyridin-3-amine (35.4 g) and pyridine (19.8 mL) in tetrahydrofuran (600 mL) was slowly added ethyl chloroformate (23.4 mL) at 0° C. The reaction mixture was stirred overnight at room temperature under nitrogen atmosphere, and poured into water, and the mixture was extracted with ethyl acetate. The extract was washed with saturated brine, and dried over anhydrous magnesium sulfate, and the solvent was evaporated under reduced pressure. To the residue was added diisopropyl ether (400 mL), the mixture was stirred at room temperature for 20 min, and the obtained solid was collected by filtration to give the title compound (29.0 g).
MS (API+):[M+H]$^+$ 245.1.

B) ethyl (5-bromo-2-nitropyridin-3-yl)carbamate

To a solution of ethyl (5-bromopyridin-3-yl)carbamate (19.0 g) in conc. sulfuric acid (37.2 mL) was slowly added fuming nitric acid (26.1 mL) at 0° C. The reaction mixture was stirred at room temperature for 72 hr under nitrogen atmosphere. The reaction mixture was slowly poured into ice, the pH of the mixture was adjusted to 9 with 28% aqueous ammonia, and the mixture was extracted with ethyl acetate. The extract was washed with saturated brine, and dried over anhydrous sodium sulfate, and the solvent was evaporated under reduced pressure. To the residue was added ethyl acetate/hexane, the mixture was stirred for 15 min, and the resulting solid was collected by filtration, and washed with hexane to give the title compound (13.9 g).
MS (API+):[M+H]$^+$ 290.1.

C) 5-methoxy-2-nitropyridin-3-amine

To a solution of ethyl (5-bromo-2-nitropyridin-3-yl)carbamate (31.1 g) in methanol (900 mL) was added 28% sodium methoxide/methanol solution (83.0 g) at room temperature. The reaction mixture was stirred at 65° C. for 4 hr under nitrogen atmosphere, and the solvent was evaporated to about 150 mL under reduced pressure. To the residue was added saturated aqueous ammonium chloride solution, and the mixture was stirred at room temperature for 20 min, and the solvent was evaporated to about 100 mL under reduced pressure. The resulting solid was collected by filtration, and washed with water to give the title compound (16.6 g).
MS (API+):[M+H]$^+$ 170.2.

D) 2-chloro-N-(5-methoxy-2-nitropyridin-3-yl)acetamide

To a solution of 5-methoxy-2-nitropyridin-3-amine (24.7 g) in N,N-dimethylformamide (740 mL) was slowly added a solution of chloroacetyl chloride (23.2 mL) in tetrahydrofuran (40 mL) at 0° C. The reaction mixture was stirred at room temperature for 3 hr under nitrogen atmosphere, and the solvent was evaporated under reduced pressure. To the residue was added saturated aqueous sodium hydrogen carbonate solution, and the mixture was extracted with ethyl acetate. The extract was washed with saturated brine, and dried over anhydrous magnesium sulfate, and the solvent was evaporated under reduced pressure. To the residue was added diisopropyl ether/hexane, and the mixture was stirred at room temperature for 30 min. The obtained solid was collected by filtration, and washed with diisopropyl ether/hexane to give the title compound (34.1 g).
MS (API+):[M+H]$^+$ 246.0.

E) N-(2-amino-5-methoxypyridin-3-yl)-2-chloroacetamide

A mixture of 2-chloro-N-(5-methoxy-2-nitropyridin-3-yl)acetamide (34.1 g), ammonium chloride (44.6 g), iron (27.1 g), ethanol (823 mL) and water (206 mL) was stirred at 75° C. for 40 min, and the solvent was evaporated under reduced pressure. To the residue were added tetrahydrofuran (500 mL) and saturated aqueous sodium hydrogen carbonate solution (300 mL), and the reaction mixture was stirred for 15 min. The insoluble substance was filtered off through Celite, to the filtrate was added saturated brine, and the mixture was extracted with ethyl acetate. The extract was washed with saturated brine, and the solvent was evaporated under reduced pressure. To the residue was added diisopropyl ether/hexane, and the obtained solid was collected by filtration, and washed with diisopropyl ether/hexane to give the title compound (26.3 g).
MS (API+):[M+H]$^+$ 216.1.

F) benzyl (3-((chloroacetyl)amino)-5-methoxypyridin-2-yl)carbamate

To a mixture of N-(2-amino-5-methoxypyridin-3-yl)-2-chloroacetamide (2.74 g), pyridine (5.14 mL) and tetrahydrofuran (85 mL) was slowly added benzyl chloroformate (2.72 mL) at 0° C. The reaction mixture was stirred at room temperature for 1 hr, and ethyl acetate was added thereto. The mixture was washed with a mixture of saturated aqueous sodium hydrogen carbonate solution and saturated brine, and the solvent was evaporated under reduced pressure. The residue was purified by silica gel column chromatography (hexane/ethyl acetate), and the obtained solid was washed with diisopropyl ether to give the title compound (3.79 g).
$^1$H NMR (300 MHz, DMSO-d$_6$) δ 3.82 (3H, s), 4.36 (2H, s), 5.13 (2H, s), 7.30-7.43 (5H, m), 7.87 (1H, d, J=3.0 Hz), 7.95 (1H, d, J=2.6 Hz), 9.46 (1H, s), 9.64 (1H, s).

G) benzyl 7-methoxy-2-oxo-2,3-dihydropyrido[2,3-b]pyrazine-4(1H)-carboxylate To a solution of benzyl (3-((chloroacetyl)amino)-5-methoxypyridin-2-yl)carbamate (200 mg) in N,N-dimethylformamide (11 mL) was added cesium carbonate (279 mg) at 50° C., and the reaction mixture was stirred at 50° C. for 30 min. The reaction mixture was diluted with ethyl acetate, and the mixture was washed with saturated brine, and the solvent was evaporated under reduced pressure. The residue was purified by silica gel column chromatography (hexane/ethyl acetate) to give the title compound (115 mg).
$^1$H NMR (300 MHz, DMSO-d$_6$) δ 3.81 (3H, s), 4.36 (2H, s), 5.20 (2H, s), 6.92 (1H, d, J=2.6 Hz), 7.27-7.43 (5H, m), 7.84 (1H, d, J=2.6 Hz), 10.72 (1H, s).

H) 7-methoxy-3,4-dihydropyrido[2,3-b]pyrazin-2(1H)-one

To a solution of benzyl 7-methoxy-2-oxo-2,3-dihydropyrido[2,3-b]pyrazine-4(1H)-carboxylate (0.722 g) in tetrahydrofuran (46.1 mL) was added 10% palladium-carbon (containing 50% water, 0.049 g), and the reaction mixture was stirred at room temperature for 15 hr under hydrogen atmosphere. To the reaction mixture was added methanol at 50° C. to dissolve the precipitated solid, the catalyst was filtered off, and the filtrate was concentrated under reduced pressure. The obtained solid was washed with diisopropyl ether to give the title compound (0.380 g).

MS (API+): [M+H]+ 180.2.

I) 2-amino-2-(3-fluoro-4-(trifluoromethoxy)phenyl) acetonitrile

3-Fluoro-4-(trifluoromethoxy)benzaldehyde (10 g) was dissolved in 2 M ammonia/methanol solution (96 mL), and titanium(IV) tetraisopropoxide (15.5 mL) was added thereto under ice-cooling. The reaction mixture was stirred at the same temperature for 15 min, trimethylsilanecarbonitrile (9.61 mL) was added thereto, and the mixture was stirred at room temperature for 20 hr. The solvent was evaporated under reduced pressure, and to the residue were added ethyl acetate and saturated aqueous sodium hydrogen carbonate solution. The insoluble substance was filtered off using Celite, and the filtrate was extracted with ethyl acetate. The extract was washed successively with water and saturated brine, and dried over anhydrous magnesium sulfate, and the solvent was evaporated under reduced pressure. The residue was purified by silica gel column chromatography (ethyl acetate/hexane) to give the title compound (9.4 g).

$^1$H NMR (300 MHz, CDCl$_3$) δ 2.01 (2H, brs), 4.93 (1H, s), 7.29-7.53 (3H, m).

J) tert-butyl (cyano(3-fluoro-4-(trifluoromethoxy) phenyl)methyl)carbamate

To a solution of 2-amino-2-(3-fluoro-4-(trifluoromethoxy)phenyl)acetonitrile (9.4 g) in tetrahydrofuran (200 mL) were added di-tert-butyl dicarbonate (10.3 mL) and triethylamine (7.27 mL) at room temperature. The reaction mixture was stirred at 40° C. for 20 hr, water was added thereto, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (8.47 g).

MS (API+): [M+H]+ 335.1.

K) tert-butyl (2-amino-1-(3-fluoro-4-(trifluoromethoxy)phenyl)-2-oxoethyl)carbamate To a mixture of tert-butyl (cyano(3-fluoro-4-(trifluoromethoxy)phenyl)methyl)carbamate (9.4 g), potassium carbonate (3.89 g) and dimethyl sulfoxide (200 mL) was added 35% aqueous hydrogen peroxide (4.66 mL) at room temperature. The reaction mixture was stirred at room temperature for 4 hr, water was added thereto, and the mixture was extracted with ethyl acetate. The extract was washed successively with water and saturated brine, and dried over anhydrous magnesium sulfate, and the solvent was evaporated under reduced pressure. The residue was purified by silica gel column chromatography (ethyl acetate/hexane) to give the title compound (3.84 g).

MS (API+), found: 253.0.

L) methyl 2-((tert-butoxycarbonyl) amino)-2-(3-fluoro-4-(trifluoromethoxy)phenyl)acetate To a solution of tert-butyl (2-amino-1-(3-fluoro-4-(trifluoromethoxy)phenyl)-2-oxoethyl)carbamate (3.84 g) in methanol (100 mL) was added 8 M aqueous sodium hydroxide solution (2.8 mL) at room temperature. The reaction mixture was heated at reflex overnight, and the methanol was evaporated under reduced pressure. The residue was neutralized with 1 M hydrochloric acid, and the mixture was extracted with ethyl acetate. The extract was washed with saturated brine, and dried over anhydrous magnesium sulfate, and the solvent was evaporated under reduced pressure. To a mixture of the residue (3.85 g) and potassium carbonate (1.81 g) in N,N-dimethylformamide (50 mL) was added methyl iodide (0.750 mL) at room temperature. The reaction mixture was stirred at room temperature for 2 hr, water was added thereto, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate) to give the title compound (1.90 g).

MS (API+), found: 268.0.

M) tert-butyl (1-(3-fluoro-4-(trifluoromethoxy)phenyl)-2-hydroxy-2-methylpropyl)carbamate To a solution of methyl 2-((tert-butoxycarbonyl) amino)-2-(3-fluoro-4-(trifluoromethoxy)phenyl)acetate (1.90 g) in tetrahydrofuran (60 mL) was slowly added 3 M methylmagnesium bromide/diethyl ether solution (5.17 mL) at 0° C. The reaction mixture was stirred at room temperature for 3 hr, 1 M hydrochloric acid at 0° C. was added thereto, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate) to give the title compound (1.53 g).

$^1$H NMR (300 MHz, CDCl$_3$) δ 1.06 (3H, s), 1.29-1.50 (13H, m), 4.38-4.52 (1H, m), 5.47-5.60 (1H, m), 7.07-7.30 (3H, m).

N) 1-amino-1-(3-fluoro-4-(trifluoromethoxy)phenyl)-2-methylpropan-2-ol hydrochloride To tert-butyl (1-(3-fluoro-4-(trifluoromethoxy)phenyl)-2-hydroxy-2-methylpropyl)carbamate (3.01 g) was added 4 M hydrogen chloride/ethyl acetate solution (30 mL). The reaction mixture was stirred at room temperature for 1 hr, and the solvent was evaporated under reduced pressure. The residue was washed with diisopropyl ether to give the title compound (2.22 g).

MS (API+), found: 268.1.

O) N-(1-(3-fluoro-4-(trifluoromethoxy)phenyl)-2-hydroxy-2-methylpropyl)-7-methoxy-2-oxo-2,3-dihydropyrido[2,3-b]pyrazine-4(1H)-carboxamide To a solution of 7-methoxy-3,4-dihydropyrido[2,3-b]pyrazin-2(1H)-one (233 mg) in tetrahydrofuran (15 mL) were added 4-nitrophenyl chloroformate (315 mg) and N,N-diisopropylethylamine (0.341 mL) at room temperature. The reaction mixture was stirred at room temperature for 24 hr, water was added thereto, and the mixture was extracted with ethyl acetate. The extract was washed successively with water and saturated brine, and dried over anhydrous magnesium sulfate, and the solvent was evaporated under reduced pressure. To a solution of the residue in N,N-dimethylformamide (15 mL) were added 1-amino-1-(3- fluoro-4-(trifluoromethoxy)phenyl)-2-methylpropan-2-ol hydrochloride (395 mg) and triethylamine (0.544 mL) at room temperature. The reaction mixture was stirred at room temperature for 20 hr, water was added thereto, and the mixture was extracted with ethyl acetate. The extract was washed successively with water and saturated brine, and dried over anhydrous magnesium sulfate, and the solvent was evaporated under reduced pressure. The residue was crystallized from hexane/ethyl acetate to give the title compound (492 mg).

MS (API+): [M+H]$^+$ 473.1.

$^1$H NMR (300 MHz, CDCl$_3$) δ 1.15 (3H, s), 1.38 (3H, s), 1.61 (1H, s), 3.89 (3H, s), 4.52-4.74 (2H, m), 4.84 (1H, d, J=8.3 Hz), 6.79 (1H, d, J=2.6 Hz), 7.14-7.31 (3H, m), 7.75 (1H, d, J=2.6 Hz), 8.44-8.60 (1H, m), 10.49 (1H, d, J=8.3 Hz).

Example 276

Optically Active N-(1-(3-fluoro-4-(trifluoromethoxy)phenyl)-2-hydroxy-2-methylpropyl)-7-methoxy-2-oxo-2,3-dihydropyrido[2,3-b]pyrazine-4(1H)-carboxamide Racemic N-(1-(3-fluoro-4-(trifluoromethoxy)phenyl)-2-hydroxy-2-methylpropyl)-7-methoxy-2-oxo-2,3-dihydropyrido[2,3-b]pyrazine-4(1H)-carboxamide (369 mg) was resolved by HPLC (column: CHIRALPAK AD, 50 mmIDx500 mmL, manufactured by Daicel Chemical Industries, Ltd., mobile phase: hexane/ethanol=850/150), and recrystallized from acetone/heptane to give the title compound having a shorter retention time (148 mg).

MS (API+): [M+H]$^+$ 473.1.

$^1$H NMR (300 MHz, CDCl$_3$) δ 1.15 (3H, s), 1.37 (3H, s), 1.64 (1H, s), 3.89 (3H, s), 4.53-4.72 (2H, m), 4.85 (1H, d, J=8.3 Hz), 6.81 (1H, d, J=2.6 Hz), 7.13-7.31 (3H, m), 7.75 (1H, d, J=2.6 Hz), 8.90 (1H, brs), 10.50 (1H, d, J=8.3 Hz).

Example 277

Optically Active N-(1-(3-fluoro-4-(trifluoromethoxy)phenyl)-2-hydroxy-2-methylpropyl)-7-methoxy-2-oxo-2,3-dihydropyrido[2,3-b]pyrazine-4(1H)-carboxamide Racemic N-(1-(3-fluoro-4-(trifluoromethoxy)phenyl)-2-hydroxy-2-methylpropyl)-7-methoxy-2-oxo-2,3-dihydropyrido[2,3-b]pyrazine-4(1H)-carboxamide (369 mg) was resolved by HPLC (column: CHIRALPAK AD, 50 mmIDx500 mmL, manufactured by Daicel Chemical Industries, Ltd., mobile phase: hexane/ethanol=850/150), and recrystallized from acetone/heptane to give the title compound having a longer retention time (144 mg).

MS (API+): [M+H]$^+$ 473.1.

$^1$H NMR (300 MHz, CDCl$_3$) δ 1.15 (3H, s), 1.37 (3H, s), 1.63 (1H, s), 3.89 (3H, s), 4.52-4.74 (2H, m), 4.85 (1H, d, J=8.3 Hz), 6.81 (1H, d, J=2.6 Hz), 7.11-7.31 (3H, m), 7.75 (1H, d, J=2.6 Hz), 8.78 (1H, brs), 10.50 (1H, d, J=8.3 Hz).

Example 278

N-(1-(3-fluoro-4-(trifluoromethoxy)phenyl)-2-methoxyethyl)-7-methoxy-6-methyl-2-oxo-2,3-dihydropyrido[2,3-b]pyrazine-4(1H)-carboxamide The title compound was obtained from 4-nitrophenyl 7-methoxy-6-methyl-2-oxo-2,3-dihydropyrido[2,3-b]pyrazine-4(1H)-carboxylate and 1-(3-fluoro-4-(trifluoromethoxy)phenyl)-2-methoxyethanamine hydrochloride in the same manner as in Step D of Example 19.

MS (API+): [M+H]$^+$ 473.1.

Example 279

N-(1-(3-fluoro-4-(trifluoromethoxy)phenyl)-2-methoxyethyl)-6-methoxy-7-methyl-2-oxo-2,3-dihydropyrido[2,3-b]pyrazine-4(1H)-carboxamide The title compound was obtained from 4-nitrophenyl 6-methoxy-7-methyl-2-oxo-2,3-dihydropyrido[2,3-b]pyrazine-4(1H)-carboxylate and 1-(3-fluoro-4-(trifluoromethoxy)phenyl)-2-methoxyethanamine hydrochloride in the same manner as in Step D of Example 19.

MS (API+): [M+H]$^+$ 473.1.

Example 280

N-(2-cyano-1-(3-fluoro-4-(trifluoromethoxy)phenyl)ethyl)-7-methoxy-2-oxo-2,3-dihydropyrido[2,3-b]pyrazine-4(1H)-carboxamide A) 3-amino-3-(3-fluoro-4-(trifluoromethoxy)phenyl)propanoic acid To a solution of 3-fluoro-4-(trifluoromethoxy)benzaldehyde (2.08 g) in ethanol (40 mL) were added malonic acid (1.35 g) and ammonium acetate (1.16 g) at room temperature, and the mixture was stirred at 80° C. for 20 hr. The reaction mixture was filtered, and the obtained solid was washed with ethanol to give the title compound (1.48 g).

MS (API+): [M+H]$^+$ 268.1.

B) tert-butyl (3-amino-1-(3-fluoro-4-(trifluoromethoxy)phenyl)-3-oxopropyl)carbamate To a solution of 3-amino-3-(3-fluoro-4-(trifluoromethoxy)phenyl)propanoic acid (1.48 g) in tetrahydrofuran (50 mL) were added di-tert-butyl dicarbonate (1.54 mL) and 2 M aqueous sodium hydroxide solution (4.0 mL), and the mixture was stirred at room temperature for 20 hr. The reaction mixture was neutralized with 1 M hydrochloric acid, and the mixture was extracted with ethyl acetate. The extract was washed successively with water and saturated brine, and dried over anhydrous magnesium sulfate, and the solvent was evaporated under reduced pressure. A mixture of the residue, 1H-benzotriazol-1-ol ammonium salt (1.01 g) and 1-(3-dimethylaminopropyl)-3-ethylcarbodiimide hydrochloride (1.27 g) in N,N-dimethylformamide (35 mL) was stirred at room temperature for 24 hr, water was added thereto, and the mixture was extracted with ethyl acetate. The extract was washed successively with water and saturated brine, and dried over anhydrous magnesium sulfate, and the solvent was evaporated under reduced pressure. The residue was crystallized from hexane/ethyl acetate to give the title compound (1.38 g).

MS (API+): [M−H]$^-$ 365.0.

C) tert-butyl (2-cyano-1-(3-fluoro-4-(trifluoromethoxy)phenyl)ethyl)carbamate

To a solution of tert-butyl (3-amino-1-(3-fluoro-4-(trifluoromethoxy)phenyl)-3-oxopropyl)carbamate (1.0 g) in toluene/tetrahydrofuran (1:1, 75 mL) was added thionyl chloride (0.498 mL) at room temperature. The reaction mixture was stirred at 60° C. for 20 hr, and the solvent was evaporated under reduced pressure. To the residue was added water, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate) to give the title compound (380 mg).

MS (API+): [M+H]$^+$ 349.1.

D) 3-amino-3-(3-fluoro-4-(trifluoromethoxy)phenyl) propanenitrile hydrochloride A mixture of tert-butyl (2-cyano-1-(3-fluoro-4-(trifluoromethoxy)phenyl)ethyl)carbamate (431 mg) and 4 M hydrogen chloride/ethyl acetate (5 mL) was stirred at room temperature for 30 min. The solvent was evaporated under reduced pressure, and the residue was washed with diisopropyl ether to give the title compound (328 mg).

MS (API+), found: 249.0.

E) N-(2-cyano-1-(3-fluoro-4-(trifluoromethoxy)phenyl)ethyl)-7-methoxy-2-oxo-2,3-dihydropyrido[2,3-b]pyrazine-4(1H)-carboxamide To a solution of 4-nitrophenyl 7-methoxy-2-oxo-2,3-dihydropyrido[2,3-b]pyrazine-4(1H)-carboxylate (275 mg) and 3-amino-3-(3-fluoro-4-(trifluoromethoxy)phenyl)propanenitrile hydrochloride (296 mg) in N,N-dimethylformamide (10 mL) was added triethylamine (0.334 mL) at room temperature. The reaction mixture was stirred at room temperature for 20 hr, and then at 60° C. for 24 hr. To the reaction mixture was added water, and the mixture was extracted with ethyl acetate. The extract was washed successively with water and saturated brine, and dried over anhydrous magnesium sulfate, and the solvent was evaporated under reduced pressure. The residue was purified by silica gel column chromatography (hexane/ethyl acetate) to give the title compound (349 mg).

MS (API+): [M+H]$^+$ 454.1.

The compounds of Examples according to the above-mentioned method or a method analogous thereto are shown in the following tables. Mass in the tables means measured value.

TABLE 1-1

| Example No. | IUPAC Name | Structure | Mass (M + 1) | Mass (M − 1) |
|---|---|---|---|---|
| 1 | N-(1-(4-methoxyphenyl)propyl)-2-oxo-2,3-dihydropyrido[2,3-b]pyrazine-4(1H)-carboxamide | 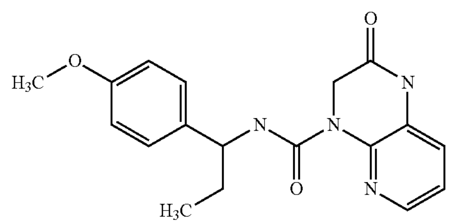 [SMILES: CCC(NC(=O)N1CC(=O)Nc2cccnc21)c1ccc(OC)cc1] | | 339.0 |
| 2 | 2-oxo-N-(1-(4-(trifluoromethoxy)phenyl)propyl)-2,3-dihydropyrido[2,3-b]pyrazine-4(1H)-carboxamide | 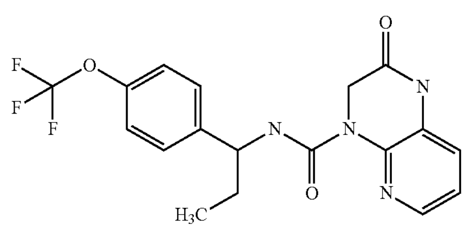 [SMILES: CCC(NC(=O)N1CC(=O)Nc2cccnc21)c1ccc(OC(F)(F)F)cc1] | | 395.2 |
| 3 | N-(1-(4-methoxyphenyl)propyl)-7-methyl-2-oxo-2,3-dihydropyrido[2,3-b]pyrazine-4(1H)-carboxamide | 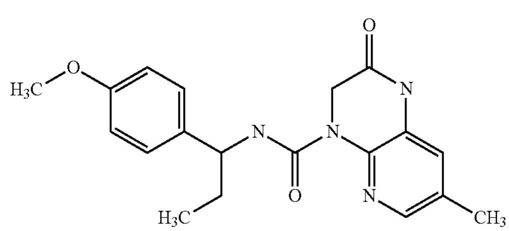 | | 355.1 |
| 4 | 7-methyl-2-oxo-N-(1-(4-(trifluoromethoxy)phenyl)propyl)-2,3-dihydropyrido[2,3-b]pyrazine-4(1H)-carboxamide | 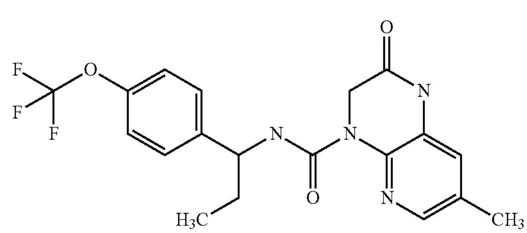 [SMILES: CCC(NC(=O)N1CC(=O)Nc2cc(C)cnc21)c1ccc(OC(F)(F)F)cc1] | | 409.2 |

TABLE 1-1-continued

| Example No. | IUPAC Name | Structure | Mass (M + 1) | Mass (M − 1) |
|---|---|---|---|---|
| 5 | optically active 7-methyl-2-oxo-N-(1-(4-(trifluoromethoxy)phenyl)propyl)-2,3-dihydropyrido[2,3-b]pyrazine-4(1H)-carboxamide | 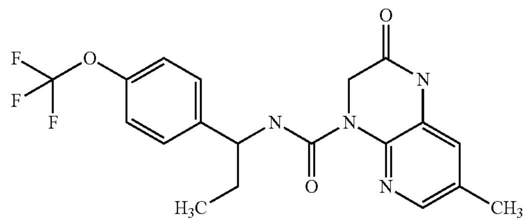 [SMILES: CCC(NC(=O)N1CC(=O)Nc2cc(C)cnc21)c1ccc(OC(F)(F)F)cc1] | 409.1 | |
| 6 | optically active 7-methyl-2-oxo-N-(1-(4-(trifluoromethoxy)phenyl)propyl)-2,3-dihydropyrido[2,3-b]pyrazine-4(1H)-carboxamide | 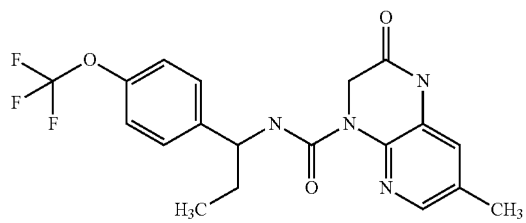 [SMILES: CCC(NC(=O)N1CC(=O)Nc2cc(C)cnc21)c1ccc(OC(F)(F)F)cc1] | 409.1 | |
| 7 | N-(2-methoxy-1-(4-(trifluoromethoxy)phenyl)ethyl)-2-oxo-2,3-dihydropyrido[2,3-b]pyrazine-4(1H)-carboxamide | 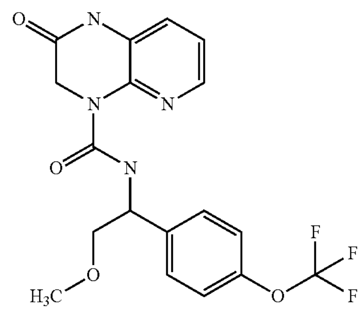 [SMILES: COCC(NC(=O)N1CC(=O)Nc2cccnc21)c1ccc(OC(F)(F)F)cc1] | 411.1 | |
| 8 | optically active 2-oxo-N-(1-(4-(trifluoromethoxy)phenyl)propyl)-2,3-dihydropyrido[2,3-b]pyrazine-4(1H)-carboxamide | 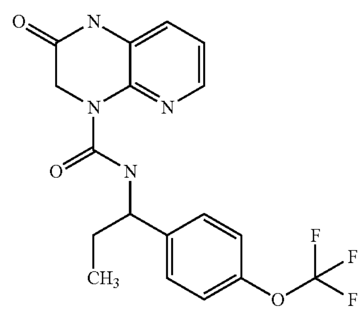 [SMILES: CCC(NC(=O)N1CC(=O)Nc2cccnc21)c1ccc(OC(F)(F)F)cc1] | 395.1 | |
| 9 | optically active 2-oxo-N-(1-(4-(trifluoromethoxy)phenyl)propyl)-2,3-dihydropyrido[2,3-b]pyrazine-4(1H)-carboxamide | 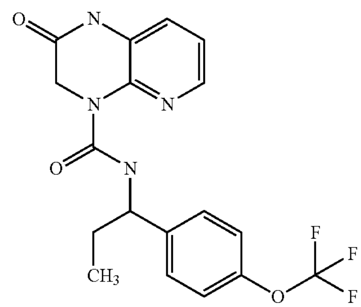 [SMILES: CCC(NC(=O)N1CC(=O)Nc2cccnc21)c1ccc(OC(F)(F)F)cc1] | 395.1 | |

TABLE 1-1-continued

| Example No. | IUPAC Name | Structure | Mass (M + 1) | Mass (M − 1) |
|---|---|---|---|---|
| 10 | 8-methyl-2-oxo-N-(1-(4-(trifluoromethoxy)phenyl)propyl)-2,3-dihydropyrido[2,3-b]pyrazine-4(1H)-carboxamide | 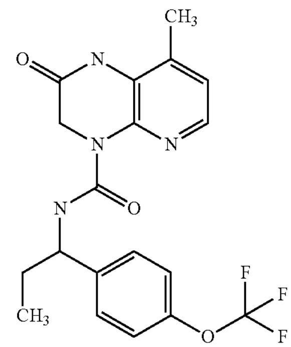 [SMILES: CCC(NC(=O)N1CC(=O)Nc2c(C)ccnc21)c1ccc(OC(F)(F)F)cc1] | 409.1 | |
| 11 | 6-methyl-2-oxo-N-(1-(4-(trifluoromethoxy)phenyl)propyl)-2,3-dihydropyrido[2,3-b]pyrazine-4(1H)-carboxamide | 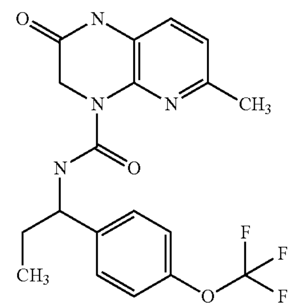 [SMILES: CCC(NC(=O)N1CC(=O)Nc2ccc(C)nc21)c1ccc(OC(F)(F)F)cc1] | 409.1 | |
| 12 | N-(2-methyl-1-(4-(trifluoromethoxy)phenyl)propyl)-2-oxo-2,3-dihydropyrido[2,3-b]pyrazine-4(1H)-carboxamide | 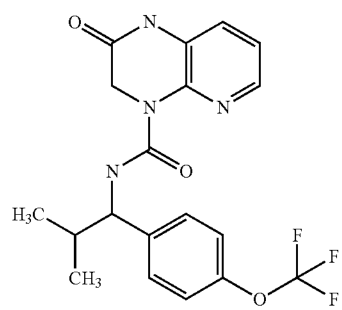 [SMILES: CC(C)C(NC(=O)N1CC(=O)Nc2cccnc21)c1ccc(OC(F)(F)F)cc1] | 409.1 | |

TABLE 1-2

| | | | | |
|---|---|---|---|---|
| 13 | N-(2-hydroxy-1-(4-(trifluoromethoxy)phenyl)ethyl)-2-oxo-2,3-dihydropyrido[2,3-b]pyrazine-4(1H)-carboxamide | | 397.1 | |

TABLE 1-2-continued

| | | | |
|---|---|---|---|
| 14 | N-(2-hydroxy-2-methyl-1-(4-(trifluoromethoxy)phenyl)propyl)-2-oxo-2,3-dihydropyrido[2,3-b]pyrazine-4(1H)-carboxamide | | 425.0 |
| 15 | N-(cyclopropyl(4-(trifluoromethoxy)phenyl)methyl)-2-oxo-2,3-dihydropyrido[2,3-b]pyrazine-4(1H)-carboxamide | | 407.0 |
| 16 | 2-oxo-N-(1-(4-(trifluoromethoxy)phenyl)butyl)-2,3-dihydropyrido[2,3-b]pyrazine-4(1H)-carboxamide | | 409.0 |
| 17 | 1-methyl-2-oxo-N-(1-(4-(trifluoromethoxy)phenyl)propyl)-2,3-dihydropyrido[2,3-b]pyrazine-4(1H)-carboxamide | | |

$^1$H NMR (300 MHz, CDCl$_3$) δ 0.97 (3H, t, J = 7.5 Hz) 1.83-1.93 (2H, m), 3.36 (3H, s), 4.69 (2H, s), 4.91 (1H, q, J = 6.9 Hz), 7.09 (1H, dd, J = 7.8, 5.1 Hz), 7.18 (2H, d, J = 8.4 Hz), 7.27-7.37 (3H, m), 8.02 (1H, d, J = 4.8 Hz), 10.31 (1H, d, J = 7.5 Hz).

TABLE 1-2-continued

| 18 | N-(1-(4-(difluoromethoxy)phenyl)propyl)-2-oxo-2,3-dihydropyrido[2,3-b]pyrazine-4(1H)-carboxamide | 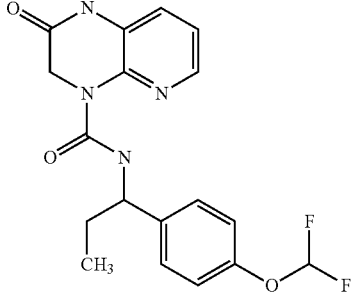 [SMILES: CCC(NC(=O)N1CC(=O)Nc2cccnc21)c1ccc(OC(F)F)cc1] | 377.1 |
| --- | --- | --- | --- |
| 19 | 2-oxo-N-(1-(4-(trifluoromethoxy)phenyl)propyl)-7-(trifluoromethyl)-2,3-dihydropyrido[2,3-b]pyrazine-4(1H)-carboxamide | 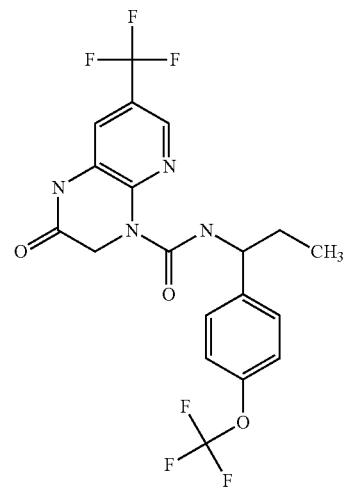 [SMILES: CCC(NC(=O)N1CC(=O)Nc2cc(C(F)(F)F)cnc21)c1ccc(OC(F)(F)F)cc1] | 463.2 |
| 20 | 2-oxo-7-phenyl-N-(1-(4-(trifluoromethoxy)phenyl)propyl)-2,3-dihydropyrido[2,3-b]pyrazine-4(1H)-carboxamide | 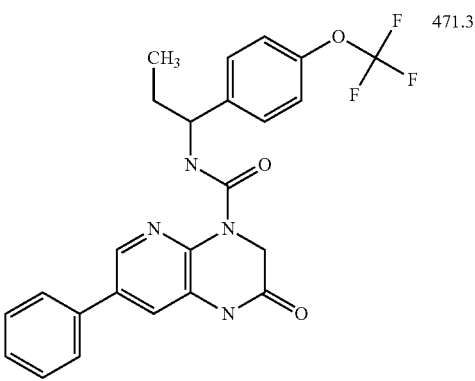 | 471.3 |
| 21 | 6-bromo-3-oxo-N-(1-(4-(trifluoromethoxy)phenyl)propyl)-3,4-dihydropyrazino[2,3-b]pyrazine-1(2H)-carboxamide | 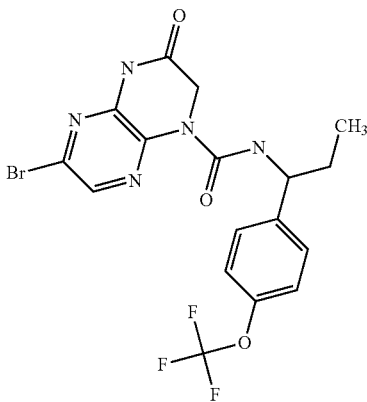 [SMILES: CCC(NC(=O)N1CC(=O)Nc2nc(Br)cnc21)c1ccc(OC(F)(F)F)cc1] | 471.9 |

TABLE 1-2-continued

| | | | |
|---|---|---|---|
| 22 | 3-oxo-N-(1-(4-(trifluoromethoxy)phenyl)propyl)-3,4-dihydropyrazine[2,3-b]pyrazine-1(2H)-carboxamide | 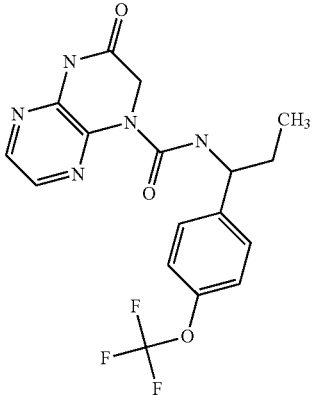 [SMILES: CCC(NC(=O)N1CC(=O)Nc2nccnc21)c1ccc(OC(F)(F)F)cc1] | 394.0 |
| 23 | 6-methyl-3-oxo-N-(1-(4-(trifluoromethoxy)phenyl)propyl)-3,4-dihydropyrazino[2,3-b]pyrazine-1(2H)-carboxamide | 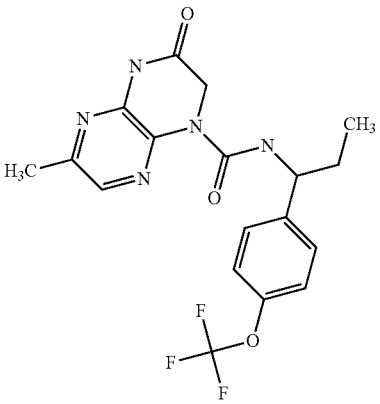 [SMILES: CCC(NC(=O)N1CC(=O)Nc2nc(C)cnc21)c1ccc(OC(F)(F)F)cc1] | 410.2 |

TABLE 1-3

| | | | |
|---|---|---|---|
| 24 | N-((1R)-2-methoxy-1-(4-(trifluoromethoxy)phenyl)ethyl)-2-oxo-2,3-dihydropyrido[2,3-b]pyrazine-4(1H)-carboxamide | 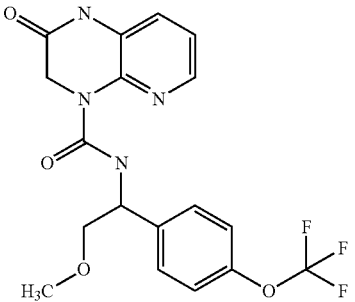 [SMILES: COCC(NC(=O)N1CC(=O)Nc2cccnc21)c1ccc(OC(F)(F)F)cc1] | 411.2 |
| 25 | N-((1S)-2-methoxy-1-(4-(trifluoromethoxy)phenyl)ethyl)-2-oxo-2,3-dihydropyrido[2,3-b]pyrazine-4(1H)-carboxamide | 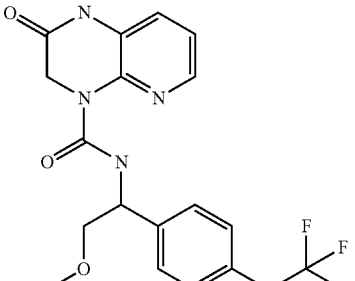 | 411.1 |

TABLE 1-3-continued
| 26 | 7-iodo-2-oxo-N-(1-(4-(trifluoromethoxy)phenyl)propyl)-2,3-dihydropyrido[2,3-b]pyrazine-4(1H)-carboxamide | 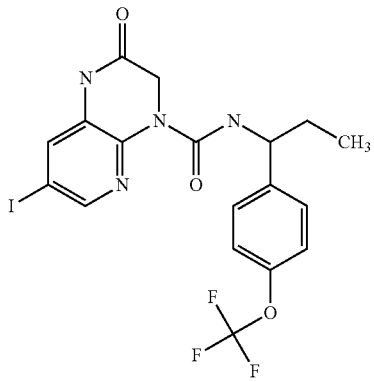 [SMILES: CCC(NC(=O)N1CC(=O)Nc2cc(I)cnc21)c1ccc(OC(F)(F)F)cc1] | 521.1 |
| 27 | 2-oxo-N-(1-(4-(trifluoromethoxy)phenyl)propyl)-7-vinyl-2,3-dihydropyrido[2,3-b]pyrazine-4(1H)-carboxamide | 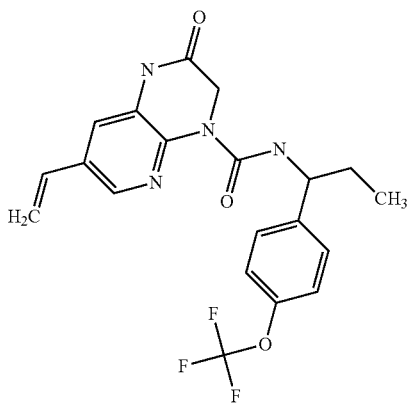 [SMILES: C=Cc1cnc2c(c1)NC(=O)CN2C(=O)NC(CC)c1ccc(OC(F)(F)F)cc1] | 421.1 |
| 28 | N-(1-(biphenyl-4-yl)propyl)-2-oxo-2,3-dihydropyrido[2,3-b]pyrazine-4(1H)-carboxamide | 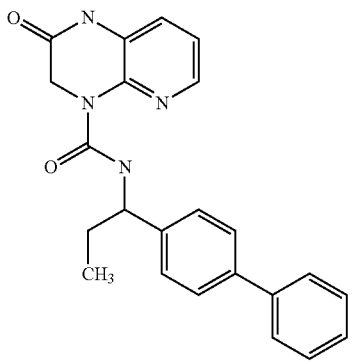 [SMILES: CCC(NC(=O)N1CC(=O)Nc2cccnc21)c1ccc(-c2ccccc2)cc1] | 387.2 |
| 29 | 7-ethyl-2-oxo-N-(1-(4-(trifluoromethoxy)phenyl)propyl)-2,3-dihydropyrido[2,3-b]pyrazine-4(1H)-carboxamide | 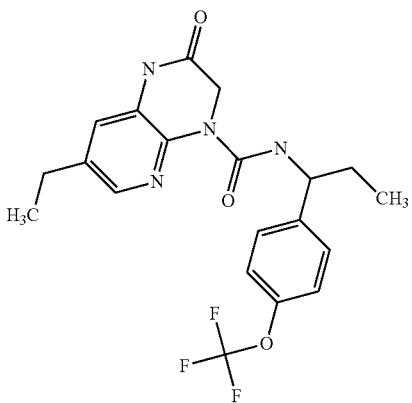 [SMILES: CCc1cnc2c(c1)NC(=O)CN2C(=O)NC(CC)c1ccc(OC(F)(F)F)cc1] | 423.1 |

TABLE 1-3-continued

| | | | |
|---|---|---|---|
| 30 | N-(1-(6-methoxypyridazin-3-yl)propyl)-2-oxo-2,3-dihydropyrido[2,3-b]pyrazine-4(1H)-carboxamide | 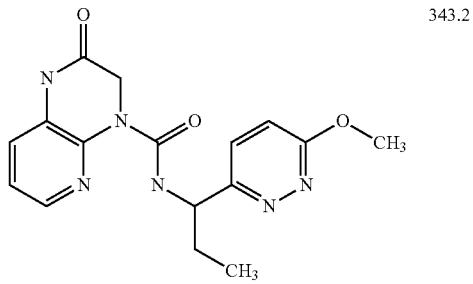 | 343.2 |
| 31 | N-(1-(3-fluoro-4-(trifluoromethoxy)phenyl)propyl)-2-oxo-2,3-dihydropyrido[2,3-b]pyrazine-4(1H)-carboxamide | 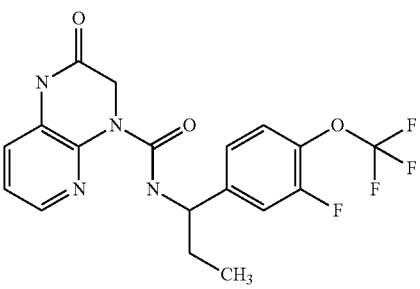 [SMILES: CCC(NC(=O)N1CC(=O)Nc2cccnc21)c1ccc(OC(F)(F)F)c(F)c1] | 413.1 |
| 32 | N-(1-(2-methoxy-4-(trifluoromethoxy)phenyl)propyl)-2-oxo-2,3-dihydropyrido[2,3-b]pyrazine-4(1H)-carboxamide | 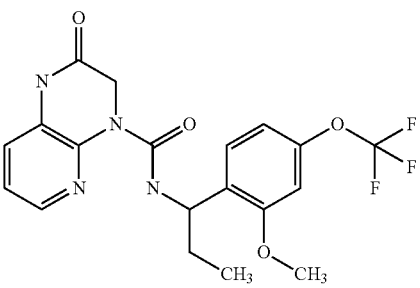 [SMILES: CCC(NC(=O)N1CC(=O)Nc2cccnc21)c1ccc(OC(F)(F)F)cc1OC] | 425.1 |
| 33 | N-(1-(4-hydroxyphenyl)propyl)-2-oxo-2,3-dihydropyrido[2,3-b]pyrazine-4(1H)-carboxamide | 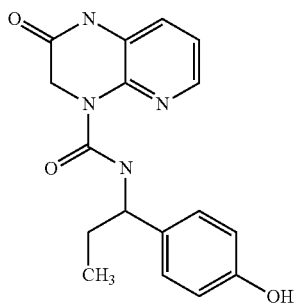 [SMILES: CCC(NC(=O)N1CC(=O)Nc2cccnc21)c1ccc(O)cc1] | 327.1 |
| 34 | N-(1-(2-fluoro-4-(trifluoromethoxy)phenyl)propyl)-2-oxo-2,3-dihydropyrido[2,3-b]pyrazine-4(1H)-carboxamide | 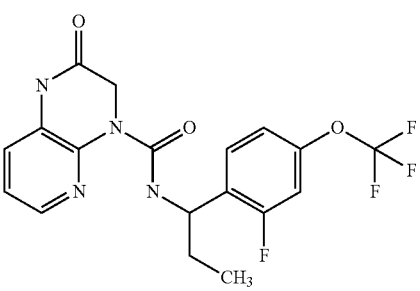 [SMILES: CCC(NC(=O)N1CC(=O)Nc2cccnc21)c1ccc(OC(F)(F)F)cc1F] | 413.2 |

TABLE 1-4
| | | | |
|---|---|---|---|
| 35 | 7-cyclopropyl-2-oxo-N-(1-(4-(trifluoromethoxy)phenyl)propyl)-2,3-dihydropyrido[2,3-b]pyrazine-4(1H)-carboxamide | 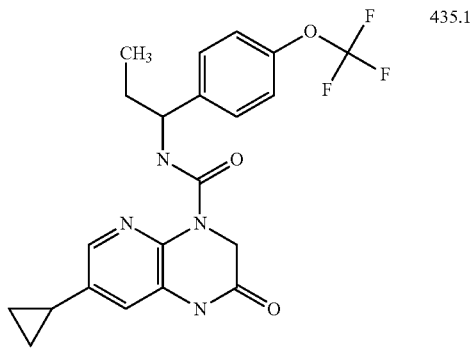 | 435.1 |
| 36 | 7-isopropyl-2-oxo-N-(1-(4-(trifluoromethoxy)phenyl)propyl)-2,3-dihydropyrido[2,3-b]pyrazine-4(1H)-carboxamide | 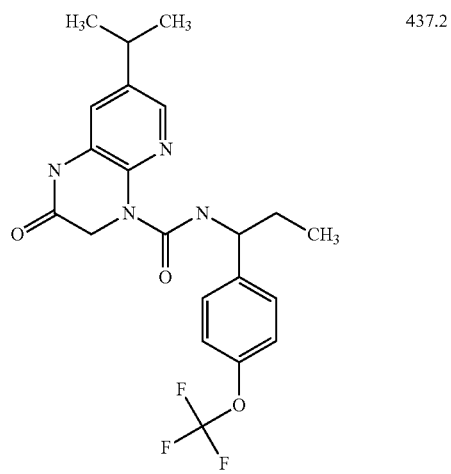 | 437.2 |
| 37 | 6-chloro-2-oxo-N-(1-(4-(trifluoromethoxy)phenyl)propyl)-2,3-dihydropyrido[2,3-b]pyrazine-4(1H)-carboxamide | 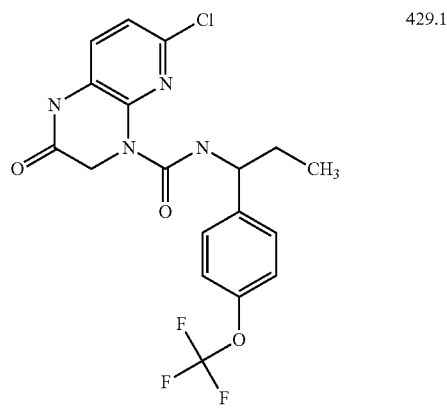 | 429.1 |
| 38 | N-(1-(4-(1-methyl-1H-pyrazol-4-yl)phenyl)propyl)-2-oxo-2,3-dihydropyrido[2,3-b]pyrazine-4(1H)-carboxamide | 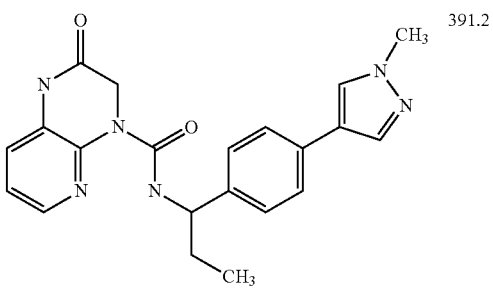 | 391.2 |

TABLE 1-4-continued

| | | | |
|---|---|---|---|
| 39 | 2-oxo-N-(1-(4-(prop-1-en-2-yl)phenyl)propyl)-2,3-dihydropyrido[2,3-b]pyrazine-4(1H)-carboxamide | 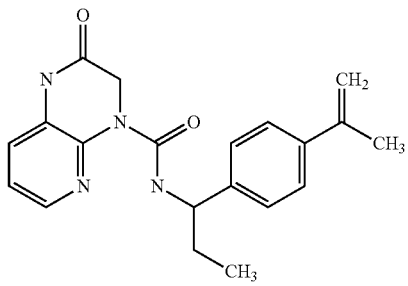 [SMILES: C=C(C)c1ccc(C(CC)NC(=O)N2CC(=O)Nc3cccnc32)cc1] | 351.2 |
| 40 | N-(1-(4-isopropylphenyl)propyl)-2-oxo-2,3-dihydropyrido[2,3-b]pyrazine-4(1H)-carboxamide | 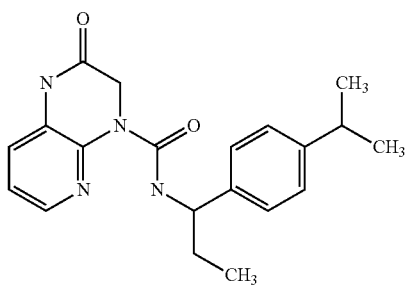 [SMILES: CCC(NC(=O)N1CC(=O)Nc2cccnc21)c1ccc(C(C)C)cc1] | 353.2 |
| 41 | N-(1-(4-(3,6-dihydro-2H-pyran-4-yl)phenyl)propyl)-2-oxo-2,3-dihydropyrido[2,3-b]pyrazine-4(1H)-carboxamide | 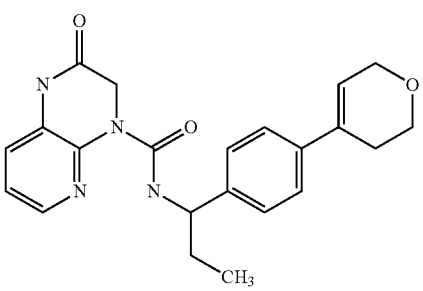 [SMILES: CCC(NC(=O)N1CC(=O)Nc2cccnc21)c1ccc(C2=CCOCC2)cc1] | 393.2 |
| 42 | N-(2-amino-2-oxo-1-(4-(trifluoromethoxy)phenyl)ethyl)-2-oxo-2,3-dihydropyrido[2,3-b]pyrazine-4(1H)-carboxamide | 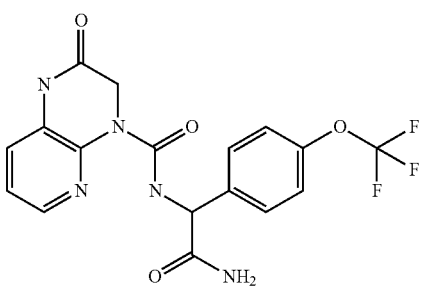 [SMILES: NC(=O)C(NC(=O)N1CC(=O)Nc2cccnc21)c1ccc(OC(F)(F)F)cc1] | 410.1 |
| 43 | N-(cyano(4-(trifluoromethoxy)phenyl)methyl)-2-oxo-2,3-dihydropyrido[2,3-b]pyrazine-4(1H)-carboxamide | 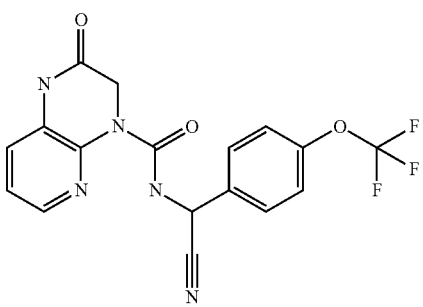 [SMILES: N#CC(NC(=O)N1CC(=O)Nc2cccnc21)c1ccc(OC(F)(F)F)cc1] | 392.1 |

TABLE 1-4-continued
| | | | |
|---|---|---|---|
| 44 | 7-cyano-2-oxo-N-(1-(4-(trifluoromethoxy)phenyl)propyl)-2,3-dihydropyrido[2,3-b]pyrazine-4(1H)-carboxamide | 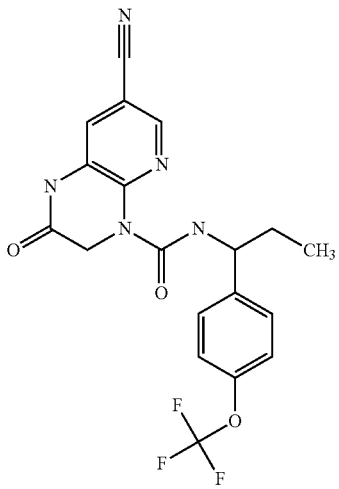 [SMILES: CCC(NC(=O)N1CC(=O)Nc2cc(C#N)cnc21)c1ccc(OC(F)(F)F)cc1] | 418.0 |
| 45 | 2-oxo-N-(1-(4-(trifluoromethoxy)phenyl)propyl)-6-(trifluoromethyl)-2,3-dihydropyrido[2,3-b]pyrazine-4(1H)-carboxamide | 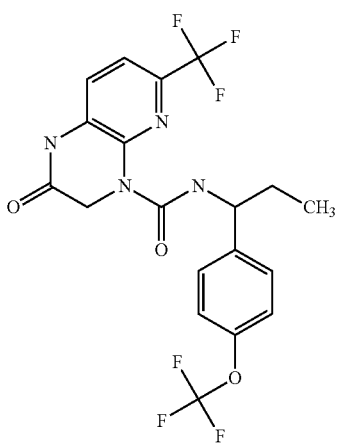 [SMILES: CCC(NC(=O)N1CC(=O)Nc2ccc(C(F)(F)F)nc21)c1ccc(OC(F)(F)F)cc1] | 463.1 |
| 46 | 2-oxo-N-(1-(4-(trifluoromethoxy)phenyl)propyl)-6-vinyl-2,3-dihydropyrido[2,3-b]pyrazine-4(1H)-carboxamide | 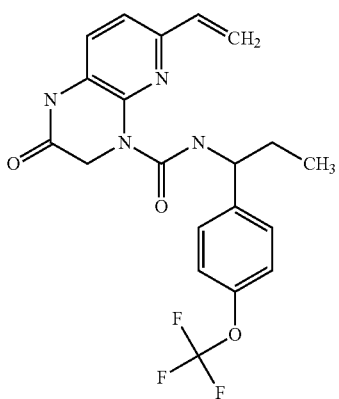 [SMILES: C=Cc1ccc2c(n1)N(C(=O)NC(CC)c1ccc(OC(F)(F)F)cc1)CC(=O)N2] | 421.2 |

TABLE 1-5
| | | | |
|---|---|---|---|
| 47 | 6-benzyl-2-oxo-N-(1-(4-(trifluoromethoxy)phenyl)propyl)-2,3-dihydropyrido[2,3-b]pyrazine-4(1H)-carboxamide | 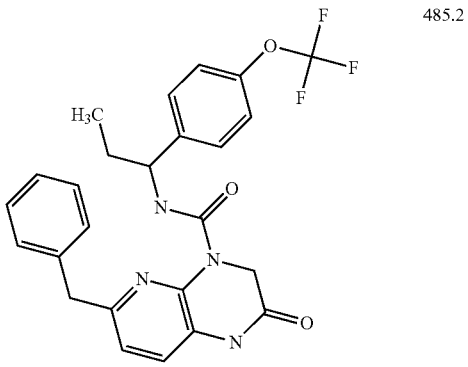 | 485.2 |
| 48 | 2-oxo-N-(1-(4-(tetrahydro-2H-pyran-4-yl)phenyl)propyl)-2,3-dihydropyrido[2,3-b]pyrazine-4(1H)-carboxamide | 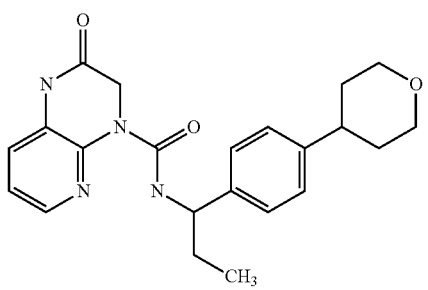 [SMILES: CCC(NC(=O)N1CC(=O)Nc2cccnc21)c1ccc(C2CCOCC2)cc1] | 395.2 |
| 49 | N-(1-(6-methoxypyridin-3-yl)propyl)-2-oxo-2,3-dihydropyrido[2,3-b]pyrazine-4(1H)-carboxamide | 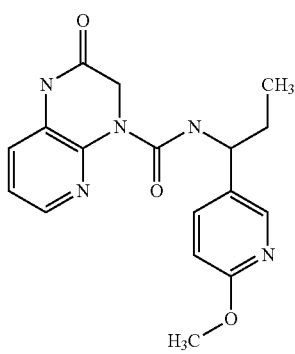 [SMILES: CCC(NC(=O)N1CC(=O)Nc2cccnc21)c1ccc(OC)nc1] | 342.1 |
| 50 | N-(1-(5-methoxypyrimidin-2-yl)propyl)-2-oxo-2,3-dihydropyrido[2,3-b]pyrazine-4(1H)-carboxamide | 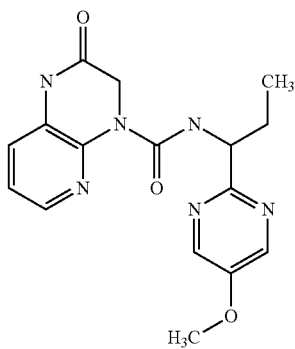 [SMILES: CCC(NC(=O)N1CC(=O)Nc2cccnc21)c1ncc(OC)cn1] | 343.2 |

TABLE 1-5-continued
| | | | |
|---|---|---|---|
| 51 | 6-ethyl-2-oxo-N-(1-(4-(trifluoromethoxy)phenyl)propyl)-2,3-dihydropyrido[2,3-b]pyrazine-4(1H)-carboxamide | 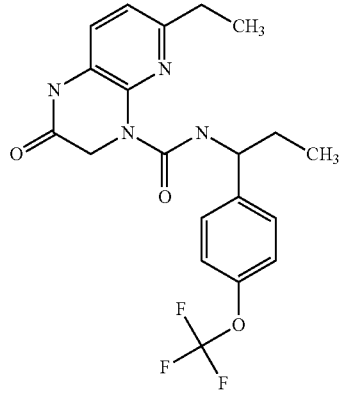 [SMILES: CCc1ccc2c(n1)N(C(=O)NC(CC)c1ccc(OC(F)(F)F)cc1)CC(=O)N2] | 423.1 |
| 52 | 6-methoxy-2-oxo-N-(1-(4-(trifluoromethoxy)phenyl)propyl)-2,3-dihydropyrido[2,3-b]pyrazine-4(1H)-carboxamide | 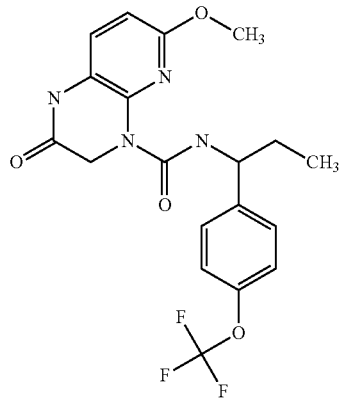 [SMILES: CCC(NC(=O)N1CC(=O)Nc2ccc(OC)nc21)c1ccc(OC(F)(F)F)cc1] | 425.1 |
| 53 | N-(1-(4-(cyclopropylmethoxy)phenyl)propyl)-2-oxo-2,3-dihydropyrido[2,3-b]pyrazine-4(1H)-carboxamide | 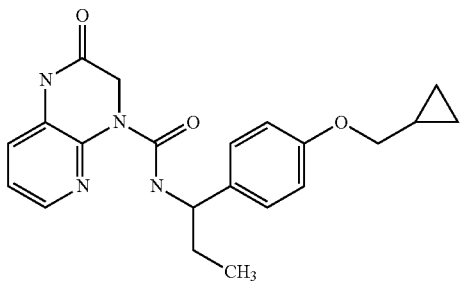 [SMILES: CCC(NC(=O)N1CC(=O)Nc2cccnc21)c1ccc(OCC2CC2)cc1] | 381.2 |
| 54 | 2-oxo-N-(1-(4-(trifluoromethyl)phenyl)propyl)-2,3-dihydropyrido[2,3-b]pyrazine-4(1H)-carboxamide | 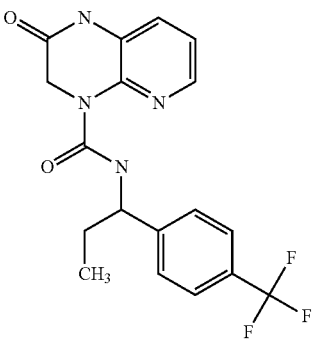 [SMILES: CCC(NC(=O)N1CC(=O)Nc2cccnc21)c1ccc(C(F)(F)F)cc1] | 379.2 |

TABLE 1-5-continued

| 55 | 2-oxo-N-(pyridin-2-yl(4-(trifluoromethoxy)phenyl)methyl)-2,3-dihydropyrido[2,3-b]pyrazine-4(1H)-carboxamide | | 444.2 |
| --- | --- | --- | --- |
| 56 | N-((3,5-dimethyl-1,2-oxazol-4-yl)(4-(trifluoromethoxy)phenyl)methyl)-2-oxo-2,3-dihydropyrido[2,3-b]pyrazine-4(1H)-carboxamide | | 462.1 |
| 57 | N-((1-methyl-1H-pyrazol-4-yl)(4-(trifluoromethoxy)phenyl)methyl)-2-oxo-2,3-dihydropyrido[2,3-b]pyrazine-4(1H)-carboxamide | | 447.2 |

TABLE 1-6

| 58 | N-(2-(dimethylamino)-1-(4-(trifluoromethoxy)phenyl)ethyl)-2-oxo-2,3-dihydropyrido[2,3-b]pyrazine-4(1H)-carboxamide | | 424.1 |
| --- | --- | --- | --- |

| | | | |
|---|---|---|---|
| 59 | N-(2-(methylsulfanyl)-1-(4-(trifluoromethoxy)phenyl)ethyl)-2-oxo-2,3-dihydropyrido[2,3-b]pyrazine-4(1H)-carboxamide | 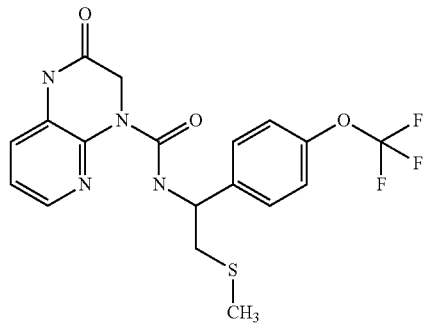 [SMILES: CSCC(NC(=O)N1CC(=O)Nc2cccnc21)c1ccc(OC(F)(F)F)cc1] | 427.1 |
| 60 | N-(2-(methylsulfonyl)-1-(4-(trifluoromethoxy)phenyl)ethyl)-2-oxo-2,3-dihydropyrido[2,3-b]pyrazine-4(1H)-carboxamide | 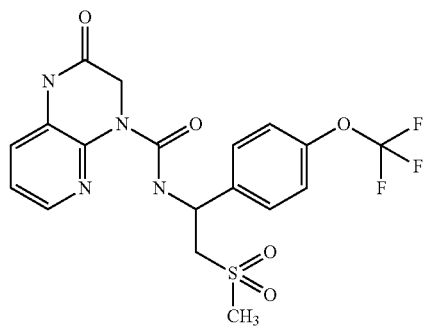 [SMILES: CS(=O)(=O)CC(NC(=O)N1CC(=O)Nc2cccnc21)c1ccc(OC(F)(F)F)cc1] | 459.2 |
| 61 | N-(1-(5-methoxypyridin-2-yl)propyl)-2-oxo-2,3-dihydropyrido[2,3-b]pyrazine-4(1H)-carboxamide | 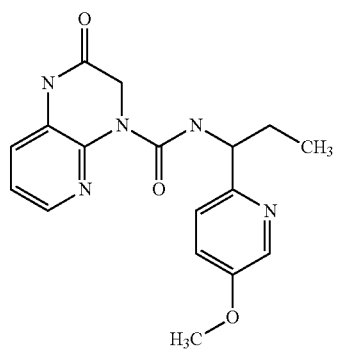 [SMILES: CCC(NC(=O)N1CC(=O)Nc2cccnc21)c1ccc(OC)cn1] | 342.1 |
| 62 | 6-cyano-2-oxo-N-(1-(4-(trifluoromethoxy)phenyl)propyl)-2,3-dihydropyrido[2,3-b]pyrazine-4(1H)-carboxamide | 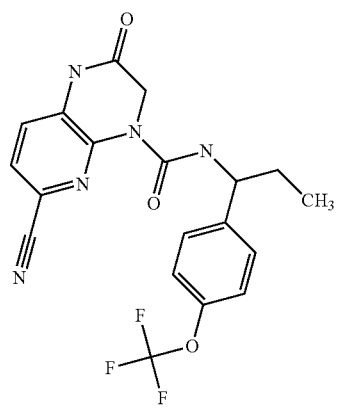 [SMILES: CCC(NC(=O)N1CC(=O)Nc2ccc(C#N)nc21)c1ccc(OC(F)(F)F)cc1] | 418.2 |

TABLE 1-6-continued

| 63 | 7-methoxy-N-(2-methoxy-1-(4-(trifluoromethoxy)phenyl)ethyl)-2-oxo-2,3-dihydropyrido[2,3-b]pyrazine-4(1H)-carboxamide | | 441.2 |
| 64 | 7-methoxy-N-((1S)-2-methoxy-1-(4-(trifluoromethoxy)phenyl)ethyl)-2-oxo-2,3-dihydropyrido[2,3-b]pyrazine-4(1H)-carboxamide | | 441.2 |
| 65 | 7-methoxy-N-((1R)-2-methoxy-1-(4-(trifluoromethoxy)phenyl)ethyl)-2-oxo-2,3-dihydropyrido[2,3-b]pyrazine-4(1H)-carboxamide | | 441.2 |
| 66 | N-(1-(3-fluoro-4-(trifluoromethoxy)phenyl)-2-methoxyethyl)-7-methoxy-2-oxo-2,3-dihydropyrido[2,3-b]pyrazine-4(1H)-carboxamide | | 459.1 |
| 67 | N-((1S)-1-(3-fluoro-4-(trifluoromethoxy)phenyl)-2-methoxyethyl)-7-methoxy-2-oxo-2,3-dihydropyrido[2,3-b]pyrazine-4(1H)-carboxamide | | 459.1 |

TABLE 1-6-continued

| | | | |
|---|---|---|---|
| 68 | N-((1R)-1-(3-fluoro-4-(trifluoromethoxy)phenyl)-2-methoxyethyl)-7-methoxy-2-oxo-2,3-dihydropyrido[2,3-b]pyrazine-4(1H)-carboxamide | 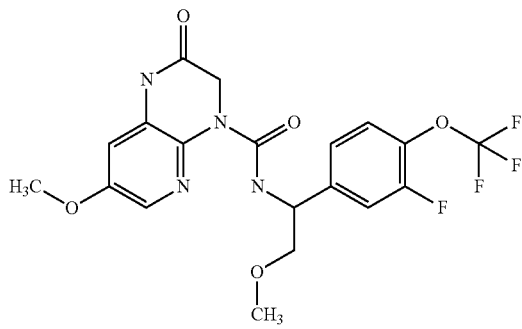 [SMILES: COCC(NC(=O)N1CC(=O)Nc2cc(OC)cnc21)c1ccc(OC(F)(F)F)c(F)c1] | 459.1 |
| 69 | 7-methoxy-N-(2-methoxy-1-(4-(trifluoromethoxy)phenyl)ethyl)-2-oxo-2,3-dihydropyrido[2,3-b]pyrazine-4(1H)-carboxamide | 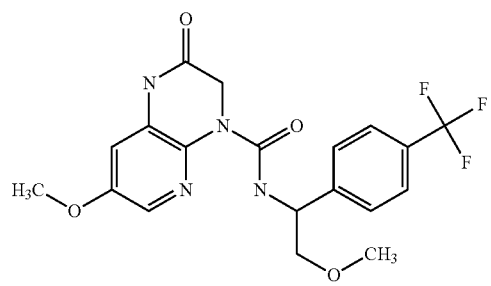 [SMILES: COCC(NC(=O)N1CC(=O)Nc2cc(OC)cnc21)c1ccc(C(F)(F)F)cc1] | 425.1 |

TABLE 1-7

| | | | |
|---|---|---|---|
| 70 | optically active 7-methoxy-N-(2-methoxy-1-(4-(trifluoromethyl)phenyl)ethyl)-2-oxo-2,3-dihydropyrido[2,3-b]pyrazine-4(1H)-carboxamide | 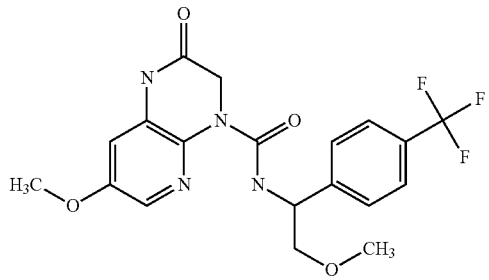 [SMILES: COCC(NC(=O)N1CC(=O)Nc2cc(OC)cnc21)c1ccc(C(F)(F)F)cc1] | 425.1 |
| 71 | optically active 7-methoxy-N-(2-methoxy-1-(4-(trifluoromethyl)phenyl)ethyl)-2-oxo-2,3-dihydropyrido[2,3-b]pyrazine-4(1H)-carboxamide | 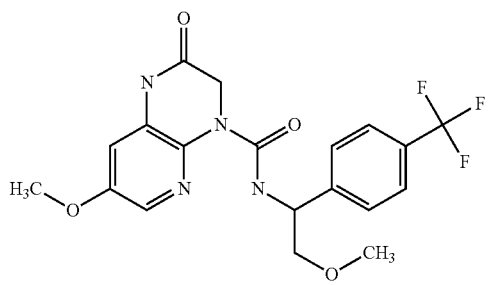 [SMILES: COCC(NC(=O)N1CC(=O)Nc2cc(OC)cnc21)c1ccc(C(F)(F)F)cc1] | 425.1 |
| 72 | 7-cyclopropyl-N-(2-hydroxy-2-methyl-1-(4-(trifluoromethoxy)phenyl)propyl)-2-oxo-2,3-dihydropyrido[2,3-b]pyrazine-4(1H)-carboxamide | 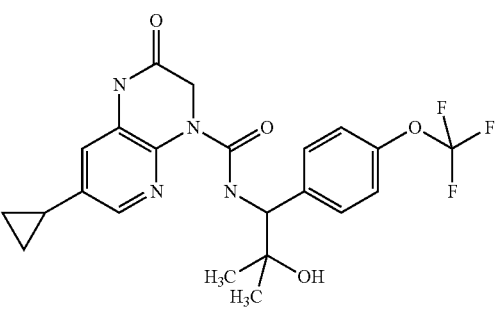 [SMILES: CC(C)(O)C(NC(=O)N1CC(=O)Nc2cc(C3CC3)cnc21)c1ccc(OC(F)(F)F)cc1] | 465.2 |

TABLE 1-7-continued

| 73 | 7-cyclopropyl-N-((1S)-2-hydroxy-2-methyl-1-(4-(trifluoromethoxy)phenyl)propyl)-2-oxo-2,3-dihydropyrido[2,3-b]pyrazine-4(1H)-carboxamide | 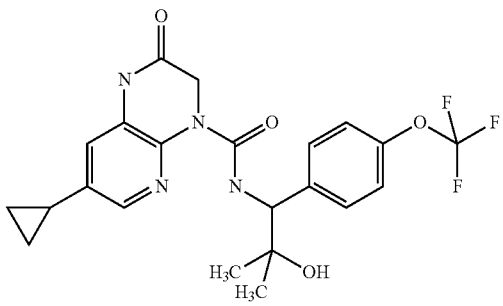 [SMILES: CC(C)(O)C(NC(=O)N1CC(=O)Nc2cc(C3CC3)cnc21)c1ccc(OC(F)(F)F)cc1] | 465.1 |
| --- | --- | --- | --- |
| 74 | 7-cyclopropyl-N-((1R)-2-hydroxy-2-methyl-1-(4-(trifluoromethoxy)phenyl)propyl)-2-oxo-2,3-dihydropyrido[2,3-b]pyrazine-4(1H)-carboxamide | 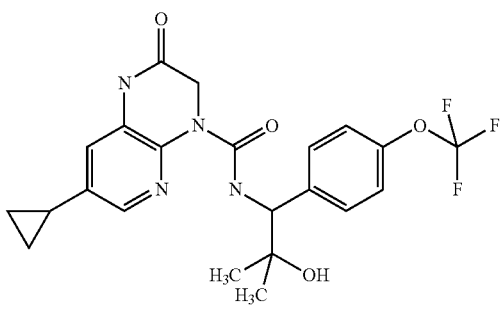 | 465.1 |
| 75 | 7-cyclopropyl-N-(1-(3-fluoro-4-(trifluoromethoxy)phenyl)-2-hydroxy-2-methylpropyl)-2-oxo-2,3-dihydropyrido[2,3-b]pyrazine-4(1H)-carboxamide | 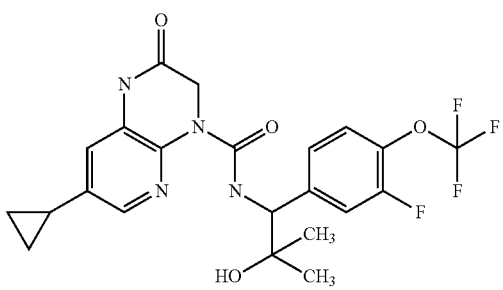 [SMILES: CC(C)(O)C(NC(=O)N1CC(=O)Nc2cc(C3CC3)cnc21)c1ccc(OC(F)(F)F)c(F)c1] | 483.2 |
| 76 | optically active 7-cyclopropyl-N-(1-(3-fluoro-4-(trifluoromethoxy)phenyl)-2-hydroxy-2-methylpropyl)-2-oxo-2,3-dihydropyrido[2,3-b]pyrazine-4(1H)-carboxamide | 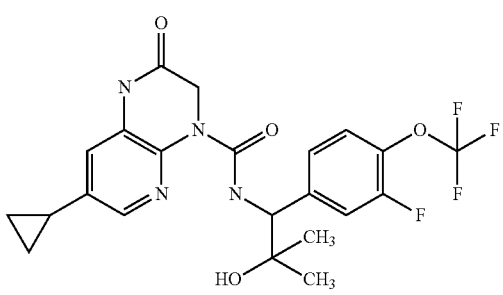 [SMILES: CC(C)(O)C(NC(=O)N1CC(=O)Nc2cc(C3CC3)cnc21)c1ccc(OC(F)(F)F)c(F)c1] | 483.2 |
| 77 | optically active 7-cyclopropyl-N-(1-(3-fluoro-4-(trifluoromethoxy)phenyl)-2-hydroxy-2-methylpropyl)-2-oxo-2,3-dihydropyrido[2,3-b]pyrazine-4(1H)-carboxamide | 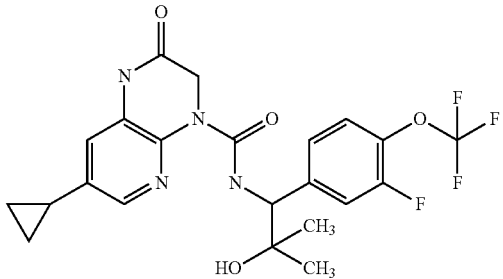 [SMILES: CC(C)(O)C(NC(=O)N1CC(=O)Nc2cc(C3CC3)cnc21)c1ccc(OC(F)(F)F)c(F)c1] | 483.2 |

TABLE 1-7-continued
| 78 | 2-oxo-N-(1-(4-(2,2,2-trifluoroethoxy)phenyl)propyl)-2,3-dihydropyrido[2,3-b]pyrazine-4(1H)-carboxamide | 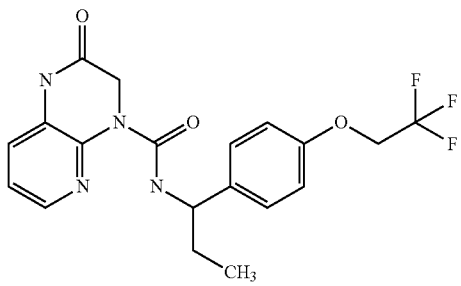 [SMILES: CCC(NC(=O)N1CC(=O)Nc2cccnc21)c1ccc(OCC(F)(F)F)cc1] | 409.1 |
| 79 | N-(2-(methylsulfinyl)-1-(4-(trifluoromethoxy)phenyl)ethyl)-2-oxo-2,3-dihydropyrido[2,3-b]pyrazine-4(1H)-carboxamide | 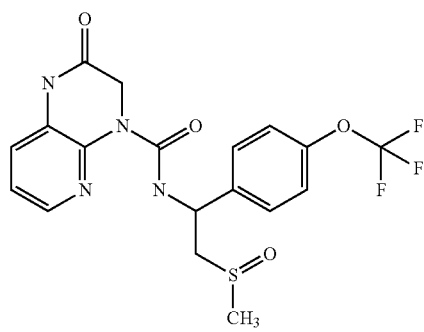 [SMILES: CS(=O)CC(NC(=O)N1CC(=O)Nc2cccnc21)c1ccc(OC(F)(F)F)cc1] | 443.1 |
| 80 | 2-oxo-N-(1-(1-(2,2,2-trifluoroethyl)-1H-imidazol-4-yl)propyl)-2,3-dihydropyrido[2,3-b]pyrazine-4(1H)-carboxamide | 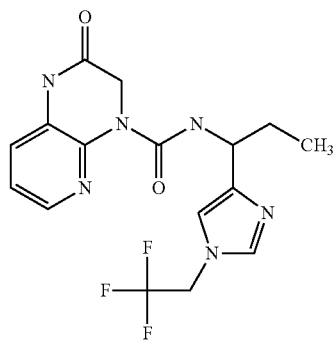 [SMILES: CCC(NC(=O)N1CC(=O)Nc2cccnc21)c1cn(CC(F)(F)F)cn1] | 383.1 |
| 81 | 2-oxo-N-(1-(1-(2,2,2-trifluoroethyl)-1H-1,2,4-triazol-3-yl)propyl)-2,3-dihydropyrido[2,3-b]pyrazine-4(1H)-carboxamide | 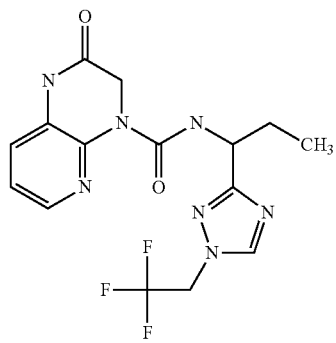 [SMILES: CCC(NC(=O)N1CC(=O)Nc2cccnc21)c1ncn(CC(F)(F)F)n1] | 384.1 |

TABLE 1-8

| 82 | N-(1-(4-isopropoxyphenyl)propyl)-2-oxo-2,3-dihydropyrido[2,3-b]pyrazine-4(1H)-carboxamide | 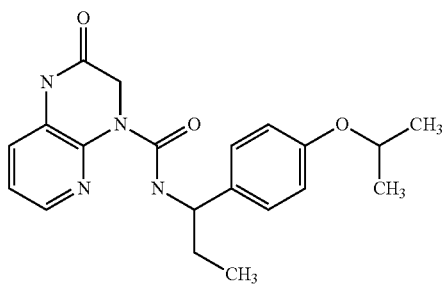 [SMILES: CCC(NC(=O)N1CC(=O)Nc2cccnc21)c1ccc(OC(C)C)cc1] | 367.2 |
| 83 | N-(1-(4-chlorophenyl)propyl)-2-oxo-2,3-dihydropyrido[2,3-b]pyrazine-4(1H)-carboxamide | 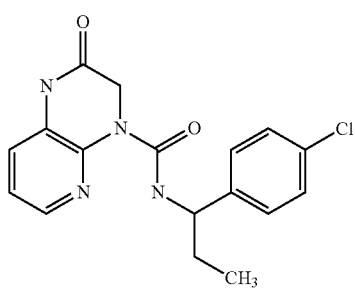 [SMILES: CCC(NC(=O)N1CC(=O)Nc2cccnc21)c1ccc(Cl)cc1] | 345.1 |
| 84 | 2-oxo-N-(1-(2-(trifluoromethoxy)phenyl)propyl)-2,3-dihydropyrido[2,3-b]pyrazine-4(1H)-carboxamide | 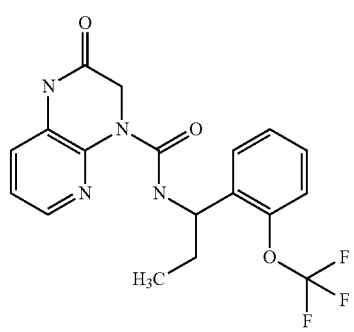 [SMILES: CCC(NC(=O)N1CC(=O)Nc2cccnc21)c1ccccc1OC(F)(F)F] | 395.1 |
| 85 | N-(1-(4-methylphenyl)propyl)-2-oxo-2,3-dihydropyrido[2,3-b]pyrazine-4(1H)-carboxamide | 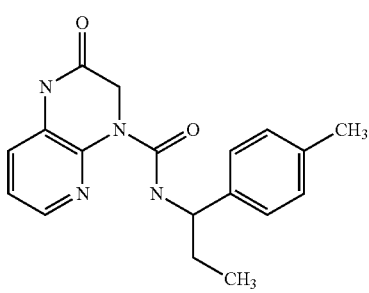 [SMILES: CCC(NC(=O)N1CC(=O)Nc2cccnc21)c1ccc(C)cc1] | 325.2 |
| 86 | 2-oxo-N-(1-(1-(2,2,2-trifluoroethyl)-1H-pyrazol-4-yl)propyl)-2,3-dihydropyrido[2,3-b]pyrazine-4(1H)-carboxamide | 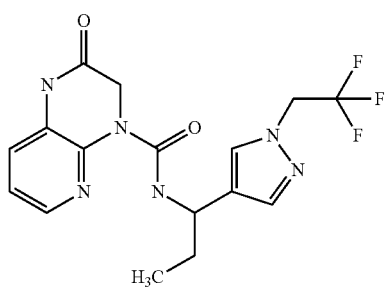 [SMILES: CCC(NC(=O)N1CC(=O)Nc2cccnc21)c1cnn(CC(F)(F)F)c1] | 383.1 |

| | | | |
|---|---|---|---|
| 87 | N-(1-(3-methyl-4-(trifluoromethoxy)phenyl)propyl)-2-oxo-2,3-dihydropyrido[2,3-b]pyrazine-4(1H)-carboxamide | | 409.1 |
| 88 | N-(2-(dimethylamino)-2-oxo-1-(4-(trifluoromethoxy)phenyl)ethyl)-2-oxo-2,3-dihydropyrido[2,3-b]pyrazine-4(1H)-carboxamide | | 438.1 |
| 89 | N-(2-(methylamino)-2-oxo-1-(4-(trifluoromethoxy)phenyl)ethyl)-2-oxo-2,3-dihydropyrido[2,3-b]pyrazine-4(1H)-carboxamide | | 424.1 |
| 90 | N-(2-isopropoxy-1-(4-(trifluoromethoxy)phenyl)ethyl)-2-oxo-2,3-dihydropyrido[2,3-b]pyrazine-4(1H)-carboxamide | | 439.2 |

TABLE 1-8-continued

| | | | |
|---|---|---|---|
| 91 | N-(2-(cyclopentyloxy)-1-(4-(trifluoromethoxy)phenyl)ethyl)-2-oxo-2,3-dihydropyrido[2,3-b]pyrazine-4(1H)-carboxamide | 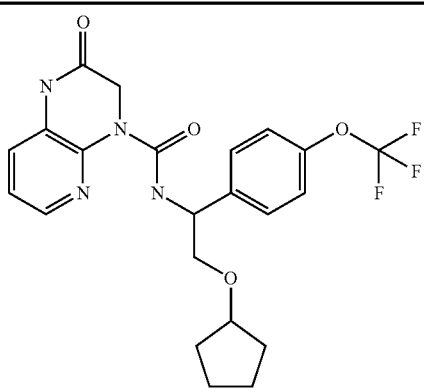 | 465.2 |
| 92 | N-(3-amino-3-oxo-1-(4-(trifluoromethoxy)phenyl)propyl)-2-oxo-2,3-dihydropyrido[2,3-b]pyrazine-4(1H)-carboxamide | 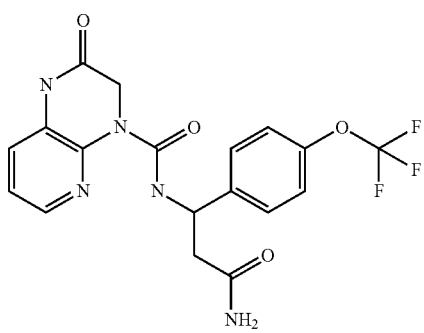 [SMILES: NC(=O)CC(NC(=O)N1CC(=O)Nc2cccnc21)c1ccc(OC(F)(F)F)cc1] | 424.1 |
| 93 | N-(3-(dimethylamino)-3-oxo-1-(4-(trifluoromethoxy)phenyl)propyl)-2-oxo-2,3-dihydropyrido[2,3-b]pyrazine-4(1H)-carboxamide | 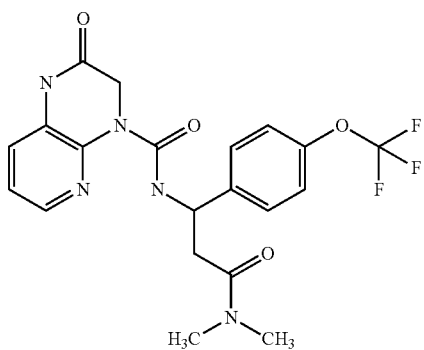 [SMILES: CN(C)C(=O)CC(NC(=O)N1CC(=O)Nc2cccnc21)c1ccc(OC(F)(F)F)cc1] | 452.2 |

TABLE 1-9

| | | | |
|---|---|---|---|
| 94 | N-(2-methoxy-1-(4-(trifluoromethoxy)phenyl)ethyl)-7-methyl-2-oxo-2,3-dihydropyrido[2,3-b]pyrazine-4(1H)-carboxamide | 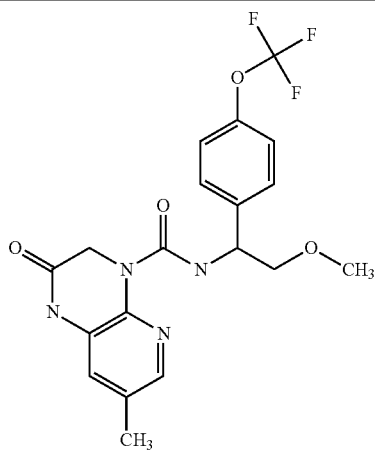 | 425.2 |

TABLE 1-9-continued

| # | Name | Structure | Mass |
|---|------|-----------|------|
| 95 | 3-methyl-2-oxo-N-(1-(4-(trifluoromethoxy)phenyl)propyl)-2,3-dihydropyrido[2,3-b]pyrazine-4(1H)-carboxamide | 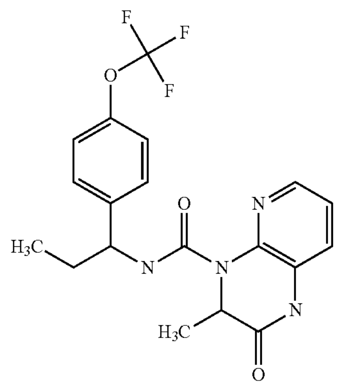 [SMILES: CCC(NC(=O)N1c2ncccc2NC(=O)C1C)c1ccc(OC(F)(F)F)cc1] | 409.1 |
| 96 | N-(1-(4-(difluoromethyl)phenyl)propyl)-2-oxo-2,3-dihydropyrido[2,3-b]pyrazine-4(1H)-carboxamide | 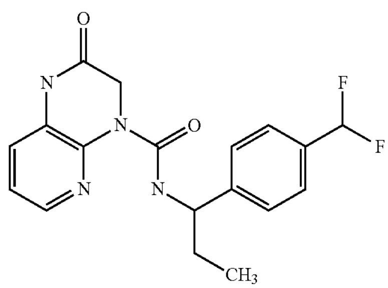 [SMILES: CCC(NC(=O)N1CC(=O)Nc2cccnc21)c1ccc(C(F)F)cc1] | 361.2 |
| 97 | N-(2-cyano-1-(4-(trifluoromethoxy)phenyl)ethyl)-2-oxo-2,3-dihydropyrido[2,3-b]pyrazine-4(1H)-carboxamide | 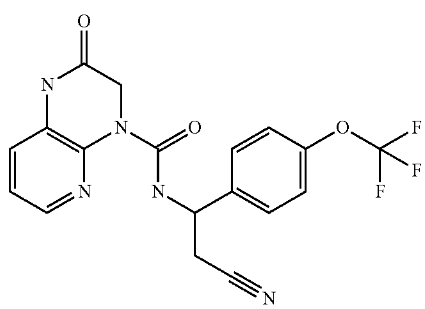 [SMILES: N#CCC(NC(=O)N1CC(=O)Nc2cccnc21)c1ccc(OC(F)(F)F)cc1] | 406.2 |
| 98 | 2-oxo-N-(1-(3-(trifluoromethoxy)phenyl)propyl)-2,3-dihydropyrido[2,3-b]pyrazine-4(1H)-carboxamide | 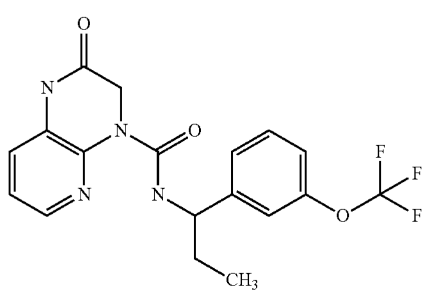 [SMILES: CCC(NC(=O)N1CC(=O)Nc2cccnc21)c1cccc(OC(F)(F)F)c1] | 395.2 |
| 99 | N-(1-(4-cyclopropylphenyl)propyl)-2-oxo-2,3-dihydropyrido[2,3-b]pyrazine-4(1H)-carboxamide | 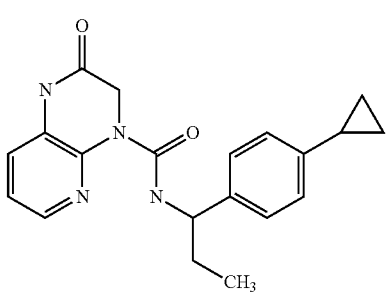 [SMILES: CCC(NC(=O)N1CC(=O)Nc2cccnc21)c1ccc(C2CC2)cc1] | 351.2 |

TABLE 1-9-continued

| 100 | N-(3-methoxy-1-(4-(trifluoromethoxy)phenyl)propyl)-2-oxo-2,3-dihydropyrido[2,3-b]pyrazine-4(1H)-carboxamide | 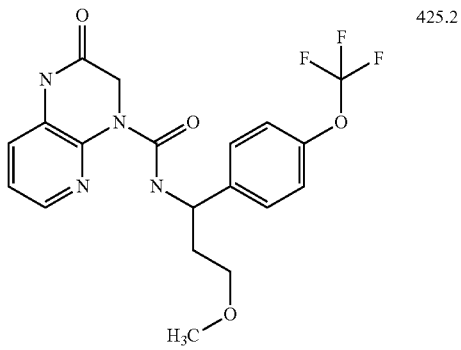 | 425.2 |
| 101 | 2-oxo-N-(2-(pyrrolidin-1-yl)-1-(4-(trifluoromethoxy)phenyl)ethyl)-2,3-dihydropyrido[2,3-b]pyrazine-4(1H)-carboxamide | 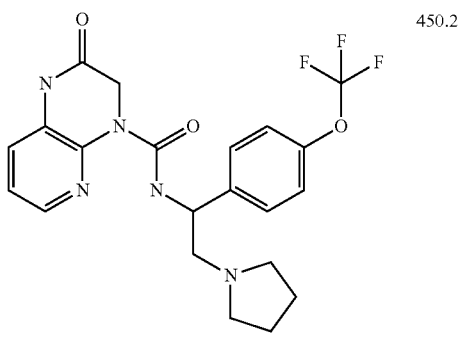 | 450.2 |
| 102 | 2-oxo-N-(2-(2-oxopyrrolidin-1-yl)-1-(4-(trifluoromethoxy)phenyl)ethyl)-2,3-dihydropyrido[2,3-b]pyrazine-4(1H)-carboxamide | 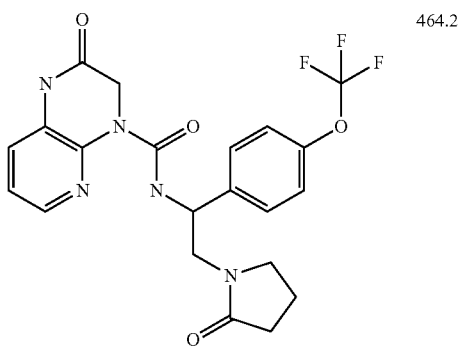 | 464.2 |
| 103 | 3-(((2-oxo-2,3-dihydropyrido[2,3-b]pyrazin-4(1H)-yl)carbonyl)amino)-3-(4-(trifluoromethoxy)phenyl)propyl acetate | 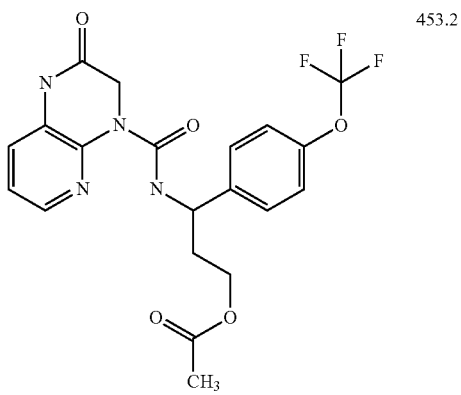 | 453.2 |

TABLE 1-9-continued

| | | | |
|---|---|---|---|
| 104 | N-(3-hydroxy-1-(4-(trifluoromethoxy)phenyl)propyl)-2-oxo-2,3-dihydropyrido[2,3-b]pyrazine-4(1H)-carboxamide | 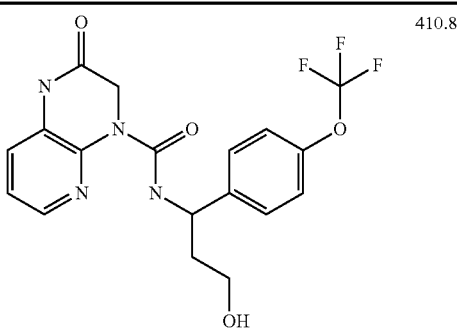 | 410.8 |
| 105 | N-(1-(4-(azetidin-1-yl)phenyl)propyl)-2-oxo-2,3-dihydropyrido[2,3-b]pyrazine-4(1H)-carboxamide | 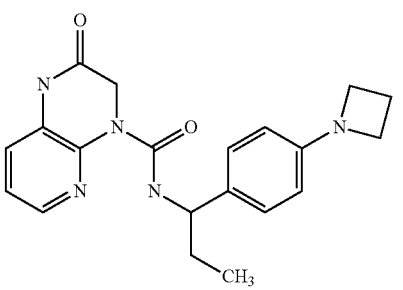 [SMILES: CCC(NC(=O)N1CC(=O)Nc2cccnc21)c1ccc(N2CCC2)cc1] | 364.2 |

TABLE 1-10

| | | | |
|---|---|---|---|
| 106 | N-((1R)-2-methoxy-1-(4-(trifluoromethoxy)phenyl)ethyl)-7-methyl-2-oxo-2,3-dihydropyrido[2,3-b]pyrazine-4(1H)-carboxamide | 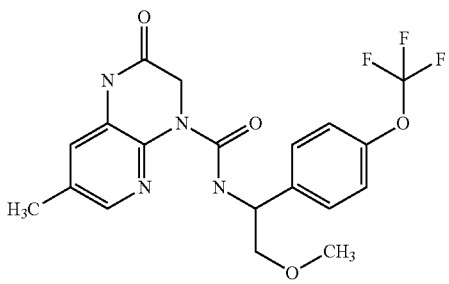 [SMILES: COCC(NC(=O)N1CC(=O)Nc2cc(C)cnc21)c1ccc(OC(F)(F)F)cc1] | 425.2 |
| 107 | N-((1S)-2-methoxy-1-(4-(trifluoromethoxy)phenyl)ethyl)-7-methyl-2-oxo-2,3-dihydropyrido[2,3-b]pyrazine-4(1H)-carboxamide | 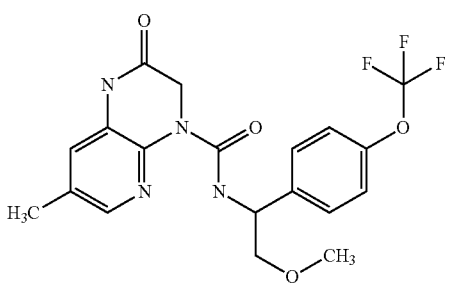 [SMILES: COCC(NC(=O)N1CC(=O)Nc2cc(C)cnc21)c1ccc(OC(F)(F)F)cc1] | 425.1 |
| 108 | N-(2-(difluoromethoxy)-1-(4-(trifluoromethoxy)phenyl)ethyl)-2-oxo-2,3-dihydropyrido[2,3-b]pyrazine-4(1H)-carboxamide | 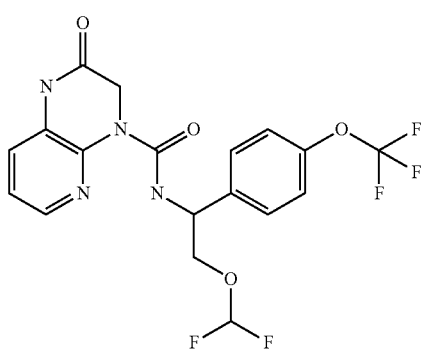 [SMILES: O=C1CN(C(=O)NC(COC(F)F)c2ccc(OC(F)(F)F)cc2)c2ncccc2N1] | 447.1 |

TABLE 1-10-continued

| | | | |
|---|---|---|---|
| 109 | N-(2-methoxy-1-(4-(trifluoromethyl)phenyl)ethyl)-2-oxo-2,3-dihydropyrido[2,3-b]pyrazine-4(1H)-carboxamide | | 395.1 |
| 110 | N-(2-methoxy-1-(4-(trifluoromethyl)phenyl)ethyl)-7-methyl-2-oxo-2,3-dihydropyrido[2,3-b]pyrazine-4(1H)-carboxamide | | 409.2 |
| 111 | N-(1-(3-fluoro-4-(trifluoromethoxy)phenyl)-2-methoxyethyl)-2-oxo-2,3-dihydropyrido[2,3-b]pyrazine-4(1H)-carboxamide | | 429.1 |
| 112 | N-(1-(3-fluoro-4-(trifluoromethoxy)phenyl)-2-methoxyethyl)-7-methyl-2-oxo-2,3-dihydropyrido[2,3-b]pyrazine-4(1H)-carboxamide | | 443.1 |
| 113 | N-(1-(3-fluoro-4-(trifluoromethoxy)phenyl)-2-methoxyethyl)-2-oxo-6-(1H-pyrazol-1-yl)-2,3-dihydropyrido[2,3-b]pyrazine-4(1H)-carboxamide | | 495.2 |

TABLE 1-10-continued

| 114 | 7-cyclopropyl-N-(2-methoxy-1-(4-(trifluoromethoxy)phenyl)ethyl)-2-oxo-2,3-dihydropyrido[2,3-b]pyrazine-4(1H)-carboxamide | 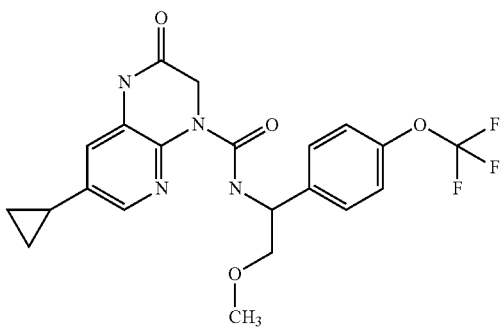 [SMILES: COCC(NC(=O)N1CC(=O)Nc2cc(C3CC3)cnc21)c1ccc(OC(F)(F)F)cc1] | 451.2 |
| 115 | 7-cyclopropyl-N-(2-methoxy-1-(4-(trifluoromethyl)phenyl)ethyl)-2-oxo-2,3-dihydropyrido[2,3-b]pyrazine-4(1H)-carboxamide | 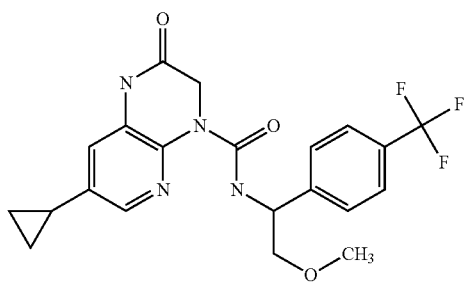 [SMILES: COCC(NC(=O)N1CC(=O)Nc2cc(C3CC3)cnc21)c1ccc(C(F)(F)F)cc1] | 435.2 |
| 116 | N-(2-methoxy-1-(4-(trifluoromethoxy)phenyl)ethyl)-2-oxo-6-(1H-pyrazol-1-yl)-2,3-dihydropyrido[2,3-b]pyrazine-4(1H)-carboxamide | 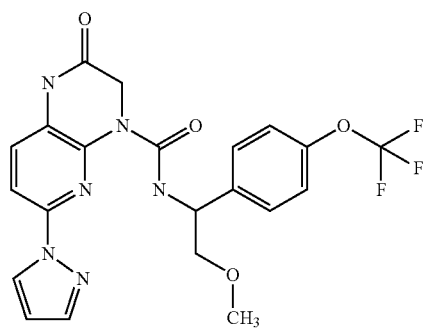 [SMILES: COCC(NC(=O)N1CC(=O)Nc2ccc(-n3cccn3)nc21)c1ccc(OC(F)(F)F)cc1] | 477.2 |
| 117 | N-((1S)-1-(3-fluoro-4-(trifluoromethoxy)phenyl)-2-methoxyethyl)-2-oxo-6-(1H-pyrazol-1-yl)-2,3-dihydropyrido[2,3-b]pyrazine-4(1H)-carboxamide | 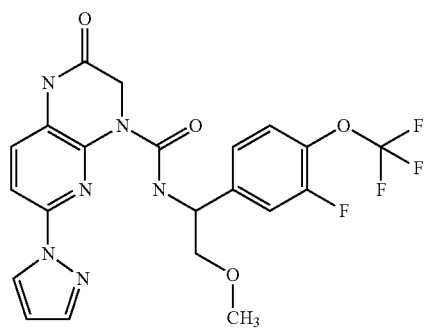 [SMILES: COCC(NC(=O)N1CC(=O)Nc2ccc(-n3cccn3)nc21)c1ccc(OC(F)(F)F)c(F)c1] | 495.2 |

TABLE 1-11

| 118 | N-((1R)-1-(3-fluoro-4-(trifluoromethoxy)phenyl)-2-methoxyethyl)-2-oxo-6-(1H-pyrazol-1-yl)-2,3-dihydropyrido[2,3-b]pyrazine-4(1H)-carboxamide | 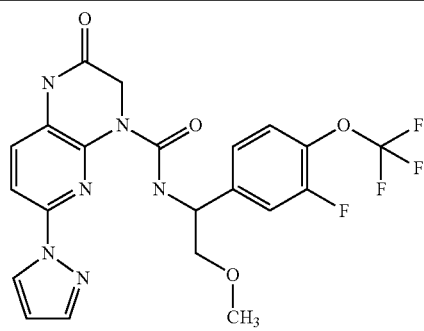 | 495.1 |
| --- | --- | --- | --- |
| 119 | 7-cyclopropyl-N-((1R)-2-methoxy-1-(4-(trifluoromethoxy)phenyl)ethyl)-2-oxo-2,3-dihydropyrido[2,3-b]pyrazine-4(1H)-carboxamide | 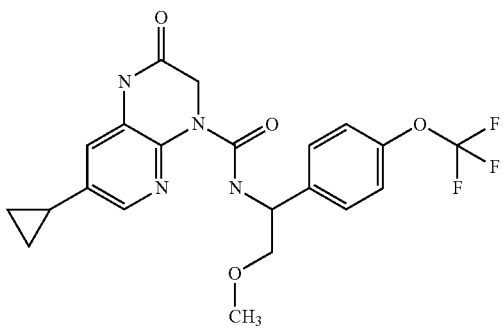 [SMILES: COCC(NC(=O)N1CC(=O)Nc2cc(C3CC3)cnc21)c1ccc(OC(F)(F)F)cc1] | 451.2 |
| 120 | 7-cyclopropyl-N-((1S)-2-methoxy-1-(4-(trifluoromethoxy)phenyl)ethyl)-2-oxo-2,3-dihydropyrido[2,3-b]pyrazine-4(1H)-carboxamide | 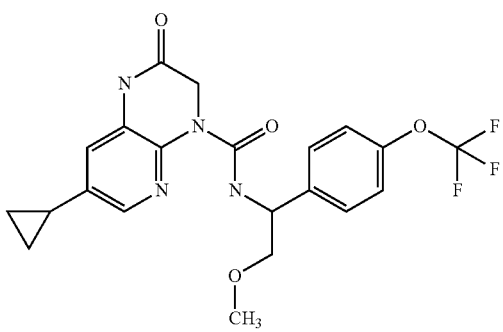 [SMILES: COCC(NC(=O)N1CC(=O)Nc2cc(C3CC3)cnc21)c1ccc(OC(F)(F)F)cc1] | 451.2 |
| 121 | N-((1S)-1-(3-fluoro-4-(trifluoromethoxy)phenyl)-2-methoxyethyl)-2-oxo-2,3-dihydropyrido[2,3-b]pyrazine-4(1H)-carboxamide | 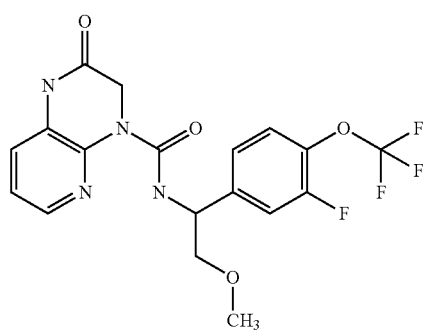 [SMILES: COCC(NC(=O)N1CC(=O)Nc2cccnc21)c1ccc(OC(F)(F)F)c(F)c1] | 429.1 |
| 122 | N-((1R)-1-(3-fluoro-4-(trifluoromethoxy)phenyl)-2-methoxyethyl)-2-oxo-2,3-dihydropyrido[2,3-b]pyrazine-4(1H)-carboxamide | 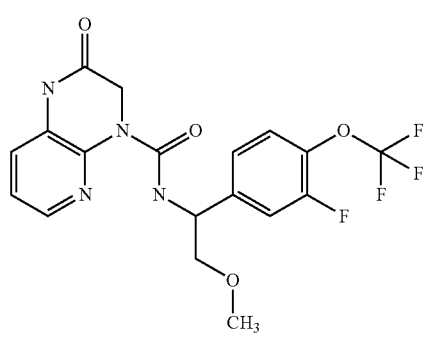 [SMILES: COCC(NC(=O)N1CC(=O)Nc2cccnc21)c1ccc(OC(F)(F)F)c(F)c1] | 429.1 |

TABLE 1-11-continued

| | | | |
|---|---|---|---|
| 123 | N-((1S)-1-(3-fluoro-4-(trifluoromethoxy)phenyl)-2-methoxyethyl)-7-methyl-2-oxo-2,3-dihydropyrido[2,3-b]pyrazine-4(1H)-carboxamide | 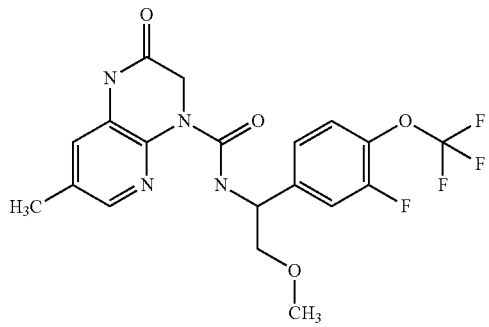 [SMILES: COCC(NC(=O)N1CC(=O)Nc2cc(C)cnc21)c1ccc(OC(F)(F)F)c(F)c1] | 443.1 |
| 124 | N-((1R)-1-(3-fluoro-4-(trifluoromethoxy)phenyl)-2-methoxyethyl)-7-methyl-2-oxo-2,3-dihydropyrido[2,3-b]pyrazine-4(1H)-carboxamide | 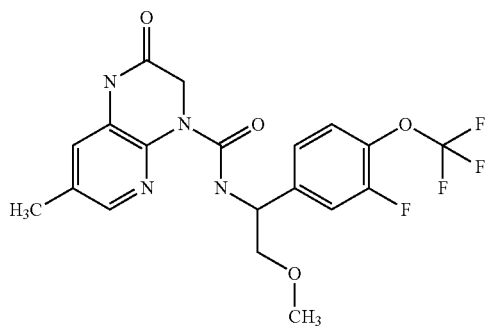 [SMILES: COCC(NC(=O)N1CC(=O)Nc2cc(C)cnc21)c1ccc(OC(F)(F)F)c(F)c1] | 443.1 |
| 125 | 7-cyclopropyl-N-(1-(3-fluoro-4-(trifluoromethoxy)phenyl)-2-methoxyethyl)-2-oxo-2,3-dihydropyrido[2,3-b]pyrazine-4(1H)-carboxamide | 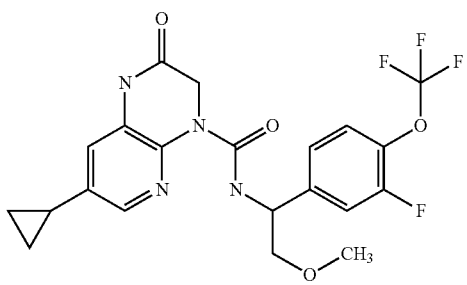 [SMILES: COCC(NC(=O)N1CC(=O)Nc2cc(C3CC3)cnc21)c1ccc(OC(F)(F)F)c(F)c1] | 469.2 |
| 126 | optically active N-(2-(difluoromethoxy)-1-(4-(trifluoromethoxy)phenyl)ethyl)-2-oxo-2,3-dihydro[2,3-b]pyrazine-4(1H)-carboxamide | 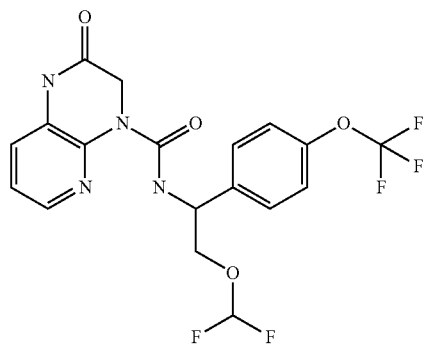 [SMILES: O=C1CN(C(=O)NC(COC(F)F)c2ccc(OC(F)(F)F)cc2)c2ncccc2N1] | 447.1 |
| 127 | optically active N-(2-(difluoromethoxy)-1-(4-(trifluoromethoxy)phenyl)ethyl)-2-oxo-2,3-dihydropyrido[2,3-b]pyrazine-4(1H)-carboxamide | 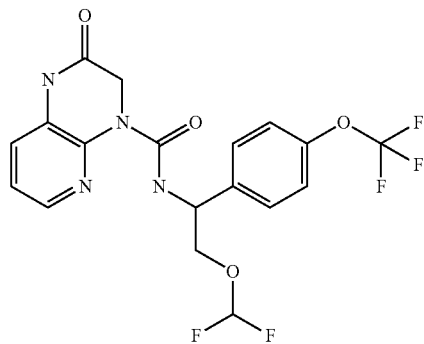 [SMILES: O=C1CN(C(=O)NC(COC(F)F)c2ccc(OC(F)(F)F)cc2)c2ncccc2N1] | 447.1 |

TABLE 1-11-continued

| 128 | 7-cyclopropyl-N-((1R)-1-(3-fluoro-4-(trifluoromethoxy)phenyl)-2-methoxyethyl)-2-oxo-2,3-dihydropyrido[2,3-b]pyrazine-4(1H)-carboxamide | | 469.2 |
| --- | --- | --- | --- |
| 129 | 7-cyclopropyl-N-((1S)-1-(3-fluoro-4-(trifluoromethoxy)phenyl)-2-methoxyethyl)-2-oxo-2,3-dihydropyrido[2,3-b]pyrazine-4(1H)-carboxamide | | 469.2 |

TABLE 1-12

| 130 | N-((1S)-2-methoxy-1-(4-(trifluoromethoxy)phenyl)ethyl)-2-oxo-6-(1H-pyrazol-1-yl)-2,3-dihydropyrido[2,3-b]pyrazine-4(1H)-carboxamide | | 477.2 |
| --- | --- | --- | --- |
| 131 | N-((1R)-2-methoxy-1-(4-(trifluoromethoxy)phenyl)ethyl)-2-oxo-6-(1H-pyrazol-1-yl)-2,3-dihydropyrido[2,3-b]pyrazine-4(1H)-carboxamide | | 477.2 |

TABLE 1-12-continued

| 132 | N-(1-(4-bromophenyl)-2-methoxyethyl)-7-methyl-2-oxo-2,3-dihydropyrido[2,3-b]pyrazine-4(1H)-carboxamide | 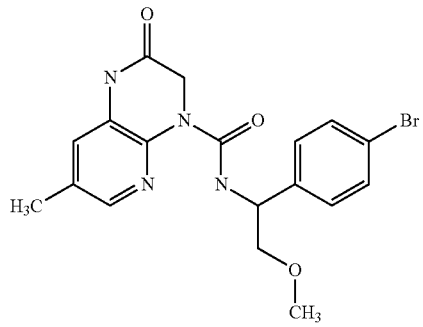 [SMILES: COCC(NC(=O)N1CC(=O)Nc2cc(C)cnc21)c1ccc(Br)cc1] | 419.1 |
| 133 | N-(2-(2-methoxyethoxy)-1-(4-(trifluoromethoxy)phenyl)ethyl)-7-methyl-2-oxo-2,3-dihydropyrido[2,3-b]pyrazine-4(1H)-carboxamide | 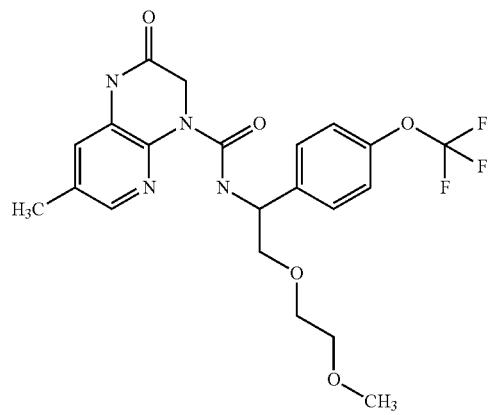 [SMILES: COCCOCC(NC(=O)N1CC(=O)Nc2cc(C)cnc21)c1ccc(OC(F)(F)F)cc1] | 469.2 |
| 134 | N-(2-methoxy-1-(4-(1H-pyrazol-1-yl)phenyl)ethyl)-7-methyl-2-oxo-2,3-dihydropyrido[2,3-b]pyrazine-4(1H)-carboxamide | 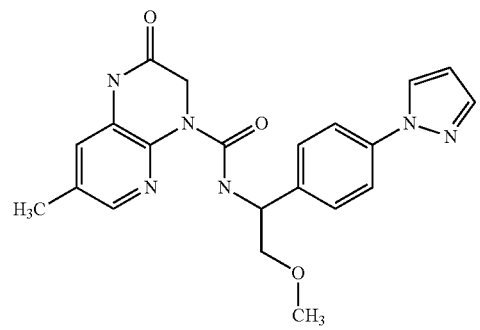 [SMILES: COCC(NC(=O)N1CC(=O)Nc2cc(C)cnc21)c1ccc(-n2cccn2)cc1] | 407.2 |
| 135 | N-(2-methoxy-1-(4-(trifluoromethoxy)phenyl)ethyl)-7-(1-methyl-1H-pyrazol-3-yl)-2-oxo-2,3-dihydropyrido[2,3-b]pyrazine-4(1H)-carboxamide | 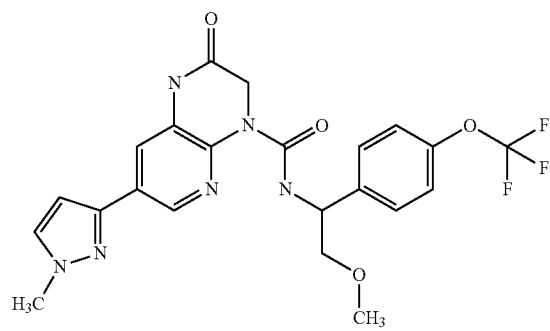 [SMILES: COCC(NC(=O)N1CC(=O)Nc2cc(-c3ccn(C)n3)cnc21)c1ccc(OC(F)(F)F)cc1] | 491.2 |

| | | | |
|---|---|---|---|
| 136 | N-(2-methoxy-1-(4-(trifluoromethoxy)phenyl)ethyl)-7-(1-methyl-1H-pyrazol-4-yl)-2-oxo-2,3-dihydropyrido[2,3-b]pyrazine-4(1H)-carboxamide | 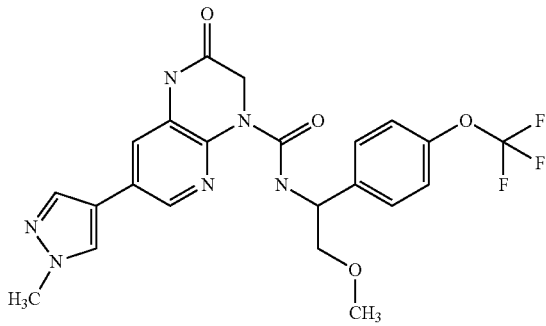 [SMILES: COCC(NC(=O)N1CC(=O)Nc2cc(-c3cnn(C)c3)cnc21)c1ccc(OC(F)(F)F)cc1] | 491.2 |
| 137 | N-(2-methoxy-1-(4-(trifluoromethoxy)phenyl)ethyl)-7-(1-methyl-1H-pyrazol-5-yl)-2-oxo-2,3-dihydropyrido[2,3-b]pryazine-4(1H)-carboxamide | 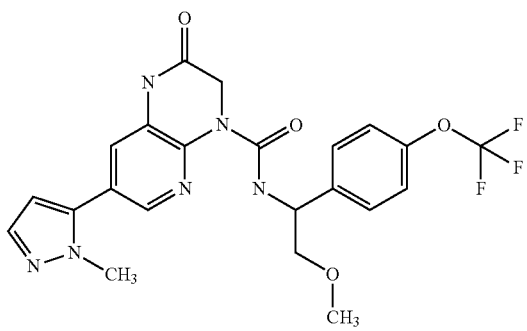 [SMILES: COCC(NC(=O)N1CC(=O)Nc2cc(-c3ccnn3C)cnc21)c1ccc(OC(F)(F)F)cc1] | 491.2 |
| 138 | 7-isopropoxy-N-(2-methoxy-1-(4-(trifluoromethoxy)phenyl)ethyl)-2-oxo-2,3-dihydropyrido[2,3-b]pyrazine-4(1H)-carboxamide | 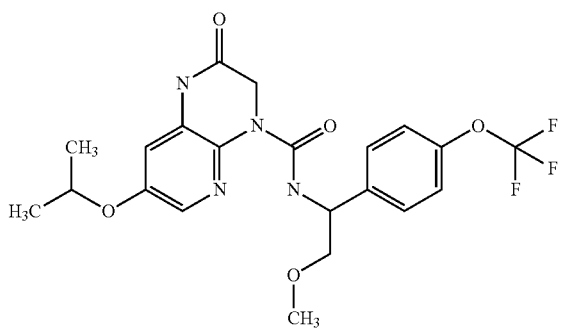 [SMILES: COCC(NC(=O)N1CC(=O)Nc2cc(OC(C)C)cnc21)c1ccc(OC(F)(F)F)cc1] | 469.1 |
| 139 | 7-(difluoromethoxy)-N-(2-methoxy-1-(4-(trifluoromethoxy)phenyl)ethyl)-2-oxo-2,3-dihydropyrido[2,3-b]pyrazine-4(1H)-carboxamide | 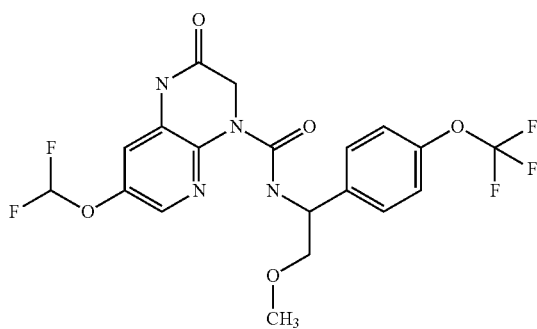 [SMILES: COCC(NC(=O)N1CC(=O)Nc2cc(OC(F)F)cnc21)c1ccc(OC(F)(F)F)cc1] | 477.2 |

TABLE 1-12-continued

| | | | |
|---|---|---|---|
| 140 | N-(2-methoxy-1-(4-(trifluoromethoxy)phenyl)ethyl)-6-oxo-6,7-dihydropteridine-8(5H)-carboxamide | 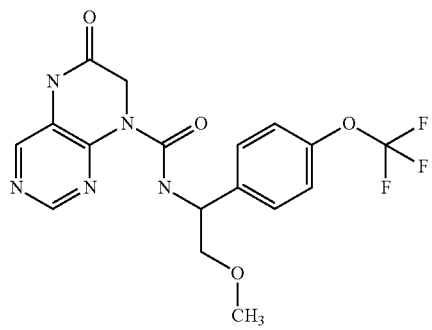 [SMILES: COCC(NC(=O)N1CC(=O)Nc2cncnc21)c1ccc(OC(F)(F)F)cc1] | 412.2 |
| 141 | 7-ethoxy-N-(2-methoxy-1-(4-(trifluoromethoxy)phenyl)ethyl)-2-oxo-2,3-dihydropyrido[2,3-b]pyrazine-4(1H)-carboxamide | 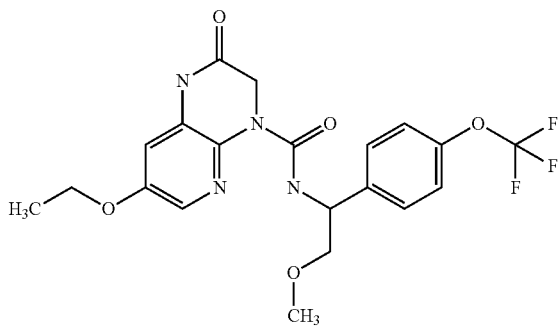 [SMILES: CCOc1cnc2c(c1)NC(=O)CN2C(=O)NC(COC)c1ccc(OC(F)(F)F)cc1] | 455.2 |

TABLE 1-13

| | | | |
|---|---|---|---|
| 142 | 7-methyl-N-(oxetan-3-yl(4-(trifluoromethoxy)phenyl)methyl)-2-oxo-2,3-dihydropyrido[2,3-b]pyrazine-4(1H)-carboxamide | 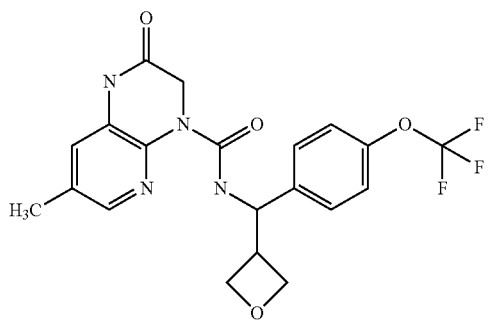 [SMILES: Cc1cnc2c(c1)NC(=O)CN2C(=O)NC(c1ccc(OC(F)(F)F)cc1)C1COC1] | 437.1 |
| 143 | N-(1-(3-fluoro-4-(1H-pyrazol-1-yl)phenyl)-2-methoxyethyl)-7-methyl-2-oxo-2,3-dihydropyrido[2,3-b]pyrazine-4(1H)-carboxamide | 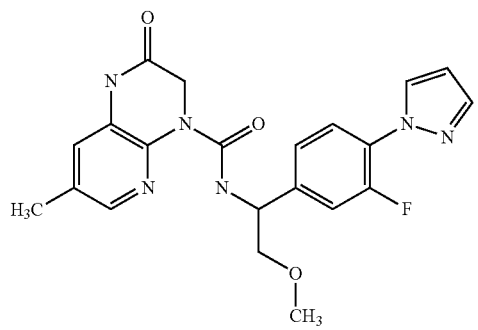 [SMILES: COCC(NC(=O)N1CC(=O)Nc2cc(C)cnc21)c1ccc(-n2cccn2)c(F)c1] | 425.2 |

| | | | |
|---|---|---|---|
| 144 | N-(2-methoxy-1-(5-(1H-pyrazol-1-yl)pyridin-2-yl)ethyl)-7-methyl-2-oxo-2,3-dihydropyrido[2,3-b]pyrazine-4(1H)-carboxamide | 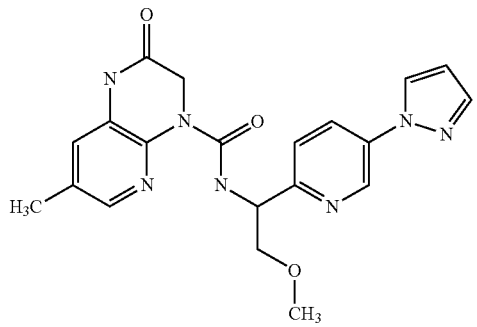 [SMILES: COCC(NC(=O)N1CC(=O)Nc2cc(C)cnc21)c1ccc(-n2cccn2)cn1] | 408.2 |
| 145 | N-((1R)-2-hydroxy-2-methyl-1-(4-(trifluoromethoxy)phenyl)propyl)-2-oxo-2,3-dihydropyrido[2,3-b]pyrazine-4(1H)-carboxamide | 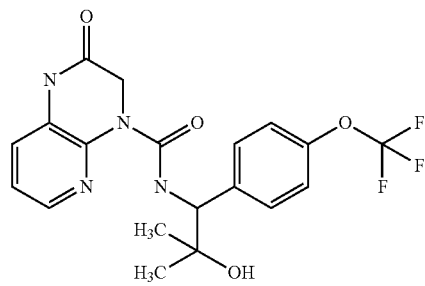 [SMILES: CC(C)(O)C(NC(=O)N1CC(=O)Nc2cccnc21)c1ccc(OC(F)(F)F)cc1] | 425.2 |
| 146 | N-((1S)-2-hydroxy-2-methyl-1-(4-(trifluoromethoxy)phenyl)propyl)-2-oxo-2,3-dihydropyrido[2,3-b]pyrazine-4(1H)-carboxamide | 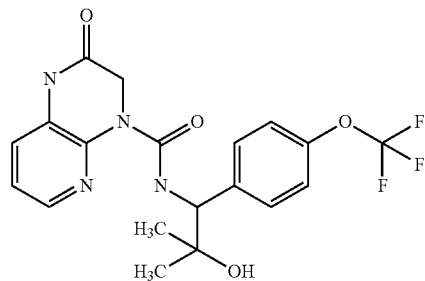 [SMILES: CC(C)(O)C(NC(=O)N1CC(=O)Nc2cccnc21)c1ccc(OC(F)(F)F)cc1] | 425.2 |
| 147 | 7-methyl-2-oxo-N-(1-(4-(1H-pyrrol-1-yl)phenyl)propyl)-2,3-dihydropyrido[2,3-b]pyrazine-4(1H)-carboxamide | 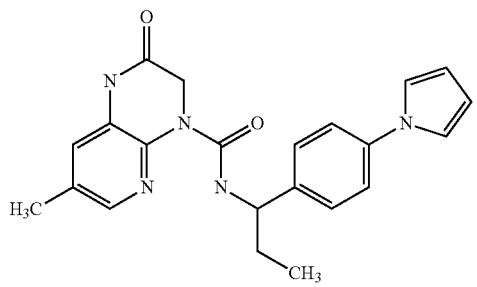 [SMILES: CCC(NC(=O)N1CC(=O)Nc2cc(C)cnc21)c1ccc(-n2cccc2)cc1] | 390.2 |
| 148 | 7-methyl-2-oxo-N-(1-(4-(pyrrolidin-1-yl)phenyl)propyl)-2,3-dihydropyrido[2,3-b]pyrazine-4(1H)-carboxamide | 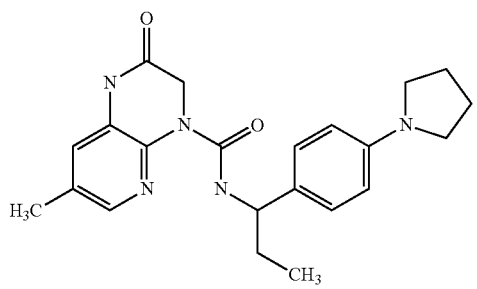 [SMILES: CCC(NC(=O)N1CC(=O)Nc2cc(C)cnc21)c1ccc(N2CCCC2)cc1] | 394.3 |

TABLE 1-13-continued

| 149 | 7-(2-hydroxypropan-2-yl)-N-(2-methoxy-1-(4-(trifluoromethoxy)phenyl)ethyl)-2-oxo-2,3-dihydropyrido[2,3-b]pyrazine-4(1H)-carboxamide | 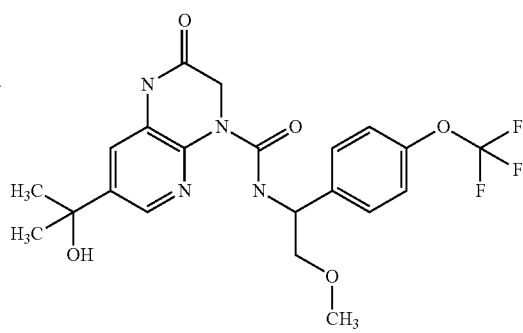 | 469.2 |
| 150 | 7-(azetidin-1-yl)-N-(2-methoxy-1-(4-(trifluoromethoxy)phenyl)ethyl)-2-oxo-2,3-dihydropyrido[2,3-b]pyrazine-4(1H)-carboxamide | 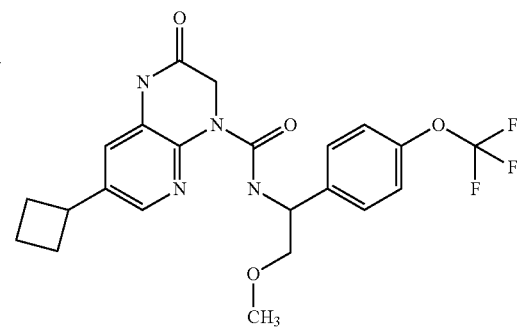 | 466.2 |
| 151 | N-(1-(imidazo[1,2-a]pyridin-7-yl)propyl)-7-methyl-2-oxo-2,3-dihydropyrido[2,3-b]pyrazine-4(1H)-carboxamide | 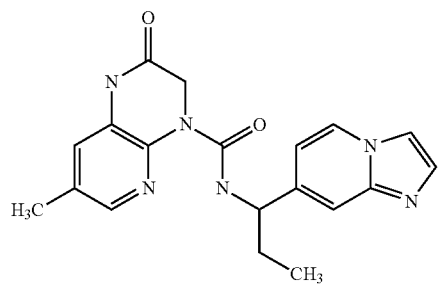 [SMILES: CCC(NC(=O)N1CC(=O)Nc2cc(C)cnc21)c1ccn2ccnc2c1] | 365.2 |
| 152 | 7-methyl-2-oxo-N-(1-(4-(trifluoromethoxy)phenyl)cyclopropyl)-2,3-dihydropyrido[2,3-b]pyrazine-4(1H)-carboxamide | 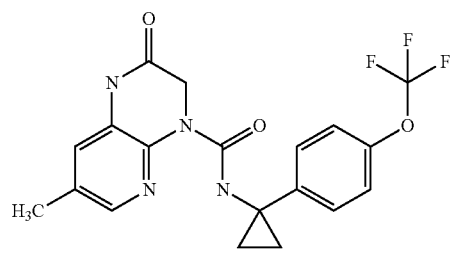 [SMILES: Cc1cnc2c(c1)NC(=O)CN2C(=O)NC1(c2ccc(OC(F)(F)F)cc2)CC1] | 407.1 |
| 153 | 7-fluoro-N-(2-methoxy-1-(4-(trifluoromethoxy)phenyl)ethyl)-2-oxo-2,3-dihydropyrido[2,3-b]pyrazine-4(1H)-carboxamide | 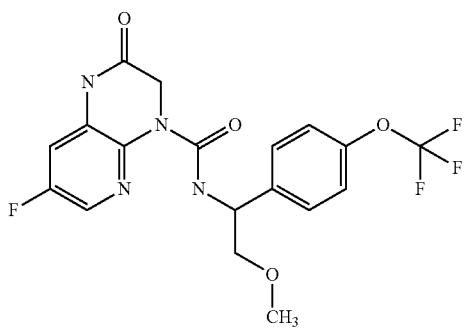 [SMILES: COCC(NC(=O)N1CC(=O)Nc2cc(F)cnc21)c1ccc(OC(F)(F)F)cc1] | 429.1 |

TABLE 1-14

| 154 | N-(2-methoxy-1-(4-(1H-pyrrol-1-yl)phenyl)ethyl)-7-methyl-2-oxo-2,3-dihydropyrido[2,3-b]pyrazine-4(1H)-carboxamide | 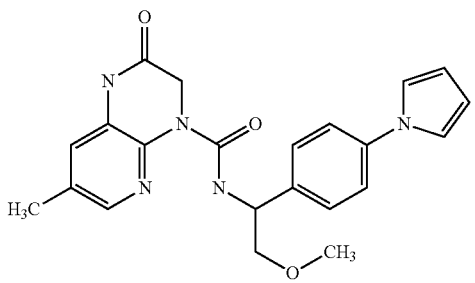 [SMILES: COCC(NC(=O)N1CC(=O)Nc2cc(C)cnc21)c1ccc(-n2cccc2)cc1] | 406.2 |
| 155 | 7-chloro-N-(2-methoxy-1-(4-(trifluoromethoxy)phenyl)ethyl)-2-oxo-2,3-dihydropyrido[2,3-b]pyrazine-4(1H)-carboxamide | 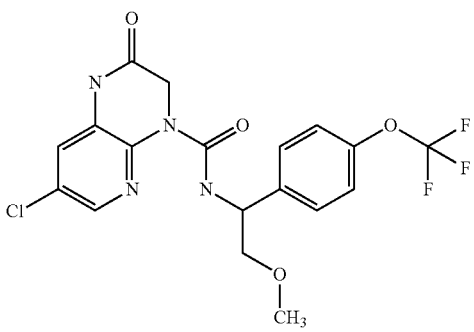 [SMILES: COCC(NC(=O)N1CC(=O)Nc2cc(Cl)cnc21)c1ccc(OC(F)(F)F)cc1] | 445.1 |
| 156 | N-(2-methoxy-1-(4-(pyrrolidin-1-yl)phenyl)ethyl)-7-methyl-2-oxo-2,3-dihydropyrido[2,3-b]pyrazine-4(1H)-carboxamide | 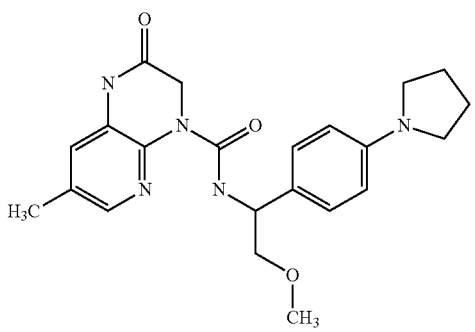 [SMILES: COCC(NC(=O)N1CC(=O)Nc2cc(C)cnc21)c1ccc(N2CCCC2)cc1] | 410.3 |
| 157 | N-(2-methoxy-1-(4-(1H-pyrrol-1-yl)phenyl)ethyl)-2-oxo-2,3-dihydropyrido[2,3-b]pyrazine-4(1H)-carboxamide | 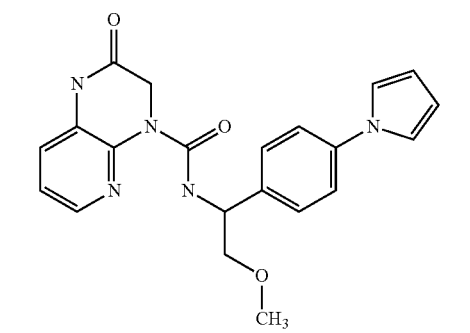 [SMILES: COCC(NC(=O)N1CC(=O)Nc2cccnc21)c1ccc(-n2cccc2)cc1] | 392.2 |
| 158 | N-(2-methoxy-1-(4-(pyrrolidin-1-yl)phenyl)ethyl)-2-oxo-2,3-dihydropyrido[2,3-b]pyrazine-4(1H)-carboxamide | 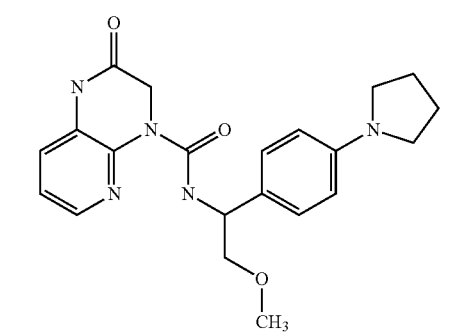 [SMILES: COCC(NC(=O)N1CC(=O)Nc2cccnc21)c1ccc(N2CCCC2)cc1] | 396.2 |

TABLE 1-14-continued

| | | | |
|---|---|---|---|
| 159 | N-(1-(2,2-difluoro-1,3-benzodioxol-5-yl)propyl)-2-oxo-2,3-dihydropyrido[2,3-b]pyrazine-4(1H)-carboxamide | 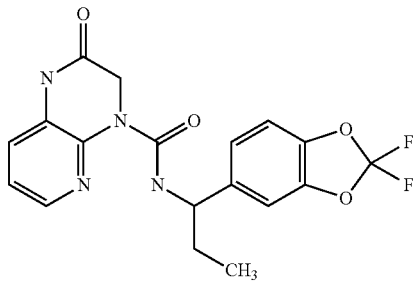 [SMILES: CCC(NC(=O)N1CC(=O)Nc2cccnc21)c1ccc2c(c1)OC(F)(F)O2] | 391.1 |
| 160 | 7-methyl-2-oxo-N-(2-(1H-pyrazol-1-yl)-1-(4-(trifluoromethoxy)phenyl)ethyl)-2,3-dihydropyrido[2,3-b]pyrazine-4(1H)-carboxamide | 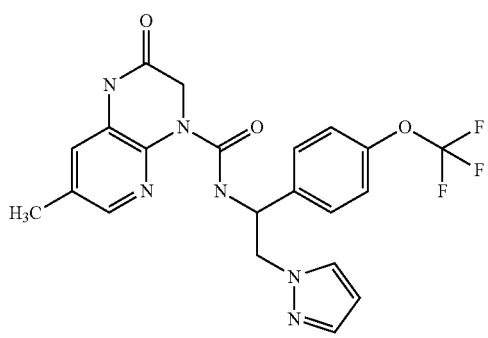 [SMILES: Cc1cnc2c(c1)NC(=O)CN2C(=O)NC(Cn1cccn1)c1ccc(OC(F)(F)F)cc1] | 461.2 |
| 161 | optically active 7-methyl-2-oxo-N-(1-(4-(1H-pyrrol-1-yl)phenyl)propyl)-2,3-dihydropyrido[2,3-b]pyrazine-4(1H)-carboxamide | 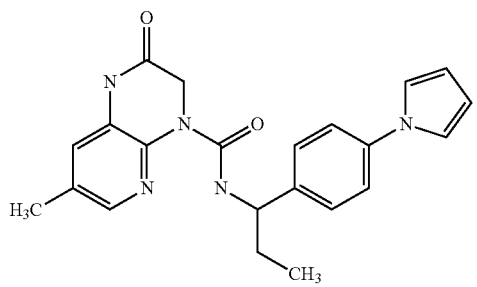 [SMILES: CCC(NC(=O)N1CC(=O)Nc2cc(C)cnc21)c1ccc(-n2cccc2)cc1] | 390.2 |
| 162 | 7-methyl-2-oxo-N-(1-(5-(1H-pyrazol-1-yl)-2-thienyl)propyl)-2,3-dihydropyrido[2,3-b]pyrazine-4(1H)-carboxamide | 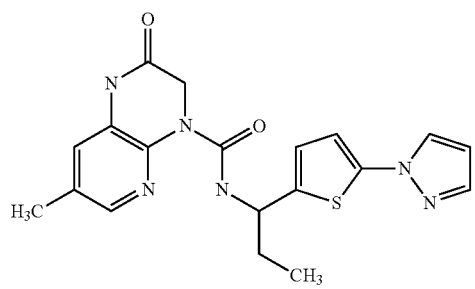 [SMILES: CCC(NC(=O)N1CC(=O)Nc2cc(C)cnc21)c1ccc(-n2cccn2)s1] | 397.0 |
| 163 | optically active 7-methyl-2-oxo-N-(1-(4-(1H-pyrrol-1-yl)phenyl)propyl)-2,3-dihydropyrido[2,3-b]pyrazine-4(1H)-carboxamide | 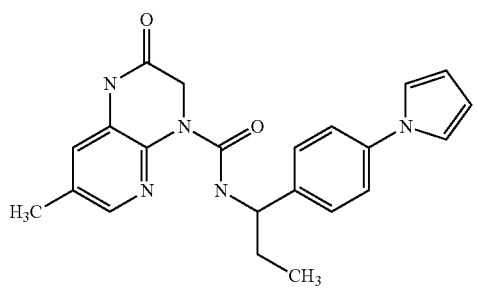 [SMILES: CCC(NC(=O)N1CC(=O)Nc2cc(C)cnc21)c1ccc(-n2cccc2)cc1] | 390.2 |

TABLE 1-14-continued

| | | | |
|---|---|---|---|
| 164 | 7-methyl-2-oxo-N-(2-(1H-(1,2,4-triazol-1-yl)-1-(4-(trifluoromethoxy)phenyl)ethyl)-2,3-dihydropyrido[2,3-b]pyrazine-4(1H)-carboxamide | 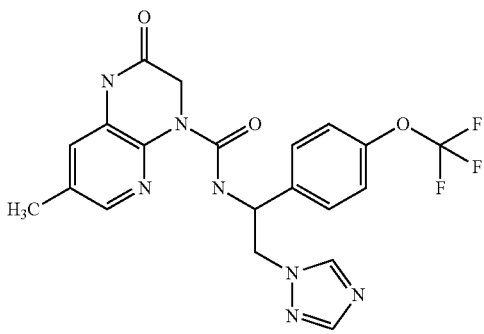 [SMILES: Cc1cnc2c(c1)NC(=O)CN2C(=O)NC(Cn1cncn1)c1ccc(OC(F)(F)F)cc1] | 462.2 |
| 165 | 7-methyl-2-oxo-N-(1-(pyrazolo[1,5-a]pyridin-5-yl)propyl)-2,3-dihydropyrido[2,3-b]pyrazine-4(1H)-carboxamide | 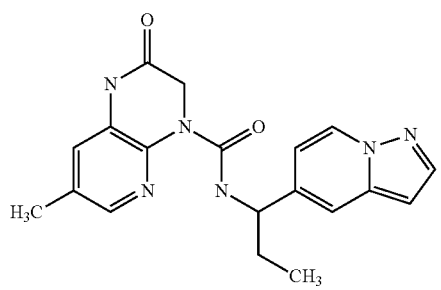 [SMILES: CCC(NC(=O)N1CC(=O)Nc2cc(C)cnc21)c1ccn2nccc2c1] | 365.2 |

TABLE 1-15

| | | | |
|---|---|---|---|
| 166 | 7-methyl-N-(2-(oxetan-3-yl)-1-(4-(trifluoromethoxy)phenyl)ethyl)-2-oxo-2,3-dihydropyrido[2,3-b]pyrazine-4(1H)-carboxamide | 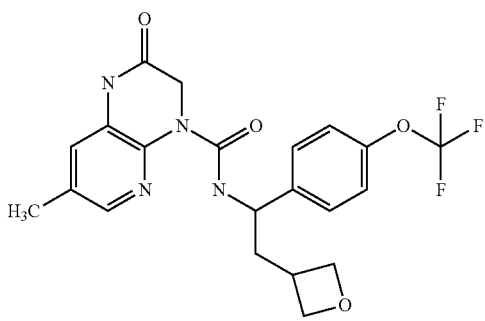 [SMILES: Cc1cnc2c(c1)NC(=O)CN2C(=O)NC(CC1COC1)c1ccc(OC(F)(F)F)cc1] | 451.2 |
| 167 | 7-(difluoromethyl)-N-(2-methoxy-1-(4-(trifluoromethoxy)phenyl)ethyl)-2-oxo-2,3-dihydropyrido[2,3-b]pyrazine-4(1H)-carboxamide | 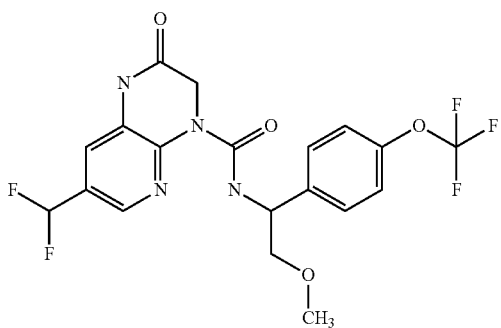 [SMILES: COCC(NC(=O)N1CC(=O)Nc2cc(C(F)F)cnc21)c1ccc(OC(F)(F)F)cc1] | 461.1 |

TABLE 1-15-continued

| | | | |
|---|---|---|---|
| 168 | 7-methyl-2-oxo-N-(tetrahydro-2H-pyran-4-yl(4-(trifluoromethoxy)phenyl)methyl)-2,3-dihydropyrido[2,3-b]pyrazine-(4H)-carboxamide | 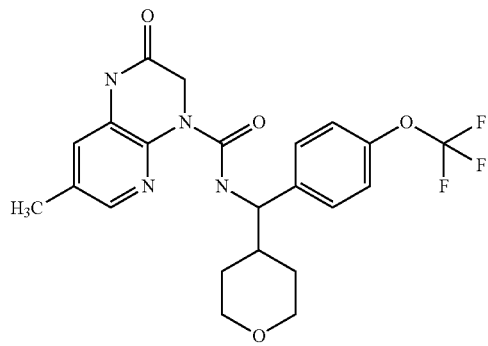 [SMILES: Cc1cnc2c(c1)NC(=O)CN2C(=O)NC(c1ccc(OC(F)(F)F)cc1)C1CCOCC1] | 465.2 |
| 169 | N-(2-(4-hydroxytetrahydro-2H-pyran-4-yl)-1-(4-(trifluoromethoxy)phenyl)ethyl)-7-methyl-2-oxo-2,3-dihydropyrido[2,3-b]pyrazine-4(1H)-carboxamide | 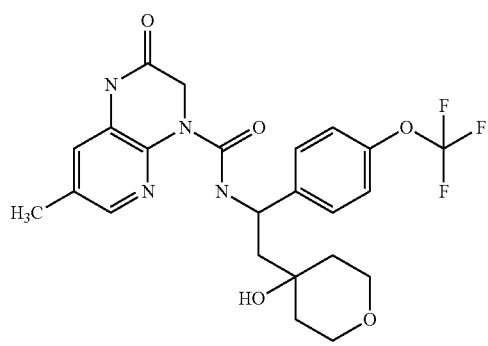 [SMILES: Cc1cnc2c(c1)NC(=O)CN2C(=O)NC(CC1(O)CCOCC1)c1ccc(OC(F)(F)F)cc1] | 495.1 |
| 170 | 7-methyl-2-oxo-N-(tetrahydrofuran-2-yl(4-(trifluoromethoxy)phenyl)methyl)-2,3-dihydropyrido[2,3-b]pyrazine-4(1H)-carboxamide | 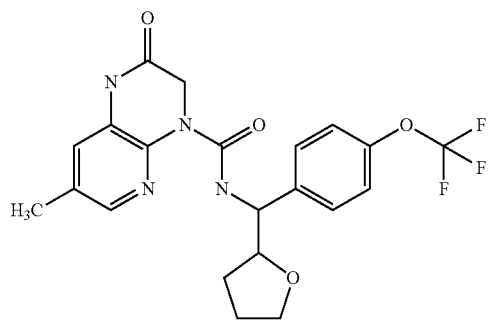 [SMILES: Cc1cnc2c(c1)NC(=O)CN2C(=O)NC(c1ccc(OC(F)(F)F)cc1)C1CCCO1] | 451.2 |
| 171 | N-(2-hydroxy-1-(4-(trifluoromethoxy)phenyl)pentyl)-7-methyl-2-oxo-2,3-dihydropyrido[2,3-b]pyrazine-4(1H)-carboxamide | 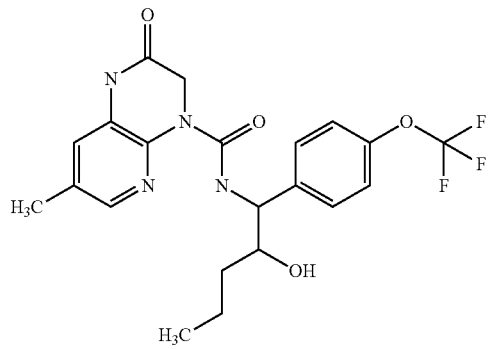 [SMILES: CCCC(O)C(NC(=O)N1CC(=O)Nc2cc(C)cnc21)c1ccc(OC(F)(F)F)cc1] | 453.2 |

TABLE 1-15-continued

| 172 | N-(3-((tert-butyl(diphenyl)silyl)oxy)-2,2-dimethyl-1-(4-(trifluoromethoxy)phenyl)propyl)-7-methyl-2-oxo-2,3-dihydropyrido[2,3-b]pyrazine-4(1H)-carboxamide | 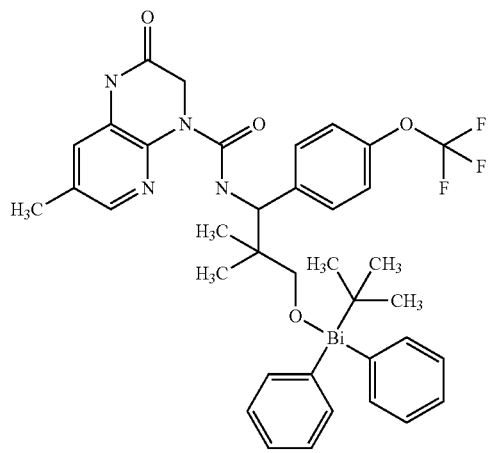 | 691.4 |
| --- | --- | --- | --- |
| 173 | N-(2-(1,3-dioxo-1,3-dihydro-2H-isoindol-2-yl)-1-(4-(trifluoromethoxy)phenyl)ethyl)-2-oxo-2,3-dihydropyrido[2,3-b]pyrazine-4(1H)-carboxamide | 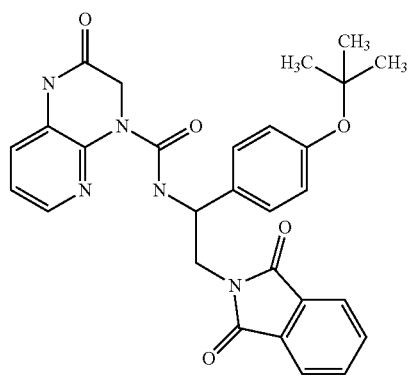 [SMILES: CC(C)(C)Oc1ccc(C(CN2C(=O)c3ccccc3C2=O)NC(=O)N2CC(=O)Nc3cccnc32)cc1] | 526.2 |
| 174 | N-(2-cyclopropyl-2-oxo-1-(4-(trifluoromethoxy)phenyl)ethyl)-2-oxo-2,3-dihydro[2,3-b]pyrazine-4(1H)-carboxamide | 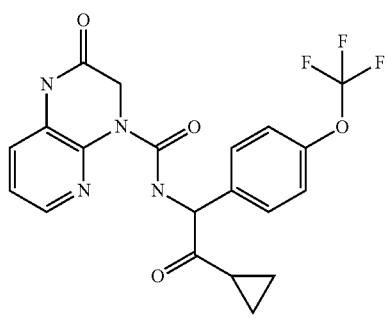 [SMILES: O=C1CN(C(=O)NC(C(=O)C2CC2)c2ccc(OC(F)(F)F)cc2)c2ncccc2N1] | 435.1 |
| 175 | N-(2-cyclopropyl-2-hydroxy-1-(4-(trifluoromethoxy)phenyl)ethyl)-2-oxo-2,3-dihydropyrido[2,3-b]pyrazine-4(1H)-carboxamide | 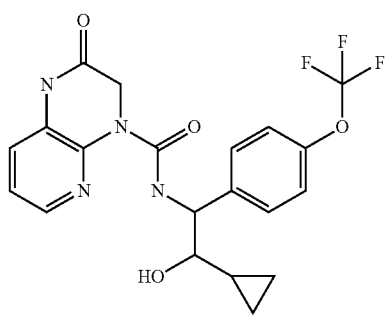 [SMILES: O=C1CN(C(=O)NC(c2ccc(OC(F)(F)F)cc2)C(O)C2CC2)c2ncccc2N1] | 437.2 |

TABLE 1-15-continued

| | | | |
|---|---|---|---|
| 176 | 7-methyl-2-oxo-N-(2-(tetrahydro-2H-pyran-4-yl)-1-(4-(trifluoromethoxy)phenyl)ethyl)-2,3-dihydropyrido[2,3-b]pyrazine-4(1H)-carboxamide | 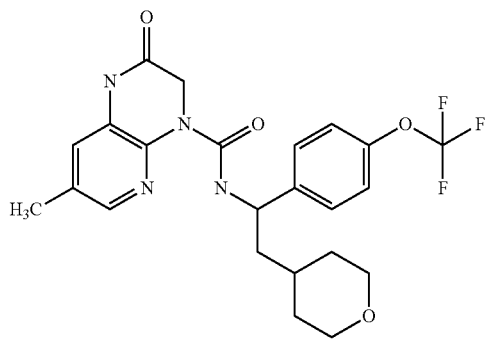 [SMILES: Cc1cnc2c(c1)NC(=O)CN2C(=O)NC(CC1CCOCC1)c1ccc(OC(F)(F)F)cc1] | 479.2 |
| 177 | 2-oxo-N-(2-oxo-1-(4-(trifluoromethoxy)phenyl)propyl)-2,3-dihydropyrido[2,3-b]pyrazine-4(1H)-carboxamide | 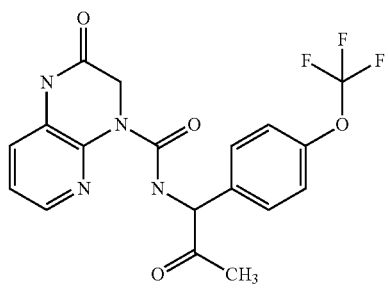 [SMILES: CC(=O)C(NC(=O)N1CC(=O)Nc2cccnc21)c1ccc(OC(F)(F)F)cc1] | 409.1 |

TABLE 1-16

| | | | |
|---|---|---|---|
| 178 | 8-methoxy-N-(2-methoxy-1-(4-(trifluoromethoxy)phenyl)ethyl)-2-oxo-2,3-dihydropyrido[2,3-b]pyrazine-4(1H)-carboxamide | 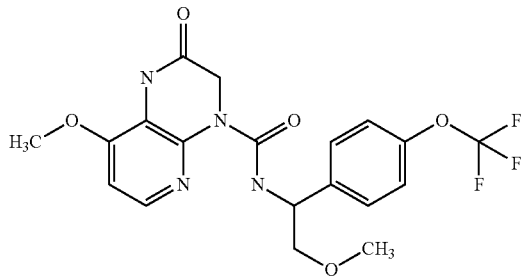 [SMILES: COCC(NC(=O)N1CC(=O)Nc2c(OC)ccnc21)c1ccc(OC(F)(F)F)cc1] | 441.2 |
| 179 | N-(2-hydroxy-1-(4-(trifluoromethoxy)phenyl)propyl)-2-oxo-2,3-dihydropyrido[2,3-b]pyrazine-4(1H)-carboxamide | 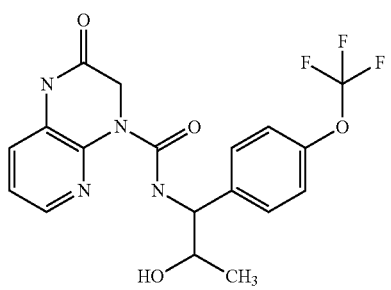 [SMILES: CC(O)C(NC(=O)N1CC(=O)Nc2cccnc21)c1ccc(OC(F)(F)F)cc1] | 411.1 |
| 180 | 2-oxo-N-(2,2,2-trifluoro-1-(4-(trifluoromethoxy)phenyl)ethyl)-2,3-dihydropyrido[2,3-b]pyrazine-4(1H)-carboxamide | 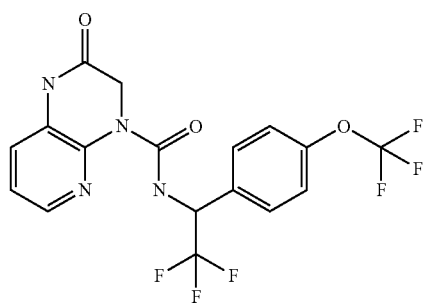 [SMILES: O=C1CN(C(=O)NC(c2ccc(OC(F)(F)F)cc2)C(F)(F)F)c2ncccc2N1] | 435.1 |

TABLE 1-16-continued

| | | | |
|---|---|---|---|
| 181 | 7-methyl-2-oxo-N-(2-(pyridin-3-yloxy)-1-(4-(trifluoromethoxy)phenyl)ethyl)-2,3-dihydropyrido[2,3-b]pyrazine-4(1H)-carboxamide | 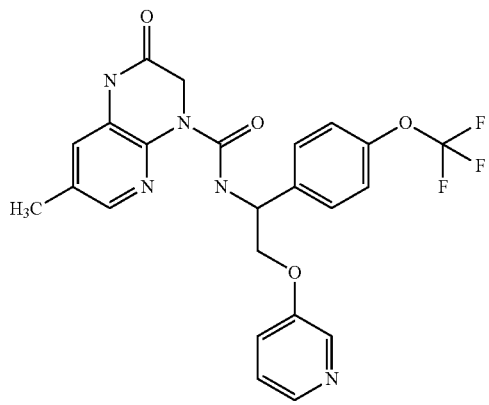 [SMILES: Cc1cnc2c(c1)NC(=O)CN2C(=O)NC(COc1cccnc1)c1ccc(OC(F)(F)F)cc1] | 488.2 |
| 182 | N-(2-hydroxy-1-(4-(trifluoromethoxy)phenyl)ethyl)-7-methyl-2-oxo-2,3-dihydropyrido[2,3-b]pyrazine-4(1H)-carboxamide | 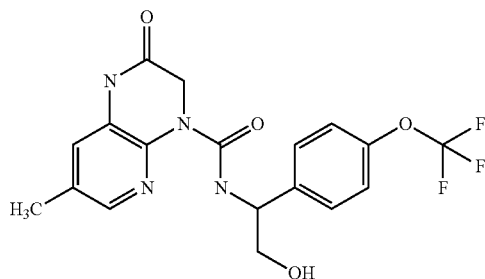 [SMILES: Cc1cnc2c(c1)NC(=O)CN2C(=O)NC(CO)c1ccc(OC(F)(F)F)cc1] | 411.1 |
| 183 | N-(1-(3,5-difluoro-4-(trifluoromethoxy)phenyl)-2-methoxyethyl)-7-methyl-2-oxo-2,3-dihydropyrido[2,3-b]pyrazine-4(1H)-carboxamide | 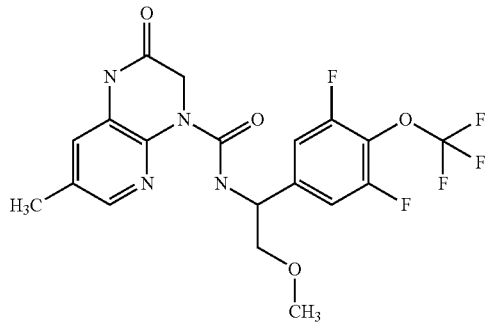 [SMILES: COCC(NC(=O)N1CC(=O)Nc2cc(C)cnc21)c1cc(F)c(OC(F)(F)F)c(F)c1] | 461.1 |
| 184 | N-(3-hydroxy-2,2-dimethyl-1-(4-(trifluoromethoxy)phenyl)propyl)-7-methyl-2-oxo-2,3-dihydropyrido[2,3-b]pyrazine-4(1H)-carboxamide | 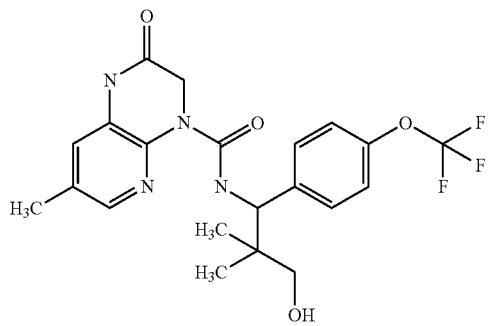 [SMILES: Cc1cnc2c(c1)NC(=O)CN2C(=O)NC(c1ccc(OC(F)(F)F)cc1)C(C)(C)CO] | 453.2 |
| 185 | N-(2-fluoro-2-methyl-1-(4-(trifluoromethoxy)phenyl)propyl)-2-oxo-2,3-dihydropyrido[2,3-b]pyrazine-4(1H)-carboxamide | 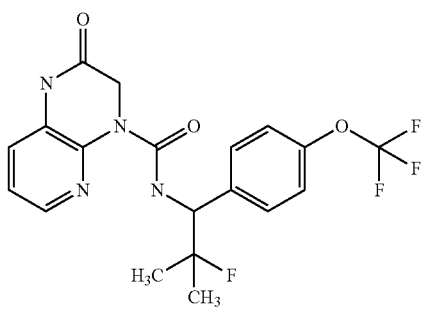 [SMILES: CC(C)(F)C(NC(=O)N1CC(=O)Nc2cccnc21)c1ccc(OC(F)(F)F)cc1] | 427.1 |

TABLE 1-16-continued

| 186 | 2-oxo-N-(1-(4-(2H-1,2,3-triazol-2-yl)phenyl)propyl)-2,3-dihydropyrido[2,3-b]pyrazine-4(1H)-carboxamide | 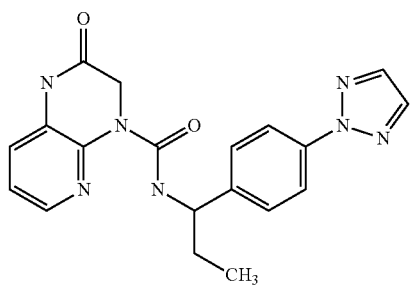 [SMILES: CCC(NC(=O)N1CC(=O)Nc2cccnc21)c1ccc(-n2nccn2)cc1] | 378.2 |
| --- | --- | --- | --- |
| 187 | N-(2-fluoro-2-methyl-1-(4-(trifluoromethoxy)phenyl)propyl)-7-methyl-2-oxo-2,3-dihydropyrido[2,3-b]pyrazine-4(1H)-carboxamide | 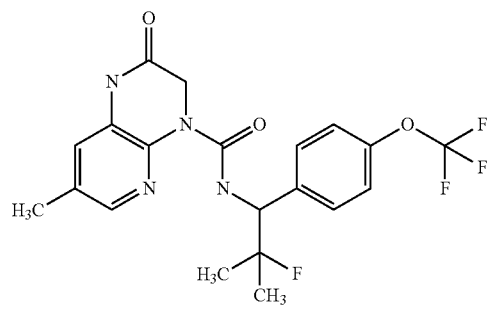 [SMILES: Cc1cnc2c(c1)NC(=O)CN2C(=O)NC(c1ccc(OC(F)(F)F)cc1)C(C)(C)F] | 441.2 |
| 188 | N-(1-(3-fluoro-4-(pyrrolidin-1-yl)phenyl)-2-methoxyethyl)-7-methyl-2-oxo-2,3-dihydropyrido[2,3-b]pyrazine-4(1H)-carboxamide | 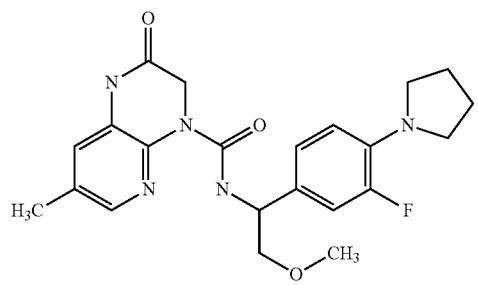 [SMILES: COCC(NC(=O)N1CC(=O)Nc2cc(C)cnc21)c1ccc(N2CCCC2)c(F)c1] | 428.2 |
| 189 | N-(1-(3-fluoro-4-(1H-pyrrol-1-yl)phenyl)-2-methoxyethyl)-7-methyl-2-oxo-2,3-dihydropyrido[2,3-b]pyrazine-4(1H)-carboxamide | 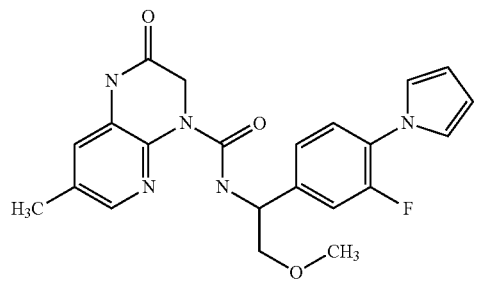 [SMILES: COCC(NC(=O)N1CC(=O)Nc2cc(C)cnc21)c1ccc(-n2cccc2)c(F)c1] | 424.2 |

TABLE 1-17

| 190 | 8-(2-hydroxypropan-2-yl)-N-(2-methoxy-1-(4-(trifluoromethoxy)phenyl)ethyl)-2-oxo-2,3-dihydropyrido[2,3-b]pyrazine-4(1H)-carboxamide | 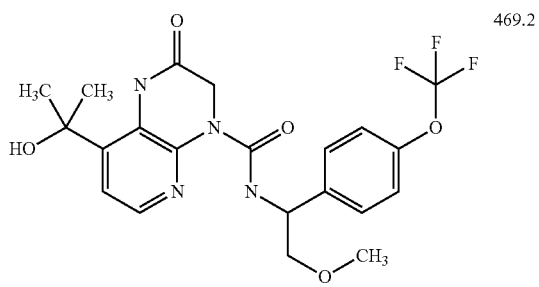 | 469.2 |
| --- | --- | --- | --- |

TABLE 1-17-continued

| # | Name | MW |
|---|---|---|
| 191 | 8-acetyl-N-(2-methoxy-1-(4-(trifluoromethoxy)phenyl)ethyl)-2-oxo-2,3-dihydropyrido[2,3-b]pyrazine-4(1H)-carboxamide | 453.1 |
| 192 | 8-(hydroxymethyl)-N-(2-methoxy-1-(4-(trifluoromethoxy)phenyl)ethyl)-2-oxo-2,3-dihydropyrido[2,3-b]pyrazine-4(1H)-carboxamide | 441.2 |
| 193 | N-(2-ethyl-2-hydroxy-1-(4-(trifluoromethoxy)phenyl)butyl)-2-oxo-2,3-dihydropyrido[2,3-b]pyrazine-4(1H)-carboxamide | 453.2 |
| 194 | N-(2-amino-1-(4-(trifluoromethoxy)phenyl)ethyl)-2-oxo-2,3-dihydropyrido[2,3-b]pyrazine-4(1H)-carboxamide | 396.1 |
| 195 | N-((2-bromo-2-fluorophenyl)(4-(trifluoromethoxy)phenyl)methyl)-7-methyl-2-oxo-2,3-dihydropyrido[2,3-b]pyrazine-4(1H)-carboxamide | 553.1 |

TABLE 1-17-continued

| | | | |
|---|---|---|---|
| 196 | N-((4-bromo-2-hydroxyphenyl)(4-(trifluoromethoxy)phenyl)methyl)-7-methyl-2-oxo-2,3-dihydropyrido[2,3-b]pyrazine-4(1H)-carboxamide | | 551.1 |
| 197 | N-(2-((5-bromopyridin-3-yl)oxy)-1-(4-(trifluoromethoxy)phenyl)ethyl)-7-methyl-2-oxo-2,3-dihydropyrido[2,3-b]pyrazine-4(1H)-carboxamide | | 566.1 |
| 198 | N-((2-fluorophenyl)(4-(trifluoromethoxy)phenyl)methyl)-7-methyl-2-oxo-2,3-dihydropyrido[2,3-b]pyrazine-4(1H)-carboxamide | | 475.2 |
| 199 | N-((2-hydroxyphenyl)(4-(trifluoromethoxy)phenyl)methyl)-7-methyl-2-oxo-2,3-dihydropyrido[2,3-b]pyrazine-4(1H)-carboxamide | | 473.2 |

TABLE 1-17-continued

| 200 | 7-methyl-2-oxo-N-(tetrahydrofuran-2-yl(4-(trifluoromethoxy)phenyl)methyl)-2,3-dihydropyrido[2,3-b]pyrazine-4(1H)-carboxamide | 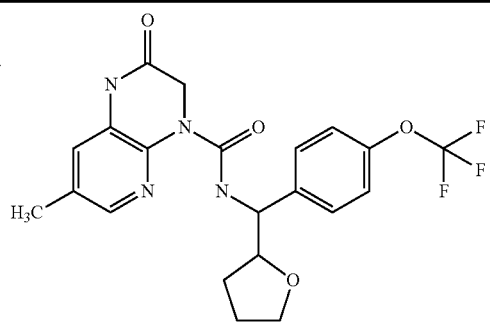 | 451.2 |
| 201 | 7-methyl-2-oxo-N-(tetrahydrofuran-2-yl(4-(trifluoromethoxy)phenyl)methyl)-2,3-dihydropyrido[2,3-b]pyrazine-4(1H)-carboxamide | 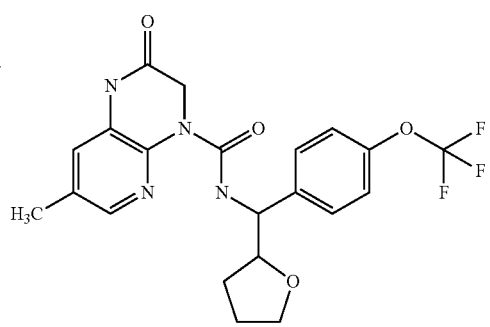 | 451.2 |

TABLE 1-18

| 202 | 7-methyl-2-oxo-N-(tetrahydrofuran-2-yl(4-(trifluoromethoxy)phenyl)methyl)-2,3-dihydropyrido[2,3-b]pyrazine-4(1H)-carboxamide | 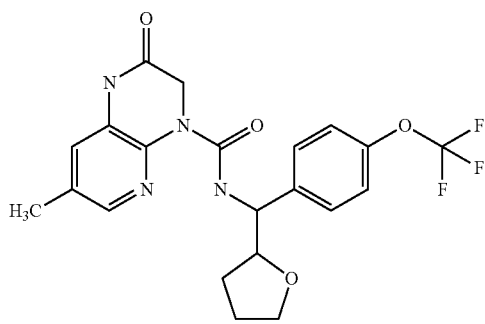 [SMILES: Cc1cnc2c(c1)NC(=O)CN2C(=O)NC(c1ccc(OC(F)(F)F)cc1)C1CCCO1] | 451.2 |
| 203 | 7-methyl-2-oxo-N-(tetrahydrofuran-2-yl(4-(trifluoromethoxy)phenyl)methyl)-2,3-dihydropyrido[2,3-b]pyrazine-4(1H)-carboxamide | 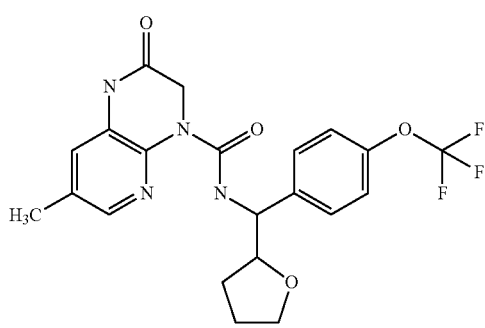 [SMILES: Cc1cnc2c(c1)NC(=O)CN2C(=O)NC(c1ccc(OC(F)(F)F)cc1)C1CCCO1] | 451.2 |

TABLE 1-18-continued

| 204 | 7-methoxy-2-oxo-N-(1-(4-(pyrrolidin-1-yl)phenyl)propyl)-2,3-dihydropyrido[2,3-b]pyrazine-4(1H)-carboxamide | 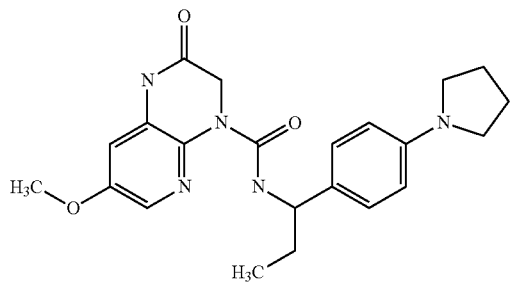 [SMILES: CCC(NC(=O)N1CC(=O)Nc2cc(OC)cnc21)c1ccc(N2CCCC2)cc1] | 408.2 |
| 205 | N-(2-hydroxy-2-methyl-1-(4-(trifluoromethoxy)phenyl)propyl)-7-methoxy-2-oxo-2,3-dihydropyrido[2,3-b]pyrazine-4(1H)-carboxamide | 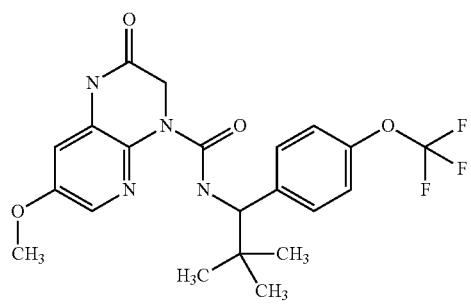 [SMILES: COc1cnc2c(c1)NC(=O)CN2C(=O)NC(c1ccc(OC(F)(F)F)cc1)C(C)(C)C] | 455.3 |
| 206 | 7-methyl-2-oxo-N-(tetrahydrofuran-3-yl(4-(trifluoromethoxy)phenyl)methyl)-2,3-dihydropyrido[2,3-b]pyrazine-4(1H)-carboxamide | 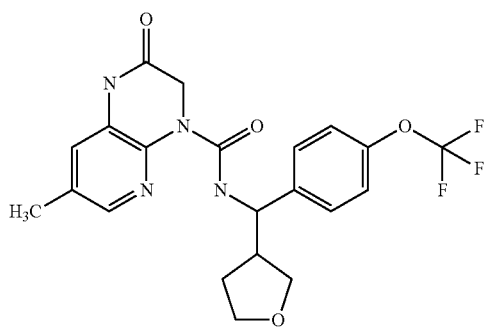 [SMILES: Cc1cnc2c(c1)NC(=O)CN2C(=O)NC(c1ccc(OC(F)(F)F)cc1)C1CCOC1] | 451.2 |
| 207 | N-((1S)-2-hydroxy-2-methyl-1-(4-(trifluoromethoxy)phenyl)propyl)-7-methoxy-2-oxo-2,3-dihydropyrido[2,3-b]pyrazine-4(1H)-carboxamide | 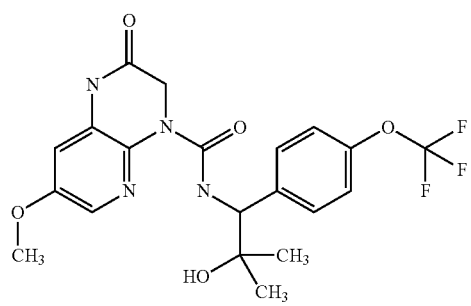 [SMILES: COc1cnc2c(c1)NC(=O)CN2C(=O)NC(c1ccc(OC(F)(F)F)cc1)C(C)(C)O] | 455.2 |
| 208 | N-((1R)-2-hydroxy-2-methyl-1-(4-(trifluoromethoxy)phenyl)propyl)-7-methoxy-2-oxo-2,3-dihydropyrido[2,3-b]pyrazine-4(1H)-carboxamide | 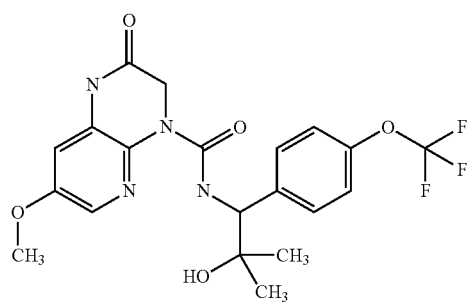 [SMILES: COc1cnc2c(c1)NC(=O)CN2C(=O)NC(c1ccc(OC(F)(F)F)cc1)C(C)(C)O] | 455.1 |

TABLE 1-18-continued

| 209 | 7-cyclopropyl-N-(1-(3-fluoro-4-(trifluoromethyl)phenyl)-2-methoxyethyl)-2-oxo-2,3-dihydropyrido[2,3-b]pyrazine-4(1H)-carboxamide | 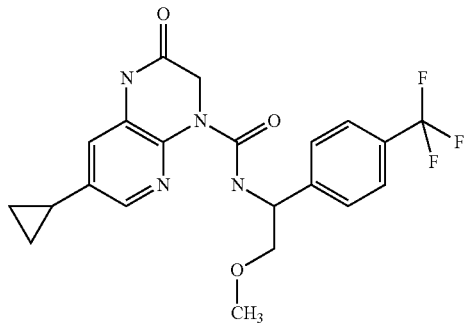 [SMILES: COCC(NC(=O)N1CC(=O)Nc2cc(C3CC3)cnc21)c1ccc(C(F)(F)F)cc1] | 453.1 |

| 210 | 7-methyl-2-oxo-N-(3,3,3-trifluoro-2-hydroxy-1-(4-(trifluoromethoxy)phenyl)propyl)-2,3-dihydropyrido[2,3-b]pyrazine-4(1H)-carboxamide | 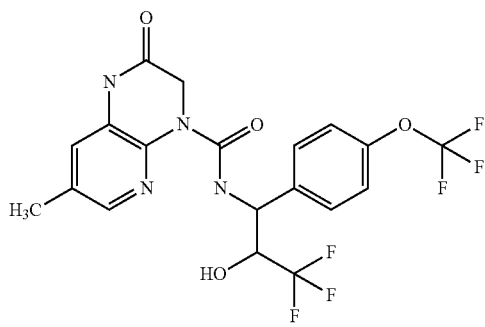 [SMILES: Cc1cnc2c(c1)NC(=O)CN2C(=O)NC(c1ccc(OC(F)(F)F)cc1)C(O)C(F)(F)F] | 479.1 |

| 211 | N-(1-(3-fluoro-4-(1H-pyrrol-1-yl)phenyl)-2-methoxyethyl)-7-methoxy-2-oxo-2,3-dihydropyrido[2,3-b]pyrazine-4(1H)-carboxamide | 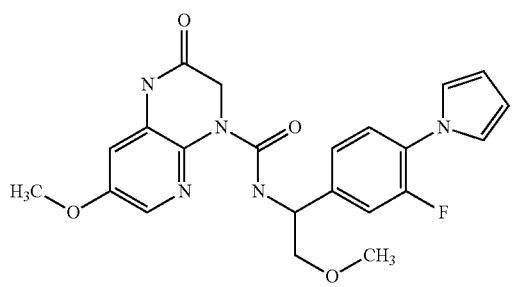 [SMILES: COCC(NC(=O)N1CC(=O)Nc2cc(OC)cnc21)c1ccc(-n2cccc2)c(F)c1] | 440.2 |

| 212 | 6-(4-methoxyphenyl)-N-(2-methoxy-1-(4-(trifluoromethoxy)phenyl)ethyl)-2-oxo-2,3-dihydropyrido[2,3-b]pyrazine-4(1H)-carboxamide | 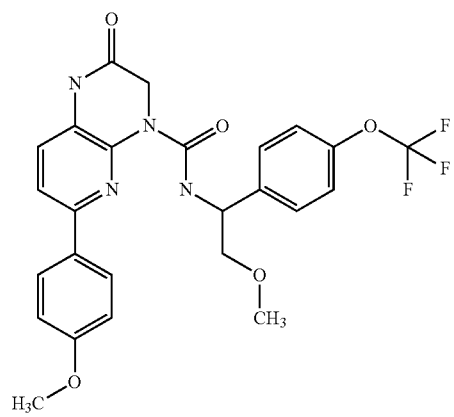 [SMILES: COCC(NC(=O)N1CC(=O)Nc2ccc(-c3ccc(OC)cc3)nc21)c1ccc(OC(F)(F)F)cc1] | 517.1 |

TABLE 1-18-continued

| 213 | N-(2-methoxy-1-(4-(trifluoromethoxy)phenyl)ethyl)-2-oxo-6-(pyridin-3-yl)-2,3-dihydropyrido[2,3-b]pyrazine-4(1H)-carboxamide | | 488.1 |
|---|---|---|---|

TABLE 1-19

| 214 | N-(2-methoxy-1-(4-(trifluoromethoxy)phenyl)ethyl)-2-oxo-6-phenyl-2,3-dihydropyrido[2,3-b]pyrazine-4(1H)-carboxamide | | 487.1 |
|---|---|---|---|
| 215 | 6-(2-methoxyphenyl)-N-(2-methoxy-1-(4-(trifluoromethoxy)phenyl)ethyl)-2-oxo-2,3-dihydropyrido[2,3-b]pyrazine-4(1H)-carboxamide | | 517.1 |
| 216 | 6-(3-methoxyphenyl)-N-(2-methoxy-1-(4-(trifluoromethoxy)phenyl)ethyl)-2-oxo-2,3-dihydropyrido[2,3-b]pyrazine-4(1H)-carboxamide | | 517.2 |

TABLE 1-19-continued

| | | | |
|---|---|---|---|
| 217 | N-(2-methoxy-1-(4-(trifluoromethoxy)phenyl)ethyl)-2-oxo-6-(pyridin-4-yl)-2,3-dihydropyrido[2,3-b]pyrazine-4(1H)-carboxamide | 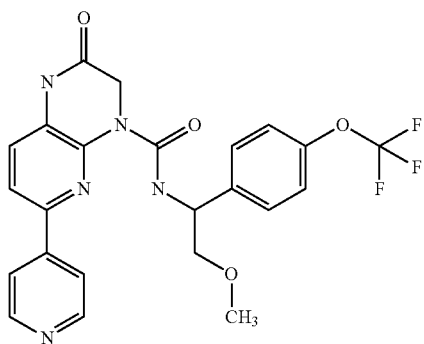 [SMILES: COCC(NC(=O)N1CC(=O)Nc2ccc(-c3ccncc3)nc21)c1ccc(OC(F)(F)F)cc1] | 488.1 |
| 218 | N-(2-methoxy-1-(4-(trifluoromethoxy)phenyl)ethyl)-2-oxo-6-(2-thienyl)-2,3-dihydropyrido[2,3-b]pyrazine-4(1H)-carboxamide | 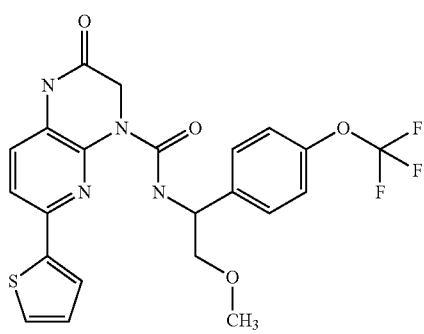 [SMILES: COCC(NC(=O)N1CC(=O)Nc2ccc(-c3cccs3)nc21)c1ccc(OC(F)(F)F)cc1] | 493.1 |
| 219 | 6-(3-furyl)-N-(2-methoxy-1-(4-(trifluoromethoxy)phenyl)ethyl)-2-oxo-2,3-dihydropyrido[2,3-b]pyrazine-4(1H)-carboxamide | 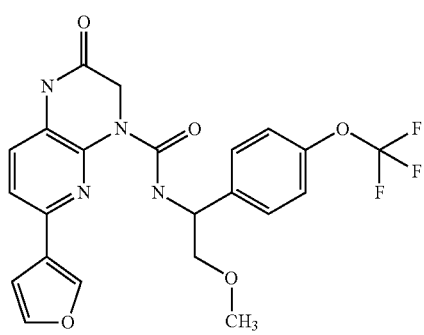 [SMILES: COCC(NC(=O)N1CC(=O)Nc2ccc(-c3ccoc3)nc21)c1ccc(OC(F)(F)F)cc1] | 477.1 |
| 220 | N-(2-methoxy-1-(4-(trifluoromethoxy)phenyl)ethyl)-2-oxo-6-(3-thienyl)-2,3-dihydropyrido[2,3-b]pyrazine-4(1H)-carboxamide | 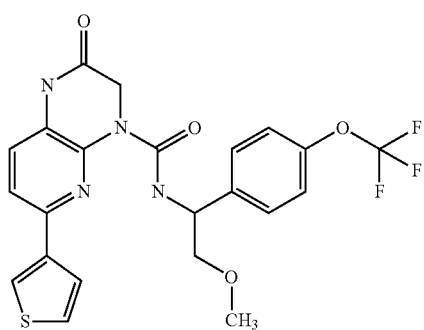 [SMILES: COCC(NC(=O)N1CC(=O)Nc2ccc(-c3ccsc3)nc21)c1ccc(OC(F)(F)F)cc1] | 493.1 |

TABLE 1-19-continued

| 221 | N-(2-methoxy-1-(4-(trifluoromethoxy)phenyl)ethyl)-6-(1-methyl-1H-pyrazol-5-yl)-2-oxo-2,3-dihydropyrido[2,3-b]pyrazine-4(1H)-carboxamide | 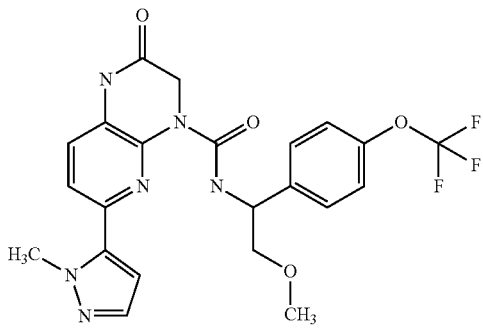 [SMILES: COCC(NC(=O)N1CC(=O)Nc2ccc(-c3ccnn3C)nc21)c1ccc(OC(F)(F)F)cc1] | 491.1 |
| --- | --- | --- | --- |
| 222 | N-(2-methoxy-1-(4-(trifluoromethoxy)phenyl)ethyl)-6-(1-methyl-1H-pyrazol-3-yl)-2-oxo-2,3-dihydropyrido[2,3-b]pyrazine-4(1H)-carboxamide | 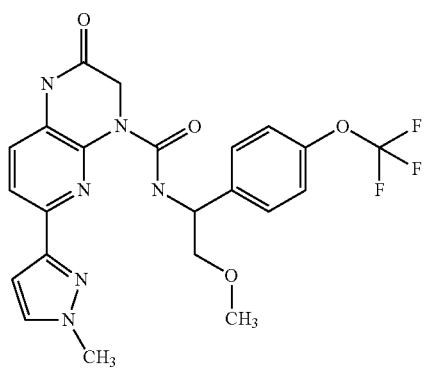 [SMILES: COCC(NC(=O)N1CC(=O)Nc2ccc(-c3ccn(C)n3)nc21)c1ccc(OC(F)(F)F)cc1] | 491.1 |
| 223 | N-(2-methoxy-1-(4-(trifluoromethoxy)phenyl)ethyl)-6-(1-methyl-1H-pyrazol-4-yl)-2-oxo-2,3-dihydropyrido[2,3-b]pyrazine-4(1H)-carboxamide | 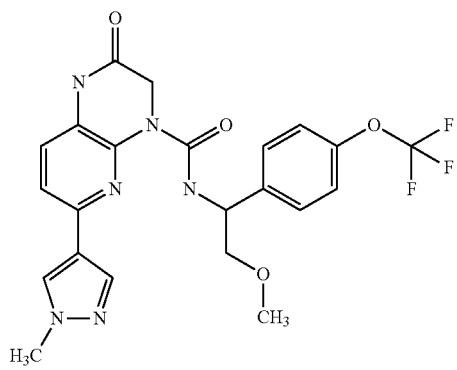 [SMILES: COCC(NC(=O)N1CC(=O)Nc2ccc(-c3cnn(C)c3)nc21)c1ccc(OC(F)(F)F)cc1] | 491.1 |
| 224 | 6-(3,5-dimethyl-1,2-oxazol-4-yl)-N-(2-methoxy-1-(4-(trifluoromethoxy)phenyl)ethyl)-2-oxo-2,3-dihydropyrido[2,3-b]pyrazine-4(1H)-carboxamide | 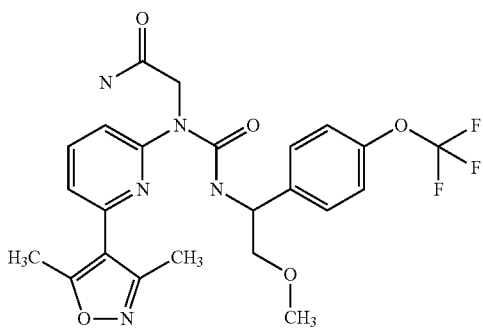 [SMILES: COCC(NC(=O)N(CC(N)=O)c1cccc(-c2c(C)noc2C)n1)c1ccc(OC(F)(F)F)cc1] | 506.1 |

TABLE 1-19-continued

| 225 | N-(1-(3-fluoro-4-(trifluoromethyl)phenyl)-2-methoxyethyl)-7-methoxy-2-oxo-2,3-dihydropyrido[2,3-b]pyrazine-4(1H)-carboxamide | 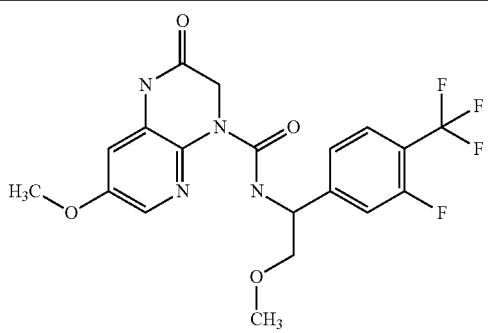 | 443.1 |

TABLE 1-20

| 226 | optically active 7-cyclopropyl-N-(1-(3-fluoro-4-(trifluoromethyl)phenyl)-2-methoxyethyl)-2-oxo-2,3-dihydropyrido[2,3-b]pyrazine-4(1H)-carboxamide | 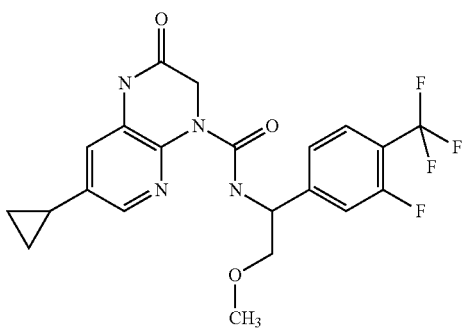 | 453.1 |
| 227 | optically active 7-cyclopropyl-N-(1-(3-fluoro-4-(trifluoromethyl)phenyl)-2-methoxyethyl)-2-oxo-2,3-dihydropyrido[2,3-b]pyrazine-4(1H)-carboxamide | 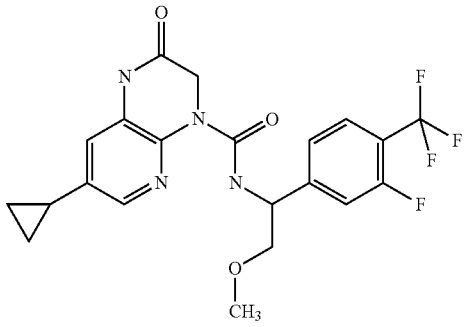 [SMILES: COCC(NC(=O)N1CC(=O)Nc2cc(C3CC3)cnc21)c1ccc(C(F)(F)F)c(F)c1] | 453.1 |
| 228 | N-(2-methoxy-2-methyl-1-(4-(trifluoromethoxy)phenyl)propyl)-7-methyl-2-oxo-2,3-dihydropyrido[2,3-b]pyrazine-4(1H)-carboxamide | 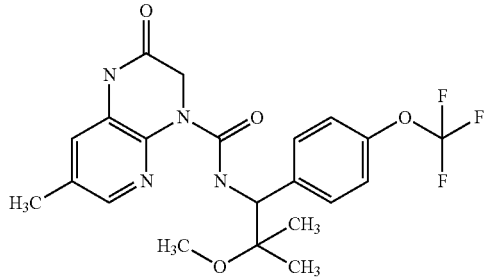 [SMILES: COC(C)(C)C(NC(=O)N1CC(=O)Nc2cc(C)cnc21)c1ccc(OC(F)(F)F)cc1] | 453.2 |

TABLE 1-20-continued

| | | | |
|---|---|---|---|
| 229 | optically active N-(1-(3-fluoro-4-(1H-pyrrol-1-yl)phenyl)-2-methoxyethyl)-7-methoxy-2-oxo-2,3-dihydropyrido[2,3-b]pyrazine-4(1H)-carboxamide | 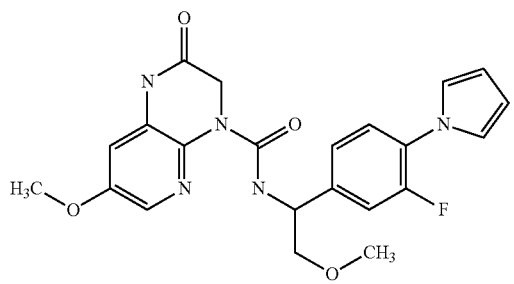 [SMILES: COCC(NC(=O)N1CC(=O)Nc2cc(OC)cnc21)c1ccc(-n2cccc2)c(F)c1] | 440.2 |
| 230 | optically active N-(1-(3-fluoro-4-(1H-pyrrol-1-yl)phenyl)-2-methoxyethyl)-7-methoxy-2-oxo-2,3-dihydropyrido[2,3-b]pyrazine-4(1H)-carboxamide | 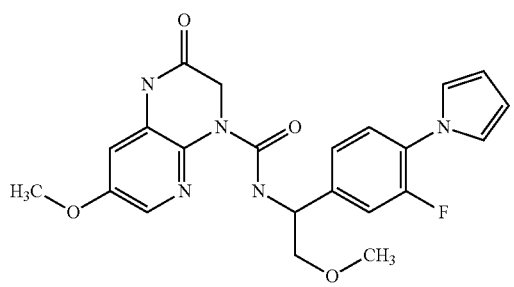 [SMILES: COCC(NC(=O)N1CC(=O)Nc2cc(OC)cnc21)c1ccc(-n2cccc2)c(F)c1] | 440.2 |
| 231 | optically active 7-cyclopropyl-N-(2-methoxy-1-(4-(trifluoromethyl)phenyl)ethyl)-2-oxo-2,3-dihydropyrido[2,3-b]pyrazine-4(1H)-carboxamide | 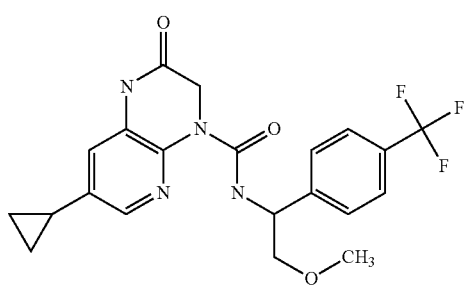 [SMILES: COCC(NC(=O)N1CC(=O)Nc2cc(C3CC3)cnc21)c1ccc(C(F)(F)F)cc1] | 435.1 |
| 232 | optically active N-(1-(3-fluoro-4-(trifluoromethyl)phenyl)-2-methoxyethyl)-7-methoxy-2-oxo-2,3-dihydropyrido[2,3-b]pyrazine-4(1H)-carboxamide | 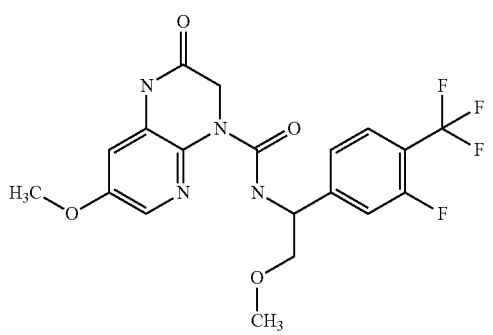 [SMILES: COCC(NC(=O)N1CC(=O)Nc2cc(OC)cnc21)c1ccc(C(F)(F)F)c(F)c1] | 443.1 |
| 233 | optically active 7-cyclopropyl-N-(2-methoxy-1-(4-(trifluoromethyl)phenyl)ethyl)-2-oxo-2,3-dihydropyrido[2,3-b]pyrazine-4(1H)-carboxamide | 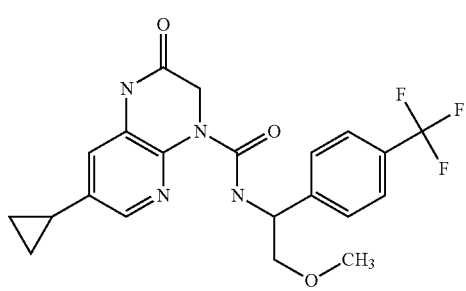 [SMILES: COCC(NC(=O)N1CC(=O)Nc2cc(C3CC3)cnc21)c1ccc(C(F)(F)F)cc1] | 435.1 |

TABLE 1-20-continued

| | | | |
|---|---|---|---|
| 234 | optically active N-(1-(3-fluoro-4-(trifluoromethyl)phenyl)-2-methoxyethyl)-7-methoxy-2-oxo-2,3-dihydropyrido[2,3-b]pyrazine-4(1H)-carboxamide | 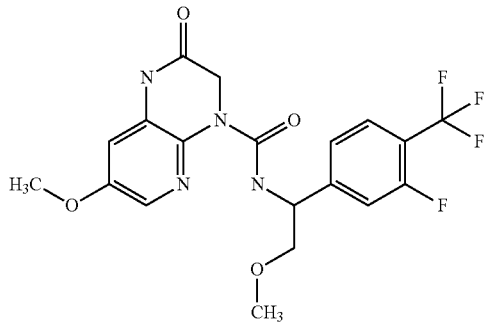 [SMILES: COCC(NC(=O)N1CC(=O)Nc2cc(OC)cnc21)c1ccc(C(F)(F)F)c(F)c1] | 443.1 |
| 235 | 6-(3,6-dihydro-2H-pyran-4-yl)-N-(2-methoxy-1-(4-(trifluoromethoxy)phenyl)ethyl)-2-oxo-2,3-dihydropyrido[2,3-b]pyrazine-4(1H)-carboxamide | 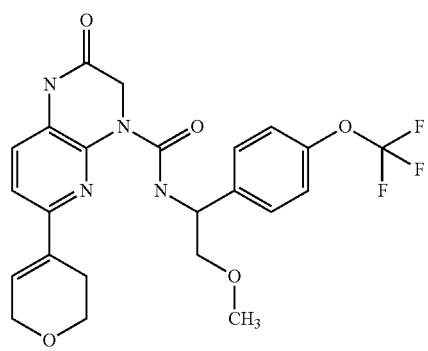 [SMILES: COCC(NC(=O)N1CC(=O)Nc2ccc(C3=CCOCC3)nc21)c1ccc(OC(F)(F)F)cc1] | 493.1 |
| 236 | N-(2-methoxy-1-(4-(trifluoromethoxy)phenyl)ethyl)-6-(1-methyl-1,2,3,6-tetrahydropyridin-4-yl)-2-oxo-2,3-dihydropyrido[2,3-b]pyrazine-4(1H)-carboxamide | 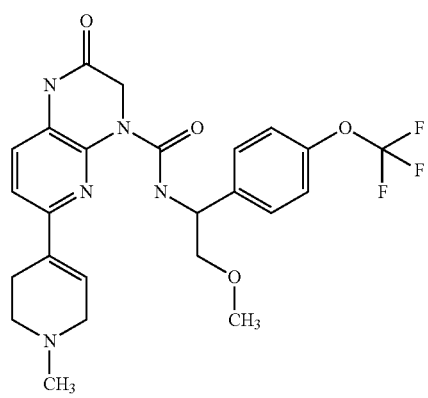 | 506.1 |
| 237 | N-(2-methoxy-1-(4-(trifluoromethoxy)phenyl)ethyl)-2-oxo-6-(1,2,3,6-tetrahydropyridin-4-yl)-2,3-dihydropyrido[2,3-b]pyrazine-4(1H)-carboxamide | 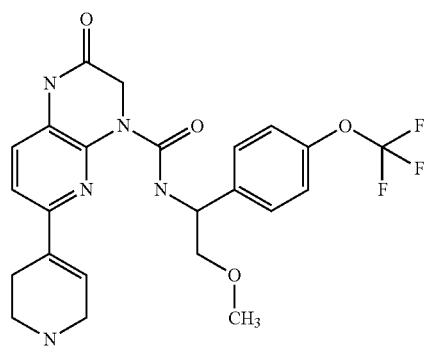 [SMILES: COCC(NC(=O)N1CC(=O)Nc2ccc(C3=CCNCC3)nc21)c1ccc(OC(F)(F)F)cc1] | 492.1 |

TABLE 1-21

| 238 | N-(2-methoxy-1-(4-(trifluoromethoxy)phenyl)ethyl)-6-methyl-2-oxo-2,3-dihydropyrido[2,3-b]pyrazine-4(1H)-carboxamide | 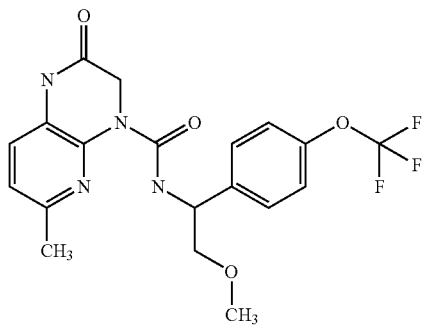 [SMILES: COCC(NC(=O)N1CC(=O)Nc2ccc(C)nc21)c1ccc(OC(F)(F)F)cc1] | 425.0 |
| 239 | N-(2-methoxy-1-(4-(trifluoromethoxy)phenyl)ethyl)-2-oxo-6-(pyridin-2-yl)-2,3-dihydropyrido[2,3-b]pyrazine-4(1H)-carboxamide | 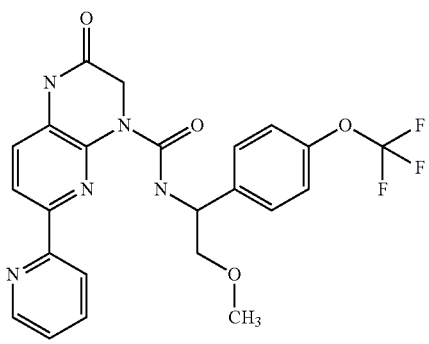 [SMILES: COCC(NC(=O)N1CC(=O)Nc2ccc(-c3ccccn3)nc21)c1ccc(OC(F)(F)F)cc1] | 488.1 |
| 240 | 6-(2-furyl)-N-(2-methoxy-1-(4-(trifluoromethoxy)phenyl)ethyl)-2-oxo-2,3-dihydropyrido[2,3-b]pyrazine-4(1H)-carboxamide | 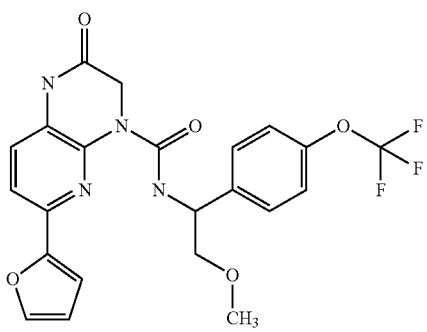 [SMILES: COCC(NC(=O)N1CC(=O)Nc2ccc(-c3ccco3)nc21)c1ccc(OC(F)(F)F)cc1] | 477.1 |
| 241 | 6-cyclopropyl-N-(2-methoxy-1-(4-(trifluoromethoxy)phenyl)ethyl)-2-oxo-2,3-dihydropyrido[2,3-b]pyrazine-4(1H)-carboxamide | 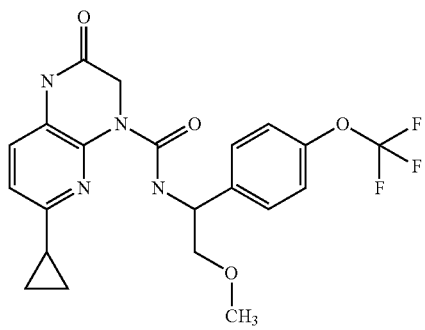 [SMILES: COCC(NC(=O)N1CC(=O)Nc2ccc(C3CC3)nc21)c1ccc(OC(F)(F)F)cc1] | 451.1 |

| | | | |
|---|---|---|---|
| 242 | N-(2-methoxy-1-(4-(trifluoromethoxy)phenyl)ethyl)-2-oxo-6-(tetrahydro-2H-pyran-4-yl)-2,3-dihydropyrido[2,3-b]pyrazine-4(1H)-carboxamide | 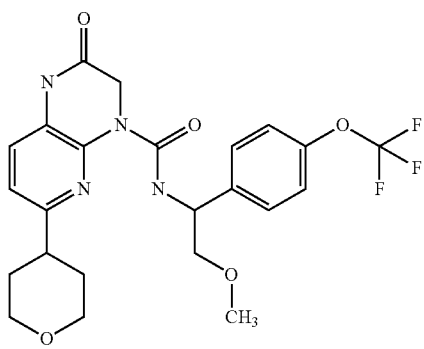 [SMILES: COCC(NC(=O)N1CC(=O)Nc2ccc(C3CCOCC3)nc21)c1ccc(OC(F)(F)F)cc1] | 495.1 |
| 243 | N-(2-methoxy-1-(4-(trifluoromethoxy)phenyl)ethyl)-6-(1-methylpiperidin-4-yl)-2-oxo-2,3-dihydropyrido[2,3-b]pyrazine-4(1H)-carboxamide | 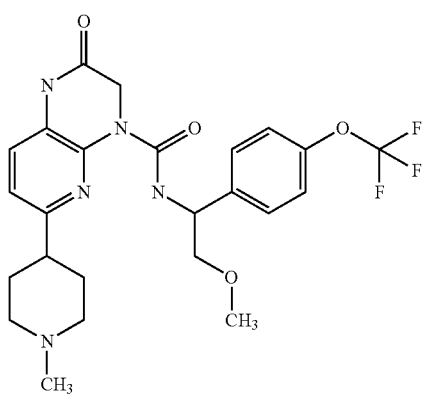 [SMILES: COCC(NC(=O)N1CC(=O)Nc2ccc(C3CCN(C)CC3)nc21)c1ccc(OC(F)(F)F)cc1] | 508.1 |
| 244 | N-(2-methoxy-1-(4-(trifluoromethoxy)phenyl)ethyl)-2-oxo-6-(piperidin-4-yl)-2,3-dihydropyrido[2,3-b]pyrazine-4(1H)-carboxamide | 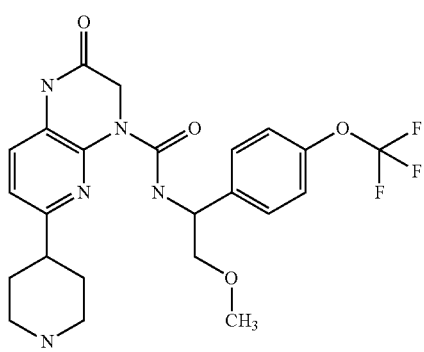 [SMILES: COCC(NC(=O)N1CC(=O)Nc2ccc(C3CCNCC3)nc21)c1ccc(OC(F)(F)F)cc1] | 494.1 |
| 245 | 6-methoxy-N-(2-methoxy-1-(4-(trifluoromethoxy)phenyl)ethyl)-7-methyl-2-oxo-2,3-dihydropyrido[2,3-b]pyrazine-4(1H)-carboxamide | 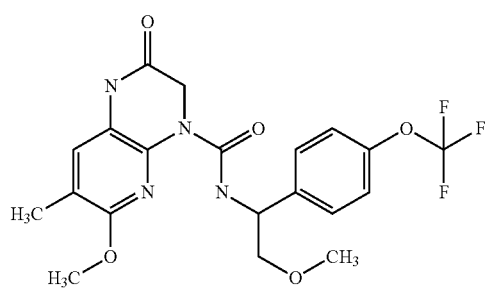 [SMILES: COCC(NC(=O)N1CC(=O)Nc2cc(C)c(OC)nc21)c1ccc(OC(F)(F)F)cc1] | 455.1 |

TABLE 1-21-continued

| 246 | 7-methoxy-N-(2-methoxy-1-(4-(trifluoromethoxy)phenyl)ethyl)-6-methyl-2-oxo-2,3-dihydropyrido[2,3-b]pyrazine-4(1H)-carboxamide | 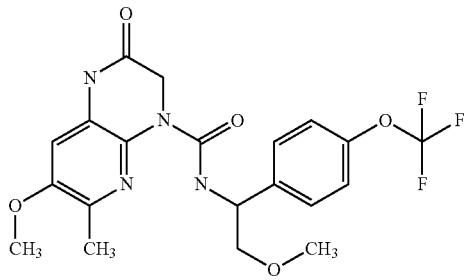 [SMILES: COCC(NC(=O)N1CC(=O)Nc2cc(OC)c(C)nc21)c1ccc(OC(F)(F)F)cc1] | 455.1 |
| 247 | N-(2-hydroxy-2-methyl-1-(4-(trifluoromethoxy)phenyl)propyl)-7-methoxy-6-methyl-2-oxo-2,3-dihydropyrido[2,3-b]pyrazine-4(1H)-carboxamide | 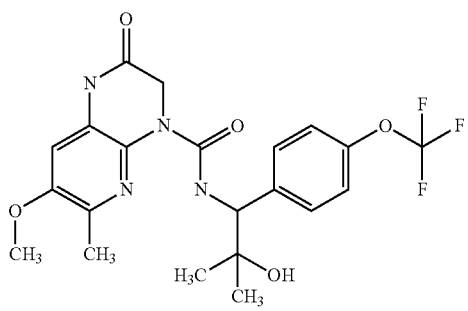 [SMILES: COc1cc2c(nc1C)N(C(=O)NC(c1ccc(OC(F)(F)F)cc1)C(C)(C)O)CC(=O)N2] | 469.1 |
| 248 | N-(2-hydroxy-2-methyl-1-(4-(trifluoromethoxy)phenyl)propyl)-6-methoxy-7-methyl-2-oxo-2,3-dihydropyrido[2,3-b]pyrazine-4(1H)-carboxamide | 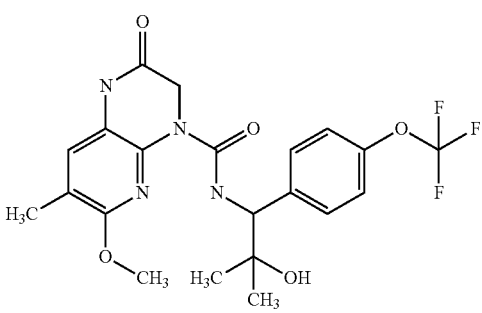 [SMILES: COc1nc2c(cc1C)NC(=O)CN2C(=O)NC(c1ccc(OC(F)(F)F)cc1)C(C)(C)O] | 469.1 |
| 249 | N-(3-methoxy-1-(4-(trifluoromethoxy)phenyl)propyl)-7-methyl-2-oxo-2,3-dihydropyrido[2,3-b]pyrazine-4(1H)-carboxamide | 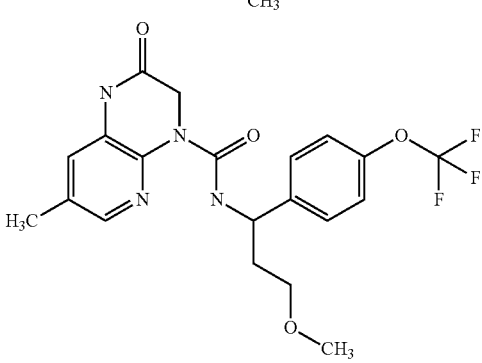 | 439.1 |

TABLE 1-22

| 250 | N-(2-hydroxy-2-methyl-1-(4-(trifluoromethoxy)phenyl)propyl)-7-methyl-2-oxo-2,3-dihydropyrido[2,3-b]pyrazine-4(1H)-carboxamide | 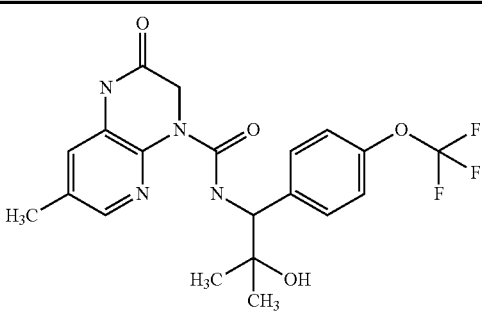 | 439.1 |

TABLE 1-22-continued

| | | | |
|---|---|---|---|
| 251 | 7-methoxy-N-((1S)-2-methoxy-1-(4-(trifluoromethoxy)phenyl)ethyl)-6-methyl-2-oxo-2,3-dihydropyrido[2,3-b]pyrazine-4(1H)-carboxamide | 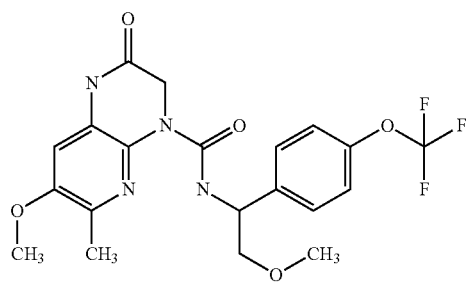 [SMILES: COCC(NC(=O)N1CC(=O)Nc2cc(OC)c(C)nc21)c1ccc(OC(F)(F)F)cc1] | 455.1 |
| 252 | 7-methoxy-N-((1R)-2-methoxy-1-(4-(trifluoromethoxy)phenyl)ethyl)-6-methyl-2-oxo-2,3-dihydropyrido[2,3-b]pyrazine-4(1H)-carboxamide | 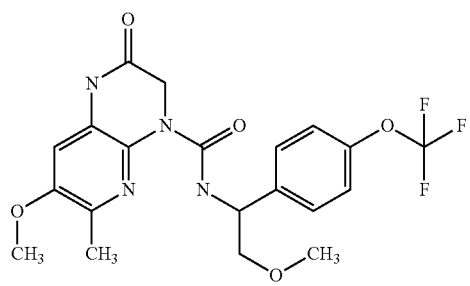 [SMILES: COCC(NC(=O)N1CC(=O)Nc2cc(OC)c(C)nc21)c1ccc(OC(F)(F)F)cc1] | 455.1 |
| 253 | N-((1S)-2-hydroxy-2-methyl-1-(4-(trifluoromethoxy)phenyl)propyl)-7-methoxy-6-methyl-2-oxo-2,3-dihydropyrido[2,3-b]pyrazine-4(1H)-carboxamide | 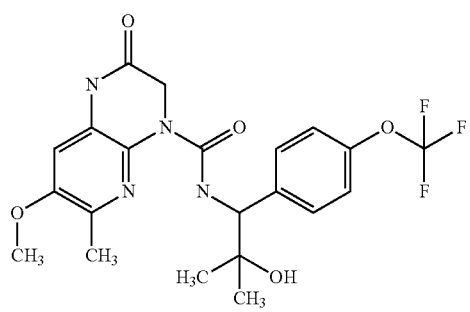 [SMILES: COc1cc2c(nc1C)N(C(=O)NC(c1ccc(OC(F)(F)F)cc1)C(C)(C)O)CC(=O)N2] | 469.1 |
| 254 | N-((1R)-2-hydroxy-2-methyl-1-(4-(trifluoromethoxy)phenyl)propyl)-7-methoxy-6-methyl-2-oxo-2,3-dihydropyrido[2,3-b]pyrazine-4(1H)-carboxamide | 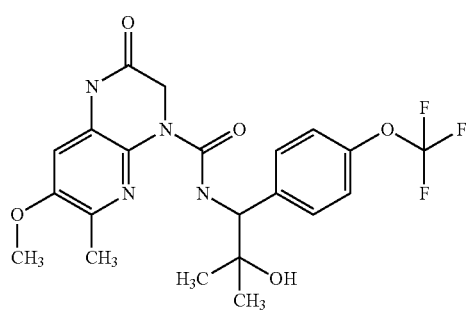 [SMILES: COc1cc2c(nc1C)N(C(=O)NC(c1ccc(OC(F)(F)F)cc1)C(C)(C)O)CC(=O)N2] | 469.1 |
| 255 | 7-methyl-2-oxo-N-(1-(5-(trifluoromethyl)pyridin-2-yl)propyl)-2,3-dihydropyrido[2,3-b]pyrazine-4(1H)-carboxamide | 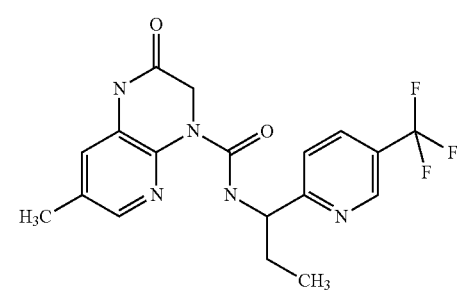 [SMILES: CCC(NC(=O)N1CC(=O)Nc2cc(C)cnc21)c1ccc(C(F)(F)F)cn1] | 394.1 |

TABLE 1-22-continued

| 256 | 7-cyclopropyl-N-(2-hydroxy-2-methyl-1-(4-(trifluoromethyl)phenyl)propyl)-2-oxo-2,3-dihydropyrido[2,3-b]pyrazine-4(1H)-carboxamide | 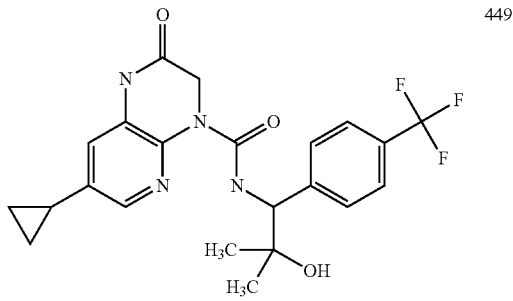 | 449.2 |
| 257 | optically active N-(3-methoxy-1-(4-(trifluoromethoxy)phenyl)propyl)-7-methyl-2-oxo-2,3-dihydropyrido[2,3-b]pyrazine-4(1H)-carboxamide | 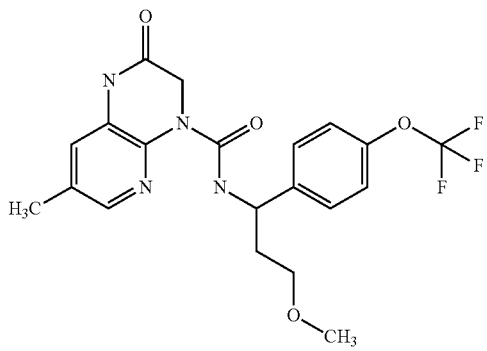 [SMILES: COCCC(NC(=O)N1CC(=O)Nc2cc(C)cnc21)c1ccc(OC(F)(F)F)cc1] | 439.1 |
| 258 | N-(3-methoxy-1-(4-(trifluoromethoxy)phenyl)propyl)-7-methyl-2-oxo-2,3-dihydropyrido[2,3-b]pyrazine-4(1H)-carboxamide | 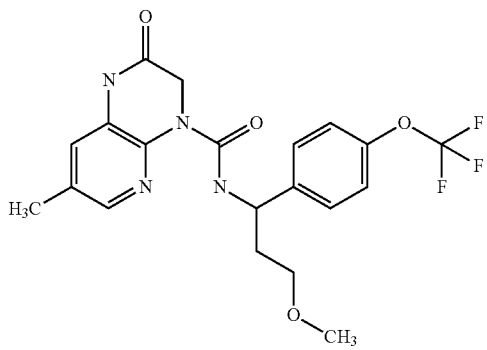 [SMILES: COCCC(NC(=O)N1CC(=O)Nc2cc(C)cnc21)c1ccc(OC(F)(F)F)cc1] | 439.1 |
| 259 | 6-methoxy-N-((1S)-2-methoxy-1-(4-(trifluoromethoxy)phenyl)ethyl)-7-methyl-2-oxo-2,3-dihydropyrido[2,3-b]pyrazine-4(1H)-carboxamide | 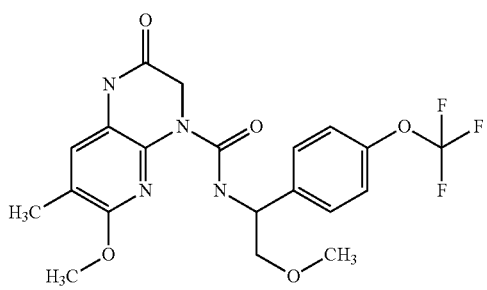 [SMILES: COCC(NC(=O)N1CC(=O)Nc2cc(C)c(OC)nc21)c1ccc(OC(F)(F)F)cc1] | 455.1 |
| 260 | 6-methoxy-N-((1R)-2-methoxy-1-(4-(trifluoromethoxy)phenyl)ethyl)-7-methyl-2-oxo-2,3-dihydropyrido[2,3-b]pyrazine-4(1H)-carboxamide | 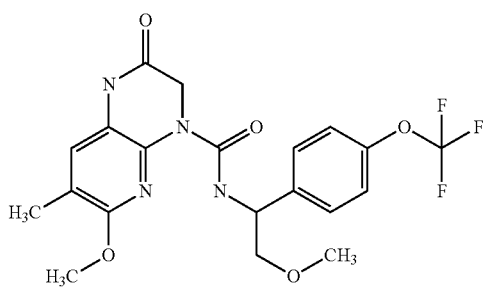 [SMILES: COCC(NC(=O)N1CC(=O)Nc2cc(C)c(OC)nc21)c1ccc(OC(F)(F)F)cc1] | 455.1 |

TABLE 1-22-continued

| 261 | N-((1S)-2-hydroxy-2-methyl-1-(4-(trifluoromethoxy)phenyl)propyl)-6-methoxy-7-methyl-2-oxo-2,3-dihydropyrido[2,3-b]pyrazine-4(1H)-carboxamide | | 469.2 |

15

TABLE 1-23

| 262 | N-((1R)-2-hydroxy-2-methyl-1-(4-(trifluoromethoxy)phenyl)propyl)-6-methoxy-7-methyl-2-oxo-2,3-dihydropyrido[2,3-b]pyrazine-4(1H)-carboxamide | | 469.2 |
| 263 | N-((1S)-2-hydroxy-2-methyl-1-(4-(trifluoromethoxy)phenyl)propyl)-7-methyl-2-oxo-2,3-dihydropyrido[2,3-b]pyrazine-4(1H)-carboxamide | | 439.1 |
| 264 | N-((1R)-2-hydroxy-2-methyl-1-(4-(trifluoromethoxy)phenyl)propyl)-7-methyl-2-oxo-2,3-dihydropyrido[2,3-b]pyrazine-4(1H)-carboxamide | | 439.1 |

TABLE 1-23-continued

| 265 | optically active 7-cyclopropyl-N-(2-hydroxy-2-methyl-1-(4-(trifluoromethyl)phenyl)propyl)-2-oxo-2,3-dihydropyrido[2,3-b]pyrazine-4(1H)-carboxamide | 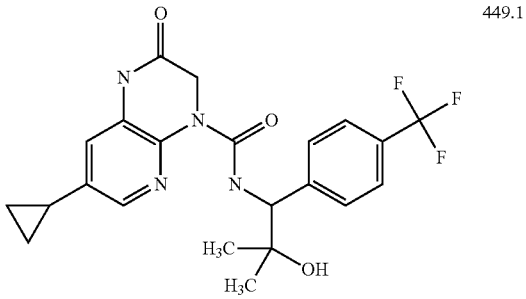 | 449.1 |
| --- | --- | --- | --- |
| 266 | optically active 7-cyclopropyl-N-(2-hydroxy-2-methyl-1-(4-(trifluoromethyl)phenyl)propyl)-2-oxo-2,3-dihydropyrido[2,3-b]pyrazine-4(1H)-carboxamide | 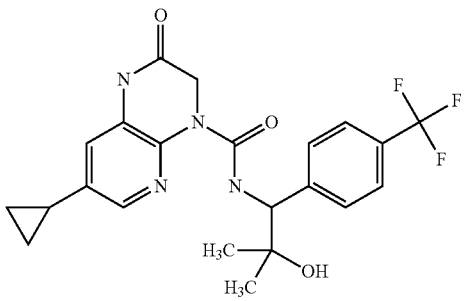 [SMILES: CC(C)(O)C(NC(=O)N1CC(=O)Nc2cc(C3CC3)cnc21)c1ccc(C(F)(F)F)cc1] | 449.1 |
| 267 | N-(2-hydroxy-2-methyl-1-(4-(trifluoromethyl)phenyl)propyl)-7-methoxy-2-oxo-2,3-dihydropyrido[2,3-b]pyrazine-4(1H)-carboxamide | 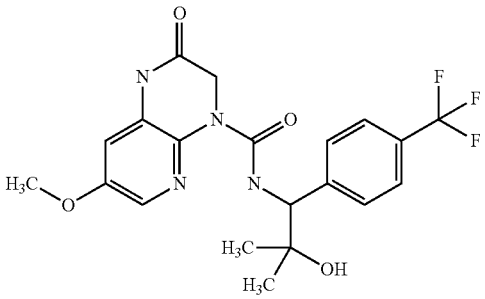 [SMILES: COc1cnc2c(c1)NC(=O)CN2C(=O)NC(c1ccc(C(F)(F)F)cc1)C(C)(C)O] | 439.2 |
| 268 | optically active N-(2-hydroxy-2-methyl-1-(4-(trifluoromethyl)phenyl)propyl)-7-methoxy-2-oxo-2,3-dihydropyrido[2,3-b]pyrazine-4(1H)-carboxamide | 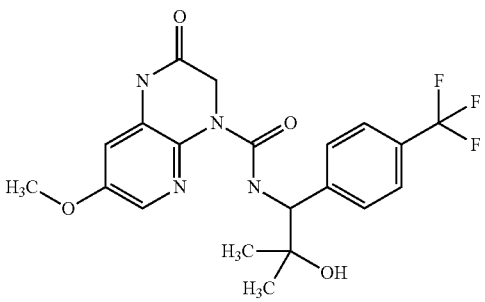 [SMILES: COc1cnc2c(c1)NC(=O)CN2C(=O)NC(c1ccc(C(F)(F)F)cc1)C(C)(C)O] | 439.2 |
| 269 | optically active N-(2-hydroxy-2-methyl-1-(4-(trifluoromethyl)phenyl)propyl)-7-methoxy-2-oxo-2,3-dihydropyrido[2,3-b]pyrazine-4(1H)-carboxamide | 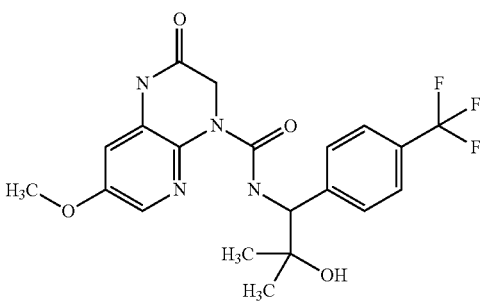 [SMILES: COc1cnc2c(c1)NC(=O)CN2C(=O)NC(c1ccc(C(F)(F)F)cc1)C(C)(C)O] | 439.2 |

TABLE 1-23-continued

| | | | |
|---|---|---|---|
| 270 | optically active 7-methyl-2-oxo-N-(1-(5-(trifluoromethyl)pyridin-2-yl)propyl)-2,3-dihydropyrido[2,3-b]pyrazine-4(1H)-carboxamide | 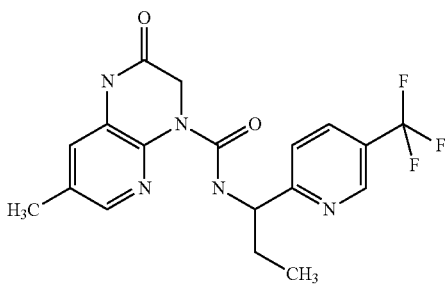 [SMILES: CCC(NC(=O)N1CC(=O)Nc2cc(C)cnc21)c1ccc(C(F)(F)F)cn1] | 394.1 |
| 271 | optically active 7-methyl-2-oxo-N-(1-(5-(trifluoromethyl)pyridin-2-yl)propyl)-2,3-dihydropyrido[2,3-b]pyrazine-4(1H)-carboxamide | 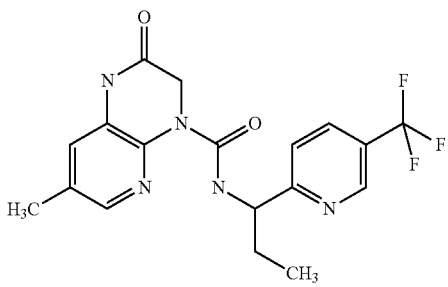 [SMILES: CCC(NC(=O)N1CC(=O)Nc2cc(C)cnc21)c1ccc(C(F)(F)F)cn1] | 394.1 |
| 272 | N-(1-(3-fluoro-4-(trifluoromethoxy)phenyl)-2-hydroxy-2-methylpropyl)-7-methyl-2-oxo-2,3-dihydropyrido[2,3-b]pyrazine-4(1H)-carboxamide | 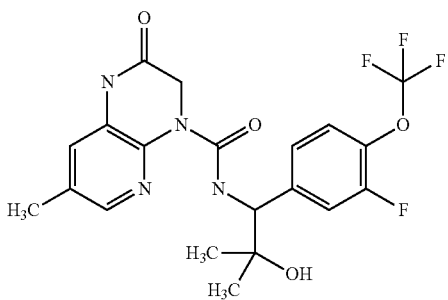 | 457.1 |
| 273 | optically active N-(1-(3-fluoro-4-(trifluoromethoxy)phenyl)-2-hydroxy-2-methylpropyl)-7-methyl-2-oxo-2,3-dihydropyrido[2,3-b]pyrazine-4(1H)-carboxamide | 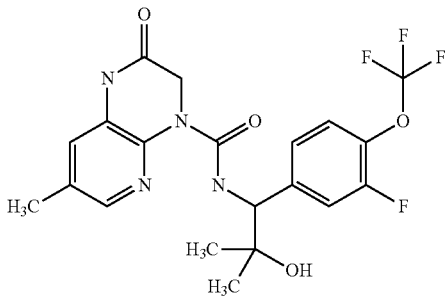 [SMILES: Cc1cnc2c(c1)NC(=O)CN2C(=O)NC(c1ccc(OC(F)(F)F)c(F)c1)C(C)(C)O] | 457.1 |

TABLE 1-24

| | | | |
|---|---|---|---|
| 274 | optically active N-(1-(3-fluoro-4-(trifluoromethoxy)phenyl)-2-hydroxy-2-methylpropyl)-7-methyl-2-oxo-2,3-dihydropyrido[2,3-b]pyrazine-4(1H)-carboxamide | 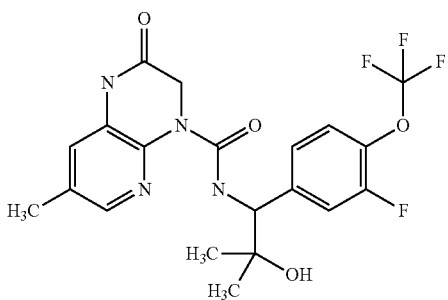 [SMILES: Cc1cnc2c(c1)NC(=O)CN2C(=O)NC(c1ccc(OC(F)(F)F)c(F)c1)C(C)(C)O] | 457.1 |

| | | | |
|---|---|---|---|
| 275 | N-(1-(3-fluoro-4-(trifluoromethoxy)phenyl)-2-hydroxy-2-methylpropyl)-7-methoxy-2-oxo-2,3-dihydropyrido[2,3-b]pyrazine-4(1H)-carboxamide | 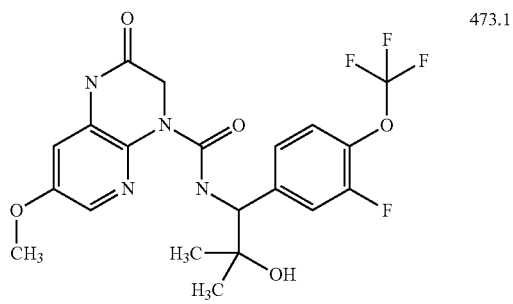 | 473.1 |
| 276 | optically active N-(1-(3-fluoro-4-(trifluoromethoxy)phenyl)-2-hydroxy-2-methylpropyl)-7-methoxy-2-oxo-2,3-dihydropyrido[2,3-b]pyrazine-4(1H)-carboxamide | 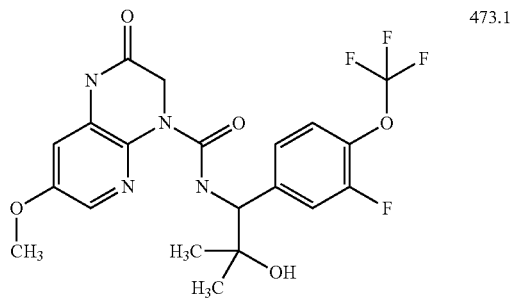 | 473.1 |
| 277 | optically active N-(1-(3-fluoro-4-(trifluoromethoxy)phenyl)-2-hydroxy-2-methylpropyl)-7-methoxy-2-oxo-2,3-dihydropyrido[2,3-b]pyrazine-4(1H)-carboxamide | 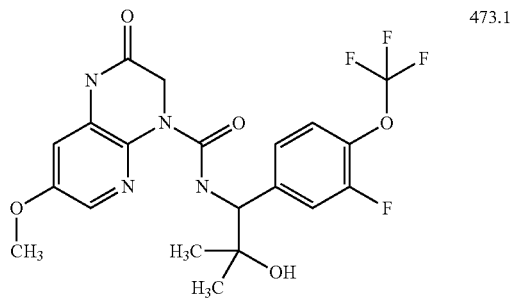 | 473.1 |
| 278 | N-(1-(3-fluoro-4-(trifluoromethoxy)phenyl)-2-methoxyethyl)-7-methoxy-6-methyl-2-oxo-2,3-dihydropyrido[2,3-b]pyrazine-4(1H)-carboxamide | 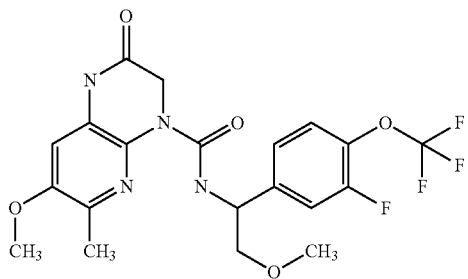 [SMILES: COCC(NC(=O)N1CC(=O)Nc2cc(OC)c(C)nc21)c1ccc(OC(F)(F)F)c(F)c1] | 473.1 |
| 279 | N-(1-(3-fluoro-4-(trifluoromethoxy)phenyl)-2-methoxyethyl)-6-methoxy-7-methyl-2-oxo-2,3-dihydropyrido[2,3-b]pyrazine-4(1H)-carboxamide | 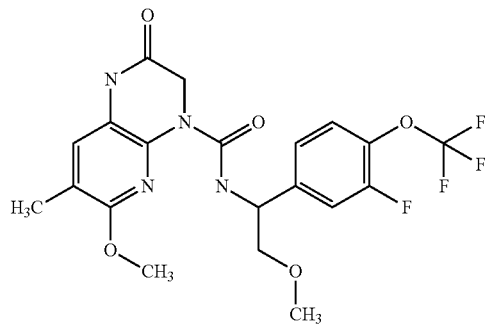 [SMILES: COCC(NC(=O)N1CC(=O)Nc2cc(C)c(OC)nc21)c1ccc(OC(F)(F)F)c(F)c1] | 473.1 |

TABLE 1-24-continued

| 280 | N-(2-cyano-1-(3-fluoro-4-(trifluoromethoxy)phenyl)ethyl)-7-methoxy-2-oxo-2,3-dihydropyrido[2,3-b]pyrazine-4(1H)-carboxamide | 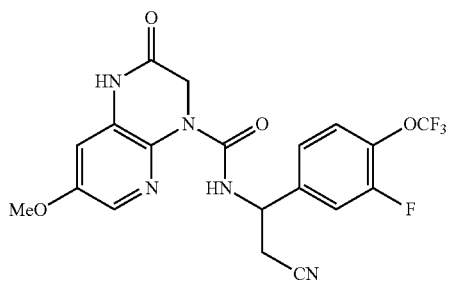 [SMILES: COc1cnc2c(c1)NC(=O)CN2C(=O)NC(CC#N)c1ccc(OC(F)(F)F)c(F)c1] | 454.1 |

Experimental Example 1

PDE Enzyme Inhibition Assay

Human PDE2A3 enzyme was generated from Sf9 cells transfected with the full-length gene. The extracted enzyme from Sf9 cells was purified by His-tag affinity column and gel filtration. The enzyme was stored at −70° C. until use. PDE activity was measured-using a SPA (Scintillation Proximity Assay) (GE Healthcare). To evaluate the inhibitory activity, 10 µl of serial diluted compounds were incubated with 20 µl of PDE enzyme in assay buffer (50 mM HEPES-NaOH, 8.3 mM $MgCl_2$, 1.7 mM EGTA, 0.1% BSA (pH 7.4)) for 30 min. at room temperature. Final concentration of DMSO in the assay was 1 percent as compounds were tested in duplicate in 96-well half-area plates (Corning) or 384-well OptiPlate (PerkinElmer). To start the reaction, 10 µl of substrate [$^3$H] cGMP (77 nM, PerkinElmer) was added for a final assay volume of 40 µl. After 60 min incubation at room temperature, 20 µl of 20 mg/ml yttrium SPA beads containing Zinc sulphate was added to terminate the PDE reaction. After being settled for further 1 hour, the assay plates were counted in a scintillation counter (PerkinElmer) to allow calculation of inhibition rate. Inhibition rate was calculated on the basis of 0% control wells with enzyme and DMSO, and 100% control wells without enzyme. The results are shown in Table 2.

TABLE 2

| Example No. | Inhibition Rate (%) (1 µM) |
| --- | --- |
| 5 | 95 |
| 9 | 96 |
| 14 | 99 |
| 15 | 94 |
| 25 | 99 |
| 31 | 96 |
| 35 | 95 |
| 52 | 93 |
| 54 | 95 |
| 60 | 97 |
| 64 | 99 |
| 66 | 101 |
| 67 | 101 |
| 70 | 98 |
| 73 | 99 |
| 76 | 100 |
| 93 | 96 |
| 107 | 99 |
| 117 | 99 |
| 120 | 99 |
| 121 | 99 |
| 123 | 98 |
| 129 | 99 |
| 130 | 99 |
| 134 | 97 |
| 136 | 99 |

TABLE 2-continued

| Example No. | Inhibition Rate (%) (1 µM) |
| --- | --- |
| 143 | 98 |
| 146 | 98 |
| 152 | 97 |
| 160 | 99 |
| 162 | 97 |
| 167 | 99 |
| 200 | 100 |
| 207 | 98 |
| 222 | 99 |
| 226 | 100 |
| 229 | 99 |
| 231 | 100 |
| 232 | 100 |
| 251 | 100 |
| 253 | 100 |
| 257 | 99 |
| 259 | 99 |
| 261 | 100 |
| 263 | 100 |
| 266 | 100 |
| 268 | 99 |
| 273 | 98 |
| 276 | 101 |

Experimental Example 2

The improvement effect on MK-801 ((5S,10R)-5-methyl-10,11-dihydro-5H-5,10-epiminodibenzo[a,d] [7]annulene)-induced disorder in contextual fear conditioning test.

Experimental Animals

Male C57BL/6 mice were purchased from CLEA Japan, Inc. They were used for an experiment after a habituation period of at least one week after carrying them in the animal experimental facility. They were bred in the animal experimental facility with environment in which 12-hours light-dark cycle was performed, humidity and temperature were controlled, and free water drinking and feeding were allowed. Handling of experimental animals and experimental procedure of this study were approved by the Experimental Animal Ethics Committee of Takeda Pharmaceutical Company Limited.

Used Drugs

A test compound was suspended in 0.5% methylcellulose solution, and orally administered. MK-801 (maleate) (Sigma-Aldrich, St Louis, Mo.) was dissolved in saline, and subcutaneously administered. All drugs were administered to mice at a dose of 10 mL/kg.

The improvement effect on MK-801-induced disorder in contextual fear conditioning test.

Contextual fear conditioning test is widely used as memory and learning test system depending on the hippocampus and amygdala. The improvement effect of test compounds on MK-801-induced disorder was investigated by contextual fear conditioning test. Administrations of 0.5% methylcellulose and saline to the control groups were carried out 60 minutes and minutes before tests, respectively. Administrations of 0.5% methylcellulose and MK-801 (maleate) to the vehicle groups were carried out 60 minutes and 30 minutes before tests, respectively. Test compounds and MK-801 (maleate) were administered 60 minutes and 30 minutes before tests. In experiments, a chamber with a floor grid for electric shock and a freezing measuring device (O'Hara & Co., Ltd.) were used. The chamber was put in a soundproof box to block the noise from outside, and tests were performed. In the training session on day 1 of the experiment, after habituation for 3 minutes in the chamber, two electric footshocks were given to mice at 1-minute interval. In the test session on day 2 of the experiment, mice were placed in the same chamber for 7 minutes, and freezing was measured during that period. The freezing was calculated as a percentage of freezing rates during measuring period with use of an automatic analysis software manufactured by the O'Hara & Co., Ltd. All data were shown as the mean+standard error (n=10-11). A comparison between two groups was tested by Student's t-test (*p≤0.05, comparison with control group. #p≤0.05, comparison with group treated with MK-801 alone.).

The compounds in FIG. 1 correspond to the following compounds.
Compound A: Example 67-II
Compound B: Example 73
Compound C: Example 76
Compound D: Example 263
Compound E: Example 273
Compound F: Example 64

The improvement effect on MK-801-induced deficits was shown by orally administering each of test compounds (A-F) to mice 60 minutes before the tests.

Formulation Example 1

| (1) Compound of the Example 1 | 10.0 g |
| (2) Lactose | 70.0 g |
| (3) Cornstarch | 50.0 g |
| (4) Soluble starch | 7.0 g |
| (5) Magnesium stearate | 3.0 g |

After 10.0 g of the compound in Embodiment 1 and 3.0 g of magnesium stearate are granulated in 70 ml aqueous solution of soluble starch (7.0 g as soluble starch) and then dried, and the resulting mixture is mixed with 70.0 g of lactose and 50.0 g of cornstarch (lactose, cornstarch, soluble starch and magnesium stearate are all products in compliance with Japanese Pharmacopoeia 14th Edition). The mixture is compressed to obtain a tablet.

INDUSTRIAL APPLICABILITY

According to the present invention, the compound having a PDE2A selective inhibitory action, which is useful as an agent for the prophylaxis or treatment of schizophrenia, Alzheimer's disease and the like, can be provided.

This application is based on patent application Nos. 100374/2012 and 283470/2012 filed in Japan, the contents of which are hereby incorporated by reference.

The invention claimed is:
1. A compound represented by the formula (1):

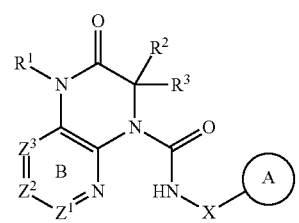

(1)

wherein
$R^1$ is a hydrogen atom,
$R^2$ and $R^3$ are each independently a hydrogen atom or a $C_{1-6}$ alkyl group,
the group represented by

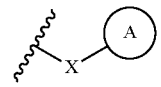

is a group represented by

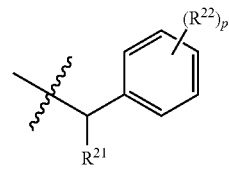

wherein
$R^{21}$ is
(1) cyano,
(2) carbamoyl,
(3) mono- or di-$C_{1-6}$ alkyl-carbamoyl,
(4) $C_{1-6}$ alkyl optionally substituted by 1 to 5 substituents selected from
  (i) a halogen atom,
  (ii) hydroxy,
  (iii) amino,
  (iv) cyano,
  (V) $C_{3-8}$ cycloalkyl,
  (vi) $C_{1-6}$ alkoxy optionally substituted by 1 to 3 substituents selected from
    (a) a halogen atom, and
    (b) $C_{1-6}$ alkoxy,
  (vii) $C_{3-8}$ cycloalkyloxy,
  (viii) mono- or di-$C_{1-6}$ alkyl-amino,
  (ix) $C_{1-6}$ alkylsulfanyl,
  (x) $C_{1-6}$ alkylsulfinyl,
  (xi) $C_{1-6}$ alkylsulfonyl,
  (xii) carbamoyl,
  (xiii) mono- or di-$C_{1-6}$ alkyl-carbamoyl,
  (xiv) a heterocyclic group optionally substituted by 1 to 3 substituents selected from
    (a) hydroxy, and
    (b) oxo,
  (xv) $C_{1-6}$ alkyl-carbonyloxy,
  (xvi) $C_{1-6}$ alkyl(diaryl)silyloxy, and
  (xvii) optionally halogenated heterocyclyl-oxy, (5) $C_{3-8}$ cycloalkyl,
(6) a heterocyclic group optionally substituted by 1 to 3 $C_{1-6}$ alkyl,
(7) $C_{1-6}$ alkyl-carbonyl,
(8) $C_{3-8}$ cycloalkyl-carbonyl, or
(9) $C_{6-14}$ aryl optionally substituted by 1 to 3 substituents selected from
  (i) a halogen atom,
  (ii) hydroxy,
  (iii) optionally halogenated $C_{1-6}$ alkoxy,
$R^{22}$ is
(1) a halogen atom,
(2) hydroxy,
(3) optionally halogenated $C_{1-6}$ alkyl,
(4) $C_{2-6}$ alkenyl,
(5) $C_{1-6}$ alkoxy optionally substituted by 1 to 3 substituents selected from
  (i) a halogen atom, and
  (ii) $C_{3-8}$ cycloalkyl,
(6) $C_{6-14}$ aryl,
(7) a heterocyclic group optionally substituted by 1 to 3 $C_{1-6}$ alkyl, or
(8) $C_{3-8}$ cycloalkyl, and
p is an integer of 1 to 3,
$Z^1$ is a group represented by $CR^{Z1}$ wherein $R^{Z1}$ is
(1) a hydrogen atom,
(2) a halogen atom,
(3) a $C_{1-6}$ alkyl group optionally substituted by 1 to 3 substituents selected from
  (i) a halogen atom, and
  (ii) $C_{6-14}$ aryl,
(4) a $C_{2-6}$ alkenyl group,
(5) a $C_{1-6}$ alkoxy group,
(6) a cyano group,
(7) a $C_{6-14}$ aryl group optionally substituted by 1 to 3 $C_{1-6}$ alkoxy,
(8) a heterocyclic group optionally substituted by 1 to 3 $C_{1-6}$ alkyl, or
(9) a $C_{3-8}$ cycloalkyl group
$Z^2$ is a group represented by $CR^{Z2}$ wherein $R^{Z2}$ is
(1) a hydrogen atom,
(2) a halogen atom,
(3) a $C_{1-6}$ alkyl group optionally substituted by 1 to 3 substituents selected from
  (i) a halogen atom, and
  (ii) hydroxy,
(4) a $C_{2-6}$ alkenyl group,
(5) an optionally halogenated $C_{1-6}$ alkoxy group,
(6) a cyano group,
(7) a $C_{6-14}$ aryl group,
(8) a $C_{3-8}$ cycloalkyl group, or
(9) a heterocyclic group optionally substituted by 1 to 3 $C_{1-6}$ alkyl, and
$Z^3$ is a group represented by $CR^{Z3}$ wherein $R^{Z3}$ is
(1) a hydrogen atom,
(2) a $C_{1-6}$ alkyl group optionally substituted by 1 to 3 hydroxy groups,
(3) a $C_{1-6}$ alkoxy group, or
(4) a $C_{1-6}$ alkyl-carbonyl group
or a salt thereof.

2. The compound or salt of claim 1, wherein $R^2$ and $R^3$ are both hydrogen atoms.

3. The compound or salt of claim 1, wherein $R^{Z1}$ and $R^{Z3}$ are both hydrogen atoms.

4. The compound or salt of claim 1, wherein $R^{Z2}$ is
(1) a $C_{1-6}$ alkyl group optionally substituted by 1 to 3 substituents selected from
  (i) a halogen atom, and
  (ii) hydroxy,
(2) an optionally halogenated $C_{1-6}$ alkoxy group, or
(3) a $C_{3-8}$ cycloalkyl group.

5. The compound or salt of claim 1, wherein
$R^1$ is a hydrogen atom,
$R^2$ and $R^3$ are both hydrogen atoms,
$Z^1$ is CH,
$Z^2$ is a group represented by $CR^{Z2}$ wherein $R^{Z2}$ is
(1) a $C_{1-6}$ alkyl group optionally substituted by 1 to 3 substituents selected from
  (i) a halogen atom, and
  (ii) hydroxy,
(2) an optionally halogenated $C_{1-6}$ alkoxy group, or
(3) a $C_{3-8}$ cycloalkyl group, and
$Z^3$ is CH.

6. A medicament comprising the compound or salt of claim 1 and a carrier.

7. The medicament of claim 6, which is a phosphodiesterase 2A inhibitor.

8. The medicament of claim 6, which is an agent for the treatment of schizophrenia.

9. A method of inhibiting phosphodiesterase 2A, which comprises administering an effective amount of a compound or salt of claim 1 to a mammal.

10. A method for the treatment of schizophrenia, which comprises administering an effective amount of a compound or salt of claim 1 to a mammal.

11. The compound or salt of claim 1, wherein
$R^1$ is a hydrogen atom;
$R^2$ and $R^3$ are both hydrogen atoms;
the group represented by

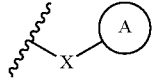

is a group represented by

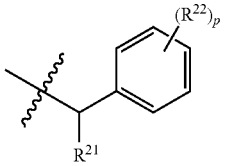

wherein
$R^{21}$ is a $C_{1-5}$ alkyl group optionally substituted by hydroxy or $C_{1-6}$ alkoxy,
$R^{22}$ is
(1) a halogen atom, or
(2) an optionally halogenated $C_{1-6}$ alkoxy group,
p is an integer of 1 or 2;
$Z^1$ is CH;
$Z^2$ is a group represented by $CR^{Z2}$ wherein $R^{Z2}$ is
(1) a $C_{1-6}$ alkoxy group,
(2) a $C_{3-8}$ cycloalkyl group, or
(3) a $C_{1-6}$ alkyl group; and
$Z^3$ is CH.

* * * * *